US008057996B2

(12) United States Patent
Raitano et al.

(10) Patent No.: US 8,057,996 B2
(45) Date of Patent: *Nov. 15, 2011

(54) NUCLEIC ACIDS AND CORRESPONDING PROTEINS ENTITLED 202P5A5 USEFUL IN TREATMENT AND DETECTION OF CANCER

(75) Inventors: Arthur B. Raitano, Los Angeles, CA (US); Mary Faris, Los Angeles, CA (US); Pia M. Challita-Eid, Encino, CA (US); Aya Jakobovits, Beverly Hills, CA (US); Wangmao Ge, Culver City, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/548,626

(22) Filed: Oct. 11, 2006

(65) Prior Publication Data

US 2008/0181885 A1 Jul. 31, 2008

Related U.S. Application Data

(63) Continuation of application No. 10/463,782, filed on Jun. 16, 2003, now abandoned.

(60) Provisional application No. 60/423,290, filed on Nov. 1, 2002, provisional application No. 60/404,306, filed on Aug. 16, 2002.

(51) Int. Cl.
*C12Q 1/68* (2006.01)
(52) U.S. Cl. .......................................................... 435/6
(58) Field of Classification Search ...................... 435/6
See application file for complete search history.

(56) References Cited

U.S. PATENT DOCUMENTS

| | | | |
|---|---|---|---|
| 5,460,951 A | 10/1995 | Kawai et al. | |
| 5,539,084 A | 7/1996 | Geysen | |
| 5,785,973 A | 7/1998 | Bixler et al. | |
| 5,840,839 A | 11/1998 | Wang et al. | |
| 6,893,818 B1 * | 5/2005 | Afar et al. | 435/6 |
| 2001/0051344 A1 * | 12/2001 | Shalon et al. | 435/6 |
| 2003/0054375 A1 | 3/2003 | Rosen et al. | |
| 2003/0087250 A1 | 5/2003 | Monahan et al. | |
| 2004/0053250 A1 | 3/2004 | Tang et al. | |
| 2007/0014801 A1 * | 1/2007 | Gish et al. | 424/155.1 |

FOREIGN PATENT DOCUMENTS

| | | |
|---|---|---|
| CN | 1412309 | 4/2003 |
| CN | 1477123 | 2/2004 |
| EP | 1 074 617 | 2/2001 |
| WO | WO9952942 | * 10/1999 |
| WO | WO-00/18916 | 4/2000 |
| WO | WO-00/58473 | 10/2000 |
| WO | WO-01/55343 | 8/2001 |
| WO | WO-01/57271 | 8/2001 |
| WO | WO-01/57272 | 8/2001 |
| WO | WO-01/60860 | 8/2001 |
| WO | WO-01/70979 | 9/2001 |
| WO | WO-01/75067 | 10/2001 |
| WO | WO-01/92581 | 12/2001 |
| WO | WO-01/94629 | 12/2001 |
| WO | WO-02/10449 | 2/2002 |
| WO | WO-02/29086 | 4/2002 |
| WO | WO-02/30268 | 4/2002 |
| WO | WO-02/59271 | 8/2002 |
| WO | WO-02/60317 | 8/2002 |
| WO | WO-02/70539 | 9/2002 |
| WO | WO-02/71928 | 9/2002 |
| WO | WO-03/006618 | 1/2003 |
| WO | WO-03/083047 | 10/2003 |
| WO | WO-03/083074 | 10/2003 |
| WO | WO-03/087768 | 10/2003 |
| WO | WO-2004/015108 | 2/2004 |
| WO | WO-2004/016736 | 2/2004 |
| WO | WO-2004/046342 | 6/2004 |
| WO | WO-2004/065545 | 8/2004 |

OTHER PUBLICATIONS

Kroese et al., Genetics in Medicine, 2004, 6: 475-480.*
Lucentini, The Scientist, 2004, vol. 18, p. 20.*
Hacker, Gut, 1997, 40: 623-627.*
Pennisi, Science, 1998, 281(5384): 1787-1789.*
Yerushalmi et al., Gene, 2001, vol. 265, pp. 55-60.*
Caillou et al., Journal of Clinical Endocrinology and Metabolism, 2001, vol. 86, pp. 3351-3358.*
Conklin et al., Briefings in Bioinformatics, 2000, vol. 1, pp. 93-99.*
Drivas et al., (Identification of Novel ras family genes in a human teratocarcinoma cell line by oligonucleotide screening In: The ras-Superfamily of GTPases, Lacal and McCormick, Eds., 1993, pp. 329-347).*
Database Geneseq, accession No. ABZ11512 (2003).
Database Geneseq, accession No. ADJ70535 (2004).
Database Geneseq, accession No. BD160241 (2003).
Database Geneseq, accession No. BD570305 (2003).
Supplementary European Search Report for EP 03737110.1, mailed Sep. 7, 2007, 5 pages.
Wilanowski et al., Mechanisms of Development (2002) 114(1-2):37-50.
Riott et al., Immunology, Fourth Edition (1996) Mosby, p. 7.9-7.11.
Jain, Sci. Am. (1994) 171:58-65.
Gura, Science (1997) 278(5340):1041-1042.
MSNBC News Services, "Mixed results on new cancer drug" Nov. 2000.
Greenbaum et al., Genome Biology (2003) 4(9):117.1-117.8.
Alberts et al., Molecular Biology of the Cell, $3^{rd}$ Edition (1994) p. 465.

(Continued)

*Primary Examiner* — Misook Yu
*Assistant Examiner* — Hong Sang
(74) *Attorney, Agent, or Firm* — Morrison & Foerster LLP

(57) ABSTRACT

A novel gene 202P5A5 and its encoded protein, and variants thereof, are described wherein 202P5A5 exhibits tissue specific expression in normal adult tissue, and is aberrantly expressed in the cancers listed in Table I. Consequently, 202P5A5 provides a diagnostic, prognostic, prophylactic and/or therapeutic target for cancer. The 202P5A5 gene or fragment thereof, or its encoded protein, or variants thereof, or a fragment thereof, can be used to elicit a humoral or cellular immune response; antibodies or T cells reactive with 202P5A5 can be used in active or passive immunization.

9 Claims, 51 Drawing Sheets

OTHER PUBLICATIONS

Mallampalli et al., Biochem. J. (1996) 38:333-341.
Fu et al., EMBO Journal (1996) 15:4392-4401.
Database Genbank, Accession No. ABP69295, Sep. 12, 2002.
Database Genbank, Accession No. Q9H8B8, Ota et al., 2005.
International Search Report for PCT/US03/18906, mailed on Aug. 4, 2006, 5 pages.

* cited by examiner

Figure 1.   202P5A5 SSH sequence of 186 nucleotides (SEQ ID NO: 1).

```
  1 GATCATGGAT TTTTTTTAAG CTTATTTGAG TTTGATTAAG GGACAAAAAA GAAGAGGCGG
 61 CAAGTTTTCC TATCTCTTTG GAGTGTTTCG CTCAGGAAAT TTTGCTCATC AAAATTCAGC
121 TAACATACAC AGCGGACACA TCAAAGGCAA ACTGGGGTGC TCCGAGGATG CAGAGGGGAA
181 TGGATC
```

Figure 2A-1

```
 1                                            M  P  S  D  P  P  F  N  T  R  R
 1 taataaaagactagtggccttagtgcccATGCCCAGTGACCCTCCATTCAATACCCGAAG
12 A  Y  T  S  E  D  E  A  W  K  S  Y  L  E  N  P  L  T  A  A
61 AGCCTACACCAGTGAGGATGAAGCCTGGAAGTCATACTTGGAGAATCCCCTGACAGCAGC
32 T  K  A  M  M  S  I  N  G  D  E  D  S  A  A  A  L  G  L  L
121 CACCAAGGCCATGATGAGCATTAATGGTGATGAGGACAGTGCTGCTGCCCTCGGCCTGCT
52 Y  D  Y  Y  K  V  P  R  D  K  R  L  L  S  V  S  K  A  S  D
181 CTATGACTACTACAAGGTTCCTCGAGACAAGAGGCTGCTGTCTGTAAGCAAAGCAAGTGA
72 S  Q  E  D  Q  E  K  R  N  C  L  G  T  S  E  A  Q  S  N  L
241 CAGCCAAGAAGACCAGGAGAAAAGAAACTGCCTTGGCACCAGTGAAGCCCAGAGTAATTT
92 S  G  G  E  N  R  V  Q  V  L  K  T  V  P  V  N  L  S  L  N
301 GAGTGGAGGAGAAAACCGAGTGCAAGTCCTAAAGACTGTTCCAGTGAACCTTTCCCTAAA
112 Q  D  H  L  E  N  S  K  R  E  Q  Y  S  I  S  F  P  E  S  S
361 TCAAGATCACCTGGAGAATTCCAAGCGGGAACAGTACAGCATCAGCTTCCCCGAGAGCTC
132 A  I  I  P  V  S  G  I  T  V  V  K  A  E  D  F  T  P  V  F
421 TGCCATCATCCCGGTGTCGGGAATCACGGTGGTGAAAGCTGAAGATTTCACACCAGTTTT
152 M  A  P  P  V  H  Y  P  R  G  D  E  E  Q  R  V  V  I  F
481 CATGGCCCCACCTGTGCACTATCCCCGGGGAGATGGGGAAGAGCAACGAGTGGTTATCTT
172 E  Q  T  Q  Y  D  V  P  S  L  A  T  H  S  A  Y  L  K  D  D
541 TGAACAGACTCAGTATGACGTGCCCTCGCTGGCCACCCACAGCGCCTATCTCAAAGACGA
192 Q  R  S  T  P  D  S  T  Y  S  E  S  F  K  D  A  A  T  E  K
601 CCAGCGCAGCACTCCGGACAGCACATACAGCGAGAGCTTCAAGGACGCAGCCACAGAGAA
212 F  R  S  A  S  V  G  A  E  E  Y  M  Y  D  Q  T  S  S  G  T
661 ATTTCGGAGTGCTTCAGTTGGGGCTGAGGAGTACATGTATGATCAGACATCAAGTGGCAC
232 F  Q  Y  T  L  E  A  T  K  S  L  R  Q  K  Q  G  E  G  P  M
721 ATTTCAGTACACCCTGGAAGCCACCAAATCTCTCCGTCAGAAGCAGGGGGAGGGCCCCAT
252 T  Y  L  N  K  G  Q  F  Y  A  I  T  L  S  E  T  G  D  N  K
781 GACCTACCTCAACAAAGGACAGTTCTATGCCATAACACTCAGCGAGACCGGAGACAACAA
272 C  F  R  H  P  I  S  K  V  R  S  V  V  M  V  V  F  S  E  D
841 ATGCTTCCGACACCCCATCAGCAAAGTCAGGAGTGTGGTGATGGTGGTCTTCAGTGAAGA
292 K  N  R  D  E  Q  L  K  Y  W  K  Y  W  H  S  R  Q  H  T  A
901 CAAAAACAGAGATGAACAGCTCAAATACTGGAAATACTGGCACTCTCGGCAGCATACGGC
312 K  Q  R  V  L  D  I  A  D  Y  K  E  S  F  N  T  I  G  N  I
961 GAAGCAGAGGGTCCTTGACATTGCCGATTACAAGGAGAGCTTTAATACGATTGGAAACAT
332 E  E  I  A  Y  N  A  V  S  F  T  W  D  V  N  E  E  A  K  I
```

Figure 2A-2

```
1021 TGAAGAGATTGCATATAATGCTGTTTCCTTTACCTGGGACGTGAATGAAGAGGCGAAGAT
 352  F  I  T  V  N  C  L  S  T  D  F  S  S  Q  K  G  V  K  G  L
1081 TTTCATCACCGTGAATTGCTTGAGCACAGATTTCTCCTCCCAAAAAGGGGTGAAAGGACT
 372  P  L  M  I  Q  I  D  T  Y  S  Y  N  N  R  S  N  K  P  I  H
1141 TCCTTTGATGATTCAGATTGACACATACAGTTATAACAATCGTAGCAATAAACCCATTCA
 392  R  A  Y  C  Q  I  K  V  F  C  D  K  G  A  E  R  K  I  R  D
1201 TAGAGCTTATTGCCAGATCAAGGTCTTCTGTGACAAAGGAGCAGAAAGAAAAATCCGAGA
 412  E  E  R  K  Q  N  R  K  K  G  K  G  Q  A  S  Q  T  Q  C  N
1261 TGAAGAGCGGAAGCAGAACAGGAAGAAAGGGAAAGGCCAGGCCTCCCAAACTCAATGCAA
 432  S  S  S  D  G  K  L  A  A  I  P  L  Q  K  K  S  D  I  T  Y
1321 CAGCTCCTCTGATGGGAAGTTGGCTGCCATACCTTTACAGAAGAAGAGTGACATCACCTA
 452  F  K  T  M  P  D  L  H  S  Q  P  V  L  F  I  P  D  V  H  F
1381 CTTCAAAACCATGCCTGATCTCCACTCACAGCCAGTTCTCTTCATACCTGATGTTCACTT
 472  A  N  L  Q  R  T  G  Q  V  Y  Y  N  T  D  D  E  R  E  G  G
1441 TGCCAAACCTGCAGAGGACCGGACAGGTCTATTACAACACGGATGATGAACGAGAAGGTGG
 492  S  V  L  V  K  R  M  F  R  P  M  E  E  E  F  G  P  V  P  S
1501 CAGTGTCCTTGTTAAACGGATGTTCCGGCCCATGGAAGAGGAGTTTGGTCCAGTGCCTTC
 512  K  Q  M  K  E  E  G  T  K  R  V  L  L  Y  V  R  K  E  T  D
1561 AAAGCAGATGAAAGAAGAAGGGACAAAGCGAGTGCTCTTGTACGTGAGGAAGGAGACTGA
 532  D  V  F  D  A  L  M  L  K  S  P  T  V  K  G  L  M  E  A  I
1621 CGATGTGTTCGATGCATTGATGTTGAAGTCTCCCACAGTGAAGGGCCTGATGGAAGCGAT
 552  S  E  K  Y  G  L  P  V  E  K  I  A  K  L  Y  K  K  S  K  K
1681 ATCTGAGAAATATGGGCTGCCCGTGGAGAAGATAGCAAAGCTTTACAAGAAAAGCAAAAA
 572  G  I  L  V  N  M  D  D  N  I  I  E  H  Y  S  N  E  D  T  F
1741 AGGCATCTTGGTGAACATGGATGACAACATCATCGAGCACTACTCGAACGAGGACACCTT
 592  I  L  N  M  E  S  M  V  E  G  F  K  V  T  L  M  E  I  *
1801 CATCCTCAACATGGAGAGCATGGTGGAGGGCTTCAAGGTCACGCTCATGGAAATCTAGcc
1861 ctgggtttggcatccgctttggctggagctctcagtgcgttcctccctgagagagacaga
1921 agcccagccccagaacctggagacccatctcccccatctcacaactgctgttacaagac
1981 cgtgctggggagtggggcaagggacaggcccactgtcggtgtgcttggcccatccactg
2041 gcacctaccacggagctgaagcctgagcccctcaggaaggtgccttaggcctgttggatt
2101 cctatttattgcccaccttttcctggagcccaggtccaggcccgccaggactctgcaggt
2161 cactgctagctccagatgagaccgtccagcgttcccccttcaagagaaacactcatcccg
2221 aacagcctaaaaaattcccatcccttctctctcacccctccatatctatctcccgagtgg
2281 ctggacaaaatgagctacgtctgggtgcagtagttataggtggggcaagaggtggatgcc
2341 cactttctggtcagacacctttaggttgctctggggaaggctgtcttgctaaatacctcc
2401 agggttcccagcaagtggccaccaggccttgtacaggaagacattcagtcaccgtgtaat
```

Figure 2A-3

```
2461 tagtaacacagaaagtctgcctgtctgcattgtacatagtgtttataatattgtaataat
2521 atattttacctgtggtatgtgggcatgtttactgccactggcctagaggagacacagacc
2581 tggagaccgttttaatgggggttttttgcctctgtgcctgttcaagagacttgcagggcta
2641 ggtagagggcctttgggatgttaaggtgactgcagctgatgccaagatggactctgcaat
2701 gggcatacctgggggctcgttccctgtccccagaggaagccccctctccttctccatggg
2761 catgactctccttcgaggccaccacgtttatctcacaatgatgtgttttgcttgactttc
2821 cctttgcgctgtctcgtgggaaaggtcattctgtctgagacccagctccttctccagct
2881 ttggctgcgggcatggcctgagctttctggagagcctctgcaggggtttgccatcaggg
2941 ccctgtggctgggtctgctgcagagctccttggctatcaggagaatcctggacactgtac
3001 tgtgcctccagtttacaaacacgcccttcatctcaagtggccctttaaaaggcctgctg
3061 ccatgtgagagctgtgaacagctcagctctgagtcggcaggctggggcttcctcctggc
3121 caccagatggaaaggggtattgtttgcctcactcctggatgctgcgttttaaggaagtg
3181 agtgagaagaatgtgccaagatacctggctcctgtgaaaccagcctcaggagggaaact
3241 gggagagagaagctgtggtctcctgctacatgccctgggagctggaagagaaaaacactc
3301 ccctaaacaatcgcaaaatgatgaaccatcatgggccactgttctctttgaggggacagg
3361 tttaggggtttgcgttcgcccttgtgggctgaagcactagcttttggtagctagacaca
3421 tcctgcacccaaaggttctctacaaaggcccagatttgtttgtaaagcactttgactctt
3481 acctggaggcccgctctctaagggcttcctgcgctcccacctcatctgtccctgagatgc
3541 agagcaggatggagggtctgcttctagctcagctgtttctccttgaggttgcggaggaat
3601 tgaattgaatgggacagagggcaggtgctgtggccaagaagatctccgagcagcagtgac
3661 ggggcaccttgctgtgtgtcctctgggcatgttaaccttctgtggggccaaaggtttgc
3721 atcgtggatccagctgtgctccagtctgtcccctcctcctccactctgactgccacgccc
3781 cggaccagcagcttggggaccctccagggtactaatggggctctgttctgagatggacaa
3841 attcagtgttggaaatacatgttgtactatgcacttcccatgctcctagggttaggaata
3901 gtttcaaacatgattggcagacataacaacggcaaatactcggactggggcataggactc
3961 cagagtaggaaaaagacaaaagatttggcagcctgacacaggcaacctacccctctctct
4021 ccagcctctttatgaaactgtttgtttgccagtcctgccctaaggcagaagatgaattga
4081 agatgctgtgcatgtttcctaagtccttgagcaatcatggtggtgacaattgccacaagg
4141 gatatgaggccagtgccaccagagggtggtgccaagtgccacatcccttccgatccattc
4201 ccctctgcatcctcggagcaccccagtttgcctttgatgtgtccgctgtgtatgttagct
4261 gaactttgatgagcaaaatttcctgagcgaaacactccaaagagataggaaaacttgccg
4321 cctcttctttttttgtcccttaatcaaactcaaataagcttaaaaaaaatccatggaagat
4381 catggacatgtgaaatgagcatttttttctttttttttttaacaaagtctgaactgaac
4441 agaacaagacttttcctcatacatctccaaattgtttaaacttactttatgagtgtttg
4501 tttagaagttcggaccaacagaaaatgcagtcagatgtcatcttggaattggtttctaa
4561 aagagtaaggcatgtccctgcccagaaacttaggaagcatgaaataaatcaaatgtttat
4621 tttccttcttatttaaaatcatgcaaatgcaacagaaatagagggtttgtgccaaatgct
4681 atgaacggccctttcttaaagacaagcaagggagattgatatatgtacaatttgctctca
4741 tgtttt
```

Figure 2B. The cDNA (SEQ ID. NO. : 4) and amino acid sequence (SEQ ID. NO. : 5) of 202P5A5 v.2. The Kozak initiation sequence is shown in bold, and the start methionine is underlined. The open reading frame extends from nucleic acid 13-1890 including the stop codon.

Figure 2B-1

```
    1                  M  S  Q  E  S  D  N  N  K  R  L  V  A  L  V  P
    1 attggatcaaacATGTCACAAGAGTCGGACAATAATAAAAGACTAGTGGCCTTAGTGCCC
   17 M  P  S  D  P  P  F  N  T  R  R  A  Y  T  S  E  D  E  A  W
   61 ATGCCCAGTGACCCTCCATTCAATACCCGAAGAGCCTACACCAGTGAGGATGAAGCCTGG
   37 K  S  Y  L  E  N  P  L  T  A  A  T  K  A  M  M  S  I  N  G
  121 AAGTCATACTTGGAGAATCCCCTGACAGCAGCCACCAAGGCCATGATGAGCATTAATGGT
   57 D  E  D  S  A  A  A  L  G  L  L  Y  D  Y  Y  K  V  P  R  D
  181 GATGAGGACAGTGCTGCTGCCCTCGGCCTGCTCTATGACTACTACAAGGTTCCTCGAGAC
   77 K  R  L  L  S  V  S  K  A  S  D  S  Q  E  D  Q  E  K  R  N
  241 AAGAGGCTGCTGTCTGTAAGCAAAGCAAGTGACAGCCAAGAAGACCAGGAGAAAAGAAAC
   97 C  L  G  T  S  E  A  Q  S  N  L  S  G  G  E  N  R  V  Q  V
  301 TGCCTTGGCACCAGTGAAGCCCAGAGTAATTTGAGTGGAGGAGAAAACCGAGTGCAAGTC
  117 L  K  T  V  P  V  N  L  S  L  N  Q  D  H  L  E  N  S  K  R
  361 CTAAAGACTGTTCCAGTGAACCTTTCCCTAAATCAAGATCACCTGGAGAATTCCAAGCGG
  137 E  Q  Y  S  I  S  F  P  E  S  S  A  I  I  P  V  S  G  I  T
  421 GAACAGTACAGCATCAGCTTCCCCGAGAGCTCTGCCATCATCCCGGTGTCGGGAATCACG
  157 V  V  K  A  E  D  F  T  P  V  F  M  A  P  P  V  H  Y  P  R
  481 GTGGTGAAAGCTGAAGATTTCACACCAGTTTTCATGGCCCCACCTGTGCACTATCCCCGG
  177 G  D  G  E  E  Q  R  V  V  I  F  E  Q  T  Q  Y  D  V  P  S
  541 GGAGATGGGGAAGAGCAACGAGTGGTTATCTTTGAACAGACTCAGTATGACGTGCCCTCG
  197 L  A  T  H  S  A  Y  L  K  D  D  Q  R  S  T  P  D  S  T  Y
  601 CTGGCCACCCACAGCGCCTATCTCAAAGACGACCAGCGCAGCACTCCGGACAGCACATAC
  217 S  E  S  F  K  D  A  A  T  E  K  F  R  S  A  S  V  G  A  E
  661 AGCGAGAGCTTCAAGGACGCAGCCACAGAGAAATTTCGGAGTGCTTCAGTTGGGGCTGAG
  237 E  Y  M  Y  D  Q  T  S  S  G  T  F  Q  Y  T  L  E  A  T  K
  721 GAGTACATGTATGATCAGACATCAAGTGGCACATTTCAGTACACCCTGGAAGCCACCAAA
  257 S  L  R  Q  K  Q  G  E  G  P  M  T  Y  L  N  K  G  Q  F  Y
  781 TCTCTCCGTCAGAAGCAGGGGGAGGGCCCCATGACCTACCTCAACAAAGGACAGTTCTAT
  277 A  I  T  L  S  E  T  G  D  N  K  C  F  R  H  P  I  S  K  V
  841 GCCATAACACTCAGCGAGACCGGAGACAACAAATGCTTCCCACACCCCATCAGCAAAGTC
  297 R  S  V  V  M  V  V  F  S  E  D  K  N  R  D  E  Q  L  K  Y
  901 AGGAGTGTGGTGATGGTGGTCTTCAGTGAAGACAAAAACAGAGATGAACAGCTCAAATAC
  317 W  K  Y  W  H  S  R  Q  H  T  A  K  Q  R  V  L  D  I  A  D
  961 TGGAAATACTGGCACTCTCGGCAGCATACGGCGAAGCAGAGGGTCCTTGACATTGCCGAT
  337 Y  K  E  S  F  N  T  I  G  N  I  E  E  I  A  Y  N  A  V  S
 1021 TACAAGGAGAGCTTTAATACGATTGGAAACATTGAAGAGATTGCATATAATGCTGTTTCC
```

Figure 2B-2

```
 357 F   T   W   D   V   N   E   E   A   K   I   F   I   T   V   N   C   L   S   T
1081 TTTACCTGGGACGTGAATGAAGAGGCGAAGATTTTCATCACCGTGAATTGCTTGAGCACA
 377 D   F   S   S   Q   K   G   V   K   G   L   P   L   M   I   Q   I   D   T   Y
1141 GATTTCTCCTCCCAAAAAGGGGTGAAAGGACTTCCTTTGATGATTCAGATTGACACATAC
 397 S   Y   N   N   R   S   N   K   P   I   H   R   A   Y   C   Q   I   K   V   F
1201 AGTTATAACAATCGTAGCAATAAACCCATTCATAGAGCTTATTGCCAGATCAAGGTCTTC
 417 C   D   K   G   A   E   R   K   I   R   D   E   E   R   K   Q   N   R   K   K
1261 TGTGACAAAGGAGCAGAAAGAAAAATCCGAGATGAAGAGCGGAAGCAGAACAGGAAGAAA
 437 G   K   G   Q   A   S   Q   T   Q   C   N   S   S   S   D   G   K   L   A   A
1321 GGGAAAGGCCAGGCCTCCCAAACTCAATGCAACAGCTCCTCTGATGGGAAGTTGGCTGCC
 457 I   P   L   Q   K   K   S   D   I   T   Y   F   K   T   M   P   D   L   H   S
1381 ATACCTTTACAGAAGAAGAGTGACATCACCTACTTCAAAACCATGCCTGATCTCCACTCA
 477 Q   P   V   L   F   I   P   D   V   H   F   A   N   L   Q   R   T   G   Q   V
1441 CAGCCAGTTCTCTTCATACCTGATGTTCACTTTGCAAACCTGCAGAGGACCGGACAGGTG
 497 Y   Y   N   T   D   D   E   R   E   G   G   S   V   L   V   K   R   M   F   R
1501 TATTACAACACGGATGATGAACGAGAAGGTGGCAGTGTCCTTGTTAAACGGATGTTCCGG
 517 P   M   E   E   E   F   G   P   V   P   S   K   Q   M   K   E   E   G   T   K
1561 CCCATGGAAGAGGAGTTTGGTCCAGTGCCTTCAAAGCAGATGAAAGAAGAAGGGACAAAG
 537 R   V   L   L   Y   V   R   K   E   T   D   D   V   F   D   A   L   M   L   K
1621 CGAGTGCTCTTGTACGTGAGGAAGGAGACTGACGATGTGTTCGATGCATTGATGTTGAAG
 557 S   P   T   V   K   G   L   M   E   A   I   S   E   K   Y   G   L   P   V   E
1681 TCTCCCACAGTGAAGGGCCTGATGGAAGCGATATCTGAGAAATATGGGCTGCCCGTGGAG
 577 K   I   A   K   L   Y   K   K   S   K   K   G   I   L   V   N   M   D   D   N
1741 AAGATAGCAAAGCTTTACAAGAAAAGCAAAAAAGGCATCTTGGTGAACATGGATGACAAC
 597 I   I   E   H   Y   S   N   E   D   T   F   I   L   N   M   E   S   M   V   E
1801 ATCATCGAGCACTACTCGAACGAGGACACCTTCATCCTCAACATGGAGAGCATGGTGGAG
 617 G   F   K   V   T   L   M   E   I   *
1861 GGCTTCAAGGTCACGCTCATGGAAATCTAGccctgggtttggcatccgctttggctggag
1921 ctctcagtgcgttcctccctgagagagacagaagccccagccccagaacctggagaccca
1981 tctcccccatctcacaactgctgttacaagaccgtgctggggagtggggcaagggacagg
2041 ccccactgtcggtgtgcttggcccatccactggcacctaccacggagctgaagcctgagc
2101 ccctcaggaaggtgccttaggcctgttggattcctatttattgcccaccttttcctggag
2161 cccaggtccaggcccgccaggactctgcaggtcactgctagctccagatgagaccgtcca
2221 gcgttccccttcaagagaaacactcatcccgaacagcctaaaaaattcccatcccttct
2281 ctctcaccccttccatatctatctcccgagtggctggacaaaatgagctacgtctgggtgc
2341 agtagttataggtggggcaagaggtggatgcccactttctggtcagacacctttaggttg
2401 ctctggggaaggctgtcttgctaaatacctccaggggttcccagcaagtggccaccaggcc
```

Figure 2B-3

```
2461 ttgtacaggaagacattcagtcaccgtgtaattagtaacacagaaagtctgcctgtctgc
2521 attgtacatagtgtttataatattgtaataatatattttacctgtggtatgtgggcatgt
2581 ttactgccactggcctagaggagacacagacctggagaccgttttaatgggggttttttgc
2641 ctctgtgcctgttcaagagacttgcagggctaggtagagggcctttgggatgttaaggtg
2701 actgcagctgatgccaagatggactctgcaatgggcatacctggggctcgttccctgtc
2761 cccagaggaagcccctctccttctccatgggcatgactctccttcgaggccaccacgtt
2821 tatctcacaatgatgtgttttgcttgactttccctttgcgctgtctcgtgggaaaggtca
2881 ttctgtctgagaccccagctccttctccagctttggctgcgggcatggcctgagctttct
2941 ggagagcctctgcaggggtttgccatcagggccctgtggctgggtctgctgcagagctc
3001 cttggctatcaggagaatcctggacactgtactgtgcctccagtttacaaacacgccct
3061 tcatctcaagtggccctttaaaaggcctgctgccatgtgagagctgtgaacagctcagct
3121 ctgagtcggcaggctggggcttcctcctgggccaccagatggaaagggggtattgtttgc
3181 ctcactcctggatgctgcgttttaaggaagtgagtgagaaagaatgtgccaagatacctg
3241 gctcctgtgaaaccagcctcaggagggaaactgggagagagaagctgtggtctcctgcta
3301 catgccctgggagctggaagagaaaaacactcccctaaacaatcgcaaaatgatgaacca
3361 tcatgggccactgttctctttgaggggacaggtttaggggtttgcgttcgccttgtggg
3421 ctgaagcactagcttttggtagctagacacatcctgcacccaaaggttctctacaaagg
3481 cccagatttgtttgtaaagcactttgactcttacctggaggcccgctctctaagggcttc
3541 ctgcgctcccacctcatctgtccctgagatgcagagcaggatggagggtctgcttctagc
3601 tcagctgtttctccttgaggttgcggaggaattgaattgaatgggacagagggcaggtgc
3661 tgtggccaagaagatctccgagcagcagtgacggggcaccttgctgtgtgtcctctgggc
3721 atgttaacccttctgtggggccaaaggtttgcatcgtggatccagctgtgctccagtctg
3781 tcccctcctcctccactctgactgccacgccccggaccagcagcttggggaccctccagg
3841 gtactaatggggctctgttctgagatggacaaattcagtgttggaaatacatgttgtact
3901 atgcacttcccatgctcctagggttaggaatagtttcaaacatgattggcagacataaca
3961 acggcaaatactcggactggggcataggactccagagtaggaaaaagacaaaagatttgg
4021 cagcctgacacaggcaacctaccctctctctccagcctctttatgaaactgtttgtttg
4081 ccagtcctgccctaaggcagaagatgaattgaagatgctgtgcatgtttcctaagtcctt
4141 gagcaatcatggtggtgacaattgccacaagggatatgaggccagtgccaccagagggtg
4201 gtgccaagtgccacatcccttccgatccattcccctctgcatcctcggagcaccccagtt
4261 tgcctttgatgtgtccgctgtgtatgttagctgaactttgatgagcaaaatttcctgagc
4321 gaaacactccaaagagataggaaaacttgccgcctcttcttttttgtcccttaatcaaac
4381 tcaaataagcttaaaaaaaatccatggaagatcatggacatgtgaaatgagcattttttt
4441 ctttttttttttaacaaagtctgaactgaacagaacaagacttttttcctcatacatctc
4501 caaattgtttaaacttactttatgagtgtttgtttagaagttcggaccaacagaaaaatg
4561 cagtcagatgtcatcttggaattggtttctaaaagagtaaggcatgtccctgcccagaaa
4621 cttaggaagcatgaaataaatcaaatgtttattttccttcttatttaaaatcatgcaaat
```

Figure 2B-4

```
4681 gcaacagaaatagagggtttgtgccaaatgctatgaacggccctttcttaaagacaagca
4741 agggagattgatatatgtacaatttgctctcatgttttaaaaaaaaaggtaaatgtaac
4801 ttaatagttttgtaaatgggagagggggaatctataaactataaatacagttattttatt
4861 ttttgtacattttttaaggagaaaaaaataaatattcataacataagaggaaaa
```

Figure 2C. The cDNA (SEQ ID. NO.: 6) and amino acid sequence (SEQ ID. NO.: 7) of 202P5A5 v.3. The Kozak initiation sequence is shown in bold, and the start methionine is underlined. The open reading frame extends from nucleic acid 121-1950 including the stop codon.

Figure 2C-1

```
   1 attggatcaaacatgtcacaagagtcggacaagtaagtggatcacacgcgccggctgctg
  61 ctactactacctttgggctgatggcaactgtaataaaagactagtggccttagtgccc
   1 M  P  S  D  P  P  F  N  T  R  R  A  Y  T  S  E  D  E  A  W
 121 ATGCCCAGTGACCCTCCATTCAATACCCGAAGAGCCTACACCAGTGAGGATGAAGCCTGG
  21 K  S  Y  L  E  N  P  L  T  A  A  T  K  A  M  M  S  I  N  G
 181 AAGTCATACTTGGAGAATCCCCTGACAGCAGCCACCAAGGCCATGATGAGCATTAATGGT
  41 D  E  D  S  A  A  A  L  G  L  L  Y  D  Y  Y  K  V  P  R  D
 241 GATGAGGACAGTGCTGCTGCCCTCGGCCTGCTCTATGACTACTACAAGGTTCCTCGAGAC
  61 K  R  L  L  S  V  K  A  S  D  S  Q  E  D  Q  E  K  R  N
 301 AAGAGGCTGCTGTCTCTAAGCAAAGCAAGTGACAGCCAAGAAGACCAGGAGAAAAGAAAC
  81 C  L  G  T  S  E  A  Q  S  N  L  S  G  G  E  N  R  V  Q  V
 361 TGCCTTGGCACCAGTGAAGCCCAGAGTAATTTGAGTGGAGGAGAAAACCGAGTGCAAGTC
 101 L  K  T  V  P  V  N  L  S  L  N  Q  D  H  L  E  N  S  K  R
 421 CTAAAGACTGTTCCAGTGAACCTTTCCCTAAATCAAGATCACCTCGAGAATTCCAAGCGG
 121 E  Q  Y  S  I  S  F  P  E  S  S  A  I  I  P  V  S  G  I  T
 481 GAACAGTACAGCATCAGCTTCCCCGAGAGCTCTGCCATCATCCCGGTGTCGGGAATCACG
 141 V  V  K  A  E  D  F  T  P  V  F  M  A  P  P  V  H  Y  P  R
 541 GTGGTGAAAGCTGAAGATTTCACACCAGTTTTCATGGCCCCACCTGTGCACTATCCCCGG
 161 G  D  G  E  E  Q  R  V  V  I  F  E  Q  T  Q  Y  D  V  P  S
 601 GGAGATGGGGAAGAGCAACGAGTGGTTATCTTTGAACAGACTCAGTATGACGTGCCCTCG
 181 L  A  T  H  S  A  Y  L  K  D  D  Q  R  S  T  P  D  S  T  Y
 661 CTGGCCACCCACAGCGCCTATCTCAAAGACGACCAGCGCAGCACTCCGGACAGCACATAC
 201 S  E  S  F  K  D  A  A  T  E  K  F  R  S  A  S  V  G  A  E
 721 AGCGAGAGCTTCAAGGACGCAGCCACAGAGAAATTTCGGAGTGCTTCAGTTGGGGCTGAG
 221 E  Y  M  Y  D  Q  T  S  S  G  T  F  Q  Y  T  L  E  A  T  K
 781 GAGTACATGTATGATCAGACATCAAGTGGCACATTTCAGTACACCCTGGAAGCCACCAAA
 241 S  L  R  Q  K  Q  G  E  G  P  M  T  Y  L  N  K  G  Q  F  Y
 841 TCTCTCCGTCAGAAGCAGGGGGAGGGCCCCATGACCTACCTCAACAAAGGACAGTTCTAT
 261 A  I  T  L  S  E  T  G  D  N  K  C  F  R  H  P  I  S  K  V
 901 GCCATAACACTCAGCGAGACCGGAGACAACAAATGCTTCCGACACCCCATCAGCAAAGTC
 281 R  S  V  V  M  V  V  F  S  E  D  K  N  R  D  E  Q  L  K  Y
 961 AGGAGTGTGGTGATGGTGGTCTTCAGTGAAGACAAAAACAGAGATGAACAGCTCAAATAC
 301 W  K  Y  W  H  S  R  Q  H  T  A  K  Q  R  V  L  D  I  A  D
1021 TGGAAATACTGGCACTCTCGGCAGCATACGGCGAAGCAGAGGGTCCTTGACATTGCCGAT
 321 Y  K  E  S  F  N  T  I  G  N  I  E  E  I  A  Y  N  A  V  S
1081 TACAAGGAGAGCTTTAATACCATTGGAAACATTGAAGAGATTGCATATAATGCTGTTTCC
```

Figure 2C-2

```
 341 F  T  W  D  V  N  E  E  A  K  I  F  I  T  V  N  C  L  S  T
1141 TTTACCTGGGACGTGAATGAAGAGGCGAAGATTTTCATCACCGTGAATTGCTTGAGCACA
 361 D  F  S  S  Q  K  G  V  K  G  L  P  L  M  I  Q  I  D  T  Y
1201 GATTTCTCCTCCCAAAAAGGGGTGAAAGGACTTCCTTTGATGATTCAGATTGACACATAC
 381 S  Y  N  N  R  S  N  K  P  I  H  R  A  Y  C  Q  I  K  V  F
1261 AGTTATAACAATCGTAGCAATAAACCCATTCATAGAGCTTATTGCCAGATCAAGGTCTTC
 401 C  D  K  G  A  E  R  K  I  R  D  E  E  R  K  Q  N  R  K  K
1321 TGTGACAAAGGAGCAGAAAGAAAAATCCGAGATGAAGAGCGGAAGCAGAACAGGAAGAAA
 421 G  K  G  Q  A  S  Q  T  Q  C  N  S  S  S  D  G  K  L  A  A
1381 GGGAAAGGCCAGGCCTCCCAAACTCAATGCAACAGCTCCTCTGATGGGAAGTTGGCTGCC
 441 I  P  L  Q  K  K  S  D  I  T  Y  F  K  T  M  P  D  L  H  S
1441 ATACCTTTACAGAAGAAGAGTGACATCACCTACTTCAAAACCATGCCTGATCTCCACTCA
 461 Q  P  V  L  F  I  P  D  V  H  F  A  N  L  Q  R  T  G  Q  V
1501 CAGCCAGTTCTCTTCATACCTGATGTTCACTTTGCAAACCTGCAGAGGACCGGACAGGTG
 481 Y  Y  N  T  D  D  E  R  E  G  G  S  V  L  V  K  R  M  F  R
1561 TATTACAACACGGATGATGAACGAGAAGGTGGCAGTGTCCTTGTTAAACGGATGTTCCGG
 501 P  M  E  E  E  F  G  P  V  P  S  K  Q  M  K  E  E  G  T  K
1621 CCCATGGAAGAGGAGTTTGGTCCAGTGCCTTCAAAGCAGATGAAAGAAGAAGGGACAAAG
 521 R  V  L  L  Y  V  R  K  E  T  D  D  V  F  D  A  L  M  L  K
1681 CGAGTGCTCTTGTACGTGAGGAAGGAGACTGACGATGTGTTCGATGCATTGATGTTGAAG
 541 S  P  T  V  K  G  L  M  E  A  I  S  E  K  Y  G  L  P  V  E
1741 TCTCCCACAGTGAAGGGCCTGATGGAAGCGATATCTGAGAAATATGGGCTGCCCGTGGAG
 561 K  I  A  K  L  Y  K  K  S  K  K  G  I  L  V  N  M  D  D  N
1801 AAGATAGCAAAGCTTTACAAGAAAAGCAAAAAAGGCATCTTGGTGAACATGGATGACAAC
 581 I  I  E  H  Y  S  N  E  D  T  F  I  L  N  M  E  S  M  V  E
1861 ATCATCGAGCACTACTCGAACGAGGACACCTTCATCCTCAACATGGAGAGCATGGTGGAG
 601 G  F  K  V  T  L  M  E  I  *
1921 GGCTTCAAGGTCACGCTCATGGAAATCTAGccctgggtttggcatccgctttggctggag
1981 ctctcagtgcgttcctccctgagagagacagaagccccagccccagaacctggagaccca
2041 tctcccccatctcacaactgctgttacaagaccgtgctggggagtggggcaagggacagg
2101 ccccactgtcggtgtgcttggcccatccactggcacctaccacggagctgaagcctgagc
2161 ccctcaggaaggtgccttaggcctgttggattcctatttattgcccaccttttcctggag
2221 cccaggtccaggcccgccaggactctgcaggtcactgctagctccagatgagaccgtcca
2281 gcgttccccttcaagagaaacactcatcccgaacagcctaaaaaattcccatcccttct
2341 ctctcacccctccatatctatctcccgagtggctggacaaaatgagctacgtctgggtgc
2401 agtagttataggtggggcaagaggtggatgcccactttctggtcagacacctttaggttg
2461 ctctggggaaggctgtcttgctaaatacctccaggggttcccagcaagtggccaccaggcc
```

Figure 2C-3

```
2521 ttgtacaggaagacattcagtcaccgtgtaattagtaacacagaaagtctgcctgtctgc
2581 attgtacatagtgtttataatattgtaataatatattttacctgtggtatgtgggcatgt
2641 ttactgccactggcctagaggagacacagacctggagaccgttttaatggggttttttgc
2701 ctctgtgcctgttcaagagacttgcagggctaggtagagggcctttgggatgttaaggtg
2761 actgcagctgatgccaagatggactctgcaatgggcatacctgggggctcgttccctgtc
2821 cccagaggaagcccctctccttctccatgggcatgactctccttcgaggccaccacgtt
2881 tatctcacaatgatgtgttttgcttgactttccctttgcgctgtctcgtgggaaaggtca
2941 ttctgtctgagacccagctccttctccagctttggctgcgggcatggcctgagctttct
3001 ggagagcctctgcaggggggtttgccatcagggccctgtggctgggtctgctgcagagctc
3061 cttggctatcaggagaatcctggacactgtactgtgcctccagtttacaaacacgccct
3121 tcatctcaagtggccctttaaaaggcctgctgccatgtgagagctgtgaacagctcagct
3181 ctgagtcggcaggctggggcttcctcctggccaccagatggaaggggtattgtttgc
3241 ctcactcctggatgctgcgttttaaggaagtgagtgagaagaatgtgccaagatacctg
3301 gctcctgtgaaaccagcctcaggagggaaactgggagagagaagctgtggtctcctgcta
3361 catgccctgggagctggaagagaaaaacactcccctaaacaatcgcaaaatgatgaacca
3421 tcatgggccactgttctctttgaggggacaggtttaggggtttgcgttcgcccttgtggg
3481 ctgaagcactagcttttggtagctagacacatcctgcacccaaaggttctctacaaagg
3541 cccagatttgtttgtaaagcactttgactcttacctggaggcccgctctctaagggcttc
3601 ctgcgctcccacctcatctgtccctgagatgcagagcaggatggagggtctgcttctagc
3661 tcagctgtttctccttgaggttgcggaggaattgaattgaatgggacagagggcaggtgc
3721 tgtggccaagaagatctccgagcagcagtgacggggcaccttgctgtgtgtcctctgggc
3781 atgttaaccttctgtggggccaaaggtttgcatcgtggatccagctgtgctccagtctg
3841 tcccctcctcctccactctgactgccacgccccggaccagcagcttggggaccctccagg
3901 gtactaatggggctctgttctgagatggacaaattcagtgttggaaatacatgttgtact
3961 atgcacttcccatgctcctaggggttaggaatagtttcaaacatgattggcagacataaca
4021 acggcaaatactcggactggggcataggactccagagtaggaaaaagacaaaagatttgg
4081 cagcctgacacaggcaacctacccctctctccagcctctttatgaaactgtttgtttg
4141 ccagtcctgccctaaggcagaagatgaattgaagatgctgtgcatgtttcctaagtcctt
4201 gagcaatcatggtggtgacaattgccacaagggatatgaggccagtgccaccagagggtg
4261 gtgccaagtgccacatcccttccgatccattccctctgcatcctcggagcacccagtt
4321 tgcctttgatgtgtccgctgtgtatgttagctgaactttgatgagcaaaatttcctgagc
4381 gaaacactccaaagagataggaaaacttgccgcctcttctttttgtcccttaatcaaac
4441 tcaaataagcttaaaaaaatccatggaagatcatggacatgtgaaatgagcatttttt
4501 ctttttttttttaacaaagtctgaactgaacagaacaagactttttcctcatacatctc
4561 caaattgtttaaacttactttatgagtgtttgtttagaagttcggaccaacagaaaaatg
4621 cagtcagatgtcatcttggaattggtttctaaaagagtaaggcatgtccctgcccagaaa
4681 cttaggaagcatgaaataaatcaaatgtttattttccttcttatttaaaatcatgcaaat
```

Figure 2C-4

```
4741 gcaacagaaatagagggtttgtgccaaatgctatgaacggccctttcttaaagacaagca
4801 agggagattgatatatgtacaatttgctctcatgttttaaaaaaaaaaggtaaatgtaac
4861 ttaatagttttgtaaatgggagaggggggaatctataaactataaatacagttattttatt
4921 ttttgtacattttttaaggagaaaaaaataaatattcataacataagaggaaaa
```

Figure 2D. The cDNA (SEQ ID. NO. : 8) and amino acid sequence (SEQ ID. NO. : 9) of 202P5A5 v.14. The Kozak initiation sequence is shown in bold, and the start methionine is underlined. The open reading frame extends from nucleic acid 29-1858 including the stop codon.

Figure 2D-1

```
                                    M  P  S  D  P  P  F  N  T  R  R
   1 taataaaagactagtggccttagtgccATGCCCAGTGACCCTCCATTCAATACCCGAAG
  12 A  Y  T  S  E  D  E  A  W  K  S  Y  L  E  N  P  L  T  A  A
  61 AGCCTACACCAGTGAGGATGAAGCCTGGAAGTCATACTTGGAGAATCCCCTGACAGCAGC
  32 T  K  A  M  M  S  I  N  G  D  E  D  S  A  A  A  L  G  L  L
 121 CACCAAGGCCATGATGAGCATTAATGGTGATGAGGACAGTGCTGCTGCCCTCGGCCTGCT
  52 Y  D  Y  Y  K  V  P  R  D  K  R  L  L  S  V  S  K  A  S  D
 181 CTATGACTACTACAAGGTTCCTCGAGACAAGAGGCTGCTGTCTGTAAGCAAAGCAAGTGA
  72 S  Q  E  D  Q  E  K  R  N  C  L  G  T  S  E  A  Q  S  N  L
 241 CAGCCAAGAAGACCAGGAGAAAAGAAACTGCCTTGGCACCAGTGAAGCCCAGAGTAATTT
  92 S  G  G  E  N  R  V  Q  V  L  K  T  V  P  V  N  L  S  L  N
 301 GAGTGGAGGAGAAAACCGAGTGCAAGTCCTAAAGACTGTTCCAGTGAACCTTTCCCTAAA
 112 Q  D  H  L  E  N  S  K  R  E  Q  Y  S  I  S  F  P  E  S  S
 361 TCAAGATCACCTGGAGAATTCCAAGCGGGAACAGTACAGCATCAGCTTCCCCGAGAGCTC
 132 A  I  I  P  V  S  G  I  T  V  V  K  A  E  D  F  T  P  V  F
 421 TGCCATCATCCCGGTGTCGGGAATCACGGTGGTGAAAGCTGAAGATTTCACACCAGTTTT
 152 M  A  P  P  V  H  Y  P  R  G  D  G  E  E  Q  R  V  V  I  F
 481 CATGGCCCCACCTGTGCACTATCCCCGGGGAGATGGGGAAGAGCAACGAGTGGTTATCTT
 172 E  Q  T  Q  Y  D  V  P  S  L  A  T  H  S  A  Y  L  K  D  D
 541 TGAACAGACTCAGTATGACGTGCCCTCGCTGGCCACCCACAGCGCCTATCTCAAAGACGA
 192 Q  R  S  T  P  D  S  T  Y  S  E  S  F  K  D  A  A  T  E  K
 601 CCAGCGCAGCACTCCGGACAGCACATACAGCGAGAGCTTCAAGGACGCAGCCACAGAGAA
 212 F  R  S  A  S  V  G  A  E  E  Y  M  Y  D  Q  T  S  S  G  T
 661 ATTTCGGAGTGCTTCAGTTGGGGCTGAGGAGTACATGTATGATCAGACATCAAGTGGCAC
 232 F  Q  Y  T  L  E  A  T  K  S  L  R  Q  K  Q  G  E  G  P  M
 721 ATTTCAGTACACCCTGGAAGCCACCAAATCTCTCCGTCAGAAGCAGGGGGAGGGCCCCAT
 252 T  Y  L  N  K  G  Q  F  Y  A  I  T  L  S  E  T  G  D  N  K
 781 GACCTACCTCAACAAAGGACAGTTCTATGCCATAACACTCAGCGAGACCGGAGACAACAA
 272 C  F  R  H  P  I  S  K  V  R  S  V  V  M  V  V  F  S  E  D
 841 ATGCTTCCGACACCCCATCAGCAAAGTCAGGAGTGTGGTGATGGTGGTCTTCAGTGAAGA
 292 K  N  R  D  E  Q  L  K  Y  W  K  Y  W  H  S  R  Q  H  T  A
 901 CAAAAACAGAGATGAACAGCTCAAATACTGGAAATACTGGCACTCTCGGCAGCATACGGC
 312 K  Q  R  V  L  D  I  A  D  Y  K  E  S  F  N  T  I  G  N  I
 961 GAAGCAGAGGGTCCTTGACATTGCCGATTACAAGGAGAGCTTTAATACGATTGGAAACAT
 332 E  E  I  A  Y  N  A  V  S  F  T  W  D  V  N  E  E  A  K  I
1021 TGAAGAGATTGCATATAATGCTGTTTCCTTTACCTGGGACGTGAATGAAGAGGCGAAGAT
```

Figure 2D-2

```
 352  F  I  T  V  N  C  L  S  T  D  F  S  S  Q  K  G  V  K  G  L
1081  TTTCATCACCGTGAATTGCTTGAGCACAGATTTCTCCTCCCAAAAAGGGGTGAAAGGACT
 372  P  L  M  I  Q  I  D  T  Y  S  Y  N  N  R  S  N  K  P  I  H
1141  TCCTTTGATGATTCAGATTGACACATACAGTTATAACAATCGTAGCAATAAACCCATTCA
 392  R  A  Y  C  Q  I  K  V  F  C  D  K  G  A  E  R  K  I  R  D
1201  TAGAGCTTATTGCCAGATCAAGGTCTTCTGTGACAAAGGAGCAGAAACAAAAATCCGAGA
 412  E  E  R  K  Q  N  R  K  K  G  K  G  Q  A  S  Q  T  Q  C  N
1261  TGAAGAGCGGAAGCAGAACAGGAAGAAAGGGAAAGGCCAGGCCTCCCAAACTCAATGCAA
 432  S  S  S  D  G  K  L  A  A  I  P  L  Q  K  K  S  D  I  T  Y
1321  CAGCTCCTCTGATGGGAAGTTGGCTGCCATACCTTTACAGAAGAAGAGTGACATCACCTA
 452  F  K  T  M  P  D  L  H  S  Q  P  V  L  F  I  P  D  V  H  F
1381  CTTCAAAACCATGCCTGATCTCCACTCACAGCCAGTTCTCTTCATACCTGATGTTCACTT
 472  A  N  L  Q  R  T  G  Q  V  Y  Y  N  T  D  D  E  R  E  G  G
1441  TGCAAACCTGCAGAGGACCGGACAGGTGTATTACAACACGGATGATGAACGAGAAGGTGG
 492  S  V  L  V  K  R  M  F  R  P  M  E  E  E  F  G  P  V  P  S
1501  CAGTGTCCTTGTTAAACGGATGTTCCGGCCCATGGAAGAGGAGTTTGGTCCAGTGCCTTC
 512  K  Q  M  K  E  E  G  T  K  R  V  L  L  Y  V  R  K  E  T  D
1561  AAAGCAGATGAAAGAAGAAGGGACAAAGCGAGTGCTCTTGTACGTGAGGAAGGAGACTGA
 532  D  V  F  D  A  L  M  L  K  S  P  T  V  K  G  L  M  E  A  I
1621  CGATGTGTTCGATGCATTGATGTTGAAGTCTCCCACAGTGAAGGGCCTGATGGAAGCGAT
 552  S  E  K  Y  G  L  P  V  E  K  I  A  K  L  Y  K  K  S  K  K
1681  ATCTGAGAAATATGGGCTGCCCGTGGAGAAGATAGCAAAGCTTTACAAGAAAAGCAAAA
 572  G  I  L  V  N  M  D  D  N  I  I  E  H  Y  S  N  E  D  T  F
1741  AGGCATCTTGGTGAACATGGATGACAACATCATCGAGCACTACTCGAACGAGGACACCTT
 592  I  L  N  M  E  S  M  V  E  G  F  K  V  T  L  M  E  I  *
1801  CATCCTCAACATGGAGAGCATGGTGGAGGGCTTCAAGGTCACGCTCATGGAAATCTAGcc
1861  ctgggtttggcatccgctttggctggagctctcagtgcgttcctccctgagagagacaga
1921  agccccagccccagaacctggagacccatctcccccatctcacaactgctgttacaagac
1981  cgtgctggggagtggggcaagggacaggccccactgtcggtgtgcttggcccatccactg
2041  gcacctaccacggagctgaagcctgagcccctcaggaaggtgccttaggcctgttggatt
2101  cctatttattgcccaccttttcctggagcccaggtccaggccgccaggactctgcaggt
2161  cactgctagctccagatgagaccgtccagcgttccccttcaagagaaacactcatcccg
2221  aacagcctaaaaaattcccatcccttctctctcaccctccatatctatatctcccgagt
2281  ggctggacaaaatgagctacgtctgggtgcagtagttataggtggggcaagaggtggatg
2341  cccactttctggtcagacacctttaggttgctctggggaaggctgtcttgctaaatacct
2401  ccagggttcccagcaagtggccaccaggccttgtacaggaagacattcagtcaccgtgta
2461  attagtaacacagaaagtctgcctgtctgcattgtacatagtgtttataatattgtaata
```

Figure 2D-3

```
2521 atatattttacctgtggtatgtgggcatgtttactgccactggcctagaggagacacaga
2581 cctggagaccgttttaatgggggttttttgcctctgtgcctgttcaagagacttgcagggc
2641 taggtagagggcctttgggatgttaaggtgactgcagctgatgccaagatggactctgca
2701 atgggcatacctgggggctcgttccctgtccccagaggaagcccctctccttctccatg
2761 ggcatgactctccttcgaggccaccacgtttatctcacaatgatgtgttttgcttgactt
2821 tcccttttgcgctgtctcgtgggaaaggtcattctgtctgagaccccagctccttctccag
2881 ctttggctgcgggcatggcctgagctttctggagagcctctgcaggggtttgccatcag
2941 ggccctgtggctgggtctgctgcagagctccttggctatcaggagaatcctggacactgt
3001 actgtgcctcccagtttacaaacacgcccttcatctcaagtggcccctttaaaaggcctgc
3061 tgccatgtgagagctgtgaacagctcagctctgagtcggcaggctggggcttcctcctgg
3121 gccaccagatggaaaggggtattgtttgcctcactcctggatgctgcgttttaaggaag
3181 tgagtgagaaagaatgtgccaagatacctggctcctgtgaaaccagcctcaggagggaaa
3241 ctgggagagagaagctgtggtctcctgctacatgccctgggagctggaagagaaaaacac
3301 tcccctaaacaatcgcaaaatgatgaaccatcatgggccactgttctctttgaggggaca
3361 ggtttaggggtttgcgttcgccttgtgggctgaagcactagcttttttggtagctagaca
3421 catcctgcacccaaaggttctctacaaaggcccagatttgtttgtaaagcactttgactc
3481 ttacctggaggcccgctctctaagggcttcctgcgctcccacctcatctgtccctgagat
3541 gcagagcaggatggagggtctgcttctagctcagctgtttctccttgaggttgcggagga
3601 attgaattgaatgggacagagggcaggtgctgtggccaagaagatctccgagcagcagtg
3661 acggggcaccttgctgtgtgtcctctgggcatgttaacccttctgtggggccaaaggttt
3721 gcatcgtggatccagctgtgctccagtctgtcccctcctcctccactctgactgccacgc
3781 cccggaccagcagcttggggaccctccagggtactaatggggctctgttctgagatggac
3841 aaattcagtgttggaaatacatgttgtactatgcacttcccatgctcctagggttaggaa
3901 tagtttcaaacatgattggcagacataacaacggcaaatactcggactggggcataggac
3961 tccagagtaggaaaaagacaaaagatttggcagcctgacacaggcaacctacccctctct
4021 ctccagcctctttatgaaactgtttgtttgccagtcctgccctaaggcagaagatgaatt
4081 gaagatgctgtgcatgtttcctaagtccttgagcaatcatggtggtgacaattgccacaa
4141 gggatatgaggccagtgccaccagagggtggtgccaagtgccacatcccttccgatccat
4201 tcccctctgcatcctcggagcaccccagtttgccttttgatgtgtccgctgtgtatgttag
4261 ctgaactttgatgagcaaaatttcctgagcgaaacactccaaagagataggaaaacttgc
4321 cgcctcttcttttttgtcccttaatcaaactcaaataagcttaaaaaaaatccatggaag
4381 atcatggacatgtgaaatgagcatttttttcttttttttttttaacaaagtctgaactga
4441 acagaacaagacttttcctcatacatctccaaattgtttaaacttactttatgagtgtt
4501 tgtttagaagttcggaccaacagaaaaatgcagtcagatgtcatcttggaattggtttct
4561 aaaagagtaaggcatgtccctgcccagaaacttaggaagcatgaaataaatcaaatgttt
4621 attttccttcttatttaaaatcatgcaaatgcaacagaaatagagggtttgtgccaaatg
4681 ctatgaacggcccttttcttaaagacaagcaagggagattgatatatgtacaatttgctct
4741 catgtttt
```

Figure 2E. The cDNA (SEQ ID. NO. : 10) and amino acid sequence (SEQ ID. NO. : 11) of 202P5A5 v.22. The Kozak initiation sequence is shown in bold, and the start methionine is underlined. The open reading frame extends from nucleic acid 29-1858 including the stop codon.

Figure 2E-1

```
  1                              M  P  S  D  P  P  F  N  T  R  R
  1 taataaaagactagtggccttagtgccATGCCCAGTGACCCTCCATTCAATACCCGAAG
 12  A  Y  T  S  E  D  E  A  W  K  S  Y  L  E  N  P  L  T  A  A
 61 AGCCTACACCAGTGAGGATGAAGCCTGGAAGTCATACTTGGAGAATCCCCTGACAGCAGC
 32  T  K  A  M  M  S  I  N  G  D  E  D  S  A  A  A  L  G  L  L
121 CACCAAGGCCATGATGAGCATTAATGGTGATGAGGACAGTGCTGCTGCCCTCGGCCTGCT
 52  Y  D  Y  Y  K  V  P  R  D  K  R  L  L  S  V  S  K  A  S  D
181 CTATGACTACTACAAGGTTCCTCGAGACAAGAGGCTGCTGTCTGTAAGCAAAGCAAGTGA
 72  S  Q  E  D  Q  E  K  R  N  C  L  G  T  S  E  A  Q  S  N  L
241 CAGCCAAGAAGACCAGGAGAAAAGAAACTGCCTTGGCACCAGTGAAGCCCAGAGTAATTT
 92  S  G  G  E  N  R  V  Q  V  L  K  T  V  P  V  N  L  S  L  N
301 GAGTGGAGGAGAAAACCGAGTGCAAGTCCTAAAGACTGTTCCAGTGAACCTTTCCCTAAA
112  Q  D  H  L  E  N  S  K  R  E  Q  Y  S  I  S  F  P  E  S  S
361 TCAAGATCACCTGGAGAATTCCAAGCGGGAACAGTACAGCATCAGCTTCCCCGAGAGCTC
132  A  I  I  P  V  S  G  I  T  V  V  K  A  E  D  F  T  P  V  F
421 TGCCATCATCCCGGTGTCGGGAATCACGGTGGTGAAAGCTGAAGATTTCACACCAGTTTT
152  M  A  P  P  V  H  Y  P  R  G  D  G  E  E  Q  R  V  V  I  F
481 CATGGCCCCACCTGTGCACTATCCCCGGGGAGATGGGGAAGAGCAACGAGTGGTTATCTT
172  E  Q  T  Q  Y  D  V  P  S  L  A  T  H  S  A  Y  L  K  D  D
541 TGAACAGACTCAGTATGACGTGCCCTCGCTGGCCACCCACAGCGCCTATCTCAAAGACGA
192  Q  R  S  T  P  D  S  T  Y  S  E  S  F  K  D  A  A  T  E  K
601 CCAGCGCAGCACTCCGGACAGCACATACAGCGAGAGCTTCAAGGACGCAGCCACAGAGAA
212  F  R  S  A  S  V  G  A  E  E  Y  M  Y  D  Q  T  S  S  G  T
661 ATTTCGGAGTGCTTCAGTTGGGGCTGAGGAGTACATGTATGATCAGACATCAAGTGGCAC
232  F  Q  Y  T  L  E  A  T  K  S  L  R  Q  K  Q  G  E  G  P  M
721 ATTTCAGTACACCCTGGAAGCCACCAAATCTCTCCGTCAGAAGCAGGGGGAGGGCCCCAT
252  T  Y  L  N  K  G  Q  F  Y  A  I  T  L  S  E  T  G  D  N  K
781 GACCTACCTCAACAAAGGACAGTTCTATGCCATAACACTCAGCGAGACCGGAGACAACAA
272  C  F  R  H  P  I  S  K  V  R  S  V  V  M  V  V  F  S  E  D
841 ATGCTTCCGACACCCCATCAGCAAAGTCAGGAGTGTGGTGATGGTGGTCTTCAGTGAAGA
292  K  N  R  D  E  Q  L  K  Y  W  K  Y  W  H  S  R  Q  H  T  A
901 CAAAAACAGAGATGAACAGCTCAAATACTGGAAATACTGGCACTCTCGGCAGCATACGGC
312  K  Q  R  V  L  D  I  A  D  Y  K  E  S  F  N  T  I  G  N  I
961 GAAGCAGAGGGTCCTTGACATTGCCGATTACAAGGAGAGCTTTAATACGATTGGAAACAT
332  E  E  I  A  Y  N  A  V  S  F  T  W  D  V  N  E  E  A  K  I
1021 TGAAGAGATTGCATATAATGCTGTTTCCTTTACCTGGGACGTGAATGAAGAGGCGAAGAT
```

Figure 2E-2

```
 352 F  I  T  V  N  C  L  S  T  D  F  S  S  Q  K  G  V  K  G  L
1081 TTTCATCACCGTGAATTGCTTGAGCACAGATTTCTCCTCCCAAAAAGGGGTGAAAGGACT
 372 P  L  M  I  Q  I  D  T  Y  S  Y  N  N  R  S  N  K  P  I  H
1141 TCCTTTGATGATTCAGATTGACACATACAGTTATAACAATCGTAGCAATAAACCCATTCA
 392 R  A  Y  C  Q  I  K  V  F  C  D  K  G  A  E  R  K  I  R  D
1201 TAGAGCTTATTGCCAGATCAAGGTCTTCTGTGACAAAGGAGCAGAAAGAAAAATCCGAGA
 412 E  E  R  K  Q  N  R  K  K  G  K  G  Q  A  S  Q  T  Q  C  N
1261 TGAAGAGCGGAAGCAGAACAGGAAGAAAGGGAAAGGCCAGGCCTCCCAAACTCAATGCAA
 432 S  S  S  D  G  K  L  A  A  I  P  L  Q  K  K  S  D  I  T  Y
1321 CAGCTCCTCTGATGGGAAGTTGGCTGCCATACCTTTACAGAAGAAGAGTGACATCACCTA
 452 F  K  T  M  P  D  L  H  S  Q  P  V  L  F  I  P  D  V  H  F
1381 CTTCAAAACCATGCCTGATCTCCACTCACAGCCAGTTCTCTTCATACCTGATGTTCACTT
 472 A  N  L  Q  R  T  G  Q  V  Y  Y  N  T  D  D  E  R  E  G  G
1441 TGCAAACCTGCAGAGGACCGGACAGGTGTATTACAACACGGATGATGAACGAGAAGGTGG
 492 S  V  L  V  K  R  M  F  R  P  M  E  E  E  F  G  P  V  P  S
1501 CAGTGTCCTTGTTAAACGGATGTTCCGGCCCATGGAAGAGGAGTTTGGTCCAGTGCCTTC
 512 K  Q  M  K  E  E  G  T  K  R  V  L  L  Y  V  R  K  E  T  D
1561 AAAGCAGATGAAAGAAGAAGGGACAAAGCGAGTGCTCTTGTACGTGAGGAAGGAGACTGA
 532 D  V  F  D  A  L  M  L  K  S  P  T  V  K  G  L  M  E  A  I
1621 CGATGTGTTCGATGCATTGATGTTGAAGTCTCCCACAGTGAAGGGCCTGATGGAAGCGAT
 552 S  E  K  Y  G  L  P  V  E  K  I  A  K  L  Y  K  K  S  K  K
1681 ATCTGAGAAATATGGGCTGCCCGTGGAGAAGATAGCAAAGCTTTACAAGAAAAGCAAAA
 572 G  I  L  V  N  M  D  D  N  I  I  E  H  Y  S  N  E  D  T  F
1741 AGGCATCTTGGTGAACATGGATGACAACATCATCGAGCACTACTCGAACGAGGACACCTT
 592 I  L  N  M  E  S  M  V  E  G  F  K  V  T  L  M  E  I  *
1801 CATCCTCAACATGGAGAGCATGGTGGAGGGCTTCAAGGTCACGCTCATGGAAATCTAGcc
1861 ctgggtttggcatccgctttggctggagctctcagtgcgttcctccctgagagagacaga
1921 agccccagccccagaacctggagacccatctcccccatctcacaactgctgttacaagac
1981 cgtgctggggagtggggcaagggacaggccccactgtcggtgtgcttggcccatccactg
2041 gcacctaccacggagctgaagcctgagcccctcaggaaggtgccttaggcctgttggatt
2101 cctatttattgcccacctttcctggagcccaggtccaggcccgccaggactctgcaggt
2161 cactgctagctccagatgagaccgtccagcgttccccttcaagagaaacactcatcccg
2221 aacagcctaaaaaattcccatcccttctctctcacccctccatatctatctcccgagtgg
2281 ctggacaaaatgagctacgtctgggtgcagtagttataggtggggcaagaggtggatgcc
2341 cactttctggtcagacaccttaggttgctctggggaaggctgtcttgctaaatacctcc
2401 agggttcccagcaagtggccaccaggccttgtacaggaagacattcagtcaccgtgtaat
2461 tagtaacacagaaagtctgcctgtctgcattgtacatagtgtttataatattgtaataat
```

Figure 2E-3

```
2521 atattttacctgtggtatgtgggcatgtttactgccactggcctagaggagacacagacc
2581 tggagaccgttttaatgggggttttttgcctctgtgcctgttcaagagacttgcagggcta
2641 ggtagagggcctttgggatgttaaggtgactgcagctgatgccaagatggactctgcaat
2701 gggcatacctgggggctcgttccctgtccccagaggaagcccctctccttctccatggg
2761 catgactctccttcgaggccaccacgtttatctcacaatgatgtgttttgcttgactttc
2821 cctttgcgctgtctcgtgggaaaggtcattctgtctgagaccccagctccttctccagct
2881 ttggctgcgggcatggcctgagctttctggagagcctctgcaggggggtttgccatcaggg
2941 ccctgtggctgggtctgctgcagagctccttggctatcaggagaatcctggacactgtac
3001 tgtgcctcccagtttacaaacacgcccttcatctcaagtggcccttttaaaaggcctgctg
3061 ccatgtgagagctgtgaacagctcagctctgagtcggcaggctggggcttcctcctgggc
3121 caccagatggaaaggggggtattgtttgcctcactcctggatgctgcgttttaaggaagtg
3181 agtgagaaagaatgtgccaagatacctggctcctgtgaaaccagcctcaggagggaaact
3241 gggagagagaagctgtggtctcctgctacatgccctgggagctggaagagaaaaacactc
3301 ccctaaacaatcgcaaaatgatgaaccatcatgggccactgttctctttgaggggacagg
3361 tttaggggtttgcgttcgcccttgtgggctgaagcactagcttttttggtagctagacaca
3421 tcctgcacccaaaggttctctacaaaggcccagatttgtttgtaaagcactttgactctt
3481 acctggaggcccgctctctaagggcttcctgcgctcccacctcatcgtccctgagatgca
3541 gagcaggatggagggtctgcttctagctcagctgtttctccttgaggttgcggaggaatt
3601 gaattgaatgggacagagggcaggtgctgtggccaagaagatctccgagcagcagtgacg
3661 gggcaccttgctgtgtgtcctctgggcatgttaaccttctgtggggccaaaggtttgca
3721 tcgtggatccagctgtgctccagtctgtccctcctcctccactctgactgccacgcccc
3781 ggaccagcagcttggggaccctccagggtactaatggggctctgttctgagatggacaaa
3841 ttcagtgttggaaatacatgttgtactatgcacttcccatgctcctaggggttaggaatag
3901 tttcaaacatgattggcagacataacaacggcaaatactcggactggggcataggactcc
3961 agagtaggaaaaagacaaaagatttggcagcctgacacaggcaacctaccctctctctc
4021 cagcctctttatgaaactgtttgtttgccagtcctgccctaaggcagaagatgaattgaa
4081 gatgctgtgcatgtttcctaagtccttgagcaatcatggtggtgacaattgccacaaggg
4141 atatgaggccagtgccaccagagggtggtgccaagtgccacatcccttccgatccattcc
4201 cctctgcatcctcggagcaccccagtttgcctttgatgtgtccgctgtgtatgttagctg
4261 aactttgatgagcaaaatttcctgagcgaaacactccaaagagataggaaaacttgccgc
4321 ctcttcttttttgtcccttaatcaaactcaaataagcttaaaaaaaatccatggaagatc
4381 atggacatgtgaaatgagcattttttctttttttttttttaacaaagtctgaactgaaca
4441 gaacaagacttttcctcatacatctccaaattgtttaaacttactttatgagtgtttgt
4501 ttagaagttcggaccaacagaaaaatgcagtcagatgtcatcttggaattggtttctaaa
4561 agagtaaggcatgtccctgcccagaaacttaggaagcatgaaataaatcaaatgtttatt
4621 ttccttcttatttaaaatcatgcaaatgcaacagaaatagagggtttgtgccaaatgcta
4681 tgaacggccctttcttaaagacaagcaagggagattgatatatgtacaatttgctctcat
4741 gtttt
```

Figure 2F. 202P5A5 v.4 through v.26, SNP variants of 202P5A5 v.1.

| Variant | Nucleic acid position | Nucleic Acid Variation | Amino Acid Position | Amino Acid Variation |
|---|---|---|---|---|
| 202P5A5 v.4 | 138 | G/T | 37 | S=>I |
| 202P5A5 v.5 | 1269 | G/A | 414 | R=>Q |
| 202P5A5 v.6 | 1288 | A/C | 420 | K=>N |
| 202P5A5 v.7 | 1552 | A/G | Silent Variant | |
| 202P5A5 v.8 | 1662 | A/T | 545 | K=>M |
| 202P5A5 v.9 | 1899 | G/A | Silent Variant | |
| 202P5A5 v.10 | 2057 | T/C | Silent Variant | |
| 202P5A5 v.11 | 2143 | C/T | Silent Variant | |
| 202P5A5 v.12 | 2144 | G/A | Silent Variant | |
| 202P5A5 v.13 | 2249 | C/T | Silent Variant | |
| 202P5A5 v.15 | 2576 | A/G | Silent Variant | |
| 202P5A5 v.16 | 2812 | T/C | Silent Variant | |
| 202P5A5 v.17 | 2836 | G/A | Silent Variant | |
| 202P5A5 v.18 | 3059 | T/C | Silent Variant | |
| 202P5A5 v.19 | 3101 | G/A | Silent Variant | |
| 202P5A5 v.20 | 3309 | A/C | Silent Variant | |
| 202P5A5 v.21 | 3332 | T/C | Silent Variant | |
| 202P5A5 v.23 | 4208 | C/T | Silent Variant | |
| 202P5A5 v.24 | 4264 | C/T | Silent Variant | |
| 202P5A5 v.25 | 4409 | C/T | Silent Variant | |
| 202P5A5 v.26 | 4645 | A/T | Silent Variant | |

Figure 3A. Amino acid sequence of 202P5A5 v.1 (SEQ ID. NO.: 12). The 202P5A5 v.1 protein has 609 amino acids.

```
  1 MPSDPPFNTR RAYTSEDEAW KSYLENPLTA ATKAMMSING DEDSAAALGL LYDYYKVPRD
 61 KRLLSVSKAS DSQEDQEKRN CLGTSEAQSN LSGGENRVQV LKTVPVNLSL NQDHLENSKR
121 EQYSISFPES SAIIPVSGIT VVKAEDFTPV FMAPPVHYPR GDGEEQRVVI FEQTQYDVPS
181 LATHSAYLKD DQRSTPDSTY SESFKDAATE KFRSASVGAE EYMYDQTSSG TFQYTLEATK
241 SLRQKQGEGP MTYLNKGQFY AITLSETGDN KCFRHPISKV RSVVMVVFSE DKNRDEQLKY
301 WKYWHSRQHT AKQRVLDIAD YKESFNTIGN IEEIAYNAVS FTWDVNEEAK IFITVNCLST
361 DFSSQKGVKC LPLMIQIDTY SYNNRSNKPI HRAYCQIKVF CDKGAERKIR DEERKQNRKK
421 GKGQASQTQC NSSSDGKLAA IPLQKKSDIT YFKTMPDLHS QPVLFIPDVH FANLQRTGQV
481 YYNTDDEREG GSVLVKRMFR PMEEEFGPVP SKQMKEEGTK RVLLYVRKET DDVFDALMLK
541 SPTVKGLMEA ISEKYGLPVE KIAKLYKKSK KGILVNMDDN IIEHYSNEDT FILNMESMVE
601 GFKVTLMEI
```

Figure 3B. Amino acid sequence of 202P5A5 v.2 (SEQ ID. NO. : 13). The 202P5A5 v.2 protein has 625 amino acids.

```
  1 MSQESDNNKR LVALVPMPSD PPFNTRRAYT SEDEAWKSYL ENPLTAATKA MMSINGDEDS
 61 AAALGLLYDY YKVPRDKRLL SVSKASDSQE DQEKRNCLGT SEAQSNLSGG ENRVQVLKTV
121 PVNLSLNQDH LENSKREQYS ISFPESSAII PVSGITVVKA EDFTPVFMAP PVHYPRGDGE
181 EQRVVIFEQT QYDVPSLATH SAYLKDDQRS TPDSTYSESF KDAATEKFRS ASVGAEEYMY
241 DQTSSGTFQY TLEATKSLRQ KQGEGPMTYL NKGQFYAITL SETGDNKCFR HPISKVRSVV
301 MVVFSEDKNR DEQLKYWKYW HSRQHTAKQR VLDIADYKES FNTIGNIEEI AYNAVSFTWD
361 VNEEAKIFIT VNCLSTDFSS QKGVKGLPLM IQIDTYSYNN RSNKPIHRAY CQIKVFCDKG
421 AERKIRDEER KQNRKKGKGQ ASQTQCNSSS DGKLAAIPLQ KKSDITYFKT MPDLHSQPVL
481 FIPDVHFANL QRTGQVYYNT DDEREGGSVL VKRMFRPMEE EFGPVPSKQM KEEGTKRVLL
541 YVRKETDDVF DALMLKSPTV KGLMEAISEK YGLPVEKIAK LYKKSKKGIL VNMDDNIIEH
601 YSNEDTFILN MESMVEGFKV TLMEI
```

Figure 3C. Amino acid sequence of 202P5A5 v.4 (SEQ ID. NO. : 14). The 202P5A5 v.4 protein has 609 amino acids.

```
  1 MPSDPPFNTR RAYTSEDEAW KSYLENPLTA ATKAMMIING DEDSAAALGL LYDYYKVPRD
 61 KRLLSVSKAS DSQEDQEKRN CLGTSEAQSN LSGGENRVQV LKTVPVNLSL NQDHLENSKR
121 EQYSISFPES SAIIPVSGIT VVKAEDFTPV FMAPPVHYPR GDGEEQRVVI FEQTQYDVPS
181 LATHSAYLKD DQRSTPDSTY SESFKDAATE KFRSASVGAE EYMYDQTSSG TFQYTLEATK
241 SLRQKQGEGP MTYLNKGQFY AITLSETGDN KCFRHPISKV RSVVMVVFSE DKNRDEQLKY
301 WKYWHSRQHT AKQRVLDIAD YKESFNTIGN IEEIAYNAVS FTWDVNEEAK IFITVNCLST
361 DFSSQKGVKG LPLMIQIDTY SYNNRSNKPI HRAYCQIKVF CDKGAERKIR DEERKQNRKK
421 GKGQASQTQC NSSSDGKLAA IPLQKKSDIT YFKTMPDLHS QPVLFIPDVH FANLQRTGQV
481 YYNTDDEREG GSVLVKRMFR PMEEEFGPVP SKQMKEEGTK RVLLYVRKET DDVFDALMLK
541 SPTVKGLMEA ISEKYGLPVE KIAKLYKKSK KGILVNMDDN IIEHYSNEDT FILNMESMVE
601 GFKVTLMEI
```

Figure 3D. Amino acid sequence of 202P5A5 v.5 (SEQ ID. NO. : 15). The 202P5A5 v.5 protein has 609 amino acids.

```
  1 MPSDPPFNTR RAYTSEDEAW KSYLENPLTA ATKAMMSING DEDSAAALGL LYDYYKVPRD
 61 KRLLSVSKAS DSQEDQEKRN CLGTSEAQSN LSGGENRVQV LKTVPVNLSL NQDHLENSKR
121 EQYSISFPES SAIIPVSGIT VVKAEDFTPV FMAPPVHYPR GDGFFQRVVI FEQTQYDVPS
181 LATHSAYLKD DQRSTPDSTY SESFKDAATE KFRSASVGAE EYMYDQTSSG TFQYTLEATK
241 SLRQKQGEGP MTYLNKGQFY AITLSETGDN KCFRHPISKV RSVVMVVFSE DKNRDEQLKY
301 WKYWHSRQHT AKQRVLDIAD YKESFNTIGN IEEIAYNAVS FTWDVNEEAK IFITVNCLST
361 DFSSQKGVKG LPLMIQIDTY SYNNRSNKPI HRAYCQIKVF CDKGAERKIR DEEQKQNRKK
421 GKGQASQTQC NSSSDGKLAA IPLQKKSDIT YFKTMPDLHS QPVLFIPDVH FANLQRTGQV
481 YYNTDDEREG GSVLVKRMFR PMEEEFGPVP SKQMKEEGTK RVLLYVRKET DDVFDALMLK
541 SPTVKGLMEA ISEKYGLPVE KIAKLYKKSK KGILVNMDDN IIEHYSNEDT FILNMESMVE
601 GFKVTLMEI
```

Figure 3E. Amino acid sequence of 202P5A5 v.6 (SEQ ID. NO. : 16). The 202P5A5 v.6 protein has 609 amino acids.

```
  1 MPSDPPFNTR RAYTSEDEAW KSYLENPLTA ATKAMMSING DEDSAAALGL LYDYYKVPRD
 61 KRLLSVSKAS DSQEDQEKRN CLGTSEAQSN LSGGENRVQV LKTVPVNLSL NQDHLENSKR
121 EQYSISFPES SAIIPVSGIT VVKAEDFTPV FMAPPVHYPR GDGEEQRVVI FEQTQYDVPS
181 LATHSAYLKD DQRSTPDSTY SESFKDAATE KFRSASVGAE EYMYDQTSSG TFQYTLEATK
241 SLRQKQGEGP MTYLNKGQFY AITLSETGDN KCFRHPISKV RSVVMVVFSE DKNRDEQLKY
301 WKYWHSRQHT AKQRVLDIAD YKESFNTIGN IEEIAYNAVS FTWDVNEEAK IFITVNCLST
361 DFSSQKGVKG LPLMIQIDTY SYNNRSNKPI HRAYCQIKVF CDKGAERKIR DEERKQNRKN
421 GKGQASQTQC NSSSDGKLAA IPLQKKSDIT YFKTMPDLHS QPVLFIPDVH FANLQRTGQV
481 YYNTDDEREG GSVLVKRMFR PMEEEFGPVP SKQMKEEGTK RVLLYVRKET DDVFDALMLK
541 SPTVKGLMEA ISEKYGLPVE KIAKLYKKSK KGILVNMDDN IIEHYSNEDT FILNMESMVE
601 GFKVTLMEI
```

Figure 3F. Amino acid sequence of 202P5A5 v.8 (SEQ ID. NO. : 17). The 202P5A5 v.8 protein has 609 amino acids.

```
  1 MPSDPPFNTR RAYTSEDEAW KSYLENPLTA ATKAMMSING DEDSAAALGL LYDYYKVPRD
 61 KRLLSVSKAS DSQEDQEKRN CLGTSEAQSN LSGGENRVQV LKTVPVNLSL NQDHLENSKR
121 EQYSISFPES SAIIPVSGIT VVKAEDFTPV FMAPPVHYPR GDGEEQRVVI FEQTQYDVPS
181 LATHSAYLKD DQRSTPDSTY SESFKDAATE KFRSASVGAE EYMYDQTSSG TFQYTLEATK
241 SLRQKQGEGP MTYLNKGQFY AITLSETGDN KCFRHPISKV RSVVMVVFSE DKNRDEQLKY
301 WKYWHSRQHT AKQRVLDIAD YKESFNTIGN IEEIAYNAVS FTWDVNEEAK IFITVNCLST
361 DFSSQKGVKG LPLMIQIDTY SYNNRSNKPI HRAYCQIKVF CDKGAERKIR DEERKQNRKK
421 GKGQASQTQC NSSSDGKLAA IPLQKKSDIT YFKTMPDLHS QPVLFIPDVH FANLQRTGQV
481 YYNTDDEREG GSVLVKRMFR PMEEEFGPVP SKQMKEEGTK RVLLYVRKET DDVFDALMLK
541 SPTVMGLMEA ISEKYGLPVE KIAKLYKKSK KGILVNMDDN IIEHYSNEDT FILNMESMVE
601 GFKVTLMEI
```

Figure 4. Alignment of 202P5A5 with known homologs

Figure 4A. Alignment of 202P5A5 (SEQ ID NO: 18) with human hypothetical protein FLJ13782 (gi 13376382) (SEQ ID NO: 19)

Score = 1194 bits (3088), Expect = 0.0
Identities = 605/609 (99%), Positives = 606/609 (99%)

```
Query:   1   MPSDPPFNTRRAYTSEDEAWKSYLENPLTAATKAMMSINGDEDSAAALGLLYDYYKVPRD   60
             MPSDPPFNTRRAYTSEDEAWKSYLENPLTAATKAMM INGDEDSAAALGLLYDYYKVPRD
Sbjct:  17   MPSDPPFNTRRAYTSEDEAWKSYLENPLTAATKAMMIINGDEDSAAALGLLYDYYKVPRD   76

Query:  61   KRLLSVSKASDSQEDQEKRNCLGTSEAQSNLSGGENRVQVLKTVPVNLSLNQDHLENSKR  120
             KRLLSVSKASDSQEDQEKRNCLGTSEAQSNLSGGENRVQVLKTVPVNLSLNQDHLENSKR
Sbjct:  77   KRLLSVSKASDSQEDQEKRNCLGTSEAQSNLSGGENRVQVLKTVPVNLSLNQDHLENSKR  136

Query: 121   EQYSISFPESSAIIPVSGITVVKAEDFTPVFMAPPVHYPRGDGEEQRVVIFEQTQYDVPS  180
             EQYSISFPESSAIIPVSGITVVKAEDFTPVFMAPPVHYPRGDGEEQRVVIFEQTQYDVPS
Sbjct: 137   EQYSISFPESSAIIPVSGITVVKAEDFTPVFMAPPVHYPRGDGEEQRVVIFEQTQYDVPS  196

Query: 181   LATHSAYLKDDQRSTPDSTYSESFKDAATEKFRSASVGAEEYMYDQTSSGTFQYTLEATK  240
             LATHSAYLKDDQRSTPDSTYSESFKDAATEKFRSASVGAEEYMYDQTSSGTFQYTLEATK
Sbjct: 197   LATHSAYLKDDQRSTPDSTYSESFKDAATEKFRSASVGAEEYMYDQTSSGTFQYTLEATK  256

Query: 241   SLRQKQGEGPMTYLNKGQFYAITLSETGDNKCFRHPISKVRSVVMVVFSEDKNRDEQLKY  300
             SLRQKQGEGPMTYLNKGQFYAITLSETGDNKCFRHPISKVRSVVMVVFSEDKNRDEQLKY
Sbjct: 257   SLRQKQGEGPMTYLNKGQFYAITLSETGDNKCFRHPISKVRSVVMVVFSEDKNRDEQLKY  316

Query: 301   WKYWHSRQHTAKQRVLDIADYKESFNTIGNIEEIAYNAVSFTWDVNEEAKIFITVNCLST  360
             WKYWHSRQHTAKQRVLDIADYKESFNTIGNIEEIAYNAVSFTWDVNEEAKIFITVNCLST
Sbjct: 317   WKYWHSRQHTAKQRVLDIADYKESFNTIGNIEEIAYNAVSFTWDVNEEAKIFITVNCLST  376

Query: 361   DFSSQKGVKGLPLMIQIDTYSYNNRSNKPIHRAYCQIKVFCDKGAERKIRDEERKQNRKK  420
             DFSSQKGVKGLPLMIQIDTYSYNNRSNKPIHRAYCQIKVFCDKGAERKIRDEE+KQNRK
Sbjct: 377   DFSSQKGVKGLPLMIQIDTYSYNNRSNKPIHRAYCQIKVFCDKGAERKIRDEEQKQNRKN  436

Query: 421   GKGQASQTQCNSSSDGKLAAIPLQKKSDITYFKTMPDLIISQPVLFIPDVHFANLQRTGQV  480
             GKGQASQTQCNSSSDGKLAAIPLQKKSDITYFKTMPDL SQPVLFIPDVHFANLQRTGQV
Sbjct: 437   GKGQASQTQCNSSSDGKLAAIPLQKKSDITYFKTMPDLHSQPVLFIPDVHFANLQRTGQV  496

Query: 481   YYNTDDEREGGSVLVKRMFRPMEEEFGPVPSKQMKEEGTKRVLLYVRKETDDVFDALMLK  540
             YYNTDDEREGGSVLVKRMFRPMEEEFGPVPSKQMKEEGTKRVLLYVRKETDDVFDALMLK
Sbjct: 497   YYNTDDEREGGSVLVKRMFRPMEEEFGPVPSKQMKEEGTKRVLLYVRKETDDVFDALMLK  556

Query: 541   SPTVKGLMEAISEKYGLPVEKIAKLYKKSKKGILVNMDDNIIEHYSNEDTFILNMESMVE  600
             SPTV GLMEAISEKYGLPVEKIAKLYKKSKKGILVNMDDNIIEHYSNEDTFILNMESMVE
Sbjct: 557   SPTVMGLMEAISEKYGLPVEKIAKLYKKSKKGILVNMDDNIIEHYSNEDTFILNMESMVE  616

Query: 601   GFKVTLMEI  609
             GFKVTLMEI
Sbjct: 617   GFKVTLMEI  625
```

Figure 4B. Alignment of 202P5A5 (SEQ ID NO: 20) with mouse BOM (gi 20502771) (SEQ ID NO: 21)

Score = 1147 bits (2966), Expect = 0.0
Identities = 576/609 (94%), Positives = 592/609 (97%)

```
Query:   1  MPSDPPFNTRRAYTSEDEAWKSYLENPLTAATKAMMSINGDEDSAAALGLLYDYYKVPRD  60
            MPSDPPFNTRRAYTSEDEAWKSYLENPLTAATKAMMSINGDEDSAAALGLLYDYYKVPRD
Sbjct:  17  MPSDPPFNTRRAYTSEDEAWKSYLENPLTAATKAMMSINGDEDSAAALGLLYDYYKVPRD  76

Query:  61  KRLLSVSKASDSQEDQEKRNCLGTSEAQSNLSGGENRVQVLKTVPVNLSLNQDHLENSKR  120
            KRLLSVSKASDSQEDQ+KRNCLGTSEAQ NLSGGENRVQVLKTVPVNL L+QDH+ENSKR
Sbjct:  77  KRLLSVSKASDSQEDQDKRNCLGTSEAQINLSGGENRVQVLKTVPVNLCLSQDHMENSKR  136

Query: 121  EQYSISFPESSAIIPVSGITVVKAEDFTPVFMAPPVHYPRGDGEEQRVVIFEQTQYDVPS  180
            EQYS+S  ESSA+IPVSGITVVKAEDFTPVFMAPPVHYPR D EEQRVVIFEQTQYD+PS
Sbjct: 137  EQYSVSITESSAVIPVSGITVVKAEDFTPVFMAPPVHYPRADSEEQRVVIFEQTQYDLPS  196

Query: 181  LATHSAYLKDDQRSTPDSTYSESFKDAATEKFRSASVGAEEYMYDQTSSGTFQYTLEATK  240
            +A+HS+YLKDDQRSTPDSTYSESFKD A+EKFRS SVGA+EY YDQT SGTFQYTLEATK
Sbjct: 197  IASHSSYLKDDQRSTPDSTYSESFKDGASEKFRSTSVGADEYTYDQTGSGTFQYTLEATK  256

Query: 241  SLRQKQGEGPMTYLNKGQFYAITLSETGDNKCFRHPISKVRSVVMVVFSEDKNRDEQLKY  300
            SLRQKQGEGPMTYLNKGQFYAITLSETGDNKCFRHPISKVRSVVMVVFSEDKNRDEQLKY
Sbjct: 257  SLRQKQGEGPMTYLNKGQFYAITLSETGDNKCFRHPISKVRSVVMVVFSEDKNRDEQLKY  316

Query: 301  WKYWHSRQHTAKQRVLDIADYKESFNTIGNIEEIAYNAVSFTWDVNEEAKIFITVNCLST  360
            WKYWHSRQHTAKQRVLDIADYKESFNTIGNIEEIAYNAVSFTWDVNEEAKIFITVNCLST
Sbjct: 317  WKYWHSRQHTAKQRVLDIADYKESFNTIGNIEEIAYNAVSFTWDVNEEAKIFITVNCLST  376

Query: 361  DFSSQKGVKGLPLMIQIDTYSYNNRSNKPIHRAYCQIKVFCDKGAERKIRDEERKQNRKK  420
            DFSSQKGVKGLPLMIQIDTYSYNNRSNKPIHRAYCQIKVFCDKGAERKIRDEERKQNRKK
Sbjct: 377  DFSSQKGVKGLPLMIQIDTYSYNNRSNKPIHRAYCQIKVFCDKGAERKIRDEERKQNRKK  436

Query: 421  GKGQASQTQCNSSSDGKLAAIPLQKKSDITYFKTMPDLHSQPVLFIPDVHFANLQRTGQV  480
            GKGQASQ QCN+SSDGK+AAIPLQKKSDITYFKTMPDLHSQPVLFIPDVHFANLQRTGQV
Sbjct: 437  GKGQASQAQCNNSSDGKMAAIPLQKKSDITYFKTMPDLHSQPVLFIPDVHFANLQRTGQV  496

Query: 481  YYNTDDEREGGSVLVKRMFRPMEEEFGPVPSKQMKEEGTKRVLLYVRKETDDVFDALMLK  540
            YYNTDDEREG SVLVKRMFRPMEEEFGP PSKQ+KEE  KRVLLYVRKE DDVFDALMLK
Sbjct: 497  YYNTDDEREGSSVLVKRMFRPMEEEFGPTPSKQIKEENVKRVLLYVRKENDDVFDALMLK  556

Query: 541  SPTVKGLMEAISEKYGLPVEKIAKLYKKSKKGILVNMDDNIIEHYSNEDTFILNMESMVE  600
            SPTVKGLMEA+SEKYGLPVEKI KLYKKSKKGILVNMDDNIIEHYSNEDTFILNMESMVE
Sbjct: 557  SPTVKGLMEALSEKYGLPVEKITKLYKKSKKGILVNMDDNIIEHYSNEDTFILNMESMVE  616

Query: 601  GFKVTLMEI  609
            GFK+TLMEI
Sbjct: 617  GFKITLMEI  625
```

Figure 4C. Alignment of 202P5A5 (SEQ ID NO: 22) with mouse grainyhead-like protein (gi 21312674) (SEQ ID NO: 23)

Score = 772 bits (1994), Expect = 0.0
Identities = 382/403 (94%), Positives = 393/403 (97%)

```
Query:   1   MPSDPPFNTRRAYTSEDEAWKSYLENPLTAATKAMMSINGDEDSAAALGLLYDYYKVPRD  60
             MPSDPPFNTRRAYTSEDEAWKSYLENPLTAATKAMMSINGDEDSAAALGLLYDYYKVPRD
Sbjct:  17   MPSDPPFNTRRAYTSEDEAWKSYLENPLTAATKAMMSINGDEDSAAALGLLYDYYKVPRD  76

Query:  61   KRLLSVSKASDSQEDQEKRNCLGTSEAQSNLSGGENRVQVLKTVPVNLSLNQDHLENSKR  120
             KRLLSVSKASDSQEDQ+KRNCLGTSEAQ NLSGGENRVQVLKTVPVNL L+QDH+ENSKR
Sbjct:  77   KRLLSVSKASDSQEDQDKRNCLGTSEAQINLSGGENRVQVLKTVPVNLCLSQDHMENSKR  136

Query: 121   EQYSISFPESSAIIPVSCITVVKAEDFTPVFMAPPVHYPRGDGEEQRVVIFEQTQYDVPS  180
             EQYS+S   ESSA+IPVSGITVVKAEDFTPVFMAPPVHYPR D EEQRVVIFEQTQYD+PS
Sbjct: 137   EQYSVSITESSAVIPVSGITVVKAEDFTPVFMAPPVHYPRADSEEQRVVIFEQTQYDLPS  196

Query: 181   LATHSAYLKDDQRSTPDSTYSESFKDAATEKFRSASVGAEEYMYDQTSSGTFQYTLEATK  240
             +A+HS+YLKDDQRSTPDSTYSESFKD A+EKFRS SVGA+EY YDQT SGTFQYTLEATK
Sbjct: 197   IASHSSYLKDDQRSTPDSTYSESFKDGASEKFRSTSVGADEYTYDQTGSGTFQYTLEATK  256

Query: 241   SLRQKQGEGPMTYLNKGQFYAITLSETGDNKCFRHPISKVRSVVMVVFSEDKNRDEQLKY  300
             SLRQKQGEGPMTYLNKGQFYAITLSETGDNKCFRHPISKVRSVVMVVFSEDKNRDEQLKY
Sbjct: 257   SLRQKQGEGPMTYLNKGQFYAITLSETGDNKCFRHPISKVRSVVMVVFSEDKNRDEQLKY  316

Query: 301   WKYWHSRQHTAKQRVLDIADYKESFNTIGNIEEIAYNAVSFTWDVNEEAKIFITVNCLST  360
             WKYWHSRQHTAKQRVLDIADYKESFNTIGNIEEIAYNAVSFTWDVNEEAKIFITVNCLST
Sbjct: 317   WKYWHSRQHTAKQRVLDIADYKESFNTIGNIEEIAYNAVSFTWDVNEEAKIFITVNCLST  376

Query: 361   DFSSQKGVKGLPLMIQIDTYSYNNRSNKPIHRAYCQIKVFCDK  403
             DFSSQKGVKGLPLMIQIDTYSYNNRSNKPIHRAYCQIKVFCDK
Sbjct: 377   DFSSQKGVKGLPLMIQIDTYSYNNRSNKPIHRAYCQIKVFCDK  419
```

Figure 5: 202P5A5 variant 1 Hydrophilicity profile
(Hopp T.P., Woods K.R., 1981.
Proc. Natl. Acad. Sci. U.S.A. 78:3824-3828)
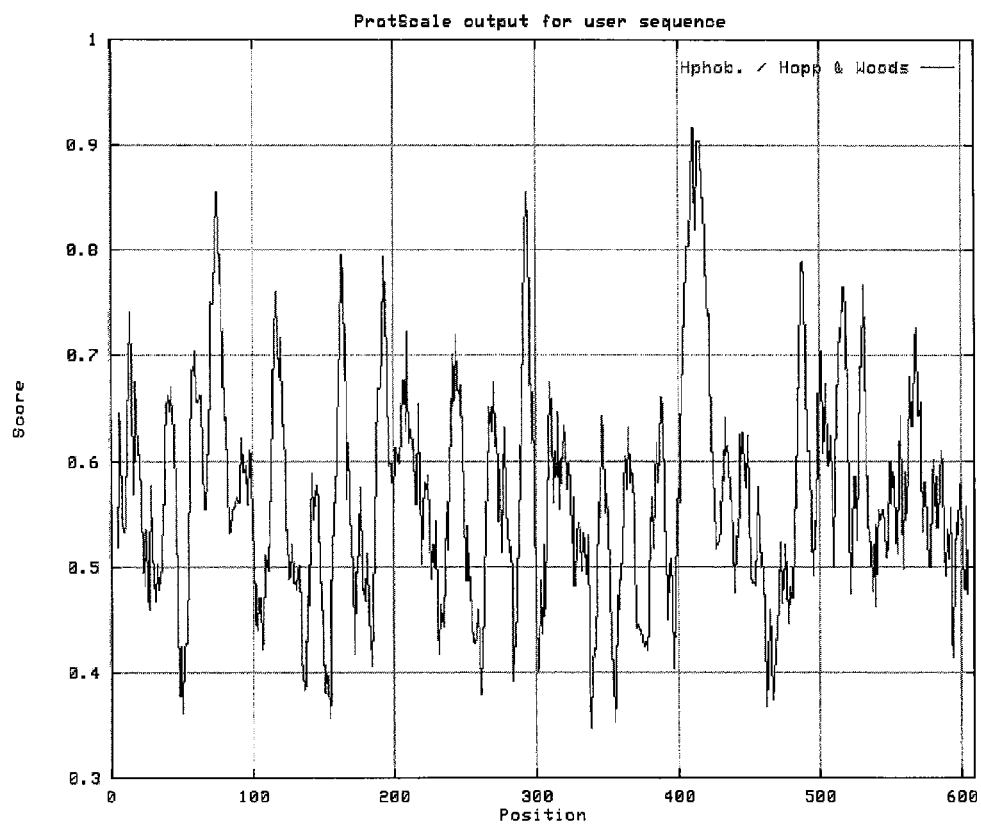

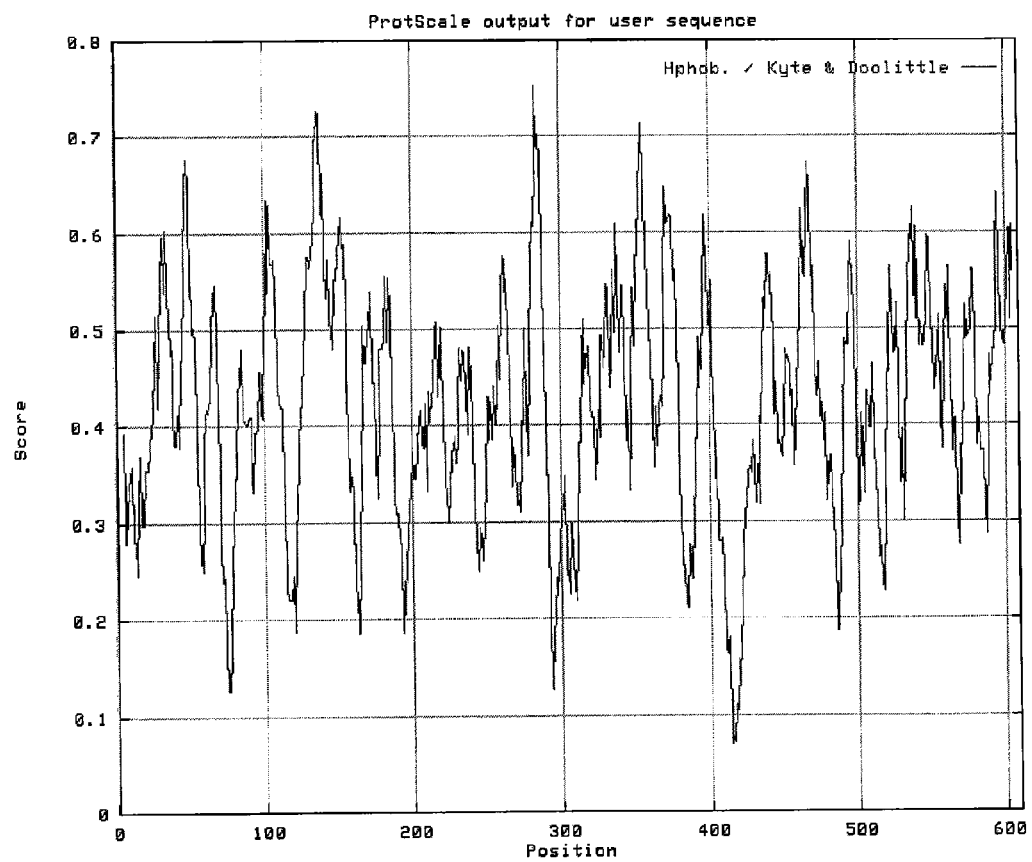
Figure 6: 202P5A5 variant 1
Hydropathicity Profile
(Kyte J., Doolittle R.F., 1982. J. Mol. Biol. 157:105-132)

Figure 7: 202P5A05 variant 1 %
Accessible Residues Profile
(Janin J., 1979. Nature 277:491-492)
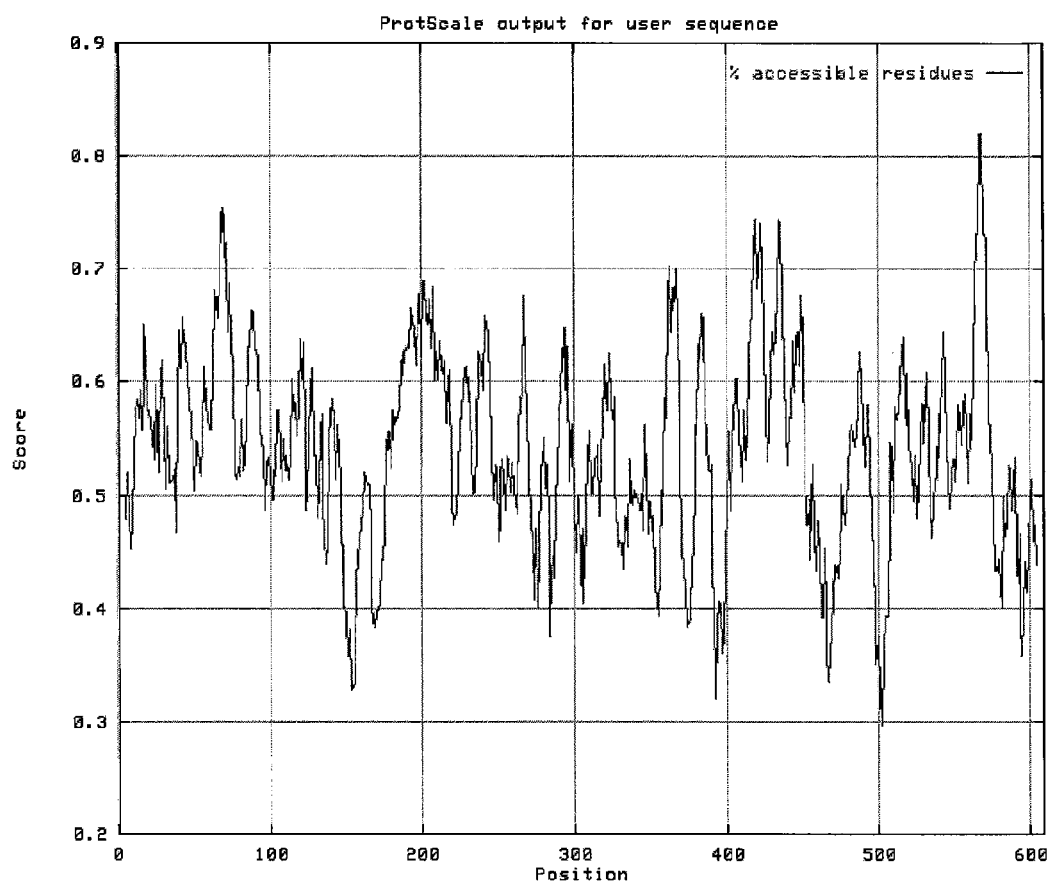

Figure 8: 202P5A5 variant 1
Average Flexibility Profile
(Bhaskaran R., Ponnuswamy P.K., 1988.
Int. J. Pept. Protein Res. 32:242-255)
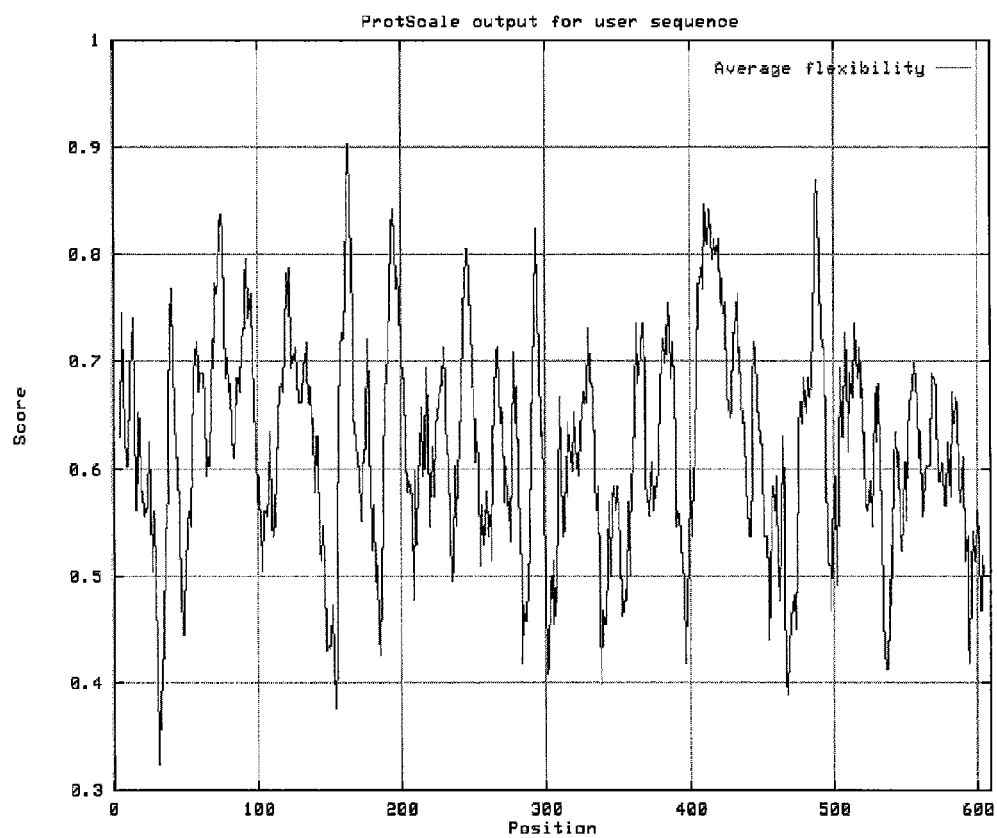

Figure 9: 202P5A5 variant 1
Beta-turn Profile
(Deleage, G., Roux B. 1987. Protein Engineering 1:289-294)
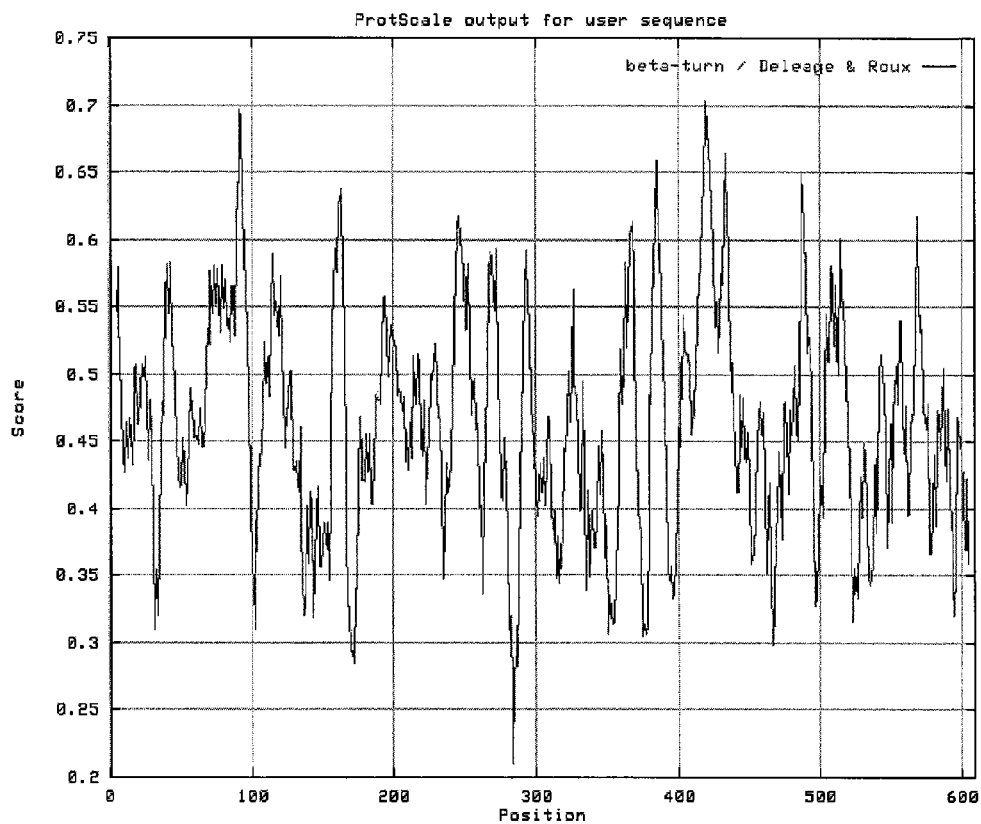

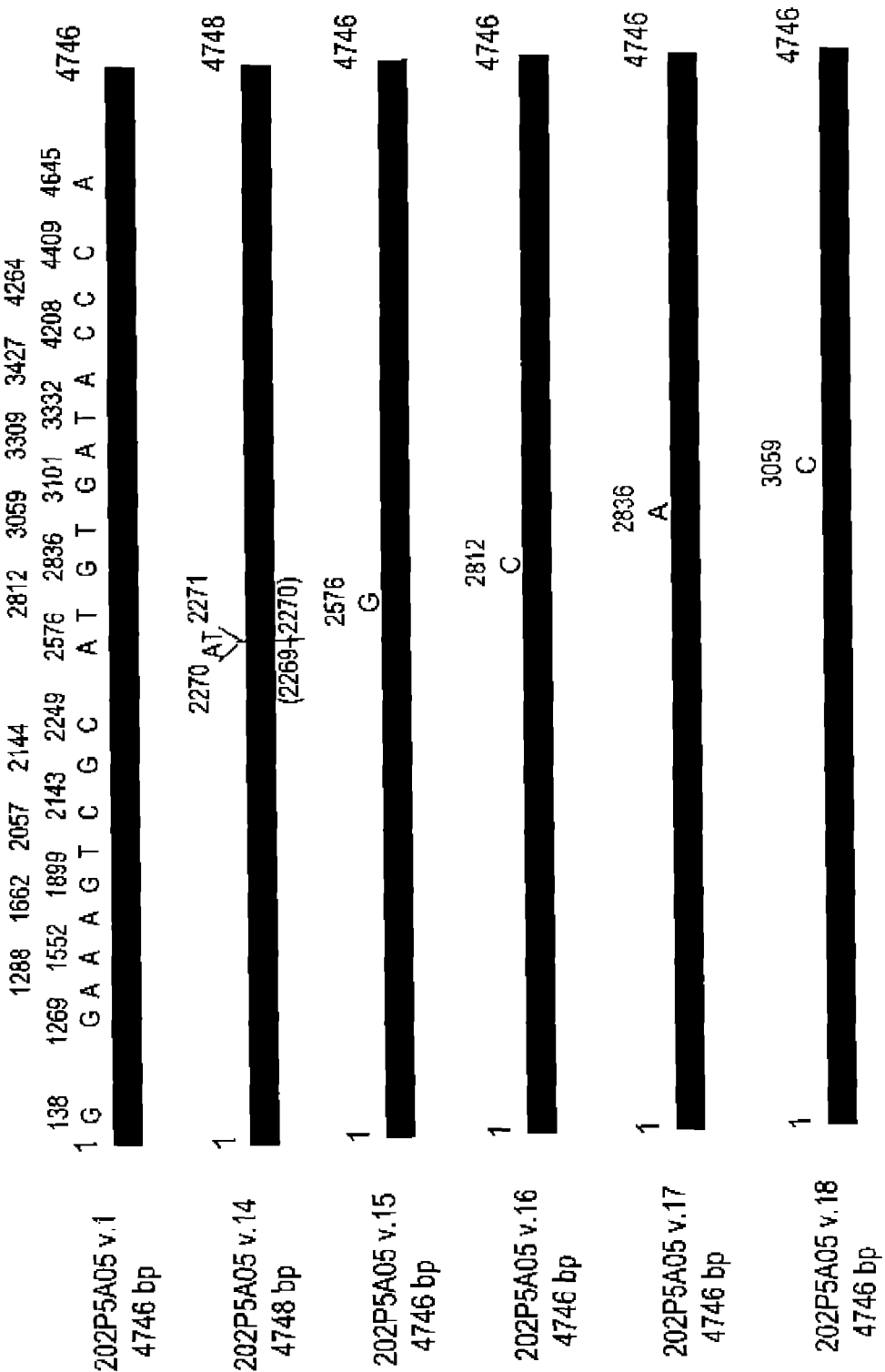

Figure 13A    Secondary structure prediction of 202P5A05 variant 1

```
         10        20        30        40        50        60        70
         |         |         |         |         |         |         |
MPSDPPFNTRRAYTSEDEAWKSYLENPLTAATKAMMSINGDEDSAAALGLLYDYKVPRDKRLLSVSKAS
cccccccccccccccchhhhhhhhhhhhhhhhhhhhhhhcccchhhhhhhhhhhhhhcccceeeeeccc
DSQEDQEKRNCLGTSEAQSNLSGGENRVQVLKTVPVNLSLNQDHLENSKREQYSISFPESSAIIPVSGIT
ccchhhhhcccccccccccccccceeeeccccccccccccccceeccccceeeeeeccccceeeeccee
VVKAEDFTPVFMAPPVHYPRGDGEEQRVVIFEQTQYDVPSLATHSAYLKDDQRSTPDSTYSESFKDAATE
eeeccccccceecccccccccccccceeeeeeeeccccccccccheccccccccccccccchhhhhhhh
KFRSASVGAEEYMYDQTSSGTFQYTLEATKSLRQKQGEGPMTYLNKGQFYAITLSETGDNKCFRHPISKV
hhhhccchhhhhhccccceeehhhhhhhhhhhcccccceeeeeecccccceeeeeeeeccccccccccce
RSVMVVFSEDKNRDEQLKYWKYWHSRQHTAKQRVLDIADYKESFNTIGNIEEIAYNAVSFTWDVNEEAK
eeeeeeecccccchhhhhcccccccccchchhhhhhhhhhccccchhhhhhhhheeeehccchhhhhhhhhc
IFITVNCLSTDFSSQKGVKGLPLMIQIDTYSYNNRSNKPIHRAYCQIKVFCDKGAERKIRDEERKQNRKK
eeeeeeecccccccccccccceeeeeeccccccccccchhhhhhhhhhhhhhhhcccchhhhhhhhhhc
GKGQASQTQCNSSSDGKLAAIPLQKKSDITYFKTMPDLHSQPVLFIPDVHFANLQRTGQVYYNTDDEREG
cccccccccccccccccccceeeeccccccccceeeeccchhhhchhcccceeeeeccccccccc
GSVLVKRMFRPMEEEFGPVPSKQMKEEGTKRVLLYVRKETDDVFDALMLKSPTVKGLMEAISEKYGLPVE
cchhhhhhhccchhccccccccchhccccceeeeeeccchhhhhhhccccchhhhhhhhccccchh
KIAKLYKKSKKGILVNMDDNIIEHYSNEDTFILNMESMVEGFKVTLMEI
hhhhhhhhhccceeeeecccheeecccccchheehhhhhhccceeeeeccc
```

Alpha helix (h): 31.69%
Extended strand (e): 19.87%
Random coil (c): 48.44%

Figure 13B Transmembrane prediction for 202P5A5 variant 1
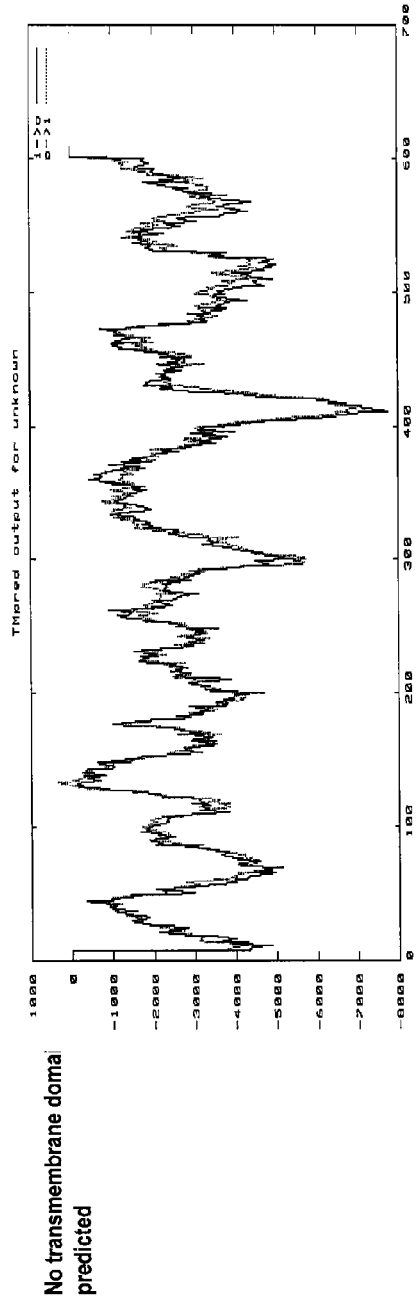
No transmembrane domain predicted
Figure 13C
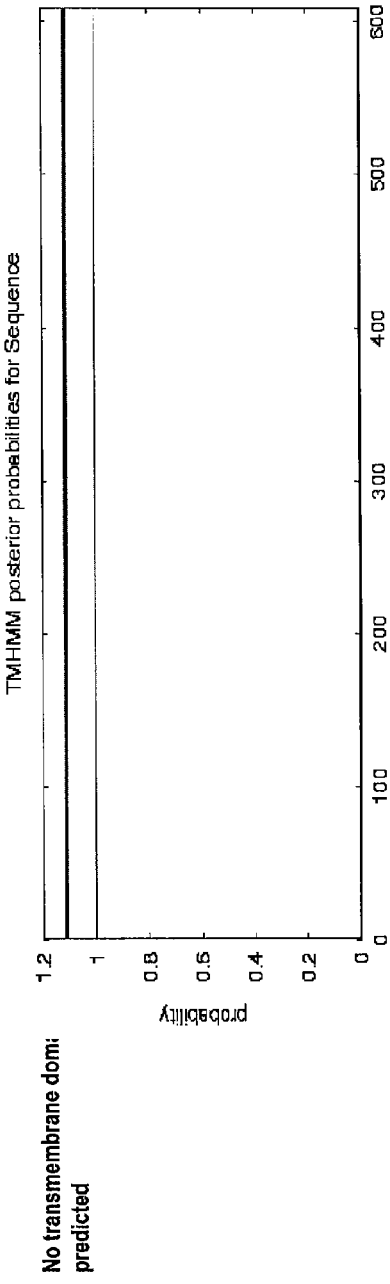
No transmembrane domain predicted

Figure 14A. 202P5A5 Expression by RT-PCR
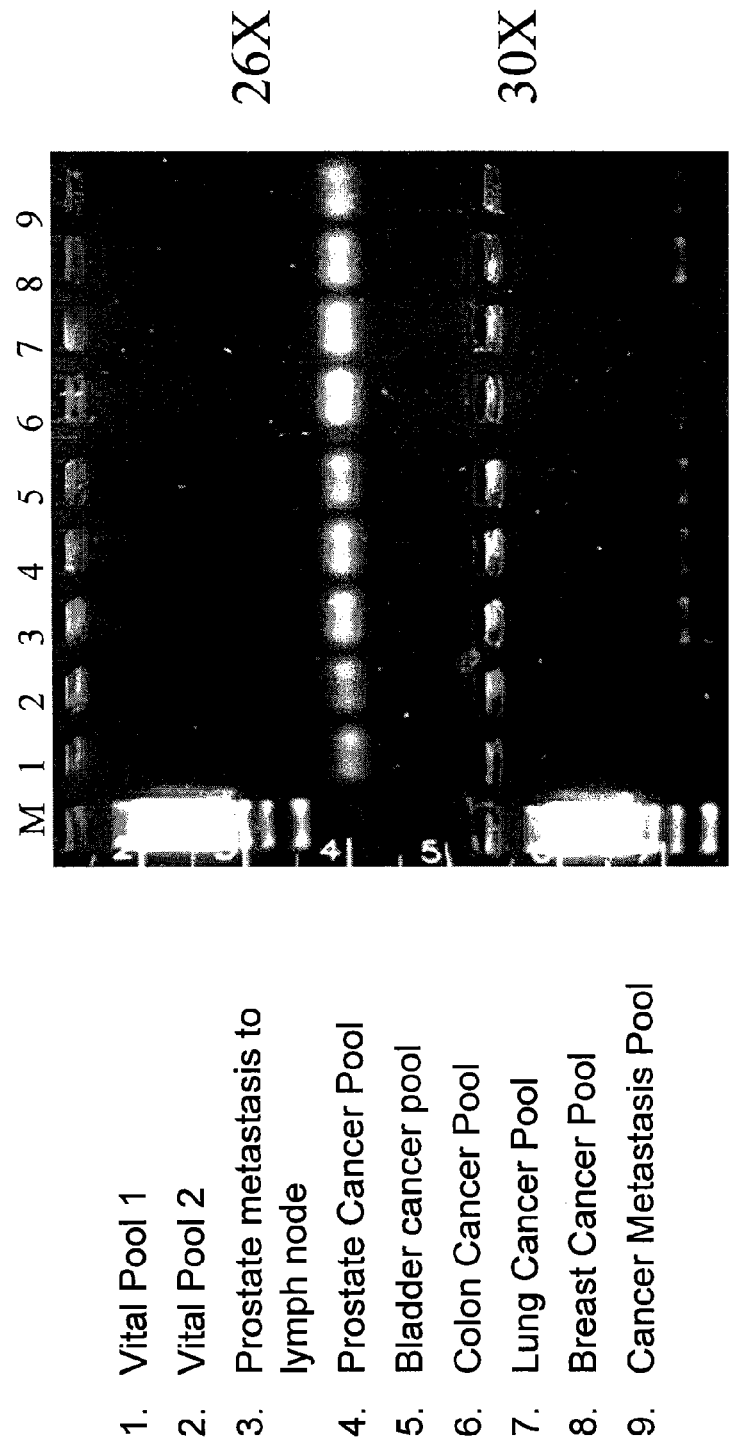
1. Vital Pool 1
2. Vital Pool 2
3. Prostate metastasis to lymph node
4. Prostate Cancer Pool
5. Bladder cancer pool
6. Colon Cancer Pool
7. Lung Cancer Pool
8. Breast Cancer Pool
9. Cancer Metastasis Pool

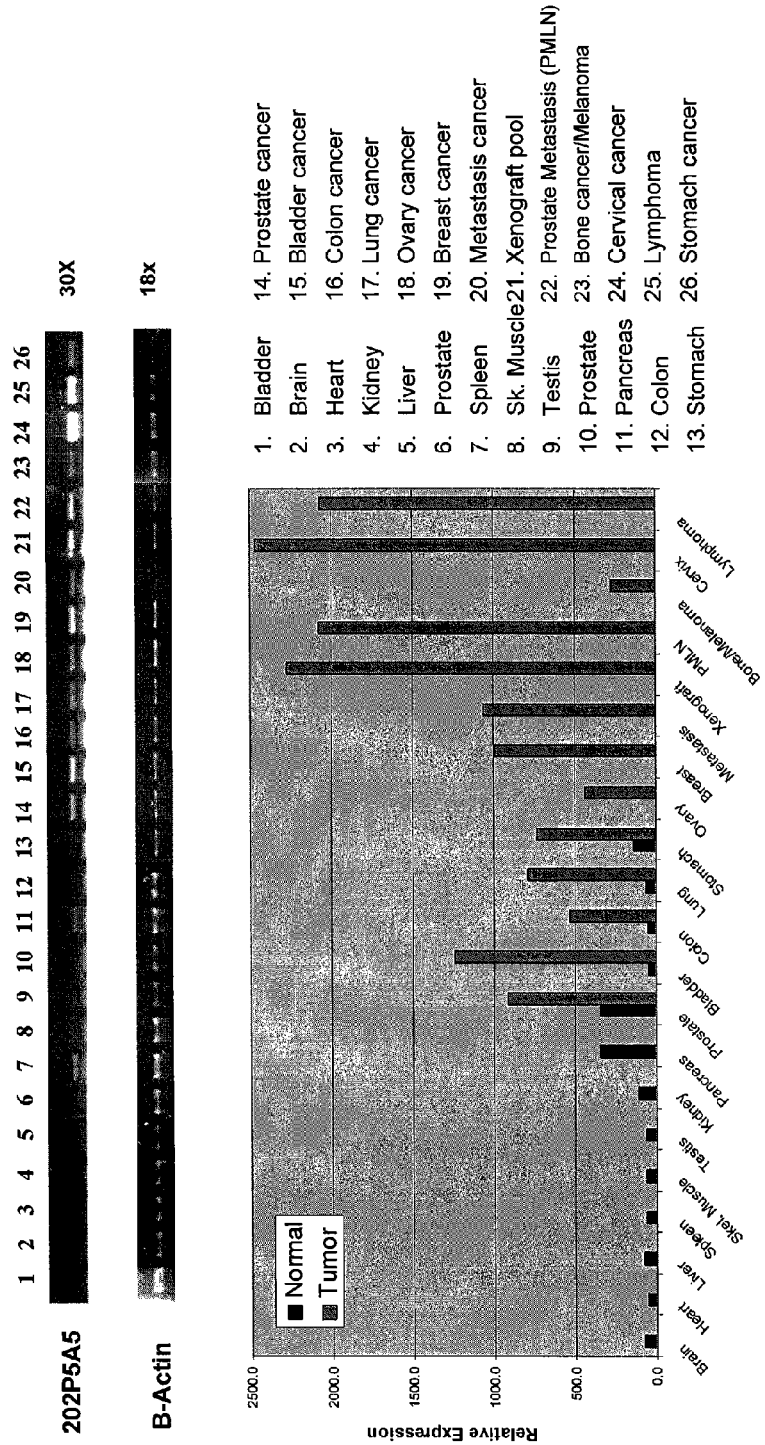
Figure 14B. Expression of 202P5A5 in Normal and Patient Cancer Tissues

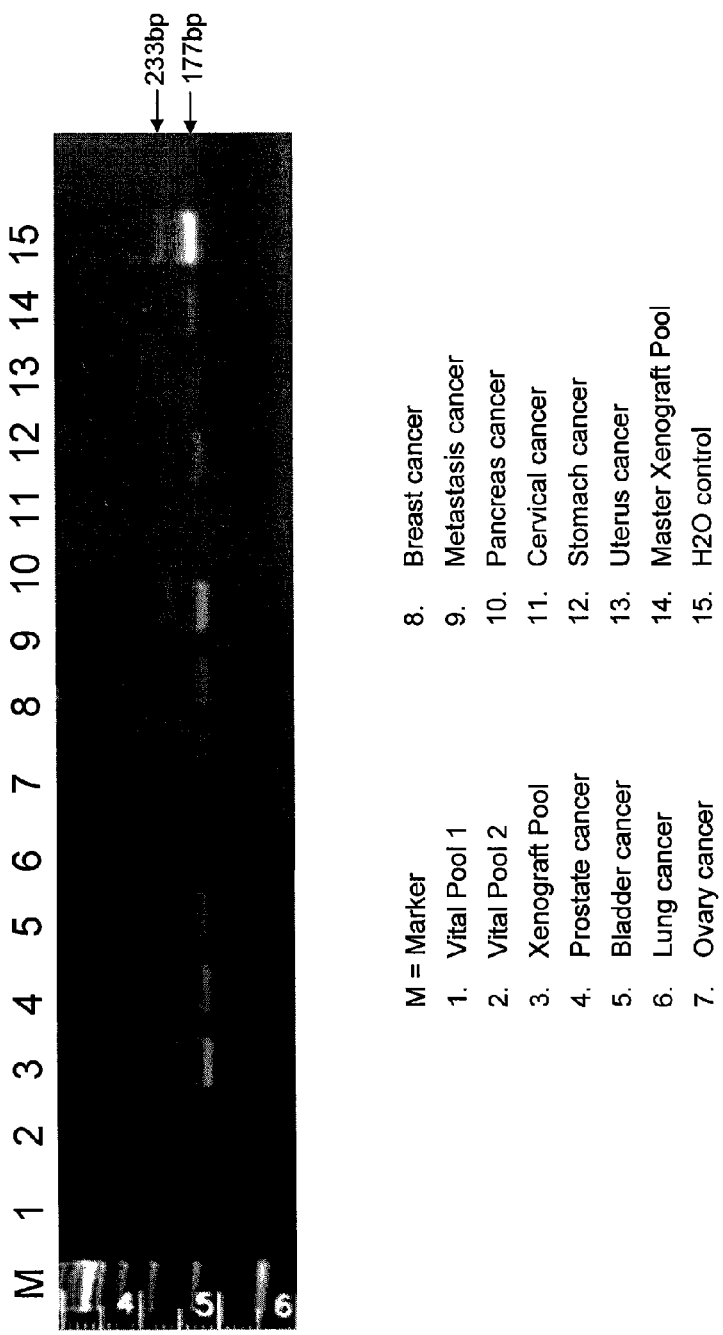
Figure 15. 202P5A5 variants Expression by RT-PCR

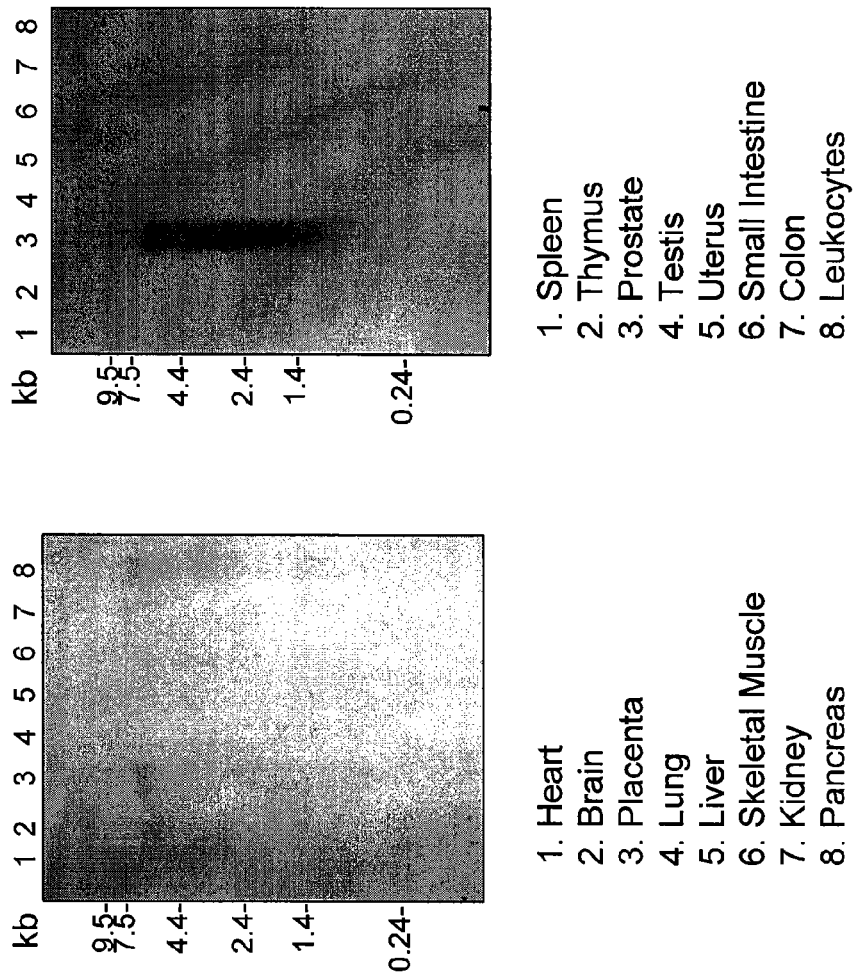
Figure 16. 202P5A5 Expression in Normal Tissues

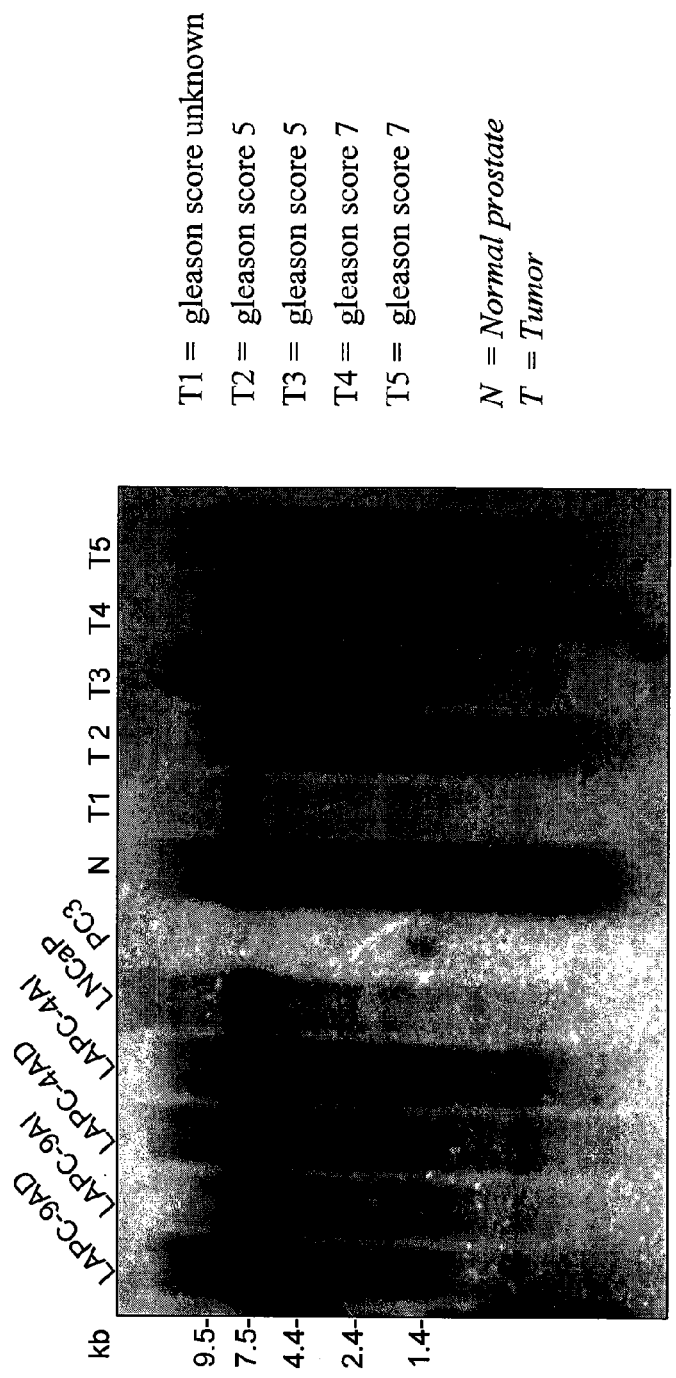
Figure 17. 202P5A5 Expression in Prostate Cancer Patient Specimens
T1 = gleason score unknown
T2 = gleason score 5
T3 = gleason score 5
T4 = gleason score 7
T5 = gleason score 7
N = *Normal prostate*
T = *Tumor*

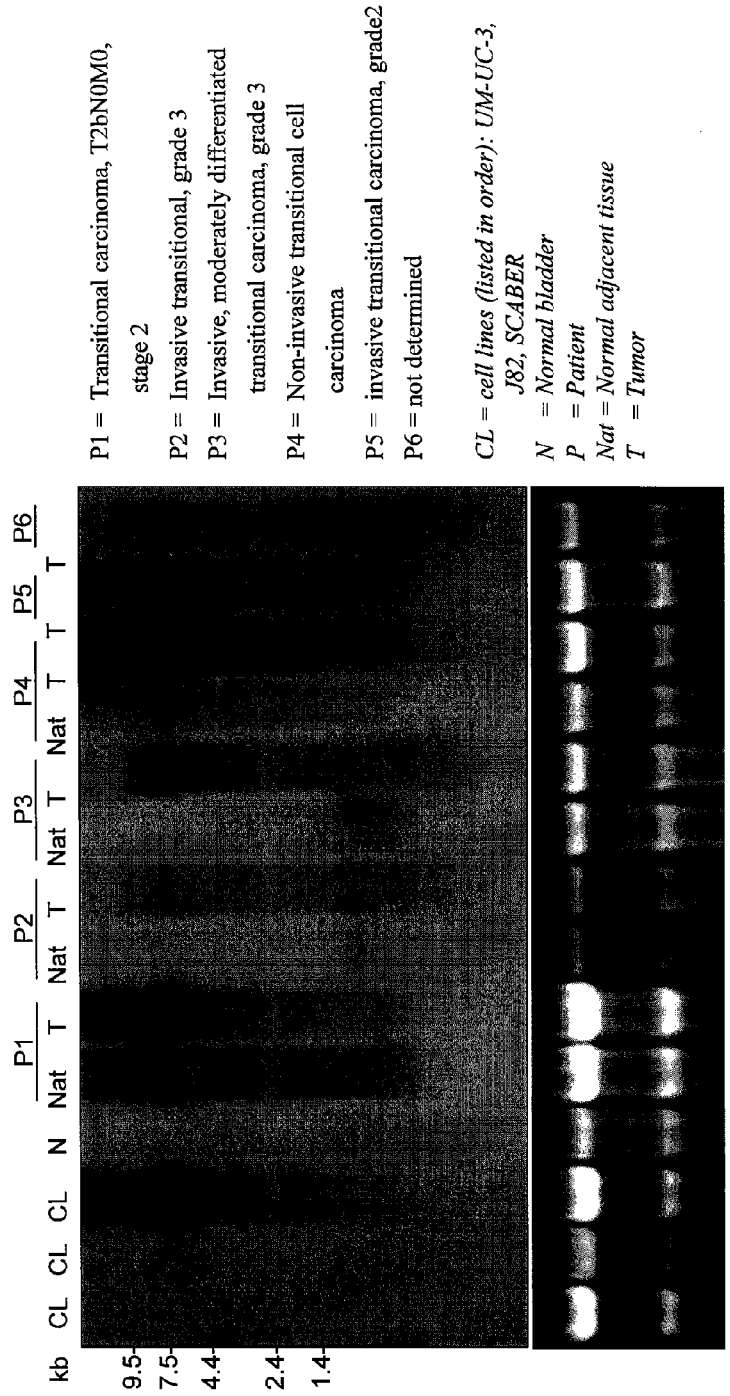
Figure 18. 202P5A5 Expression in Bladder Cancer Patient Specimens

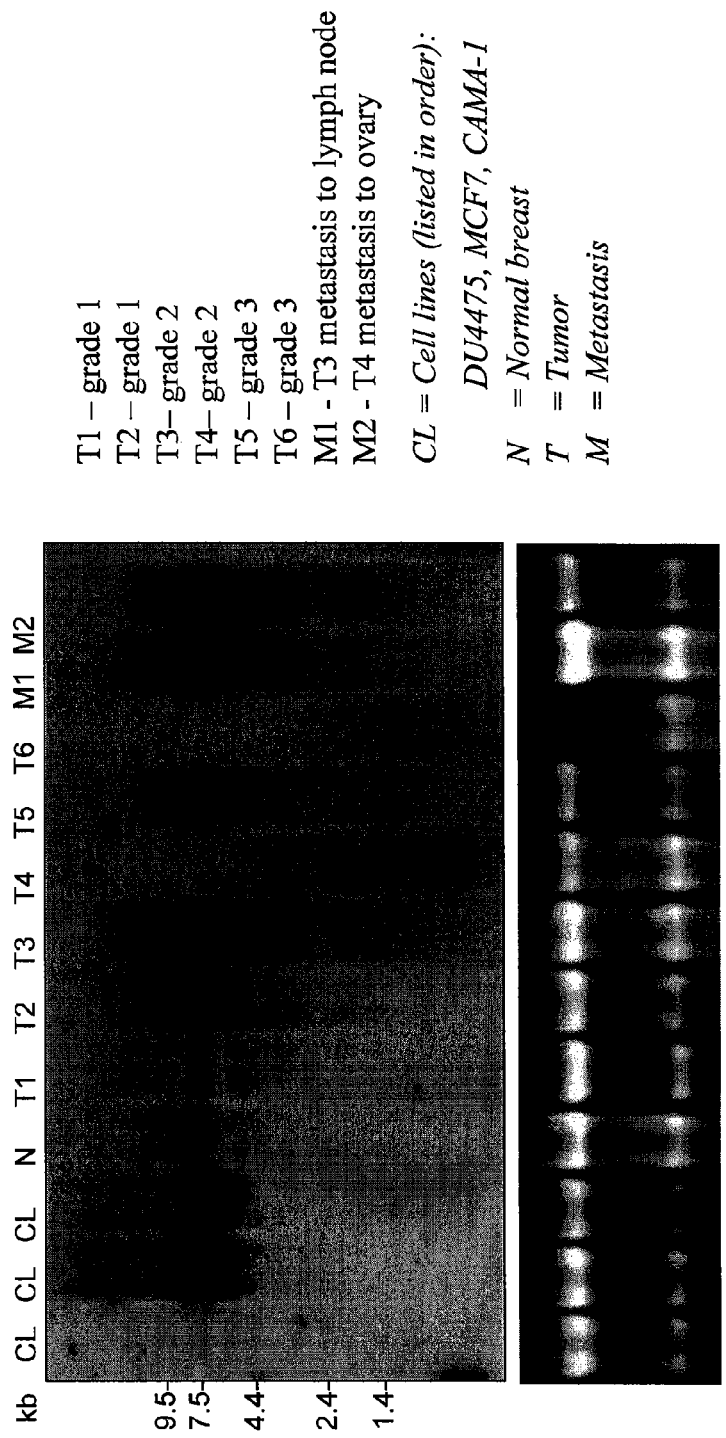
Figure 19. 02P5A5 Expression in Breast Cancer Patient Specimens

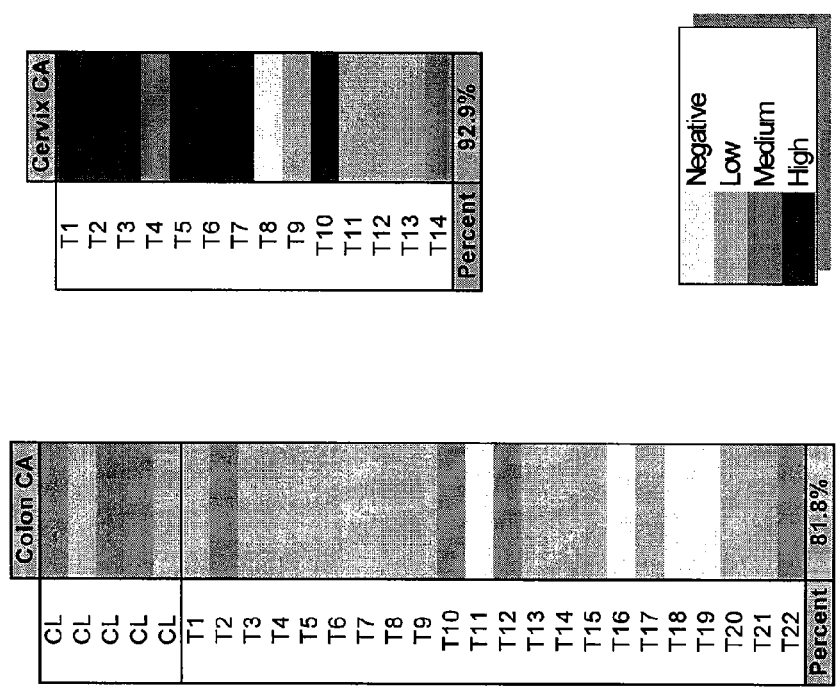
Figure 20. 202P5A5 Expression in Colon and Cervical Cancer Patient Specimens

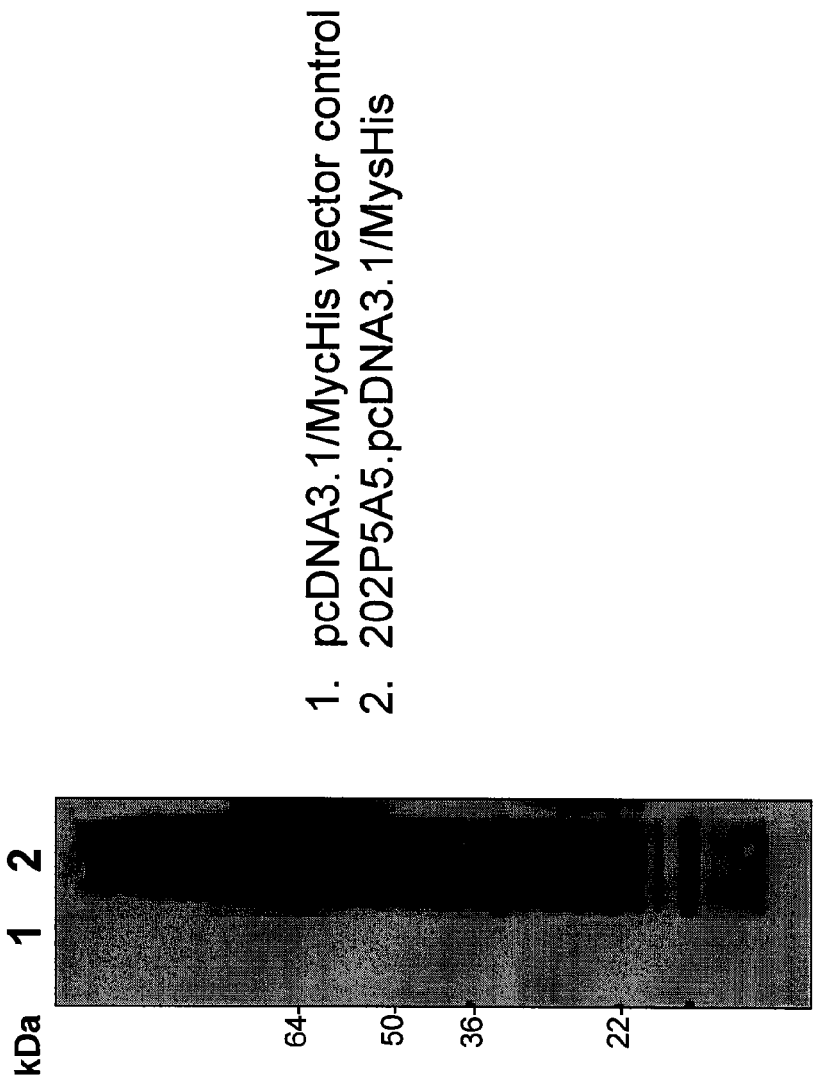
Figure 21. Expression of 202P5A5.pcDNA3.1/MycHis Following Transfection into 293T Cells.

NUCLEIC ACIDS AND CORRESPONDING PROTEINS ENTITLED 202P5A5 USEFUL IN TREATMENT AND DETECTION OF CANCER

CROSS-REFERENCE TO RELATED APPLICATIONS

This application is a continuation of U.S. Ser. No. 10/463,782 filed 16 Jun. 2003 which is a non-provisional utility patent application, now abandoned, that claims priority from U.S. provisional patent application Ser. No. 60/404,306, filed 16 Aug. 2002 and this application claims priority from U.S. provisional patent application Ser. No. 60/423,290, filed 1 Nov. 2002. The contents of the applications listed in this paragraph are fully incorporated by reference herein.

STATEMENT OF RIGHTS TO INVENTIONS MADE UNDER FEDERALLY SPONSORED RESEARCH

Not applicable.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 511582008601seqlist.txt | Oct. 5, 2007 | 229,695 bytes |

FIELD OF THE INVENTION

The invention described herein relates to genes and their encoded proteins, termed 202P5A5 and variants thereof, expressed in certain cancers, and to diagnostic and therapeutic methods and compositions useful in the management of cancers that express 202P5A5.

BACKGROUND OF THE INVENTION

Cancer is the second leading cause of human death next to coronary disease. Worldwide, millions of people die from cancer every year. In the United States alone, as reported by The American Cancer Society, cancer causes the death of well over a half-million people annually, with over 1.2 million new cases diagnosed per year. While deaths from heart disease have been declining significantly, those resulting from cancer generally are on the rise, in the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has teen improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al. 19971 Nat. Med. 3:402). More recently identified prostate cancer markers include PCTA-1 (Su et al., 1996 Proc. Natl. Acad. Sci. USA 93:7252), prostate-specific membrane (PSM) antigen (Pinto et al., Clin Cancer Res 1996 September 2 (9): 1445-51), STEAP (Hubert, et al., Proc Natl Acad Sci USA. 1999 Dec. 7; 96 (25): 14523-8) and prostate stem cell antigen (PSCA) (Reiter et al. 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men end women, incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1964 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of alt cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long tasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnoses in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequalae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all infra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among woman.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

SUMMARY OF THE INVENTION

The present invention relates to a gene, designated 202P5A5, that has now been found to be over-expressed in the cancer(s) listed in Table I. Northern blot expression analysis of 202P5A5 gene expression in normal tissues shows a restricted expression pattern in adult tissues. The nucleotide (FIG. 2) and amino acid (FIG. 2, and FIG. 3) sequences of 202P5A5 are provided. The tissue-related profile of 202P5A5 in normal adult tissues, combined with the over-expression observed in the tissues listed in Table I, shows that 202P5A5 is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 202P5A5 genes, mRNAs, and/or coding sequences, preferably in isolated form, including polynucleotides encoding 202P5A5-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 202P5A5-related protein, as well as the peptides/proteins themselves; DNA, RNA, DNA/RNA hybrids, and related molecules, polynucleotides or oligonucleotides complementary or having at least a 90% homology to the 202P5A5 genes or mRNA sequences or parts thereof, and polynucleotides or oligonucleotides that hybridize to the 202P5A5 genes, mRNAs, or to 202P5A5-encoding polynucleotides. Also provided are means for isolating cDNAs and the genes encoding 202P5A5. Recombinant DNA molecules containing 202P5A5 polynucleotides, cells transformed or transduced with such molecules, and host-vector systems for the expression of 202P5A5 gene products are also provided. The invention further provides antibodies that bind to 202P5A5 proteins and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments, there is a proviso that the entire nucleic acid sequence of FIG. 2 is not encoded and/or the entire amino acid sequence of FIG. 2 is not prepared, in certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of 202P5A5 polynucleotides and proteins in various biological samples, as well as methods for identifying cells that express 202P5A5. A typical embodiment of this invention provides methods for monitoring 202P5A5 gene products in a tissue or hematology sample having or suspected of having some form of growth dysregulation such as cancer.

The invention further provides various immunogenic or therapeutic compositions and strategies for treating cancers that express 202P5A5 such as cancers of tissues listed in Table I, including therapies aimed at inhibiting the transcription, translation, processing or function of 202P5A5 as well as cancer vaccines. In one aspect, the invention provides compositions, and methods comprising them, for treating a cancer that expresses 202P5A5 in a human subject wherein the composition comprises a earner suitable for human use and a human unit dose of one or more than one agent that inhibits the production or function of 202P5A5. Preferably, the carrier is a uniquely human carrier. In another aspect of the invention, the agent is a moiety that is immunoreactive with 202P5A5 protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety, in another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to 202P5A5 and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with 202P5A5 as described above. The one or more than one nucleic acid molecule may also be, or encodes a molecule that inhibits production of 202P5A5. Non-limiting examples of such molecules include, but are not limited to, those complementary to a nucleotide sequence essential for production of 202P5A5 (e.g., antisense sequences or molecules that form a triple helix with a nucleotide double helix essential for 202P5A5 production) or a ribozyme effective to lyse 202P5A5 mRNA.

Note that to determine the starting position of any peptide set forth in Tables VIII-XXI and XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides in Table VII. Generally, a unique Search Peptide is used to obtain HLA peptides of a particular for a particular variant. The position of each Search Peptide relative to its respective parent molecule is listed in Table VII. Accordingly, if a Search Peptide begins at position "X", one must add the value "X−1" to each position in Tables VIII-XXI and XXII to XLIX to obtain the actual position of the HLA peptides in their parental molecule. For example, if a particular Search Peptide begins at position 150 of its parental molecule, one must add 150−1, i.e., 149 to each HLA peptide amino acid position to calculate the position of that amino acid in the parent molecule.

One embodiment of the invention comprises an HLA peptide, that occurs at least twice in Tables VIII-XXI and XXII to XLIX collectively, or an oligonucleotide that encodes the HLA peptide. Another embodiment of the invention comprises an HLA peptide that occurs at least once in Tables VIII-XXII and at least once in tables XXII to XLIX, or an oligonucleotide that encodes the HLA peptide.

Another embodiment of the invention is antibody epitopes, which comprise a peptide regions, or an oligonucleotide encoding the peptide region, that has one two, three, four, or five of the following characteristics:

i) a peptide region of at least 5 amino acids of a particular peptide of FIG. 3, in any whole number increment up to the full length of that protein in FIG. 3, that includes an ammo acid position having a value equal to or greater than 0.5, 0.6, 0.7, 0.8, 0.9, or having a value equal to 1.0, in the Hydrophilicity profile of FIG. 5;

ii) a peptide region of at least 5 amino adds of a particular peptide of FIG. 3, in any whole number increment up to the full length of that protein FIG. 3, that includes an amino acid position having a value equal to or less than 0.5, 0.4, 0.3, 0.2, 0.1, or having a value equal to 0.0, in the Hydropathicity profile of FIG. 6;

iii) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the percent Accessible Residues profile of FIG. 7;

iv) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or v) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0 in the Beta-turn profile of FIG. 9.

Figure 10:
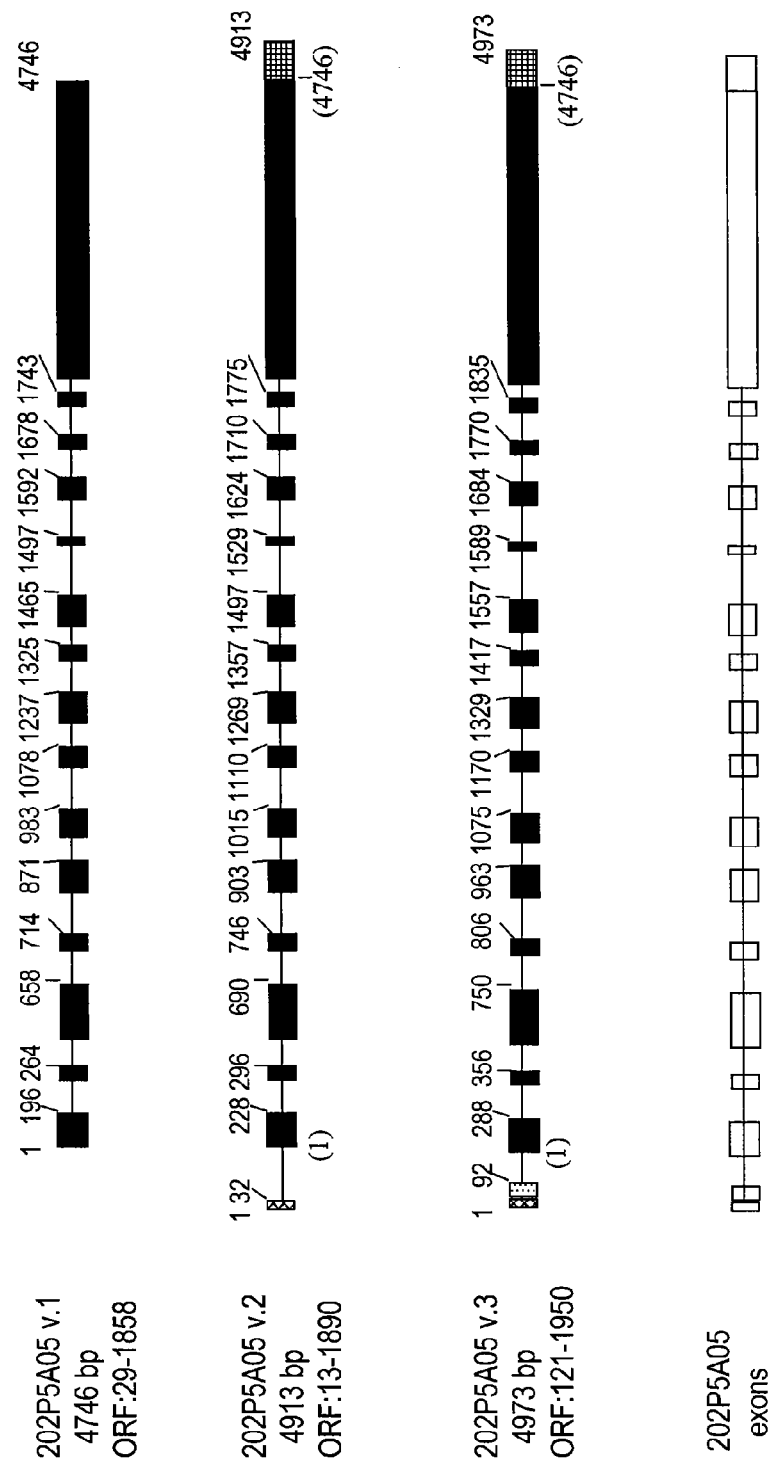

B) The cDNA and amino acid sequence of 202P5A5 variant 2 (also called "202P5A5 v.2") is shown in FIG. 2B. The codon for the start methionine is underlined. The open reading frame extends from nucleic acid 13-1890 including the stop codon.

C) The cDNA and amino acid sequence of 202P5A5 variant 3 (also called "202P5A5 v.3:") is shown in FIG. 2C. The codon for the start methionine is underlined. The open reading frame extends from nucleic acid 121-1950 including the stop codon.

D) The cDNA and amino acid sequence of 202 P5A5 variant 14 (also called "202P5A5 v.14") is shown in FIG. 2D. The codon for the start methionine is underlined. The open reading frame extends from nucleic acid 29-1858 including the stop codon.

E) The cDNA and amino acid sequence of 202P5A5 variant 22 (also called "202P5A5 v.22") is shown in FIG. 2E. The codon for the start methionine is underlined. The open reading frame extends from nucleic acid 29-1858 including the stop codon.

F) 202P5A5 v.4 through v.26, SNP variants of 202P5A5 v.1. The 202P5A5 v.4 through v.23 are variants with single nucleotide difference from 202P5A5 v.1. 202P5A5 v.4, v.5, v.6 and v.8 differ from 202P5A5 v.1 by one amino acid. 202P5A5 v.7, and v.9 through v.9 code for the same protein as v.1. Though these SNP variants are shown separately, they can also occur in any combinations and in any of the transcript variants listed above in FIGS. 2A through 2C.

FIG. 3.
A) The amino acid sequence of 202P5A5 v.1 is shown in FIG. 3A; it has 609 amino acids.
B) The amino acid sequence of 202P5A5 v.2 is shown in FIG. 3B; it has 625 amino acids.
C) The amino acid sequence of 202P5A5 v.4 is shown in FIG. 3C; it has 609 amino acids.
D) The amino acid sequence of 202P5A5 v.5 is shown in FIG. 3D; it has 609 amino acids.
E) The amino acid sequence of 202P5A5 v.5 is shown in FIG. 3E; it has 609 amino acids.
F) The amino acid sequence of 202P5A5 v.8 is shown in FIG. 3F; it has 609 amino acids.

As used herein, a reference to 202P5A5 includes all variants thereof, including those shown in FIGS. 2, 3, 10, and 11, unless the context clearly indicates otherwise.

Figures 1, 12:
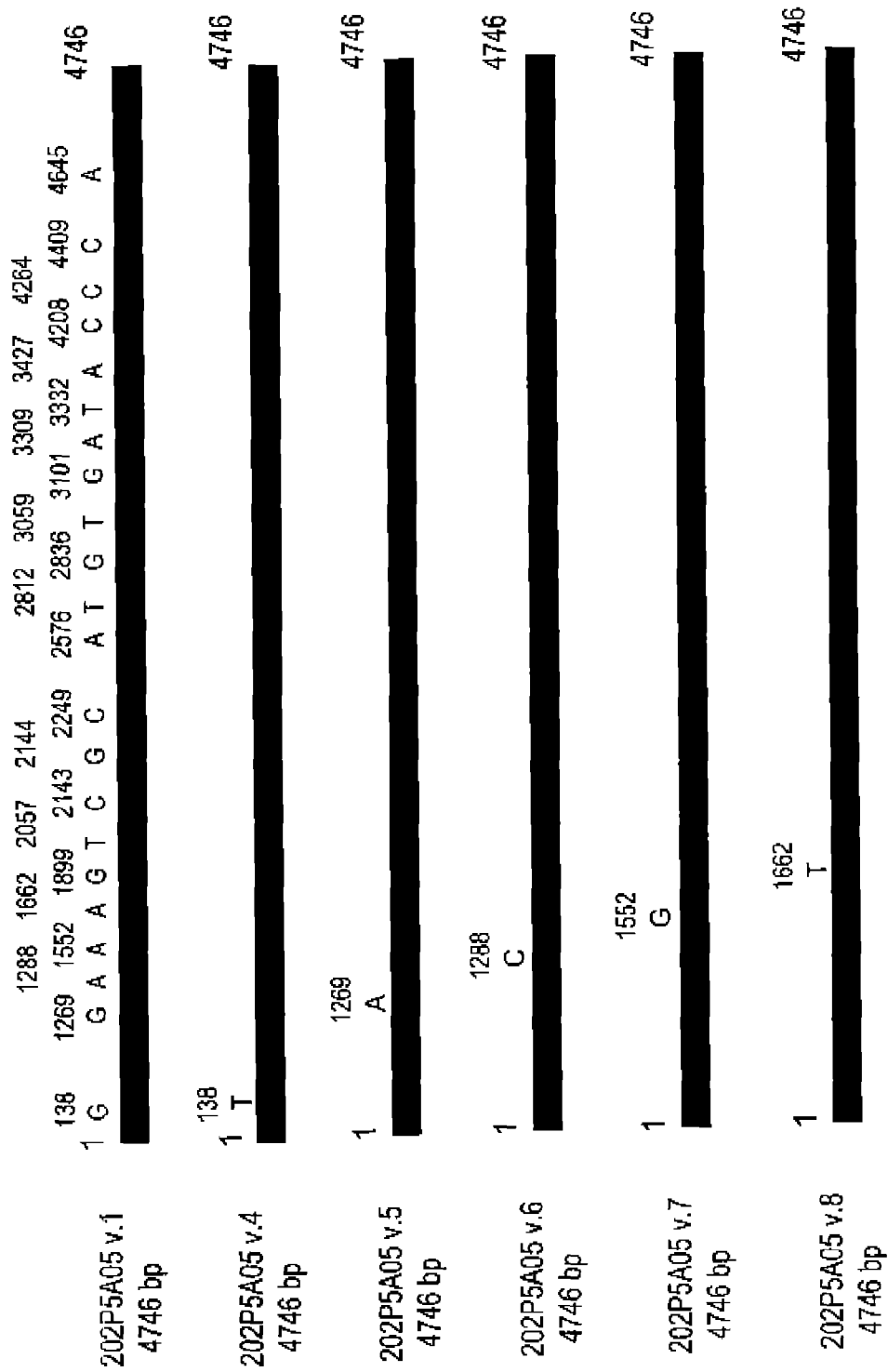
FIG. 1. The 202P5A5 SSH sequence of 186 nucleotides.
Figures 2, 12:
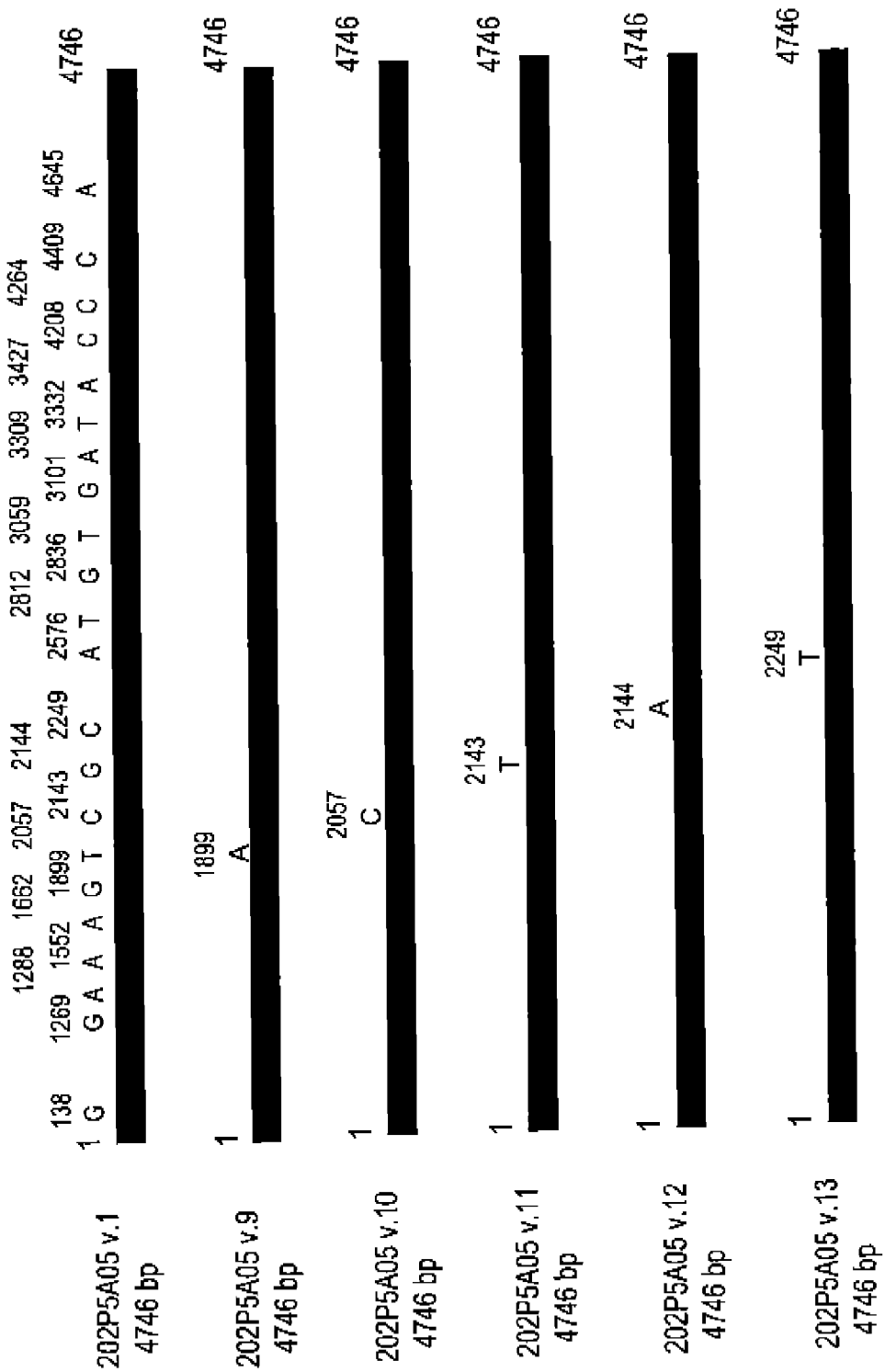
FIG. 2. A) The cDNA and amino acid sequence of 202P5A5 variant 1 (also called "202P5A5 v.1" or "202P5A5 variant 1") is shown in FIG. 2A. The start methionine is underlined. The open reading frame extends from nucleic acid 29-1858 including the stop codon.
Figures 4, 12:
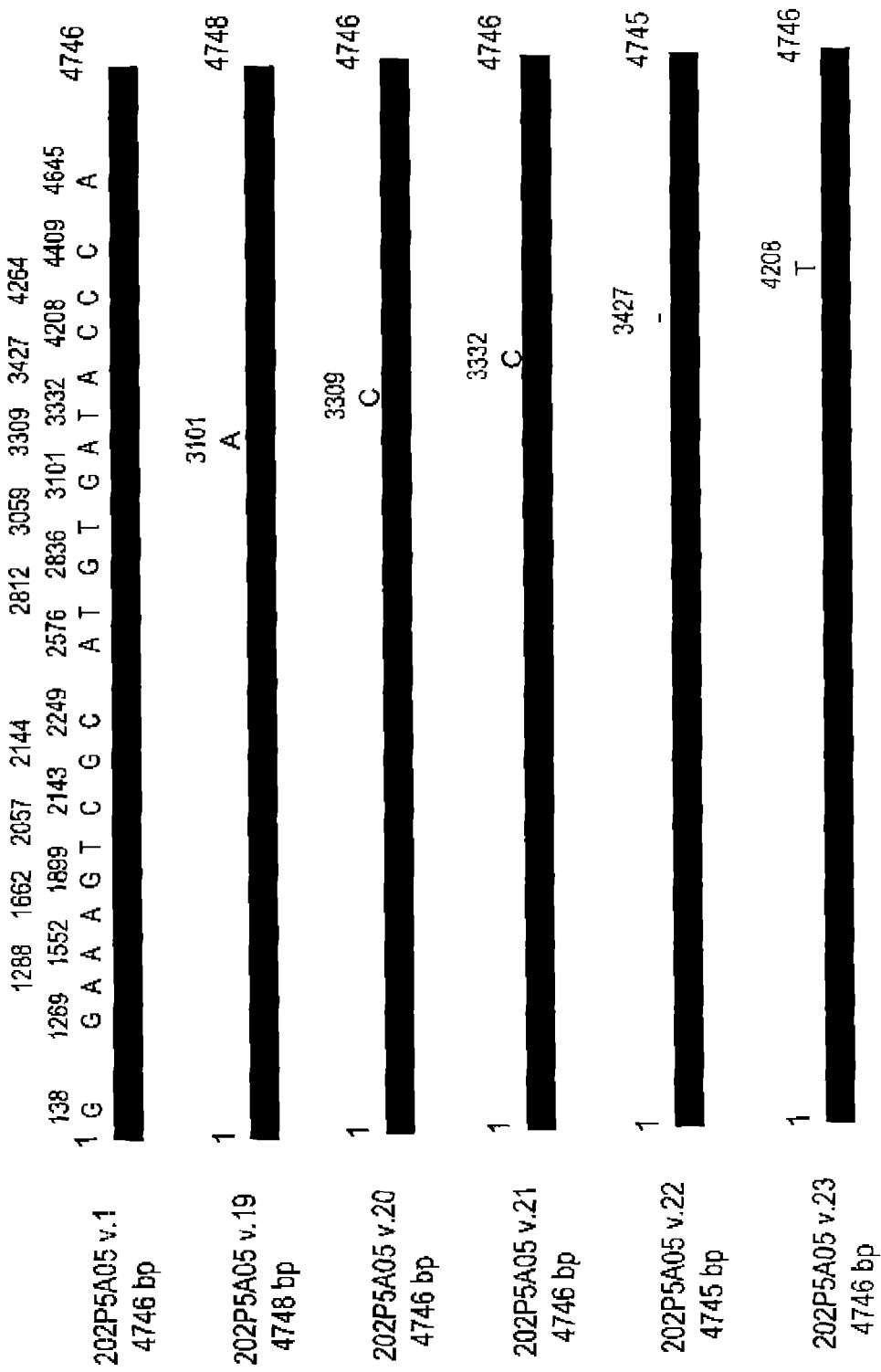

FIG. 4. Alignment of 202P5A5 with known homologs. FIG. 4A) Alignment of 202P5A5 with human hypothetical protein FLJ13782(gi 13376382). FIG. 4B) Alignment of 202P5A5 with mouse BOM (gi 20502771). FIG. 4C) Alignment of 202P5A5 with mouse grainyhead-like protein (gi 21312674).

Figures 5, 12:
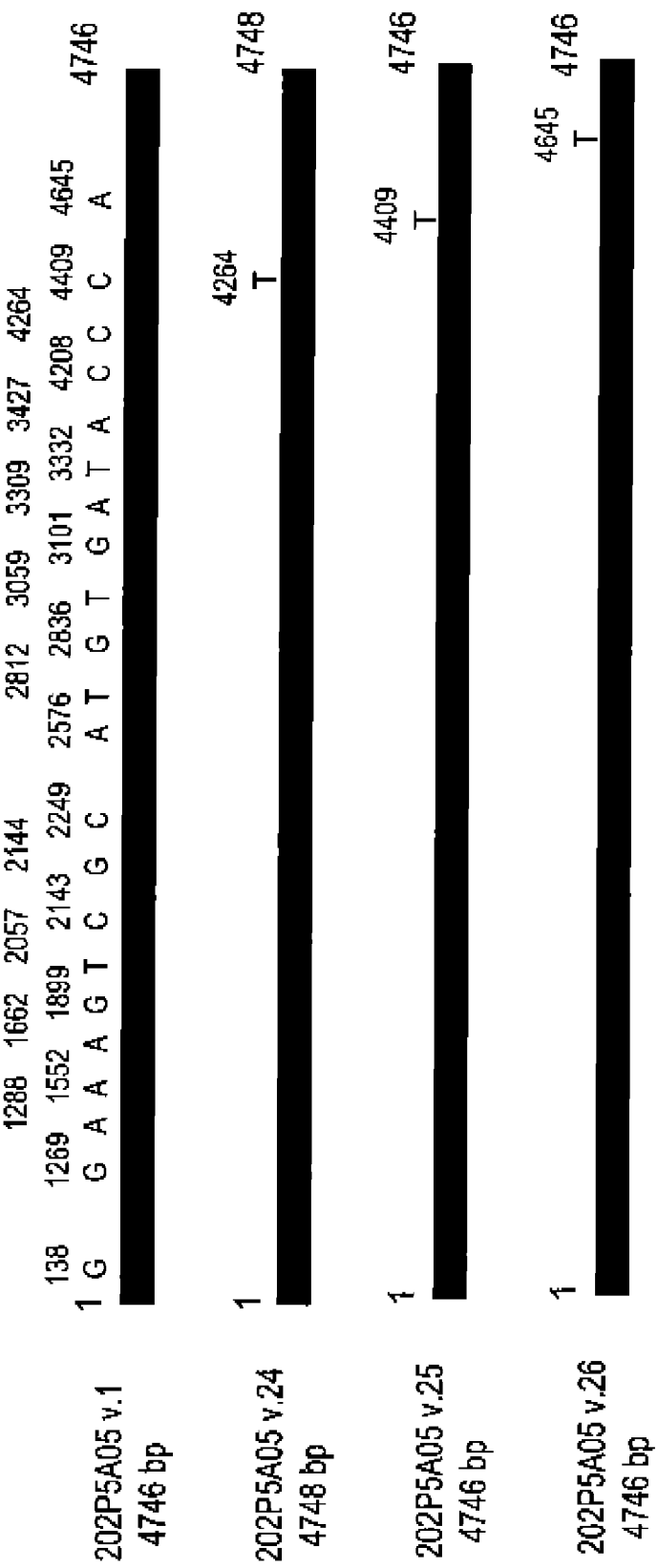

FIG. 5. Hydrophilicity amino acid profile of 202P5A5 v.1 determined by computer algorithm sequence analysis using the method of Hopp and Woods (Hopp T. P., Woods K. R., 1981 Proc. Natl. Acad. Sci, U.S.A. 78:3824-3823) accessed on the Protscale website located on the World Wide Web at (expasy.ch/cgi-bin/protscale.pl) through the ExPasy molecular biology server.

FIG. 6. Hydropathicity amino acid profile of 202P5A5 v.1 determined by computer algorithm sequence analysis using the method of Kyte and Doolittle (Kyte J., Doolittle R. F., 1982. J. Mol. Biol. 157:105-132) accessed on the ProtScale website located on the World Wide Web at (expasy.ch/cgi-bin/protscale.pl) through the ExPasy molecular biology server.

FIG. 7. Percent accessible residues amino acid profile of 202P5A5 v.1 determined by computer algorithm sequence analysis using the method of Janin (Janin J., 1979 Nature 277:491-492) accessed on the ProtScale website located on the World Wide Web at (expasy.ch/cgi-bin/protscale.pl) through the ExPasy molecular biology server.

FIG. 8. Average flexibility amino acid profile of 202P5A5 v.1 determined by computer algorithm sequence analysis using the method of Bhaskaran and Ponnuswamy (Bhaskaran R., and Ponnuswamy P. K., 1988. Int. J. Pept. Protein Res. 32:242-255) accessed on the ProtScale website located on the World Wide Web at (expasy.ch/cgi-bin/protscale.pl) through the ExPasy molecular biology server.

FIG. 9. Beta-turn amino acid profile of 202P5A5 v.1 determined by computer algorithm sequence analysis using the method of Deleage and Roux (Deleage, G., Roux B. 1987 Protein Engineering 1:289-294) accessed on the ProtScale website located on the World Wide Web at (expasy.ch/cgi-bin/protscale.pl) through the ExPasy molecular biology server.

FIG. 10. Structures of transcript variants of 202P5A5. Variants 202P5A5 v.2 and v.3 are transcript variants of 202PA05 v.1. Variant 202PA05 v.2 added an exon to the 5' end of variant v.1. Variant v.3 further extended exon 1 of v.2 into intron 1. Poly A tails are not shown in this figure. Numbers in "( )" underneath the boxes correspond to those of 202P5A05 v.1. Lengths of introns and exons are not proportional.

Figure 11:
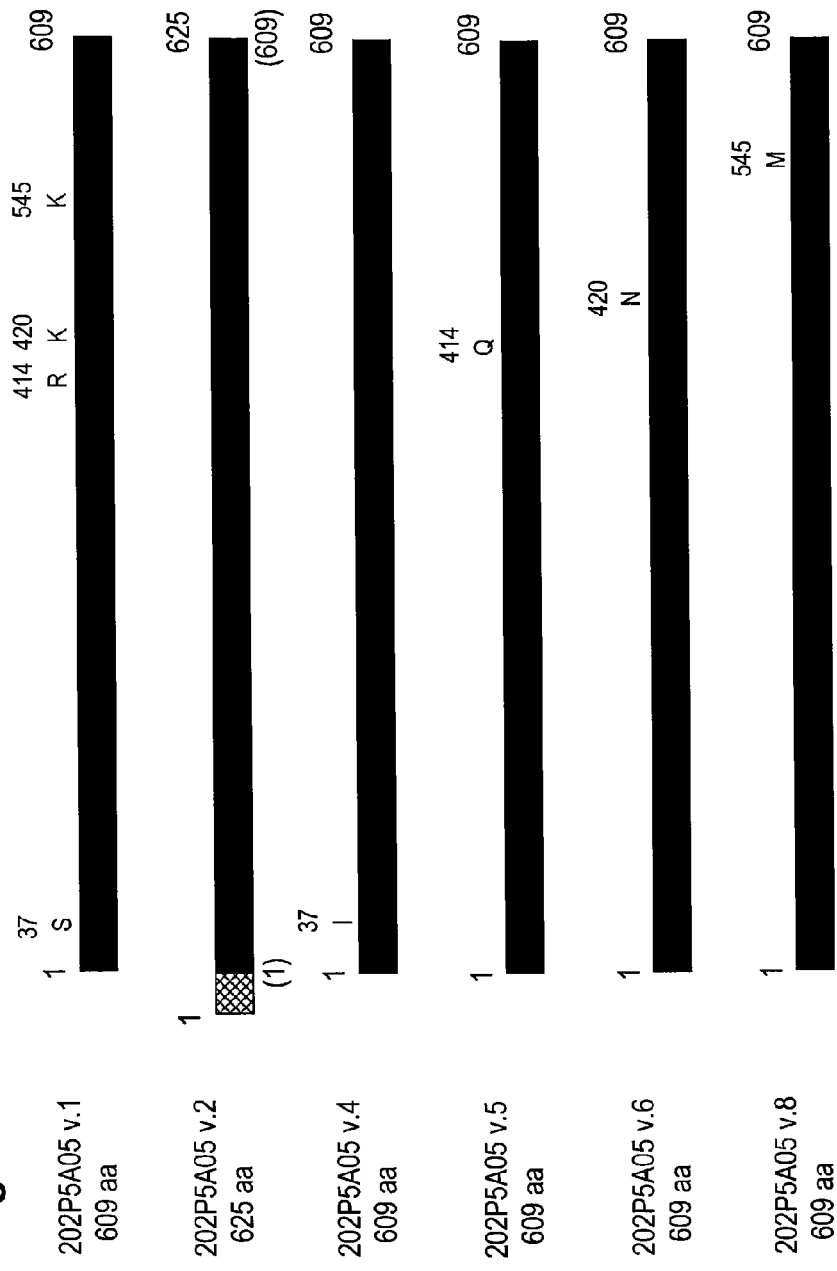

FIG. 11. Schematic alignment of protein variants of 202P5A5. Protein variants correspond to nucleotide variants. Nucleotide variants 202P5A5 v.3, v.7, and v.9 through v.26 coded the same protein as v.1. Variant v.2 coded a protein that was 16 amino acids longer and contained the whole protein of v.1. Nucleotide variants 202P5A5 v.2 and v.3 were transcript variants of v.1, as shown in FIG. 10. SNP in v.1 also existed in v.2 and v.3. Single amino acid differences were indicated above the boxes. Black boxes represent the same sequence as 202P5A5 v.1. Numbers underneath the box correspond to 202P5A5 v.1.

FIG. 12. Schematic alignment of SNP variants of 202P5A5. Variants 202P5A5 v.4 through v.26 are variants with single nucleotide differences as compared to variant v.1 (ORF: 29-1858). Variant v.14 inserted two base pairs at 2269-2270 while variant v.22 deleted one base pair at 3427. Though these SNP variants were shown separately, they could also occur in any combinations and in any transcript variants, such as v.3 shown in FIG. 10, that contained the base pairs. Numbers correspond to those of 202P5A5 v.1. The black box shows the same sequence as 202P5A5 v.1. SNPs are indicated above the box.

FIG. 13. Secondary structure and transmembrane domains prediction for 202P5A05 protein variant 1.

FIG. 13A: The secondary structure of 202P5A5 protein variant 1 (FIG. 13A) (SEQ ID NO: 108) was predicted using the HNN—Hierarchical Neural Network method (NPS@: Network Protein Sequence Analysis TIBS 2000 March Vol. 25, No 3 [291]: 147-150 Combet C., Blanchet C., Geourjon C. and Deléage G., located on the World Wide Web at pbil.ibcp.fr/cgi-bin/npsa_automat.pl?page=npsa_nn.html), accessed from the ExPasy molecular biology server located on the World Wide Web at (.expasy.ch/tools/). This method predicts the presence and location of alpha helices, extended strands, and random coils from the primary protein sequence. The percent of the protein in a given secondary structure is also listed.

FIG. 13B: Schematic representation of the probability of existence of transmembrane regions of 202P5A5 variant 1 based on the TMpred algorithm of Hofmann and Stoffel which utilizes TMBASE (K. Hofmann, W. Stoffel. TMBASE—A database of membrane spanning protein segments Biol. Chem. Hoppe-Seyler 374:166, 1993), FIG. 13C: Schematic representation of the probability of the existence of transmembrane regions of 202P5A05 variant 1, based on the TMHMM algorithm of Sonnhammer, von Heijne, and Krogh (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998). The TMpred and TMHMM algorithms are accessed from the ExPasy molecular biology server located on the World Wide Web at (.expasy.ch/tools/). Both algorithms do not predict the presence of transmembrane regions in 202P5A5 variant 1.

FIG. 14. Expression of 202P5A5 by RT-PCR. FIG. 14A: First strand cDNA was prepared from vital pool 1 (liver, lung and kidney), vital pool 2 (pancreas, colon and stomach), prostate cancer metastasis to lymph node, prostate cancer pool, bladder cancer pool, colon cancer pool, lung cancer pool, breast cancer pool, and cancer metastasis pool. Normalization was performed by PCR using primers to actin and GAPDH, Semi-quantitative PCR, using primers to 202P5A5, was performed at 26 and 30 cycles of amplification. Expression was detected in prostate cancer metastasis to lymph node, prostate cancer pool, bladder cancer pool, colon cancer pool, lung cancer pool, breast cancer pool, and cancer metastasis pool. Low expression was also detected in vital pool 1 but not in vital pool 2. FIG. 14B: Semi-quantitative PCR, using primers to 202P5A5, was performed on a panel of 13 normal tissues and 13 cancer pools. Samples were run on an agarose gel, and PCR products were quantitated using the AlphaImager software. Results show strong expression of 202P5A5 in prostate cancer, bladder cancer, colon cancer, lung cancer, ovary cancer, breast cancer, metastasis cancer, xenograft pool, prostate metastasis to lymph node (PMLN), bone cancer/melanoma pool, cervical cancer, lymphoma and stomach cancer compared to all normal tissues tested.

FIG. 15. Expression of 202P5A5 variants by RT-PCR. Primers were designed to differentiate between 202P5A5 v.2 and 202P5A5 v.3. 202P5A5 leads to a PCR product of 173 bp, whereas 202P5A5 v.3 leads to a PCR product of 233 bp in size. First strand cDNA was prepared from vital pool 1 (liver, lung and kidney), vital pool 2 (pancreas, colon and stomach), LAPC prostate xenograft pool (LAPC-4AD. LAPC-4AI, LAPC-9AD and LAPC-9AI), prostate cancer pool, bladder cancer pool, lung cancer pool, ovary cancer pool, breast cancer pool, cancer metastasis pool, cervical cancer pool, stomach cancer pool, uterus cancer pool, and master xenograft pool (LAPC xenograft pool, bladder cancer xenograft, kidney cancer xenograft). Normalization was performed by PCR using primers to actin and GAPDH. Semi-quantitative PCR, using the variant specific primers was performed at 26 and 30 cycles of amplification. Stronger expression of the 173 bp product was detected in ail cancer pools tested and weakly in vital pools. The larger 233 bp product was mostly detected in the cancer pools and not in the vital tissues, and at a frequency of 20-30% compared to the smaller product.

FIG. 16. Expression of 202P5A5 in normal tissues. Two multiple tissue northern blots (Clontech) both with 2 ug of mRNA/lane were probed with the 202P5A5 sequence. Size standards in kilobases (kb) are indicated on the side. Results show expression of an approximately 7kb 202P5A5 transcript in normal prostate and normal placenta but not in any other normal tissue tested.

FIG. 17. Expression of 202P5A5 in Prostate Cancer Patient Specimens. RNA was extracted from prostate cancer xenografts (LAPC-4AD, LAPC-4AI, LAPC-9AD, and LAPC-9AI), prostate cancer cell lines (LNCaP and PC3), normal prostate (N), and prostate cancer patient tumors (T). Northern blots with 10 ug of total RNA were probed with the 202P5A5 SSH fragment. Size standards in kilobases are on the side. Results show expression of 202P5A5 in all prostate cancer specimens tested as well as in the normal prostate, prostate cancer xenografts and LNCaP, but not in the PC3 cell line.

FIG. 18. Expression of 202P5A5 in Bladder Cancer Patient Specimens. RNA was extracted from bladder cancer cell lines (CL), normal bladder (N), bladder cancer patient tumors (T) as well as their adjacent normal tissues (Nat). Northern blots with 10 ug of total RNA were probed with the 202P5A5 sequence. Size standards in kilobases are on the side. Results show expression of 202P5A5 in all bladder cancer patient tumor specimens tested but not in normal bladder. Expression was also detected in SCABER but not in the other cancer cell lines tested.

FIG. 19. Expression of 202P5A5 in Breast Cancer Patient Specimens. RNA was extracted from breast cancer cell lines (CL), normal breast (N), breast cancer patient tumors (T), and breast cancer metastasis specimens (M). Northern blots with 10 ug of total RNA were probed with the 202P5A5 sequence. Size standards in kilobases are on the side. Results show expression of 202P5A5 in the breast cancer patient tumors and metastasis specimens. Expression was also detected in MCF-7 and CAMA-1 but not in the DU4475 cell line. Lower level expression was also detected in normal breast.

FIG. 20. Expression of 202P5A5 in Colon and Cervical Cancer Patient Specimens. First strand cDNA was prepared from a panel of patient cancer specimens. Normalization was performed by PCR using primers to actin. Semi-quantitative PCR, using primers to 202P5A5, was performed at 26 and 30 cycles of amplification. Samples were run on an agarose gel, and PCR products were quantitated using the AlphaImager software. Expression was recorded as absent, low, medium or strong. Results show expression of 202P5A5 in the majority of patient cancer specimens tested.

FIG. 21. Expression of 202P5A5.pcDNA3.1/MycHis following transfection into 293T cells. 293T cells were transfected with either 202P5A5.pcDNA3.1/MycHis or pcDNA3.1/MycHis vector control. Forty hours later, cell lysates were collected. Samples were run on an SDS-PAGE acrylamide gel, blotted and stained with anti-his antibody. The blot was developed using the ECL chemiluminescence kit and visualized by autoradiography. Results show expression of 202P5A5 from the 202P5A5.pcDNA3.1/MycHis construct in the lysates of transfected cells but not in the control pcDNA3.1/MycHis transfected cells.

DETAILED DESCRIPTION OF THE INVENTION

Outline of Sections

I.) Definitions
II.) 202P5A5 Polynucleotides
II.A.) Uses of 202P5A5 Polynucleotides
II.A.1.) Monitoring of Genetic Abnormalities
II.A.2.) Antisense Embodiments
II.A.3.) Primers and Primer Pairs
II.A.4.) Isolation of 202P5A5-Encoding Nucleic Acid Molecules
II.A.5.) Recombinant Nucleic Acid Molecules and Host-Vector Systems
III.) 202P5A5-related Proteins
III.A.) Motif-bearing Protein Embodiments
III.B.) Expression of 202P5A5-related Proteins
III.C) Modifications of 202P5A5-related Proteins
III.D.) Uses of 202P5A5-related Proteins
IV.) 202P5A5 Antibodies
V.) 202P5A5 Cellular Immune Responses
VI.) 202P5A5 Transgenic Animals
VII.) Methods for the Detection of 202P5A5
VIII.) Methods far Monitoring the Status of 202P5A5-related Genes and Their Products
IX.) Identification of Molecules That Interact With 202P5A5
X.) Therapeutic Methods and Compositions
X.A.) Anti-Cancer Vaccines
X.B.) 202P5A5 as a Target for Antibody-Based Therapy
X.C.) 202P5A5 as a Target for Cellular Immune Responses
X.C.1. Minigene Vaccines
X.C.2. Combinations of CTL Peptides with Helper Peptides
X.C.3 Combinations of CTL Peptides with T Cell Priming Agents
X.C.4. Vaccine Compositions Comprising DC Pulsed with CTL and/or HTL Peptides
X.D.) Adoptive Immunotherapy
X.E.) Administration of Vaccines for Therapeutic or Prophylactic Purposes
XI.) Diagnostic and Prognostic Embodiments of 202P5A5.
XI.) Inhibition of 202P5A5 Protein Function
XII.A.) Inhibition of 202P5A5 With Intracellular Antibodies
XII.B.) Inhibition of 202P5A5 with Recombinant Proteins
XII.C.) Inhibition of 202P5A5 Transcription or Translation
XII.D.) General Considerations for Therapeutic Strategies
XIII.) Identification, Characterization and Use of Modulators of 202P5A5
XIV.) KITS/Articles of Manufacture

I. DEFINITIONS

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general surgery is not recommended for patients with locally advanced disease, and these patients have substantially less favorable outcomes compared to patients with locally advanced disease, and these patients have substantially less favorable outcomes identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 202P5A5 (either by removing the underlying glycosylation site or by deleting the glycosylation by chemical and/or enzymatic means), and/or adding one or more glycosylate sites that are not present in the native sequence 202P5A5. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 202P5A5-related protein). For example, an analog of a 202P5A5 protein can be specifically bound by an antibody or T cell that specifically binds to 202P5A5.

The term "antibody" is used in the broadest sense. Therefore, an "antibody" can be naturally occurring or man-made such as monoclonal antibodies produced by conventional hybridoma technology. Anti-202P5A5 antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment ft specifically covers single anti-202P5A5 antibodies and clones thereof (including agonist, antagonist and neutralizing antibodies) and anti-202P5A5 antibody compositions with polyepitopic specificity.

The term "codon optimized sequences" refers to nucleotide sequences that have been optimized for a particular host species by replacing any codons having a usage frequency of less than about 20%. Nucleotide sequences that have been optimised for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

A "combinatorial library" is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound), numerous chemical compounds are synthesized through such combinatorial mixing of chemical building blocks (Gallop et al., J. Med. Chem. 37(9); 1233-1251 (1994)).

Preparation and screening of combinatorial libraries is well known to those of skill in the art. Such combinatorial chemical libraries include, but are not limited to peptide libraries (see, e.g., U.S. Pat. No. 5,010,175. Furka. Pept. Prot. Res. 37:437-493 (1991), Houghton et al, Nature, 354:84-88 (1991)), peptoids (PCT Publication No WO 91/15735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et. al., J. Amer. Chem. Soc. 114:6568 (1992)), nonpeptidal peptidomimetics with a Beta-D-Glucose scaffolding (Hirschmann et al., J. Amer. Chem. Soc. 114:9217-9218 (1992)), analogous organic syntheses of small compound libraries (Chen et al., J. Amer. Chem. Soc. 116:2561 (1994)), oligocarbamates (Cho, et al., Science 261: 1303 (1993)), and/or peptidyl phosphonates (Campbell et al., J. Org. Chem. 59:658 (1994)). See, generally, Gordon et al., J. Med. Chem. 37:1335 (1994), nucleic acid libraries (see, e.g., Stratagene, Corp.), peptide nucleic acid libraries (see, e.g., U.S. Pat. No. 5,539,083), antibody libraries (see, e.g., Vaughn et al., Nature Biotechnology 14(3):309-314 (1996), and PCT/US96/10287), carbohydrate libraries (see, e.g., Liang et al., Science 274:1520-1522 (1996), and U.S. Pat. No. 5,593,353), and small organic molecule libraries (see, e.g., benzodiazepines, Baum, C&EN, January 18, page 33 (1993), isoprenoids, U.S. Pat. No. 5,559,588; thiazolidinones and metathiazanones, U.S. Pat. No. 5,549,974: pyrrolidines, U.S. Pat. Nos. 5,525,735 and 5,519,134; morpholino compounds, U.S. Pat. No. 5,506,337; benzodiazepines, U.S. Pat. No. 5,238,514; and the like).

Devices for me preparation of combinatorial libraries are commercially available (see, e.g., 357 NIPS, 390 NIPS, Advanced Chem Tech, Louisville Ky.; Symphony, Rainin, Woburn, Mass.; 433A, Applied Biosystems, Foster City, Calif.; 9050, Plus, Millipore, Bedford. NIA). A number of well-known robotic systems have also been developed for solution phase chemistries. These systems include automated workstations such as the automated synthesis apparatus developed by Takeda Chemical Industries, LTD, (Osaka, Japan) and many robotic systems utilizing robotic arms (Zymate H, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinational libraries are themselves commercially available (see, e.g., ComGenex, Princeton, N.J.; Asinex, Moscow, RU; Tripos, Inc., St Louis, Mo.; Chem Star, Ltd, Moscow, RU; 3D Pharmaceuticals, Exton, Pa.; Martek Biosciences, Columbia, Md.; etc), The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auromycins, maytansinoids, yttrium, bismuth, ricin, ricin A-chain, combrestatin, duocarmycins, dolostatins, doxorubicin, daunorubicin, taxol, cisplatin, cc1065, ethidium bromide, mitomycin, etoposide, tenoposide, vincristine, vinblastine, colchicine, dihydroxy anthracin dione, actinomycin, diphtheria toxin. Pseudomonas exotoxin (PE) A, PE40, abrin, abrin A chain, modeccin A chain, alpha-sarcin, gelonin, mitogellin, restrictocin, phenomycin, enomycin, curicin, crotin, calicheamicin, *Sapaonana officinalis* inhibitor, and glucocorticoid and other chemotherapeutic agents, as well as radioisotopes such as $At^{211}, I^{13'}, I^{125}, Y^{50}, Re^{1R5}, Re^{188}, Sm^{153}, Bi^{212\ or\ 213}, P^{32}$ and radioactive isotopes of Lu including $Lu^{177}$. Antibodies may also be conjugated to an anti-cancer pro-drug activating enzyme capable of converting the pro-drug to its active form.

The "gene product" is some times referred to herein as a protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc, In one embodiment, the cancer protein is encoded by a nucleic acid of FIG. 2. The cancer protein can be a fragment, or alternatively, be the full-length protein to the fragment encoded by the nucleic acids of FIG. 2. In one embodiment, a cancer amino acid sequence is used to determine sequence identity or similarity. In another embodiment, the sequences are naturally occurring allelic variants of a protein encoded by a nucleic acid of FIG. 2. In another embodiment, the sequences are sequence variants as further described herein.

"High throughput screening" assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins; U.S. Pat. No. 5,585,639 discloses high throughput screening methods for nucleic acid binding (i.e., in arrays); while U.S. Pat. Nos. 5,573,220 and 5,541,061 disclose high throughput methods of screening for ligand/antibody binding, In addition, high throughput screening systems are commercially available (see, e.g., Amersham Biosciences, Piscataway, N. J; Zymark Corp., Hopkinton, Mass.; Air Technical Industries, Mentor, Ohio; Beckman Instruments, Inc. Fullerton, Calif.; Precision Systems, Inc., Natick, Mass.; etc.). These systems typically automate entire procedures, including all sample and reagent pipetting, liquid dispensing, timed incubations, and final readings of the microplate in detectors) appropriate for the assay. These configurable systems provide high throughput and rapid start up as well as a high degree of flexibility and customization. The manufacturers of such systems provide detailed protocols for various high throughput systems. Thus, e.g., Zymark Corp, provides technical bulletins describing screening systems for detecting the modulation of gene transcription, ligand binding, and the like.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., Immunology, 8$^y$-Ed., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6XSSC/0.1% SDS/100 μg/ml ssDNA, in which temperatures for hybridization are above 37 degrees C. and temperatures for washing in 0.1XSSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond ore are complementary to genes other than the 202P5A5 genes or that encode polypeptides other than 202P5A5 product or fragments thereof. A skilled artisan can readily employ nucleic acid isolation procedures to obtain an isolated 202P5A5 polynucleotide. A protein is said to be "isolated," for example, when physical, mechanical or chemical methods are employed to remove the 202P5A5 proteins from cellular constituents that are normally associated with the protein. A skilled artisan can readily employ standard purification methods to obtain an isolated 202P5A5 protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by die femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "modulator" or "test compound" or "drug candidate" or grammatical equivalents as used herein describe any molecule. e.g., protein, oligopeptide, small organic molecule, polysaccharide, polynucleotide, etc, to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways, in one embodiment, the modulator suppresses a cancer phenotype, e.g. to a normal tissue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary far structural interaction with proteins, particularly hydrogen bonding and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides, In a preferred embodiment, peptide/protein-based modulators are antibodies, and fragments thereof, as defined herein.

Modulators of cancer can also be nucleic acids. Nucleic acid modulating agents can be naturally occurring nucleic acids, random nucleic acids, or "biased" random nucleic acids. For example, digests of prokaryotic or eukaryotic genomes can be used in an approach analogous to that outlined above for proteins.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of a 202P5A5-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated, or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 ammo acids for a class I HLA motif and from a bout 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term is often used interchangeably with "oligonucleotide". A polynucleotide can comprise a nucleotide sequence disclosed herein wherein thymidine (T), as shown for example in FIG. 2, can also be uracil (U); this definition pertains to the differences between the chemical structures of DNA and RNA, in particular the observation that one of the four major bases in RNA is uracil (U) instead of thymidine (T).

The term "polypeptide" means a polymer of at least 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. Alternatively, in another embodiment, the primary anchor residues of a peptide binds an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV, Such analogs are used to modulate the binding affinity and/or population coverage of a peptide comprising a particular HLA motif or supermotif.

"Radioisotopes" include, but are not limited to the following (non-limiting exemplary uses are also set forth):

Examples of Medical Isotopes:

| Isotope | Description of use |
| --- | --- |
| Actinium-225 (AC-225) | See Thorium-229 (Th-229) |
| Actinium-227 (AC-227) | Parent of Radium-223 (Ra-223) which is an alpha emitter used to treat metastases in the skeleton resulting from cancer (i.e., breast and prostate cancers), and cancer radioimmunotherapy |
| Bismuth-212 (Bi-212) | See Thorium-228 (Th-228) |
| Bismuth-213 (Bi-213) | See Thorium-229 (Th-229) |
| Cadmium-109 (Cd-109) | Cancer detection |
| Cobalt-60 (Co-60) | Radiation source for radiotherapy of cancer, for food irradiators, and for sterilization of medical supplies |
| Copper-64 (Cu-64) | A positron emitter used for cancer therapy and SPECT imaging |
| Copper-67 | Beta/gamma emitter used in cancer radioimmunotherapy and diagnostic studies (i.e., breast |

-continued

Examples of Medical Isotopes:

| Isotope | Description of use |
| --- | --- |
| (Cu-67) | and colon cancers, and lymphoma) |
| Dysprosium-166 (Dy-166) | Cancer radioimmunotherapy |
| Erbium-169 (Er-169) | Rheumatoid arthritis treatment, particularly for the small joints associated with fingers and toes |
| Europium-152 (Eu-152) | Radiation source for food irradiation and for sterilization of medical supplies |
| Europium-154 (Eu-154) | Radiation source for food irradiation and for sterilization of medical supplies |
| Gadolinium-153 (Gd-153) | Osteoporosis detection and nuclear medical quality assurance devices |
| Gold-198 (Au-198) | Implant and intracavity therapy of ovarian, prostate, and brain cancers |
| Holmium-166 (Ho-166) | Multiple myeloma treatment in targeted skeletal therapy, cancer radioimmunotherapy, bone marrow ablation, and rheumatoid arthritis treatment |
| Iodine-125 (I-125) | Osteoporosis detection, diagnostic imaging, tracer drugs, brain cancer treatment, radiolabeling, tumor imaging, mapping of receptors in the brain, interstitial radiation therapy, brachytherapy for treatment of prostate cancer, determination of glomerular filtration rate (GFR), determination of plasma volume, detection of deep vein thrombosis of the legs |
| Iodine-131 (I-131) | Thyroid function evaluation, thyroid disease detection, treatment of thyroid cancer as well as other non-malignant thyroid diseases (i.e., Graves disease, goiters, and hyperthyroidism), treatment of leukemia, lymphoma, and other forms of cancer (e.g., breast cancer) using radioimmunotherapy |
| Iridium-192 (Ir-192) | Brachytherapy, brain and spinal cord tumor treatment, treatment of blocked arteries (i.e., arteriosclerosis and restenosis), and implants for breast and prostate tumors |
| Lutetium-177 (Lu-177) | Cancer radioimmunotherapy and treatment of blocked arteries (i.e., arteriosclerosis and restenosis) |
| Molybdenum-99 (Mo-99) | Parent of Technetium-99m (Tc-99m) which is used for imaging the brain, liver, lungs, heart, and other organs. Currently, Tc-99m is the most widely used radioisotope used for diagnostic imaging of various cancers and diseases involving the brain, heart, liver, lungs; also used in detection of deep vein thrombosis of the legs |
| Osmium-194 (Os-194) | Cancer radioimmunotherapy |
| Palladium-103 (Pd-103) | Prostate cancer treatment |
| Platinum-195m (Pt-195m) | Studies on biodistribution and metabolism of cisplatin, a chemotherapeutic drug |
| Phosphorus-32 (P-32) | Polycythemia rubra vera (blood cell disease) and leukemia treatment, bone cancer diagnosis/treatment; colon, pancreatic, and liver cancer treatment; radiolabeling nucleic acids for in vitro research, diagnosis of superficial tumors, treatment of blocked arteries (i.e., arteriosclerosis and restenosis), and intracavity therapy |
| Phosphorus-33 (P-33) | Leukemia treatment, bone disease diagnosis/treatment, radiolabeling, and treatment of blocked arteries (i.e., arteriosclerosis and restenosis) |
| Radium-223 (Ra-223) | See Actinium-227 (Ac-227) |
| Rhenium-186 (Re-186) | Bone cancer pain relief, rheumatoid arthritis treatment, and diagnosis and treatment of lymphoma and bone, breast, colon, and liver cancers using radioimmunotherapy |
| Rhenium-188 (Re-188) | Cancer diagnosis and treatment using radioimmunotherapy, bone cancer pain relief, treatment of rheumatoid arthritis, and treatment of prostate cancer |
| Rhodium-105 (Rh-105) | Cancer radioimmunotherapy |
| Samarium-145 (Sm-145) | Ocular cancer treatment |
| Samarium-153 (Sm-153) | Cancer radioimmunotherapy and bone cancer pain relief |
| Scandium-47 (Sc-47) | Cancer radioimmunotherapy and bone cancer pain relief |
| Selenium-75 (Se-75) | Radiotracer used in brain studies, imaging of adrenal cortex by gamma-scintigraphy, lateral locations of steroid secreting tumors, pancreatic scanning, detection of hyperactive parathyroid glands, measure rate of bile acid loss from the endogenous pool |
| Strontium-85 (Sr-85) | Bone cancer detection and brain scans |
| Strontium-89 (Sr-89) | Bone cancer pain relief, multiple myeloma treatment, and osteoblastic therapy |
| Technetium-99m (Tc-99m) | See Molybdenum-99 (Mo-99) |
| Thorium-228 (Th-228) | Parent of Bismuth-212 (Bi-212) which is an alpha emitter used in cancer radioimmunotherapy |
| Thorium-229 (Th-229) | Parent of Actinium-225 (Ac-225) and grandparent of Bismuth-213 (Bi-213) which are alpha emitters used in cancer radioimmunotherapy |
| Thulium-170 (Tm-170) | Gamma source for blood irradiators, energy source for implanted medical devices |
| Tin-117m (Sn-117m) | Cancer immunotherapy and bone cancer pain relief |
| Tungsten-188 | Parent for Rhenium-188 (Re-188) which is used for cancer diagnostics/treatment, bone |

-continued

Examples of Medical Isotopes:

| Isotope | Description of use |
|---|---|
| (W-188) | cancer pain relief, rheumatoid arthritis treatment, and treatment of blocked arteries (i.e., arteriosclerosis and restenosis) |
| Xenon-127 (Xe-127) | Neuroimaging of brain disorders, high resolution SPECT studies, pulmonary function tests, and carebral blood flow studies |
| Ytterbium-175 (Yb-175) | Cancer radioimmunotherapy |
| Yttrium-90 (Y-90) | Microseeds obtained from irradiating Yttrium-89 (Y-89) for liver cancer treatment |
| Yttrium-91 (Y-91) | A gamma-emitting label for Yttrium-90 (Y-90) which is used for cancer radioimmunotherapy (i.e., lymphoma, breast, colon, kidney, lung, ovarian, prostate, pancreatic, and inoperable liver cancers) |

By "randomized" or grammatical equivalents as herein applied to nucleic acids and proteins is meant that each nucleic acid and peptide consists of essentially random nucleotides and amino acids, respectively. These random peptides (or nucleic acids, discussed herein) can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, a library is "fully randomized," with no sequence preferences or constants at any position. In another embodiment, the library is a "biased random" library. That is, some positions within the sequence either are held constant, or are selected from a limited number of possibilities. For example, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

A "recombinant" DNA or RNA molecule is a DNA or RNA molecule that has been subjected to molecular manipulation in vitro.

Non-limiting examples of small molecules include compounds that bind or interact with 202P5A5, ligands including hormones, neuropeptides, chemokines, colorants, phospholipids, and functional equivalents thereof that bind and preferably inhibit 202P5A5 protein function. Such non-limiting small molecules preferably have a molecular weight of less than about 10 kDA, more preferably below about 9, about 8, about 7, about 6, about 5 or about 4 kDa. In certain embodiments, small molecules physically associate with, or bind, 202P5A5 protein, are not found in naturally occurring metabolic pathways; and/or are more soluble in aqueous than non-aqueous solutions.

"Stringency" of hybridization reactions is readily determinable by one of ordinary skill in the art, and generally is an empirical calculation dependent upon probe length, washing temperature, and salt concentration. In general, longer probes require higher temperatures (or proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% v/v formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5 X SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2 X SSC (sodium chloride/sodium, citrate) and 50% formamide at 55° C. followed by a high-stringency wash consisting of 0.1 X SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5 X SSC (150 mM NaCl, 15 mM trisodium citrate), 50 mM sodium phosphate (pH 7.6). 5×Denhardt's solution, 10% dextran sulfate, and 20 mg/mL denatured sheared salmon sperm DNA, followed by washing the filters in 1 X SSC at about 37-50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles. Overall phenotypic frequencies of HLA-supertypes in different ethnic populations are set forth in Table IV (F). The non-limiting constituents of various supertypes are as follows:

A2: A*0201, A*0202, A*203, A*204, A*0205, A*206, A*6802, A*6901, A*0207

A3: A3, A11, A31, A*3301, A*6801, A*0301, A*1101, A*3101

B7: B7, B*3501-03, B*51, B*5301, B*5401, B*5501, B*5502, B*5601, B*6701, B*7801, B*0702, B*5101, B*5602

B44: B*3701; B*4402, B*4403, B*60 (B*4001), B61 (B*4006)

A1: A*0102, A*2604, A*3601, A*4301, A*8001

A24: A*24, A*30, A*2403, A*2404, A*3002, A3003

B27: B*1401-02, B*1503, B*1509, B*1510, B*1518, B*3801-02, B*3901, B*3902, B*3903-04, B*4801-02, B*7301, B*2701-08

B58: B*1518, B*1517, B*5701, B*6702, B58

B62: B*4601, B52, B*1501 (B62), B*1502 (B75), B*1513 (B77)

Calculated population coverage afforded by different HLA-supertype combinations are set forth in Table IV (G).

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g. a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides, one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences, HLA class I peptides of the invention can e admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 202P5A5 protein shown in FIG. 2 or FIG. 3. An analog is an example of a variant protein. Splice isoforms and single nucleotides polymorphisms (SNPs) are further examples of variants.

The "202P5A5-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 202P5A5 proteins or fragments thereof, as well as fusion proteins of a 202P5A5 protein and a heterologous polypeptide are also included. Such 202P5A5 proteins are collectively referred to as the 202P5A5-related proteins, the proteins of the invention, or 202P5A5. The term "202P5A5-related protein" refers to a polypeptide fragment or a 202P5A5 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, or 576 or more amino acids.

II.) 202P5A5 POLYNUCLEOTIDES

One aspect of the invention provides polynucleotides corresponding or complementary to all or part of a 202P5A5 gene, mRNA, and/or coding sequence, preferably in isolated form, including polynucleotides encoding a 202P5A5 related protein and fragments thereof, DNA, RNA, DNA/RNA hybrid, and related molecules, polynucleotides or oligonucleotides complementary to a 202P5A5 gene or mRNA sequence or a part thereof, and polynucleotides or oligonucleotides that hybridize to a 202P5A5 gene, mRNA, or to a 202P5A5 encoding polynucleotide (collectively, "202P5A5 polynucleotides"). In all instances when referred to in this section. T can also be U in FIG. 2.

Embodiments of a 202P5A5 polynucleotide include: a 202P5A5 polynucleotide having the sequence shown in FIG. 2, the nucleotide sequence of 202P5A5 as shown in FIG. 2 wherein T is U; at least 10 contiguous nucleotides of a polynucleotide having the sequence as shown in FIG. 2; or at least 10 contiguous nucleotides of a polynucleotide having the sequence as shown in FIG. 2 where T is U. For example, embodiments of 202P5A5 nucleotides comprise, without limitation:

(I) a polynucleotide comprising, consisting essentially of, or consisting of a sequence as shown in FIG. 2, wherein T can also be U;

(II) a polynucleotide comprising, consisting essentially of, or consisting of the sequence as shown in FIG. 2A, from nucleotide residue number 29 through nucleotide residue number 1858, including the stop codon, wherein T can also be U;

(III) a polynucleotide comprising, consisting essentially of, or consisting of the sequence as shown in FIG. 2B, from nucleotide residue number 13 through nucleotide residue number 1890, including the stop codon, wherein T can also be U.

(IV) a polynucleotide comprising, consisting essentially of, or consisting of the sequence as shown in FIG. 2C, from nucleotide residue number 121 through nucleotide residue number 1950, including the stop codon, wherein T can also be U.

(V) a polynucleotide comprising, consisting essentially of, or consisting of the sequence as shown in FIG. 2D, from nucleotide residue number 29 through nucleotide residue number 1858, including the stop codon, wherein T can also be U.

(VI) a polynucleotide comprising, consisting essentially of, or consisting of the sequence as shown in FIG. 2E, from nucleotide residue number 29 through nucleotide residue number 1858, including the stop codon, wherein T can also be U.

(VII) a polynucleotide comprising, consisting essentially of, or consisting of the sequence as shown in FIGS. 2F and 2A, from nucleotide residue number 29 through nucleotide residue number 1858, including the stop codon, wherein T can also be U.

(VIII) a polynucleotide that encodes a 202 P5 A5-related protein that is at least 90, 91, 92, 93, 94, 95, 96, 97, 98, 99 or 100% homologous to an entire amino acid sequence shown in FIGS. 2A-F;

(IX) a polynucleotide that encodes a 202P5A5-related protein that is at least 90, 91, 92, 93, 94, 95, 96, 97, 98, 99 or 100% identical to an entire amino acid sequence shown in FIGS. 2A-F;

(X) a polynucleotide that encodes at least one peptide set forth in Tables VIII-XXI and XXII-XLIX;

(XI) a polynucleotide mat encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A and 3C-3F in any whole number increment up to 609 that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XII) a polynucleotide that encodes a peptide region of at least 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35 amino acids of a peptide of FIGS. 3A and 3C-3F in any whole number increment up to 609 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid positions) having a value less than 0.5 in the Hydrophilicity profile of FIG. 6;

(XIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A and 3C-3F in any whole number increment up to 609 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XIV) a polynucleotide that encodes a peptide region of at least 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35 amino acids of a peptide of FIGS. 3A and 3C-3F in any whole number increment up to 609 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Average Flexibility profile of FIG. 8;

(XV) a polynucleotide that encodes a peptide region of at least 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35 amino acids of a peptide of FIGS. 3A and 3C-3F in any whole number increment up to 609 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Beta-turn profile of FIG. 9;

(XVI) a polynucleotide that encodes a peptide region of at least 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35 amino acids of a peptide of FIG. 3B in any whole number increment up to 625 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydrophilicity profile of FIG. 5;

(XVII) a polynucleotide that encodes a peptide region of at least 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35 amino acids of a peptide of FIG. 3B in any whole number increment up to 625 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydrophilicity profile of FIG. 6;

(XVIII) a polynucleotide that encodes a peptide region of at least 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35 amino acids of a peptide of FIG. 3B in any whole number increment up to 625 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Percent Accessible Residues profile of FIG. 7;

(XIX) a polynucleotide that encodes a peptide region of at least 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35 amino acids of a peptide of FIG. 3B in any whole number increment up to 625 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Average Flexibility profile of FIG. 8;

(XX) a polynucleotide that encodes a peptide region of at least 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35 amino acids of a peptide of FIG. 3B in any whole number increment up to 625 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Beta-turn profile of FIG. 9;

(XXI) a polynucleotide that is fully complementary to a polynucleotide of any one of (I)-(XX);

(XXII) a polynucleotide that is fully complementary to a polynucleotide of any one of (I)-(XXI);

(XXIII) a peptide that is encoded by any of (I) to (XXII); and;

(XXIV) a composition comprising a polynucleotide of any of (I)-(XXII) or peptide of (XXIII) together with a pharmaceutical excipient and/or in a human unit dose form;

(XXV) a method of using a polynucleotide of any (I)-(XXIII) or peptide of (XXIII) or a composition of (XXIV) in a method to modulate a cell expressing 202P5A5;

(XXVI) a method of using a polynucleotide of any (I)-(XXII) or peptide of (XXIII) or a composition of (XXIV) in a method to diagnose, prophylax, prognose, or treat an individual who bears a cell expressing 202P5A5;

(XXVII) a method of using a polynucleotide of any (I)-(XXII) or peptide of (XXIII) or a composition of (XXIV) in a method to diagnose, prophylax, prognose, or treat an individual who bears a cell expressing 202P5A5, said cell from a cancer of a tissue listed in Table I;

(XXVIII) a method of using a polynucleotide of any (I)-(XXII) or peptide of (XXIII) or a composition of (XXIV) in a method to diagnose, prophylax, prognose, or treat a cancer;

(XXIX) a method of using a polynucleotide of any (I)-(XXII) or peptide of (XXIII) or a composition of (XXIV) in a method to diagnose, prophylax, prognose, or treat a cancer of a tissue listed in Table I; and;

(XXX) a method of using a polynucleotide of any (I)-(XXII) or peptide of (XXIII) or a composition of (XXIV) in a method to identify or characterize a modulator of a cell expressing 202P5A5.

As used herein, a range is understood to disclose specifically all whole unit positions thereof.

Typical embodiments of the invention disclosed herein include 202P5A5 polynucleotides that encode specific portions of 202P5A5 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 605, 609 or more contiguous amino acids of 202P5A5 variant 1; the maximal lengths relevant for other variants are: variant 2, 625 amino acids; variant 4, 609 amino acids, variant 5, 609 amino acids, variant 6, 609 amino acids, and variant 8, 609 amino acids.

For example, representative embodiments of the invention disclosed herein include: polynucleotides and their encoded peptides themselves encoding about amino acid 1 to about amino acid 10 of the 202P5A5 protein shown in FIG. 2 or FIG. 3, polynucleotides encoding about amino acid 10 to about amino acid 20 of the 202P5A5 protein shown in FIG. 2 or FIG. 3, polynucleotides encoding about amino acid 20 to about amino acid 30 of the 202P5A5 protein shown in FIG. 2 or FIG. 3, polynucleotides encoding about amino acid 30 to about amino acid 40 of the 202P5A5 protein shown in FIG. 2 or FIG. 3, polynucleotides encoding about amino acid 40 to about amino acid 50 of the 202P5A5 protein shown in FIG. 2 or FIG. 3, polynucleotides encoding about amino acid 50 to about amino acid 60 of the 202P5A5 protein shown in FIG. 2 or FIG. 3, polynucleotides encoding about amino acid 60 to about amino add 70 of the 202P5A5 protein shown in FIG. 2 or FIG. 3, polynucleotides encoding about amino acid 70 to about amino acid 80 of the 202P5A5 protein shown in FIG. 2 or FIG. 3, polynucleotides encoding about amino acid 80 to about amino acid 90 of the 202P5A5 protein shown in FIG. 2 or FIG. 3, polynucleotides encoding about amino acid 90 to about amino acid 100 of the 202P5A5 protein shown in FIG. 2 or FIG. 3, in increments of about 10 amino acids, ending at the carboxyl terminal amino acid set forth in FIG. 2 or FIG. 3. Accordingly, polynucleotides encoding portions of the amino acid sequence (of about 10 amino acids), of amino acids; 100 through the carboxyl terminal amine acid of the 202P5A5 protein are embodiments of the invention. Wherein it is understood that each particular amino acid position discloses that position plus or minus five amino acid residues.

Polynucleotides encoding relatively long portions of a 202P5A5 protein are also within the scope of the invention. For example, polynucleotides encoding from about amino acid 1 (or 20 or 30 or 40 etc.) to about amino acid 20, (or 30, or 40 or 50 etc.) of the 202P5A5 protein "or variant" shown in FIG. 2 or FIG. 3 can be generated by a variety of techniques well known in the art. These polynucleotide fragments can include any portion of the 202P5A5 sequence as shown in FIG. 2.

Additional illustrative embodiments of the invention disclosed herein include 202P5A5 polynucleotide fragments encoding one or more of the biological motifs contained within a 202P5A5 protein "or variant" sequence, including one or more of the motif-bearing subsequences of a 202P5A5 protein "or variant" set forth in Tables VIII-XXI and XXII-XLIX. In another embodiment, typical polynucleotide fragments of the invention encode one or more of the regions of 202P5A5 protein or variant that exhibit homology to a known molecule. In another embodiment of the invention, typical polynucleotide fragments can encode one or more of the 202P5A5 protein or variant N-glycosylation sites, cAMP and cGMP-dependent protein kinase phosphorylation sites, casein kinase II phosphorylation sites or N-myristoylation site and amidation sites.

Note that to determine the starting position of any peptide set forth in Tables VIII-XXI and Tables XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides listed in Table VII. Generally, a unique Search Peptide is used to obtain HLA peptides for a particular variant. The position of each Search Peptide relative to its respective parent molecule is listed in Table VII. Accordingly, if a Search Peptide begins at position "X", one must add the value "X minus 1" to each position in Tables VIII-XXI and Tables XXII-IL to obtain the actual position of the HLA peptides in their parental molecule, For example if a particular Search Peptide begins at position 150 of its parental molecule, one must add 150–1, i.e., 149 to each HLA peptide amino acid position to calculate the position of that amino acid in the parent molecule.

II.A.) Uses of 202P5A5 Polynucleotides

II.A.1.) Monitoring of Genetic Abnormalities

The polynucleotides of the preceding paragraphs have a number of different specific uses. The human 202P5A5 gene maps to the chromosomal location set forth in the Example entitled "Chromosomal Mapping of 202P5A5." For example, because the 202P5A5 gene maps to this chromosome, polynucleotides that encode different regions of the 202P5A5 proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 88(10): 3905-3914 (1995) and Finger et al., P.N.A.S. 85(23): 9158-9162 (1988)). Thus, polynucleotides encoding specific regions of the 202P5A5 proteins provide new tools that can be used to delineate, with greater precision than previously possible, cytogenetic abnormalities in the chromosomal region that encodes 202P5A5 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994).

Furthermore, as 202P5A5 was shown to be highly expressed in prostate and other cancers, 202P5A5 polynucleotides are used in methods assessing the status of 202P5A5 gene products in normal versus cancerous tissues. Typically, polynucleotides that encode specific regions of the 202P5A5 proteins are used to assess the presence of perturbations (such as deletions, insertions, point mutations, or alterations resulting in a loss of an antigen etc.) in specific regions of the 202P5A5 gene, such as regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 202P5A5. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skied artisan can readily obtain these classes of nucleic acid molecules using the 202P5A5 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 202P5A5. See for example, Jack Cohen, Oligodeoxynucleotides. Antisense Inhibitors of Gene Expression, CRC Press 1989; and Synthesis 1:1-5 (1988). The 202P5A5 antisense oligonucleotides of the present invention include derivatives such as S-oligonucleotides (phosphorothioate derivatives or S-oligos, see. Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Iyer, R. P. et al., J. Am. Chem. SOC. 112:1253-1254 (1990). Additional 202P5A5 antisense oligonucleotides of the present invention include morpholino antisense oligonucleotides known in the art (see, e.g., Partridge et al., 1996, Antisense & Nucleic Acid Drug Development 6: 169-175).

The 202P5A5 antisense oligonucleotides of the present invention typically can be RNA or DNA that is complementary to and stably hybridizes with the first 100 5' codons or last 100 3' codons of a 202P5A5 genomic sequence or the corresponding mRNA. Absolute complementarity is not required, although high degrees of complementarity are preferred. Use of an oligonucleotide complementary to this region allows for the selective hybridization to 202P5A5 mRNA and not to mRNA specifying other regulatory subunits of protein kinase, In one embodiment, 202P5A5 antisense oligonucleotides of the present invention are 15 to 30-mer fragments of the antisense DNA molecule that have a sequence that hybridizes to 202P5A5 mRNA, Optionally, 202P5A5 antisense oligonucleotide is a 30-mer oligonucleotide that is complementary to a region in the first 10 5' codons or last 10 3' codons of 202P5A5. Alternatively, the antisense molecules are modified to employ ribozymes in the inhibition of 202P5A5 expression, see, e.g., L. A. Couture & D. T. Stinchcomb; *Trends Genet.* 12:510-515 (1996).

II.A.3.) Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 202P5A5 polynucleotide in a sample and as a means for detecting a cell expressing a 202P5A5 protein.

Examples of such probes include polypeptides comprising all or part of the human 202P5A5 cDNA sequence shown in FIG. 2. Examples of primer pairs capable of specifically amplifying 202P5A5 mRNAs are also described in the Examples. As will be understood by die skilled artisan, a great many different primers and probes can be prepared based on the sequences provided herein and used effectively to amplify and/or detect a 202P5A5 mRNA.

The 202P5A5 polynucleotides of the invention are useful for a variety of purposes, including but not limited to their use as probes and primers for the amplification and/or detection of the 202P5A5 gene(s), mRNA(s), or fragments thereof; as reagents for the diagnosis and/or prognosis of prostate cancer and other cancers; as coding sequences capable of directing the expression of 202P5A5 polypeptides; as tools for modulating or inhibiting the expression of the 202P5A5 gene(s) and/or translation of the 202P5A5 transcripts); and as therapeutic agents.

The present invention includes the use of any probe as described herein to identify and isolate a 202P5A5 or 202P5A5 related nucleic acid sequence from a naturally occurring source, such as humans or other mammals, as well as the isolated nucleic acid sequence per se, which would comprise all or most of the sequences found in the probe used.

II.A.4.) Isolation of 202P5A5-Encoding Nucleic Acid Molecules

The 202P5A5 cDNA sequences described herein enable the isolation of other polynucleotides encoding 202P5A5 gene produces), as well as the isolation of polynucleotides encoding 202P5A5 gene product homologs, alternatively spliced isoforms, allelic variants, and mutant forms of a 202P5A5 gene product as well as polynucleotides that encode analogs of 202P5A5 related proteins. Various molecular cloning methods that can be employed to isolate full length cDNAs encoding a 202P5A5 gene are well known (see, for example, Sambrook, J. et al. Molecular Cloning: A Laboratory Manual, 2d edition. Cold Spring Harbor Press, New York, 1989; Current Protocols in Molecular Biology, Ausubel et al. Eds., Wiley and Sons, 1995). For example, lambda phage cloning methodologies can be conveniently employed, using commercially available cloning systems)(e.g., Lambda ZAP Express, Stratagene), Phage clones containing 202P5A5 gene cDNAs can be identified by probing with a labeled 202P5A5 cDNA or a fragment thereof. For example, in one embodiment, a 202P5A5 cDNA (e.g., FIG. 2) or a portion thereof can be synthesized and used as a probe to retrieve overlapping and full-length cDNAs corresponding to a 202P5A5 gene. A 202P5A5 gene itself can be isolated by screening genomic DNA libraries, bacterial artificial chromosome libraries (BACs), yeast artificial chromosome libraries (YACs), and the like, with 202P5A5 DNA probes or primers.

II.A.5.) Recombinant Nucleic Acid Molecules and Host-Vector Systems

The invention also provides recombinant DNA or RNA molecules containing a 202P5A5 polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 202P5A5 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 202P5A5 or a fragment, analog or homolog thereof can be used to generate 202P5A5 proteins or fragments thereof using any number of host-vector systems routinely used and widely known in the art.

A wide range of host-vector systems suitable for the expression of 202P5A5 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 202P5A5 can be expressed in several prostate cancer and non-prostate cell lines, including for example 293, 293T, rat-1, NIH 3T3 and TsuPr1. The host-vector systems of the invention are useful for the production of a 202P5A5 protein or fragment thereof. Such host-vector systems can be employed to study the functional properties of 202P5A5 and 202P5A5 mutations or analogs.

Recombinant human 202P5A5 protein or an analog or homolog or fragment thereof can be produced by mammalian cells transfected with a construct encoding a 202P5A5-related nucleotide. For example, 293T cells can be transfected with an expression plasmid encoding 202P5A5 or fragment, analog or homolog thereof, a 202P5A5-related protein is expressed in the 293T cells, and the recombinant 202P5A5 protein is isolated using standard purification methods (e.g., affinity purification using anti-202P5A5 antibodies). In another embodiment, a 202P5A5 coding sequence is subcloned into the retroviral vector pSRαMSVtkneo and used to intact various mammalian cell lines, such as NIH 3T3, TsuPr1, 293 and rat-1 in order to establish 202P5A5 expressing cell lines. Various other expression systems well known in the art can also be employed. Expression constructs encoding a leader peptide joined in frame to a 202P5A5 coding sequence can be used for the generation of a secreted form of recombinant 202P5A5 protein.

As discussed herein, redundancy in the genetic code permits variation in 202P5A5 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at URL dna.affrc.go.jp/~nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Bio.*, 9:5073-5080 (1989). Skilled artisans understand that the general rule that eukaryotic ribosomes initiate translation exclusively at the 5' proximal AUG codon is abrogated only under rare conditions (see, e.g., Kozak *PNAS* 92(7):2662-2666, (1995) and Kozak NAR 15(20): 8125-8148 (1987).

III.) 202P5A5-RELATED PROTEINS

Another aspect of the present invention provides 202P5A5-related proteins. Specific embodiments of 202P5A5 proteins comprise a polypeptide having all or part of the amino acid sequence of human 202P5A5 as shown in FIG. 2 or FIG. 3. Alternatively, embodiments of 202P5A5 proteins comprise variant, homolog or analog polypeptides that have alterations in the amino acid sequence of 202P5A5 shown in FIG. 2 or FIG. 3.

Embodiments of a 202P5A5 polypeptide include: a 202P5A5 polypeptide having a sequence shown in FIG. 2, a peptide sequence of a 202P5A5 as shown in FIG. 2 wherein T is U; at least 10 contiguous nucleotides of a polypeptide having the sequence as shown in FIG. 2, or, at least 10 contiguous peptides of a polypeptide having the sequence as shown in FIG. 2 where T is U. For example, embodiments of 202P5A5 peptides comprise, without limitation:

(I) a protein comprising, consisting essentially of, or consisting of an amino acid sequence as shown in FIG. 2A-F or FIGS. 3A-F;

(II) a 202P5A5-related protein that is at least 90, 91, 92, 93, 94, 95, 96, 97, 98, 99 or 100% homologous to an entire amino acid sequence shown in FIG. 2A-F or 3A-F;

(III) a 202P5A5-related protein that is at least 90, 81, 92, 93, 94, 95, 96, 97, 98, 99 or 100% identical to an entire amino acid sequence shown in FIG. 2A-F or 3A-F;

(IV) a protein that comprises at least one peptide set forth in Tables VIII to XLIX optionally with a proviso that it is not an entire protein of FIG. 2;

(V) a protein that comprises at least one peptide set forth in Tables VIII-XXI, collectively, which peptide is also set forth in Tables XXII to XLIX, collectively, optionally with a proviso that it is not an entire protein of FIG. 2;

(VI) a protein that comprises at least two peptides selected from the peptides set forth in Tables VIII-XLIX, optionally with a proviso that it is not an entire protein of FIG. 2;

(VII) a protein that comprises at least two peptides selected from the peptides set forth in Tables VIII to XLIX collectively, with a proviso that the protein is not a contiguous sequence from an amino acid sequence of FIG. 2;

(VIII) a protein that comprises at least one peptide selected from the peptides set forth in Tables VIII-XXI; and at least one peptide selected from the peptides set forth in Tables XXIII to XLIX, with a proviso that the protein is not a contiguous sequence from an amino acid sequence of FIG. 2;

(IX) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3C-3F in any whole number increment up to 609 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(X) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3C-3F in any whole number increment up to 609 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 6;

(XI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3C-3F in any whole number increment up to 609 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 7;

(XII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3C-3F in any whole number increment up to 609 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XIII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIGS. 3A, 3C-3F in any whole number increment up to 609 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIV) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3B, in any whole number increment up to 625 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XV) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3B, in any whole number increment up to 625 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 6;

(XVI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3B, in any whole number increment up to 625 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XVII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3B, in any whole number increment up to 625 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the the Average Flexibility profile of FIG. 8;

(XVIII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 amino acids of a protein of FIG. 3B, in any whole number increment up to 625 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIX) a peptide that occurs at least twice in Tables VIII-XXI and XXII to XLIX, collectively;

(XX) a peptide that occurs at least three times in Tables VIII-XXI and XXII to XLIX, collectively;

(XXI) a peptide that occurs at least four times in Tables VIII-XXI and XXII to XLIX, collectively;

(XXII) a peptide that occurs at least five times in Tables VIII-XXI and XXII to XLIX, collectively;

(XXIII) a peptide that occurs at least once in Tables VIII-XXI and at least once in tables XXII to XLIX;

(XXIV) a peptide that occurs at least once in Tables VIII-XXI and at least twice in tables XXII to XLIX;

(XXV) a peptide that occurs at least twice in Tables VIII-XXI and at least once in tables XXII to XLIX;

(XXVI) a peptide that occurs at least twice in Tables VIII-XXI and at least twice in tables XXII to XLIX;

(XXVII) a peptide which comprises one two, three, four, or five of the following characteristics, or an oligonucleotide encoding such peptide:

i) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 6;

ii) a region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of of FIG. 7;

iv) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or, v) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9;

(XXVIII) a composition comprising a peptide of (I)-(XX-VII) or an antibody or binding region thereof together with a pharmaceutical excipient and/or in a human unit dose form.

(XXIX) a method of using a peptide of (I)-(XXVII), or an antibody or binding region thereof or a composition of (XXVIII) in a method to modulate a cell expressing 202P5A5;

(XXX) a method of using a peptide of (I)-(XXVII) or an antibody or binding region thereof or a composition of (XXVIII) in a method to diagnose, prophylax, prognose, or treat an individual who bears a cell expressing 202P5A5;

(XXXI) a method of using a peptide of (I)-(XXVII) or an antibody or binding region thereof or a composition (XXVIII) in a method to diagnose, prophylax, prognose, or treat an individual who bears a cell expressing 202P5A5, said cell from a cancer of a tissue listed in Table I;

(XXXII) a method of using a peptide of (I)-(XXVII) or an antibody or binding region thereof or a composition of (XXVIII) in a method to diagnose, prophylax, prognose, or treat a cancer;

(XXXIII) a method of using a peptide of (I)-(XXVII) or an antibody or binding region thereof or a composition of (XXVIII) in a method to diagnose, prophylax, prognose, or treat a cancer of a tissue listed in Table I; and;

(XXXIV) a method of using a peptide of (I)-(XXVII) or an antibody or binding region thereof or a composition (XXVIII) in a method to identify or characterize a modulator of a cell expressing 202P5A5

As used herein, a range is understood to specifically disclose all whole unit positions thereof., Typical embodiments of the invention disclosed herein include 202P5A5 polynucleotides that encode specific portions of 202P5A5 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 605, and 609 or more contiguous amino acids of 202P5A5 variant 1; the maximal lengths relevant for other variants are; variant 2, 625 amino acids; variant 4, 609 amino acids, variant 5, 609 amino acids, variant 6, 609 amino acids, and variant 8, 309 amino acids.

In general, naturally occurring allelic variants of human 202P5A5 share a high degree of structural identity and homology (e.g., 90% or more homology). Typically, allelic variants of a 202P5A5 protein contain conservative amino acid substitutions within the 202P5A5 sequences described herein or contain a substitution of an amino acid from a corresponding position in a homologue of 202P5A5. One class of 202P5A5 allelic variants are proteins that share a high degree of homology with at least a small region of a particular 202P5A5 amino acid sequence, but further contain a radical departure from the sequence, such as a non-conservative substitution, truncation, insertion or frame shift. In comparisons of protein sequences, the terms, similarity, identify, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids, aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" $2^{nd}$ ED Lubert Stryer ed (Stanford University); Henikoff et al., PNAS 1992 Vol 89 10915-10919; Lei et al., J Biol Chem 1995 May 19; 270(20): 11882-6).

Embodiments of the invention disclosed herein include a wide variety of art-accepted variants or analogs of 202P5A5 proteins such as polypeptides having amino acid insertions, deletions and substitutions. 202P5A5 variants can be made using methods known in the art such as site-directed mutagenesis, alanine scanning, and PCR mutagenesis. Site-directed mutagenesis (Carter et al., *Nucl. Acids Res.* 13:4331 (1986); Zoller et al., *Nucl. Acids Res.*, 10:6487 (1987)), cassette mutagenesis (Wells et al. Gene, 34:315 (1985)), restriction selection mutagenesis (Wells et al., *Philos. Trans. R. Soc. London SerA,* 317:415 (1985)) or other known techniques can be performed on the cloned DNA to produce the 202P5A5 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

As defined herein, 202P5A5 variants, analogs or homologs, have the distinguishing attribute of having at least one epitope that is "cross reactive" with a 202P5A5 protein having an amino acid sequence of FIG. 3. As used in this sentence, "cross reactive" means that an antibody or T cell that specifically binds to a 202P5A5 variant also specifically binds to a 202P5A5 protein having an amino acid sequence set forth in FIG. 3. A polypeptide ceases to be a variant of a protein shown in FIG. 3, when it no longer contains any epitope capable of being recognized by an antibody or T cell that specifically binds to the starting 202P5A5 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165(12):6949-6955; Hebbes et al., Mol. Immunol (1989)25(9:865-73; Schwartz et al., J. Immunol (1985)135(4):2598-608.

Other classes of 202P5A5-related protein variants share 70%, 75%, 80%, 85% or 90% or more similarity with an amino acid sequence of FIG. 3, or a fragment thereof. Another specific class of 202P5A5 protein variants or analogs comprises one or more of the 202P5A5 biological motifs described herein or presently known in the art. Thus, encompassed by the present invention are analogs of 202P5A5 fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a 202P5A5 protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of a 202P5A5 protein shown in FIG. 2 or FIG. 3.

Moreover, representative embodiments of the invention disclosed herein include polypeptides consisting of about amino acid 1 to about amino acid 10 of a 202P5A5 protein shown in FIG. 2 or FIG. 3, polypeptides consisting of about amino acid 10 to about amino acid 20 of a 202P5A5 protein shown in FIG. 2 or FIG. 3, polypeptides consisting of about amino acid 20 to about amino acid 30 of a 202P5A5 protein shown in FIG. 2 or FIG. 3, polypeptides consisting of about amino acid 30 to about amino acid 40 of a 202P5A5 protein shown in FIG. 2 or FIG. 3, polypeptides consisting of about amino acid 40 to about amino acid 50 of a 202P5A5 protein shown in FIG. 2 or FIG. 3, polypeptides consisting of about amino acid 50 to about amino acid 60 of a 202P5A 5 protein shown in FIG. 2 or FIG. 3, polypeptides consisting of about amino add 60 to about amino acid 70 of a 202P5A5 protein shown in FIG. 2 or FIG. 3, polypeptides consisting of about amino acid 70 to about amino acid 80 of a 202P5A5 protein shown in FIG. 2 or FIG. 3, polypeptides consisting of about amino acid 80 to about amino acid 90 of a 202P5A5 protein shown in FIG. 2 or FIG. 3, polypeptides consisting of about amino acid 90 to about amino acid 100 of a 202P5A5 protein shown in FIG. 2 or FIG. 3, etc. throughout the entirety of a 202P5A5 amino acid sequence. Moreover, polypeptides consisting of about amino acid 1 (or 20 or 30 or 40 etc.) to about amino acid 20, (or 130, or 140 or 150 etc.) of a 202P5A5 protein shown in FIG. 2 or FIG. 3 are embodiments of the invention. It is to be appreciated that the starting and stopping positions in this paragraph refer to the specified position as well as that position plus or minus 5 residues.

202P5A5-related proteins are generated using standard peptide synthesis technology or using chemical cleavage methods well known in the art. Alternatively, recombinant methods can be used to generate nucleic acid molecules that encode a 202P5A5-related protein. In one embodiment, nucleic acid molecules provide a means to generate defined fragments of a 202P5A5 protein (or variants, homologs or analogs thereof).

III.A) Motif-bearing Protein Embodiments

Additional illustrative embodiments of the invention disclosed herein include 202P5A5 polypeptides comprising the amino acid residues of one or more of the biological motifs contained within a 202P5A5 polypeptide sequence set forth in FIG. 2 or FIG. 3. Various motifs are known in the art, and a protein can be evaluated for the presence of such motifs by a number of publicly available Internet sites (see, e.g., URL addresses: pfam.wustl.edu/; searchlauncher.bcm.tmc.edu/ seq-search/struc-predict.html; psort.ims.u-tokyo.ac.jp/; cbs-.dtu.dk/; ebl.ac.uk/interpro/scan.html; expasy.ch/tools/ scnpsit1.html; Epimatrix® and Epimer®, Brown University, brown.edu/Research/TB-HIV Lab/epimatrix/epimatrix.html; and BIMAS, bimas.dcrt.nih.gov/.).

Motif bearing subsequences of all 202P5A5 variant proteins are set forth and identified in Tables VIII-XXI and XXII-XIIX.

Table V sets forth several frequently occurring motifs based on pfam searches (see URL address pfam.wustl.edu/). The columns of Table V list (1) motif name abbreviation, (2) percent identity found amongst the different member of the motif family, (3) motif name or description and (4) most common function; location information is included if the motif is relevant for location.

Polypeptides comprising one or more of the 202P5A5 motifs discussed above are useful in elucidating the specific characteristics of a malignant phenotype in view of the observation that the 202P5A5 motifs discussed above are associated with growth dysregulation and because 202P5A5 is overexpressed in certain cancers (See, e.g., Table I). Casein kinase II, cAMP and camp-dependent protein kinase, and Protein Kinase C, for example, are enzymes known to be associated with the development of the malignant phenotype (see e.g., Chen et al., Lab Invest, 78(2): 165-174 (1998); Gaiddon et al., Endocrinology 136(10):4331-4338 (1995); Hall et al., Nucleic Acids Research 24(6):1119-1128(1996); Peterziel et al., Oncogene 18(48):6322-6329 (1999) and O'Brian, Oncol. Rep. 5(2);305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables VIII-XXI and XXII-XLIX. CTL epitopes can be determined using specific algorithms to identify peptides within a 202P5A5 protein that are capable of optimally binding to specified HLA alleles (e.g., Table IV; Epimatrix® and Epimer®, Brown University, URL brown.edu/Research/ TB-HIV_Lab/epimatrix/epimatrix.html, and BIMAS, URL bimas.dcrt.nih.gov/.) Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenic. For example, one begins with an epitope that bears a CTL or HTL motif (see, e.g., the HLA Class I and HLA Glass II motifs/ supermotifs of Table IV). The epitope is analoged by substituting out an amino acid at one of the specified positions, and replacing it with another amino acid specified for that position, For example, on the basis of residues defined in Table IV, one can substitute out a deleterious residue in favor of any other residue, such as a preferred residue; substitute a less-preferred residue with a preferred residue; or substitute an originally-occurring preferred residue with another preferred residue. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, Immunogenetics 1999 50(3-4):201-212; Sette et al., J. Immunol, 2001 166 (2):1389-1397; Sidney et al., Hum. Immunol. 1997 58 (1): 12-20; Kondo et al., Immunogenetics 1997 45 (4):249-258: Sidney et al., J. Immunol. 1995 157 (8):3480-90; and Falk et al., Nature 351:290-6 (1991); Hunt et al., Science 255:1231-3 (1992); Parker et al., J. Immunol. 149:3580-7 (1992); Parker et al., J. Immunol. 152:163-75 (1994)); Kast et al., 1994 152 (8):3904-12; Borras-Cuesta et al., Hum. Immunol. 2000 61 (3):286-278; Alexander et al., J. Immunol. 2000 164 (3);154 (3):1625-1633; Alexander et al., PMID: 7895164, UI: 95202582; O'Sullivan et al., J. Immunol. 1991 147 (8): 2863-2369; Alexander et al., Immunity 1994 1(9): 751-761 and Alexander et al., Immunol, Res. 1998 18(2): 79-92.

Related embodiments of the invention include polypeptides comprising combinations of the different motifs set forth in Table VI, and/or, one or more of the predicted CTL epitopes of Tables VIII-XXI and XXII-XLIX, and/or, one or more of the predicted HTL epitopes of Tables XLVI-XLIX, and/or, one or more of the T cell binding motifs known in the art. Preferred embodiments contain no insertions, deletions or substitutions either within the motifs or within the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically, the number of N-terminal and/or C-terminal amino acid residues on either side of a motif is between about 1 to about 100 amino acid residues, preferably 5 to about 50 amino acid residues.

202P5A5-related proteins are embodied in many forms, preferably in isolated form. A purified 202P5A5 protein molecule will be substantially free of other proteins or molecules that impair the binding of 202P5A5 to antibody, T cell or other ligand. The nature and degree of isolation and purification will depend on the intended use. Embodiments of a 202P5A5-related proteins include purified 202P5A5-related proteins and functional, soluble 202P5A5-related proteins. In one embodiment, a functional, soluble 202P5A5 protein or fragment thereof retains the ability to be bound by antibody, T cell or other ligand.

The invention also provides 202P5A5 proteins comprising biologically active fragments of a 202P5A5 amino acid sequence shown in FIG. 2 or FIG. 3. Such proteins exhibit properties of the starting 202P5A5 protein, such as the ability to elicit the generation of antibodies that specifically bind an epitope associated with the starting 202P5A5 protein; to be bound by such antibodies; to elicit the activation of HTL or CTL; and/or, to be recognized by HTL or CTL that also specifically bind to the starting protein.

202P5A5-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or based on immunogenicity. Fragments that contain such structures are particularly useful in generating subunit-specific anti-202P5A5 antibodies or T cells or in identifying cellular factors that bind to 202P5A5.

For example, hydrophilicity profiles can be generated, and immunogenic peptide fragments identified, using the method of Hopp, T. P. and Woods, K. R., 1961, Proc. Natl. Acad. Sci. U.S.A. 75:3824-3828. Hydropathicity profiles can be generated, and immunogenic peptide fragments identified, using the method of Kyte. J. and Doolittle, R. F., 1982, J. Mol. Biol, 157:105-132. Percent (%) Accessible Residues profiles can be generated, and immunogenic peptide fragments identified, using the method of Janin J., 1979, Nature 277:491-492. Average Flexibility profiles can be generated, and immunogenic peptide fragments identified, using the method of Bhaskaran R., Ponnuswamy P. K., 1983, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within a 202P5A5 protein that are capable of optimally binding to specified HLA alleles (e.g., by using the SYMPATHY site at World Wide Web URL syfpeithi.bmi-heidelberg.com/; the listings in Table IV (A)-(E); Epimatrix® and Epimatrix®, Brown University, URL (brown.edu/Research/TB-HIV Lab/epimatrix/epimatrix.html); and BIMAS, URL bimas.dcrt.nih.gov/). Illustrating this, peptide epitopes from 202P5A5 that are presented in the context of human MHC Class I molecules, e.g., HLA-A1, A2, A3, A11, A24, B7 and B35 were predicted (see, e.g., Tables VIII-XXI, XXII-XLIX). Specifically, the complete amino acid sequence of the 202P5A5 protein and relevant portions of other variants, i.e., for HLA Class I predictions 9 flanking residues on either side of a point mutation or exon junction, and for HLA Class II predictions 14 flanking residues on either side of a point mutation or exon junction corresponding to that variant, were entered into the HLA Peptide Motif Search algorithm found in the Bioinformatics and Molecular Analysis Section (BIMAS) web site listed above; in addition to the site SYFPEITHI, at URL syfpeithi.bmi-heidelberg.com/.

The HLA peptide motif search algorithm was developed by Dr. Ken Parker based on binding of specific peptide sequences in the groove of HLA Class I molecules, in particular HLA-A2 (see, e.g., Falk et al., Nature 351:290-6 (1991); Hunt et al., Science 255:1261-3 (1992); Parker et al., J. Immunol. 149:3580-7 (1992); Parker et al., J. Immunol. 152:163-75 (1994). This algorithm allows location and ranking of 8-mer, 9-mer, and 10-mer peptides from a complete protein sequence for predicted binding to HLA-A2 as well as numerous other HLA Class I molecules. May HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., J. Immunol. 149: 3580-7 (1992). Selected results of 202P5A5 predicted binding peptides are shown in Tables VII-XXI and XXII-XLIX herein. In Tables VIII-XXI and XXII-XLVII, selected candidates, 9-mers and 10-mers, for each family member are shown along with their location, the amino acid sequence of each specific peptide, and an estimated binding score. In Tables XLVI-XLIX, selected candidates, 15-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets to T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998). Immunogenicity of specific peptides can be evaluated in vitro by stimulation of CD8+ cytotoxic T lymphocytes (CTL) in the presence of antigen presenting cells such as dendritic cells.

It is to be appreciated every epitope predicted by the BIMAS site, Epimer™ and Epimatrix™ sites, or specified by the HLA class I or class I motifs available in the art or which become part of the art such as set forth in Table IV (or determined using World Wide Web site URL syfpeilhi.bmi-heidelberg.com/, or BIMAS, bimas.dcrt.nih.gov/) are to be "applied" to a 202P5A5 protein in accordance with the invention. As used in this context "applied" means that a 202P5A5 protein is evaluated, e.g., visually or by computer-based patterns finding methods, as appreciated by those of skill in the relevant art. Every subsequence of a 202P5A5 protein of 8, 9, 10, or 11 amino acid residues that bears an HLA Class I motif, or a subsequence of 9 or more amino acid residues that bear an HLA Class II motif, are within the scope of the invention.

III.B.) Expression of 202P5A5-related Proteins

In an embodiment described in the examples that follow, 202P5A5 can be conveniently expressed in cells (such as 283T cells) transfected with a commercially available expression vector such as a CMV-driven expression vector encoding 202P5A5 with a C-terminal 6XHis and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 202P5A5 protein in transfected cells. The secreted HIS-tagged 202P5A5 in the culture media can be purified, e.g., using a nickel column using standard techniques.

III.C.) Modifications of 202P5A5-related Proteins

Modifications of 202P5A5-related proteins such as covalent modifications are included within the scope of this invention. One type of covalent modification includes reacting targeted amino acid residues of a 202P5A5 polypeptide with an organic derivatizing agent that is capable of reacting with selected side chains or the N- or C-terminal residues of a 202P5A5 protein. Another type of covalent modification of a 202P5A5 polypeptide includes within the scope of this invention comprises altering the native glycosylation pattern of a protein of the invention. Another type of covalent modification of 202P5A5 comprises linking a 202P5A5 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689, 4,301,144; 4,670,417; 4,791,192 or 4,179,337.

The 202P5A5-related proteins of the present invention can also be modified to form a chimeric molecule comprising 202P5A5 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 202P5A5 sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 202P5A5. A chimeric molecule can comprise a fusion of a 202P5A5-related protein with a polyhistidine epitope tag, which provides an epitope to which immobilized nickel can selectively bind, with cytokines or with growth factors. The epitope tag is generally placed at the amino- or carboxyl-terminus of a 202P5A5 protein. In an alternative embodiment, the chimeric molecule can comprise a fusion of a 202P5A5-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 202P5A5 polypeptide in place of at least one variable region within an Ig molecule. In a preferred embodiment, the immunoglobulin fusion includes the hinge, CH2 and CH3, or the hinge, CH1, CH2 and CH3 regions of an IgG1 molecule. For the production of immunoglobulin fusions see, e.g., U.S. Pat. No. 5,428,130 issued Jun. 27, 1995.

III.D.) Uses of 202P5A5-related Proteins

The proteins of the invention have a number of different specific uses. As 202P5A5 is highly expressed in prostate and other cancers, 202P5A5-related proteins are used in methods that assess the status of 202P5A5 gene products in normal versus cancerous tissues, thereby elucidating the malignant phenotype. Typically, polypeptides from specific regions of a 202P5A5 protein are used to assess the presence of perturbations (such as deletions, insertions, point mutations etc.) in those regions (such as regions containing one or more motifs). Exemplary assays utilize antibodies or T cells targeting 202P5A5-related proteins comprising the amino acid residues of one or more of the biological motifs contained within a 202P5A5 polypeptide sequence in order to evaluate the characteristics of this region in normal versus cancerous tissues or to elicit an immune response to the epitope. Alternatively, 202P5A5-related proteins that contain the amino acid residues of one or more of the biological motifs in a 202P5A5 protein are used to screen for factors that interact with that region of 202P5A5.

202P5A5 protein fragments/subsequences are particularly useful in generating and characterizing domain-specific antibodies (e.g., antibodies recognizing an extracellular or intracellular epitope of a 202P5A5 protein), for identifying agents or cellular factors that bind to 202P5A5 or a particular structural domain thereof, and in various therapeutic and diagnostic contexts, including but not limited to diagnostic assays, cancer vaccines and methods of preparing such vaccines.

Proteins encoded by the 202P5A5 genes, or by analogs, homo logs or fragments thereof, have a variety of uses, including but not limited to generating antibodies and in methods for identifying ligands and other agents and cellular constituents that bind to a 202P5A5 gene product Antibodies raised against a 202P5A5 protein or fragment thereof are useful in diagnostic and prognostic assays, and imaging methodologies in the management of human cancers characterized by expression of 202P5A5 protein, such as those listed in Table I. Such antibodies can be expressed intracellularly and used in methods of treating patients with such cancers. 202P5A5-related nucleic acids or proteins are also used in generating HTL or CTL responses.

Various immunological assays useful for the detection of 202P5A5 proteins are used, including but not limited to various types of radio immunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 202P5A5-expressing cells (e.g., in radioscinligraphic imaging methods), 202P5A5 pro-

IV.) 202P5A5 ANTIBODIES

Another aspect of the invention provides antibodies that bind to 202P5A5-related proteins. Preferred antibodies specifically bind to a 202P5A5-related protein and do not bind (or bind weakly) to peptides or proteins that are not 202P5A5-related proteins under physiological conditions. In this context, examples of physiological conditions include: 1) phosphate buffered saline; 2) Tris-buffered saline containing 25 mM Tris and 150 mM NaCl; or normal saline (0.9% NaCl); 4) animal serum such as human serum; or, 5) a combination of any of 1) through 4); these reactions preferably taking place at pH 7.5, alternatively in a range of pH 7.0 to 8.0, or alternatively in a range of pH 6.5 to 8.5; also, these reactions taking place at a temperature between 4° C. to 37° C. For example, antibodies that bind 202P5A5 can bind 202P5A5-related proteins such as the homologs or analogs thereof.

202P5A5 antibodies of the invention are particularly useful in cancer (see, e.g., Table I) diagnostic and prognostic assays, and imaging methodologies. Similarly, such antibodies are useful in the treatment, diagnosis, and/or prognosis of other cancers, to the extent 202P5A5 is also expressed or overexpressed in these other cancers. Moreover, intracellularly expressed antibodies (e.g., single chain antibodies) are therapeutically useful in treating cancers in which the expression of 202P5A5 is involved, such as advanced or metastatic prostate cancers.

The invention also provides various immunological assays useful for the defection and quantification of 202P5A5 and mutant 202P5A5-related proteins. Such assays can comprise one or more 202P5A5 antibodies capable of recognizing and binding a 202P5A5-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as wail as major histocompatibility complex (MHC) binding assays.

In addition, immunological imaging methods capable of detecting prostate cancer and other cancers expressing 202P5A5 are also provided by the invention, including but not limited to radioscinligraphic imaging methods using labeled 202P5A5 antibodies. Such assays are clinically useful in the detection, monitoring, and prognosis of 202P5A5 expressing cancers such as prostate cancer, 202P5A5 antibodies are also used in methods for purifying a 202P5A5-related protein and for isolating 202P5A5 homologues and related molecules. For example, a method of purifying a 202P5A5-related protein comprises incubating a 202P5A5 antibody, which has bean coupled to a solid matrix, with a lysate or other solution containing a 202P5A5-related protein under conditions that permit the 202P5A5 antibody to bind to the 202P5A5-related protein; washing the solid matrix to eliminate impurities and eluting the 202P5A5-related protein from the coupled antibody. Other uses of 202P5A5 antibodies in accordance with the invention include generating anti-idiotypic antibodies that mimic a 202P5A5 protein.

Various methods for the preparation of antibodies are well known in the art. For example, antibodies can be prepared by immunizing a suitable mammalian host using a 202P5A5-related protein, peptide, or fragment, in isolated or immunoconjugated form (Antibodies: A Laboratory Manual, CSH Press, Eds., Harlow, and Lane (1988), Harlow, Antibodies, Cold Spring Harbor Press, N.Y. (1989). In addition, fusion proteins of 202P5A5 can also be used, such as a 202P5A5 GST-fusion protein. In a particular embodiment, a GST fusion protein comprising all or most of the amino acid sequence of FIG. 2 or FIG. 3 is produced, then used as an immunogen to generate appropriate antibodies, In another embodiment, a 202P5A5-related protein is synthesized and used as an immunogen.

In addition, naked DNA immunization techniques known in the art are used (with or without purified 202P5A5-related protein or 202P5A5 expressing cells) to generate an immune response to the encoded immunogen (for review, see Donnelly et al., 1997, Ann. Rev. Immunol. 15:617-648).

The amino acid sequence of a 202P5A5 protein as shown in FIG. 2 or FIG. 3 can be analyzed to select specific regions of the 202P5A5 protein for generating antibodies. For example, hydrophobicity and hydrophilicity analyses of a 202P5A5 amino acid sequence are used to identify hydrophilic regions in the 202P5A5 structure. Regions of a 202P5A5 protein that show immunogenic structure, as well as other regions and domains, can readily be identified using various other methods known in the art, such as Chou-Fasman, Garnier-Robson, Kyte-Doolittle. Eisenberg. Karplus-Schultz or Jameson-Wolf analysis. Hydrophilicity profiles can be generated using the method of Hopp, T. P. and Woods, K. R., 1961, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept, Protein Res. 32:242-255. Beta-turn profiles can be generated using the method of Deleage, G. Roux B., 1937, Protein Engineering 1:289-294. Thus, each region identified by any of these programs or methods is within the scope of the present invention. Methods for the generation of 202P5A5 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodimide reagents are used; in other instances linking reagents such as those supplied by Pierce Chemical Co., Rockford, Ill., are effective. Administration of a 202P5A5 immunogen is often conducted by injection over a suitable time period and with use of a suitable adjuvant, as is understood in the art. During the immunization schedule, liters of antibodies can be taken to determine adequacy of antibody formation.

202P5A5 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known, immortalized cell lines that secrete the desired antibodies are screened by immunoassay in which the antigen is a 202P5A5-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 202P5A5 protein can also be produced in the context of chimeric or complementarity-determining region (CDR) grafted antibodies of multiple species origin. Humanized or human 202P5A5 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321:522-525; Riechmann et al., 1988, Nature 332:323-327; Verhoeyen et al., 1988, Science 239:1534-1533). See also, Carter et al., 1993, Proc. Natl. Acad. Sci. USA 89:4285 and Sims et al., 1993, J. Immunol. 151:2296.

Methods for producing fully human monoclonal antibodies include phage display and transgene methods (for review, see Vaughan et al., 1998, Nature Biotechnology 16:535-539), Fully human 202P5A5 monoclonal antibodies can be generated using cloning technologies employing large human Ig gene combinatorial libraries (i.e., phage display) (Griffiths and Hoogenboom, Building an in vitro immune system: human antibodies from phage display libraries. In; Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries, Id., pp 65-82). Fully human 202P5A5 monoclonal antibodies can also be produced using transgenic mice engineered to contain human immunoglobulin gene loci as described in PCT Patent Application WO096/24893, Kucherlapati and Jakobovits et al., published Dec. 3, 1997(see also, Jakobovits, 1993, Exp. Opin. Invest. Drugs 7(4):607-614; U.S. Pat. No. 6,162,963 issued 19 Dec. 2000; U.S. Pat. No. 6,150,584 issued 12 Nov. 2000; and, U.S. Pat. No. 6,114,598 issued 5 Sep. 2000). This method avoids the in vitro manipulation required with phage display technology and efficiently produces high affinity authentic human antibodies.

Reactivity of 202P5A5 antibodies with a 202P5A5-related protein can be established by a number of well known means, including Western blot, immunoprecipitation, ELISA, and FACS analyses using, as appropriate, 202P5A5-related proteins, 202P5A5-expressing cells or extracts thereof. A 202P5A5 antibody or fragment thereof can be labeled with a detectable marker or conjugated to a second molecule. Suitable detectable markers include, but are not limited to, a radioisotope, a fluorescent compound, a bio luminescent compound, chemiluminescent compound, a metal chelator or an enzyme. Further, bi-specific antibodies specific for two or more 202P5A5 epitopes are generated using methods generally known in the art. Homodimeric antibodies can also be generated by cross-linking techniques known in the art (e.g., Wolff et al., Cancer Res. 53:2560-2565).

V.) 202P5A5 CELLULAR IMMUNE RESPONSES

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., Cell 47:1071, 1986: Babbitt, B. P. et al., Nature 317: 359, 1985; Townsend, A. and Bodmer, H., Annu. Rev. Immunol. 7:601, 1989; Germain, R. N., Annu. Rev. Immunol. 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., J. Immunol. 160: 3363, 1993; Rammensee, et al., Immunogenetics 41:176, 1995; Rammensee et al., SYFPEITHI, access via World Wide Web at URL (134.2.96.221/scripts.hlaserver.dll/home.htm); Sette, A. and Sidney, J. Curr. Opin. Immunol. 10:476, 1998; Engelhard, V. H. Curr. Opin. Immunol. 6:13, 1994; Sette, A. and Grey, H. M., Curr. Opin. Immunol. 4:79, 1992; Sinigaglia, F. and Hammer, J. Curr. Biol. 6:52, 1994; Ruppert et al., Cell 74:929-937, 1993, Kondo et al., J. Immunol. 155: 4307-4312, 1995; Sidney et al., J. Immunol. 157:3480-3490, 1996; Sidney et al., Human Immunol. 45:79-93, 1996; Sette, A. and Sidney, J. Immunogenetics 1999 November; 50 (3-4): 201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. Annu. Rev. Immunol. 13:587, 1995; Smith, et al., Immunity 4:203, 1996; Fremont et al., Immunity 8:305, 1998; Stem et al., Structure 2:245, 1994: Jones, E. Y. Curr. Opin. Immunol 9:75, 1997:Brown, J. H. et al., Nature 364:33, 1993; Guo, H. C. et al., Proc. Natl. Acad. Sci. USA 90:8053, 1993; Guo, H. C. et al., Nature 360:364, 1992; Silver, M. L. et al., Nature 380:367, 1992; Matsumura, M. et al., Science 257:927, 1992; Madden et al., Cell 70:1035, 1992; Fremont, D. H. et al., Science 257:919, 1992; Saper, M. A., Bjorkman, P. J. and Wiley, D.C., J. Mol. Biol. 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified, such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., Mol. Immunol. 32:603, 1995; Celis, E. et al., Proc. Natl. Acad. Sci. USA 91; 2105, 1994; Tsai, V. et al., J. Immunol. 153:1796, 1997; Kawashima, I. et al., Human Immunol. 59:1, 1998). This procedure involves the stimulation of peripheral blood lymphocytes (PBL) from normal subjects with a test peptide in the presence of antigen presenting cells in vitro over a period of several weeks. T cells specific for the peptide became activated during this time and are detected using, e.g., a lymphokine- or $^{51}$Cr-release assay involving peptide sensitized target cells.

2) Immunization of HLA transgenic mice (see, e.g. Wentworth, P. A. et al., J. Immunol. 26:97, 1996; Wentworth, P. A. et al., Int. Immunol. 8:651, 1996; Alexander, J. et al., J. Immunol 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., *J. Exp. Med.* 181:1047, 1995; Doolan, D. L, et al., Immunity 7.97, 1997; Bertoni, R. et al., *J. Clin. Invest.* 100:503, 1987; Threlkeld, S. C. et al., J. Immunol. 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) 202P5A5 TRANSGENIC ANIMALS

Nucleic acids that encode a 202P5A5-related protein can also be used to generate either transgenic animals or "knock out" animals that, in turn, are useful in the development and screening of therapeutically useful reagents. In accordance with established techniques, cDNA encoding 202P5A5 can be used to clone genomic DNA that encodes 202P5A5. The cloned genomic sequences can then be used to generate transgenic animals containing cells that express DNA that encode 202P5A5. Methods for generating transgenic animals, particularly animals such as mice or rats, have become conventional in the art and are described, for example, in U.S. Pat. Nos. 4,736,866 issued 12 Apr. 1988, and U.S. Pat. No. 4,870, 009 issued 28 Sep. 1989. Typically, particular cells would be targeted for 202P5A5 transgene incorporation with tissue-specific enhancers.

Transgenic animals that include a copy of a transgene encoding 202P5A5 can be used to examine the effect of Increased expression of DNA that encodes 202P5A5. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 202P5A5 can be used to construct a 202P5A5 "knock out" animal that has a defective or altered gene encoding 202P5A5 as a result of homologous recombination between the endogenous gene encoding 202P5A5 and altered genomic DNA encoding 202P5A5 introduced into an embryonic cell of the animal. For example, cDNA that encodes 202P5A5 can be used to clone genomic DNA encoding 202P5A5 in accordance with established techniques. A portion of the genomic DNA encoding 202P5A5 can be deleted or replaced with another gene, such as a gene encoding a selectable marker that can be used to monitor integration. Typically, several kilobases of unaltered flanking DNA (both at the 5' and 3' ends) are included in the vector (see. e.g., Thomas and Capecchi, *Cell*, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell*, 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 202P5A5 polypeptide.

VII.) METHODS FOR THE DETECTION OF 202P5A5

Another aspect of the present invention relates to methods for detecting 202P5A5 polynucleotides and 202P5A5-related proteins, as well as methods for identifying a cell that expresses 202P5A5. The expression profile of 202P5A5 makes it a diagnostic marker for metastasized disease. Accordingly, the status of 202P5A5 gene products provides information useful for predicting a variety of factors including susceptibility to advanced stage disease, rate of progression, and/or turner aggressiveness. As discussed in detail herein, the status of 202P5A5 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 202P5A5 polynucleotides in a biological sample, such as serum, bone, prostate, and other tissues, urine, semen, cell preparations, and the like, Detectable 202P5A5 polynucleotides include, for example, a 202P5A5 gene or fragment thereof, 202P5A5 mRNA, alternative splice variant 202P5A5 mRMAs, and recombinant DNA or RNA molecules that contain a 202P5A5 polynucleotide. A number of methods for amplifying and/or detecting the presence of 202P5A5 polynucleotides are well known in the art and can be employed in the practice of this aspect of the invention.

In one embodiment, a method for defecting a 202P5A5 mRNA in a biological sample comprises producing cDNA from the sample by reverse transcription using at least one primer; amplifying the cDNA so produced using a 202P5A5 polynucleotides as sense and antisense primers to amp lily 202P5A5 cDNAs therein; and detecting the presence of the amplified 202P5A5 cDNA. Optionally, the sequence of the amplified 202P5A5 cDNA can be determined.

In another embodiment, a method of detecting a 202P5A5 gene in a biological sample comprises first isolating genomic DNA from the sample; amplifying the isolated genomic DNA using 202P5A5 polynucleotides as sense and antisense primers; and detecting the presence of the amplified 202P5A5 gene. Any number of appropriate sense and antisense probe combinations can be designed from a 202P5A5 nucleotide sequence (see, e.g., FIG. 2) and used for this purpose.

The invention also provides assays for detecting the presence of a 202P5A5 protein in a tissue or other biological sample such as serum, semen, bone, prostate, urine, cell preparations, and the like. Methods for detecting a 202P5A5-related protein are also well known and include, for example, immune precipitation, immunohistochemical analysis, Western blot analysis, molecular binding assays, ELISA, ELIFA and the like. For example, a method of detecting the presence of a 202P5A5-related protein in a biological sample comprises first contacting the sample with a 202P5A5 antibody, a 202P5A5-reactive fragment thereof, or a recombinant protein containing an antigen-binding region of a 202P5A5 antibody; and then detecting the binding of 202P5A5-related protein in the sample.

Methods for identifying a cell that expresses 202P5A5 are also within the scope of the invention. In one embodiment, an assay for identifying a cell that expresses a 202P5A5 gene comprises detecting the presence of 202P5A5 mRNA in the cell. Methods for the detection of particular mRNAs in cells are well known and include, for example, hybridization assays using complementary DNA probes (such as in situ hybridization using labeled 202P5A5 riboprobes, Northern blot and related techniques) and various nucleic acid amplification assays (such as RT-PCR using complementary primers specific for 202P5A5, and other amplification type detection methods, such as, for example, branched DNA SISBA, TMA and the like). Alternatively, an assay for identifying a cell that expresses a 202P5A5 gene comprises detecting the presence of 202P5A5-related protein in the cell or secreted by the cell. Various methods for the detection of proteins are well known in the art and are employed for the detection of 202P5A5-related proteins and cells that express 202P5A5 related proteins.

202P5A5 expression analysis is also useful as a tool for identifying and evaluating agents that modulate 202P5A5 gene expression. For example, 202P5A5 expression is significantly unregulated in prostate cancer, and is expressed in cancers of the tissues listed in Table I. Identification of a molecule or biological agent that inhibits 202P5A5 expression or over-expression in cancer cells is of therapeutic value. For example, such an agent can be identified by using a screen that quantifies 202P5A5 expression by RT-PCR, nucleic acid hybridization or antibody binding.

VIII.) METHODS FOR MONITORING THE STATUS OF 202P5A5-RELATED GENES AND THEIR PRODUCTS

Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer. Surv. 23: 19-32 (1995)). In this context, examining a biological sample for evidence of dysregulated cell growth (such as aberrant 202P5A5 expression in cancers) allows for early detection of such aberrant physiology, before a pathologic state such as cancer has progressed to a stage that therapeutic options are more limited and or the prognosis is worse, In such examinations, the status of 202P5A5 in a biological sample of interest can be compared, for example, to the status of 202P5A5 in a corresponding normal sample (e.g. a sample from that individual or alternatively another individual that is not affected by a pathology). An alteration in the status of 202P5A5 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp, Neurol. 1996 Dec. 9; 376(2): 306-14 and U.S. Pat. No. 5,837,501) to compare 202P5A5 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 202P5A5 expressing cells) as well as the level, and biological activity of expressed gene products (such as 202P5A5 mRNA, polynucleotides and polypeptides). Typically, an alteration in the status of 202P5A5 comprises a change in the location of 202P5A5 and/or 202P5A5 expressing cells and/or an increase in 202P5A5 mRNA and/or protein expression.

202P5A5 status in a sample can be analyzed by a number of means well known in the art including without limitation, Immunohistochemical analysis, in situ hybridization, RT-PCR analysis on laser capture micro-dissected samples, Western blot analysis, and tissue array analysis. Typical protocols for evaluating the status of a 202P5A5 gene and gene products are found, for example in Ausubel et al. eds., 1995, Current Protocols In Molecular Biology; Units 2 (Northern Blotting), 4 (Southern Blotting), 15 (Immunoblotting) and 18 (PCR Analysis). Thus, the status of 202P5A5 in a biological sample is evaluated by various methods utilized by skilled artisans including, but not limited to genomic Southern analysis (to examine, for example perturbations in a 202P5A5 gene), Northern analysis and/or PCR analysis of 202P5A5 mRNA (to examine, for example alternations in the polynucleotide sequences or expression levels of 202P5A5 mRNAs), and, Western and/or immunohistochemical analysis (to examine, for example alterations in polypeptide sequences, alterations in polypeptide localization within a sample, alterations in expression levels of 202P5A5 proteins and/or associations of 202P5A5 proteins with polypeptide binding partners). Detectable 202P5A5 polynucleotides include, for example, a 202P5A5 gene or fragment thereof, 202P5A5 mRNA, alternative splice variants, 202P5A5 mRNAs, and recombinant DNA or RNA molecules containing a 202P5A5 polynucleotide.

The expression profile of 202P5A5 makes it a diagnostic marker for local and/or metastasized disease, and provides information on the growth or oncogenic potential of a biological sample. In particular, the status of 202P5A5 provides information useful for predicting susceptibility to particular disease stages, progression, and/or tumor aggressiveness. The invention provides methods and assays for determining 202P5A5 status and diagnosing cancers that express 202P5A5, such as cancers of the tissues located in Table I. For example, because 202P5A5 mRNA is so highly expressed in possible and other cancers relative to normal prostate tissue, assays that evaluate the levels of 202P5A5 mRNA transcripts or proteins in a biological sample can be used to diagnose a disease associated with 202P5A5 dysregulation, and can provide prognostic information useful in defining appropriate therapeutic options.

The expression status of 202P5A5 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 202P5A5 in biological samples such as those from individuals suffering from, or suspected of suffering from a pathology characterized by dysregulated cellular growth, such as cancer.

As described above, the status of 202P5A5 in a biological sample can be examined by a number of well-known procedures in the art, For example, the status of 202P5A5 in a biological sample taken from a specific location in the body can be examined by evaluating the sample for the presence or absence of 202P5A5 expressing cells (e.g. those that express 202P5A5 mRNAs or proteins). This examination can provide evidence of dysregulated cellular growth, for example, when 202P5A5-expressing cells are found in a biological sample that does not normally contain such cells (such as a lymph node), because such alterations in the status of 202P5A5 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000); Su et al., Semin. Surg. Oncol. 18(1): 17-28 (2000) and Freeman et al., J Urol 1995 August 154(2 Pt 1);474-8).

In one aspect, the invention provides methods for monitoring 202P5A5 gene products by determining the status of 202P5A5 gene products expressed by cells from an individual suspected of having a disease associated with dysregulated cell growth (such as hyperplasia or cancer) and then comparing the status so determined to the status of 202P5A5 gene products in a corresponding normal sample. The presence of aberrant 202P5A5 gene products in the test sample relative to the normal sample provides an indication of the presence of dysregulated cell growth within the cells of the individual.

In another aspect, the invention provides assays useful in determining the presence of cancer in an individual, comprising detecting a significant increase in 202P5A5 mRNA or protein expression in a test cell or tissue sample relative to expression levels in the corresponding normal cell or tissue. The presence of 202P5A5 mRNA can, for example, be evaluated in tissues including but not limited to those listed in Table I. The presence of significant 202P5A5 expression in any of these tissues is useful to indicate the emergence, presence and/or severity of a cancer, since the corresponding normal tissues do not express 202P5A5 mRNA or express it at lower levels.

In a related embodiment, 202P5A5 status is determined at the protein level rather than at the nucleic acid level. For example, such a method comprises determining the level of 202P5A5 protein expressed by cells in a test tissue sample and comparing the level so determined to the level of 202P5A5 expressed in a corresponding normal sample. In one embodiment, the presence of 202P5A5 protein is evaluated, for example, using immunohistochemical methods. 202P5A5 antibodies or binding partners capable of detecting 202P5A5 protein expression are used in a variety of assay formats well known in the art for this purpose.

In a further embodiment, one can evaluate the status of 202P5A5 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(B):369-378). For example, a mutation in the sequence of 202P5A5 may be indicative of the presence or promotion of a tumor. Such assays therefore have diagnostic and predictive value where a mutation in 202P5A5 indicates a potential loss of function or increase in tumor growth.

A wide variety of assays for observing perturbations in nucleotide and amino acid sequences are well known in the art. For example, the size and structure of nucleic acid or amino acid sequences of 202P5A5 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. No. 5,382,510 issued 7 Sep. 1999, and U.S. Pat. No. 5,952,170 issued 17 Jan. 1995).

Additionally, one can examine the methylation status of a 202P5A5 gene in a biological sample. Aberrant demethylation and/or hypermethylation of CpG islands In gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of eases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 202P5A5. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 202P5A5 expression. The presence of RT-PCR amplifiable 202P5A5 mRNA provides an indication of the presence of cancer. RT-PCR assays are well known in the art. RT-PCR detection assays for tumor cells in peripheral blood are currently being evaluated for use in the diagnosis and management of a number of human solid tumors, in the prostate cancer field, these include RT-PCR assays for the detection of cells expressing PSA and PSM (Verkaik et al., 1997, Urol. Res. 25:373-354; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 202P5A5 mRNA or 202P5A5 protein in a tissue sample, its presence indicating susceptibility to cancer, wherein the degree of 202P5A5 mRNA expression correlates to the degree of susceptibility. In a specific embodiment, the presence of 202P5A5 in prostate or other tissue is examined, with the presence of 202P5A5 in the sample providing an indication of prostate cancer susceptibility (or the emergence or existence of a prostate tumor). Similarly, one can evaluate the integrity 202P5A5 nucleotide and amino acid sequences in a biological sample, in order to identify perturbations in the structure of these molecules such as insertions, deletions, substitutions and the like. The presence of one or more perturbations in 202P5A5 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 202P5A5 mRNA or 202P5A5 protein expressed by tumor cells, comparing the level so determined to the level of 202P5A5 mRNA or 202P5A5 protein expressed in a corresponding normal tissue taken from the same individual or a normal tissue reference sample, wherein the degree of 202P5A5 mRNA or 202P5A5 protein expression in the tumor sample relative to the normal sample indicates the degree of aggressiveness. In a specific embodiment, aggressiveness of a tumor is evaluated by determining the extent to which 202P5A5 is expressed in the tumor cells, with higher expression levels indicating more aggressive tumors. Another embodiment is the evaluation of the integrity of 202P5A5 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 202P5A5 mRNA or 202P5A5 protein expressed by cells in a sample of the tumor, comparing the level so determined to the level of 202P5A5 mRNA or 202P5A5 protein expressed in an equivalent tissue sample taken from the same individual at a different time, wherein the degree of 202P5A5 mRNA or 202P5A5 protein expression in the tumor sample over time provides information on the progression of the cancer. In a specific embodiment, the progression of a cancer is evaluated by determining 202P5A5 expression in the tumor cells over time, where increased expression over time indicates a progression of the cancer. Also, one can evaluate the integrity 202P5A5 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with anyone of a wide variety of prognostic and diagnostic protocols known in the art. For example, another embodiment of the invention is directed to methods for observing a coincidence between the expression 202P5A5 gene and 202P5A5 gene products (or perturbations in 202P5A5 gene and 202P5A5 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et. al., 1984, Anal. Quant. Cytol. 6 (2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of 202P5A5 gene and 202P5A5 gene products (or perturbations in 202P5A5 gene and 202P5A5 products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 202P5A5 gene and 202P5A5 gene products (or perturbations in 202P5A5 gene and 202P5A5 gene products) and another factor associated with malignancy entails detecting the overexpression of 202P5A5 mRNA or protein in a tissue sample, detecting the overexpression of PSA mRNA or protein in a tissue sample (or PSCA or PSM expression), and observing a coincidence of 202P5A5 mRNA or protein and PSA mRNA or protein overexpression (or PSCA or PSM expression). In a specific embodiment, the expression of 202P5A5 and PSA mRNA in prostate tissue is examined, where the coincidence of 202P5A5 and PSA mRNA overexpression in the sample indicates the existence of prostate cancer, prostate cancer susceptibility or the emergence or status of a prostate tumor, Methods for detecting and quantifying the expression of 202P5A5 mRNA or protein are described herein, and standard nucleic acid and protein detection and quantification technologies are well known in the art. Standard methods for the detection and quantification of 202P5A5 mRNA include m situ hybridization using labeled 202P5A5 riboprobes, Northern blot and related techniques using 202P5A5 polynucleotide probes, RT-PCR analysis using primers specific for 202P5A5, and other amplification type detection methods, such as, for example, branched DNA, SISBA, TMA and the like. In a specific embodiment, semi-quantitative RT-PCR is used to detect and quantify 202P5A5 mRNA expression. Any number of primers capable of amplifying 202P5A5 can be used for this purpose, including but not limited to the various primer sets specifically described herein. In a specific embodiment, polyclonal or monoclonal antibodies specifically reactive with the wild-type 202P5A5 protein can be used in an immunohistochemical assay of biopsied tissue.

IX.) IDENTIFICATION OF MOLECULES THAT INTERACT WITH 202P5A5

The 202P5A5 protein and nucleic acid sequences disclosed herein allow a skilled artisan to identify proteins, small molecules and other agents that interact with 202P5A5, as well as pathways activated by 202P5A5 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. No. 5,955,280 issued 21 Sep. 1999, U.S. Pat. No. 5,925,523 issued 20 Jul. 1999, U.S. Pat. No. 5,846,722 issued 8 Dec. 1993 and U.S. Pat. No. 6,004,746 issued 21 Dec. 1999. Algorithms are also available in the art for genome-based predictions of protein function (see, e.g., Marcotte, et al., Nature 402:4 Nov. 1999, 83-86).

Alternatively one can screen peptide libraries to identify molecules that interact with 202P5A5 protein sequences in such methods, peptides that bind to 202P5A5 are identified by screening libraries that encode a random or controlled collector of amino acids. Peptides encoded by the libraries are expressed as fusion proteins of bacteriophage coat proteins, the bacteriophage particles are it en screened against the 202P5A5 protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 202P5A5 protein sequences are disclosed for example in U.S. Pat. No. 5,723,286 issued 3 Mar. 1998 and U.S. Pat. No. 5,733,731 issued 31 Mar. 1998.

Alternatively, cell lines that express 202P5A5 are used to identify protein-protein interactions mediated by 202P5A5. Such interactions can be examined using immunoprecipitation techniques (see, e.g., Hamilton B. J., et al. Biochem. Biophys. Res. Commun. 1999, 261:646-51). 202P5A5 protein can be immunoprecipitated from 202P5A5-expressing cell lines us inn anti-202P5A5 antibodies. Alternatively, antibodies against His-tag can be used in a cell line engineered to express fusions of 202P5A5 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 202P5A5 can be identified through related embodiments of such screening assays. For example, small molecules can be identified that interfere with protein function, including molecules that interfere with 202P5A5's ability to mediate phosphorylation and de-phosphorylation, interaction with DNA or RNA molecules as an indication of regulation of cell cycles, second messenger signaling or tumorigenesis. Similarly, small molecules that modulate 202P5A5-related ion channel, protein pump, or cell communication functions are identified and used to treat patients that have a cancer that expresses 202P5A5 (see, e.g., Hille, B., Ionic Channels of Excitable Membranes $2^{nd}$ Ed., Sinauer Assoc., Sunderland, Mass., 1992), Moreover, ligands that regulate 202P5A5 function can be identified based on their ability to bind 202P5A5 and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 202P5A5 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit 202P5A5.

An embodiment of this invention comprises a method of screening for a molecule that interacts with a 202P5A5 amino acid sequence shown in FIG. 2 or FIG. 3, comprising the steps of contacting a population of molecules with a 202P5A5 amino acid sequence, allowing the population of molecules and the 202P5A5 amino acid sequence to interact under conditions that facilitate an interaction, determining the presence of a molecule that interacts with the 202P5A5 amino acid sequence, and then separating molecules that do not interact with the 202P5A5 amino acid sequence from molecules that do. In a specific embodiment, the method further comprises purifying, characterizing and identifying a molecule that interacts with the 202P5A5 amino acid sequence. The identified molecule can be used to modulate a function performed by 202P5A5. In a preferred embodiment, the 202P5A5 amino acid sequence is contacted with a library of peptides.

X.) THERAPEUTIC METHODS AND COMPOSITIONS

The identification of 202P5A5 as a protein that is normally expressed in a restricted set of tissues, but which is also expressed in cancers such as those listed in Table I, opens a number of therapeutic approaches to the treatment of such cancers.

Of note, targeted antitumor therapies have been useful even when the targeted protein is expressed on normal tissues, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

For example, Herceptin® is an FDA approved pharmaceutical that has as its active ingredient an antibody which is immunoreactive with the protein variously known as HER2, HER2/neu, and erb-b-2. It is marketed by Genentech and has been a commercially successful antitumor agent. Herceptin safes reached almost $400 million in 2002. Herceptin is a treatment for HER2 positive metastatic breast cancer. However, the expression of HER2 is not limited to such tumors. The same protein is expressed in a number of normal tissues. In particular, it is known that HER2/neu is present in normal kidney and heart, thus these tissues are present in all human recipients of Herceptin. The presence of HER2/neu in normal kidney is also confirmed by Latif, Z., et al., *B. J. U. International* (2002) 89:5-9. As shown in this article (which evaluated whether renal cell carcinoma should be a preferred indication for anti-HER2 antibodies such as Herceptin) both protein and mRNA are produced in benign renal tissues, Notably, HER2/neu protein was strongly overexpressed in benign renal tissue. Despite the fact that HER2/neu is expressed in such vital tissues as heart and kidney, Herceptin is a very useful, FDA approved, and commercially successful drug. The effect of Herceptin on cardiac tissue, i.e., "cardiotoxicity," has merely been a side effect to treatment. When patients were treated with Herceptin alone, significant cardiotoxicity occurred in a very low percentage of patients.

Of particular note, although kidney tissue is indicated to exhibit normal expression, possibly even higher expression than cardiac tissue, kidney has no appreciable Herceptin side effect whatsoever. Moreover, of the diverse array of normal tissues in which HER2 is expressed, there is very little occurrence of any side effect. Only cardiac tissue has manifested any appreciable side effect at all. A tissue such as kidney, where HER2/neu expression is especially notable, has not been the basis for any side effect, Furthermore, favorable therapeutic effects have been found for antitumor therapies that target epidermal growth factor receptor (EGFR), EGFR is also expressed in numerous normal tissues. There have been very limited side effects in normal tissues following use of anti-EGFR therapeutics.

Thus, expression of a target protein in normal tissue, even vital normal tissue, does not defeat the utility of a targeting agent for the protein as a therapeutic for certain tumors in which the protein is also overexpressed.

Accordingly, therapeutic approaches that inhibit the activity of a 202P5A5 protein are useful for patients suffering from a cancer that expresses 202P5A5. These therapeutic approaches generally fall into two classes. One class comprises various methods for inhibiting the binding or association of a 202P5A5 protein with its binding partner or with other proteins. Another class comprises a variety of methods for inhibiting the transcription of a 202P5A5 gene or translation of 202P5A5 mRNA.

X.A.) Anti-Cancer Vaccines

The invention provides cancer vaccines comprising a 202P5A5-related protein or 202P5A5-related nucleic acid. In view of the expression of 202P5A5, cancer vaccines prevent and/or treat 202P5A5-expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Such methods can be readily practiced by employing a 202P5A5-related protein, or a 202P5A5-encoding nucleic acid molecule and recombinant vectors capable of expressing and presenting the 202P5A5 immunogen (which typically comprises a number of antibody or T cell epitopes). Skilled artisans understand that a wide variety of vaccine systems for delivery of immunoreactive epitopes are known in the art (see, e.g., Heryln et al., Ann Med 1999 Feb. 31(1):68-73; Maruyama et al., Cancer Immunol Immunother 2000 June 49(3):123-32). Briefly, such methods of generating an immune response (e.g. humoral and/or cell-mediated) in a mammal, comprise the steps of: exposing the mammal's immune system to an immunoreactive epitope (e.g. an epitope present in a 202P5A5 protein shown in FIG. 3 or analog or homolog thereof) so that the mammal generates an immune response that is specific for that epitope (e.g. generates antibodies that specifically recognize that epitope). In a preferred method, a 202P5A5 immunogen contains a biological motif, see e.g., Tables VIII-XXI and XXII-XLIX, or a peptide of a size range from 202P5A5 indicated in FIG. 5, FIG. 6, FIG. 7, FIG. 8, and FIG. 9.

The entire 202P5A5 protein, immunogenic regions or epitopes thereof can be combined and delivered by various means. Such vaccine compositions can include, for example, lipopeptides (e.g., Vitiello, A. et al., J. Clin. Invest. 95:341, 1995), peptide compositions encapsulated in poly(DL-lactide-co-glycolide) ("PLG") microspheres (see, e.g., Eldridge, et al., Molec. Immunol. 28:287-294, 1991: Alonso et al., Vaccine 12:299-308, 1994; Jones et al., Vaccine 13:675-681, 1995), peptide compositions contained in immune stimulating complexes (ISCOMS) (see, e.g., Takahashi et al., Nature 344:873-875, 1990: Hu et al., Clin Exp Immunol. 113:235-243, 1998), multiple antigen peptide systems (MAPs) (see e.g., Tam, J. P., Proc. Natl. Acad. Sci. U.S.A. 85:5409-5413, 1988; Tam, J. P., J. Immunol. Methods 196:17-32, 1993), peptides formulated as multivalent peptides; peptides for use in ballistic delivery systems, typically crystallized peptides, viral delivery vectors (Perkus, M. E. et al., In: Concepts in vaccine development, Kaufmann, S. H. E., ed. p. 379, 1996; Chakrabarti S. et al., Nature 320:535, 1988; Hu, S. L, et al., Nature 320:537, 1986; Kieny, M.-P. et al., AIDS Bio/Technology 4:790, 1986; Top, F. H. et al., J. Infect. Dis. 124:148, 1971; Chanda, P. K. et al., Virology 175:35, 1990), particles of viral or synthetic origin (e.g., Kofler, N. et al., J. Immunol. Methods. 192:25, 1996; Eldridge, J. H. et al., Sem. Hematol. 30:16, 1993; Falo, L. D., Jr. et al., Nature Med. 7:649, 1995), adjuvants (Warren, H. S., Vogel, F. R., and Chedid, L. A. Annu. Rev. Immunol. 4:369, 1986; Gupta, R. K. et al., Vaccine 11:293, 1993), liposomes (Reddy, R. et al., J. Immunol. 148: 1585, 1992; Rock, K. L., Immunol. Today 17:131, 1996), or, naked or particle absorbed cDNA (Ulmer, J. B. et al. Science 259:1745, 1993; Robinson, H. L., Hunt, L. A., and Webster, R. G., Vaccine 11:957, 1993; Shiver, J. W. et al., In: Concepts in vaccine development, Kaufmann, S. H. E., p. 423, 1996; Cease, K. B., and Berzofsky, J. A.: Annu. Rev. Immunol. 12:923, 1994 and Eldridge, J. H. et al., Sem. Hematol. 30:16, 1993). Toxin-targeted delivery technologies, also known as receptor mediated targeting, such as those of Avant Immunotherapeutics, Inc. (Needham, Mass.) may also be used.

In patients with 202P5A5-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 202P5A5 protein that bind corresponding HLA alleles (see e.g., Table IV; Epimer™ and Epimatrix™, Brown University (URL brown.edu/Research/TB-HIV_Lab/epimatrix/epimatrix.html.); and, BIMAS, (URL bimas.dcrt.nih.gov/; SYFPEITHI at URL syfpeithi.bmi-heidelberg.com/). In a preferred embodiment, a 202P5A5 immunogen contains one or more amino acid sequences identified using techniques well known in the art, such as the sequences shown in Tables VIII-XXI and XXII-XLIX or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. 202P5A5 protein) so that an immune response is generated. A typical embodiment consists of a method for generating an immune response to 202P5A5 in a host, by contacting the host with a sufficient amount of at least one 202P5A5 B cell or cytotoxic T-cell epitope or analog thereof; and at least one periodic interval thereafter re-contacting the host with the 202P5A5 B cell or cytotoxic T-cell epitope or analog thereof. A specific embodiment consists of a method of generating a immune response against a 202P5A5-related protein or a man-made multiepitopic peptide comprising: administering 202P5A5 immunogen (e.g. a 202P5A5 protein or a peptide fragment thereof, a 202P5A5 fusion protein or an analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3): 164(3): 1625-1633; Alexander et al. Immunity 1994(9): 751-761 and Alexander et. al., Immunol. Res. 1998 18(2): 79-92). An alternative method comprises generating an immune response in an individual against a 202P5A5 immunogen by: administering in vivo to muscle or skin of the individual's body a DNA molecule that comprises a DNA sequence that encodes a 202P5A5 immunogen, the DNA sequence operatively linked to regulatory sequences which control the expression of the DNA sequence; wherein the DNA molecule is taken up by cells, the DNA sequence is expressed in the cells and an immune response is generated against the immunogen (see. e.g., U.S. Pat. No. 5,962,428). Optionally a genetic vaccine facilitator such as anionic lipids; saponins; lectins: estrogenic compounds: hydroxylated lower alkyls; dimethyl sulfoxide; and urea is also administered. In addition, an antiidiotypic antibody can be administered that mimics 202P5A5, in order to generate a response to the target antigen, Nucleic Acid Vaccines:

Vaccine compositions of the invention include nucleic acid-mediated modalities. DNA or RNA that encode protein (s) of the invention can be administered to a patient. Genetic immunization methods can be employed to generate prophylactic or therapeutic humoral and cellular immune responses directed against cancer cells expressing 202P5A5. Constructs comprising DNA encoding a 202P5A5-related protein/immunogen and appropriate regulatory sequences can be injected directly into muscle or skin of an individual, such that the cells of the muscle or skin take-up the construct and express the encoded 202P5A5 protein/immunogen. Alternatively, a vaccine comprises a 202P5A5-related protein. Expression of the 202P5A5-related protein immunogen results in the generation of prophylactic or therapeutic humoral and cellular immunity against cells that bear a 202P5A5 protein. Various prophylactic and therapeutic genetic immunization techniques known in the art can be used (for review, see information and references published at Internet address genweb.com). Nucleic acid-based delivery is described, for instance, in Wolff et. al., Science 247:1465 (1990) as well as U.S. Pat. Nos. 5,580,859; 5,589,466; 5,804, 566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifa, 1996, Curr. Opin. Immunol. 8:358-663; Tsang et. al., *J. Natl. Cancer Inst.* 87:982-990 (1995)). Non-viral delivery systems can also be employed by introducing naked DNA encoding a 202P5A5-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et at., *Nature* 351:458-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 202P5A5-related nucleic acid molecule. In one embodiment, the full-length human 202P5A5 cDNA is employed. In another embodiment, 202P5A5 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 202P5A5 antigen to a patient'immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et. al., 1996, Prostate 26:65-69; Murphy et. al., 1996, Prostate 29:371-380). Thus, dendritic cells can be used to present 202P5A5 peptides to T cells in the context of MHC class I or II molecules. In one embodiment, autologous dendritic cells are pulsed with 202P5A5 peptides capable of binding to MHC class I and/or class II molecules. In another embodiment, dendritic cells are pulsed with the complete 202P5A5 protein. Yet another embodiment involves engineering the overexpression of a 202P5A5 gene in dendritic cells using various implementing vectors know in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2665-2869), or tumor-derived RNA transfection (Ashley et al., 1997, J. Exp. Med. 186: 1177-1182). Cells that express 202P5A5 can also be engineered to express immune modulators, such as GM-CSF, and used as immunizing agents.

X.B.) 202P5A5 as a Target for Antibody-Based Therapy

202P5A5 is an attractive target for antibody-based therapeutic strategies. A number of antibody strategies are known in the art for targeting both extracellular and intracellular molecules (see, e.g., complement and ADCC mediated killing as well as the use of intrabodies). Because 202P5A5 is expressed by cancer cells of various lineages relative to corresponding normal cells, systemic administration of 202P5A5-immunoreactive compositions are prepared that exhibit excellent sensitivity without toxic, non-specific and/or non-target effects caused by binding of the immunoreactive composition to non-target organs and tissues. Antibodies specifically reactive with domains of 202P5A5 are useful to treat 202P5A5-expressing cancers systemically, either as conjugates with a toxin or therapeutic agent, or as naked antibodies capable of inhibiting cell proliferation or function.

202P5A5 antibodies can be introduced into a patient such that the antibody binds to 202P5A5 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 202P5A5, inhibition of ligand binding or signal transduction pathways, modulation of tumor cell differentiation, alteration of turn or angiogenesis factor profiles, and/or apoptosis.

Those skilled in the art understand that antibodies can be used to specifically target and bind immunogenic molecules such as an immunogenic region of a 202P5A5 sequence shown in FIG. 2 or FIG. 3. In addition, skilled artisans understand that it is routine to conjugate antibodies to cytotoxic agents (see, e.g., Slevers, et al. *Blood* 93:11 3678-3684 (Jun. 1, 1999)). When cytotoxic and/or therapeutic agents are delivered directly to cells, such as by conjugating them to antibodies specific for a molecule expressed by that cell (e.g. 202P5A5), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-202P5A5 antibody) that binds to a market (e.g. 202P5A5) expressed, accessible to binding or localized on the cell surfaces. A typical embodiment is a method of delivering a cytotoxic and/or therapeutic agent to a cell expressing 202P5A5, comprising conjugating the cytotoxic agent to an antibody that immunospecifically binds to a 202P5A5 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-202P5A5 antibodies can be done in accordance with various approaches that have been successfully employed in the treatment of other types of cancer, including but not limited to colon cancer (Arlen et at. 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-539), colorectal cancer (Moun et al., 1994, Cancer Res. 54:6160-6166; Velders et. al., 1995, Cancer Res. 55:4398-4403), and breast cancer (Shepard et al. 1991, J. Clin. Immunol. 11:117-127), Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp, or Bexxar™, Coulter Pharmaceuticals), while others involve co-administration of antibodies and other therapeutic agents, such as Herceptin™ (trastuzumab) with paclitaxel (Genentech, Inc.). The antibodies can be conjugated to a therapeutic agent. To treat prostate cancer, for example, 202P5A5 antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized $IgG_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064).

Although 202P5A5 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

Although 202P5A5 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 202P5A5 expression, preferably using immunohistochemical assessments of tumor tissue, quantitative 202P5A5 imaging, or other techniques that reliably indicate the presence and degree of 202P5A5 expression. Immunohistochemical analysis of tumor biopsies or surgical specimens is preferred for this purpose. Methods for immunohistochemical analysis of tumor tissues are well known in the art, Anti-202P5A5 monoclonal antibodies that treat prostate and other cancers include those that initiate a potent immune response against the tumor or those that are directly cytotoxic, in this regard, anti-202P5A5 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-202P5A5 mAbs that exert a direct biological effect on tumor growth are useful to treat cancers that express 202P5A5. Mechanisms by which directly cytotoxic mAbs act include: inhibition of cell growth, modulation of cellular differentiation, modulation of tumor angiogenesis factor profiles, and the induction of apoptosis. The mechanism (s) by which a particular anti-202P5A5 mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other n on-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 202P5A5 antigen with high affinity but exhibit low or no antigenicity in the patient.

Therapeutic methods of the invention contemplate the administration of single anti-202P5A5 mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-202P5A5 mAbs can be administered concomitantly with other therapeutic modalities, including but not limited to various chemotherapeutic agents, androgen-blockers, immune modulators (e.g., IL-2, GM-CSF), surgery or radiation. The anti-202P5A5 mAbs are administered in their "naked" or unconjugated form, or can have a therapeutic agent(s) conjugated to them.

Anti-202P5A5 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-202P5A5 antibody preparation, via an acceptable route of administration such as intravenous injection (IV), typically at a dose in the range of about 0, 1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg mAb per week are effective and wall tolerated.

Based on clinical experience with the Herceptin™ mAb in the treatment of metastatic breast cancer, an initial loading dose of approximately 4 mg/kg patient body weight IV. followed by weekly doses of about 2 mg/kg IV of the anti-202P5A5 mAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 202P5A5 expression in the patient, the extent of circulating shed 202P5A5 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 202P5A5 in a given sample (e.g. the levels of circulating 202P5A5 antigen and/or 202P5A5 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-202P5A5 antibodies can also be used in anti-cancer therapy as a vaccine for inducing an immune response to cells expressing a 202P5A5-related protein. In particular, the generation of anti-idiotypic antibodies is well known in the art, this methodology can readily be adapted to generate anti-idiotypic anti-202P5A5 antibodies that mimic an epitope on a 202P5A5 related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody an be used in cancer vaccine strategies.

X.C.) 202P5A5 as a Target for Cellular Immune Responses

Vaccines and methods of preparing vaccines that contain an immunogenically effective amount of one or more HLA-binding peptides as described herein are further embodiments of the invention, Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinants or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphonothiolated-guanine-containing (CpG) oligonucleotides has been found to increase CTL responses 10- to 100-fold, (see, e.g. Davila and Cells, J. Immunol. 165:539-547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen, Consequently, the host becomes at least partially immune to later development of cells that express or overexpress 202P5A5 antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA), For HLA Class II a similar rationale is employed; again 3-4 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that is does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1 Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 152:3915-3925, 1999; An, L. and Whitton, J. L, *J. Virol.* 71:2292, 1997; Thomson, S. A. et. al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 202P5A5, the PADRE® universal helper T cell epitope or multiple HTL epitopes from 202P5A5 (see e.g., Tables VIII-XXI and XXII to XLIX), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g., poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an E. coli origin of replication; and an E. coli selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate E. coli strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence. If desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in E. coli followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, Bio Techniques 6(7):682 (1988); U.S. Pat. No. 5,279,833; WO 91/06309; and Felgner, et. al., Proc. Nat'l Acad. Sci. USA 84:7413 (1987). In addition, peptides and compounds referred to collectively as protective, interactive, non-condensing compounds (PINC) could also be completed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines, cytolysis, detected by $^{51}$Cr release, indicated both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to mini gene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No.

5,204,253. Using tills technique, particles comprised solely of DNA are administered, in a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at me amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class ii molecules. Examples of such amino acid bind many HLA Class II molecules include sequences from antigens such as tetanus toxoid at positions 830-843 (QYIKANSKFIGITE; SEQ ID NO: 24), *Plasmodium falciparum* circumsporozoite (CS) protein at positions 378-398 (DIEKKIAKMEKASSVFNVVNS; SEQ ID NO: 25): and *Streptococcus* 18 kD protein at positions 116-131 (GAVDSILGGVATYGAA; SEQ ID NO: 26). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed, most preferably, to bind most HLA-DR (human HLA class II) molecules. For instance, a pan-DR-binding epitope peptide having the formula: aKXVAAWTLKAa (SEQ ID NO: 27), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes b lymphocytes or T lymphocytes. Lipids have been identified as agents capable of priming CTL in vivo. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinyl-seryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to prime specifically an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment a vaccine comprises peptide-pulsed DCs which present the pulsed peptide epitopes completed with HLA molecules on their surfaces.

The DC can be pulsed ex vivo with a cocktail of peptides, some of which stimulate CTL responses to 202P5A5. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 202P5A5.

X.D. Adoptive Immunotherapy

Antigenic 202P5A5-related peptides are used to elicit a CTL and/or HTL response ex vivo, as well. The resulting CTL or HTL cells, can be used to treat turners in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC) such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 202P5A5. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and seventy of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 202P5A5. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 202P5A5-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 202P5A5, a vaccine comprising 202P5A5-specific CTL may be more efficacious in killing tumor cells in patient with advanced disease than alternative embodiments.

It is generally important to provide an amount of the peptide epitope delivered by a mode of administration sufficient to stimulate effectively a cytotoxic T cell response, compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µper 70 kilogram patient. Boosting dosages of between about 1.0 µg to about 50,000 µg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these states dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, 17$^{th}$ Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5\text{-}10^1$ to $5\times10^9$ pfu.

For antibodies, a treatment generally involves repeated administration of the anti-202P5A5 antibody preparation, via an acceptable route of administration such as intravenous injection (IV). Typically at a dose in the range of about 0.1 to about 10 mg/kg body weight. In general, doses in the range of 10-500 mg mAb per week are effective and well tolerated. Moreover, an initial loading dose of approximately 4 mg/kg patient body weight IV, followed by weekly doses of about 2 mg/kg IV of the anti-202P5A5 mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 202P5A5 expression in the patient, the extent of circulating shed 202P5A5 antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 µg-1 mg, 1 mg-50 mg, 50 mg-100 mg, 100 mg-200 mg, 200 mg-300 mg, 400 mg-500 mg, 500 mg-500 mg, 600 mg-700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 8, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg m$^2$ of body weight, e.g., followed in tow, three or four weeks by weekly of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg, Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^a$ cells, about $10^{11}$ to about $10^{11}$ cells, or about $10^a$ to about $5\times10^{10}$ cells. A dose may also about $10^6$ cells/m$^2$ to about $10^{10}$ cells/m$^2$, or about $10^6$ cells/m$^2$ to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:457 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, an generally 10-95% of active ingredient, that is, one or more peptides of the invention, and more preferably at a concentration of 25%-76%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) DIAGNOSTIC AND PROGNOSTIC EMBODIMENTS OF 202P5A5

As disclosed herein, 202P5A5 polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of 202P5A5 in normal tissues, and patient specimens").

202P5A5 can be analogized to a prostate associated antigen PSA, the archetypal marker that has been used by medical practitioners for years to identify and monitor the presence of prostate cancer (see, e.g., Merrill et al., J. Urol. 163(2):503-5120 (2000); Polascik et al., J. Urol. August; 162(21:293-306 (1999) and Fortier et al., J. Nat. Cancer Inst. 91(19): 1635-1640 (1999)). A variety of other diagnostic markers are also used in similar contexts including p53 and K-ras (see, e.g., Tulchinsky e al., Int J Mol Med 1999 July 4(1):99-102 and Minimoto et al., Cancer Detect Prev 2000; 24(1):1-12). Therefore, this disclosure of 202P5A5 polynucleotides and polypeptides (as well as 202P5A5 polynucleotide probes and anti-202P5A5 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 202P5A5 polynucleotides, polypeptides, reactive T cells and antibodies are analogous to those methods from well-established diagnostic assays, which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):537-74(1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 202P5A5 polynucleotides described herein can be utilized in the same way to detect 202P5A5 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192 (3):233-7 (1995)), the 202P5A5 polypeptides described herein can be utilized to generate antibodies for use in detecting 202P5A5 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 202P5A5 polynucleotides and/or polypeptides can be used to provide evidence of metastasis. For example, when a biological sample from tissue that does not normally contain 202P5A5-expressing cells (lymph node) is found to contain 202P5A5-expressing cells such as the 202P5A5 expression seen in LAPC4 and LAPC9, xenografts isolated from lymph node and bone metastasis, respectively, this finding is indicative of metastasis.

Alternatively 202P5A5 polynucleotides and/or polypeptides can be used to provide evidence of cancer, for example, when cells in a biological sample that do not normally express 202P5A5 or express 202P5A5 at a different level are found to express 202P5A5 or have an increased expression of 202P5A5 (see, e.g., the 202P5A5 expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 202P5A5) such as PSA, PSCA etc. (see, e.g., Alan en et al., Pathol. Res. Pract. 192(3): 233-237(1996).

The use of immunohistochemistry to identify the presence of a 202P5A5 polypeptide within a tissue section can indicate an altered state of certain cells within that tissue. It is well understood in the art that the ability of an antibody to localize to a polypeptide that is expressed in cancer cells is a way of diagnosing presence of disease, disease stage, progression and/or tumor aggressiveness. Such an antibody can also detect an altered distribution of the polypeptide within the cancer cells, as compared to corresponding non-malignant tissue.

The 202P5A5 polypeptide and immunogenic compositions are also useful in view of the phenomena of altered subcellular protein localization in disease states. Alteration of cells from normal to diseased state causes changes in cellular morphology and is often associated with changes in subcellular protein localization/distribution. For example, cell membrane proteins that are expressed in a polarized manner in normal cells can be altered in disease, resulting in distribution of the protein in a n on-polar manner over the whole cell surface.

The phenomenon of altered subcellular protein localization in a disease state has been demonstrated with MUC1 and Her2 protein expression by use of immunohistochemical means. Normal epithelial cells have a typical apical distribution of MUC1, in addition to some supranuclear localization of the glycoprotein, whereas malignant lesions often demonstrate an apolar staining pattern (Diaz et al., The Breast Journal. 7; 40-45 (2001); Zhang et al, Clinical Cancer Research, 4; 2669-2676 (1993): Cao, et al., The Journal of Histochemistry and Cytochemistry, 45:1547-1557 (1997)). In addition, normal breast epithelium is either negative for Her2 protein or exhibits only a basolateral distribution whereas malignant cells can express the protein over the whole cell surface (De Potter, et al., International Journal of Cancer, 44: 1547-1557 (1989). McCormick et al, 117; 935-943 (2002). Alternatively, distribution of the protein may be altered from a surface only localization to include diffuse cytoplasmic expression in the diseased state. Such an example can be seen with MUC1 (Diaz, et al, The Breast Journal, 7: 40-45 (2001)).

Alteration in the localization/distribution of a protein in the cell, as detected by immunohistochemical methods, can also provide valuable information concerning the favorability of certain treatment modalities. This last point is illustrated by a situation where a protein may be intracellular in normal tissue, but cell surface in malignant cells; the cell surface location makes the cells favorably amenable to antibody-based diagnostic and treatment regimens. When such an alteration of protein localization occurs for 202P5A5, the 202P5A5 protein and immune responses related thereto are very useful. Accordingly, the ability to determine whether alteration of subcellular protein localization occurred for 24P4C12 make the 202P5A5 protein and immune responses related thereto very useful. Use of (tie 202P5A5 compositions allows those skilled in the art to make important diagnostic and therapeutic decisions.

Immunohistochemical reagents specific to 202P5A5 are also useful to detect metastases of tumors expressing 202P5A5 when the polypeptide appears in tissues where 202P5A5 is not normally produced.

Thus, 202P5A5 polypeptides and antibodies resulting from immune responses thereto are useful in a variety of important contexts such as diagnostic, prognostic, preventative and/or therapeutic purposes known to those skilled in the art.

Just as PSA polynucleotide fragments and polynucleotide variants are employed by skilled artisans for use in methods of monitoring PSA, 202P5A5 polynucleotide fragments and polynucleotide variants are used in an analogous manner, in particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G, Biotechniques 25(3), 472-476, 478-480 (1998); Robertson et al., Methods Mol. Biol. 96:121-154 (1998)). An additional illustration of the use of such fragments is provided in the Example entitled "Expression analysis of 202P5A5 in normal tissues, and patient specimens," where a 202P5A5 polynucleotide fragment is used as a probe to show the expression of 202P5A5 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November-December 11(6):407-13 and Current Protocols In Molecular Biology, Volume 2, Unit 2, Frederick M. Ausubel et al. eds., 1995)), Polynucleotide fragments and variants are useful in this context where they are capable of binding to a target polynucleotide sequence (e.g., a 202P5A5 polynucleotide shown in FIG. 2 or variant thereof) under conditions of high stringency.

Furthermore, PSA polypeptides which contain an epitope that can be recognized by an antibody or T cell that specifically binds to that epitope are used in methods of monitoring PSA. 202P5A5 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols in Molecular Biology, Volume 2, Unit 16, Frederick M. Ausubel et al. eds., 1996). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g. U.S. Pat. No. 5,840,501 and U.S. Pat. No. 5,939,533). For example it may be preferable to utilize a polypeptide comprising one of the 202P5A5 biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cells specific for a target polypeptide sequence (e.g., a 202P5A5 polypeptide shown in FIG. 3).

As shown herein, the 202P5A5 polynucleotides and polypeptides (as well as the 202P5A5 polynucleotide probes and anti-202P5A5 antibodies or T cells used to identify the presence of these molecules) exhibit specific properties that make them useful in diagnosing cancers such as those listed in Table I. Diagnostic assays that measure the presence of 202P5A5 gene products, in order to evaluate the presence or onset of a disease condition described herein, such as prostate cancer, are used to identify patients for preventive measures or further monitoring, as has been done so successfully with PSA, Moreover, these materials satisfy a need in the art for molecules having similar of complementary characteristics to PSA in situations where, for example, a definite diagnosis of metastasis of prostatic origin cannot be made on the bases of a test for PSA alone (see, e.g., Alanen et al., Pathol. Res. Pract. 192(3): 233-237 (1996)), and consequently, materials such as 202P5A5 polynucleotides and polypeptides (as well as the 202P5A5 polynucleotide probes and anti-202P5A5 antibodies used to identify the presence of these molecules) need to be employed to confirm a metastases of prostatic origin.

Finally, in addition to their use in diagnostic assays, the 202P5A5 polynucleotides disclosed herein have a number of other utilities such as their use in the identification of ontogenetic associated chromosomal abnormalities in the chromosomal region to which the 202P5A5 gene maps (see the Example entitled "Chromosomal Mapping of 202P5A5" below). Moreover, in addition to their use in diagnostic assays, the 202P5A5-related proteins and polynucleotides disclosed herein have other utilities such as their use in the forensic analysis of tissues of unknown origin (see, e.g., Takahama K Forensic Sci Int 1996 Jun. 28; 80(1-2): 63-9).

Additionally, 202P5A5-related proteins or polynucleotides of the invention can be used to treat a pathologic condition characterized by the over-expression of 202P5A5. For example, the amino acid or nucleic acid sequence of FIG. 2 or FIG. 3, or fragments of either, can be used to generate an immune response to a 202P5A5 antigen. Antibodies or other molecules that react with 202P5A5 can be used to modulate the function of this molecule, and thereby provide a therapeutic benefit.

XII.) INHIBITION OF 202P5A5 PROTEIN FUNCTION

The invention includes various methods and compositions for inhibiting the binding of 202P5A5 to its binding partner or its association with other protein(s) as well as methods for inhibiting 202P5A5 function.

XII.A.) Inhibition of 202P5A5 With Intracellular Antibodies

In one approach, a recombinant vector that encodes single chain antibodies that specifically bind to 202P5A5 are introduced into 202P5A5 expressing cells via gene transfer technologies. Accordingly, the encoded single chain anti-202P5A5 antibody is expressed intracellularly, binds to 202P5A5 protein, and thereby inhibits its function. Methods for engineering such intracellular single chain antibodies are well know. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1996, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to target precisely the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic intrabodies are used to sequester factors within the cytosol, thereby preventing them from being transported to their natural cellular destination.

one embodiment, intra bodies are used to capture 202P5A5 in the nucleus, thereby preventing its activity within the nucleus. Nuclear targeting signals are engineered into such 202P5A5 intrabodies in order to achieve the desired targeting. Such 202P5A5 intrabodies are designed to bind specifically to a particular 202P5A5 domain. In another embodiment, cytosolic intrabodies that specifically bind to a 202P5A5 protein are used to prevent 202P5A5 from gaining access to the nucleus, thereby preventing it from exerting any biological activity within the nucleus (e.g., preventing 202P5A5 from forming transcription complexes with other factors.

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 8 Jul. 1999).

XII.B.) Inhibition of 202P5A5 with Recombinant Proteins

In another approach, recombinant molecules bind to 202P5A5 and thereby inhibit 202P5A5 function. For example, these recombinant molecules prevent or inhibit 202P5A5 from accessing/binding to its binding partners) or associating with other protein(s). Such recombinant molecules can, for example, contain the reactive part(s) of a 202P5A5 specific antibody molecule. In a particular embodiment, the 202P5A5 binding domain of a 202P5A5 binding partner is engineered into a dimeric fusion protein, whereby the fusion protein comprises two 202P5A5 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 202P5A5, whereby the dimeric fusion protein specifically binds to 202P5A5 and blocks 202P5A5 interaction with a binding partner. Such dimeric fusion proteins are further continued into multimeric proteins using known antibody linking technologies.

XII.C.) Inhibition of 202P5A5 Transcription or Translation

The present invention also comprises various methods and compositions for inhibiting the transcription of the 202P5A5 gene. Similarly, the invention also provides methods and compositions for inhibiting the translation of 202P5A5 mRNA into protein.

In one approach, a method of inhibiting the transcription of the 202P5A5 gene comprises contacting the 202P5A5 gene with a 202P5A5 antisense polynucleotide. In another approach, a method of inhibiting 202P5A5 mRNA translation comprises contacting a 202P5A5 mRNA with an antisense polynucleotide. In another approach, a 202P5A5 specific ribozyme is used to cleave a 202P5A5 message, thereby inhibiting translation. Such antisense and ribozyme based methods can also be directed to the regulatory regions of the 202P5A5 gene, such as 202P5A5 promoter and/or enhancer elements. Similarly, proteins capable of inhibiting a 202P5A5 gene transcription factor are used to inhibit 202P5A5 mRNA transcription. The various polynucleotides and compositions useful in the aforementioned methods have been described above. The use of antisense and ribozyme molecules to inhibit transcription and translation is well known in the art.

Other factors that inhibit the transcription of 202P5A5 by interfering with 202P5A5 transcriptional activation are also useful to treat cancers expressing 202P5A5. Similarly, factors that interfere with 202P5A5 processing are useful to treat cancers that express 202P5A5. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 202P5A5 (i.e., antisense, ribozyme, polynucleotides encoding intrabodies and other 202P5A5 inhibitory molecules). A number of gene therapy approaches are known in the art. Recombinant vectors encoding 202P5A5 antisense polynucleotides, ribozymes, factors capable of interfering with 202P5A5 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems, in vitro assays that evaluate therapeutic activity include cell growth assays, soft agar assays and other assays indicative of tumor promoting activity, binding assays capable of determining the extent to which a therapeutic composition will inhibit the binding of 202P5A5 to a binding partner, etc.

In vivo, the effect of a 202P5A5 therapeutic composition can be evaluated in a suitable animal model. For example, xenogeneic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition, The therapeutic compositions used in the practice of the foregoing methods can be formulated into pharmaceutical compositions comprising a carrier suitable for the desired delivery method. Suitable carriers include any material that when non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal. Ed., 1980), Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection, Dosages and administration protocols for the treatment of cancers using the foregoing methods will vary with the method and the target cancer, and will generally depend on a number of other factors appreciated in the art.

XIII.) IDENTIFICATION, CHARACTERIZATION AND USE OF MODULATORS of 202P5A5

Methods to Identify and Use Modulators

In one embodiment, screening is performed to identify modulators that induce or suppress a particular expression profile, suppress or induce specific pathways, preferably generating the associated phenotype thereby. In another embodiment, having identified differentially expressed genes important in a particular state, screens are performed to identify modulators that alter expression of individual genes, either increase or decrease. In another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition, screens are done for genes that are induced in response to a candidate agent. After identifying a modulator (one that suppresses a cancer expression pattern leading to a normal expression pattern, or a modulator of a cancer gene that leads to expression of the gene as in normal tissue) a screen is performed to identify genes that are specifically modulated in response to the agent. Comparing expression profiles between normal tissue and agent treated cancer tissue reveals genes that are not expressed in normal tissue or cancer tissue, but are expressed in agent treated tissue, and vice versa. These agent-specific sequences are identified and used by methods described herein for cancer genes or proteins. In particular these sequences and the proteins they encode are used in marking or identifying agent-treated cancer tissue sample.

Modulator-Related Identification and Screening Assays
Gene Expression-Related Assays Proteins, nucleic acids, and antibodies of the invention are used in screening assays. The cancer-associated proteins, antibodies, nucleic acids, modified proteins and cells containing these sequences are used in screening assays, such as evaluating the effect of drug candidates on a "gene expression profile," expression profile of polypeptides or alteration of biological function. In one embodiment, the expression profiles are used, preferably in conjunction with high throughput screening techniques to allow monitoring for expression profile genes after treatment with a candidate agent (e.g., Davis, G F, et al, J Biol Screen 7:69 (2002); Zlokarnik, et. al., Science 279:84-8 (1993); Heid, Genome Res 6:966-94, 1996).

The cancer proteins, antibodies, nucleic acids, modified proteins and cells containing the native or modified cancer proteins or genes are used in screening assays. That is, the present invention comprises methods for screening for compositions which modulate the cancer phenotype or a physiological function of a cancer protein of the invention. This is done on a gene itself or by evaluating the effect of drug candidates on a "gene expression profile" or biological function. In one embodiment, expression profiles are used, preferably in conjunction with high throughput screening techniques to allow monitoring after treatment with a candidate agent, see Zlokarnik, supra.

A variety of assays are executed directed to the genes and proteins of the invention. Assays are run on an individual nucleic acid or protein level. That is, having identified a particular gene as up regulated in cancer, test compounds are screened for the ability to modulate gene expression or for binding to the cancer protein of the invention. "Modulation" in this context includes an increase or a decrease in gene expression. The preferred amount of modulation will depend on the original change of the gene expression in normal versus tissue undergoing cancer, with changes of at least 10%, preferably 50%, more preferably 100-300%, and in some embodiments 300-1000% or greater. Thus, if a gene exhibits a 4-fold increase in cancer tissue compared to normal tissue, a decrease of about four-fold is often desired; similarly, a 10-fold decrease in cancer tissue compared to normal tissue a target value of a 10-fold increase in expression by the test compound is often desired. Modulators that exacerbate the type of gene expression seen in cancer are also useful, e.g., as an upregulated target in further analyses.

The amount of gene expression is monitored using nucleic acid probes and the quantification of gene expression levels, or, alternatively, a gene product itself is monitored, e.g., through the use of antibodies to the cancer protein and standard immunoassays. Proteomics and separation techniques also allow for quantification of expression.

Expression Monitoring to Identify Compounds that Modify Gene Expression

In one embodiment, gene expression monitoring, i.e., an expression profile, is monitored simultaneously for a number of entities. Such profiles will typically involve one or more of the genes of FIG. 2. In this embodiment, e.g., cancer nucleic and probes are attached to biochips to detect and quantify cancer sequences in a particular cell. Alternatively, PCR can be used. Thus, a series, e.g., wells of a microtiter plate, can be used with dispensed primers in desired wells. A PCR reaction can then be performed and analyzed for each well.

Expression monitoring is performed to identify compounds that modify the expression of one or more cancer-associated sequences, e.g., a polynucleotide sequence set out in FIG. 2. Generally, a test modulator is added to the cells prior to analysis. Moreover, screens are also provided to identify agents that modulate cancer, modulate cancer proteins of the invention, bind to a cancer protein of the invention, or interfere with the binding of a cancer protein of the invention and an antibody or other binding partner.

In one embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds," as compounds for screening, or as therapeutics.

In certain embodiments, combinatorial libraries of potential modulators are screened for an ability to bind to a cancer polypeptide or to modulate activity. Conventionality, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

As noted above, gene expression monitoring is conveniently used to test candidate modulators (e.g., protein, nucleic acid or small molecule). After the candidate agent has been added and the cells allowed to incubate for a period, the sample containing a target sequence to be analyzed is, e.g., added to a biochip.

If required, the target sequence is prepared using known techniques. For example, a sample is treated to lyse the cells, using known lysis buffers, electroporation, etc, with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

The target sequence can be labeled with, e.g., a fluorescent, a chemiluminescent, a chemical, or a radioactive signal, to provide a means of detecting the target sequence's specific binding to a probe. The label also can be an enzyme, such as alkaline phosphatase or horseradish peroxidase, which when provided with an appropriate substrate produces a product that is detected. Alternatively, the label is a labeled compound or small molecule, such as an enzyme inhibitor, that binds but is not catalyzed or altered by the enzyme. The label also can be a moiety or compound, such as an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697. In this embodiment, in general, the target nucleic acid is prepared as outlined above, and then added to the biochip comprising a plurality of nucleic acid probes, under conditions that allow the formation of a hybridization complex.

A variety of hybridization conditions are used in the present invention, including high, moderate and low stringency conditions as outlined above. The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S. Pat. No. 5,681,697. Thus, it can be desirable to perform certain steps at higher stringency conditions to reduce non-specific binding.

The reactions outlined herein can be accomplished in a variety of ways. Components of the reaction can be added simultaneously, or sequentially, in different orders, with preferred embodiments outlined below. In addition, the reaction may include a variety of other reagents. These include salts, buffers, neutral proteins, e.g. albumin, detergents, etc. which can be used to facilitate optimal hybridization and detection, and/or reduce nonspecific or background interactions. Reagents dial otherwise improve the efficiency of the assay, such as protease inhibitors, nuclease inhibitors, anti-microbial agents, etc., may also be used as appropriate, depending on the sample preparation methods and purity of the target. The assay data are analyzed to determine the expression levels of individual genes, and changes in expression levels as between states, forming a gene expression profile.

Biological Activity-Related Assays

The invention provides methods identify or screen for a compound that modulates the activity of a cancer-related gene or protein of the invention. The methods comprise adding a test compound, as defined above, to a cell comprising a cancer protein of the invention. The cells contain a recombinant nucleic acid that encodes a cancer protein of the invention. In another embodiment, a library of candidate agents is tested on a plurality of cells.

In one aspect, the assays are evaluated in the presence or absence or previous or subsequent exposure of physiological signals, e.g. hormones, antibodies, peptides, antigens, cytokines, growth factors, action potentials, pharmacological agents including chemotherapeutics, radiation, carcinogenics, or other cells (i.e., cell-cell contacts). In another example, the determinations are made at different stages of the cell cycle process. In this way compounds that modulate genes or proteins of the invention are identified. Compounds with pharmacological activity are able to enhance or interfere with the activity of the cancer protein of the invention. Once identified, similar structures are evaluated to identify critical structural features of the compound.

In one embodiment, a method of modulating (inhibiting) cancer cell division is provided; the method comprises administration of a cancer modulator. In another embodiment, a method of modulating (e.g., inhibiting) cancer is provided: the method comprises administration of a cancer modulator. In a further embodiment, methods of treating cells or individuals with cancer are provided; the method comprises administration of a cancer modulator.

In one embodiment, a method for modulating the status of a cell that expresses a gene of the invention is provided. As used herein status comprises such art-accepted parameters such as growth, proliferation, survival, function, apoptosis, senescence, location, enzymatic activity, signal transduction, etc, of a cell. In one embodiment, a cancer inhibitor is an antibody as discussed above. In another embodiment, the cancer inhibitor is an antisense molecule. A variety of cell growth, proliferation, and metastasis assays are known to those of skill in the art, as described herein.

High Throughput Screening to Identify Modulators

The assays to identify suitable modulators are amenable to high throughput screening. Preferred assays thus detect enhancement or inhibition of cancer gene transcription, inhibition or enhancement of polypeptide expression, and inhibition or enhancement of polypeptide activity.

In one embodiment, modulators evaluated in high throughput screening methods are proteins, often naturally occurring proteins or fragments of naturally occurring proteins. Thus, e.g., cellular extracts containing proteins, or random or directed digests of proteinaceous cellular extracts, are used. In this way, libraries of proteins are made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes, or ligands and receptors.

Use of Soft Agar Growth and Colony Formation to Identify and Characterize Modulators Normal cells require a solid substrate to attach and grow. When cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, can regenerate normal phenotype and once again require a solid substrate to attach to and grow. Soft agar growth or colony formation in assays are used to identify modulators of cancer sequences, which when expressed in host cells, inhibit abnormal cellular proliferation and transformation. A modulator reduces or eliminates the host cells' ability to grow suspended in solid or semisolid media, such as agar.

Techniques for soft agar growth or colony formation in suspension assays are described in Freshney, Culture of Animal Cells a Manual of Basic Technique (3rd ed., 1994). See also, the methods section of Garkavtsev et al. 1996), supra.

Evaluation of Contact Inhibition and Growth Density Limitation to Identify and Characterize Modulators Normal cells typically grow in a flat and organized pattern in cell culture until they touch other cells, when the cells touch one another, they are contact inhibited and stop growing. Transformed cells, however, are not contact inhibited and continue to grow to high densities in disorganized foci. Thus, transformed cells grow b a higher saturation density than corresponding normal cells. This is defected morphologically by the formation of a disoriented monolayer of cells or cells in foci. Alternatively, labeling index with ($^3$H)-thymidine at saturation density is used to measure density limitation of growth, similarly an MTT or Alamar blue assay will reveal proliferation capacity of cells and the ability of modulators to affect same. See Freshney (1994), supra. Transformed cells, when transfected with tumor suppressor genes, can regenerate a normal phenotype and become contact inhibited and would grow to a lower density.

In this assay, labeling index with $^3$H-thymidine at saturation density is a preferred method of measuring density limitation of growth. Transformed host cells are transfected with a cancer-associated sequence and are grown for 24 hours at saturation density in non-limiting medium conditions. The percentage of cells labeling with ($^3$H)-thymidine is determined by incorporated cpm.

Contact independent growth is used to identify modulators of cancer sequences, which had led to abnormal cellular proliferation and transformation. A modulator reduces or eliminates contact independent growth, and returns the cells to a normal phenotype.

Evaluation of Growth Factor or Serum Dependence to Identify and Characterize Modulators Transformed cells have lower serum dependence than their normal counterparts (see, e.g., Tamin, J. Natl. Cancer Inst. 37:167-175 (1966); Eagle et al., J. Exp. Med 131:836-879 (1970)); Freshney, supra. This is in part due to release of various growth factors by the transformed cells. The degree of growth factor or serum dependence of transformed host cells can be compared with that of control. For example, growth factor or serum dependence of a cell is monitored in methods to identify and characterize compounds that modulate cancer-associated sequences of the invention.

Use of Tumor-specific Marker Levels to Identify and Characterize Modulators

Tumor cells release an increased amount of certain factors (hereinafter "tumor specific markers") than their normal counterparts, For exam pie, plasminogen activator (PA) is released from human glioma at a higher level than from normal brain cells (see, e.g., Gullino, Angiogenesis, Tumor Vascularization, and Potential Interference with Tumor Growth, in Biological Responses in Cancer, pp, 178-184 (Mihich (ed.) 1985)). Similarly, Tumor Angiogenesis Factor (TAF) is released at a higher level in tumor cells than their normal counterparts. See, e.g., Folkman, Angiogenesis and Cancer, Sem Cancer Biol. (1992)), while bFGF is released from endothelial tumors (Ensoli, B et al).

Various techniques which measure the release of these factors are described in Freshney (1994), supra. Also, see, Unkless et al., J. Biol, Chem. 249:4295-4305(1974); Strickland & Beers, J. Biol. Chem. 251:5694-5702 (1976), Whur et al., Br. J. Cancer 42:305-312 (1980); Gullino, Angiogenesis, Tumor Vascularization, and Potential Interference with Tumor Growth, in Biological Responses in Cancer, pp, 178-184 (Mihich (ed.) 1985): Freshney, Anticancer Res, 5:111-130 (1985). For example, tumor specific marker levels are monitored in methods to identify and characterize compounds that modulate cancer-associated sequences of the invention.

Invasiveness into Matrigel to Identify and Characterize Modulators

The degree of invasiveness into Matrigel or an extracellular matrix constituent can be used as an assay to identify and characterize compounds that modulate cancer associated sequences. Tumor cells exhibit a positive correlation between malignancy and invasiveness of cells into Matrigel or some other extracellular matrix, constituent. In this assay, tumorigenic cells are typically used as host cells. Expression of a tumor suppressor gene in these host cells would decrease invasiveness of the host cells. Techniques described in Cancer Res. 1999; 59:6010; Freshney (1994), supra, can be used. Briefly, the level of invasion of host cells is measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}1$ and counting the radioactivity on the distal side of the filter or bottom of the dish. See, e.g., Freshney (1984), supra.

Evaluation of Tumor Growth in Vivo to Identify and Characterize Modulators

Effects of cancer-associated sequences on cell growth are tested in transgenic or immune-suppressed organisms. Transgenic organisms are prepared in a variety of art-accepted ways. For example, knock-out transgenic organisms, e.g., mammals such as mice, are made, in which a cancer gene is disrupted or in which a cancer gene is inserted. Knock-out transgenic mice are made by insertion of a marker gene or other heterologous gene into the endogenous cancer gene site in the mouse genome via homologous recombination. Such mice can also be made by substituting the endogenous cancer gene with a mutated version of the cancer gene, or by mutating the endogenous cancer gene, e.g., by exposure to carcinogens.

To prepare transgenic chimeric animals, e.g., mice, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells some of which are derived from the mutant cell line. Therefore, by breeding the chimeric mice it is possible to obtain a new line of mice containing the introduced genetic lesion (see, e.g., Capecchi et al., Science 244:1288 (1989)). Chimeric mice can be derived according to U.S. Pat. No. 6,386,797, issued 2 Apr. 2002; U.S. Pat. 6,107,540 issued 22 Aug. 2000; Hogan et al., Manipulating the Mouse Embryo: A laboratory Manual, Cold Spring Harbor Laboratory (1988) and Teratocarcinomas and Embryonic Stem Cells: A Practical Approach, Robertson, ed., IRL Press, Washington, D.C., (1987).

Alternatively, various immune-suppressed or immune-deficient host animals can be used, For example, a genetically athymic "nude" mouse (see, e.g., Giovanella et. al., J. Natl. Cancer Inst. 52:921 (1974)), a SCID mouse, a thymectornized mouse, or an irradiated mouse (see, e.g., Bradley et al., Br. J. Cancer 38:263 (1978); Selby et al., Br. J. Cancer 41:52 (1980)) can be used as a host. Transplantable tumor cells (typically about $10^6$ cells) injected into isogenic hosts produce invasive tumors in a high proportion of cases, while normal cells of similar origin will not. In hosts which developed invasive tumors, cells expressing cancer-associated sequences are injected subcutaneously or orthotopically. Mice are then separated into groups, including control groups and treated experimental groups) e.g. treated with a modulator). After a suitable length of time, preferably 4-8 weeks, tumor growth is measured (e.g., by volume or by its two largest dimensions, or weight) and compared to the control. Tumors that have statistically significant reduction (using, e.g., Student's T test) are said to have inhibited growth.

In Vitro Assays to Identify and Characterize Modulators

Assays to identify compounds with modulating activity can be performed in vitro. For example, a cancer polypeptide is first contacted with a potential modulator and incubated for a suitable amount of time, e.g., from 0.5 to 48 hours. In one embodiment, the cancer polypeptide levels are determined in vitro by measuring the level of protein or mRNA, The level of protein is measured using immunoassays such as Western blotting, ELISA and the like with an antibody that selectively binds to the cancer polypeptide or a fragment thereof. For measurement of mRNA, amplification, e.g., using PCR, LCR, or hybridization assays, e.g., Northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a cancer protein promoter operably linked to a reporter gene such as luciferase, green fluorescent protein, CAT, or P-gal. The reporter construct is typically transfected into a cell. After treatment with a potential modulator, the amount of reporter gene transcription, translation, or activity is measured according to standard techniques known to those of skill in the art (Davis G F, supra; Gonzalez, J. & Negulescu, P. Curr. Opin. Biotechnol. 1998:9:624).

As outlined above, in vitro screens are done on individual genes and gene products. That is, having identified a particular differentially expressed gene as important in a particular state, screening of modulators of the expression of the gene or the gene product itself is performed.

In one embodiment, screening for modulators of expression of specific gene(s) is performed. Typically, the expression of only one or a few genes is evaluated, in another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships, Binding Assays to Identify and Characterize Modulators In binding assays in accordance with the invention, a purified or isolated gene product of the invention is generally used. For example, antibodies are generated to a protein of the invention, and immunoassays are run to determine the amount and/or location of protein. Alternatively, cells comprising the cancer proteins are used in the assays.

Thus, the methods comprise combining a cancer protein of the invention and a candidate compound such as a ligand, and determining the binding of the compound, to the cancer protein of the invention. Preferred embodiments utilize the human cancer protein; animal models of human disease of can also be developed and used. Also, other analogous mammalian proteins also can be used as appreciated by those of skill in the art. Moreover, in some embodiments variant or derivative cancer proteins are used.

Generally, the cancer protein of the invention, or the ligand, is non-diffusibly bound to an insoluble support. The support can e.g., be one having isolated sample receiving areas (a microtiter plate, an array, etc.). The insoluble supports can be made of any composition to which the compositions can be bound, is readily separated from soluble material, and is otherwise compatible with the overall method of screening. The surface of such supports can be solid or porous and of any convenient shape.

Examples of suitable insoluble supports include microtiter plates, arrays, membranes and beads. These are typically made of glass, plastic (e.g., polystyrene), polysaccharide, nylon, nitrocellulose, or Teflon™, etc. Microliter plates and arrays are especially convenient because a large number of assays can be carried out simultaneously, using small amounts of reagents and samples. The particular manner of binding of the composition to the support is not crucial so long as it is compatible with the reagents and overall methods of the invention, maintains the activity of the composition and is nondiffusable. Preferred methods of binding include the use of antibodies which do not sterically block either the ligand binding site or activation sequence when attaching the protein to the support, direct binding to "sticky" or ionic supports, chemical crosslinking, the synthesis of the protein or agent on the surface, etc. Following binding of the protein or ligand/binding agent to the support, excess unbound material is removed by washing. The sample receiving areas may then be blocked through incubation with bovine serum albumin (BSA), casein or other innocuous protein or other moiety.

Once a cancer protein of the invention is bound to the support, and a test compound is added to the assay. Alternatively, the candidate binding agent is bound to the support and the cancer protein of the invention is then added. Binding agents include specific antibodies, non-natural binding agents identified in screens of chemical libraries, peptide analogs, etc.

Of particular interest are assays to identify agents that have a low toxicity for human cells. A wide variety of assays can be used for this purpose, including proliferation assays, cAMP assays, labeled in vitro protein-protein binding assays, electrophoretic mobility shift assays, immunoassays for protein binding, functional assays (phosphorylation assays, etc.) and the like.

A determination of binding of the test compound (ligand, binding agent, modulator, etc) to a cancer protein of the invention can be done in a number of ways. The test compound can be labeled, and binding determined directly, e.g., by attaching all or a portion of the cancer protein of the invention to a solid support, adding a labeled candidate compound (e.g., a fluorescent label), washing off excess reagent, and determining whether the label is present on the solid support. Various blocking and washing steps can be utilized as appropriate.

In certain embodiments, only one of the components is labeled, e.g., a protein of the invention or ligands labeled. Alternatively, more than one component is labeled with different labels, e.g., $I^{125}$, for the proteins and a fluorophor for the compound. Proximity reagents, e.g., quenching or energy transfer reagents are also useful.

Competitive Binding to Identify and Characterize Modulators

In one embodiment, the binding of the "test compound" is determined by competitive binding assay with a "competitor." The competitor is a binding moiety that binds to the target molecule (e.g., a cancer protein of the invention). Competitors include compounds such as antibodies, peptides, binding partners, ligands, etc. Under certain circumstances, the competitive binding between the test compound and the competitor displaces the test compound. In one embodiment, the test compound is labeled. Either the test compound, the competitor, or both, is added to the protein for a time sufficient to allow binding. Incubations are performed at a temperature that facilitates optimal activity, typically between four and 40° C. Incubation periods are typically optimized, e.g., to facilitate rapid high throughput screening; typically between zero and one hour will be sufficient. Excess reagent is generally removed or washed away. The second component is then added, and the presence or absence of the labeled component is followed, to indicate binding.

In one embodiment, the competitor is added first, followed by the test compound. Displacement of the competitor is an indication that the test compound is binding to the cancer protein and thus is capable of binding to, and potentially modulating, the activity of the cancer protein. In this embodiment, either component can be labeled. Thus, e.g., if the competitor is labeled, the presence of label in the post-test compound wash solution indicates displacement by the test compound. Alternatively, if the test compound is labeled, the presence of the label on the support indicates displacement.

In an alternative embodiment, the test compound is added first, with incubation and washing, followed by the competitor. The absence of binding by the competitor indicates that the test compound binds to the cancer protein with higher affinity than the competitor. Thus, if the test compound is labeled, the presence of the label on the support, coupled with a lack of competitor binding, indicates that the test compound binds to and thus potentially modulates the cancer protein of the invention.

Accordingly, the competitive binding methods comprise differential screening to identity agents that are capable of modulating the activity of the cancer proteins of the invention. In this embodiment, the methods comprise combining a cancer protein and a competitor in a first sample. A second sample comprises a test compound, the cancer protein, and a competitor. The binding of the competitor is determined for both samples, and a change, or difference in binding between the two samples indicates the presence of an agent capable of binding to the cancer protein and potentially modulating its activity. That is, if the binding of the competitor is different in the second sample relative to the first sample, the agent is capable of binding to the cancer protein.

Alternatively, differential screening is used to identify drug candidates that bind to the native cancer protein, but cannot bind to modified cancer proteins. For example the structure of the cancer protein is modeled and used in rational drug design to synthesize agents that interact with that site, agents which generally do not bind to site-modified proteins. Moreover, such drug candidates that affect the activity of a native cancer protein are also identified by screening drugs for the ability to either enhance or reduce the activity of such proteins.

Positive controls and negative controls can be used in the assays, Preferably control and test samples are performed in at least triplicate to obtain statistically significant results, incubation of all samples occurs for a time sufficient to allow for the binding of the agent to the protein. Following incubation, samples are washed free of non-specifically bound material and the amount of bound, generally labeled agent determined. For example, where a radio label is employed, the samples can be counted in a scintillation counter to determine the amount of bound compound.

A variety of other reagents can be included in the screening assays. These include reagents like salts, neutral proteins, e.g. albumin, detergents, etc, which are used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components is added in an order that provides for the requisite binding.

Use of Polynucleotides to Down-regulate or Inhibit a Protein of the Invention

Polynucleotide modulators of cancer can be introduced into a cell containing the target nucleotide sequence by formation of a conjugate with a ligand-binding molecule, as described in WO 91/04753. Suitable ligand-binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of cancer can be introduced into a cell containing the target nucleic acid sequence, e.g., by formation of a polynucleotide-lipid complex, as described in WO 90/10448. It is understood that the use of antisense molecules or knock out and knock in models may also be used in screening assays as discussed above, in addition to methods of treatment.

Inhibitory and Antisense Nucleotides

In certain embodiments, the activity of a cancer-associated protein is down-regulated, or entirely inhibited, by the use of antisense polynucleotide or inhibitory small nuclear RNA (snRNA), i.e., a nucleic acid complementary to, and which can preferably hybridize specifically to, a coding mRNA nucleic acid sequence, e.g., a cancer protein of the invention, mRNA, or a subsequence thereof. Binding of the antisense polynucleotide to the mRNA reduces the translation and/or stability of the mRNA.

In the context of this invention, antisense polynucleotides can comprise naturally occurring nucleotides, or synthetic species formed from naturally occurring subunits or their close homologs. Antisense polynucleotides may also have altered sugar moieties or inter-sugar linkages. Exemplary among these are the phosphorothioate and other sulfur containing species which are known for use in the art. Analogs are comprised by this invention so long as they function effectively to hybridize with nucleotides of the invention. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art, Antisense molecules are used herein include antisense or sense oligonucleotides. Sense oligonucleotides can, e.g., be employed to block transcription by binding to the anti-sense strand. The antisense and sense oligonucleotide comprise a single stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 12 nucleotides, preferably from about 12 to 30 nucleotides. The ability to derive an antisense or a sense oligonucleotide, based upon a cDNA sequence encoding a given protein is described in, e.g., Stein & Cohen (Cancer Res. 45:2659 (1988 and van der Krol et al. (BioTechniques 6:958 (1988)).

Ribozymes

In addition to antisense polynucleotides, ribozymes can be used to target and inhibit transcription of cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al., Adv. in Pharmacology 25:289-317 (1994) for a general review of the properties of different ribozymes).

The general features of hairpin ribozymes are described, e.g., in Hampel et al., Nucl. Acids Res, 13:299-304 (1990); European Patent Publication No, 0360257; U.S. Pat. No. 5,254,678, Methods of preparing are well known to those of skill in the art (see, e.g., WO 94/26877; Ojwang et al., Proc. Natl. Acad. Sci. USA 92:6340-6344 (1993): Yamada et al., Human Gene Therapy 1:39-45 (1994); Leavitt et al., Proc Natl. Acad Sci, USA 92:699-703 (1995); Leavitt et al., Human Gene Therapy 5:1151-120 (1994); and Yamada et al., Virology 205:121-125 (1994)).

Use of Modulators in Phenotypic Screening

In one embodiment, a test compound is administered to a population of cancer cells, which have an associated cancer expression profile. By "administration" or "contacting" herein is meant that file modulator is added to the cells in such a manner as to allow the modulator to act upon the cell, whether by uptake and intracellular action, or by action at the cell surface. In some embodiments, a nucleic acid encoding a proteinaceous agent (i.e., a peptide) is put into a viral construct such as an adenoviral or retroviral construct, and added to the cell, such that expression of the peptide agent is accomplished, e.g., PCT US97/01019. Regulatable gene therapy systems can also be used. Once the modulator has been administered to the cells, the cells are washed if desired and are allowed to incubate under preferably physiological conditions for some period. The cells are then harvested and a new gene expression profile is generated. Thus, e.g., cancer tissue is screened for agents that modulate, e.g., induce or suppress, the cancer phenotype. A change in at least one gene, preferably many, of the expression profile indicates that the agent has an effect on cancer activity. Similarly, altering a biological function or a signaling pathway is indicative of modulator activity. By defining such a signature for the cancer phenotype, screens for new drugs that alter the phenotype are devised. With this approach, the drug target need not be known and need not be represented in the original gene/protein expression screening platform, nor does the level of transcript for the target protein need to change. The modulator inhibiting function will serve as a surrogate marker As outlined above, screens are done to assess genes or gene products. That is, having identified a particular differentially expressed gene as important in a particular state, screening of modulators of either the expression of the gene or the gene product itself is performed.

Use of Modulators to Affect Peptides of the Invention

Measurements of cancer polypeptide activity, or of the cancer phenotype are performed using a variety of assays. For example, the effects of modulators upon the function of a cancer polypeptide(s) are measured by examining parameters described above. A physiological change that affects activity is used to assess the influence of a test compound on the polypeptides of this invention. When the functional outcomes are determined using intact cells or animals, a variety of effects can be assesses such as, in the case of a cancer associated with solid tumors, tumor growth, tumor metastasis, neovascularization, hormone release, transcriptional changes to both known and uncharacterized genetic markers (e.g., by Northern blots), changes in cell metabolism such as cell growth or pH changes, and changes in intracellular second messengers such as cGNIP.

Methods of Identifying Characterizing Cancer-Associated Sequences

Expression of various gene sequences is correlated with cancer. Accordingly, disorders based on mutant or variant cancer genes are determined. In one embodiment, the invention provides methods for identifying cells containing variant cancer genes, e.g., determining the presence of, all or part, the sequence of at least one endogenous cancer gene in a cell. This is accomplished using any number of sequencing techniques. The invention comprises methods of identifying the cancer genotype of an individual, e.g., determining ail or pad of the sequence of at least one gene of the invention in the individual. This is generally done in at least one tissue of the individual, e.g., a tissue set forth in Table I, and may include the evaluation of a number of tissues or different samples of the same tissue. The method may include comparing the sequence of the sequenced gene to a known cancer gene, i.e., a wild-type gene to determine the presence of family members, homologies, mutations or variants. The sequence of all or part of the gene can then be compared to the sequence of a known cancer gene to determine if any differences exist. This is done using any number of known homology programs, such as BLAST, Bestfit, etc. The presence of a difference in the sequence between the cancer gene of the patient and the known cancer gene correlates with a disease state or a propensity for a disease state, as outlined herein.

In a preferred embodiment, the cancer genes are used as probes to determine the number of copies of the cancer gene in the genome The cancer genes are used as probes to determine the chromosomal localization of the cancer genes. Information such as chromosomal localization finds use in providing a diagnosis or prognosis in particular when chromosomal abnormalities such as translocations, and the like are identified in the cancer gene locus.

XIV.) KITS/ARTICLES OF MANUFACTURE

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a probe that is or can be detectably labeled. Such probe can be an antibody or polynucleotide specific for a protein or a gene or message of the invention, respectively. Where the method utilizes nucleic acid hybridization to detect the target nucleic acid, the kit can also have containers containing nucleotide(s) for amplification of the target nucleic acid sequence. Kits can comprise a container comprising a reporter, such as a biotin-binding protein, such as avidin or streptavidin, bound to a reporter molecule, such as an enzymatic, fluorescent, or radioisotope label; such a reporter can be used with, e.g., a nucleic acid or antibody. The kit can include all or part of the amino acid sequences in FIG. 2 or FIG. 3 or analogs thereof, or a nucleic acid molecule that encodes such amino acid sequences.

The kit of the invention wilt typically comprise the container described above and one or more other containers associated therewith that comprise materials desirable from a commercial and user standpoint including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself, a label can be associated with a container when it is present within a receptacle or carrier that also holds the container, e.g., as a package insert. The label can indicate that the composition is used for diagnosing, treating, prophylaxing or prognosing a condition, such as a neoplasia of a tissue set forth in Table I.

The terms "kit" and "article of manufacture" can be used as synonyms.

In another embodiment of the invention, an article(s) of manufacture containing compositions, such as amino acid sequence(s), small molecule(s), nucleic acid sequencers), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and teat tubes. The containers can be formed from a variety of materials such as glass, metal or plastic. The container can hold amino acid sequence(s), small molecule(s), nucleic acid sequence(i) cell population(s) and/or antibody(s). In one embodiment, the container holds a polynucleotide for use in examining the mRNA expression profile of a cell, together with reagents used for this purpose. In another embodiment a container comprises an antibody, binding fragment thereof or specific binding protein for use in evaluating protein expression of 282P1G3 in cells and tissues, or for relevant laboratory, prognostic, diagnostic, prophylactic and therapeutic purposes, indications and/or directions for such uses can be included on or with such container, as can reagents and other compositions or tools used for these purposes. In another embodiment, a container comprises materials for eliciting a cellular or humoral immune response, together with associated indications and/or directions. In another embodiment, a container comprises materials for adoptive immunotherapy, such as cytotoxic T cells (CTL) or helper T cells (HTL), together with associated indications and/or directions; reagents and other compositions or tools used for such purpose can also be included.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding 282P1G3 and modulating the function of 282P1G3.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1

SSH-Generated Isolation of cDNA Fragment of the 202P5A5 Gene

To isolate genes that are over-expressed in prostate cancer the Suppression Subtracts Hybridization (SSH) procedure was performed using cDNA derived from prostate cancer tissues. The 202P5A5 SSH cDNA sequence was derived from prostate tumor minus cDNAs derived from normal prostate. The 202P5A5 cDNA was identified as highly expressed in prostate cancer as well as in other cancers listed in Table I.

Materials and Methods

Human Tissues:
The patient cancer and normal tissues were purchased from different sources such as the NDRI (Philadelphia, Pa.). mRNA for some normal tissues was purchased from Clontech, Palo Alto, Calif.

RNA Isolation:

Tissues were homogenized in Trizol reagent (Life Technologies, Gibco BRL) using 10 mg/g tissue to isolate total RNA. Poly A RNA was purified from total RNA using Qiagen's Oligotex mRNA Mini and Midi kits. Total and mRNA were quantified by spectrophotometric analysis (O.D. 280/280 nm) and analyzed by gel electrophoresis.

Oligonucleotides:

The following HPLC purified oligonucleotides were used.

```
DPNCDN (cDNA synthesis primer):
                                    (SEQ ID NO: 28)
5'TTTTGATCAAGCTT₃₀3'

Adaptor 1:
                                    (SEQ ID NO: 29)
5'CTAATACGACTCACTATAGGGCTCGAGCGGCCGCCCGGGCAG3'

(SEQ ID NO: 30)
3'GGCCCGTCCTAG5'

Adaptor 2:
                                    (SEQ ID NO: 31)
5'GTAATACGACTCACTATAGGGCAGCGTGGTCGCGGCCGAG3'

(SEQ ID NO: 32)
3'CGGCTCCTAG5'

PCR primer 1:
                                    (SEQ ID NO: 33)
5'CTAATACGACTCACTATAGGGC3'

Nested primer (NP)1:
                                    (SEQ ID NO: 34)
5'TCGAGCGGCCGCCCGGGCAGGA3'

Nested primer (NP)2:
                                    (SEQ ID NO: 35)
5'AGCGTGGTCGCGGCCGAGGA3'
```

Suppression Subtractive Hybridization:

Suppression Subtractive Hybridization (SSH) was used to identify cDNAs corresponding to genes that may be differentially expressed in prostate cancer. The SSH reaction utilized cDNA from prostate cancer and normal tissues.

The gene 202P5A5 sequence was derived from prostate cancer minus normal prostate cDNA subtraction. The SSH DNA sequence (FIG. 1) was identified.

The cDNA derived from normal prostate mixed with a pool ft 9 normal tissues was used as the source of the "driver" cDNA, while the cDNA from prostate cancer was used as the source of the "tester" cDNA. Double stranded cDNAs corresponding to tester and driver cDNAs were synthesized from 2 μg of poly (A)* RNA isolated from the relevant xenograft tissue, as described above, using CLONTECH's PCR-Select cDNA Subtraction Kit and 1 μg of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Driver cDNA was generated by combining in a 1:1 ratio Dpn II digested cDNA from normal prostate with a mix of digested cDNAs derived from the nine normal tissues: stomach, skeletal muscle, lung, brain, liver, kidney, pancreas, small intestine, and heart.

Tester cDNA was generated by diluting 1 μl of Dpn II digested cDNA from prostate cancer 400 ng) in 5 μl of water. The diluted cDNA (2 μl, 180 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (800 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 658° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PC-R amplifications were performed, in the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 μl of bacterial culture using the conditions of PCR1 and NP1 and NP2 as primers. PCR products were analyzed using 2% agarose gel electrophoresis.

Bacterial clones were stored in 20% glycerol in a 95 well format. Plasmid DNA, was prepared, sequenced, and subjected to nucleic acid homology searches of the GenBank, dBest, and NCI-CGAP databases.

RT-PCR Expression Analysis:

First strand cDNAs can be generated from 1 of mRNA with oligo (dT) 12-18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 μl with water prior to normalization. First strand cDNAs from 16 different normal human tissues can be obtained from Clontech.

Normalization of the first strand cDNAs from multiple tissues was performed by using the primers 5'atatcgccgcgctcgtcgtcgacaa3' (SEQ ID NO: 36) and 5'agccacacgcagctcattgtagaagg 3' (SEQ ID NO: 37) to amplify β-actin. First strand cDNA (5 μl) were amplified in a total volume of 50 μl containing 0.4 μM primers, 0.2 μM each dNTPs, 1XPCR buffer (Clontech, 10 mM Tris-HCL, 1.5 mM MgCl₂, 50 mM KCl, pH 8.3) and 1× Klentaq DNA polymerase (Clontech). Five μl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 b.p. β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 202P5A5 gene, 5 μl of normalized first strand cDNA were analyzed by PCR using 26, and 30 cycles of amplification. Semi-quantitative expression analysis can be achieved by comparing the PCR products at cycle numbers that give light band intensities. The primers used for RT-PCR were designed using the 202P5A5 SSH sequence and are listed below:

```
202P5A5.1
5'- CATTTCACATGTCCATGATCTTCC-3'    (SEQ ID NO: 38)

202P5A5.2
5'- CTTTGATGTGTCCGCTGTGTATGT-3'    (SEQ ID NO: 39)
```

A typical RT-PCR expression analysis is shown in FIG. 14A. First strand cDNA was prepared from vital pool 1 (liver, lung and kidney), vital pool 2 (pancreas, colon and stomach), prostate cancer metastasis to lymph node, prostate cancer pool, bladder cancer pool, colon cancer pool, lung cancer pool, breast cancer pool, and cancer metastasis pool. Normalization was performed by PCR using primers to actin and GAPDH. Semi-quantitative PCR, using primers to 202P5A5, was performed at 25 and 30 cycles of amplification. Expression was detected in prostate cancer metastasis to lymph node, prostate cancer pool, bladder cancer pool, colon cancer pool, lung cancer pool, breast cancer pool, and cancer metastasis pool. Low expression was also defected in vital pool 1 but not in vital pool 2.

Example 2

Full Length Cloning of 202P5A5

The 202P5A5 SSH cDNA sequence was derived from a subtraction consisting of prostate cancer minus normal prostate. The SSH cDNA sequence of 186 bp (FIG. 1) was designated 202P5A5.

202P5A5 v.3 of 4973 bp was cloned from a pool of bladder cancer cDNA library, revealing an ORF of 609 amino acids (FIG. 2 and FIG. 3). Other variants of 202P5A5 were also identified and these and listed in FIG. 2 and FIG. 3.

202P5A5 v.1, v.4, v.5, v.6, and v.8 proteins are 609 amino acids in length and differ from each other by one amino acid as shown in FIG. 11. 202P5A5 v.7 and v.9 through v.26, are SNP variants and code for the same protein as 202P5A5 v.1. 202P5A5 v.2 is a splice variant adding extra 15 amino acids to the amino terminus of v.1 and thereby codes for a 625 amino acids protein.

202P5A5 v.1 shows 99% identity over 609 nucleotides, and 99% identity over 609 amino acids, to cDNA FLJ13782, a gene similar to gene ceding for Grainy Head protein. 202P5A5 v.2 shows 99% identity over 4792 nucleotides, and 99% identity over 625 amino acids., to cDNA FLJ13782.

Example 3

Chromosomal Mapping of 202P5A5

Chromosomal localization can implicate genes in disease pathogenesis. Several chromosome mapping approaches are known in the art including fluorescent in situ hybridization (FISH), human/hamster radiation hybrid (RH) panels (Walter et al., 1994; Nature Genetics 7:22; Research Genetics. Huntsville Ala.), human-rodent somatic cell hybrid panels available from the Cornell Institute (Camden, N.J.), and genomic viewers utilizing BLAST homologies to sequenced and mapped genomic clones (NCBI, Bethesda, Md.).

Accordingly, 202P5A5 maps to chromosome Bq22.3 using 202P5A5 sequence and the NCBI BLAST tool located on the World Wide Web at (.ncbi.nlm.nih.gov/genome/seq/page.cgi?F=HsBlast.html&&ORG=Hs).

Example 4

Expression Analysis of 202P5A5 in Normal Tissues and Patient Specimens

Expression analysis by RT-PCR demonstrated that 202P5A5 is strongly expressed in patient cancer specimens (FIG. 14). In FIG. 14A, first strand cDNA was prepared from vital pool 1 (liver, lung and kidney), vital pool 2 (pancreas, colon and stomach), prostate cancer metastasis to lymph node, prostate cancer pool, bladder cancer pool, colon cancer pool, lung cancer pool, breast cancer pool, and cancer metastasis pool. Normalization was performed by PCR using primers to actin and GAPDH. Semi-quantitative PCR, using primers to 202P5A5, was performed at 26 and 30 cycles of amplification. Expression was detected in prostate cancer metastasis to lymph node, prostate cancer pool, bladder cancer pool, colon cancer pool, lung cancer pool, breast cancer pool, aid cancer metastasis pool. Low expression was detected in vital pool 1 but not in vital pool 2.

In FIG. 14B, semi-quantitative PCR, using primers to 202P5A5, was performed on a panel of 13 normal tissues and 13 cancer pools. Samples were run on an agarose gel, and PCR products were quantitated using the AlphaImager software. Results show strong expression of 202P5A5 in prostate cancer, bladder cancer, colon cancer, lung cancer, ovary cancer, breast cancer, metastasis cancer, xenograft pool, prostate metastasis to lymph node (PMLN), bone cancer/melanoma pool, cervical cancer, lymphoma and stomach cancer compared to all normal tissues tested.

In order to assay relative expression of 202P5A5 v.2 compared to the other variants, primers were designed spanning the 80 bp insertion at position 32-92 of 202P5A5 v.3 (FIG. 15), 202P5A5 v.2 leads to a PCR product of 173 base pairs in size, whereas other 202P5A5 variants lead to a PCR product of 233 base pairs in size. First strand cDNA was prepared from vital pool 1 (liver, lung and kidney), vital pool 2 (pancreas, colon and stomach), LAPC prostate xenograft pool (LAPC-4AD. LAPC-4AI, LAPC-9AD and LAPC-9AI), prostate cancer pool, bladder cancer pool, lung cancer pool, ovary cancer pool, breast cancer pool, cancer metastasis pool, cervical cancer pool, stomach cancer pool, uterus cancer pool, and master xenograft pool (LAPC xenograft pool, bladder cancer xenograft, kidney cancer xenograft). Normalization was performed by PCR using primers to actin and GAPDH, Semi-quantitative PCR, using the variant specific primers was performed at 26 and 30 cycles of amplification. Stronger expression of the 173 bp product was detected in ail cancer pools tested and weakly in vital pools. The larger 233 bp product was mostly detected in the cancer pools and not in the vital tissues, and at a frequency of 20-50% compared to the smaller product Extensive expression of 202P5A5 in normal tissues is shown in FIG. 16. Two multiple tissue northern blots (Clontech) both with 1 μg of mRNA/lane were probed with the 202P5A5 sequence. Size standards in kilobases (kb) are indicated on the side. Results show expression of an approximately 7 kb 202P5A5 transcript in normal prostate and normal placenta but not in any other normal tissue tested.

Expression of 202P5A5 in prostate cancer patient specimens is shown in FIG. 17. RNA was extracted from prostate cancer xenografts (LAPC-4AD, LAPC-4AI, LAPC-9AD, and LAPC-9AI), prostate cancer cell lines (LNCaP and PC3), normal prostate (N), and prostate cancer patient tumors (T). Northern blots with 10 μg of total RNA were probed with the 202P5A5 SSH fragment. Size standards in kilobases are on the side. Results show expression of 202P5A5 in all prostate cancer specimens tested as well as in the normal prostate, prostate cancer xenografts and LNCaP, but not in the PC3 cell line.

Expression of 202P5A5 was also detected in bladder cancer patient specimens (FIG. 18). RNA was extracted from bladder cancer cell lines (CL), normal bladder (N), bladder cancer patient tumors (T) as well as their adjacent normal tissues (Nat). Northern blots with 10 μg of total RNA were probed with the 202P5A5 sequence. Size standards in kilobases are on the side. Results show expression of 202P5A5 in all bladder cancer patient tumor specimens tested but not in normal bladder. Expression was also detected in SCABER hut not in the other cancer cell lines tested.

FIG. 19 shows expression of 202P5A5 in breast cancer patient specimens, RNA was extracted from breast cancer cell lines (CL), normal breast (N), breast cancer patient tumors (T), and breast cancer metastasis specimens (M), Northern blots with 10 μg of total RNA were probed with the 202P5A5 sequence. Size standards in kilobases are on the side. Results show expression of 202P5A5 in the breast cancer patient tumors and metastasis specimens. Expression was also detected in MCF-7 and CAMA-1 but not in the DU4475 cell line. Weaker expression was detected in normal breast.

FIG. 20 shows expression of 202P5A5 in colon and cervical cancer patient specimens. First strand cDNA was prepared from a panel of patient cancer specimens. Normalization was performed by PCR using primers to actin. Semi-quantitative PCR, using primers to 202P5A5, was performed at 26 and 30 cycles of amplification. Samples were run on an agarose gel, and PCR products were quantitated using the Alpha Imager software. Expression was recorded as absent, low, medium or strong, Results show expression of 202P5A5 in the majority of the colon and cervical cancer patient specimens tested.

The restricted expression of 202P5A5 in normal tissues and the expression detected in cancer patient specimens suggest that 202P5A5 is a potential therapeutic target and a diagnostic prognostic, and/or preventative marker for human cancers.

Example 5

Transcript Variants of 202P5A5

Transcript variants are variants of mature mRNA from the same gene which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or can encode proteins with different functions, and can be expressed in the same tissue at the same time, or in different tissues at the same time, or in the same tissue at different times, or in different tissues at different times. Proteins encoded by transcript variants can have similar or different cellular or extracellular localizations, e.g., secreted versus intracellular.

Transcript variants are identified by a variety of art-accepted methods. For example, alternative transcripts and splice variants are identified by full-length cloning experiments, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Even when a variant is identified that is not a full-length clone, that portion of the variant is very useful for antigen generation and for further cloning of the full-length splice variant, using techniques known to those skilled in the art.

Moreover, computer programs are available to those skilled in the art in at identify transcript variants based on genomic sequences, Genomic-based transcript variant identification programs include FgenesH (A. Salamov and V. Solovyev, "Ab initio gene finding in Drosophila genomic DNA," Genome Research. 2000 April; 10(4):516-22), Grail (URL compbio.oml.gov/Grail-bin/EmptyGrailForm) and GenScan (URL.genes.mlt.edu/GENSCAN.html). For a general discussion of splice variant identification protocols see., e.g., Southan, C., A genomic perspective on human proteases, FEBS Lett. 2001 Jun. 8; 498 (2-3):214-8; de Souza, S. J., et al., identification of human chromosome 22 transcribed sequences with ORF expressed sequence tags, Proc. Natl Acad Sci USA. 2000 Nov. 7; 97 (23):12890-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et al., Albumin banks peninsula: a new termination variant characterized by electrospray mass spectrometry, Biochem Biophys Acta. 1999 Aug. 17; 1433(1-2): 321-6; Ferranti P, et al., Differential splicing of pre-messenger RNA produces multiple forms of mature caprine alpha(s1)-casein, Eur J Biochem. 1997 Oct. 1; 249 (1):1-7. For PCR-based Validation: Wellmann S, et al., Specific reverse transcription-PCR quantification of vascular endothelial growth factor (VEGF) splice variants by LightCycler technology, Clin Chem. 2001 April, 47 (4):654-60, Jia, H. P., et al., Discovery of new human beta-defensins using a genomics-based approach, Gene. 2001 Jan. 24; 263(1-2): 211-8. For PCR-based and 5' RACE Validation; Brigle, K. E., et el., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is that 202P5A5 has a particular expression profile related to cancer (See, Table I). Alternative transcripts and splice variants of 202P5A5 may also be involved in cancers in the same or different tissues, thus serving as tumor-associated markers/antigens.

Using the full-length gene and EST sequences, two additional transcript variants were identified, designated as 202P5A5 v.2 and v.3. The boundaries of exons in the original transcript, 202P5A5 v.1 are shown in Table LI. The structures of the transcript variants are shown in FIG. 10. Variant 202P5A5 v.2 added an exon to the 5' end of variant v.1. Variants v.3 further extended exon 1 of v.2 into intron 1.

Tables LII(a)-(b) through LV(a)-(b) are set forth on a variant-by-variant bases. LII(a)-(b) shows nucleotide sequence of the transcript variant. Table LIII(a)-(b) shows the alignment of the transcript variant with nucleic acid sequence of 202P5A5 v.1. Table LIV(a)-(b) lays out amino acid translation of the transcript variant for the identified reading frame orientation. Table LV(a)-(b) lays out amino and translation of the transcript variant for the identified reading frame 202P5A5 v.1.

Example 6

Single Nucleotide Polymorphisms of 202P5A5

A Single Nucleotide Polymorphism (SNP) is a single base pair variation in a nucleotide sequence at a specific location. At any given point of the genome, there are four possible nucleotide base pairs: A/T, C/G, G/C and T/A. Genotype refers to the specific base pair sequence of one or more locations in the genome of an individual. Haplotype refers to the base pair sequence of more than one location on the same DNA molecule (or the same chromosome in higher organisms), often in the context of one gene or in the context of several tightly linked genes. SNPs that occur on a cDNA are called cSNP. This cSNPs may change amino acids of the protein encoded by the gene and thus change the functions of the protein. Some SNP cause inherited diseases; others contribute to quantitative variations in phenotype and reactions to environmental factors including diet and drugs among individuals. Therefore, SNP and/or combinations of alleles (called haplotypes) have many applications, including diagnosis of inherited diseases, determination of drug reactions and dosage, identification of genes responsible for diseases, and analysis of the genetic relationship between individuals (P. Nowotny, J. M. Kwon and A. M. Goate, "SNP analysis to dissect human traits," Curr. Opin. Neurobiol. 2001 October; 11(5):637-641; M. Pirmohamed and B. K. Park, "Genetic susceptibility to adverse drug reactions," Trends Pharmacol. Sci, 2001 June: 22(6);298-305; J. H. Riley, C. J. Allan, E. Lai and A. Roses, "The use of single nucleotide polymorphisms in the isolation of common disease genes," Pharmacogenomics. 2000 February; 1(1):39-47; R. Judson, J. C. Stephens and A. Windemuth, "The predictive power of haplotypes in clinical response," Pharmacogenomics. 2000 February; 1(1):15-26).

SNPs are identified by a variety of art-accepted methods (P. Bean, "The promising voyage of SNP target discovery," Am. Clin. Lab. 2001 October-November; 20(9): 18-20; K. M. Weiss, "In search of human variation," Genome Res. 1993 July; 3(7):691-697; M. M. She, "Enabling large-scale pharmacogenetic studies by high-throughput mutation detection and genotyping technologies," Clin. Chem. 2001 February; 47(2):164-172). For example, SNPs can be identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L, Hillier and P. Y. Kwok, "Single nucleotide polymorphism hunting in cyberspace," Hum. Mutat. 1998; 12(4):221-225), SNPs can be verified and genotype or haplotype of an individual can be determined by a variety of methods including direct sequencing and high throughput microarrays (P. Y. Kwok, "Methods for genotyping single nucleotide polymorphisms," Annu. Rev. Genomics Hum. Genet. 2001 1; 2: 235-258; M. Kokoris, K, Dix, K, Moynihan, J, Mathis, B. Erwin, P, Grass, 8. Hines and A. Duesterhoeft "High-throughput SNP genotyping with the Mass-code system," Mol. Diagn. 2000 December; 5(4);329-340). Using the methods described above, twenty-four SNPs were identified in the transcript, 202P5A5 v.1, as shown in Table LVI. The transcripts or proteins with alternative alleles were designated as variant 202P5A5 v.4 through v.26, as shown in Table LVI and FIG. 12. Table LVI also lists the amino acid changes of protein sequence in the corresponding transcript variants v.2 and v.3. These alleles of the SNP, though shown separately here, can occur in different combinations (haplotypes) and in any one of the transcript variants (such as 202P5A5 v.2 and v.3, as listed in table LVI) that contains the site of the SNP, as set forth in FIGS. 11 and 12.

Example 7

Production of Recombinant 202P5A5 in Prokaryotic Systems

To express recombinant 202P5A5 and 202P5A5 variants in prokaryotic cells, the full or partial length 202P5A5 and 202P5A5 variant cDNA sequences are cloned into any one of a variety of expression vectors known in the art. One or more of the following regions of 202P5A5 variants are expressed: the full length sequence presented in FIGS. 2 and 3, or any 8, 9, 10, 11, 12, 13, 14, 15, 16, 17, 18, 19, 20, 21, 22, 23, 24, 25, 26, 27, 28, 29, 30 or more contiguous amino acids from 202P5A5, variants, or analogs thereof.

A. In Vitro Transcription and Translation Constructs:

pCRII: To generate 202P5A5 sense and anti-sense RNA probes for RNA in situ investigations, pCRII constructs (Invitrogen, Carlsbad Calif.) are generated encoding either all or fragments of the 202P5A05 cDNA. The pCRII vector has Sp6 and T7 promoters flanking the insert to drive the transcription of 202P5A05 RNA for use as probes in RNA in situ hybridization experiments. These probes are used to analyze the cell and tissue expression of 202P5A05 at the RNA level. Transcribed 202P5A05 RNA representing the cDNA amino acid coding region of the 202P5A05 gene is used in in vitro translation systems such as the TnT™ Coupled Reticulolysate System (Promega, Corp., Madison, Wis.) to synthesize 202P5A05 protein.

B. Bacterial Constructs:

pGEX Constructs: To generate recombinant 202P5A5 proteins in bacteria that are fused to the Glutathione S-transferase (GST) protein, all or parts of the 202P5A5 cDNA protein coding sequence are cloned into the pGEX family of GST-fusion vectors (Amersham Pharmacia Biotech, Piscataway, N.J.). These constructs allow controlled expression of recombinant 202P5A5 protein sequences with GST fused at the amino-terminus and a six histidine epitope (6 X His) at the carboxyl-terminus. The GST and 6 X His tags permit purification of the recombinant fusion protein from induced bacteria with the appropriate affinity matrix and allow recognition of the fusion protein with anti-GST and anti-His antibodies. The 6 X His tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 202P5A05-related protein. The ampicillin resistance gene and pBR322 origin permits selection and maintenance of the pGEX plasmids in *E. coli*.

pMAL Constructs: To generate, in bacteria, recombinant 202P5A5 proteins that are fused to maltose-binding protein (MBP), all or parts of the 202P5A5 cDNA protein coding sequence are fused to the MBP gene by cloning into the pMAL-c2X and pMAL-p2X vectors (New England Biolabs, Beverly, Mass.). These constructs allow controlled expression of recombinant 202P5A5 protein sequences with MBP fused at the amino-terminus and a 5 X His epitope tag at the carboxyl-terminus. The MBP and 6 X His tags permit purification of the recombinant protein from induced bacteria with the appropriate affinity matrix and allow recognition of the fusion protein with anti-MBF and anti-His antibodies. The 6 X His epitope tag is generated by adding 6 histidine codons to the 3' cloning primer. A Factor Xa recognition site permits cleavage of the pMAL tag from 202P5A5. The pMAL-c2X and pMAL-p2X vectors are optimized to express the recombinant protein in the cytoplasm or periplasm respectively. Periplasm expression enhances folding of proteins with disulfide bonds.

pET Constructs: To express 202P5A05 in bacterial cells, all or parts of the 202P5A05 cDNA protein coding sequence are cloned into the pET family of vectors (Novagen, Madison, Wis.). These vectors allow tightly controlled expression of recombinant 202P5A05 protein in bacteria with and without fusion to proteins that enhance solubility, such as NusA and thioredoxin (Trx), and epitope tags, such as 6 X His and S-Tag™ that aid purification and detection of the recombinant protein. For example, constructs are made utilizing pET NusA fusion system 43.1 such that regions of the 202P5A05 protein are expressed as amino-terminal fusions to NusA.

C. Yeast Constructs:

pESC Constructs: To express 202P5A5 in the yeast species *Saccharomyces cersvisiae* for generation of recombinant protein and functional studies, all or parts of the 202P5A05 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of 202P5A5. In addition, expression in yeast yields similar post-translational modifications, such as glycosylations and phosphorylations that are found when expressed in eukaryotic cells.

pESP Constructs: To express 202P5A5 in the yeast species *Saccharomyces pombe*, all or parts of the 202P5A5 cDNA protein coding sequence are cloned into the pESP family of vectors. These vectors allow controlled high level of expression of a 202P5A5 protein sequence that is fused at either the amino terminus or at the carboxyl terminus to GST which aids purification of the recombinant protein. A Flag™ epitope tag allows detadion of the recombinant protein with anti-Flag™ antibody.

Example 8

Production of Recombinant 202P5A5 in Higher Eukaryotic Systems

A. Mammalian Constructs:

To express recombinant 202P5A5 in eukaryotic cells, the full or partial length 202P5A5 cDNA sequences were cloned into any one of a variety of expression vectors known in the art. One or more of the following regions of 202P5A5 were expressed in these constructs, amino adds 1 to 609, or any 8, 9, 10, 11, 12, 13, 14, 15, 16, 17, 18, 19, 20, 21, 22, 23, 24, 25, 26, 27, 28, 29, 30 or more contiguous amino acids from 202P5A5 v.1, v.4, v.5, v.6 and v.8; amino acids 1 to 625, or any 8, 9, 10, 11, 12, 13, 14, 15, 16, 17, 18, 19, 20, 21, 22, 23, 24, 25, 26, 27, 28, 29, 30 or more contiguous amino acids from 202P5A5 v.2 variants, or analogs thereof.

The constructs can be transfected into any one of a wide variety of mammalian cells such as 293T cells. Transfected 293T cell lysates can be probed with the anti-202P5A5 polyclonal serum, described herein.

pcDNA4/HisMax Constructs: To express 202P5A5 in mammalian cells, a 202P5A5 ORF, or portions thereof, of 202P5A5 are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6 X His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli*.

pcDNA3.1/MycHis Constructs: To express 202P5A5 in mammalian cells, a 202P5A5 ORF, or portions thereof, 202P5A5 with a consensus Kozak translation initiation site is cloned into pcDNA3.1/MycHis Version A (Invitrogen, Carlsbad, Calif.). Protein expression is driven from the cytomegalovirus (CMV) promoter. The recombinant proteins have the myc epitope and 6 X His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli*.

The complete ORF of 202P5A5 v.1 was cloned into the pcDNA3.1/MycHis construct to generate 202P5A5.pcDNA3.1/MycHis. FIG. 21 shows expression of 202P5A5.pcDNA3.1/MycHis. 293T cells were transfected with either 202P5A5.pcDNA3.1/MycHis or pcDNA3.1/MycHis vector control. Forty hours later, cell lysates were collected. Samples were run on an SDS-PAGE acrylamide gel, blotted and stained with anti-his antibody. The blot was developed using the ECL chemiluminescence kit and visualized by autoradiography. Results show expression of 202P5A5 from the 202P5A5.pcDNA3.1/MycHis construct in the lysates of transfected cells.

pcDNA3.1/CT-GFP-TOPO Construct: To express 202P5A5 in mammalian cells and to allow detection of the recombinant proteins using fluorescence, a 202P5A5 ORF, or portions thereof, with a consensus Kozak translation initiation site are cloned into pcDNA3.1/CT-GFP-TOPO (Invitrogen, Calif.). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in E. coli. Additional constructs with an amino-terminal GFP fusion are made in pcDNA3.1/NT-GFP-TOPO spanning the entire length of a 202P5A5 protein.

PAPtag: A 202P5A5 ORF, or portions thereof, is cloned into pAPtag-5 (GenHunter Corp. Nashville, Tenn.). This construct generates an alkaline phosphatase fusion at the carboxyl-terminus of a 202P5A5 protein while fusing the IgGκ signal sequence to the amino-terminus. Constructs are also generated in which alkaline phosphatase with an amino-terminal IgGκ signal sequence is fused the amino-terminus of a 202P5A5 protein. The resulting recombinant 202P5A5 proteins are optimized for secretion into the media of transfected mammalian cells and can be used to identify proteins such as ligands or receptors that interact with 202P5A5 proteins. Protein expression is driven from the CMV promoter and the recombinant proteins also contain myc and 6 X His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in E. coli.

pTag5: A 202P5A5 ORF, or portions thereof, is cloned into pTag-5. This vector is similar to pAPtag but without the alkaline phosphatase fusion. This construct generates 202P5A5 protein with an amino-terminal IgGκ signal sequence and myc and 6 X His epitope tags at the carboxyl-terminus that facilitate detection and affinity purification. The resulting recombinant 202P5A5 protein is optimized for secretion into the media of transfected mammalian cells, and is used as immunogen or ligand to identify proteins such as ligands or receptors that interact with the 202P5A5 proteins. Protein expression is driven from the CMV promoter. The Zeocin resistance gene present in the vector allows for selection of mammalian cells expressing the protein, and the ampicillin resistance gene permits selection of the plasmid in E. coli.

PsecFc: A 202P5A5 ORF, or portions thereof, is also cloned into psecFc. The psecFc vector was assembled by cloning the human immunoglobulin G1 (IgG) Fc (hinge CH2, CH3 regions) into pSecTag2 (Invitrogen, Calif.). This construct generates an IgG 1 Fc fusion at the carboxyl-terminus of the 202P5A5 proteins, while fusing the IgGK signal sequence to N-terminus. 202P5A5 fusions utilizing the murine IgG 1 Fc region are also used. The resulting recombinant 202P5A5 proteins are optimized for secretion into the media of transfected mammalian cells, and can be used as immunogens or to identify proteins such as ligands or receptors that interact with 202P5A5 protein. Protein expression is driven from the CMV promoter. The hygromycin resistance gene present in the vector allows for selection of mammalian cells that express the recombinant protein, and the ampicillin resistance gene permits selection of the plasmid in E. coli.

Retroviral Constructs: To generate mammalian cell lines that express 202P5A5 constitutively, 202P5A5 ORF, or portions thereof, of 202P5A5 were cloned into pQCXIN (Clontech) constructs. Amphotropic and ecotropic retroviruses were generated by transaction of pQCXIN constructs into the 293T-10A1 packaging line or co-transfection of pQCXIN and a helper plasmid (containing deleted packaging sequences) into the 293 cells, respectively. The retrovirus is used to infect a variety of mammalian cell lines, resulting in the integration of the cloned gene, 202P5A5, into the host cell-lines. Protein expression is driven from the CMV promoter. The Neomycin resistance gene present in the vector allows for selection of mammalian cells that express the protein, and the ampicillin resistance gene and ColE1 origin permit selection and maintenance of the plasmid in E. coli. The retroviral vectors can thereafter be used for infection and generation of various cell lines using, for example, PC3, NIH 3T3, TsuPr1, 293 or rat-1 cells.

Additional pQCXIN constructs are made that fuse an epitope tag such as the FLAG™ tag to the carboxyl-terminus of 202P5A5 sequences to allow detection using anti-Flag antibodies, For example, the FLAG™ sequence 5' gat tac aag gat gac gac gat aag 3': (SEQ ID NO: 40) is added to cloning primer at the 3' end of the ORF. Additional retroviral constructs are made to produce both amino-terminal and carboxyl-terminal GFP and myc/6 X His fusion proteins of the full-length 202P5A5 proteins and under various selection methods.

Additional Viral Vectors: Additional constructs are made for viral-mediated delivery and expression of 202P5A5. High virus titer leading to high level expression of 202P5A5 is achieved in viral delivery systems such as adenoviral vectors and herpes amplicon vectors. A 202P5A5 coding sequences or fragments thereof are amplified by PCR and subcloned into the AdEasy shuttle vector (Stratagene). Recombination and virus packaging are performed according to the manufacturer's instructions to generate adenoviral vectors. Alternatively, 202P5A5 coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of 202P5A5 in mammalian cells, coding sequences of 202P5A5, or portions thereof, are cloned into regulated mammalian expression systems such as the T-Rex System (Invitrogen), the Gene Switch System (Invitrogen) and the tightly-regulated Ecdysone System (Sratagene). These systems allow the study of the temporal and concentration dependent effects of recombinant 202P5A5. These vectors are thereafter used to control expression of 202P5A5. In various cell lines such as PC3, NIH 3T3, 293 or rat-1 cells.

B. Baculovirus Expression Systems

To generate recombinant 202P5A5 proteins in a baculovirus expression system, 202P5A5 ORF, or portions thereof, are cloned into the baculovirus transfer vector pBlueBac4.5 (Invitrogen), which provides a His-tag at the N-terminus. Specifically, pBlueBac-202P5A5 is co-transfected with helper plasmid pBac-N-Blue (Invitrogen) into SF9 (*Spodoptere frugiperde*) insect cells to generate recombinant baculovirus (see Invitrogen instruction manual for details). Baculovirus is then collected from cell supernatant and purified by plaque assay.

Recombinant 202P5A5 protein is then generated by infection of High Five insect cells (Invitrogen) with purified baculovirus. Recombinant 202P5A5 protein can be detected using anti-202P5A5 or anti-His-tag antibody, 202P5A5 protein can be purified and used in various cell-based assays or as immunogen to generate polyclonal and monoclonal antibodies specific for 202P5A5.

Example 9

Antigenicity Profiles and Secondary Structure

FIG. 5, FIG. 6, FIG. 7, FIG. 8, and FIG. 9 depict graphically five amino acid profiles of 202P5A5 variant 1, each assessment available by accessing the ProlScale website located on the World Wide Web at (.expasy.ch/cgi-bin/prolscale.pl) on the ExPasy molecular biology server.

These profiles: FIG. 5, Hydrophilicity, (Hopp T. P., Woods K. R., 1981. Proc. Natl. Acad. Sci. U.S.A. 78:3824-3828), FIG. 6., Hydropathicity, (Kyte J., Doolittle R. F., 1982. J. Mol. Biol. 157:105-132), FIG. 7, Percentage Accessible Residues (Janin J., 1979 Nature 277:491-492); FIG. 8, Average Flexibility, (Bhaskaran R., and Ponnuswamy P. K., 1988. Int. J. Pept. Protein Res. 32:242-255); FIG. 9, Beta-turn (Deleage, G., Roux B. 1987 Protein Engineering 1:289-294); and optionally others available in the art, such as on the ProtScale website, were used to identify antigenic regions of each of the 202P5A5 valiant proteins. Each of the above amino acid profiles of 202P5A5 variants were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility (FIG. 3) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the 202P5A5 variant proteins indicated, e.g., by the profiles set forth in FIG. 5, FIG. 6, FIG. 7, FIG. 6, and/or FIG. 9 are used to prepare immunogens, either peptides or nucleic acids that encode them, to generate therapeutic and diagnostic anti-202P5A5 antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 202P5A5 protein variants listed in FIGS. 2 and 3. In particular, peptide immunogens of the invention can comprise, a peptide region of at least 5 amino adds of FIGS. 2 and 3 in any whole number increment that includes an amino acid position having a value greater than 0.5 in the Hydrophilicity profiles of FIG. 5; a peptide region of at least 5 amino acids of FIGS. 2 and 3 in any whole number increment that includes an ammo acid position having a value less than 0-5 in the Hydropathicity profile of FIG. 6; a peptide region of at least 5 amino acids of FIGS. 2 and 3 in any whole number increment that includes an amino acid position having a value greater than 0.5 in the Percent Accessible Residues profiles of FIG. 7; a peptide region of at least 5 amino acids of FIGS. 2 and 3 in any whole number increment that includes an amino acid position having a value greater than 0.5 in the Average Flexibility profiles on FIG. 8; and, a peptide region of at least 5 amino acids of FIGS. 2 and 3 in any whole number increment that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 202P5A5 protein variant 1, namely the predicted presence and location of alpha helices, extended strands, and random coils, is predicted from the primary amino acid sequence using the HNN—Hierarchical Neural Network method (NPS@: Network Protein Sequence Analysis TIBS 2000 March Vol. 25, No 3 [291]:147-150 Combet C., Blanchet C., Geourjon C. and Deléage G., located on the World Wide Web at pbil.ibcp.fr/cgi-bin/npsa_automat.pl?page=npsa_nn.html), accessed from the ExPasy molecular biology server located on the World Wide Web at (.expasy.ch/tools/). The analysis indicates that 202P5A5 variant 1 is composed of 31.69% alpha helix, 19.87% extended strand, and 48.44% random coil (FIG. 13A).

Analysis for the potential presence of transmembrane domains in the 202P5A5 variant proteins was carried out using a variety of transmembrane prediction algorithms accessed from the ExPasy molecular biology server located on the Wold Wide Web at (.expasy.ch/tools/). Shown graphically in FIGS. 13B and 13C are the results of analysis of 202P5A5 variant 1 using the TMpred program (FIG. 13B) and TMHMM program (FIG. 13C). Neither of the programs predicted the presence of transmembrane domains, suggesting that 202P5A5 is a soluble protein. The results of structural analysis programs are summarized in Table VI.

Example 10

Generation of 202P5A5 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with a full length 202P5A5 protein variant, computer algorithms are employed in design of immunogens that, based on amino acid sequence analysis contain characteristics of being antigenic and available for recognition by the immune system of the immunized host (see the Example entitled "Antigenicity Profiles and Secondary Structures"). Such regions would be predicted to be hydrophilic, flexible, in beta-turn conformations, and be exposed on the surface of the protein (see, e.g., FIG. 5, FIG. 6, FIG. 7, FIG. 8, or FIG. 9 for amino acid profiles that indicate such regions of 202P5A5 protein variant 1).

For example, recombinant bacterial fusion proteins or peptides containing hydrophilic, flexible, beta-turn regions of 202P5A5 protein variants are used as antigens to generate polyclonal antibodies in New Zealand White rabbits or monoclonal antibodies as described in the Example entitled "Generation of 202P5A5 Monoclonal Antibodies (mAbs)". For example, in 202P5A5 variant 1, such regions include, but are not limited to, amino acids 1-22, amino acids 55-84, amino acids 181-225, amino acids 399-450, and amino acids 496-538. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 1-22 of 202P5A5 variant 1 was conjugated to KLH and used to immunize a rabbit. Alternatively the immunizing agent may include all or portions of the 202P5A5 variant proteins, analogs or fusion proteins thereof. For example, the 202P5A5 variant 1 amino acid sequence can be fused using recombinant DNA techniques to any one of a variety of fusion protein partners that are well known in the art, such as glutathione-S-transferase (GST) and HIS tagged fusion proteins. In another embodiment, the complete cDNA of 202P5A5 variant 1 is fused to GST using recombinant techniques and the pGEX expression vector, expressed, purified and used to immunize a rabbit. Such fusion proteins are purified from induced bacteria using the appropriate affinity matrix.

Other recombinant bacterial fusion proteins that may be employed include maltose binding protein, LacZ, thioredoxin, NusA, or an immunoglobulin constant region (see the section entitled "Production of 202P5A5 in Prokaryotic Systems" and Current Protocols In Molecular Biology, Volume 2, Unit 16, Frederick M. Ausubul et al. eds., 1995; Linsley, P. S., Brady, W., Umes, M., Grosmaire, L., Damle, N., and Ledbetter, L. (1991) J. Exp. Med. 174, 561-565).

In addition to bacterial derived fusion proteins, mammalian expressed protein antigens are also used. These antigens are expressed from mammalian expression vectors such as the Tag5 and Fc-fusion vectors (see the section entitled "Production of Recombinant 202P5A5 in Eukaryotic Systems"), and retain post-translational modifications such as glycosylations found in native protein. In one embodiment, the complete cDNA of 202P5A5 variant 1 is cloned into the Tag5 mammalian secretion vector, and expressed in 293T cells. The recombinant protein is purified by metal chelate chromatography from tissue culture supernatants of 293T cells stably expressing the recombinant vector. The purified Tag5 202P5A5 protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 μg, typically 100-200 μg, of fusion protein or peptide conjugated to KLH mixed in complete Freund's adjuvant (CFA). Rabbits are then injected subcutaneously every two weeks with up to 200 μg, typically 100-200 μg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as the rabbit serum derived from immunization with the GST fusion of 202P5A5 variant 1 protein, the full-length 202P5A5 variant 1 cDNA is cloned into pCDNA 3.1 myc-his expression vector (Invitrogen, see the Example entitled "Production of Recombinant 202P5A05 in Eukaryotic Systems"). After transfection of the constructs into 293T cells, cell lysates are probed with the anti-202P5A5 serum and with anti-His antibody (FIG. 21); Santa Cruz Biotechnologies, Santa Cruz, Calif.) to determine specific reactivity to denatured 202P5A5 protein using the Western blot technique. In addition, the immune serum is tested by fluorescence microscopy, flow cytometry and immunoprecipitation against 293T and other recombinant 202P5A5-expressing cells to determine specific recognition of native protein. Western blot, immunoprecipitation, florescent microscopy, and flow cytometric techniques using cells that endogenously express 202P5A5 are also carried out to test reactivity and specificity.

Anti-serum from rabbits immunized with 202P5A5 variant fusion proteins, such as GST and MBP fusion proteins, are purified by depletion of antibodies reactive to the fusion partner sequence by passage over an affinity column containing the fusion partner either alone or in the context of an irrelevant fusion protein. For example, antiserum derived from a GST-202P5A5 variant 1 fusion protein is first purified by passage over a column of GST protein covalently coupled to AffiGel matrix (BioRad, Hercules, Calif.). The antiserum is then affinity purified by passage over a column composed of a MBP-202P5A5 fusion protein covalently coupled to Affigel matrix. The serum is then further purified by protein G affinity chromatography to isolate the IgG fraction, Sera from other His-tagged antigens and peptide immunized rabbits as well as fusion partner depleted sera are affinity purified by passage over a column matrix composed of the original protein immunogen or free peptide.

Example 11

Generation of 202P5A5 Monoclonal Antibodies (mAbs)

In One embodiment, therapeutic mAbs to 202P5A5 variants comprise those that react with epitopes specific for each variant protein or specific to sequences in common between the variants that would disrupt or modulate the biological function of the 202P5A5 variants, for example those that would disrupt the interaction with ligands and binding partners. Immunogens for generation of such mAbs include those designed to encode or contain the entire 202P5A5 protein variant sequence, regions of the 202P5A5 protein variants predicted to be antigenic from computer analysis of the amino acid sequence (see, e.g., FIG. 5, FIG. 6, FIG. 7, FIG. 6, or FIG. 9, and the Example entitled "Antigenicity Profiles and Secondary Structures"). Immunogens include peptides, recombinant bacterial proteins, and mammalian expressed Tag 5 proteins and human and murine IgG FC fusion proteins. In ad ditto n, cells engineered to express high levels of a respective 202P5A5 variant, such as 293T-202P5AD5 variant 1 or 300.19-202P5A5 variant 1 murine Pre-B cells, are used to immunize mice.

To generate mAbs to a 202P5A5 variant, mice are first immunized intraperitoneally (IP) with, typically, 10-50 μg of protein immunogen or 107 202P5A5-expressing cells mixed in complete Freund's adjuvant. Mice are then subsequently immunized IP every 2-4 weeks with, typically, 10-50 μg of protein immunogen or $10^7$ cells mixed in incomplete Freund's adjuvant. Alternatively, MPL-TDM adjuvant is used in immunizations. In addition to the above protein and cell-based immunization strategies, a DNA-based immunization protocol is employed in which a mammalian expression vector encoding a 202P5A5 variant sequence is used to immunize mice by direct injection of the plasmid DNA. For example, the complete cDNA of 202P5A5 of variant 1 (amino acids 1-609) is cloned into the Tag5 mammalian secretion vector and the recombinant vector will then be used as immunogen. In another example, the same amino acids are cloned into an Fc-fusion secretion vector in which the 202P5A5 variant 2 sequence is fused at the amino-terminus to an IgK leader sequence and at the carboxyl-terminus to the coding sequence of the human or murine IgG Fc region. This recombinant vector is then used as immunogen. The plasmid immunization protocols are used in combination with purified proteins expressed from the same vector and with cells expressing the respective 202P5A5 variant.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

In one embodiment for generating 202P5A5 monoclonal antibodies, a GST-fusion of variant 1 antigen encoding amino acids 1-609, is expressed and then purified from stably transfected 293T cells, Balb C mice are initially immunized intra peritoneally with 25 μg of the Tag5-202P5A05 variant 1 protein mixed in complete Freund's adjuvant. Mice are subsequently immunized every two weeks with 25 μg of the antigen mixed in incomplete Freund's adjuvant for a total of three immunizations. ELISA using the GST-fusion antigen and a cleavage product from which the GST portion is removed determines the titer of serum from immunized mice. Reactivity and specificity of serum to full length 202P5A5 variant 1 protein is monitored by Western blotting, immunoprecipitation and flow cytometry using 293T cells transfected with an expression vector encoding the 202P5A5 variant 1 cDNA (see e.g., the Example entitled "Production of Recombinant 202P5A05 in Eukaryotic Systems" and FIG. 21). Other recombinant 202P5A5 variant 1-expressing cells or cells endogenously expressing 202P5A5 variant 1 are also used. Mice showing the strongest reactivity are rested and given a final injection of Tag5 antigen in PBS and then sacrificed four days later. The spleens of the sacrificed mice are harvested and fused to SPO/2 myeloma cells using standard procedures (Harlow and Lane, 1988). Supernatants from HAT selected growth wells are screened by ELISA, Western blot, immunoprecipitation, fluorescent microscopy, and flow cytometry to identify 202P5A5 specific antibody-producing clones.

To generate monoclonal antibodies that are specific for 202P5A5 variant 2 protein, immunogens are designed to encode the sequence unique to that variant. For example, a peptide encoding amino acids 1-16 of 202P5A5 variant 2 is synthesized, conjugated to KLH and used as immunogen. Hybridoma supernatants are then screened on the peptide antigen and then further screened on cells expressing the 202P5A5 variant 2 and cross-screened on cells expressing 202P5A5 variant 1 to derive variant 2-specific monoclonal antibodies.

The binding affinity of a 202P5A5 variant monoclonal antibody is determined using standard technologies. Affinity measurements quantify the strength of antibody to epitope binding and are used to help define which 202P5A5 variant monoclonal antibodies preferred for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 12

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 mM) are incubated with various unlabeled peptide inhibitors and 1-10 nM, $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and $IC_{50} \geqq$ [HLA], the measured $IC_{50}$ values are reasonable approximations of the true $K_D$ values. Peptide inhibitors are typically tested at concentrations ranging from 120 μg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides (see Table IV).

Example 13

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-bearing Epitopes The searches performed to identify the motif-bearing peptide sequences in the Example entitled "Antigenicity Profiles" and Tables VIII-XXI and XXII-XLIX employ the protein sequence data from the gene product of 202P5A5 set forth in FIGS. 2 and 3, the specific search peptides used to generate the tables are listed in Table VII.

Computer searches for epitopes bearing HLA Class I or Class II supermotifs or motifs are performed as follows, All translated 202P5A5 protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or $\Delta G$) of peptide-HLA molecule interactions can be approximated as a linear polynomial function of the type:

"$\Delta G$"=a1i×a2i×a3i ... ×aji where aji is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount j; to the free energy of binding of the peptide irrespective of the sequence of the rest of the peptide.

The method of derivation of specific algorithm coefficients has been described in Gulukota et al., *J. Mol. Biol.* 267-1258-126, 1997; (see also Sidney et al., *Human Immunol.* 45:79-93, 1996; and Southwood et al., J. Immunol. 160:3363-3373, 1998). Briefly, for all i positions, anchor and non-anchor alike, the geometric mean of the average relative binding (ARB) of all peptides carrying j is calculated relative to the remainder of the group, and used as the estimate of j. For Class II peptides, if multiple alignments are possible, only the highest scoring alignment is utilized, following an iterative procedure. To calculate an algorithm score of a given peptide in a test set, the ARB values corresponding to the sequence of the peptide are multiplied, if this product exceeds a chosen threshold, the peptide is predicted to bind. Appropriate thresholds are chosen as a function of the degree of stringency of prediction desired.

Selection of HLA-A2 Supertype Cross-reactive Peptides

Protein sequences from 202P5A5 are scanned utilizing motif identification software, to identify 8-, 9- 10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

Those peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-bearing Epitopes

The 202P5A5 protein sequence(s) scanned above is also examined for the presence of peptides with the HLA-A3-supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of ≦500 nM, often ≦200 nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The 202P5A5 protein(s) scanned above is also analyzed for the presence of 8-, 9- 10-, or 11-mer peptides with the HLA-B7-supermotif. Corresponding peptides are synthesized and tested for binding to HLA-B*0702, the molecule encoded by the most common B7-supertype allele (i.e., the prototype B7 supertype allele). Peptides binding B*0702 with $IC_{50}$ of <500 nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-bearing Epitopes

To further increase population coverage, HLA-A1 and -A24 epitopes can also be incorporated into vaccine compositions. An analysis of the 202P5A5 protein can also be performed to identify HLA-A1- and A24-motif-containing sequences.

High affinity and/or cross-reactive binding epitopes that bear other motif and/or supermotifs are identified using analogous methodology.

Example 14

Confirmation of Immunogenicity

Cross-reactive candidate CTL A2-supermotif-bearing peptides that are identified as described herein are selected to confirm in vitro immunogenicity. Confirmation is performed using the following methodology;

Target Cell Lines for Cellular Screening:

The 221A2.1 cell line, produced by transferring the HLA-A2.1 gene into the HLA-A, -B, -C null mutant human B-lymphoblastoid cell line 721.221, is used as the peptide-loaded target to measure activity or HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 µg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating 10×10⁸ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNF α is added to the DCs on day 6 at 75 ng/ml and the cells are used for CTL induction cultures on day 7.

Induction of CTL with DC and Peptide: CD8+T-cells are isolated by positive selection with Dynal Immunomagnetic beads (Dynabeads® M-450) and the Detacha-Bead® reagent. Typically about 200-250×10$^6$ PBMC are processed to obtain 24×10$^5$ CD8+T-cells (enough for a 48-well plate culture). Briefly, the PBMCs are thawed in RPMI with 30 µg/ml DNAse, washed once with PBS containing 1% human AB serum and resuspended in PBS/1% AB serum at a concentration of 20×10$^5$ cells/ml. The magnetic beads are washed 3 times with PBS/AB serum, added to the cells (140 µl beads/20/×10$^5$ cells) and incubated for 1 hour at 4° C. with continuous mixing. The beads and cells are washed 4× with PBS/AB serum to remove the nonadherent cells and resuspended at 100×10$^6$ cells/ml (based on the original cell number) in PBS/AB serum containing 100 µl/ml Detacha-Bead® reagent and 30 µg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5-7 minutes, washed once with PBS with 1% BSA, counted and pulsed with 40 µg/ml of peptide at a cell concentration of 1-2×10$^8$/ml in the presence of 3 µg/ml microglobulin for 4 hours at 20° C. The DC are then irradiated (4,200 rads), washed 1 time with medium and counted again.

Setting up induction cultures: 0.25 ml cytokine-generated DC (at 1×10$^5$ cells/ml) are co-cultured with 0.25 ml of CD8+ T-cells (at 2×10$^6$ cell/ml) in each well of a 48-well plate in the presence of 10 ng/ml of IL-7. Recombinant human IL-10 is added the next day at a final concentration of 10 ng/ml and rhuman IL-2 is added 4B hours later at 10 IU/ml.

Restimulation of the induction cultures with peptide-pulsed adherent cells: Seven and fourteen days after the primary induction, the cells are restimulated with peptide-pulsed adherent cells. The PBMCs are thawed and washed twice with RPMI and DNAse. The cells are resuspended at 5×10$^6$ cells/ml and irradiated at −4200 rads. The PBMCs are plated at 2×10$^6$ in 0.5 ml complete medium per well and incubated for 2 hours at 37° C. The plates are washed mice with RPMI by tapping the plate gently to remove the nonadherent cells and the adherent cells pulsed with 10 µg/ml of peptide in the presence of 3 µg ml β$_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2-3 days later at 50 IU/ml (Tsai et al., *Critical Reviews in Immunology* 18(1-2):65-75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 µg/ml peptide overnight at 37° C.

Adherent target cells are removed from culture flasks with trypsin-EDTA, Target cells are labeled with 200 µCi of $^{51}$Cr sodium chromate (Dupont, Wilmington, Del.) for 1 hour at 37° C. Labeled target cells are resuspended at 10$^6$ per ml and diluted 1:10 with K662 cells at a concentration of 3.3×10$^6$/ml (an NK-sensitive erythroblastoma cell line used to reduce non-specific lysis). Target cell is (100 µl) and effectors (100 µl) are plated in 96 well round-bottom plates and incubated for 5 hours at 37° C. At that time, 100 µl of supernatant are collected from each well and percent lysis is determined according to the formula:

$$[(\text{cpm of the test sample} - \text{cpm of the spontaneous } ^{51}\text{Cr release sample})/(\text{cpm of the maximal } ^{51}\text{Cr release sample} - \text{cpm of the spontaneous } ^{51}\text{Cr release sample})] \times 100.$$

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-specific and Endogenous Recognition Immulon 2 plates are coated with mouse anti-human IFNγ monoclonal antibody (4 µg/ml 0.1M NaHCO$_3$. pH 3.2) overnight at 4° C. The plates are washed with Ca$^{2+}$, Mg$^{2+}$-free PBS/0.05% Tween 20 and blocked with PBS/10% FCS for two hours, after which the CTLs (100 µl/well) and targets (100 µd/well) are added to each well, leaving empty wells for the standards and blanks (which received media only). The target cells, either peptide-pulsed or endogenous targets, are used at a concentration of 1×10$^6$ cells/ml. The plates are incubated for 48 hours at 37° C. with 5% CO$_2$.

Recombinant human IFN-gamma is added to the standard wells starting at 400 pg or 1200 pg/100 microtiter/well and the plate incubated for two hours at 37° C. The plates are washed and 100 µl of biotinylated mouse anti-human IFN-gamma monoclonal antibody (2 microgram/ml in PBS/3% FCS/0.05% Tween 20) are added and incubated for 2 hours at room temperature. After washing again, 100 microtiter HRP-streptavidin (1:4000) are added and the plates incubated for one hour at room temperature. The plates are then washed 6× with wash buffer, 100 micro liter/well developing solution (1:1) are added, and the plates allowed to develop for 5-15 minutes. The reaction is stopped with 50 microliter/well 1M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, 5×10$^4$ CDB+ cells are added to a T25 flask containing the following: 1×10$^6$ irradiated (4,200 rad) PBMC (autologous or allogeneic) per ml, 2×10$^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 26 µM 2-mercaptoethanol, L-glutamine and penicillin/streptomycin. Recombinant human IL2 is added 24 hours later at a final concentration of 200 IU/ml and every three days thereafter with fresh media at 50 IU/ml. The cells are split if the cell concentration exceeds 1×10$^5$/ml and the cultures are assayed between days 13 and 15 at E:T ratios of 30, 10, 3 and 1:1 in the $^{51}$Cr release assay or at 1×10$^6$/ml in the in situ IFNγ assay using the same targets as before the expansion.

Cultures are expanded in the absence of anti-CD3+ as follows. Those cultures that demonstrate specific lytic activity against peptide and endogenous targets are selected and 5×10$^4$ CDB+ cells are added to a T25 flask containing the following: 1×10$^6$ autologous PBMC per ml which have been peptide-pulsed with 10 µg/ml peptide for two hours at 37° C. and irradiated (4,200 rad); 2×10$^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 202P5A5. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 screening of the B7-supertype cross-reactive binding peptides identified as set forth herein are methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology.

Example 15

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and super motifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analog at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an $IC_{50}$ of 5000 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., *J. Immunol.* 157:2539, 1996; and Pogue et al., Proc. Natl. Acad Sci. USA 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-Supermotif-Bearing Peptides

Analogs of HLA-A3 supermotif-bearing epitopes are generated using strategies similar to those employed in analoging HLA-A2 supermotif-bearing peptides. For example, peptides binding to ⅗ of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate ≦500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et. al., (*J. Immunol* 157:3480-3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with 202P5A5-expressing tumors.

Other Analoging Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of α-amino butyric acid for cysteine not only alleviates this problem, but has been shown to improve binding and crossbinding capabilities in some instances (see, e.g., the review by Sette et al., In: Persistent Viral Infections, Eds. R. Ahmed an d I. Chen, John Wiley & Sons, England, 1999).

Thus, by the use of single amino acid substitutions, the binding properties and/or cross-reactivity of peptide ligands for HLA supertype molecules can be modulated.

Example 16

Identification and Confirmation of 202P5A5-derived Sequences with HLA-DR Binding Motifs Peptide epitopes bearing an HLA class II supermotif or motif are identified and confirmed as outlined below using methodology similar to that described for HLA Class I peptides.

Selection of HLA-DR-Supermotif-Bearing Epitopes.

To identify 202P5A5-derived, HLA class II HTL epitopes, a 202P5A5 antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160: 3363-3373, 1998). These protocols, specific for individual DR molecules, allow the scoring, and ranking, of 9-mer core regions. Each protocol not only scores peptide sequences for the presence of DR-super motif primary anchors (i.e., at position 1 and position 6) within a 9-mer core, but additionally evaluates sequences for the presence of secondary anchors. Using allele-specific selection tables (see, e.g., Southwood et al., ibid), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 202P5A5-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 202P5A5-derived peptides found to bind common HLA-DR alleles are of particular interest.

Selection of DR3 Motif Peptides

Because HLA-DR3 is an allele that is prevalent in Caucasian, Black and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 202P5A5 antigens are analyzed for sequences carrying one of the two DR3-specific binding motifs reported by Geluk et al. (*J. Immunol.* 152:5742-5748, 1994). The corresponding peptides are then synthesized and confirmed as having the ability to bind DR3 with an affinity or 1 μM or better, i.e., less in an 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 17

Immunogenicity of 202P5A5-Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.1) in vitro primary induction using normal PBMC or 2.) recall responses from patients who have 202P5A5-expressing tumors.

Example 18

Calculation of Phenotypic Frequencies of HLA-Supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1−(SQRT(1-af)) (see, e.g., Sidney et al., *Human Immunol.* 45:75-93, 1996). To obtain overall phenolypic frequencies, cumulative gene frequencies are calculated, and the cumulative antigen frequencies derived by the use of the inverse formula [$af=1-(1-Cgf)^2$].

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1−A)). Confirmed members of the A3-like supertype are A3, A11, A31, A*3301, and A*6801. Although the A3-like supertype may also include A34, A66, and A*401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B5401, B*5501-2, B*5801, B*6701, and B7801 (potentially also B*1401, B*3501-08, B4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%, see, e.g. Table IV (G). An analogous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159-1848, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%, A more preferred percentage is 95%.

Example 19

CTL Recognition Of Endogenously Processed Antigens After Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K=target cells in the absence or presence of peptide, and also tested on $^{51}$Cr labeled target cells bearing the endogenously synthesized antigen, i.e. cells that are stably transfected with 202P5A5 expression vectors.

The results demonstrate that CTL lines obtained from animals primed with peptide epitope recognize endogenously synthesized 202P5A5 antigen. The choice of transgenic mouse model to be used for such an analysis depends upon the epitope(s) that are being evaluated. In addition to HLA-A*0201/K$^t$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 20

Activity Of CTL-HTL Conjugated Epitopes In Transgenic Mice

This example illustrates the induction of CTLs and HTLs in transgenic mice, by use of a 202P5A5-derived CTL and HTL peptide vaccine compositions. The vaccine composition used herein comprise peptides to be administered to a patient with a 202P5A5-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures: Immunization of transgenic mice is performed as described (Alexander et al., *J. Immunol* 159:4753-4761, 1997). For example, A2/K$^D$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in incomplete Freund's Adjuvant, or if the peptide composition is a lipidated CTU/HTL conjugate, in DMSO/saline, or if the peptide composition is a polypeptide, in PBS or incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/K$^b$ chimeric gene (e.g., Vitiello et al., *J. Exp. Med.* 173:1007, 1991)

In vitro CTL activation: One week after priming, spleen cells (30×10$^6$ cells/flask) are co-cultured at 37° C. with syngenic, irradiated (3000 rads), peptide coated lymphoblasts (10×10$^5$ cells/flask) in 10 ml of culture medium/T25 flask. After six days, effector cells are harvested and assayed for cytotoxic activity.

Assay for cytotoxic activity: Target cells (1.0 to 1.5×10$^6$) are incubated at 37° C. in the presence of 200 µl of $^{51}$Cr. After 60 minutes, cells are washed three times and resuspended in R10 medium. Peptide is added where required at a concentration of 1 µg/ml. For the assay, 10$^4$ 51Cr-labeled target cells are added to different concentrations of effector cells (final volume of 200 µl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula; percent specific release=100× (experimental release−spontaneous release)/ (maximum release−spontaneous release). To facilitate comparison between separate CTL assays run under the same conditions, % $^{51}$Cr release data is expressed as lytic units, 10$^6$ cells. One lytic unit is arbitrarily defined as the number of effector cells required to achieve 30% lysis of 10,000 target cells in a six hour $^{51}$Cr release assay. To obtain specific lytic units/10$^6$, the lytic units/10$^6$ obtained in the absence of peptide is subtracted from the lytic units/10$^5$ obtained in the presence of peptide. For example, if 30% $^{51}$Cr release is obtained at the effector (E): target (T) ratio of 50:1 (i.e., $5\times10^5$ effector cells for 10,000 targets) in the absence of peptide and 5:1 (i.e., $5\times10^4$ effector cells for 10,000 targets) in the presence of peptide, the specific lytic units would be: $[(1/50,000)-(1/500,000)]\times10^6=18$ LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity." Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 21

Selection of CTL and HTL Epitopes for Inclusion in a 202P5A5-Specific Vaccine

This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 202P5A5 clearance. The number of epitopes used depends on observations of patients who spontaneously clear 202P5A5. For example, if it has been observed that patients who spontaneously clear 202P5A5-expressing cells genera be an immune response to at least three (3) epitopes from 202P5A5 antigen, then at least three epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores from the BIMAS web site, at URL bimas.dcrt.nih.gov/.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 50% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes, For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 202P5A5, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress 202P5A5.

Example 22

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived 202P5A5, are selected such that multiple supermotifs/motifs are represented to ensure broad population coverage. Similarly, HLA class II epitopes are selected from 202P5A5 to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 µg of each of two oligonucleotides are annealed and extended: In an example using eight oligonucleotides, i.e., four pairs of primers, oligonucleotides 1+2, 3+4, 5+3, and 7+8 are combined in 100 µl reactions containing Pfu polymerase buffer (1×10 mM KCL, 10 mM $(NH4)_2SO_4$, 20 mM Tris-chloride, pH 8.75, 2 mM $MgSO_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 23

The Plasmid Construct and the Degree to Which It Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol* 155:663-692, 1996; Demotz et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et. al., *Immunity* 1:751-761, 1994).

For example, to confirm the capacity of a DNA minigene construct containing at least one HLA-A2 supermotif peptide to induce CTLs in vitro, HLA-A2.1/$K^b$ transgenic mice, for example, are immunized intramuscularly with 100 µg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}Cr$ release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-$A^b$-restricted mice, for example, are immunized intramuscularly with 100 µg of plasmid DNA. As a means of comparing a the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3H$-thymidine incorporation proliferation assay, (see, e.g., Alexander et al. Immunity 1:751-751, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retroviruses* 14, Supplement 3:S299-S309, 1998) or recombinant vaccinia, for example, expressing a minigene or DNA encoding the complete protein of interest (see, e.g., Hanke et al., *Vaccine* 16:439-445, 1998; Sedegah et al., *Proc. Natl. Acad. Sci USA* 95:7648-53, 1998; Hanke and McMichael, *Immunol. Letters* 66:177-131, 1999; and Robinson et. al., *Nature Med.* 5:526-34, 1999).

For example, the efficacy of the DNA minigene used in a prime boost protocol is initially evaluated in transgenic mice, in this example, A2.1/$K^b$ transgenic mice are immunized IM with 100 µg of a DNA minigene encoding the immunogenic peptides including at least one HLA-A2 supermotif-bearing peptide. After an incubation period (ranging from 3-9 weeks), the mice are boosted IP with $10^7$ pfu/mouse of a recombinant vaccinia virus expressing the same sequence encoded by the DNA minigene. Control mice are immunized with 100 ng of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 24

Peptide Compositions for Prophylactic Uses

Vaccine compositions of the present invention can be used to prevent 202P5A5 expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 202P5A5-associated tumor.

For example, a peptide-based composition is provided as a single polypeptide that encompasses multiple epitopes. The vaccine is typically administered in a physiological solution that comprises an adjuvant, such as incomplete Freunds Adjuvant. The dose of peptide for the initial immunization is from about 1 to about 50,000 µg, generally 100-5,000 µg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 202P5A5-associated disease.

Alternatively, a composition typically comprising transfecting agents is used for the administration of a nucleic acid-based vaccine in accordance with methodologies known in the art and disclosed herein.

Example 25

Polyepitopic Vaccine Compositions Derived from Native 202P5A5 Sequences

A native 202P5A5 poly protein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide, Such a vaccine composition is administered For therapeutic or prophylactic purposes.

The vaccine composition will include, for example, multiple CTL epitopes from 202P5A5 antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally, such an embodiment provides for the possibility of motif-bearing epitopes for an HLA makeup(s) that is presently unknown. Furthermore, this embodiment (excluding an analoged embodiment) directs the immune response to multiple peptide sequences that are actually present in native 202P5A5, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequences length.

Example 26

Polyepitopic Vaccine Compositions from Multiple Antigens

The 202P5A5 peptide epitopes of the present invention are used in conjunction with epitopes from other target tumor-associated antigens, to create a vaccine composition that is useful for the prevention or treatment of cancer that expresses 202P5A5 and such other antigens. For example, a vaccine composition can be provided as a single polypeptide that incorporates multiple epitopes from 202P5A5 as well as tumor-associated antigens that are often expressed with a target cancer associated with 202P5A5 expression, or can be administered as a composition comprising a cocktail of one or more discrete epitopes. Alternatively, the vaccine can be administered as a minigene constructor as dendritic cells which have been loaded with the peptide epitopes in vitro.

Example 27

Use of Peptides to Evaluate an Immune Response

Peptides of the invention may be used to analyze an immune response for the presence of specific antibodies, CTL or HTL directed to 202P5A5. Such an analysis can be performed in a manner described by Ogg et al., *Science* 279: 2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, 202P5A5 HLA-A*0201-specific CTL frequencies from HLA A*0201-positive individuals at different stages of disease or following immunization comprising a 202P5A5 peptide containing an A*0201 motif. Tetrameric complexes are synthesized as described (Musey et. al., W. Engl. J. Med. 337:1267, 1997). Briefly, purified HLA heavy chain (A*0201 in this example) and (β-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain. β2-microglobulin, and peptide are refolded by dilution. The 45-kD refolded product is isolated by fast protein liquid chromatography and then biotinylated by BirA in the presence of biotin (Sigma, St, Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 μl of cold phosphate-buffered saline. Tricolor analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 202P5A5 epitope, and thus the status of exposure to 202P5A5, or exposure to a vaccine that elicits a protective or therapeutic response.

Example 28

Use of Peptide Epitopes to Evaluate Recall Responses

The peptide epitopes of the invention are used as reagents to evaluate T cell responses, such as acute or recall responses, in patients. Such an analysis may be performed on patients who have recovered from 202P5A5-associated disease or who have been vaccinated with a 202P5A5 vaccine.

For example, the class I restricted CTL response of persons who have been vaccinated may be analyzed. The vaccine may be any 202P5A5 vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50/ml), streptomycin (50 μg/ml), and Hepes (10 mM) containing 10% heat-inactivated human AB serum (complete RPMI) and plated using microculture formats. A synthetic peptide comprising an epitope of the invention is added at 10 μg/ml to each well and HBV core 128-140 epitope is added at 1 μg/ml to each well as a source of T cell help during the first week of stimulation.

In the microculture formal, $4\times10^5$ PBMC are stimulated with peptide in 8 replicate cultures in 96-well round bottom plate in 100 μl/well of complete RPMI. On days 3 and 10, 100 μl of complete RPMI and 20 U/ml final concentration of rIL-2 are added to each well. On day 7 the cultures are transferred into a 96-well flat-bottom plate and restimulated with peptide, rIL-2 and $10^6$ irradiated (3,000 rad) autologous feeder calls. The cultures are tested for cytotoxic activity on day 14. A positive CTL response requires two or more of the eight replicate cultures to display greater than 10% specific $^{51}Cr$ release, based on comparison with non-diseased control subjects as previously described (Rehermann, et. al., *Nature Med.* 2:1104, 1108, 1996; Rehermann et al., *J. Clin. Invest* 97:1655-1665, 1996; and Rehermann et al. *J. Clin. Invest.* 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670-2673, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 μM, and labeled with 100 μCi of $^{51}Cr$ (Amersham Corp., Arlington Heights, Ill.) for 1 hour after which they are washed four times with HBSS.

Cytolytic activity is determined in a standard 4-h, split well $^{51}Cr$ release assay using U-bottomed 96 well plates containing 3,000 targets/well. Stimulated PBMC are tested at effector/target (E/T) ratios of 20-50:1 on day 14. Percent cytotoxicity is determined from the formula: 100× [(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 202P5A5 or a 202P5A5 vaccine.

Similarly, Class II restricted HTL responses may also be analyzed. Purified PBMC are cultured in a 96-well flat bottom plate at a density of $1.5\times10^5$ cells/well and are stimulated with 10 μg/ml synthetic peptide of the invention, whole 202P5A5 antigen, or PHA. Cells are routinely plated in replicates of 4-6 welts for each condition. After seven days of culture, the medium is removed and replaced with fresh medium containing 10 U/ml IL-2. Two days later, 1 μCi $^3H$-thymidine is added to each well and incubation is continued for an additional 16 hours. Cellular DNA is then harvested on glass fiber mats and analyzed for $^3H$-thymidine incorporation. Antigen-specific T cell proliferation is calculated as the ratio of $^3H$-thymidine incorporation in the presence of antigen divided by the $^3H$-thymidine incorporation in the absence of antigen.

Example 29

Induction of Specific CTL Response in Humans

A human clinical trial for an immunogenic composition comprising CTL and HTL epitopes of the invention is set up as an IND Phase I, dose escalation study and earned out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 μg of peptide composition;

Group II: 3 subjects are injected with placebo and 6 subjects are injected with 50 μg peptide composition;

Group III: 3 subjects are injected with placebo and 6 subjects are injected with 500 μg of peptide composition, After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safely and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear calls are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 30

Phase II Trials In Patients Expressing 202P5A5

Phase II trials are performed to study the effect of administering the CTL-HTL peptide compositions to patients having cancer that expresses 202P5A5. The main objectives of the trial are to determine an effective dose and regimen for inducing CTLs in cancer patients that express 202P5A5, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-55 and represent diverse ethnic backgrounds. All of them have a tumor that expresses 202P5A5.

Clinical manifestations or antigen-specific T-cell responses are monitored to assess the effects of administering the peptide compositions. The vaccine composition is found to be both safe and efficacious in the treatment of 202P5A5-associated disease.

Example 31

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used far the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of "Minigene" Multi-Epitope DNA Plasmids" in the form of naked nucleic acid administered IM (or SC or ID) in the amounts of 0.5-5 mg at multiple sites. The nucleic acid (0.1 to 1000 μg) can also be administered using a gene gun. Following an incubation period of 3-4 weeks, a booster dose is then administered. The booster can be recombinant fowl pox virus administered at a dose of $5\text{-}10^7$ to $5\times10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugal Lon, aliquoted in freezing media and stored frozen. Samples are assayed for CTL and HTL activity.

Analysis of the results indicates that a magnitude of response sufficient to achieve a therapeutic or protective immunity against 202P5A5 is generated.

Example 32

Administration of Vaccine Compositions Using Dendritic Calls (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back Into the patient to elicit CTL and HTL responses in vivo. The induced CTL and HTL then destroy or facilitate destruction, respectively, of the target cells that bear the 202P5A5 protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g. *Nature Med.* 4:328, 1998; *Nature Med*, 2:52, 1996 and Prostate 32:272, 1997). Although $2\text{-}50\times10^6$ DC per patient are typically administered, larger number of DC, such as $10^7$ or $10^8$ can also be provided. Such cell populations typically contain between 50-90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive 5×10⁶ DC, then the patient will be injected with a total of 2.5×10⁸ peptide-loaded PBMC. The percent DC mobilized by an agent such as Progenipoietin™ is typically estimated to be between 2-10%, but can vary as appreciated by one of skill in the art.

Ex Vivo Activation of CTL/HTL Responses

Alternatively, ex vivo CTL or HTL responses to 202P5A5 antigens can be induced by incubating, in tissue culture, the patient's, or genetically compatible, CTL or HTL precursor cells together with a source of APC, such as DC, and immunogenic peptides. After an appropriate incubation time (typically about 7-28 days), in which the precursor cells are activated and expanded into effector cells, the cells are infused into the patient, where they will destroy (CTL) or facilitate destruction (HTL) of their specific target cells, i.e., tumor cells.

Example 33

An Alternative Method of Identifying and Confirming Motif-Bearing Peptides

Another method of identifying and confirming motif-bearing peptides is to elute them from cells bearing defined MHC molecules. For example. EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 202P5A5. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et. al., *J. Immunol.* 152:3313, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 202P5A5 to isolate peptides corresponding to 202P5A5 that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 34

Complementary Polynucleotides

Sequences complementary to the 202P5A5-encoding sequences, or any parts thereof, are used to detect, decrease, or inhibit expression of naturally occurring 202P5A5. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 202P5A5. To inhibit transcription, a complementary oligonucleotide is designed from the most unique 5' sequence and used to prevent promoter binding to the coding sequence. To inhibit translation, a complementary oligonucleotide is designed to prevent ribosomal binding to a 202P5A5-encoding transcript.

Example 35

Purification of Naturally-Occurring or Recombinant 202P5A5 Using 202P5A5-Specific Antibodies Naturally occurring or recombinant 202P5A5 is substantially purified by immunoaffinity chromatography using antibodies specific for 202P5A5. An immunoaffinity column is constructed by covalently coupling anti-202P5A5 antibody to an activated chromatographic resin, such as CNBr-activated SEPHAROSE (Amersham Pharmacia Biotech). After the coupling, the resin is blocked and washed according to the manufacturer's instructions.

Media containing 202P5A5 are passed over the immunoaffinity column, and the column is washed under conditions that allow the preferential absorbance of 202P5A5 (e.g., high ionic strength buffers in the presence of detergent). The column is eluted under conditions that disrupt antibody/202P5A5 binding (e.g., a buffer of pH 2 to pH 3, or a high concentration of a chaotrope, such as urea or thiocyanate ion), and GCR.P is collected.

Example 36

Identification of Molecules Which Interact with 202P5A5

202P5A5, or biologically active fragments (hereof, are labeled with 121 1 Bolton-Hunter reagent. (See, e.g., Bolton et al. (1973) Biochem. J. 133:529.) Candidate molecules previously arrayed in the wells of a multi-well plate are incubated with the labeled 202P5A5, washed, and any wells with labeled 202P5A5 complex are assayed. Data obtained using different concentrations of 202P5A5 are used to calculate values for the number, affinity, and association of 202P5A5 with the candidate molecules.

Example 37

In Vivo Assay for 202P5A5 Tumor Growth Promotion

The effect of the 202P5A5 protein on tumor cell growth is evaluated in vivo by evaluating tumor development and growth of cells expressing or lacking 202P5A5. For example, SCID mice are injected subcutaneously on each flank with 1×10⁶ of either 3T3, prostate (e.g. PC3 cells), bladder (e.g. UM-UC3 cells) or breast (e.g. DU4475 cells) cancer cell lines containing tkNeo empty vector or 202P5A5. At least two strategies may be used: (1) Constitutive 202P5A5 expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as acdysone, tetracycline, etc., provided such promoters are compatible with the host cell systems. Tumor volume is then monitored by caliper measurement at the appearance of palpable tumors and followed overtime to determine if 202P5A5-expressing cells grow at a faster rate and whether tumors produced by 202P5A5-expressing cells demonstrate characteristics of altered aggressiveness (e.g. enhanced metastasis, vascularization, reduced responsiveness to chemotherapeutic drugs).

Additionally, mice can be implanted with $1 \times 10^5$ of the same cells orthotopically to determine if 202P5A5 has an effect on local growth in the pancreas, and whether 202P5A5 affects the ability of the cells to metastasize, specifically to lymph nodes, and bone (Miki T et al, Oncol Res. 2001; 12:209; Fu X et al, Int J Cancer. 1991, 49:938). The effect of 202P5A5 on bone tumor formation and growth may be assessed by injecting tumor cells intratibially. The assay is also useful to determine the 202P5A5 inhibitory effect of candidate therapeutic compositions, such as for example, 202P5A5 intrabodies, 202P5A5 antisense molecules and ribozymes.

Example 38

202P5A5 Monoclonal Antibody-Mediated Inhibition of Tumors In Vivo

The significant expression of 202P5A5 in cancer tissues, together with its restrictive expression in normal tissues makes 202P5A5 a good target for antibody therapy. Similarly, 202P5A5 is a target for T cell-based immunotherapy. Thus, the therapeutic efficacy of anti-202P5A5 mAbs in human cancer xenograft mouse models, including prostate, bladder and breast (e.g. DU4475 cells) and other 202P5A5 cancers listed in table I, is evaluated by using recombinant cell lines such as PC3-202P5A5, UM-UC3-202P5A5, DU4475-202P5A5, and 3T3-202P5A5 (see, e.g., Kaighn, M. E., et. al., Invest Urol. 1979. 17 (1): 16-23), as well as human xenograft models (Saffran et al. PNAS 1999, 10:1073-1078).

Antibody efficacy on tumor growth and metastasis formation is studied, e.g., in a mouse orthotopic ovary, pancreas, or blood cancer xenograft models. The antibodies can be unconjugated, as discussed in this Example, or can be conjugated to a therapeutic modality, as appreciated in the art. Anti-202P5A5 mAbs inhibit formation of tumors in mouse xenografts. Anti-202P5A5 mAbs also retard the growth of established orthotopic tumors and prolonged survival of tumor-bearing mice. These results indicate the utility of anti-202P5A5 mAbs in the treatment of local and advanced stages several solid tumors. (See, e.g., Saffran, D., et al., PNAS 10:1073-1078 or world wide web URL pnas.org/cgi/dol/10.1073/pnas.051624698).

Administration of the anti-202P5A5 mAbs led to retardation of established orthotopic tumor growth and inhibition of metastasis to distant sites, resulting in a significant prolongation in the survival of tumor-bearing mice. These studies indicate that 202P5A5 as an attractive target for immunotherapy and demonstrate the therapeutic potential of anti-202P5A5 mAbs for the treatment of local and metastatic cancer. This example indicates that unconjugated 202P5A5 monoclonal antibodies are effective to inhibit the growth of human pancreatic, ovarian, and lymphomas tumor xenografts grown in SCID mice; accordingly a combination of such efficacious monoclonal antibodies is also effective.

Tumor Inhibition Using Multiple Unconjugated 202P5A5 mAbs

Materials and Methods

202P5A5 Monoclonal Antibodies:

Monoclonal antibodies are raised against 202P5A5 as described in the Example entitled "Generation of 202P5A5 Monoclonal Antibodies (mAbs)." The antibodies are characterized by ELISA. Western blot, FACS, and immunoprecipitation for their capacity to bind 202P5A5. Epitope mapping data for the anti-202P5A5 mAbs, as determined by ELISA and Western analysis recognize epitopes on the 202P5A5 protein. Immunohistochemical analysis of cancer tissues and cells with these antibodies is performed.

The monoclonal antibodies are purified from ascites or hybridoma tissue culture supernatants by Protein-G Sepharose chromatography, dialyzed against PBS, filter sterilized, and stored at $-20°$ C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of PC3, UM-UC3, CaKi and A4271 tumor xenografts.

Cell Lines and Xenografts

The LAPC-9 xenograft, which expresses a wild-type androgen receptor and produces prostate-specific antigen (PSA), is passage din 6- to 8-week-old male ICR-severe combined immunodeficient (SCID) mice (Taconic Farms) by s.c. trocar implant (Craft, N., et al., 1999, Cancer Res. 59:5030-5030). The AGS-K3 and AGS-K6 kidney xenografts are also passaged by subcutaneous implants in 6- to 8-week old SCID mice. Single-cell suspensions of tumor cells are prepared as described in Craft, et al.

The cancer cell lines PC3, UM-UC3 and DU4475 cell lines, as well as the fibroblast line NIH 3T3 (American Type Culture Collection). The prostate carcinoma cell line PC3 is maintained in RPMI supplemented with L-glutamine and 10% FBS, and the bladder and breast carcinoma lines, UM-UC3 and DU4475 respectively, are maintained in DMEM supplemented with L-glutamine and 10% FBS. PC3-202P5A5, UM-UC3-202P5A5, DU 4475-202P5A5 and 3T3-202P5A5 cell populations are generated by retroviral gene transfer as described in Hubert, R. S., et al., Proc Natl Acad Sci USA, 1999. 96(25): 14523.

Xenograft Mouse Models

Subcutaneous (s.c.) tumors are generated by injection of $2 \times 10^5$ cancer cells mixed at a 1:1 dilution with Matrigel (Collaborative Research) in the right flank of male SCID mice. To test antibody efficacy on tumor formation, antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between IgG or PBS on tumor growth. Tumor sizes are determined by caliper measurements, and the tumor volume is calculated as length×width×height. Mice with Subcutaneous tumors greater than 1.5 cm in diameter are sacrificed.

Orthotopic injections are performed under anesthesia by using ketamine/xylazine. For prostate orthotopic studies, an incision is made through the abdominal muscles to expose the bladder and seminal vesicles, which then are delivered through the incision to expose the dorsal prostate. LAPC-9 cells (5×105) mixed with Matrigel are injected into each dorsal lobe in a 10 µl volume. To monitor tumor growth, mice are bled on a weekly basis for determination of PSA levels. For the breast orthopotic model, an incision is made through the abdominal muscles to expose the mammary tissues and a single cell suspension of breast cancer cells is injected into the mammary pad. For the bladder orthotopic model, AGS-B1 bladder cancer tissue is adhered onto the bladder wall. Following tumor implantation, the mice are segregated into groups for the appropriate treatments, with anti-202P5A5 or control mAbs being injected i.p. To monitor tumor growth, mice are palpated and blood is collected on a weekly basis to measure hCG levels.

Anti-202P5A5 mAbs Inhibit Growth of 202P5A5-Expressing Xenograft-Cancer Tumors

The effect of anti-202P5A5 mAbs on tumor formation is tested by using cell line (e.g. PC3, UM-UC3, DU4475 and 3T3) and patient-derived tumor orthotopic models. As compared with the s.c. tumor model, the orthotopic model, which requires injection of tumor cells directly in the mouse organ that results in a local tumor growth, development of metastasis in distal sites, deterioration of mouse health, and subsequent death (Saffran, D., et al., PNAS supra). The features make the orthotopic model more representative of human disease progression and allowed the therapeutic effect of mAbs on clinically relevant end points to be followed more easily.

A major advantage of the orthotopic cancer models is the ability to study the development of metastases. Formation of metastasis in mice bearing established orthotopic tumors is studies by IHC analysis on lung sections using an antibody against a tumor-specific cell-surface protein such as anti-CK20 for prostate cancer (Lin S et al, Cancer Detect Prev. 2001; 25; 202).

Another advantage of xenograft cancer models is the ability to study neovascularization and angiogenesis. Tumor growth is partly dependent on new blood vessel development. Although the capillary system and developing blood network is of host origin, the initiation and architecture of the neovasculature is regulated by the xenograft tumor (Davidoff A M et al, Clin Cancer Res. 2001; 7:2870; Solesvik O et al, Eur J Cancer Clin Oncol. 1984, 20:1295). The effect of antibody and small molecule on neovascularization is studied in accordance with procedures known in the art, such as by IHC analysis of tumor tissues and their surrounding microenvironment.

Mice bearing established orthotopic tumors are administered 1000 µg injections of either anti-202P5A5 mAb or PBS over a 4-week period. Mice in both groups are allowed to establish a high tumor burden, to ensure a high frequency of metastasis formation in mouse lungs. Mice then are killed and their bladders, livers, bone, and lungs are analyzed for the presence of tumor cells by IHC analysis. These studies demonstrate a broad anti-tumor efficacy of anti-202P5A5 antibodies on initiation and progression of prostate cancer in xenograft mouse models. Anti-202P5A5 antibodies inhibit tumor formation of tumors as welt as retarding the growth of already established tumors and prolong the survival of treated mice. Moreover, anti-202P5A5 mAbs demonstrate a dramatic inhibitory effect on the spread of local prostate tumor to distal sites, even in the presence of a large tumor burden.

Thus, anti-202P5A5 mAbs are efficacious on major clinically relevant end points (tumor growth), prolongation of survival, and health.

Example 39

Therapeutic and Diagnostic use of Anti-202P5A5 Antibodies in Humans

Anti-202P5A5 monoclonal antibodies are safely and effectively used for diagnostic, prophylactic, prognostic and/or therapeutic purposes in humans. Western blot and immunohistochemical analysis of cancer tissues and cancer xenografts with anti-202P5A5 mAb show strong extensive staining in carcinoma but significantly lower or undetectable levels in normal tissues. Detection of 202P5A5 in carcinoma and in metastatic disease demonstrates the usefulness of the mAb as a diagnostic and/or prognostic indicator. Anti-202P5A5 antibodies are therefore used in diagnostic applications such as immunohistochemistry of kidney biopsy specimens to detect cancer from suspect patients.

As determined by flow cytometry, anti-202P5A5 mAb specifically binds to carcinoma cells. Thus, anti-202P5A5 antibodies are used in diagnostic whole body imaging applications, such as radioimmunoscintigraphy and radioimmunotherapy. (see, e.g., Potamianos S., et. al. Anticancer Res 20(2A):925-948 (2000)) for the detection of localized and metastatic cancers that exhibit expression of 202P5A5. Shedding or release of an extracellular domain of 202P5A5 into the extracellular milieu, such as that seen for alkaline phosphodiesterase B10 (Meerson, N. R., Hepatology 27:563-568 (1998)), allows diagnostic detection of 202P5A5 by anti-202P5A5 antibodies in serum and/or urine samples from suspect patients.

Anti-202P5A5 antibodies that specifically bind 202P5A5 are used in therapeutic applications for the treatment of cancers that express 202P5A5. Anti-202P5A5 antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-202P5A5 antibodies are tested for efficacy of tumor prevention and growth inhibition in the SCID mouse cancer xenograft models, e.g., kidney cancer models AGS-K3 and AGS-K6, (see, e.g., the Example entitled "202P5A5 Monoclonal Antibody-mediated inhibition of Bladder and Lung Tumors In Vivo"). Either conjugated and unconjugated anti-202P5A5 antibodies are used as a therapeutic modality in human clinical trials either alone or in combination with other treatments as described in following Examples.

Example 40

Human Clinical Trials for the Treatment and Diagnosis of Human Carcinomas through use of Human Anti-202P5A5 Antibodies In vivo Antibodies are used in accordance with the present invention which recognize an epitope on 202P5A5, and are used in the treatment of certain tumors such as those listed in Table I. Based upon a number of factors, including 202P5A5 expression levels, tumors such as those listed in Table I are presently preferred indications. In connection with each of these indications, three clinical approaches are successfully pursued.

I.) Adjunctive therapy: In adjunctive therapy, patients are treated with anti-202P5A5 antibodies in combination with a chemotherapeutic or antineoplastic agent and/or radiation therapy. Primary cancer targets, such as those listed in Table I, are treated under standard protocols by the addition anti-202P5A5 antibodies to standard first and second line therapy.

Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-202P5A5 antibodies are utilized in several adjunctive clinical trials in combination with the chemotherapeutic or antineoplastic agents adriamycin (advanced prostate carcinoma), cisplatin (advanced head and neck and lung carcinomas), taxol (breast cancer), and doxorubicin (preclinical).

II.) Monotherapy: In connection with the use of the anti-202P5A5 antibodies in monotherapy of tumors, the antibodies are administered to patients without a chemotherapeutic or antineoplastic agent. In one embodiment monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-202P5A5 antibodies, the radiolabeled antibodies are utilized as a diagnostic and/or imaging agent. In such a role, the labeled antibodies localize to both solid tumors, as well as, metastatic lesions of cells expressing 202P5A5. In connection with the use of the anti-202P5A5 antibodies as imaging agents, the antibodies are used as an adjunct to surgical treatment of solid tumors, as both a pre-surgical screen as well as a post-operative follow-up to determine what tumor remains and/or returns, in one embodiment, a ($^{111}$In)-202P5A5 antibody is used as an imaging agent in a Phase I human clinical trial in patients having a carcinoma that expresses 202P5A5 (by analogy see, e.g., Divgi et al. *J. Natl. Cancer Inst.* 83:97-104 (1991)). Patients are followed with standard anterior and posterior gamma camera. The results indicate that primary lesions and metastatic lesions are identified.

Dose and Route of Administration

As appreciated by those or ordinary skill in the art, dosing considerations can be determined through comparison with the analogous products that are in the clinic. Thus, anti-202P5A5 antibodies can be administered with doses in the range of 5 to 400 mg/m$^2$, with the lower doses used, e.g., in connection with safety studies. The affinity of anti-202P5A5 antibodies relative to the affinity of a known antibody for its target is one parameter used by those of skill in the art for determining analogous dose regimens. Further, anti-202P5A5 antibodies that are fully human antibodies, as compared to the chimeric antibody, have slower clearance; accordingly, dosing in patients with such fully human anti-202P5A5 antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of anti-202P5A5 antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-202P5A5 antibodies in connection with adjunctive therapy, monotherapy, and as an imaging agent. Trials initially demonstrate safety and thereafter confirm efficacy in repeat doses. Trails are open label comparing, standard chemotherapy with standard therapy plus anti-202P5A5 antibodies. As will be appreciated, one criteria that can be utilized in connection with enrollment of patients is 202P5A5 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 202P5A5. Standard tests and follow-up are utilized to monitor each of these safety concerns. Anti-202P5A5 antibodies are found to be safe upon human administration.

Example 41

Human Clinical Trial Adjunctive Therapy with Human Anti-202P5A5 Antibody and Chemotherapeutic Agent A phase I human clinical trial is initiated to assess the safety of six intravenous doses of a human anti-202P5A5 antibody in connection with the treatment of a solid tumor, e.g., a cancer of a tissue listed in Table I. In the study, the safety of single doses of anti-202P5A5 antibodies when utilized as an adjunctive therapy to an antineoplastic or chemotherapeutic agent as defined herein, such as, without limitation: cisplatin, topotecan, doxorubicin, adriamycin, taxol, or the like, is assessed. The trial design includes delivery of six single doses of an anti-202P5A5 antibody with dosage of antibody escalating from approximately about 25 mg/m$^2$ to about 275 mg/m$^2$ over the course of the treatment in accordance with the following schedule:

|  | Day 0 | Day 7 | Day 14 | Day 21 | Day 28 | Day 35 |
|---|---|---|---|---|---|---|
| mAb Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express 202P5A5. Standard tests and follow-up are utilized to monitor each of these safety concerns. Patients are also assessed for clinical outcome, and particularly reduction in tumor mass as evidenced by MRI or other imaging.

The anti-202P5A5 antibodies are demonstrated to be safe and efficacious, Phase II trials confirm the efficacy and refine optimum dosing.

Example 42

Human Clinical Trial: Monotherapy with Human Anti-202P5A5 Antibody

Anti-202P5A5 antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-202P5A5 antibodies.

Example 43

Human Clinical Trial: Diagnostic Imaging with Anti-202P5A5 Antibody

Once again, as the adjunctive therapy discussed above is safe wish in the safety criteria discussed above, a human clinical trial is conducted concerning the use of anti-202P5A5 antibodies as a diagnostic imaging agent. The protocol is designed in a substantially similar manner to those described in the art, such as in Divgi et al. *J. Natl. Cancer Inst.* 83:97-104 (1991). The antibodies are found to be both safe and efficacious when used as a diagnostic modality.

Example 44

Homology Comparison of 202P5A5 to Known Sequences

The 202P5A5 gene encodes a 609 amino acid protein. The human 202P5A5 protein exhibits a high degree of homology to a human protein of unknown function, namely hypothetical protein FLJ13782 (gi 13376382), exhibiting 99% identity to 202P5A5 at the protein level (FIG. 4A). The mouse homolog of 202P5A5 has been identified as immune BOM (gi 20502771), and shows 94% identity and 97% homology to 202P5A5 (FIG. 4B). Mouse BOM and human 202P5A5 show significant homology to a slightly smaller protein named grainyhead protein or NTF1 (gi 21312674; Shirra M K, Hansen U. J Biol. Chem. 1998, 273:19260) (FIG. 4C).

Grainyhead proteins were first identified in *Drosophila melanogaster*, where they were found to function as transcription factors regulating embryo development (Uv AE, Thompson C R, Bray S J. Mol Cell Biol. 1994, 24:4020; Uv AE, Harrison E J, Bray S J. Mol Cell Biol. 1997, 17:6727). Similarly, mammalian grainyhead-like proteins have been identified in mammalian cells and found to function as transcription factors in these cells. For example, CP2 (LBP-1c) and LBP-1a regulate transcription of diverse genes involved in hematopoietic differentiation, T-cell activation, metabolism and cell growth (Ramamurthy L et al, J Biol Chem. 2001, 276:7836; Volker J L., et. al., Genes Dev. 1997, 11:1435). Grainyhead proteins have recently been shown to participate in the Notch pathways as they participate in the regulation of Notch-mediated gene expression (Fusse B, Hoch M. Curr Biol. 2002, 12:171).

The 202P5A5 protein has several variants (FIG. 11). These include five SNPs, namely 202P5A5 v.1, v.4, v.5, v.6 and v.8, in addition to splice variants, namely 202P5A5 v.2 and v.3. The 202P5A5 v.2 protein encompasses 16 additional aa at the N-terminus of the protein relative to 202P5A5 v.1. 202P5A5 v.3 further extended exxon 1 of v.2 into intron 1 (FIG. 10).

Bioinformatic analysis using topology prediction programs indicate that 202P5A5 is a soluble protein with no transmembrane domains (Table L).

Motif analysis revealed the presence of several protein functional motifs in the 202P5A5 protein (Table L). A fibronectin type III repeat has been identified in addition to a CP2 transcription factor motif.

Fibronectin type III repeats are 100 ammo acid domains with binding sites for various molecules, including DNA, heparin, basement membrane, and cell surface proteins (Kimizuka et al., J Biol Chem. 1991, 266:3045; Yokosaki et al, J Biol Chem, 1998, 273:11423). Proteins containing fibronectin III motifs participate in cell surface binding, binding to specific substrates including heparin, collagen, DNA, actin, and fibrin, are involved in binding to fibronectin receptors. Fibronectins have been reported to function in wound healing; cell adhesion, cell differentiation, cell migration, and tumor metastasis (Bloom et al, Mot Biol Cell. 1999, 10:1521; Brodt P, Cancer Met Rev 1991, 10:23).

CP2-related proteins are DNA-binding transcription factors. They regulate transcription by homo-oligomerizing and hetero-oligomerizing with transcription factors, thereby forming a stable DNA-protein complex (Shirra, J Biol. Chem. 1998, 273:19260). In addition, transcriptional activation of LBP-1, a member of the CP2 family, is regulated by phosphorylation (Volker J, et al. Genes Dev 1997, 11:1435). As indicated above, CP2 proteins regulate transcription of diverse genes, including those regulating hematopoietic differentiation, immune response, and cell growth (Ramamurthy L et al, J Biol Chem. 2001, 276:7636; Volker J L. Rameh L E. et al, Genes Dev. 1997, 11: 1435). Recent studies have implicated CP2 in Alzheimer's disease (Taylor et al, J Med Genet 2001, 38:232).

The motifs found in 202P5A5 indicate that 202P5A5 participates in tumor growth, and progression by transcriptionally regulating the expression of tumor-related genes, thereby regulating tumor establishment, tumor growth, adhesion, migration, metastasis, differentiation, immune response, and cell growth.

Accordingly, when 202P5A5 functions as a transcription factor regulating embryo development, a regulator of tumor establishment, tumor growth, tumor invasion, cell survival, cell signaling, differentiation, immune response, and cell growth, 202P5A5 is used for therapeutic, diagnostic, prognostic, and/or preventative purposes. In addition, when a molecule, such as a splice variant or SNP of 202P5A5 is expressed in cancerous tissues, such as those listed in Table I, they are used for therapeutic, diagnostic, prognostic and/or preventative purposes.

Example 45

Regulation of Transcription

The nuclear localization of 202P5A5 coupled to the presence of CP2 domains within its sequence indicate that 202P5A5 modulates the transcriptional regulation of eukaryotic genes. Regulation of gene expression is confirmed, e.g., by studying gene expression in cells expressing or lacking 202P5A5. For this purpose, two types of experiments are performed.

In the first set of experiments, RNA from parental and 202P5A5-expressing cells are extracted and hybridized to commercially available gene arrays (Clontech)(Smid-Koopman E et al, Br J Cancer. 2000. 83:246). Resting cells as well as cells treated with FBS, androgen or growth factors are compared. Differentially expressed genes are identified in accordance with procedures known in the art. The differentially expressed genes are then mapped to biological pathways (Chen K et al, Thyroid, 2001. 11:41).

In the second set of experiments, specific transcriptional pathway activation is evaluated using commercially available (Stratagene) luciferase reporter constructs including: NFkB-luc, SRE-luc, ELK1-luc, ARE-luc, p53-luc, and CRE-luc. These transcriptional reporters contain consensus binding sites for known transcription factors that lie downstream of well-characterized signal transduction pathways: and represent a good tool to ascertain pathway activation and screen for positive and negative modulators of pathway activation.

Thus, 202P5A5 plays a role in gene regulation, and it is used as a target for diagnostic, prognostic, preventative and/or therapeutic purposes.

Example 46

Identification and Confirmation of Potential Signal Transduction Pathways

Many mammalian proteins have bean reported to interact with signaling molecules and to participate in regulating signaling pathways. (J Neurochem. 2001; 78:217-223). Using immunoprecipitation and Western blotting techniques, proteins are identified that associate with 202P5A5 and mediate signaling events. Several pathways known to play a role in cancer biology can be regulated by 202P5A5, including phospholipid pathways such as PI3K, AKT, etc, adhesion and migration pain ways, including FAK, Rho, Rac-1, catenin, etc, as well as mitogenic/survival cascades such as ERK, p38, etc (Cell Growth Differ. 2000, 11:279; J Biol Chem. 1999, 274:801; Oncogene. 2000, 19:3003, J. Cell Biol. 1997, 138: 913). In order to determine whether expression of 202P5A5 is sufficient to regulate specific signaling pathways not otherwise active in resting cancer cells, the effect of 202P5A5 on the activation of the signaling cascade is investigated in the cancer cell lines PA-1, Panc1 and Daudi. Cancer cells stably expressing 202P5A5 or neo are stimulated with growth factor, FBS or other activating molecules. Whole cell lysates are analyzed by western blotting.

To confirm that 202P5A5 directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, Signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK, growth/differentiation/apoptosis
6. CRE-luc, CREB/ATF2; PKA/p3B; growth/apoptosis/stress
7. TCF-luc, TCF/Lef; ]-catenin, Adhesion/invasion Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrata and luminescence of the reaction is monitored in a luminometer.

Signaling pathways activated by 202P5A5 are mapped and used for the identification and validation of therapeutic targets. When 202P5A5 is involved in cell signaling, it is used as target for diagnostic, prognostic, preventative and/or therapeutic purposes.

Example 47

Involvement in Tumor Progression

Based on the role of CP2 domains and fibronectin motifs in cell growth and protein interactions, the 202P5A5 gene can contribute to the growth, invasion, and transformation of cancer cells. The role of 202P5A5 in tumor growth is confirmed in a variety of primary and transfected cell lines including prostate cell lines, as well as NIH 3T3 cells engineered to stably express 202P5A5. Parental cells lacking 202P5A5 and cells expressing 202P5A5 are evaluated for cell growth using a well-documented proliferation assay (Fraser S P, Grimes J A, Djamgoz M B. Prostate. 2000; 44:61, Johnson D E, Ochieng J, Evans S L. Anticancer Drugs. 1996; 7:288).

To confirm the role of 202P5A5 in the transformation process, its effect in colony forming assays is investigated, Parental NIH-3T3 cells lacking 202P5A5 are compared to NIH-3T3 cells expressing 202P5A5, using a soft agar assay under stringent and more permissive conditions (Song Z. et al, Cancer Res. 2000; 60:6730).

To confirm the role of 202P5A5 in invasion and metastasis of cancer cells, a well-established assay is used, e.g., a Transwell insert System assay (Becton Dickinson) (Cancer Res. 1999; 59:6010). Control cells, including prostate, breast, and kidney cell lines lacking 202P5A5 are compared to cells expressing 202P5A5. Cells are loaded with the fluorescent dye, calcein, and plated in the top well of the Transwell insert coated with a basement membrane analog. Invasion is determined by fluorescence of cells in the lower chamber relative to the fluorescence of the entire cell population.

202P5A5 can also play a role in cell cycle and apoptosis. Parental cells and cells expressing 202P5A5 are compared for differences in cell cycle regulation using a well-established BrdU assay (Abdel-Malek Z A. J Cell Physiol. 1983, 136: 247). In short, cells are grown under both optimal (full serum) and limiting (low serum) conditions are labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing 202P5A5, including normal and tumor prostate cells. Engineered and parental cells are treated with various chemotherapeutic agents, such as etoposide, taxol, etc, and protein synthesis inhibitors, such as cycloheximide. Cells are stained with annex in V-FITC and cell death is measured by FACS analysis. The modulation of cell death by 202P5A5 can play a critical role in regulating tumor progression and tumor load.

When 202P5A5 plays a role in cell growth, transformation, invasion or apoptosis, it is used as a target for diagnostic, prognostic, preventative and/or therapeutic purposes.

Example 48

Involvement in Angiogenesis

Angiogenesis or new capillary blood vessel formation is necessary for tumor growth (Hanahan D, Folkman J. Cell, 1996, 86:353; Folkman J. Endocrinology. 1998 139:441). Based on the effect of fibronectins on tumor cell adhesion and their interaction with endothelial cells, 202P5A5 plays a role in angiogenesis (Mareel and Leroy: Physiol Rev, 83:337; DeFouw L et al, Microvasc Res 2001, 62:263). Several assays have been developed to measure angiogenesis in vitro and in vivo, such as the tissue culture assays endothelial cell tube formation and endothelial cell proliferation. Using these assays as well as in vitro neo-vascularization, the role of 202P5A5 in angiogenesis, enhancement or inhibition, is confirmed.

For example, endothelial cells engineered to express 202P5A5 are evaluated using tube formation and proliferation assays. The effect of 202P5A5 is also confirmed in animal models in vivo. For example, cells either expressing or lacking 202P5A5 are implanted subcutaneously in immunocompromised mice. Endothelial cell migration and angiogenesis are evaluated 5-15 days later using immunohistochemistry techniques. Thus, 202P5A5 affects angiogenesis, and it is used as a target for diagnostic, prognostic, preventative and/or therapeutic purposes.

Example 49

Involvement in Protein-Protein Interactions

CP2 domains and fibronectin motifs have been shown to mediate interaction with other proteins. Using immunoprecipitation techniques as well as two yeast hybrid systems, proteins are identified that associate with 202P5A5. Immunoprecipitates from cells expressing 202P5A5 and cells lacking 202P5A5 are compared for specific protein-protein associations.

Studies are performed to confirm the extent of association of 202P5A5 with effector molecules, such as nuclear proteins, transcription factors, kinases, phosphates etc. Studies comparing 202P5A5 positive and 202P5A5 negative cells as well as studies comparing unstimulated/resting cells and cells treated with epithelial cell activators, such as cytokines, growth factors, androgen and anti-integrin Ab reveal unique interactions.

In addition, protein-protein interactions are confirmed using two yeast hybrid methodology (Curr Opin Chem Biol. 1999, 3:64). A vector carrying a library of proteins fused to the activation domain of a transcription factor is introduced into yeast expressing a 202P5A5-DNA-binding domain fusion protein and a reporter construct. Protein-protein interaction is detected by colorimetric reporter activity. Specific association with effector molecules and transcription factors directs one of skill to the mode of action of 202P5A5, and thus identifies therapeutic, prognostic, preventative and/or diagnostic targets for cancer. This and similar assays are also used to identify and screen for small molecules that interact with 202P5A5.

Thus, it is found that 202P5A5 associates with proteins and small molecules. Accordingly, 202P5A5 and these proteins and small molecules are used for diagnostic, prognostic, preventative and/or therapeutic purposes.

Example 50

Involvement of 202P5A5 in Cell-Cell Communication

Cell-cell communication is essential in maintaining organ integrity and homeostasis, both of which become deregulated during tumor formation and progression. Based on the presence of a fibronectin motif in 202P5A5, a motif known to be involved in cell interaction and cell-cell adhesion, as well as the role of CP2 in gene expression, 202P5A5 can regulate cell communication. Intercellular communications con be measured using two types of assays (J. Biol. Chem, 2000, 275: 25207). In the first assay, cells loaded with a fluorescent dye are incubated in the presence of unlabeled recipient cells and the cell populations are examined under fluorescent microscopy. This qualitative assay measures the exchange of dye between adjacent cells. In the second assay system, donor and recipient cell populations are treated as above and quantitative measurements of the recipient cell population are performed by FACS analysis. Using these too assay systems, cells expressing 202P5A5 are compared to controls that do not express 202P5A5, and it is found that 202P5A5 enhances cell communications. Small molecules and/or antibodies that modulate cell-cell communication mediated by 202P5A5 are used as therapeutics for cancers that express 202P5A5.

Thus, 202P5A5 functions in cell-cell communication and small molecule transport, it is used as a target or marker for diagnostic, prognostic, preventative and/or therapeutic purposes.

Throughout this application, various website data content, publications, patent applications and patents are referenced. (Websites are referenced by their Uniform Resource Locator or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLES

TABLE I

| Tissues that Express 202P5A5:<br>a. Malignant Tissues |
|---|
| Prostate |
| Bladder |
| Colon |
| Lung |
| Ovary |
| Breast |
| Stomach |
| Cervix |
| Lymphoma |
| Bone |
| Skin |

TABLE II

| Amino Acid Abbreviations | | |
|---|---|---|
| SINGLE LETTER | THREE LETTER | FULL NAME |
| F | Phe | phenylalanine |
| L | Leu | leucine |
| S | Ser | serine |

TABLE II-continued

Amino Acid Abbreviations

| SINGLE LETTER | THREE LETTER | FULL NAME |
|---|---|---|
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix
Adapted from the GCG Software 9.0 BLOSUM62 amino acid substitution matrix (block substitution matrix). The higher the value, the more likely a substitution is found in related, natural proteins.
(See world wide web URL ikp.unibe.ch/manual/blosum62.html)

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
|  | 9 | −3 | −4 | −2 | −3 | −3 | −1 | −3 | −1 | −1 | −3 | −3 | −3 | −3 | −1 | −1 | −1 | −2 | −2 | C |
|  |  | 6 | 2 | −3 | −1 | −1 | −3 | −1 | −4 | −3 | 1 | −1 | 0 | −2 | 0 | −1 | −3 | −4 | −3 | D |
|  |  |  | 5 | −3 | −2 | 0 | −3 | 1 | −3 | −2 | 0 | −1 | 2 | 0 | 0 | −1 | −2 | −3 | −2 | E |
|  |  |  |  | 6 | −3 | −1 | 0 | −3 | 0 | 0 | −3 | −4 | −3 | −3 | −2 | −2 | −1 | 1 | 3 | F |
|  |  |  |  |  | 6 | −2 | −4 | −2 | −4 | −3 | 0 | −2 | −2 | −2 | 0 | −2 | −3 | −2 | −3 | G |
|  |  |  |  |  |  | 8 | −3 | −1 | −3 | −2 | 1 | −2 | 0 | 0 | −1 | −2 | −3 | −2 | 2 | H |
|  |  |  |  |  |  |  | 4 | −3 | 2 | 1 | −3 | −3 | −3 | −3 | −2 | −1 | 3 | −3 | −1 | I |
|  |  |  |  |  |  |  |  | 5 | −2 | −1 | 0 | −1 | 1 | 2 | 0 | −1 | −2 | −3 | −2 | K |
|  |  |  |  |  |  |  |  |  | 4 | 2 | −3 | −3 | −2 | −2 | −2 | −1 | 1 | −2 | −1 | L |
|  |  |  |  |  |  |  |  |  |  | 5 | −2 | −2 | 0 | −1 | −1 | −1 | 1 | −1 | −1 | M |
|  |  |  |  |  |  |  |  |  |  |  | 6 | −2 | 0 | 0 | 1 | 0 | −3 | −4 | −2 | N |
|  |  |  |  |  |  |  |  |  |  |  |  | 7 | −1 | −2 | −1 | −1 | −2 | −4 | −3 | P |
|  |  |  |  |  |  |  |  |  |  |  |  |  | 5 | 1 | 0 | −1 | −2 | −2 | −1 | Q |
|  |  |  |  |  |  |  |  |  |  |  |  |  |  | 5 | −1 | −1 | −3 | −3 | −2 | R |
|  |  |  |  |  |  |  |  |  |  |  |  |  |  |  | 4 | 1 | −2 | −3 | −2 | S |
|  |  |  |  |  |  |  |  |  |  |  |  |  |  |  |  | 5 | 0 | −2 | −2 | T |
|  |  |  |  |  |  |  |  |  |  |  |  |  |  |  |  |  | 4 | −3 | −1 | V |
|  |  |  |  |  |  |  |  |  |  |  |  |  |  |  |  |  |  | 11 | 2 | W |
|  |  |  |  |  |  |  |  |  |  |  |  |  |  |  |  |  |  |  | 7 | Y |

TABLE IV (A)

HLA Class I Supermotifs/Motifs

| | POSITION 2 (Primary Anchor) | POSITION 3 (Primary Anchor) | POSITION C Terminus (Primary Anchor) |
|---|---|---|---|
| SUPERMOTIF | | | |
| A1 | T*ILVMS* | | FWY |
| A2 | LIVM*ATQ* | | IV*MATL* |
| A3 | VSMA*TLI* | | RK |
| A24 | YF*WIVLMT* | | FI *YWLM* |
| B7 | P | | VILF*MWYA* |
| B27 | RHK | | FYL*WMIVA* |
| B44 | ED | | FWYLIMVA |
| B58 | ATS | | FWY*LIVMA* |
| B62 | QL*IVMP* | | FWY*MIVLA* |
| MOTIFS | | | |
| A1 | TSM | | Y |
| A1 | | DE*AS* | Y |
| A2.1 | LM*VQIAT* | | V*LIMAT* |
| A3 | LMVISATF*CGD* | | KYR*HFA* |
| A11 | VTMLISAGN*CDF* | | KR*YH* |
| A24 | YF*WM* | | FLIW |
| A*3101 | MVT*ALIS* | | RK |
| A*3301 | MVALF*IST* | | RK |
| A*6801 | AVT*MSLI* | | RK |
| B*0702 | P | | LMF*WYAIV* |

TABLE IV (A)-continued

HLA Class I Supermotifs/Motifs

| | POSITION 2 (Primary Anchor) | POSITION 3 (Primary Anchor) | POSITION C Terminus (Primary Anchor) |
|---|---|---|---|
| B*3501 | P | | LMFWY_IVA_ |
| B51 | P | | LIVF_WYAM_ |
| B*5301 | P | | IMFWY_ALV_ |
| B*5401 | P | | ATIV_LMFWY_ |

Bolded residues are preferred, italicized residues are less preferred: A peptide is considered motif-bearing if it has primary anchors at each primary anchor position for a motif or supermotif as specified in the above table.

TABLE IV (B)

HLA Class II Supermotif

| 1 | 6 | 9 |
|---|---|---|
| W, F, Y, V, I, L | A, V, I, L, P, C, S, T | A, V, I, L, C, S, T, M, Y |

TABLE IV (C)

HLA Class II Motifs

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY_LIVW_ | M | T | | I | VST_CPALIM_ | MH | | MH |
| | deleterious | | | | W | | | R | | WDE |
| DR1 | preferred | MF_LIVWY_ | | | PAMQ | | VMAT_SPLIC_ | M | | AVM |
| | deleterious | | C | CH | FD | CWD | | GDE | D | |
| DR7 | preferred | MF_LIVWY_ | M | W | A | | IVMSA_CTPL_ | M | | IV |
| | deleterious | | C | | G | | | GRD | N | G |

| DR3 | MOTIFS | 1° anchor 1 | 2 | 3 | 1° anchor 4 | 5 | 1° anchor 6 |
|---|---|---|---|---|---|---|---|
| Motif a preferred | | LIVMFY | | | D | | |
| Motif b preferred | | LIVMFAY | | | DNQEST | | KRH |
| DR Supermotif | | MF_LIVWY_ | | | | | VMSTA_CPLI_ |

Italicized residues indicate less preferred or "tolerated" residues

TABLE IV (D)

HLA Class I Supermotifs

| SUPER-MOTIFS | | 1 | 2 | 3 | 4 | 5 | 6 | 7 | 8 | C-terminus |
|---|---|---|---|---|---|---|---|---|---|---|
| A1 | | | 1° Anchor T_ILVMS_ | | | | | | | 1° Anchor FWY |
| A2 | | | 1° Anchor LIVM_ATQ_ | | | | | | | 1° Anchor LIVMAT |
| A3 | Preferred | | 1° Anchor VSMA_TLI_ | YFW (4/5) | | | YFW (3/5) | YFW (4/5) | P (4/5) | 1° Anchor RK |
| | deleterious | DE(3/5); P(5/5) | | DE (4/5) | | | | | | |
| A24 | | | 1° Anchor YF_WIVLMT_ | | | | | | | 1° Anchor FIY_WLM_ |
| B7 | Preferred | FWY(5/5) LIVM(3/5) | 1° Anchor P | FWY (4/5) | | | | | FWY (3/5) | 1° Anchor VILF_MWYA_ |
| | deleterious | DE(3/5); P(5/5); G(4/5); A(3/5); QN(3/5) | | | | DE (3/5) | G (4/5) | QN (4/5) | DE (4/5) | |
| B27 | | | 1° Anchor RHK | | | | | | | 1° Anchor FYL_WMIVA_ |
| B44 | | | 1° Anchor E_D_ | | | | | | | 1° Anchor FWYLIMVA |
| B58 | | | 1° Anchor ATS | | | | | | | 1° Anchor FWY_LIVMA_ |

TABLE IV (D)-continued

HLA Class I Supermotifs

| SUPER-MOTIFS | POSITION: | | | | | | | | |
|---|---|---|---|---|---|---|---|---|---|
| | 1 | 2 | 3 | 4 | 5 | 6 | 7 | 8 | C-terminus |
| B62 | | 1° Anchor QL*IVMP* | | | | | | | 1° Anchor FWY*MIVLA* |

Italicized residues indicate less preferred or "tolerated" residues

TABLE IV (E)

HLA Class I Motifs

| | | POSITION | | | | |
|---|---|---|---|---|---|---|
| | | 1 | 2 | 3 | 4 | 5 |
| A1 9-mer | preferred | GFYW | 1° Anchor STM | DEA | YEW | |
| | deleterious | DE | | RHKLIVMP | A | G |
| A1 9-mer | preferred | GRHK | ASTCLIVM | 1° Anchor DE*AS* | GSTC | |
| | deleterious | A | RHKDEPYFW | | DE | PQN |
| A1 10-mer | preferred | YFW | 1° Anchor STM | DEAQN | A | YFWQN |
| | deleterious | GP | | RHKGLIVM | DE | RHK |
| A1 10-mer | preferred | YFW | STCLIVM | 1° Anchor DE*AS* | A | YFW |
| | deleterious | RHK | RHKDEPYFW | | | P |
| A2.1 9-mer | preferred | YFW | 1° Anchor LM*IVQAT* | YFW | STC | YFW |
| | deleterious | DEP | | DERKH | | |
| A2.1 10-mer | preferred | AYFW | 1° Anchor LM*IVQAT* | LVIM | G | |
| | deleterious | DEP | | DE | RKHA | P |
| A3 | preferred | RHK | 1° Anchor LMVISATFCGD | YFW | PRHKYFW | A |
| | deleterious | DEP | | DE | | |
| A11 | preferred | A | 1° Anchor VTLMISAGN*CDF* | YFW | YFW | A |
| | deleterious | DEP | | | | |
| A24 9-mer | preferred | YFWRHK | 1° Anchor YFW*M* | | STC | |
| | deleterious | DEG | | DE | G | QNP |
| A24 10-mer | Preferred | | 1° Anchor YFW*M* | | P | YFWP |
| | Deleterious | | | GDE | QN | RHK |
| A3101 | Preferred | RHK | 1° Anchor MVT*ALIS* | YFW | P | |
| | Deleterious | DEP | | DE | | ADE |
| A3301 | Preferred | | 1° Anchor MVALF*IST* | YFW | | |
| | Deleterious | GP | | DE | | |
| A6801 | Preferred | YFWSTC | 1° Anchor AVT*MSLI* | | | YFWLIVM |
| | deleterious | GP | | DEG | | RHK |
| B0702 | Preferred | RHKFWY | 1° Anchor P | RHK | | RHK |
| | deleterious | DEQNP | | DEP | DE | DE |
| B3501 | Preferred | FWYLIVM | 1° Anchor P | FWY | | |
| | deleterious | AGP | | | | G |
| B51 | Preferred | LIVMFWY | 1° Anchor P | FWY | STC | FWY |
| | deleterious | AGPDERHKSTC | | | | DE |
| B5301 | preferred | LIVMFWY | 1° Anchor P | FWY | STC | FWY |
| | deleterious | AGPQN | | | | P |
| B5401 | preferred | FWY | 1° Anchor P | FWYLIVM | | LIVM |
| | deleterious | GPQNDE | | GDESTC | | RHKDE |

TABLE IV (E)-continued

HLA Class I Motifs

| | | \multicolumn{5}{c}{POSITION} |
|---|---|---|---|---|---|---|
| | | 6 | 7 | 8 | 9 or C-terminus | C-terminus |
| A1 9-mer | preferred | P | DEQN | YFW | 1° Anchor Y | |
| | deleterious | A | G | A | | |
| A1 9-mer | preferred | ASTC | LIVM | DE | 1° Anchor Y | |
| | deleterious | RHK | PG | GP | | |
| A1 10-mer | preferred | | PASTC | GDE | P | 1° Anchor Y |
| | deleterious | QNA | RHKYFW | RHK | A | |
| A1 10-mer | preferred | | PG | G | YFW | 1° Anchor Y |
| | deleterious | G | | PRHK | QN | |
| A2.1 9-mer | preferred | | A | P | 1° Anchor VLIMAT | |
| | deleterious | RKH | DERKH | | | |
| A2.1 10-mer | preferred | G | | FYWLVIM | | 1° Anchor VLIMAT |
| | deleterious | | RKH | DERKH | RKH | |
| A3 | preferred | YFW | | P | 1° Anchor KYRHFA | |
| | deleterious | | | | | |
| A11 | preferred | YFW | YFW | P | 1° Anchor KRYH | |
| | deleterious | | A | G | | |
| A24 9-mer | preferred | | YFW | YFW | 1° Anchor FLIW | |
| | deleterious | DERHK | G | AQN | | |
| A24 10-mer | Preferred | | P | | | 1° Anchor FLIW |
| | Deleterious | DE | A | QN | DEA | |
| A3101 | Preferred | YFW | YFW | AP | 1° Anchor RK | |
| | Deleterious | DE | DE | DE | | |
| A3301 | Preferred | | AYFW | | 1° Anchor RK | |
| | Deleterious | | | | | |
| A6801 | Preferred | | YFW | P | 1° Anchor RK | |
| | deleterious | | | A | | |
| B0702 | Preferred | RHK | RHK | PA | 1° Anchor LMFWYAIV | |
| | deleterious | GDE | QN | DE | | |
| B3501 | Preferred | | FWY | | 1° Anchor LMFWYIVA | |
| | deleterious | G | | | | |
| B51 | Preferred | | G | FWY | 1° Anchor LIVFWYAM | |
| | deleterious | G | DEQN | GDE | | |
| B5301 | preferred | | LIVMFWY | FWY | 1° Anchor IMFWYALV | |
| | deleterious | G | RHKQN | DE | | |
| B5401 | preferred | | ALIVM | FWYA P | 1° Anchor ATIVLMFWY | |
| | deleterious | DE | QNDGE | DE | | |

TABLE IV (F)

Summary of HLA-supertypes
Overall phenotypic frequencies of HLA-supertypes in different ethnic populations

| | Specificity | | \multicolumn{5}{c}{Phenotypic frequency} | |
|---|---|---|---|---|---|---|---|---|
| Supertype | Position 2 | C-Terminus | Caucasian | N.A. Black | Japanese | Chinese | Hispanic | Average |
| B7 | P | AILMVFWY | 43.2 | 55.1 | 57.1 | 43.0 | 49.3 | 49.5 |
| A3 | AILMVST | RK | 37.5 | 42.1 | 45.8 | 52.7 | 43.1 | 44.2 |
| A2 | AILMVT | AILMVT | 45.8 | 39.0 | 42.4 | 45.9 | 43.0 | 42.2 |
| A24 | YF (WIVLMT) | FI (YWLM) | 23.9 | 38.9 | 58.6 | 40.1 | 38.3 | 40.0 |
| B44 | E (D) | FWYLIMVA | 43.0 | 21.2 | 42.9 | 39.1 | 39.0 | 37.0 |

TABLE IV (F)-continued

Summary of HLA-supertypes
Overall phenotypic frequencies of HLA-supertypes in different ethnic populations

| | Specificity | | Phenotypic frequency | | | | | |
|---|---|---|---|---|---|---|---|---|
| Supertype | Position 2 | C-Terminus | Caucasian | N.A. Black | Japanese | Chinese | Hispanic | Average |
| A1 | TI (LVMS) | FWY | 47.1 | 16.1 | 21.8 | 14.7 | 26.3 | 25.2 |
| B27 | RHK | FYL (WMI) | 28.4 | 26.1 | 13.3 | 13.9 | 35.3 | 23.4 |
| B62 | QL (IVMP) | FWY (MIV) | 12.6 | 4.8 | 36.5 | 25.4 | 11.1 | 18.1 |
| B58 | ATS | FWY (LIV) | 10.0 | 25.1 | 1.6 | 9.0 | 5.9 | 10.3 |

TABLE IV (G)

Calculated population coverage afforded by different HLA-supertype combinations

| | Phenotypic frequency | | | | | |
|---|---|---|---|---|---|---|
| HLA-supertypes | Caucasian | N.A Blacks | Japanese | Chinese | Hispanic | Average |
| A2, A3 and B7 | 83.0 | 86.1 | 87.5 | 88.4 | 86.3 | 86.2 |
| A2, A3, B7, A24, B44 | 99.5 | 98.1 | 100.0 | 99.5 | 99.4 | 99.3 |
| and A1 | 99.9 | 99.6 | 100.0 | 99.8 | 99.9 | 99.8 |
| A2, A3, B7, A24 B44, A1, B27, B62, and B58 | | | | | | |

Motifs indicate the residues defining supertype specificites. The motifs incorporate residues determined on the basis of published data to be recognized by multiple alleles within the supertype. Residues within brackets are additional residues also predicted to be tolerated by multiple alleles within the supertype.

TABLE V

Frequently Occurring Motifs

| Name | avrg. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| Ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a 12 residue loop flanked on both sides by a 12 residue alpha-helical domain |
| Rvp | 79% | Retroviral aspartyl protease | Aspartyl or acid proteases, centered on a catalytic aspartyl residue |

TABLE V-continued

Frequently Occurring Motifs

| Name | avrg. % identity | Description | Potential Function |
|---|---|---|---|
| Collagen | 42% | Collagen triple helix repeat (20 copies) | extracellular structural proteins involved in formation of connective tissue. The sequence consists of the G-X-Y and the polypeptide chains forms a triple helix. |
| Fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE VI

Post-translational modifications of 202P5A5

N-glycosylation site

| | | |
|---|---|---|
| 90-93 | NLSG | (SEQ ID NO: 41) |
| 107-110 | NLSL | (SEQ ID NO: 42) |
| 384-387 | NRSN | (SEQ ID NO: 43) |
| 431-424 | NSSS | (SEQ ID NO: 44) |

Tyrosine sulfation site

| | | |
|---|---|---|
| 215-229 | ASVGAEEYMYDQTSS | (SEQ ID NO: 45) |
| 217-231 | VGAEEYMYDQTSSGT | (SEQ ID NO: 46) |
| 314-328 | RVLDIADYKESFNTI | (SEQ ID NO: 47) |
| 578-592 | DDNIIEHYSNEDTFI | (SEQ ID NO: 48) | cAMP- and cGMP-dependent protein kinase phosphorylation site

| | | |
|---|---|---|
| 527-530 | RKET | (SEQ ID NO: 49) |

Protein kineaseC phosphorylation site

| | |
|---|---|
| 9-11 | TRR |
| 118-120 | SKR |
| 203-205 | SFK |
| 209-211 | TEK |
| 241-243 | SLR |
| 310-312 | TAK |
| 364-366 | SQK |
| 386-388 | SNK |
| 519-521 | TKR |
| 543-545 | TVK |
| 552-554 | SEK |
| 569-571 | SKK |

Casein kinase II phosphorylation site

| | | |
|---|---|---|
| 14-17 | TSED | (SEQ ID NO: 50) |
| 15-18 | SEDE | (SEQ ID NO: 51) |

TABLE VI-continued

Post-translational modifications of 202P5A5

| | | |
|---|---|---|
| 22-25 | SYLE | (SEQ ID NO: 52) |
| 72-75 | SQED | (SEQ ID NO: 53) |
| 92-95 | SGGE | (SEQ ID NO: 54) |
| 118-121 | SKRE | (SEQ ID NO: 55) |
| 126-129 | SEPE | (SEQ ID NO: 55) |
| 174-177 | TQYD | (SEQ ID NO: 57) |
| 194-197 | STPD | (SEQ ID NO: 58) |
| 203-206 | SFKD | (SEQ ID NO: 60) |
| 263-266 | TLSE | (SEQ ID NO: 61) |
| 432-435 | SSSD | (SEQ ID NO: 62) |
| 454-457 | TMPD | (SEQ ID NO: 63) |
| 484-487 | TDDE | (SEQ ID NO: 64) |
| 586-589 | SNED | (SEQ ID NO: 65) |
| 597-600 | SMVE | (SEQ ID NO: 66) |
| 605-608 | TLME | (SEQ ID NO: 67) |

Tyrosine kinase phosphorylation site

| | | |
|---|---|---|
| 193-200 | RSTPDSTY | (SEQ ID NO: 68) |
| 292-300 | KNRDEQLKY | (SEQ ID NO: 69) |
| 314-321 | RVLDIADY | (SEQ ID NO: 70) |
| 445-451 | KKSDITY | (SEQ ID NO: 71) |

N-myristoylation site

| | | |
|---|---|---|
| 83-88 | GTSEAQ | (SEQ ID NO: 72) |
| 257-262 | GQFYAI | (SEQ ID NO: 73) |
| 546-551 | GLMEAI | (SEQ ID NO: 74) |
| 572-577 | GILVNM | (SEQ ID NO: 75) |

Bipartite nuclear targeting sequence

| | | |
|---|---|---|
| 407-423 | RKIRDEERKQNRKKGKG | (SEQ ID NO: 76) |

Cell attachment sequence

| | |
|---|---|
| 160-162 | RGD |

TABLE VII

Search Peptides

202P5A05 v.1
9-mers, 10-mers and 15 mers

```
                                                              (SEQ ID NO: 77)
        MPSDPPFNTR RAYTSEDEAW KSYLENPLTA ATKAMMSING CEDSAAALGL LYDYYKVPRD  60
        KRLLSVSKAS DSQEDQEKRN CLGTSEAQSN LSGGENRVQV LKTVPVNLSL NQDHLENSKR 120
        EQYSISFPES SAKIPVSGIF VVKAEDFTPV FMAPPVHYPR GDGEEQRVVI FEQTQYDVPS 180
        LATHSAYLKD DQRSTPDSTY SESFKDAATE KFRSASVGAE EYMYDQTSSG TFQYTLEATK 240
        SLRQKQGEGP MTYLNKGQFY AITLSETGDN DCFRHPISKV RSVVMVVESE DKNRDEQLKY 300
        WKYWESRQHT AKQRVLDEAD YKESFNTIGN TEEIAYNAVS FTWDVNEEAK IFITVNCLST 360
        CFSSQKGVKG LPIMIQIDTY SYNNRSNKPI RRAYCQIKVF CDKGAERKIR DEERKQNRKK 420
```

TABLE VII-continued

Search Peptides

```
GKGQASCYQC NSSSDGKLAA TPLQKKSDIT YFKTMDDLHS QPVLFIPDVE FANLQRTGQV 480
YYNTDDERDG GSVLVKRYFR PMEEEFGPVP SKQMKEEGTK RVLLYVRKET DDVFDALMRK 540
SPTVKGLMEA ISEKYGLFVF KIAKLYKKSK KGILVNMDDN IIEHYSNEDT FYLNMESMVD 600
GFKVTLMFI                                                        609
```

202P5A5 v.2 ORF:13-1890
9-mers, aa 1-24

(SEQ ID NO: 78)
MSQESDNNKR RVALVPMPSD PPFN 10-mers, aa 1-25

(SEQ ID NO: 79)
MSQESDNNKR LVALVPMPSD PPFNT 25-mers, aa 1-30

(SEQ ID NO: 80)
MSQEDSNNKR LVALVPMPSD PPFNTRRAYT

202P5A5 v.4 ORF:121-1950
9-mers, aa 29-45

(SEQ ID NO: 81)
TTATKAMMIINGDEDSA 10-mers, aa 28-46

(SEQ ID NO: 82)
LTAATKAMMIINGDEDSAA 14-mers, aa 22-51

(SEQ ID NO: 83)
YLENDLTAATKAMMIINGDEDSAAALGLL

202P5A5 v.5
9-mers, aa 406-422

(SEQ ID NO: 84)
ERKIRDEEQKQNRKKGK 10-mers, aa 405-423

(SEQ ID NO: 85)
AERKIRDEEQKQNRKKGKG 15-mers, aa 400-428

(SEQ ID NO: 86)
FCDKGAERKIRDEEQKQNRKKGKGQASQT

202P5A5 v.6
9-mers, aa 412-428

(SEQ ID NO: 87)
EERKQNRKKGKGGASQT 10-mers, aa 411-429

(SEQ ID NO: 88)
DEERKQNRKNGKGQASQTQ 15-mers, aa 406-434

(SEQ ID NO: 89)
ERKIEDLEERKQNRKNGKGQASQTQCNSSS

202P515 V5/6
9-mers, aa 412-422

(SEQ ID NO: 90)
EEQKQNRKNGK 10-mers, aa 411-423

(SEQ ID NO: 91)
DEEQKQNRKNGKG 15-mers, aa 406-428

(SEQ ID NO: 92)
ERKIRDEFQKQNRKNGKGQASQT

202P5A5 v.8
9-mers, aa 537-553

(SEQ ID NO: 93)
LMLKSPTVMGLMEAISE 10-mers, aa 536-554

(SEQ ID NO: 94)
AEMLKSPTVMGLMEAISEK 15-mers, aa 531-559

(SEQ ID NO: 95)
DDVFDALMLKSPTVMGLMEAISEKYGLPV

TABLE VIII-V1

HLA-A1-9mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 547 | LMEAISEKY | 22.500 |
| 143 | KAEDFTPVF | 18.000 |
| 235 | TLEATKSLR | 9.000 |
| 2 | PSDPPFNTR | 7.500 |
| 226 | QTSSGTFQY | 6.250 |
| 594 | NMESMVEGF | 4.500 |
| 446 | KSDITYFKT | 3.750 |
| 44 | SAAALGLLY | 2.500 |
| 119 | KREQYSISF | 2.250 |
| 152 | MAPPVHYPR | 2.000 |
| 598 | MVEGFKVTL | 1.800 |
| 294 | RDEQLKYWK | 1.800 |
| 218 | GAEEYMYDQ | 1.800 |
| 330 | NIEEIAYNA | 1.800 |
| 433 | SSDGKLAAI | 1.500 |
| 111 | NQDHLENSK | 1.500 |
| 200 | YSESFKDAA | 1.350 |
| 264 | LSETGDNKC | 1.350 |
| 14 | TSEDEAWKS | 1.350 |
| 84 | TSEAQSNLS | 1.350 |
| 529 | ETDDVFDAL | 1.250 |
| 102 | KTVPVNLSL | 1.250 |
| 483 | NTDDEREGG | 1.250 |
| 576 | NMDDNIIEH | 1.250 |
| 15 | SEDEAWKSY | 1.250 |
| 577 | MDDNIIEHY | 1.250 |
| 359 | STDFSSQKG | 1.250 |
| 345 | VNEEAKIFI | 1.125 |
| 586 | SNEDTFILN | 1.125 |
| 46 | AALGLLYDY | 1.000 |
| 532 | DVFDALMLK | 1.000 |
| 400 | FCDKGAERK | 1.000 |
| 216 | SVGAEEYMY | 1.000 |
| 376 | QIDTYSYNN | 1.000 |
| 556 | GLPVEKIAK | 1.000 |

TABLE VIII-V1-continued

HLA-A1-9mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 437 | KLAAIPLQK | 1.000 |
| 374 | MIQIDTYSY | 1.000 |
| 13 | YTSEDEAWK | 1.000 |
| 163 | GEEQRVVIF | 0.900 |
| 114 | HLENSKREQ | 0.900 |
| 23 | YLENPLTAA | 0.900 |
| 551 | ISEKYGLPV | 0.675 |
| 328 | IGNIEEIAY | 0.625 |
| 267 | TGDNKCFRH | 0.625 |
| 468 | DVHFANLQR | 0.500 |
| 168 | VVIFEQTQY | 0.500 |
| 342 | TWDVNEEAK | 0.500 |
| 214 | SASVGAEEY | 0.500 |
| 318 | IADYKESFN | 0.500 |
| 492 | SVLVKRMFR | 0.500 |
| 47 | ALGLLYDYY | 0.500 |
| 51 | LYDYYKVPR | 0.500 |
| 507 | GPVPSKQMK | 0.500 |
| 558 | PVEKIAKLY | 0.450 |
| 182 | DGEEQRVVI | 0.450 |
| 410 | RDEERKQNT | 0.450 |
| 181 | LATHSAYLK | 0.400 |
| 245 | KQGEGPMTY | 0.375 |
| 380 | YSYNNRSNK | 0.300 |
| 358 | LSTDFSSQK | 0.300 |
| 197 | DSTYSESFK | 0.300 |
| 453 | KTMPDLHSQ | 0.250 |
| 39 | NGDEDSAAA | 0.250 |
| 266 | ETGDNKCFR | 0.250 |
| 248 | EGPMTYLNK | 0.250 |
| 204 | FKDAATEKF | 0.250 |
| 466 | IPDVHFANL | 0.250 |
| 251 | MTYLNKGQF | 0.250 |
| 139 | ITVVKAEDF | 0.250 |

TABLE VIII-V1-continued

HLA-A1-9mers-202P5A5
Each peptide is a portion of
SEQ ID NO: 3; each start
position is specified, the
length of peptide is 9 amino
acids, and the end position
for each peptide is the start
position plus eight.

| Start | Subsequence | Score |
|---|---|---|
| 346 | NEEAKIFIT | 0.225 |
| 246 | QGEGPMTYL | 0.225 |
| 93 | GGENRVQVL | 0.225 |
| 208 | ATEKFRSAS | 0.225 |
| 263 | TLSERGDNK | 0.200 |
| 314 | RVLDIADYK | 0.200 |
| 546 | GLMEAISEK | 0.200 |
| 438 | LAAIPLQKK | 0.200 |
| 457 | DLHSQPVLF | 0.200 |
| 463 | VLFIPDVHF | 0.200 |
| 333 | EIAYNAVSF | 0.200 |
| 429 | QCNSSSDGK | 0.200 |
| 71 | DSQEDQEKR | 0.150 |
| 125 | ISFPESSAI | 0.150 |
| 491 | GSVLVKRMF | 0.150 |
| 193 | RSTPDSTYS | 0.150 |
| 288 | FSEDKNRDE | 0.135 |
| 72 | SQEDQEKRN | 0.135 |
| 589 | DTFILNMES | 0.125 |
| 533 | VFDALMLKS | 0.125 |
| 175 | QYDVPSLAT | 0.125 |
| 386 | SNKPIHRAY | 0.125 |
| 230 | GTFQYTLEA | 0.125 |
| 587 | NEDTFILNM | 0.125 |
| 369 | KGLPLMIQI | 0.125 |
| 455 | MPDLHSQPV | 0.125 |
| 195 | TPDSTYSES | 0.125 |
| 160 | RGDGEEQRV | 0.125 |
| 127 | FPESSAIIP | 0.113 |
| 315 | VLDIADYKE | 0.100 |
| 354 | TVNCLSTDF | 0.100 |

TABLE VIII-V2

HLA-A1-9mers-202P5A5
Each peptide is a portion of
SEQ ID NO: 5; each start
position is specified, the
length of peptide is 9 amino
acids, and the end position
for each peptide is the start
position plus eight.

| Start | Subsequence | Score |
|---|---|---|
| 2 | SQESDNNKR | 1.350 |
| 4 | ESDNNKRLV | 0.750 |
| 15 | VPMPSDPPF | 0.500 |
| 1 | MSQESDNNK | 0.300 |
| 11 | LVALVPMPS | 0.050 |
| 13 | ALVPMPSDP | 0.010 |
| 5 | SDNNKRLVA | 0.003 |
| 12 | VALVPMPSD | 0.002 |
| 10 | RLVALVPMP | 0.002 |
| 9 | KRLVALVPM | 0.001 |
| 16 | PMPSDPPFN | 0.001 |
| 14 | LVPMPSDPP | 0.001 |
| 3 | QESDNNKRL | 0.001 |
| 6 | DNNKRLVAL | 0.001 |
| 7 | NNKRLVALV | 0.000 |
| 8 | NKRLVALVP | 0.000 |

TABLE VIII-V4

HLA-A1-9mers-202P5A5
Each peptide is a portion of
SEQ ID NO: 3; each start
position is specified, the
length of peptide is 9 amino
acids, and the end position
for each peptide is the start
position plus eight.

| Start | Subsequence | Score |
|---|---|---|
| 1 | TAATKAMMI | 0.050 |
| 3 | ATKAMMIIN | 0.013 |
| 8 | MIINGDEDS | 0.010 |
| 9 | IINGDEDSA | 0.010 |
| 2 | AATKAMMII | 0.005 |
| 4 | TKAMMIING | 0.003 |
| 5 | KAMMIINGD | 0.001 |
| 6 | AMMIINGDE | 0.001 |
| 7 | MMIINGDED | 0.001 |

TABLE VIII-V5

HLA-A1-9mers-202P5A5
Each peptide is a portion of
SEQ ID NO: 3; each start
position is specified, the
length of peptide is 9 amino
acids, and the end position
for each peptide is the start
position plus eight.

| Start | Subsequence | Score |
|---|---|---|
| 6 | DEEQKQNRK | 0.900 |
| 5 | RDEEQKQNR | 0.450 |
| 4 | IRDEEQKQN | 0.025 |
| 9 | QKQNRKKGK | 0.010 |
| 7 | EEQKQNRKK | 0.001 |
| 2 | RKIRDEEQK | 0.001 |
| 3 | KIRDEEQKQ | 0.001 |
| 8 | EQKQNRKKG | 0.000 |
| 1 | ERKIRDEEQ | 0.000 |

TABLE VIII-V5&6

HLA-A1-9mers-202P5A5
Each peptide is a portion of
SEQ ID NO: 3; each start
position is specified, the
length of peptide is 9 amino
acids, and the end position
for each peptide is the start
position plus eight.

| Start | Subsequence | Score |
|---|---|---|
| 3 | QKQNRKNGK | 0.010 |
| 2 | EQKQNRKNG | 0.000 |
| 1 | EEQKQNRKN | 0.000 |

TABLE VIII-V6

HLA-A1-9mers-202P5A5
Each peptide is a portion of
SEQ ID NO: 3; each start
position is specified, the
length of peptide is 9 amino
acids, and the end position
for each peptide is the start
position plus eight.

| Start | Subsequence | Score |
|---|---|---|
| 3 | RKQNRKNGK | 0.010 |
| 8 | KNGKGQASQ | 0.001 |
| 7 | RKNGKGQAS | 0.001 |
| 9 | NGKGQASQT | 0.000 |
| 4 | KQNRKNGKG | 0.000 |
| 2 | ERKQNRKNG | 0.000 |
| 6 | NRKNGKGQA | 0.000 |

TABLE VIII-V6-continued

HLA-A1-9mers-202P5A5
Each peptide is a portion of
SEQ ID NO: 3; each start
position is specified, the
length of peptide is 9 amino
acids, and the end position
for each peptide is the start
position plus eight.

| Start | Subsequence | Score |
|---|---|---|
| 5 | QNRKNGKGQ | 0.000 |
| 1 | EERKQNRKN | 0.000 |

TABLE VIII-V8

HLA-A1-9mers-202P5A5
Each peptide is a portion of
SEQ ID NO: 3; each start
position is specified, the
length of peptide is 9 amino
acids, and the end position
for each peptide is the start
position plus eight.

| Start | Subsequence | Score |
|---|---|---|
| 3 | LKSPTVMGL | 0.025 |
| 4 | KSPTVMGLM | 0.015 |
| 6 | PTVMGLMEA | 0.013 |
| 7 | TVMGLMEAI | 0.010 |
| 8 | VMGLMEAIS | 0.010 |
| 2 | MLKSPTVMG | 0.002 |
| 9 | MGLMEAISE | 0.001 |
| 5 | SPTVMGLME | 0.001 |
| 1 | LMLKSPTVM | 0.001 |

TABLE IX-V1

HLA-A1-10mers-202P5A5
Each peptide is a portion of
SEQ ID NO: 3; each start
position is specified, the
length of peptide is 10 amino
acids, and the end position for
each peptide is the start
position plus nine.

| Start | Subsequence | Score |
|---|---|---|
| 14 | TSEDEAWKSY | 67.500 |
| 114 | HLENSKREQY | 45.000 |
| 69 | ASDSQEDQEK | 15.000 |
| 264 | LSETGDNKCF | 13.500 |
| 576 | NMDDNIIEHY | 12.500 |
| 93 | GGENRVQVLK | 9.000 |
| 594 | NMESMVEGFK | 9.000 |
| 2 | PSDPPFNTRR | 7.500 |

TABLE IX-V1-continued

HLA-A1-10mers-202P5A5
Each peptide is a portion of
SEQ ID NO: 3; each start
position is specified, the
length of peptide is 10 amino
acids, and the end position for
each peptide is the start
position plus nine.

| Start | Subsequence | Score |
|---|---|---|
| 84 | TSEAQSNLSG | 6.750 |
| 376 | QIDTYSYNNR | 5.000 |
| 235 | TLEATKSLRQ | 4.500 |
| 487 | EREGGSVLVK | 4.500 |
| 162 | DGEEQRVVIF | 4.500 |
| 43 | DSAAALGLLY | 3.750 |
| 200 | YSESFKDAAT | 2.700 |
| 327 | TIGNIEEIAY | 2.500 |
| 529 | ETDDVFDALM | 2.500 |
| 555 | YGLPVEKIAK | 2.500 |
| 318 | IADYKESFNT | 2.500 |
| 294 | RDEQLKYWKY | 2.250 |
| 503 | EEEFGPVPSK | 1.800 |
| 143 | KAEDFTPVFM | 1.800 |
| 23 | YLENPLTAAT | 1.800 |
| 215 | ASVGAEEYMY | 1.500 |
| 288 | FSEDKNRDEQ | 1.350 |
| 251 | MTYLNKGQFY | 1.250 |
| 359 | STDFSSQKGV | 1.250 |
| 195 | TPDSTYSESF | 1.250 |
| 483 | NTDDEREGGS | 1.250 |
| 345 | VNEEAKIFIT | 1.125 |
| 127 | FPESSAIIPV | 1.125 |
| 586 | SNEDTFILNM | 1.125 |
| 151 | FMAPPVHYPR | 1.000 |
| 293 | NRDEQLKYWK | 1.000 |
| 45 | AAALGLLYDY | 1.000 |
| 598 | MVEGFKVTLM | 0.900 |
| 410 | RDEERKQNRK | 0.900 |
| 218 | GAEEYMYDQT | 0.900 |
| 330 | NIEEIAYNAV | 0.900 |
| 558 | PVEKIAKLYK | 0.900 |
| 581 | IIEHYSNEDT | 0.900 |
| 213 | RSASVGAEEY | 0.750 |
| 446 | KSDITYFKTM | 0.750 |

TABLE IX-V1-continued

HLA-A1-10mers-202P5A5
Each peptide is a portion of
SEQ ID NO: 3; each start
position is specified, the
length of peptide is 10 amino
acids, and the end position for
each peptide is the start
position plus nine.

| Start | Subsequence | Score |
|---|---|---|
| 491 | GSVLVKRMFR | 0.750 |
| 111 | NQDHLENSKR | 0.750 |
| 132 | AIIPVSGITV | 0.500 |
| 46 | AALGLLYDYY | 0.500 |
| 546 | GLMEAISEKY | 0.500 |
| 167 | RVVIFEQTQY | 0.500 |
| 315 | VLDIADYKES | 0.500 |
| 373 | LMIQIDTYSY | 0.500 |
| 262 | ITLSETGDNK | 0.500 |
| 247 | GEGPMTYLNK | 0.500 |
| 208 | ATEKFRSASV | 0.450 |
| 547 | LMEAISEKYG | 0.450 |
| 246 | QGEGPMTYLN | 0.450 |
| 180 | SLATHSAYLK | 0.400 |
| 47 | ALGLLYDYYK | 0.400 |
| 225 | DQTSSGTFQY | 0.375 |
| 125 | ISFPESSAII | 0.300 |
| 223 | MYDQTSSGTF | 0.250 |
| 39 | NGDEDSAAAL | 0.250 |
| 353 | ITVNCLSTDF | 0.250 |
| 234 | YTLEATKSLR | 0.250 |
| 204 | FKDAATEKFR | 0.250 |
| 102 | KTVPVNLSLN | 0.250 |
| 409 | IRDEERKQNR | 0.250 |
| 455 | MPDLHSQPVL | 0.250 |
| 346 | NEEAKIFITV | 0.225 |
| 527 | RKETDDVFDA | 0.225 |
| 321 | YKESFNTIGN | 0.225 |
| 536 | ALMLKSPTVK | 0.200 |
| 152 | MAPPVHYPRG | 0.200 |
| 24 | LENPLTAATK | 0.200 |
| 50 | LLYDYYKVPR | 0.200 |
| 283 | VVMVVFSEDK | 0.200 |
| 357 | CLSTDFSSQK | 0.200 |

TABLE IX-V1-continued

HLA-A1-10mers-202P5A5
Each peptide is a portion of
SEQ ID NO: 3; each start
position is specified, the
length of peptide is 10 amino
acids, and the end position for
each peptide is the start
position plus nine.

| Start | Subsequence | Score |
|---|---|---|
| 394 | YCQIKVFCDK | 0.200 |
| 398 | KVFCDKGAER | 0.200 |
| 437 | KLAAIPLQKK | 0.200 |
| 88 | QSNLSGGENR | 0.150 |
| 184 | HSAYLKDDQR | 0.150 |
| 433 | SSDGKLAAIP | 0.150 |
| 72 | SQEDQEKRNC | 0.135 |
| 41 | DEDSAAALGL | 0.125 |
| 466 | IPDVHFANLQ | 0.125 |
| 244 | QKQGEGPMTY | 0.125 |
| 371 | LPLMIQIDTY | 0.125 |
| 557 | LPVEKIAKLY | 0.125 |
| 160 | RGDGEEQRVV | 0.125 |
| 28 | LTAATKAMMS | 0.125 |
| 144 | AEDFTPVFMA | 0.125 |
| 472 | ANLQRTGQVY | 0.125 |
| 530 | TDDVFDALML | 0.125 |
| 4 | DPPFNTRRAY | 0.125 |
| 516 | EEGTKRVLLY | 0.125 |
| 178 | VPSLATHSAY | 0.125 |
| 266 | ETGDNKCFRH | 0.125 |
| 134 | IPVSGITVVK | 0.100 |
| 149 | PVFMAPPVHY | 0.100 |

TABLE IX-V2

HLA-A1-10mers-202P5A5
Each peptide is a portion of
SEQ ID NO: 5; each start
position is specified, the
length of peptide is 10 amino
acids, and the end position for
each peptide is the start
position plus nine.

| Start | Subsequence | Score |
|---|---|---|
| 4 | ESDNNKRLVA | 3.750 |
| 14 | LVPMPSDPPF | 0.200 |
| 1 | MSQESDNNKR | 0.150 |
| 2 | SQESDNNKRL | 0.135 |

TABLE IX-V2-continued

HLA-A1-10mers-202P5A5
Each peptide is a portion of
SEQ ID NO: 5; each start
position is specified, the
length of peptide is 10 amino
acids, and the end position for
each peptide is the start
position plus nine.

| Start | Subsequence | Score |
|---|---|---|
| 15 | VPMPSDPPFN | 0.050 |
| 10 | RLVALVPMPS | 0.050 |
| 13 | ALVPMPSDPP | 0.010 |
| 16 | PMPSDPPFNT | 0.003 |
| 11 | LVALVPMPSD | 0.002 |
| 5 | SDNNKRLVAL | 0.001 |
| 12 | VALVPMPSQP | 0.001 |
| 3 | QESDNNKRLV | 0.001 |
| 6 | DNNKRLVALV | 0.001 |
| 8 | NKRLVALVPM | 0.000 |
| 9 | KRLVALVPMP | 0.000 |
| 7 | NNKRLVALVP | 0.000 |

TABLE IX-V4

HLA-A1-10mers-202P5A5
Each peptide is a portion of
SEQ ID NO: 3; each start
position is specified, the
length of peptide is 10 amino
acids, and the end position for
each peptide is the start
position plus nine.

| Start | Subsequence | Score |
|---|---|---|
| 1 | LTAATKAMMI | 0.125 |
| 2 | TAATKAMMII | 0.050 |
| 4 | ATKAMMIING | 0.013 |
| 9 | MIINGDEDSA | 0.010 |
| 10 | IINGDEDSAA | 0.010 |
| 8 | MMIINGDEDS | 0.005 |
| 3 | AATKAMMIIN | 0.005 |
| 6 | KAMMIINGDE | 0.001 |
| 7 | AMMIINGDED | 0.001 |
| 5 | TKAMMIINGD | 0.000 |

TABLE IX-V5

HLA-A1-10mers-202P5A5
Each peptide is a portion of
SEQ ID NO: 3; each start
position is specified, the
length of peptide is 10 amino
acids, and the end position for
each peptide is the start
position plus nine.

| Start | Subsequence | Score |
|---|---|---|
| 6 | RDEEQKQNRK | 0.900 |
| 7 | DEEQKQNRKK | 0.900 |
| 5 | IRDEEQKQNR | 0.250 |
| 9 | EQKQNRKKGK | 0.003 |
| 2 | ERKIRDEEQK | 0.001 |
| 4 | KIRDEEQKQN | 0.001 |
| 10 | QKQNRKKGKG | 0.001 |
| 3 | RKIRDEEQKQ | 0.000 |
| 8 | EEQKQNRKKG | 0.000 |
| 1 | AERKIRDEEQ | 0.000 |

TABLE IX-V5&6

HLA-A1-10mers-202P5A5
Each peptide is a portion of
SEQ ID NO: 3; each start
position is specified, the
length of peptide is 10 amino
acids, and the end position for
each peptide is the start
position plus nine.

| Start | Subsequence | Score |
|---|---|---|
| 1 | DEEQKQNRKN | 0.045 |
| 3 | EQKQNRKNGK | 0.003 |
| 4 | QKQNRKNGKG | 0.001 |
| 2 | EEQKQNRKNG | 0.000 |

TABLE IX-V6

HLA-A1-10mers-202P5A5
Each peptide is a portion of
SEQ ID NO: 3; each start
position is specified, the
length of peptide is 10 amino
acids, and the end position for
each peptide is the start
position plus nine.

| Start | Subsequence | Score |
|---|---|---|
| 2 | ERKQNRKNGK | 0.001 |
| 7 | RKNGKGQASQ | 0.001 |
| 3 | RKQNRKNGKG | 0.001 |
| 8 | KNGKGQASQT | 0.000 |
| 4 | KQNRKNGKGQ | 0.000 |

TABLE IX-V6-continued

HLA-A1-10mers-202P5A5
Each peptide is a portion of
SEQ ID NO: 3; each start
position is specified, the
length of peptide is 10 amino
acids, and the end position for
each peptide is the start
position plus nine.

| Start | Subsequence | Score |
|---|---|---|
| 6 | NRKNGKGQAS | 0.000 |
| 5 | QNRKNGKGQA | 0.000 |
| 1 | EERKQNRKNG | 0.000 |

TABLE IX-V8

HLA-A1-10mers-202P5A5
Each peptide is a portion of
SEQ ID NO: 3; each start
position is specified, the
length of peptide is 10 amino
acids, and the end position for
each peptide is the start
position plus nine.

| Start | Subsequence | Score |
|---|---|---|
| 10 | MGLMEAISEK | 0.050 |
| 8 | TVMGLMEAIS | 0.020 |
| 6 | SPTVMGLMEA | 0.013 |
| 1 | ALMLKSPTVM | 0.010 |
| 5 | KSPTVMGLME | 0.007 |
| 3 | MLKSPTVMGL | 0.005 |
| 4 | LKSPTVMGLM | 0.005 |
| 7 | PTVMGLMEAI | 0.003 |
| 9 | VMGLMEAISE | 0.003 |
| 2 | LMLKSPTVMG | 0.001 |

TABLE X-V1

HLA-A0201-9mers-202P5A5
Each peptide is a portion of
SEQ ID NO: 3; each start
position is specified, the
length of peptide is 9 amino
acids, and the end position for
each peptide is the start
position plus eight.

| Start | Subsequence | Score |
|---|---|---|
| 253 | YLNKGQFYA | 729.004 |
| 49 | GLLYDYYKV | 386.014 |
| 536 | ALMLKSPTV | 257.342 |
| 591 | FILNMESMV | 162.769 |
| 180 | SLATHSAYL | 117.493 |
| 350 | KIFITVNCL | 87.488 |

TABLE X-V1-continued

HLA-A0201-9mers-202P5A5
Each peptide is a portion of
SEQ ID NO: 3; each start
position is specified, the
length of peptide is 9 amino
acids, and the end position for
each peptide is the start
position plus eight.

| Start | Subsequence | Score |
|---|---|---|
| 90 | NLSGGENRV | 69.552 |
| 522 | VLLYVRKET | 46.873 |
| 337 | NAVSFTWDV | 27.531 |
| 234 | YTLEATKSL | 20.704 |
| 528 | KETDDVFDA | 18.492 |
| 597 | SMVEGFKVT | 17.190 |
| 133 | IIPVSGITV | 16.258 |
| 98 | VQVLKTVPV | 11.988 |
| 107 | NLSLNQDHL | 10.468 |
| 573 | ILVNMDDNI | 8.691 |
| 334 | IAYNAVSFT | 7.122 |
| 307 | RQHTAKQRV | 7.052 |
| 174 | TQYDVPSLA | 6.609 |
| 585 | YSNEDTFIL | 6.254 |
| 341 | FTWDVNEEA | 5.293 |
| 352 | FITVNCLST | 4.713 |
| 461 | QPVLFIPDV | 3.968 |
| 23 | YLENPLTAA | 3.364 |
| 222 | YMYDQTSSG | 3.248 |
| 557 | LPVEKIAKL | 2.236 |
| 369 | KGLPLMIQI | 2.028 |
| 1 | MPSDPPFNT | 1.967 |
| 140 | TVVKAEDFT | 1.757 |
| 279 | KVRSVVMVV | 1.527 |
| 56 | KVPRDKRLL | 1.308 |
| 142 | VKAEDFTPV | 1.279 |
| 100 | VLKTVPVNL | 1.271 |
| 83 | GTSEAQSNL | 1.216 |
| 465 | FIPDVHFAN | 1.121 |
| 525 | TVRKETDDV | 1.043 |
| 102 | KTVPVNLSL | 1.038 |
| 187 | YLKDDQRST | 0.984 |
| 564 | KLYKKSKKG | 0.835 |
| 598 | MVEGFKVTL | 0.773 |
| 134 | IPVSGITVV | 0.728 |

TABLE X-V1-continued

HLA-A0201-9mers-202P5A5
Each peptide is a portion of
SEQ ID NO: 3; each start
position is specified, the
length of peptide is 9 amino
acids, and the end position for
each peptide is the start
position plus eight.

| Start | Subsequence | Score |
|---|---|---|
| 124 | SISFPESSA | 0.683 |
| 173 | QTQYDVPSL | 0.682 |
| 574 | LVNMDDNII | 0.636 |
| 151 | FMAPPVHYP | 0.626 |
| 446 | KSDITYFKT | 0.592 |
| 21 | KSYLENPLT | 0.545 |
| 228 | SSGTFQYTL | 0.530 |
| 546 | GLMEAISEK | 0.520 |
| 227 | TSSGTFQYT | 0.508 |
| 373 | LMIQIDTYS | 0.503 |
| 256 | KGQFYAITL | 0.488 |
| 463 | VLFIPDVHF | 0.469 |
| 148 | TPVFMAPPV | 0.454 |
| 375 | IQIDTYSYN | 0.434 |
| 441 | IPLQKKSDI | 0.428 |
| 125 | ISFPESSAI | 0.428 |
| 518 | GTKRVLLYV | 0.428 |
| 599 | VEGFKVTLM | 0.378 |
| 360 | TDFSSQKGV | 0.357 |
| 567 | KKSKKGILV | 0.338 |
| 493 | VLVKRMFRP | 0.338 |
| 587 | NEDTFILNM | 0.338 |
| 37 | SINGDEDSA | 0.335 |
| 131 | SAIIPVSGI | 0.333 |
| 30 | AATKAMMSI | 0.333 |
| 363 | SSQKGVKGL | 0.321 |
| 362 | YNNRSNKPI | 0.313 |
| 455 | MPDLHSQPV | 0.309 |
| 371 | LLPLMIQIDT | 0.306 |
| 47 | ALGLLYDYY | 0.301 |
| 169 | VIFEQTQYD | 0.291 |
| 82 | RLLSVSKAS | 0.276 |
| 366 | KGVKGLPLM | 0.261 |
| 230 | GTFQYTLEA | 0.255 |

TABLE X-V1-continued

HLA-A0201-9mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 24 | LENPLTAAT | 0.246 |
| 555 | YGLPVEKIA | 0.226 |
| 38 | INGDEDSAA | 0.226 |
| 278 | SKVRSVVMV | 0.222 |
| 331 | IEEIAYNAV | 0.221 |
| 472 | ANLQRTGQV | 0.218 |
| 144 | AEDFTPVFM | 0.213 |
| 50 | LLYDYYKVP | 0.204 |
| 576 | NMDDNIIEH | 0.203 |
| 347 | EEAKIFITV | 0.193 |
| 319 | ADYKESFNT | 0.192 |
| 160 | RGDGEEQRV | 0.182 |
| 466 | IPDVHFANL | 0.180 |
| 330 | NIEEIAYNA | 0.179 |
| 345 | VNEEAKIFI | 0.167 |
| 326 | NTIGNIEEI | 0.163 |
| 458 | LHSQPVLFI | 0.156 |
| 476 | RTGQVYYNT | 0.155 |
| 506 | FGPVPSKQM | 0.149 |
| 201 | SESFKDAAT | 0.145 |
| 327 | TIGNIEEIA | 0.137 |
| 55 | YKVPRDKRL | 0.136 |
| 20 | WKSYLENPL | 0.136 |

TABLE X-V2

HLA-A0201-9mers-202P5A5
Each peptide is a portion of SEQ ID NO: 5; each start position is specified, the length of peptide is 9 amino acids, and the end position for each peptide is the start position plus eight.

| Start | Subsequence | Score |
|---|---|---|
| 3 | QESDNNKRL | 1.703 |
| 7 | NNKRLVALV | 0.037 |
| 10 | RLVALVPMP | 0.034 |
| 6 | DNNKRLVAL | 0.024 |

TABLE X-V2-continued

HLA-A0201-9mers-202P5A5
Each peptide is a portion of SEQ ID NO: 5; each start position is specified, the length of peptide is 9 amino acids, and the end position for each peptide is the start position plus eight.

| Start | Subsequence | Score |
|---|---|---|
| 9 | KRLVALVPM | 0.021 |
| 13 | ALVPMPSDP | 0.015 |
| 11 | LVALVPMPS | 0.011 |
| 16 | PMPSDPPFN | 0.007 |
| 15 | VPMPSDPPF | 0.003 |
| 12 | VALVPMPSD | 0.003 |
| 5 | SDNNKRLVA | 0.003 |
| 4 | ESDNNKRLV | 0.003 |
| 14 | LVPMPSDPP | 0.001 |
| 1 | MSQESDNNK | 0.001 |
| 2 | SQESDNNKR | 0.000 |
| 8 | NKRLVALVP | 0.000 |

TABLE X-V4

HLA-A0201-9mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 9 | IINGDEDSA | 0.569 |
| 1 | TAATKAMMI | 0.145 |
| 2 | AATKAMMII | 0.137 |
| 7 | MMIINGDED | 0.009 |
| 8 | MIINGDEDS | 0.009 |
| 5 | KAMMIINGD | 0.006 |
| 6 | AMMIINGDE | 0.005 |
| 4 | TKAMMIING | 0.000 |
| 3 | ATKAMMIIN | 0.000 |

TABLE X-V5

HLA-A0201-9mers-202P5A5
Each peptide is a portion of SEQ ID NO: 3;
each start position is specified, the
length of peptide is 9 amino acids, and
the end position for each peptide is the
start position plus eight.

| Start | Subsequence | Score |
|---|---|---|
| 3 | KIRDEEQKQ | 0.002 |
| 4 | IRDEEQKQN | 0.000 |
| 9 | QKQNRKKGK | 0.000 |
| 8 | EQKQNRKKG | 0.000 |
| 2 | RKIRDEEQK | 0.000 |
| 5 | RDEEQKQNR | 0.000 |
| 7 | EEQKQNRKK | 0.000 |
| 6 | DEEQKQNRK | 0.000 |
| 1 | ERKIRDEEQ | 0.000 |

TABLE X-V5&6

HLA-A0201-9mers-202P5A5
Each peptide is a portion of SEQ ID NO: 3;
each start position is specified, the
length of peptide is 9 amino acids, and
the end position for each peptide is the
start position plus eight.

| Start | Subsequence | Score |
|---|---|---|
| 1 | EEQKQNRKN | 0.000 |
| 3 | QKQNRKNGK | 0.000 |
| 2 | EQKQNRKNG | 0.000 |

TABLE X-V6

HLA-A0201-9mers-202P5A5
Each peptide is a portion of SEQ ID NO: 3;
each start position is specified, the
length of peptide is 9 amino acids, and
the end position for each peptide is the
start position plus eight.

| Start | Subsequence | Score |
|---|---|---|
| 4 | KQNRKNGKG | 0.003 |
| 9 | NGKGQASQT | 0.002 |
| 8 | KNGKGQASQ | 0.000 |
| 7 | RKNGKGQAS | 0.000 |
| 3 | RKQNRKNGK | 0.000 |
| 5 | QNRKNGKGQ | 0.000 |
| 6 | NRKNGKGQA | 0.000 |
| 1 | EERKQNRKN | 0.000 |
| 2 | ERKQNRKNG | 0.000 |

TABLE X-V8

HLA-A0201-9mers-202P5A5
Each peptide is a portion of SEQ ID NO: 3;
each start position is specified, the
length of peptide is 9 amino acids, and
the end position for each peptide is the
start position plus eight.

| Start | Subsequence | Score |
|---|---|---|
| 1 | LMLKSPTVM | 9.253 |
| 7 | TVMGLMEAI | 3.807 |
| 3 | LKSPTVMGL | 0.116 |
| 8 | VMGLMEAIS | 0.038 |
| 4 | KSPTVMGLM | 0.034 |
| 2 | MLKSPTVMG | 0.004 |
| 6 | PTVMGLMEA | 0.003 |
| 9 | MGLMEAISE | 0.001 |
| 5 | SPTVMGLME | 0.000 |

TABLE XI-V1

HLA-A0201-10mers-202P5A5
Each peptide is a portion of SEQ ID NO: 3;
each start position is specified, the
length of peptide is 10 amino acids, and
the end position for each peptide is the
start position plus nine.

| Start | Subsequence | Score |
|---|---|---|
| 463 | VLFIPDVHFA | 395.296 |
| 245 | KQGEGPMTYL | 393.172 |
| 222 | YMYDQTSSGT | 324.814 |
| 169 | VIFEQTQYDV | 246.631 |
| 597 | SMVEGFKVTL | 240.374 |
| 454 | TMPDLHSQPV | 205.951 |
| 564 | KLYKKSKKGI | 116.847 |
| 465 | FIPDVHFANL | 105.256 |
| 253 | YLNKGQFYAI | 91.183 |
| 460 | SQPVLFIPDV | 61.633 |
| 336 | YNAVSFTWDV | 59.522 |
| 556 | GLPVEKIAKL | 49.134 |
| 550 | AISEKYGLPV | 39.210 |
| 263 | TLSETGDNKC | 20.369 |
| 133 | IIPVSGITVV | 15.331 |
| 271 | KCFRHPISKV | 13.523 |
| 595 | MESMVEGFKV | 13.335 |
| 174 | TQYDVPSLAT | 9.913 |
| 457 | DLHSQPVLFI | 9.898 |
| 132 | AIIPVSGITV | 9.563 |

TABLE XI-V1-continued

HLA-A0201-10mers-202P5A5
Each peptide is a portion of SEQ ID NO: 3;
each start position is specified, the
length of peptide is 10 amino acids, and
the end position for each peptide is the
start position plus nine.

| Start | Subsequence | Score |
|---|---|---|
| 370 | GLPLMIQIDT | 7.452 |
| 573 | ILVNMDDNII | 7.272 |
| 513 | QMKEEGTKRV | 7.208 |
| 99 | QVLKTVPVNL | 6.916 |
| 97 | RVQVLKTVPV | 6.086 |
| 528 | KETDDVFDAL | 5.549 |
| 147 | FTPVFMAPPV | 4.444 |
| 48 | LGLLYDYYKV | 4.284 |
| 330 | NIEEIAYNAV | 3.764 |
| 15 | SEDEAWKSYL | 3.747 |
| 449 | ITYFKTMPDL | 3.712 |
| 493 | VLVKRMFRPM | 3.209 |
| 538 | MLKSPTVKGL | 2.923 |
| 572 | GILVNMDDNI | 2.601 |
| 521 | RVLLYVRKET | 2.413 |
| 23 | YLENPLTAAT | 2.194 |
| 500 | RPMEEEFGPV | 1.701 |
| 89 | SNLSGGENRV | 1.680 |
| 344 | DVNEEAKIFI | 1.544 |
| 362 | FSSQKGVKGL | 1.475 |
| 440 | AIPLQKKSDI | 1.435 |
| 124 | SISFPESSAI | 1.435 |
| 445 | KKSDITYFKT | 1.292 |
| 392 | RAYCQIKVFC | 1.214 |
| 226 | QTSSGTFQYT | 1.082 |
| 333 | EIAYNAVSFT | 0.972 |
| 91 | LSGGENRVQV | 0.772 |
| 548 | MEAISEKYGL | 0.706 |
| 141 | VVKAEDFTPV | 0.688 |
| 37 | SINGDEDSAA | 0.683 |
| 432 | SSSDGKLAAI | 0.642 |
| 471 | FANLQRTGQV | 0.578 |
| 546 | GLMEAISEKY | 0.554 |
| 57 | VPRDKRLLSV | 0.553 |
| 92 | SGGENRVQVL | 0.539 |

TABLE XI-V1-continued

HLA-A0201-10mers-202P5A5
Each peptide is a portion of SEQ ID NO: 3;
each start position is specified, the
length of peptide is 10 amino acids, and
the end position for each peptide is the
start position plus nine.

| Start | Subsequence | Score |
|---|---|---|
| 227 | TSSGTFQYTL | 0.530 |
| 144 | AEDFTPVFMA | 0.515 |
| 139 | ITVVKAEDFT | 0.474 |
| 230 | GTFQYTLEAT | 0.432 |
| 517 | EGTKRVLLYV | 0.431 |
| 106 | VNLSLNQDHL | 0.430 |
| 198 | STYSESFKDA | 0.420 |
| 473 | NLQRTGQVYY | 0.410 |
| 318 | IADYKESFNT | 0.408 |
| 359 | STDFSSQKGV | 0.386 |
| 172 | EQTQYDVPSL | 0.374 |
| 21 | KSYLENPLTA | 0.363 |
| 388 | KPIHRAYCQI | 0.358 |
| 325 | FNTIGNIEEI | 0.353 |
| 143 | KAEDFTPVFM | 0.349 |
| 537 | LMLKSPTVKG | 0.339 |
| 29 | TAATKAMMSI | 0.333 |
| 94 | GENRVQLKT | 0.333 |
| 50 | LLYDYYKVPR | 0.332 |
| 127 | FPESSAIIPV | 0.307 |
| 592 | ILNMESMVEG | 0.291 |
| 535 | DALMLKSPTV | 0.268 |
| 366 | KGVKGLPLMI | 0.238 |
| 82 | LGTSEAQSNL | 0.237 |
| 39 | NGDEDSAAAL | 0.229 |
| 38 | INGDEDSAAA | 0.226 |
| 322 | KESFNTIGNI | 0.212 |
| 214 | SASVGAEEYM | 0.186 |
| 307 | RQHTAKQRVL | 0.178 |
| 125 | ISFPESSAII | 0.176 |
| 73 | QEDQEKRNCL | 0.166 |
| 346 | NEEAKIFITV | 0.164 |
| 130 | SSAIIPVSGI | 0.167 |
| 301 | WKYWHSRQHT | 0.152 |
| 123 | YSISFPESSA | 0.149 |
| 13 | YTSEDEAWKS | 0.146 |

TABLE XI-V1-continued

HLA-A0201-10mers-202P5A5
Each peptide is a portion of SEQ ID NO: 3;
each start position is specified, the
length of peptide is 10 amino acids, and
the end position for each peptide is the
start position plus nine.

| Start | Subsequence | Score |
|---|---|---|
| 374 | MIQIDTYSYN | 0.144 |
| 329 | GNIEEIAYNA | 0.133 |
| 350 | KIFITVNCLS | 0.133 |
| 63 | LLSVSKASDS | 0.127 |
| 26 | NPLTAATKAM | 0.120 |
| 437 | KLAAIPLQKK | 0.120 |
| 345 | VNEEAKIFIT | 0.119 |
| 468 | DVHFANLQRT | 0.112 |
| 232 | FQYTLEATKS | 0.111 |

TABLE XI-V2

HLA-A0201-10mers-202P5A5
Each peptide is a portion of SEQ ID NO: 5;
each start position is specified, the
length of peptide is 10 amino acids, and
the end position for each peptide is the
start position plus nine.

| Start | Subsequence | Score |
|---|---|---|
| 3 | QESDNNKRLV | 1.109 |
| 16 | PMPSDPPFNT | 0.687 |
| 2 | SQESDNNKRL | 0.139 |
| 6 | DNNKRLVALV | 0.078 |
| 10 | RLVALVPMPS | 0.075 |
| 5 | SDNNKRLVAL | 0.068 |
| 15 | VPMPSDPPFN | 0.017 |
| 14 | LVPMPSDPPF | 0.011 |
| 13 | ALVPMPSDPP | 0.007 |
| 11 | LVALVPMPSD | 0.005 |
| 12 | VALVPMPSDP | 0.001 |
| 8 | NKRLVALVPM | 0.001 |
| 1 | MSQESDNNKR | 0.001 |
| 4 | ESDNNKRLVA | 0.000 |
| 9 | KRLVALVPMP | 0.000 |
| 7 | NNKRLVALVP | 0.000 |

TABLE XI-V4

HLA-A0201-10mers-202P5A5
Each peptide is a portion of SEQ ID NO: 3;
each start position is specified, the
length of peptide is 10 amino acids, and
the end position for each peptide is the
start position plus nine.

| Start | Subsequence | Score |
|---|---|---|
| 10 | IINGDEDSAA | 1.161 |
| 9 | MIINGDEDSA | 0.569 |
| 1 | LTAATKAMMI | 0.246 |
| 2 | TAATKAMMII | 0.137 |
| 8 | MMIINGDEDS | 0.045 |
| 7 | AMMIINGDED | 0.020 |
| 3 | AATKAMMIIN | 0.001 |
| 6 | KAMMIINGDE | 0.000 |
| 4 | ATKAMMIING | 0.000 |
| 5 | TKAMMIINGD | 0.000 |

TABLE XI-V5

HLA-A0201-10mers-202P5A5
Each peptide is a portion of SEQ ID NO: 3;
each start position is specified, the
length of peptide is 10 amino acids, and
the end position for each peptide is the
start position plus nine.

| Start | Subsequence | Score |
|---|---|---|
| 4 | KIRDEEQKQN | 0.011 |
| 8 | EEQKQNRKKG | 0.000 |
| 3 | RKIRDEEQKQ | 0.000 |
| 10 | QKQNRKKGKG | 0.000 |
| 1 | AERKIRDEEQ | 0.000 |
| 5 | IRDEEQKQNR | 0.000 |
| 6 | RDEEQKQNRK | 0.000 |
| 9 | EQKQNRKKGK | 0.000 |
| 7 | DEEQKQNRKK | 0.000 |
| 2 | ERKIRDEEQK | 0.000 |

TABLE XI-V5&6

HLA-A0201-10mers-202P5A5
Each peptide is a portion of SEQ ID NO: 3;
each start position is specified, the
length of peptide is 10 amino acids, and
the end position for each peptide is the
start position plus nine.

| Start | Subsequence | Score |
|---|---|---|
| 2 | EEQKGNRKNG | 0.000 |
| 4 | QHQNRKNGKG | 0.000 |

TABLE XI-V5&6-continued

HLA-A0201-10mers-202P5A5
Each peptide is a portion of SEQ ID NO: 3;
each start position is specified, the
length of peptide is 10 amino acids, and
the end position for each peptide is the
start position plus nine.

| Start | Subsequence | Score |
|---|---|---|
| 3 | EQKQNRKNGK | 0.000 |
| 1 | DEEQKQNRKN | 0.000 |

TABLE XI-V6

HLA-A0201-10mers-202P5A5
Each peptide is a portion of SEQ ID NO: 3,
each start position is specified, the
length of peptide is 10 amino acids, and
the end position for each peptide is the
start position plus nine.

| Start | Subsequence | Score |
|---|---|---|
| 8 | KNGKGQASQT | 0.170 |
| 4 | KQNRKNGKGQ | 0.005 |
| 5 | QNRKNGKGQA | 0.000 |
| 7 | RKNGKGQASQ | 0.000 |
| 3 | RKQNRKNGKG | 0.000 |
| 1 | EERKQNRKNG | 0.000 |
| 6 | NRKNGKGQAS | 0.000 |
| 2 | ERKQNRKNGK | 0.000 |

TABLE XI-V8

HLA-A0201-10mers-202P5A5
Each peptide is a portion of SEQ ID NO: 3,
each start position is specified, the
length of peptide is 10 amino acids, and
the end position for each peptide is the
start position plus nine.

| Start | Subsequence | Score |
|---|---|---|
| 1 | ALMLKSPTVM | 7.536 |
| 3 | MLKSPTVMGL | 2.923 |
| 2 | LMLKSPTVMG | 0.339 |
| 6 | SPTVMGLMEA | 0.075 |
| 9 | VMGLMEAISE | 0.018 |
| 8 | TVMGLMEAIS | 0.010 |
| 7 | PTVMGLMEAI | 0.004 |
| 4 | LKSPTVMGLM | 0.004 |
| 10 | MGLMEAISEK | 0.001 |
| 5 | KSPTVMGLME | 0.000 |

TABLE XII-V1

HLA-A3-9mers-202P5A5
Each peptide is a portion of SEQ ID NO: 3,
each start position is specified, the
length of peptide is 9 amino acids, and
the end position for each peptide is the
start position plus eight.

| Start | Subsequence | Score |
|---|---|---|
| 546 | GLMEAISEK | 202.500 |
| 437 | KLAAIPLQK | 180.000 |
| 556 | GLPVEKIAK | 120.000 |
| 284 | VMVVFSEDK | 90.000 |
| 263 | TLSETGDNK | 30.000 |
| 537 | LMLKSPTVK | 30.000 |
| 463 | VLFIPDVHF | 15.000 |
| 532 | DVFDALMLK | 9.000 |
| 594 | NMESMVEGF | 6.000 |
| 547 | LMEAISEKY | 6.000 |
| 513 | QMKEEGTKR | 6.000 |
| 271 | KCFRHPISK | 6.000 |
| 314 | RVLDIADYK | 4.500 |
| 395 | CQIKVFCDK | 4.050 |
| 235 | TLEATKSLR | 4.000 |
| 473 | NLQRTGQVY | 4.000 |
| 47 | ALGLLYDYY | 4.000 |
| 232 | FQYTLEATK | 3.000 |
| 350 | KIFITVNCL | 2.700 |
| 49 | GLLYDYYKV | 2.700 |
| 297 | QLKYWKYWH | 1.800 |
| 13 | YTSEDEAWK | 1.500 |
| 507 | GPVPSKQMK | 1.350 |
| 216 | SVGAEEYMY | 1.200 |
| 492 | SVLVKRMFR | 1.200 |
| 374 | MIQIDTYSY | 1.200 |
| 245 | KQGEGPMTY | 1.080 |
| 286 | VVFSEDKNR | 1.000 |
| 230 | GTFQYTLEA | 0.900 |
| 372 | PLMIQIDTY | 0.900 |
| 100 | VLKTVPVNL | 0.900 |
| 573 | ILVNMDDNI | 0.900 |
| 512 | KQMKEEGTK | 0.810 |
| 102 | KTVPVNLSL | 0.608 |
| 504 | EEFGPVPSK | 0.607 |
| 180 | SLATHSAYL | 0.600 |

TABLE XII-V1-continued

HLA-A3-9mers-202P5A5
Each peptide is a portion of SEQ ID NO: 3,
each start position is specified, the
length of peptide is 9 amino acids, and
the end position for each peptide is the
start position plus eight.

| Start | Subsequence | Score |
|---|---|---|
| 457 | DLHSQPVLF | 0.600 |
| 226 | QTSSGTFQY | 0.600 |
| 107 | NLSLNQDHL | 0.600 |
| 168 | VVIFEQTQY | 0.600 |
| 111 | NQDHLENSK | 0.600 |
| 576 | NMDDNIIEH | 0.600 |
| 181 | LATHSAYLK | 0.600 |
| 253 | YLNKGQFYA | 0.600 |
| 279 | KVRSVVMVV | 0.540 |
| 367 | GVKGLPLMI | 0.540 |
| 488 | REGGSVLVK | 0.540 |
| 380 | YSYNNRSNK | 0.500 |
| 438 | LAAIPLQKK | 0.450 |
| 135 | PVSGITVVK | 0.450 |
| 23 | YLENPLTAA | 0.450 |
| 46 | AALGLLYDY | 0.405 |
| 597 | SMVEGFKVT | 0.338 |
| 358 | LSTDFSSQK | 0.300 |
| 562 | IAKLYKKSK | 0.300 |
| 536 | ALMLKSPTV | 0.300 |
| 90 | NLSGGENRV | 0.300 |
| 48 | LGLLYDYYK | 0.270 |
| 94 | GENRVQVLK | 0.270 |
| 445 | KKSDITYFK | 0.270 |
| 152 | MAPPVHYPR | 0.270 |
| 598 | MVEGFKVTL | 0.270 |
| 468 | DVHFANLQR | 0.240 |
| 443 | LQKKSDITY | 0.240 |
| 497 | RMFRPMEEE | 0.225 |
| 354 | TVNCLSTDF | 0.200 |
| 400 | FCDKGAERK | 0.200 |
| 185 | SAYLKDDQR | 0.200 |
| 429 | QCNSSSDGK | 0.200 |
| 299 | KYWKYWHSR | 0.180 |
| 143 | KAEDFTPVF | 0.180 |
| 317 | DIADYKESF | 0.180 |
| 564 | KLYKKSKKG | 0.150 |
| 50 | LLYDYYKVP | 0.150 |
| 251 | MTYLNKGQF | 0.150 |
| 139 | ITVVKAEDF | 0.150 |
| 543 | TVKGLMEAI | 0.135 |
| 151 | FMAPPVHYP | 0.135 |
| 83 | GTSEAQSNL | 0.135 |
| 518 | GTKRVLLYV | 0.135 |
| 330 | NIEEIAYNA | 0.135 |
| 493 | VLVKRMFRP | 0.135 |
| 559 | VEKIAKLYK | 0.120 |
| 474 | LQRTGQVYY | 0.120 |
| 522 | VLLYVRKET | 0.113 |
| 326 | NTIGNIEEI | 0.101 |
| 523 | LLYVRKETD | 0.100 |
| 222 | YMYDQTSSG | 0.100 |
| 520 | KRVLLYVRK | 0.090 |
| 373 | LMIQIDTYS | 0.090 |
| 370 | GLPLMIQID | 0.090 |
| 173 | QTQYDVPSL | 0.090 |
| 44 | SAAALGLLY | 0.080 |
| 341 | FTWDVNEEA | 0.075 |
| 392 | RAYCQIKVF | 0.075 |
| 294 | RDEQLKYWK | 0.060 |
| 390 | IHRAYCQIK | 0.060 |
| 333 | EIAYNAVSF | 0.060 |
| 574 | LVNMDDNII | 0.060 |
| 315 | VLDIADYKE | 0.060 |

TABLE XII-V2

HLA-A3-9mers-202P5A5
Each peptide is a portion of SEQ ID NO: 5, each start position is specified, the length of peptide is 9 amino acids, and the end position for each peptide is the start position plus eight.

| Start | Subsequence | Score |
|---|---|---|
| 1 | MSQESDNNK | 0.150 |
| 2 | SQESDNNKR | 0.120 |
| 10 | RLVALVPMP | 0.090 |
| 13 | ALVPMPSDP | 0.045 |
| 15 | VPMPSDPPF | 0.045 |
| 11 | LVALVPMPS | 0.012 |
| 14 | LVPMPSDPP | 0.003 |
| 16 | PMPSDPPFN | 0.002 |
| 9 | KRLVALVPM | 0.001 |
| 7 | NNKRLVALV | 0.001 |
| 3 | QESDNNKRL | 0.001 |
| 12 | VALVPMPSD | 0.001 |
| 6 | DNNKRLVAL | 0.001 |
| 5 | SDNNKRLVA | 0.000 |
| 8 | NKRLVALVP | 0.000 |
| 4 | ESDNNKRLV | 0.000 |

TABLE XII-V4

HLA-A3-9mers-202P5A5
Each peptide is a portion of SEQ ID NO: 3, each start position is specified, the length of peptide is 9 amino acids, and the end position for each peptide is the start position plus eight.

| Start | Subsequence | Score |
|---|---|---|
| 9 | IINGDEDSA | 0.030 |
| 7 | MMIINGDED | 0.030 |
| 2 | AATKAMMII | 0.018 |
| 6 | AMMIINGDE | 0.013 |
| 1 | TAATKAMMI | 0.012 |
| 8 | MIINGDEDS | 0.006 |
| 3 | ATKAMMIIN | 0.003 |
| 5 | KAMMIINGD | 0.002 |
| 4 | TKAMMIING | 0.000 |

TABLE XII-V5

HLA-A3-9mers-202P5A5
Each peptide is a portion of SEQ ID NO: 3, each start position is specified, the length of peptide is 9 amino acids, and the end position for each peptide is the start position plus eight.

| Start | Subsequence | Score |
|---|---|---|
| 2 | RKIRDEEQK | 0.030 |
| 6 | DEEQKQNRK | 0.018 |
| 9 | QKQNRKKGK | 0.010 |
| 5 | RDEEQKQNR | 0.006 |
| 3 | KIRDEEQKQ | 0.006 |
| 7 | EEQKQNRKK | 0.002 |
| 8 | EQKQNRKKG | 0.000 |
| 4 | IRDEEQKQN | 0.000 |
| 1 | ERKIRDEEQ | 0.000 |

TABLE XII-V5&6

HLA-A3-9mers-202P5A5
Each peptide is a portion of SEQ ID NO: 3, each start position is specified, the length of peptide is 9 amino acids, and the end position for each peptide is the start position plus eight.

| Start | Subsequence | Score |
|---|---|---|
| 3 | QKQNRKNGK | 0.020 |
| 2 | EQKQNRKNG | 0.000 |
| 1 | EEQKQNRKN | 0.000 |

TABLE XII-V6

HLA-A3-9mers-202P5A5
Each peptide is a portion of SEQ ID NO: 3, each start position is specified, the length of peptide is 9 amino acids, and the end position for each peptide is the start position plus eight.

| Start | Subsequence | Score |
|---|---|---|
| 3 | RKQNRKNGK | 0.020 |
| 4 | KQNRKNGKG | 0.001 |
| 9 | NGKGQASQT | 0.000 |
| 8 | KNGKGQASQ | 0.000 |
| 7 | RKNGKGQAS | 0.000 |
| 6 | NRKNGKGQA | 0.000 |
| 5 | QNRKNGKGQ | 0.000 |
| 2 | ERKQNRKNG | 0.000 |
| 1 | EERKQNRKN | 0.000 |

TABLE XII-V8

HLA-A3-9mers-202P5A5
Each peptide is a portion of SEQ ID NO: 3, each start position is specified, the length of peptide is 9 amino acids, and the end position for each peptide is the start position plus eight.

| Start | Subsequence | Score |
|---|---|---|
| 1 | LMLKSPTVM | 0.300 |
| 7 | TVMGLMEAI | 0.203 |
| 8 | VMGLMEAIS | 0.040 |
| 2 | MLKSPTVMG | 0.030 |
| 3 | LKSPTVMGL | 0.005 |
| 6 | PTVMGLMEA | 0.005 |
| 4 | KSPTVMGLM | 0.002 |
| 5 | SPTVMGLME | 0.000 |
| 9 | MGLMEAISE | 0.000 |

TABLE XIII-V1

HLA-A3-10mers-202P5A5
Each peptide is a portion of SEQ ID NO: 3, each start position is specified, the length of peptide is 10 amino acids, and the end position for each peptide is the start position plus nine.

| Start | Subsequence | Score |
|---|---|---|
| 47 | ALGLLYDYYK | 180.000 |
| 437 | KLAAIPLQKK | 135.000 |
| 50 | LLYDYYKVPR | 60.000 |
| 180 | SLATHSAYLK | 60.000 |
| 357 | CLSTDFSSQK | 60.000 |
| 546 | GLMEAISEKY | 40.500 |
| 536 | ALMLKSPTVK | 30.000 |
| 151 | FMAPPVHYPR | 27.000 |
| 373 | LMIQIDTYSY | 18.000 |
| 497 | RMFRPMEEEF | 10.000 |
| 561 | KIAKLYKKSK | 9.000 |
| 283 | VVMVVFSEDK | 9.000 |
| 594 | NMESMVEGFK | 9.000 |
| 576 | NMDDNIIEHY | 9.000 |
| 398 | KVFCDKGAER | 6.000 |
| 253 | YLNKGQFYAI | 5.400 |
| 341 | FTWDVNEEAK | 5.000 |
| 564 | KLYKKSKKGI | 4.500 |
| 597 | SMVEGFKVTL | 4.050 |

TABLE XIII-V1-continued

HLA-A3-10mers-202P5A5
Each peptide is a portion of SEQ ID NO: 3, each start position is specified, the length of peptide is 10 amino acids, and the end position for each peptide is the start position plus nine.

| Start | Subsequence | Score |
|---|---|---|
| 473 | NLQRTGQVYY | 4.000 |
| 114 | HLENSKREQY | 4.000 |
| 463 | VLFIPDVHFA | 3.000 |
| 518 | GTKRVLLYVR | 2.700 |
| 556 | GLPVEKIAKL | 2.700 |
| 479 | QVYYNTDDER | 2.000 |
| 457 | DLHSQPVLFI | 1.620 |
| 262 | ITLSETGDNK | 1.500 |
| 279 | KVRSVVMVVF | 1.350 |
| 251 | MTYLNKGQFY | 1.000 |
| 573 | ILVNMDDNII | 0.900 |
| 394 | YCQIKVFCDK | 0.900 |
| 538 | MLKSPTVKGL | 0.900 |
| 370 | GLPLMIQIDT | 0.900 |
| 327 | TIGNIEEIAY | 0.800 |
| 442 | PLQKKSDITY | 0.800 |
| 428 | TQCNSSSDGK | 0.600 |
| 167 | RVVIFEQTQY | 0.600 |
| 389 | PIHRAYCQIK | 0.600 |
| 138 | GITVVKAEDF | 0.600 |
| 312 | KQRVLDIADY | 0.540 |
| 512 | KQMKEEGTKR | 0.540 |
| 247 | GEGPMTYLNK | 0.540 |
| 222 | YMYDQTSSGT | 0.500 |
| 234 | YTLEATKSLR | 0.450 |
| 134 | IPVSGITVVK | 0.450 |
| 169 | VIFEQTQYDV | 0.450 |
| 376 | QIDTYSYNNR | 0.400 |
| 558 | PVEKIAKLYK | 0.400 |
| 149 | PVFMAPPVHY | 0.300 |
| 285 | MVVFSEDKNR | 0.300 |
| 263 | TLSETGDNKC | 0.300 |
| 572 | GILVNMDDNI | 0.270 |
| 559 | VEKIAKLYKK | 0.270 |
| 436 | GKLAAIPLQK | 0.270 |

TABLE XIII-V1-continued

HLA-A3-10mers-202P5A5
Each peptide is a portion of SEQ ID NO: 3,
each start position is specified, the
length of peptide is 10 amino acids, and
the end position for each peptide is the
start position plus nine.

| Start | Subsequence | Score |
|---|---|---|
| 449 | ITYFKTMPDL | 0.225 |
| 562 | IAKLYKKSKK | 0.200 |
| 526 | YVRKETDDVF | 0.200 |
| 454 | TMPDLHSQPV | 0.200 |
| 245 | KQGEGPMTYL | 0.182 |
| 1 | MPSDPPFNTR | 0.180 |
| 491 | GSVLVKRMFR | 0.180 |
| 465 | FIPDVHFANL | 0.180 |
| 45 | AAALGLLYDY | 0.180 |
| 309 | HTAKQRVLDI | 0.180 |
| 560 | AISEKYGLPV | 0.180 |
| 100 | VLKTVPVNLS | 0.180 |
| 202 | ESFKDAATEK | 0.150 |
| 353 | ITVNCLSTDF | 0.150 |
| 513 | QMKEEGTKRV | 0.150 |
| 49 | GLLYDYYKVP | 0.135 |
| 215 | ASVGAEEYMY | 0.135 |
| 545 | KGLMEAISEK | 0.135 |
| 99 | QVLKTVPVNL | 0.135 |
| 297 | QLKYWKYWHS | 0.120 |
| 111 | NQDHLENSKR | 0.120 |
| 230 | GTFQYTLEAT | 0.113 |
| 225 | DQTSSGTFQY | 0.108 |
| 23 | YLENPLTAAT | 0.100 |
| 69 | ASDSQEDQEK | 0.100 |
| 523 | LLYVRKETDD | 0.100 |
| 293 | NRDEQLKYWK | 0.090 |
| 444 | QKKSDITYFK | 0.090 |
| 93 | GGENRVQVLK | 0.090 |
| 555 | YGLPVEKIAK | 0.090 |
| 46 | AALGLLYDYY | 0.090 |
| 598 | MVEGFKVTLM | 0.090 |
| 443 | LQKKSDITYF | 0.090 |
| 493 | VLVKRMFRPM | 0.090 |
| 350 | KIFITVNCLS | 0.090 |
| 132 | AIIPVSGITV | 0.090 |

TABLE XIII-V1-continued

HLA-A3-10mers-202P5A5
Each peptide is a portion of SEQ ID NO: 3,
each start position is specified, the
length of peptide is 10 amino acids, and
the end position for each peptide is the
start position plus nine.

| Start | Subsequence | Score |
|---|---|---|
| 371 | LPLMIQIDTY | 0.090 |
| 24 | LENPLTAATK | 0.090 |
| 503 | EEEFGPVPSK | 0.081 |
| 198 | STYSESFKDA | 0.075 |
| 557 | LPVEKIAKLY | 0.068 |
| 271 | KCFRHPISKV | 0.068 |
| 124 | SISFPESSAI | 0.060 |
| 552 | SEKYGLPVEK | 0.060 |
| 109 | SLNQDHLENS | 0.060 |
| 195 | TPDSTYSESF | 0.060 |

TABLE XIII-V2

HLA-A3-10mers-202P5A5
Each peptide is a portion of SEQ ID NO: 5;
each start position is specified, the length
of peptide is 10 amino acids, and the end
position for each peptide is the start
position plus nine.

| Start | Subsequence | Score |
|---|---|---|
| 14 | LVPMPSDPPF | 0.200 |
| 10 | RLVALVPMPS | 0.180 |
| 13 | ALVPMPSDPP | 0.068 |
| 16 | PMPSDPPFNT | 0.045 |
| 1 | MSQESDNNKR | 0.030 |
| 2 | SQESDNNKRL | 0.009 |
| 11 | LVALVPMPSD | 0.005 |
| 5 | SDNNKRLVAL | 0.001 |
| 4 | ESDNNKRLVA | 0.001 |
| 15 | VPMPSDPPFN | 0.000 |
| 6 | DNNKRLVALV | 0.000 |
| 8 | NKRLVALVPM | 0.000 |
| 12 | VALVPMPSDP | 0.000 |
| 9 | KRLVALVPMP | 0.000 |
| 7 | NNKRLVALVP | 0.000 |
| 3 | QESDNNKRLV | 0.000 |

TABLE XIII-V4

HLA-A3-10mers-202P5A5
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 1 | LTAATKAMMI | 0.060 |
| 8 | MMIINGDEDS | 0.060 |
| 7 | AMMIINGDED | 0.030 |
| 9 | MIINGDEDSA | 0.030 |
| 10 | IINGDEDSAA | 0.030 |
| 2 | TAATKAMMII | 0.018 |
| 4 | ATKAMMIING | 0.003 |
| 3 | AATKAMMIIN | 0.001 |
| 6 | KAMMIINGDE | 0.000 |
| 5 | TKAMMIINGD | 0.000 |

TABLE XIII-V5

HLA-A3-10mers-202P5A5
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 9 | EQKQNRKKGK | 0.090 |
| 6 | RDEEQKQNRK | 0.030 |
| 5 | IRDEEQKQNR | 0.006 |
| 2 | ERKIRDEEQK | 0.006 |
| 4 | KIRDEEQKQN | 0.003 |
| 7 | DEEQKQNRKK | 0.002 |
| 1 | AERKIRDEEQ | 0.000 |
| 3 | RKIRDEEQKQ | 0.000 |
| 8 | EEQKQNRKKG | 0.000 |
| 10 | QKQNRKKGKG | 0.000 |

TABLE XIII-V5&6

HLA-A3-10mers-202P5A5
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 3 | EQKQNRKNGK | 0.180 |
| 2 | EEQKQNRKNG | 0.000 |

TABLE XIII-V5&6-continued

HLA-A3-10mers-202P5A5
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 4 | QKQNRKNGKG | 0.000 |
| 1 | DEEQKQNRKN | 0.000 |

TABLE XIII-V6

HLA-A3-10mers-202P5A5
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 2 | ERKQNRKNGK | 0.006 |
| 4 | KQNRKNGKGQ | 0.001 |
| 8 | KNGKGQASQT | 0.001 |
| 5 | QNRKNGKGQA | 0.000 |
| 6 | NRKNGKGQAS | 0.000 |
| 7 | RKNGKGQASQ | 0.000 |
| 1 | EERKQNRKNG | 0.000 |
| 3 | RKQNRKNGKG | 0.000 |

TABLE XIII-V8

HLA-A3-10mers-202P5A5
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 3 | MLKSPTVMGL | 3.600 |
| 1 | ALMLKSPTVM | 0.300 |
| 10 | MGLMEAISEK | 0.045 |
| 2 | LMLKSPTVMG | 0.045 |
| 9 | VMGLMEAISE | 0.040 |
| 8 | TVMGLMEAIS | 0.009 |
| 7 | PTVMGLMEAI | 0.007 |
| 6 | SPTVMGLMEA | 0.006 |
| 5 | KSPTVMGLME | 0.001 |
| 4 | LKSPTVMGLM | 0.000 |

TABLE XIV-V1

HLA-A1101-9mers-202P5A5
Each peptide is a portion of SEQ ID NO: 3;
each start position is specified, the length
of peptide is 9 amino acids, and the end
position for each peptide is the start
position plus eight.

| Start | Subsequence | Score |
| --- | --- | --- |
| 314 | RVLDIADYK | 9.000 |
| 512 | KQMKEEGTK | 3.600 |
| 556 | GLPVEKIAK | 2.400 |
| 271 | KCFRHPISK | 2.400 |
| 546 | GLMEAISEK | 2.400 |
| 532 | DVFDALMLK | 2.400 |
| 437 | KLAAIPLQK | 2.400 |
| 492 | SVLVKRMFR | 1.200 |
| 232 | FQYTLEATK | 1.200 |
| 13 | YTSEDEAWK | 1.000 |
| 395 | CQIKVFCDK | 0.900 |
| 507 | GPVPSKQMK | 0.900 |
| 111 | NQDHLENSK | 0.600 |
| 284 | VMVVFSEDK | 0.600 |
| 537 | LMLKSPTVK | 0.600 |
| 299 | KYWKYWHSR | 0.480 |
| 263 | TLSETGDNK | 0.400 |
| 286 | VVFSEDKNR | 0.400 |
| 181 | LATHSAYLK | 0.400 |
| 488 | REGGSVLVK | 0.360 |
| 468 | DVHFANLQR | 0.240 |
| 429 | QCNSSSDGK | 0.200 |
| 400 | FCDKGAERK | 0.200 |
| 135 | PVSGITVVK | 0.200 |
| 203 | SFKDAATEK | 0.200 |
| 438 | LAAIPLQKK | 0.200 |
| 94 | GENRVQVLK | 0.180 |
| 480 | VYYNTDDER | 0.160 |
| 445 | KKSDITYFK | 0.120 |
| 294 | RDEQLKYWK | 0.120 |
| 279 | KVRSVVMVV | 0.120 |
| 559 | VEKIAKLYK | 0.120 |
| 367 | GVKGLPLMI | 0.120 |
| 230 | GTFQYTLEA | 0.120 |
| 562 | IAKLYKKSK | 0.100 |
| 407 | RKIRDEERK | 0.090 |

TABLE XIV-V1-continued

HLA-A1101-9mers-202P5A5
Each peptide is a portion of SEQ ID NO: 3;
each start position is specified, the length
of peptide is 9 amino acids, and the end
position for each peptide is the start
position plus eight.

| Start | Subsequence | Score |
| --- | --- | --- |
| 520 | KRVLLYVRK | 0.090 |
| 102 | KTVPVNLSL | 0.090 |
| 185 | SAYLKDDQR | 0.080 |
| 54 | YYKVPRDKR | 0.080 |
| 152 | MAPPVHYPR | 0.080 |
| 51 | LYDYYKVPR | 0.080 |
| 513 | QMKEEGTKR | 0.080 |
| 235 | TLEATKSLR | 0.080 |
| 48 | LGLLYDYYK | 0.060 |
| 266 | ETGDNKCFR | 0.060 |
| 361 | DFSSQKGVK | 0.060 |
| 595 | MESMVEGFK | 0.060 |
| 518 | GTKRVLLYV | 0.060 |
| 399 | VFCDKGAER | 0.040 |
| 216 | SVGAEEYMY | 0.040 |
| 380 | YSYNNRSNK | 0.040 |
| 504 | EEFGPVPSK | 0.036 |
| 245 | KQGEGPMTY | 0.036 |
| 49 | GLLYDYYKV | 0.036 |
| 563 | AKLYKKSKK | 0.030 |
| 414 | RKQNRKKGK | 0.030 |
| 168 | VVIFEQTQY | 0.030 |
| 83 | GTSEAQSNL | 0.030 |
| 226 | QTSSGTFQY | 0.030 |
| 53 | DYYKVPRDK | 0.024 |
| 350 | KIFITVNCL | 0.024 |
| 341 | FTWDVNEEA | 0.020 |
| 390 | IHRAYCQIK | 0.020 |
| 304 | WHSRQHTAK | 0.020 |
| 543 | TVKGLMEAI | 0.020 |
| 354 | TVNCLSTDF | 0.020 |
| 342 | TWDVNEEAK | 0.020 |
| 70 | SDSQEDQEK | 0.020 |
| 251 | MTYLNKGQF | 0.020 |
| 574 | LVNMDDNII | 0.020 |

TABLE XIV-V1-continued

HLA-A1101-9mers-202P5A5
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 358 | LSTDFSSQK | 0.020 |
| 598 | MVEGFKVTL | 0.020 |
| 525 | YVRKETDDV | 0.020 |
| 243 | RQKQGEGPM | 0.018 |
| 411 | DEERKQNRK | 0.018 |
| 307 | RQHTAKQRV | 0.018 |
| 560 | EKIAKLYKK | 0.018 |
| 139 | ITVVKAEDF | 0.015 |
| 326 | NTIGNIEEI | 0.015 |
| 410 | RDEERKQNR | 0.012 |
| 89 | SNLSGGENR | 0.012 |
| 253 | YLNKGQFYA | 0.012 |
| 11 | RAYTSEDEA | 0.012 |
| 336 | AYNAVSFTW | 0.012 |
| 398 | KVFCDKGAE | 0.012 |
| 601 | GFKVTLMEI | 0.012 |
| 553 | EKYGLPVEK | 0.012 |
| 554 | KYGLPVEKI | 0.012 |
| 248 | EGPMTYLNK | 0.012 |
| 25 | ENPLTAATK | 0.012 |
| 174 | TQYDVPSLA | 0.012 |
| 22 | SYLENPLTA | 0.012 |
| 443 | LQKKSDITY | 0.012 |
| 28 | LTAATKAMM | 0.010 |
| 173 | QTQYDVPSL | 0.010 |
| 98 | VQVLKTVPV | 0.009 |
| 282 | SVVMVVFSE | 0.009 |
| 167 | RVVIFEQTQ | 0.009 |
| 536 | ALMLKSPTV | 0.008 |

TABLE XIV-V2

HLA-A1101-9mers-202P5A5
Each peptide is a portion of SEQ ID NO: 5;
each start position is specified, the length
of peptide is 9 amino acids, and the end
position for each peptide is the start
position plus eight.

| Start | Subsequence | Score |
|---|---|---|
| 2 | SQESDNNKR | 0.120 |
| 1 | MSQESDNNK | 0.020 |
| 15 | VPMPSDPPF | 0.004 |
| 11 | LVALVPMPS | 0.004 |
| 14 | LVPMPSDPP | 0.002 |
| 10 | RLVALVPMP | 0.002 |
| 9 | KRLVALVPM | 0.001 |
| 13 | ALVPMPSDP | 0.001 |
| 7 | NNKRLVALV | 0.000 |
| 5 | SDNNKRLVA | 0.000 |
| 12 | VALVPMPSD | 0.000 |
| 3 | QESDNNKRL | 0.000 |
| 6 | DNNKRLVAL | 0.000 |
| 16 | PMPSDPPFN | 0.000 |
| 8 | NKRLVALVP | 0.000 |
| 4 | ESDNNKRLV | 0.000 |

TABLE XIV-V4

HLA-A1101-9mers-202P5A5
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 9 | IINGDEDSA | 0.004 |
| 1 | TAATKAMMI | 0.004 |
| 2 | AATKAMMII | 0.004 |
| 3 | ATKAMMIIN | 0.002 |
| 5 | KAMMIINGD | 0.001 |
| 6 | AMMIINGDE | 0.001 |
| 8 | MILNGDEDS | 0.001 |
| 7 | MMIINGDED | 0.001 |
| 4 | TKAMMIING | 0.000 |

TABLE XIV-V5

HLA-A1101-9mers-202P5A5
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 2 | RKIRDEEQK | 0.090 |
| 6 | DEEQKQNRK | 0.018 |
| 5 | RDEEQKQNR | 0.012 |
| 9 | QKQNRKKGK | 0.010 |
| 7 | EEQKQNRKK | 0.002 |
| 3 | KIRDEEQKQ | 0.001 |
| 8 | EQKQNRKKG | 0.000 |
| 4 | IRDEEQKQN | 0.000 |
| 1 | ERKIRDEEQ | 0.000 |

TABLE XIV-V5&6

HLA-A1101-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 3 | QKQNRKNGK | 0.020 |
| 2 | EQKQNRKNG | 0.000 |
| 1 | EEQKQNRKN | 0.000 |

TABLE XIV-V6

HLA-A1101-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 3 | RKQNRKNGK | 0.060 |
| 4 | KQNRKNGKG | 0.002 |
| 6 | NRKNGKGQA | 0.000 |
| 8 | KNGKGQASQ | 0.000 |
| 7 | RKNGKGQAS | 0.000 |
| 9 | NGKGQASQT | 0.000 |
| 5 | QNRKNGKGQ | 0.000 |

TABLE XIV-V6-continued

HLA-A1101-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 2 | ERKQNRKNG | 0.000 |
| 1 | EERKQNRKN | 0.000 |

TABLE XIV-V8

HLA-A1101-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 7 | TVMGLMEAI | 0.040 |
| 1 | LMLKSPTVM | 0.006 |
| 6 | PTVMGLMEA | 0.003 |
| 4 | KSPTVMGLM | 0.001 |
| 8 | VMGLMEAIS | 0.000 |
| 5 | SPTVMGLME | 0.000 |
| 3 | LKSPTVMGL | 0.000 |
| 2 | MLKSPTVMG | 0.000 |
| 9 | MGLMEAISE | 0.000 |

TABLE XV-VI

HLA-A1101-10mers-202P5A5
Each peptide is a portion of
SEQ ID NO: 3; each start
position is specified, the length
of peptide is 10 amino acids,
and the end position for each
peptide is the start position
plus nine.

| Start | Subsequence | Score |
|---|---|---|
| 283 | VVMVVFSEDK | 4.000 |
| 398 | KVFCDKGAER | 2.400 |
| 341 | FTWDVNEEAK | 2.000 |
| 262 | ITLSETGDNK | 1.500 |
| 518 | GTKRVLLYVR | 1.200 |
| 437 | KLAAIPLQKK | 1.200 |
| 536 | ALMLKSPTVK | 0.800 |
| 160 | SLATHSAYLK | 0.800 |

TABLE XV-VI-continued

HLA-A1101-10mers-202P5A5
Each peptide is a portion of
SEQ ID NO: 3; each start
position is specified, the length
of peptide is 10 amino acids,
and the end position for each
peptide is the start position
plus nine.

| Start | Subsequence | Score |
|---|---|---|
| 479 | QVYYNTDDER | 0.800 |
| 47 | ALGLLYDYYK | 0.800 |
| 512 | KQMKEEGTKR | 0.720 |
| 428 | TQCNSSSDGK | 0.600 |
| 561 | KIAKLYKKSK | 0.600 |
| 379 | TYSYNNRSNK | 0.400 |
| 12 | AYTSEDEAWK | 0.400 |
| 357 | CLSTDFSSQK | 0.400 |
| 594 | NMESMVEGFK | 0.400 |
| 558 | PVEKIAKLYK | 0.400 |
| 247 | GEGPMTYLNK | 0.360 |
| 234 | YTLEATKSLR | 0.300 |
| 134 | IPVSGITVVK | 0.300 |
| 265 | MVVFSEDKNR | 0.300 |
| 231 | TFQYTLEATK | 0.200 |
| 399 | VFCDKGAERK | 0.200 |
| 562 | IAKLYKKSKK | 0.200 |
| 394 | YCQIKVFCDK | 0.200 |
| 436 | GKLAAIPLQK | 0.180 |
| 151 | FMAPPVHYPR | 0.160 |
| 50 | LLYDYYKVPR | 0.160 |
| 659 | VEDIAKLYKK | 0.120 |
| 111 | NQDHLENSKR | 0.120 |
| 545 | KGLMEAISEK | 0.090 |
| 167 | RVVIFEQYQY | 0.090 |
| 376 | QIDTYSYNNR | 0.080 |
| 59 | RDKRLLSVSK | 0.060 |
| 555 | YGLPVEKIAK | 0.060 |
| 410 | RDEERKQNRK | 0.060 |
| 93 | GGENRVQVLK | 0.060 |
| 279 | KVRSVVMVVF | 0.060 |
| 24 | LENPLTAATK | 0.060 |
| 97 | RVQVLKTVPV | 0.060 |
| 552 | SEKYGLPVEK | 0.060 |

TABLE XV-VI-continued

HLA-A1101-10mers-202P5A5
Each peptide is a portion of
SEQ ID NO: 3; each start
position is specified, the length
of peptide is 10 amino acids,
and the end position for each
peptide is the start position
plus nine.

| Start | Subsequence | Score |
|---|---|---|
| 53 | DYYKVPRDKR | 0.048 |
| 270 | NKCFRHPISK | 0.040 |
| 389 | PIHRAYCQIK | 0.040 |
| 444 | QKKSDITYFK | 0.040 |
| 110 | LNQDHLENSK | 0.040 |
| 360 | TDFSSQKGVK | 0.040 |
| 293 | NRDEQLKYWK | 0.040 |
| 158 | YPRGDGEEQR | 0.040 |
| 1 | MPSDPPFNTR | 0.040 |
| 491 | GSVLVKRMFR | 0.036 |
| 488 | REGGSVLVKR | 0.036 |
| 313 | QRVLDIADYK | 0.030 |
| 99 | QVLKTVPVNL | 0.030 |
| 302 | KYWHSRQHTA | 0.024 |
| 497 | RMFRPMEEEF | 0.024 |
| 546 | GLMEAISEKY | 0.024 |
| 303 | YWHSRQHTAK | 0.020 |
| 449 | ITYFKTMPDL | 0.020 |
| 519 | TKRVLLYVRK | 0.020 |
| 272 | CFRHPISKVR | 0.020 |
| 251 | MTYLNKGQFY | 0.020 |
| 69 | ASDSQEDQEK | 0.020 |
| 506 | FGPVPSKQMK | 0.020 |
| 596 | MVEGFKVTLM | 0.020 |
| 511 | SKQMKEEGTK | 0.020 |
| 141 | VVKAEDFTPV | 0.020 |
| 309 | HTAKQRVLDI | 0.020 |
| 525 | YVRKETDDVF | 0.020 |
| 314 | RVLDIADYKE | 0.018 |
| 252 | TYLNKGQFYA | 0.018 |
| 572 | GILVNMDDNI | 0.018 |
| 312 | KQRVLDIADY | 0.018 |
| 531 | DDVFDALMLK | 0.018 |
| 245 | KQGEGPMTYL | 0.018 |
| 503 | EEEFGPVPSK | 0.018 |

TABLE XV-VI-continued

HLA-A1101-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 169 | VIFEQTQYDV | 0.016 |
| 383 | NNRSNKPIHR | 0.016 |
| 326 | NTIGNIEEIA | 0.015 |
| 353 | ITVNCLSTDF | 0.015 |
| 556 | GLPVEDIAKL | 0.012 |
| 265 | SETGDNKCFR | 0.012 |
| 202 | ESFKDAATEK | 0.012 |
| 500 | RPMEEEFGPV | 0.012 |
| 487 | EREGGSVLVK | 0.012 |
| 344 | DVNEEAKIFI | 0.012 |
| 138 | GITVVKAEDF | 0.012 |
| 271 | KCFRHPISKV | 0.012 |
| 11 | RAYTSEDEAW | 0.012 |
| 564 | KLYKKSKKGI | 0.012 |
| 364 | SQKGVKGLPL | 0.012 |
| 405 | AERKIRDEER | 0.012 |
| 367 | GVKGLPLMIQ | 0.012 |
| 132 | AIIPVSGITV | 0.012 |
| 373 | LMIQIDTYSY | 0.012 |
| 56 | KVPRDKRLLS | 0.012 |
| 334 | IAYNAVSFTW | 0.012 |
| 584 | HYSNEDTFIL | 0.012 |
| 208 | ATEKFRSASV | 0.010 |

TABLE XV-V2

HLA-A1101-10mers-202P5A5
Each peptide is a portion of SEQ ID NO: 5; each start position is specified, the length of peptide is 10 amino acids, and the end position for each peptide is the start position plus nine.

| Start | Subsequence | Score |
|---|---|---|
| 14 | LVPMPSDPPF | 0.020 |
| 1 | MSQESDNNKR | 0.004 |
| 2 | SQESDNNKRL | 0.003 |

TABLE XV-V2-continued

HLA-A1101-10mers-202P5A5
Each peptide is a portion of SEQ ID NO: 5; each start position is specified, the length of peptide is 10 amino acids, and the end position for each peptide is the start position plus nine.

| Start | Subsequence | Score |
|---|---|---|
| 11 | LVALVPMPSK | 0.002 |
| 13 | ALVPMPSDPP | 0.001 |
| 15 | VPMPSDPPFN | 0.000 |
| 12 | VALVPMPSDP | 0.000 |
| 5 | SDNNKRLVAL | 0.000 |
| 8 | NKRLVALVPM | 0.000 |
| 16 | PMPSDPPFNT | 0.000 |
| 6 | DNNKRLVALV | 0.000 |
| 4 | ESDNNKRLVA | 0.000 |
| 9 | KRLVALVPMP | 0.000 |
| 7 | NNKRLVALVP | 0.000 |
| 3 | QESDNNKRLV | 0.000 |

TABLE XV-V4

HLA-A1101-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 1 | LTAATKAMMI | 0.020 |
| 9 | MIINGDEDSA | 0.006 |
| 10 | IINGDEDSAA | 0.004 |
| 2 | TAATKAMMII | 0.004 |
| 4 | ATKAMMIING | 0.002 |
| 6 | KAMMIINGDE | 0.001 |
| 7 | AMMIINGDED | 0.001 |
| 8 | MMIINGDEDS | 0.001 |
| 3 | AATKAMMIIN | 0.000 |
| 5 | TKAMMIINGD | 0.000 |

TABLE XV-V5

HLA-A1101-10mers-202P5A5
Each peptide is a portion of
SEQ ID NO: 3; each start
position is specified, the length
of peptide is 10 amino acids,
and the end position for each
peptide is the start position
plus nine.

| Start | Subsequence | Score |
|---|---|---|
| 9 | EQKQNRKKGK | 0.090 |
| 6 | RDEEQKQNRK | 0.060 |
| 2 | ERKIRDEEQK | 0.060 |
| 5 | IRDEEQKQNR | 0.004 |
| 7 | DEEQKQNRKK | 0.002 |
| 4 | KIRDEEQKQN | 0.001 |
| 3 | RKIRDEEQKQ | 0.000 |
| 1 | AERKIRDEEQ | 0.000 |
| 10 | QKQNRKKGKG | 0.000 |
| 8 | EEQKQNRKKG | 0.000 |

TABLE XV-V5&6

HLA-A1101-10mers-202P5A5
Each peptide is a portion of
SEQ ID NO: 3; each start
position is specified, the length
of peptide is 10 amino acids,
and the end position for each
peptide is the start position
plus nine.

| Start | Subsequence | Score |
|---|---|---|
| 3 | EQKQNRKNGK | 0.180 |
| 4 | QKQNRKNGKG | 0.000 |
| 2 | EEQKQNRKNG | 0.000 |
| 1 | DEEQKQNRKN | 0.000 |

TABLE XV-V6

HLA-A1101-10mers-202P5A5
Each peptide is a portion of
SEQ ID NO: 3; each start
position is specified, the length
of peptide is 10 amino acids,
and the end position for each
peptide is the start position
plus nine.

| Start | Subsequence | Score |
|---|---|---|
| 3 | RKQNRKNGK | 0.080 |
| 4 | KQNRKNGKG | 0.002 |
| 6 | NRKNGKQA | 0.000 |
| 8 | KNGKGQASQ | 0.000 |
| 7 | RKNGKGQAS | 0.000 |

TABLE XV-V6-continued

HLA-A1101-10mers-202P5A5
Each peptide is a portion of
SEQ ID NO: 3; each start
position is specified, the length
of peptide is 10 amino acids,
and the end position for each
peptide is the start position
plus nine.

| Start | Subsequence | Score |
|---|---|---|
| 9 | NGKGQASQT | 0.000 |
| 5 | QNRKNGKGQ | 0.000 |
| 2 | ERKQNRKNG | 0.000 |
| 1 | EERKQNRKN | 0.000 |

TABLE XV-V8

HLA-A1101-10mers-202P5A5
Each peptide is a portion of
SEQ ID NO: 3; each start
position is specified, the length
of peptide is 10 amino acids,
and the end position for each
peptide is the start position
plus nine.

| Start | Subsequence | Score |
|---|---|---|
| 10 | MGLMEAISEK | 0.030 |
| 1 | ALMLKSPTVM | 0.008 |
| 3 | MLKSPTVMGL | 0.008 |
| 8 | TVMGLMEAIS | 0.004 |
| 6 | SPTVMGLMEA | 0.004 |
| 7 | PTVMGLMEAI | 0.002 |
| 9 | VMGLMEAISE | 0.001 |
| 2 | LMLKSPTVMG | 0.001 |
| 4 | LKSPTVMGLM | 0.000 |
| 5 | KSPTVMGLME | 0.000 |

TABLE XVI-V1

HLA-A24-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 450 | TYFKTMPDL | 200.000 |
| 554 | KYGLPVEKI | 110.000 |
| 320 | DYKESFNTI | 88.400 |
| 565 | LYKKSKKGI | 50.000 |
| 584 | HYSNEDTFI | 50.000 |

TABLE XVI-V1-continued

HLA-A24-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 102 | KTVPVNLSL | 20.160 |
| 498 | MFRPMEEEF | 13.200 |
| 302 | KYWHSRQHT | 12.000 |
| 56 | KVPRDKRLL | 12.000 |
| 256 | KGQFYAITL | 12.000 |
| 335 | AYNAVSFTW | 10.500 |
| 350 | KIFITVNCL | 9.600 |
| 22 | SYLENPLTA | 9.000 |
| 186 | AYLKDDQRS | 9.000 |
| 126 | SFPESSAII | 9.000 |
| 252 | TYLNKGQFY | 9.000 |
| 529 | ETDDVFDAL | 9.064 |
| 557 | LPVEKIAKL | 7.920 |
| 221 | EYMYDQTSS | 7.500 |
| 234 | YTLEATKSL | 7.200 |
| 199 | TYSESFKDA | 7.200 |
| 93 | GGENRVQVL | 7.200 |
| 585 | YSNEDTFIL | 7.200 |
| 143 | KAEDFTPVF | 7.200 |
| 393 | AYCQIDVFC | 7.000 |
| 122 | QYSISFPES | 6.600 |
| 363 | SSQKGVKGL | 6.000 |
| 598 | MVEGFKVTL | 6.000 |
| 549 | EAISEKYGL | 6.000 |
| 246 | QGEGPMTYL | 6.000 |
| 173 | QTQYDVPSL | 6.000 |
| 100 | VLKTVPVNL | 5.800 |
| 259 | FYAITLSET | 5.500 |
| 233 | QYTLEATKS | 5.500 |
| 601 | GFKVTLMEI | 5.500 |
| 12 | AYTSEDEAW | 5.000 |
| 175 | QYDVPSLAT | 5.000 |
| 223 | MYDQTSSGT | 5.000 |
| 379 | TYSYNNRSN | 5.000 |
| 83 | GTSEAQSNL | 4.800 |

TABLE XVI-V1-continued

HLA-A24-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 466 | IPDVHFANL | 4.800 |
| 430 | CNSSSDGKL | 4.400 |
| 369 | KGLPLMIQI | 4.320 |
| 491 | GSVLVKRMF | 4.200 |
| 180 | SLATHSAYL | 4.000 |
| 435 | DGKLAAIPL | 4.000 |
| 228 | SSGTFQYTL | 4.000 |
| 392 | RAYCQIKVF | 4.000 |
| 107 | NLSLNQDHL | 4.000 |
| 43 | DSAAALGLL | 4.000 |
| 590 | TFILNMESM | 3.750 |
| 344 | DVNEEAKIF | 3.600 |
| 354 | TVNCLSTDF | 3.600 |
| 139 | ITVVKAEDF | 3.000 |
| 594 | NMESMVEGF | 3.000 |
| 317 | DIADYKESF | 2.400 |
| 540 | KSPTVKGLM | 2.100 |
| 463 | VLFIPDVHF | 2.000 |
| 333 | EIAYNAVSF | 2.000 |
| 457 | DLHSQPVLF | 2.000 |
| 251 | MTYLNKGQF | 2.000 |
| 345 | VNEEAKIFI | 1.800 |
| 574 | LVNMDDNII | 1.800 |
| 162 | DGEEQRVVI | 1.800 |
| 326 | NTIGNIEEI | 1.650 |
| 382 | YNNRSNKPI | 1.500 |
| 573 | ILVNMDDNI | 1.500 |
| 131 | SAIIPVSGI | 1.500 |
| 366 | KGVKGLPLM | 1.500 |
| 441 | IPLQKKSDI | 1.500 |
| 515 | KEEGTKRVL | 1.200 |
| 543 | TVKGLMEAI | 1.200 |
| 125 | ISFPESSAI | 1.200 |
| 367 | GVKGLPLMI | 1.200 |

TABLE XVI-V1-continued

HLA-A24-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 254 | LNKGQFYAI | 1.200 |
| 351 | IFITVNCLS | 1.050 |
| 30 | AATKAMMSI | 1.000 |
| 310 | TAKQRVLDI | 1.000 |
| 323 | ESFNTIGNI | 1.000 |
| 211 | KFRSASVGA | 1.000 |
| 117 | NSKREQYSI | 1.000 |
| 243 | RQKQGEGPM | 1.000 |
| 299 | KYWKYWHSR | 1.000 |
| 269 | DNKCFRHPI | 1.000 |
| 433 | SSDGKLAAI | 1.000 |
| 361 | SYNNRSNKP | 0.990 |
| 464 | LFIPDVHFA | 0.900 |
| 74 | EDQEKRNCL | 0.864 |
| 157 | HYPRGDGEE | 0.825 |
| 150 | VFMAPPVHY | 0.750 |
| 170 | IFEQTQYDV | 0.750 |
| 524 | LYVRKETDD | 0.750 |
| 215 | ASVGAEEYM | 0.750 |
| 481 | YYNTDDERE | 0.750 |
| 231 | TFQYTLEAT | 0.750 |
| 506 | FGPVPSKQM | 0.750 |
| 40 | GDEDSAAAL | 0.720 |
| 55 | YKVPRDKRL | 0.720 |
| 53 | DYYKVPRDK | 0.700 |
| 533 | VFDALMLKS | 0.660 |

TABLE XVI-V2

HLA-A24-9mers-202P5A5
Each peptide is a portion of
SEQ ID NO: 5; each start
position is specified, the length
of peptide is 9 amino acids,
and the end position for each
peptide is the start position
plus eight.

| Start | Subsequence | Score |
|---|---|---|
| 6 | DNNKRLVAL | 6.000 |
| 15 | VPMPSDPPF | 3.600 |

TABLE XVI-V2-continued

HLA-A24-9mers-202P5A5
Each peptide is a portion of
SEQ ID NO: 5; each start
position is specified, the length
of peptide is 9 amino acids,
and the end position for each
peptide is the start position
plus eight.

| Start | Subsequence | Score |
|---|---|---|
| 3 | QESDNNKRL | 0.480 |
| 9 | KRLVALVPM | 0.150 |
| 11 | LVALVPMPS | 0.140 |
| 7 | NNKRLVALV | 0.120 |
| 4 | ESDNNKRLV | 0.100 |
| 10 | RLVALVPMP | 0.036 |
| 1 | MSQESDNNK | 0.022 |
| 2 | SQESDNNKR | 0.020 |
| 13 | ALVPMPSDP | 0.018 |
| 5 | SDNNKRLVA | 0.015 |
| 12 | VALVPMPSD | 0.015 |
| 16 | PMPSDPPFN | 0.015 |
| 14 | LVPMPSDPP | 0.015 |
| 8 | NKRLVALVP | 0.001 |

TABLE XVI-V4

HLA-A24-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 1 | TAATKAMMI | 1.000 |
| 2 | AATKAMMII | 1.000 |
| 8 | MIINGDEDS | 0.150 |
| 9 | IINGDEDSA | 0.150 |
| 3 | ATKAMMIIN | 0.100 |
| 5 | KAMMIINGD | 0.050 |
| 6 | AMMIINGDE | 0.021 |
| 7 | MMIINGDED | 0.017 |
| 4 | TKAMMIING | 0.001 |

TABLE XVI-V5

HLA-A24-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 3 | KIRDEEQKQ | 0.032 |
| 4 | IRDEEQKQN | 0.012 |
| 8 | EQKQNRKKG | 0.011 |
| 5 | RDEEQKQNR | 0.004 |
| 2 | RKIRDEEQK | 0.003 |
| 6 | DEEQKQNRK | 0.002 |
| 7 | EEQKQNRKK | 0.002 |
| 9 | QKQNRKKGK | 0.002 |
| 1 | ERKIRDEEQ | 0.001 |

TABLE XVI-5&6

HLA-A24-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 1 | EEQKQNRKN | 0.017 |
| 2 | EQKQNRKNG | 0.010 |
| 3 | QKQNRKNGK | 0.002 |

TABLE XVI-V6

HLA-A24-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 9 | NGKGQASQT | 0.100 |
| 7 | RKNGKGQAS | 0.036 |
| 4 | KQNRKNGKG | 0.033 |
| 8 | KNGKGQASQ | 0.020 |
| 1 | EERKQNRKN | 0.011 |
| 6 | NRKNGKGQA | 0.010 |
| 5 | QNRKNGKGQ | 0.010 |

TABLE XVI-V6-continued

HLA-A24-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 3 | RKQNRKNGK | 0.004 |
| 2 | ERKQNRKNG | 0.001 |

TABLE XVI-V8

HLA-A24-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 4 | KSPTVMGLM | 2.100 |
| 7 | TVMGLMEAI | 1.800 |
| 1 | LMLKSPTVM | 0.750 |
| 3 | LKSPTVMGL | 0.480 |
| 8 | VMGLMEAIS | 0.100 |
| 6 | PTVMGLMEA | 0.017 |
| 9 | MGLMEAISE | 0.015 |
| 2 | MLKSPTVMG | 0.010 |
| 5 | SPTVMGLME | 0.010 |

TABLE XVII-V1

HLA-A24-10mers-202P5A5
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 565 | LYKKSKKGIL | 200.000 |
| 584 | HYSNEDTFIL | 200.000 |
| 54 | YYKVPRDKRL | 200.000 |
| 233 | QYTLEATKSL | 200.000 |
| 223 | MYDQTSSGTF | 100.000 |
| 381 | SYNNRSNKPI | 75.000 |
| 554 | KYGLPVEKIA | 14.000 |
| 203 | SFKDAATEKF | 13.200 |
| 302 | KYWHSRQHTA | 100.000 |

TABLE XVII-V1-continued

HLA-A24-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 245 | KQGEGPMTYL | 9.600 |
| 22 | SYLENPLTAA | 9.000 |
| 465 | FIPDVHFANL | 8.640 |
| 99 | QVLKTVPVNL | 8.400 |
| 307 | RQHTAKQRVL | 8.000 |
| 252 | TYLNKGQFYA | 7.500 |
| 524 | LYVRKETDDV | 7.500 |
| 186 | AYLKDDQRST | 7.500 |
| 597 | SMVEGFKVTL | 7.200 |
| 556 | GLPVEKIAKL | 6.600 |
| 429 | QCNSSSDGKL | 6.600 |
| 106 | VNLSLNQDHL | 6.000 |
| 199 | TYSESFKDAA | 6.000 |
| 19 | AWKSYLENPL | 5.760 |
| 92 | SGGENRVQVL | 5.760 |
| 279 | KVRSVVMVVF | 5.600 |
| 122 | QYSISFPESS | 5.000 |
| 39 | NGDEDSAAAL | 4.800 |
| 497 | RMFRPMEEEF | 4.400 |
| 449 | ITYFKTMPDL | 4.000 |
| 227 | TSSGTFQYTL | 4.000 |
| 538 | MLKSPTVKGL | 4.000 |
| 456 | MPDLHSQPVL | 4.000 |
| 364 | SQKGVKGLPL | 4.000 |
| 172 | EQTQYDVPSL | 4.000 |
| 82 | LGTSEAQSNL | 4.000 |
| 362 | FSSQKGVKGL | 4.000 |
| 353 | ITVNCLSTDF | 3.600 |
| 162 | DGEEQRVVIF | 3.600 |
| 593 | LNMESMVEGF | 3.600 |
| 366 | KGVKGLPLMI | 3.600 |
| 388 | KPIHRAYCQI | 3.000 |
| 264 | LSETGDNKCF | 3.000 |
| 505 | EFGPVPSKQM | 3.000 |
| 490 | GGSVLVKRMF | 2.800 |

TABLE XVII-V1-continued

HLA-A24-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 138 | GITVVKAEDF | 2.000 |
| 195 | TPDSTYSESF | 2.000 |
| 564 | KLYKKSKKGI | 2.000 |
| 443 | LQKKSDITYF | 2.000 |
| 525 | YVRKETDDVF | 2.000 |
| 253 | YLNKGQFYAI | 1.800 |
| 344 | DVNEEAKIFI | 1.800 |
| 573 | ILVNMDDNII | 1.800 |
| 143 | KAEDFTPVFM | 1.800 |
| 528 | KETDDVFDAL | 1.613 |
| 440 | AIPLQKKSDI | 1.500 |
| 572 | GILVNMDDNI | 1.500 |
| 568 | KSKKGILVNM | 1.400 |
| 464 | LFIPDVHFAN | 1.260 |
| 446 | KSDITYFKTM | 1.200 |
| 125 | ISFPESSAII | 1.200 |
| 515 | KEEGTKRVLL | 1.200 |
| 432 | SSSDGKLAAI | 1.200 |
| 325 | FNTIGNIEEI | 1.100 |
| 342 | TWDVNEEAKI | 1.100 |
| 400 | FCDKGAERKI | 1.100 |
| 600 | EGFKVTLMEI | 1.100 |
| 116 | ENSKREQYSI | 1.000 |
| 299 | KYWKYWHSRQ | 1.000 |
| 457 | DLHSQPVLFI | 1.000 |
| 309 | HTAKQRVLDI | 1.000 |
| 124 | SISFPESSAI | 1.000 |
| 29 | TAATKAMMSI | 1.000 |
| 130 | SSAIIPVSGI | 1.000 |
| 493 | VLVKRMFRPM | 0.900 |
| 586 | SNEDTFILNM | 0.900 |
| 335 | AYNAVSFTWD | 0.900 |
| 157 | HYPRGDGEEQ | 0.825 |
| 481 | YYNTDDEREG | 0.825 |
| 340 | SFTWDVNEEA | 0.770 |

TABLE XVII-V1-continued

HLA-A24-10mers-202P5A5
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 26 | NPLTAATKAM | 0.750 |
| 221 | EYMYDQTSSG | 0.750 |
| 598 | MVEGFKVTLM | 0.750 |
| 351 | IFITVNCLST | 0.750 |
| 590 | TFILNMESMV | 0.750 |
| 55 | YKVPRDKRLL | 0.720 |
| 514 | MKEEGTKRVL | 0.720 |
| 349 | AKIFITVNCL | 0.720 |
| 485 | DDEREGGSVL | 0.600 |
| 259 | FYAITLSETG | 0.600 |
| 320 | DYKESFNTIG | 0.600 |
| 489 | EGGSVLVKRM | 0.600 |
| 179 | PSLATHSAYL | 0.600 |
| 101 | LKTVPVNLSL | 0.560 |
| 53 | DYYKVPRDKR | 0.550 |
| 258 | QFYAITLSET | 0.550 |
| 451 | YFKTMPDLHS | 0.500 |
| 175 | QYDVPSLATH | 0.500 |
| 379 | TYSYNNRSNK | 0.500 |
| 589 | DTFILNMESM | 0.500 |

TABLE XVII-V2

HLA-A24-10mers-202P5A5
Each peptide is a portion of
SEQ ID NO: 5; each start position
is specified, the length of peptide
is 10 amino acids, and the end
position for each peptide is the
start position plus nine.

| Start | Subsequence | Score |
|---|---|---|
| 2 | SQESDNNKRL | 6.000 |
| 14 | LVPMPSDPPF | 3.000 |
| 5 | SDNNKRLVAL | 0.600 |
| 10 | RLVALVPMPS | 0.420 |
| 6 | DNNKRLVALV | 0.180 |
| 15 | VPMPSDPPFN | 0.180 |
| 4 | ESDNNKRLVA | 0.100 |

TABLE XVII-V2-continued

HLA-A24-10mers-202P5A5
Each peptide is a portion of
SEQ ID NO: 5; each start position
is specified, the length of peptide
is 10 amino acids, and the end
position for each peptide is the
start position plus nine.

| Start | Subsequence | Score |
|---|---|---|
| 8 | NKRLVALVPM | 0.050 |
| 1 | MSQESDNNKR | 0.024 |
| 13 | ALVPMPSDPP | 0.018 |
| 16 | PMPSDPPFNT | 0.015 |
| 12 | VALVPMPSDP | 0.015 |
| 7 | NNKRLVALVP | 0.014 |
| 3 | QESDNNKRLV | 0.012 |
| 11 | LVALVPMPSD | 0.010 |
| 9 | KRLVALVPMP | 0.004 |

TABLE XVII-V4

HLA-A24-10mers-202P5A5
Each peptide is a portion of
SEQ ID NO: 3; each start position
is specified, the length of peptide
is 10 amino acids, and the end
position for each peptide is the
start position plus nine.

| Start | Subsequence | Score |
|---|---|---|
| 1 | LTAATKAMMI | 1.000 |
| 2 | TAATKAMMII | 1.000 |
| 8 | MMIINGDEDS | 0.150 |
| 9 | MIINGDEDSA | 0.150 |
| 10 | IINGDEDSAA | 0.150 |
| 3 | AATKAMMIIN | 0.100 |
| 6 | KAMMIINGDE | 0.042 |
| 7 | AMMIINGDED | 0.017 |
| 4 | ATKAMMIING | 0.010 |
| 5 | TKAMMIINGD | 0.002 |

TABLE XVII-V5

HLA-A24-10 mers-202P5A5
Each peptide is a portion of SEQ ID NO: 3; each
start position is specified, the length of peptide
is 10 amino acids, and the end position for each
peptide is the start position plus nine.

| Start | Subsequence | Score |
|---|---|---|
| 4 | KIRDEEQKQN | 0.240 |
| 9 | EQKQNRKKGK | 0.010 |
| 6 | RDEEQKQNRK | 0.004 |

TABLE XVII-V5-continued

HLA-A24-10 mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 3 | RKIRDEEQKQ | 0.004 |
| 8 | EEQKQNRKKG | 0.002 |
| 10 | QKQNRKKGKG | 0.002 |
| 7 | DEEQKQNRKK | 0.002 |
| 5 | IRDEEQKQNR | 0.001 |
| 1 | AERKIRDEEQ | 0.001 |
| 2 | ERKIRDEEQK | 0.001 |

TABLE XVII-V5&6

HLA-A24-10 mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 1 | DEEQKQNRKN | 0.017 |
| 3 | EQKQNRKNGK | 0.012 |
| 4 | QKQNRKNGKG | 0.002 |
| 2 | EEQKQNRKNG | 0.002 |

TABLE XVII-V6

HLA-A24-10 mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 8 | KNGKGQASQT | 0.200 |
| 5 | QNRKNGKGQA | 0.100 |
| 4 | KQNRKNGKGQ | 0.030 |
| 6 | NRKNGKGQAS | 0.012 |
| 3 | RKQNRKNGKG | 0.003 |
| 7 | RKNGKGQASQ | 0.003 |
| 2 | ERKQNRKNGK | 0.001 |

TABLE XVII-V8

HLA-A24-10 mers-202P515
Each peptide is a portion of SEQ ID NO:3; each start position is specified, the length of peptide is 10 amino acids, and the end position for each peptide is the start postion plus nine.

| Start | Subsequence | Score |
|---|---|---|
| 1 | EERKQNRKNG | 0.001 |

TABLE XVII-V8

HLA-A24-10 mers-202P5A5
Each peptide is a portion of SEQ ID NO:3; each start position is specified, the length of peptide is 10 amino acids, and the end postion for each peptide is the start postion plus nine.

| Start | Subsequence | Score |
|---|---|---|
| 3 | MLKSPTVMGL | 4.000 |
| 1 | ALMLKSPTVM | 0.750 |
| 7 | PTVMGLMEAI | 0.180 |
| 8 | TVMGLMEAIS | 0.150 |
| 6 | SPTVMGLMEA | 0.110 |
| 4 | LKSPTVMGLM | 0.084 |
| 5 | KSPTVMGLME | 0.030 |
| 10 | MGLMEAISEK | 0.017 |
| 2 | LMLKSPTVMG | 0.015 |
| 9 | VMGLMEAISE | 0.010 |

TABLE XVIII-V1

HLA-B7-9 mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 557 | LPVEKIAKL | 80.000 |
| 466 | IPDVHFANL | 24.000 |
| 56 | KVPRDKRLL | 20.000 |
| 549 | EAISEKYGL | 12.000 |
| 525 | YVRKETDDV | 10.000 |
| 279 | KVRSVVMVV | 10.000 |
| 441 | IPLQKKSDI | 8.000 |
| 598 | MVEGFKVTL | 6.000 |
| 57 | VPRDKRLLS | 6.000 |
| 494 | LVKRMFRPM | 5.000 |
| 461 | QPVLFIPDV | 4.000 |
| 256 | KGQFYAITL | 4.000 |

TABLE XVIII-V1-continued

HLA-B7-9 mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 43 | DSAAALGLL | 4.000 |
| 100 | VLKTVPVNL | 4.000 |
| 275 | HPISKVRSV | 4.000 |
| 148 | TPVFMAPPV | 4.000 |
| 107 | NLSLNQDHL | 4.000 |
| 435 | DGKLAAIPL | 4.000 |
| 363 | SSQKGVKGL | 4.000 |
| 486 | DEREGGSVL | 4.000 |
| 83 | GTSEAQSNL | 4.000 |
| 585 | YSNEDTFIL | 4.000 |
| 234 | YTLEATKSL | 4.000 |
| 180 | SLATHSAYL | 4.000 |
| 173 | QTQYDVPSL | 4.000 |
| 228 | SSGTFQYTL | 4.000 |
| 134 | IPVSGITVV | 4.000 |
| 102 | KTVPVNLSL | 4.000 |
| 350 | KIFITVNCL | 4.000 |
| 430 | CNSSSDGKL | 4.000 |
| 30 | AATKAMMSI | 3.600 |
| 215 | ASVGAEEYM | 3.000 |
| 1 | MPSDPPFNT | 3.000 |
| 26 | NPLTAATKA | 2.000 |
| 371 | LPLMIQIDT | 2.000 |
| 158 | YPRGDGEEQ | 2.000 |
| 543 | TVKGLMEAI | 2.000 |
| 4 | DPPFNTRRA | 2.000 |
| 178 | VPSLATHSA | 2.000 |
| 574 | LVNMDDNII | 2.000 |
| 367 | GVKGLPLMI | 2.000 |
| 246 | QGEGPMTYL | 1.800 |
| 131 | SAIIPVSGI | 1.800 |
| 536 | ALMLKSPTV | 1.800 |
| 506 | FGPVPSKQM | 1.500 |
| 529 | ETDDVFDAL | 1.200 |
| 310 | TAKQRVLDI | 1.200 |
| 93 | GGENRVQVL | 1.200 |
| 455 | MPDLHSQPV | 1.200 |
| 490 | GGSVLVKRM | 1.000 |
| 277 | ISKVRSVVM | 1.000 |
| 366 | KGVKGLPLM | 1.000 |
| 95 | ENRVQVLKT | 1.000 |
| 540 | KSPTVKGLM | 1.000 |
| 191 | DQRSTPDST | 1.000 |
| 28 | LTAATKAMM | 1.000 |
| 243 | RQKQGEGPM | 1.000 |
| 207 | AATEKFRSA | 0.900 |
| 472 | ANLQRTGQV | 0.600 |
| 74 | EDQEKRNCL | 0.600 |
| 269 | DNKCFRHPI | 0.600 |
| 153 | APPVHYPRG | 0.600 |
| 337 | NAVSFTWDV | 0.600 |
| 516 | EEGTKRVLL | 0.600 |
| 596 | ESMVEGFKV | 0.600 |
| 500 | RPMEEEFGP | 0.600 |
| 249 | GPMTYLNKG | 0.600 |
| 140 | TVVKAEDFT | 0.500 |
| 125 | ISFPESSAI | 0.400 |
| 531 | DDVFDALML | 0.400 |
| 539 | LKSPTVKGL | 0.400 |
| 573 | ILVNMDDNI | 0.400 |
| 290 | EDKNRDEQL | 0.400 |
| 566 | YKKSKKGIL | 0.400 |
| 254 | LNKGQFYAI | 0.400 |
| 382 | YNNRSNKPI | 0.400 |
| 326 | NTIGNIEEI | 0.400 |
| 369 | KGLPLMIQI | 0.400 |
| 55 | YKVPRDKRL | 0.400 |
| 308 | QHTAKQRVL | 0.400 |
| 20 | WKSYLENPL | 0.400 |
| 365 | QKGVKGLPL | 0.400 |
| 42 | EDSAAALGL | 0.400 |
| 450 | TYFKTMPDL | 0.400 |

TABLE XVIII-V1-continued

HLA-B7-9 mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 323 | ESFNTIGNI | 0.400 |
| 117 | NSKREQYSI | 0.400 |
| 334 | IAYNAVSFT | 0.300 |
| 338 | AVSFTWDVN | 0.300 |
| 11 | RAYTSEDEA | 0.300 |
| 92 | SGGENRVQV | 0.300 |
| 272 | CFRHPISKV | 0.300 |
| 535 | DALMLKSPT | 0.300 |
| 132 | AIIPVSGIT | 0.300 |
| 541 | SPTVKGLME | 0.200 |
| 591 | FILNMESMV | 0.200 |
| 518 | GTKRVLLYV | 0.200 |
| 90 | NLSGGENRV | 0.200 |
| 104 | VPVNLSLNQ | 0.200 |
| 307 | RQHTAKQRV | 0.200 |
| 509 | VPSKQMKEE | 0.200 |

TABLE XVIII-V2

HLA-B7-9 mers-202P5A5
Each peptide is a portion of SEQ ID NO: 5; each start position is specified, the length of peptide is 9 amino acids, and the end position for each peptide is the start position plus eight.

| Start | Subsequence | Score |
|---|---|---|
| 6 | DNNKRLVAL | 4.000 |
| 15 | VPMPSDPPF | 1.200 |
| 3 | QESDNNKRL | 0.400 |
| 7 | NNKRLVALV | 0.200 |
| 11 | LVALVPMPS | 0.100 |
| 9 | KRLVALVPM | 0.100 |
| 14 | LVPMPSDPP | 0.075 |
| 4 | ESDNNKRLV | 0.060 |
| 12 | VALVPMPSD | 0.045 |
| 13 | ALVPMPSDP | 0.030 |
| 5 | SDNNKRLVA | 0.015 |
| 10 | RLVALVPMP | 0.010 |
| 8 | NKRLVALVP | 0.010 |

TABLE XVIII-V2-continued

HLA-B7-9 mers-202P5A5
Each peptide is a portion of SEQ ID NO: 5; each start position is specified, the length of peptide is 9 amino acids, and the end position for each peptide is the start position plus eight.

| Start | Subsequence | Score |
|---|---|---|
| 1 | MSQESDNNK | 0.010 |
| 2 | SQESDNNKR | 0.003 |
| 16 | PMPSDPPFN | 0.002 |

TABLE XVIII-V4

HLA-B7-9 mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 2 | AATKAMMII | 3.600 |
| 1 | TAATKAMMI | 1.200 |
| 9 | IINGDEDSA | 0.100 |
| 6 | AMMIINGDE | 0.090 |
| 5 | KAMMIINGD | 0.090 |
| 3 | ATKAMMIIN | 0.060 |
| 8 | MIINGDEDS | 0.020 |
| 7 | MMIINGDED | 0.010 |
| 4 | TKAMMIING | 0.001 |

TABLE XVIII-V5

HLA-B7-9 mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 3 | KIRDEEQKQ | 0.100 |
| 8 | EQKQNRKKG | 0.015 |
| 7 | EEQKQNRKK | 0.001 |
| 9 | QKQNRKKGK | 0.001 |
| 1 | ERKIRDEEQ | 0.001 |
| 2 | RKIRDEEQK | 0.001 |
| 4 | IRDEEQKQN | 0.001 |
| 6 | DEEQKQNRK | 0.000 |
| 5 | RDEEQKQNR | 0.000 |

TABLE XVIII-V5&6

HLA-B7-9 mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 2 | EQKQNRKNG | 0.015 |
| 1 | EEQKQNRKN | 0.002 |
| 3 | QKQNRKNGK | 0.001 |

TABLE XVIII-V6

HLA-B7-9 mers-202P5A5
Each peptide is a portion of SEQ ID NO: 3; each start position is specified, the length of peptide is 9 amino acids, and the end position for each peptide is the start position plus eight.

| Start | Subsequence | Score |
|---|---|---|
| 9 | KGKGQASQT | 0.100 |
| 5 | QNRKNGKGQ | 0.100 |
| 1 | EERKQNRKN | 0.020 |
| 6 | NRKNGKGQA | 0.010 |
| 8 | KNGKGQASQ | 0.010 |
| 4 | KQNRKNGKG | 0.010 |
| 7 | RKNGKGQAS | 0.002 |
| 2 | ERKQNRKNG | 0.002 |
| 3 | RKQNRKNGK | 0.001 |

TABLE XVIII-V8

HLA-B7-9mers-202P5A5
Each peptide is a portion of SEQ ID NO: 3; each stat position is specified, the length of peptide is 9 amino acids, and the end position for each peptide is the start position plus eight.

| Start | Subsequence | Score |
|---|---|---|
| 7 | TVMGLMEAI | 6.000 |
| 1 | LMLKSPTVM | 1.000 |
| 4 | KSPTVMGLM | 1.000 |
| 3 | LKSPTVMGL | 0.400 |
| 5 | SPTVMGLME | 0.200 |
| 8 | VMGLMEAIS | 0.020 |
| 2 | MLKSPTVMG | 0.015 |
| 6 | PTVMGLMEA | 0.010 |
| 9 | MGLMEAISE | 0.010 |

TABLE XIX-VI

HLA-B7-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 57 | VPRDKRLLSV | 40.000 |
| 455 | MPDLHSQPVL | 24.000 |
| 99 | QVLTVPVNL | 20.000 |
| 26 | NPLTAATKAM | 20.000 |
| 500 | RPMEEEFGPV | 12.000 |
| 388 | KPIHRAYCQI | 8.000 |
| 245 | KQGEGPMTYL | 6.000 |
| 275 | HPISKVRSVV | 6.000 |
| 364 | SQKGVKGLPL | 4.000 |
| 92 | SGGENRVQVL | 4.000 |
| 429 | QCNSSSDGKL | 4.000 |
| 449 | ITYFKTMPDL | 4.000 |
| 556 | GLPVEKIAKL | 4.000 |
| 172 | EQTQYDVPSL | 4.000 |
| 538 | MLKSPTVKGL | 4.000 |
| 106 | VNLSLNQDHL | 4.000 |
| 227 | TSSGTFQYTL | 4.000 |
| 362 | FSSQKGVKGL | 4.000 |
| 465 | FIPDVHFANL | 4.000 |
| 597 | SMVEGFKVTL | 4.000 |
| 82 | LGTSEAQSNL | 4.000 |
| 307 | RQHTAKQRVL | 4.000 |
| 214 | SASVGAEEYM | 3.000 |
| 95 | ENRVQVLKTV | 2.000 |
| 158 | YPRGDGEEQR | 2.000 |
| 441 | IPLQKKSDIT | 2.000 |
| 541 | SPTVKGLMEA | 2.000 |
| 344 | DVNEEAKIFI | 2.000 |
| 598 | MVEGFKVTLM | 1.500 |
| 29 | TAATKAMMSI | 1.200 |
| 39 | NGDEDSAAAL | 1.200 |
| 440 | AIPLQKKSDI | 1.200 |
| 19 | AWKSYLENPL | 1.200 |
| 127 | FPESSAIIPV | 1.200 |
| 349 | AKIFITVNCL | 1.200 |

TABLE XIX-VI-continued

HLA-B7-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 416 | QNRKKGKGQA | 1.000 |
| 279 | KVRSVVMVVF | 1.000 |
| 525 | YVRKETDDVF | 1.000 |
| 493 | VLVKRMFRPM | 1.000 |
| 165 | EQRVVIFEQT | 1.000 |
| 97 | RVQVLKTVPV | 1.000 |
| 568 | KSKKGILVNM | 1.000 |
| 589 | DTFILNMESM | 1.000 |
| 489 | EGGSVLVKRM | 1.000 |
| 141 | VVKAEDFTPV | 1.000 |
| 143 | KAEDFTPVFM | 0.900 |
| 521 | RVLLYVRKET | 0.750 |
| 153 | APPVHYPRGD | 0.600 |
| 249 | GPMTYLNKGQ | 0.600 |
| 457 | DLHSQPVLFI | 0.600 |
| 535 | DALMLKSPTV | 0.600 |
| 130 | SSAIIPVSGI | 0.600 |
| 4 | DPPFNTRRAY | 0.600 |
| 132 | AIIPVSGITV | 0.600 |
| 471 | FANLQRTGQV | 0.600 |
| 550 | AISEKYGLPV | 0.600 |
| 177 | DVPSLATHSA | 0.500 |
| 468 | DVHFANLQRT | 0.500 |
| 600 | EGFKVTLMEI | 0.400 |
| 564 | KLYKKSKKGI | 0.400 |
| 309 | HTAKQRVLDI | 0.400 |
| 54 | YYKVPRDKRL | 0.400 |
| 584 | HYSNEDTFIL | 0.400 |
| 255 | NKGQFYAITL | 0.400 |
| 366 | KGVKGLPLMI | 0.400 |
| 434 | SDGKLAAIPL | 0.400 |
| 565 | LYKKSKKGIL | 0.400 |
| 371 | LPLMIQIDTY | 0.400 |
| 528 | KETDDVFDAL | 0.400 |

TABLE XIX-VI-continued

HLA-B7-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 325 | FNTIGNIEEI | 0.400 |
| 233 | QYTLEATKSL | 0.400 |
| 557 | LPVEKIAKLY | 0.400 |
| 178 | VPSLATHSAY | 0.400 |
| 42 | EDSAAALGLL | 0.400 |
| 179 | PSLATHSAYL | 0.400 |
| 432 | SSSDGKLAAI | 0.400 |
| 572 | GILVNMDDNI | 0.400 |
| 573 | ILVNMDDNII | 0.400 |
| 124 | SISFPESSAI | 0.400 |
| 55 | YKVPRDKRLL | 0.400 |
| 253 | YLNKGQFYAI | 0.400 |
| 548 | MEAISEKYGL | 0.400 |
| 116 | ENSKREQYSI | 0.400 |
| 125 | ISFPESSAII | 0.400 |
| 101 | LKTVPVNLSL | 0.400 |
| 271 | KCFRHPISKV | 0.300 |
| 408 | KIRDEERKQN | 0.300 |
| 5 | PPFNTRRAYT | 0.300 |
| 586 | SNEDTFILNM | 0.300 |
| 191 | DQRSTPDSTY | 0.300 |
| 392 | RAYCQIKVFC | 0.300 |
| 596 | ESMVEGFKVT | 0.300 |
| 1 | MPSDPPFNTR | 0.300 |
| 310 | TAKQRVLDAI | 0.300 |
| 131 | SAIIPVSGIT | 0.300 |
| 91 | LSGGENRVQV | 0.300 |
| 206 | DAATEKFRSA | 0.300 |
| 348 | EAKIFITVNC | 0.300 |
| 446 | KSDITYFKTM | 0.300 |
| 529 | ETDDVFDALM | 0.300 |

TABLE XIX-V2

HLA-B7-10mers-202P5A5
Each peptide is a portion of
SEQ D NO: 5; each start
position is specified, the length
of peptide is 10 amino acids,
and the end position for each
peptide is the start position plus nine.

| Start | Subsequence | Score |
|---|---|---|
| 2 | SQESDNNKRL | 1.200 |
| 15 | VPMPSDPPFN | 1.200 |
| 8 | NKRLVALVPM | 1.000 |
| 5 | SDNNKRLVAL | 0.400 |
| 6 | DNNKRLVALV | 0.200 |
| 14 | LVPMPSDPPF | 0.100 |
| 11 | LVALVPMPSD | 0.075 |
| 13 | ALVPMPSDPP | 0.045 |
| 4 | ESDNNKRLVA | 0.045 |
| 12 | VALVPMPSDP | 0.030 |
| 10 | RLVALVPMPS | 0.020 |
| 3 | QESDNNKRLV | 0.020 |
| 16 | PMPSDPPFNT | 0.015 |
| 7 | NNKRLVALVP | 0.010 |
| 1 | MSQESDNNKR | 0.010 |
| 9 | KRLVALVFMP | 0.001 |

TABLE XIX-V4

HLA-B7-10mers-202P5A5
Each peptide is a portion of
SEQ ID NO: 3; each start
position is specified, the length
of peptide is 10 amino acids,
and the end position for each
peptide is the start position plus nine.

| Start | Subsequence | Score |
|---|---|---|
| 2 | TAATKAMMII | 1.200 |
| 1 | LTAATKAMMI | 0.400 |
| 3 | AATKAMMIIN | 0.180 |
| 9 | MIINGDEDSA | 0.100 |
| 10 | IINGDEDSAA | 0.100 |
| 6 | KAMMIINGDF | 0.090 |
| 7 | AMMIINGDED | 0.090 |
| 4 | ATKAMMIING | 0.030 |
| 8 | MMIINGDEDS | 0.020 |
| 5 | TKAMMIINGD | 0.001 |

TABLE XIX-V5

HLA-B7-10mers-202P5A5
Each peptide is a portion of
SEQ ID NO: 3; each start
position is specified, the length
of peptide is 10 amino acids,
and the end position for each
peptide is the start position plus nine.

| Start | Subsequence | Score |
|---|---|---|
| 4 | KIRDEEQKQN | 0.200 |
| 1 | AERKIRDEEQ | 0.030 |
| 9 | EQKQNRKKGK | 0.010 |
| 8 | EEQKQNRKKG | 0.002 |
| 2 | ERKIRDEEQK | 0.001 |
| 10 | QKQNRKKGKG | 0.001 |
| 3 | RKIRDEEQKQ | 0.001 |
| 7 | DEEQKQNRKK | 0.000 |
| 6 | RDEEQKQNRK | 0.000 |
| 5 | IRDEEQKQNR | 0.000 |

TABLE XIX-V5&6

HLA-B7-10mers-202P5A5
Each peptide is a portion of
SEQ ID NO: 3; each start
position is specified, the length
of peptide is 10 amino acids,
and the end position for each
peptide is the start position plus nine.

| Start | Subsequence | Score |
|---|---|---|
| 3 | EQKQNRKNGK | 0.010 |
| 2 | EEQKQNRKNG | 0.002 |
| 4 | QKQNRKNGKG | 0.001 |
| 1 | DEEQKQNRKN | 0.001 |

TABLE XIX-V6

HLA-B7-10mrs-202P545
Each peptide is a portion of
SEQ ID NO: 3; each start
position is specified, the length
of peptide is 10 amino acids,
and the end position for each
peptide is the start position plus nine.

| Start | Subsequence | Score |
|---|---|---|
| 5 | QNRKNGKGQA | 1.000 |
| 8 | KNGKGQASQT | 0.100 |
| 1 | EERKQNRKNG | 0.015 |
| 4 | KQNRKNGKGQ | 0.015 |
| 6 | NRKNGKGQAS | 0.002 |
| 7 | RKNGKGQASQ | 0.001 |

TABLE XIX-V6-continued

HLA-B7-10mrs-202P545
Each peptide is a portion of
SEQ ID NO: 3; each start
position is specified, the length
of peptide is 10 amino acids,
and the end position for each
peptide is the start position plus nine.

| Start | Subsequence | Score |
|---|---|---|
| 2 | ERKQNRKNGK | 0.001 |
| 3 | RKQNRKINGKG | 0.001 |

TABLE XIX-V8

HLA-B7-10mers-202P5A5
Each peptide is a portion of
SEQ ID NO: 3; each start
position is specified, the length
of peptide is 10 amino acids,
and the end position for each
peptide is the start position plus nine.

| Start | Subsequence | Score |
|---|---|---|
| 1 | ALMLKSPTVM | 9.000 |
| 3 | MLKSPTVMGL | 4.000 |
| 6 | SPTVMGLMEA | 2.000 |
| 8 | TVMGLMEAIS | 0.300 |
| 4 | LKSPTVMGLM | 0.100 |
| 7 | PTVMGLMEAI | 0.040 |
| 2 | LMLKSPTVMG | 0.015 |
| 10 | MGLMEAISEK | 0.010 |
| 9 | VMGLMEAISE | 0.010 |
| 5 | KSPTVMGLME | 0.010 |

TABLE XX-V1

HLA-B3501-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 557 | LPVEKIAKL | 40.000 |
| 292 | KNRDEQLKY | 36.000 |
| 277 | ISKVRSVVM | 30.000 |
| 540 | KSPTVKGLM | 20.000 |
| 585 | YSNEDTFIL | 15.000 |
| 243 | RQKQGEGPM | 12.000 |
| 57 | VPRDKRLLS | 12.000 |
| 215 | ASVGAEEYM | 10.000 |

TABLE XX-V1-continued

HLA-B3501-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 117 | NSKREQYSI | 9.000 |
| 245 | KQGEGPMTY | 8.000 |
| 441 | IPLQKKSDI | 8.000 |
| 214 | SASVGAEEY | 6.000 |
| 46 | AALGLLYDY | 6.000 |
| 443 | LQKKSDITY | 6.000 |
| 466 | IPDVHFANL | 6.000 |
| 386 | SNKPIHRAY | 6.000 |
| 392 | RAYCQIKVF | 8.000 |
| 474 | LQRTGQVYY | 8.000 |
| 494 | LVKRMFRPM | 6.000 |
| 44 | SAAALGLLY | 6.000 |
| 43 | DSAAALGLL | 5.000 |
| 491 | GSVLVKRMF | 5.000 |
| 228 | SSGTFQYTL | 5.000 |
| 363 | SSQKGVKGL | 5.000 |
| 549 | EAISEKYGL | 4.500 |
| 148 | TPVFMAPPV | 4.000 |
| 134 | IPVSGITVV | 4.000 |
| 5 | PPFNTRRAY | 4.000 |
| 1 | MPSDPPFNT | 4.000 |
| 366 | KGVKGLPLM | 4.000 |
| 275 | HPISKVRSV | 4.000 |
| 461 | QPVLFIPDV | 4.000 |
| 143 | KAEDFTPVF | 3.600 |
| 310 | TAKQRVLDI | 3.600 |
| 216 | SVGAEEYMY | 3.000 |
| 56 | KVPRDKRLL | 3.000 |
| 374 | MIQIDTYSY | 3.000 |
| 344 | DVNEEAKIF | 3.000 |
| 100 | VLKTVPVNL | 3.000 |
| 125 | ISFPESSAI | 3.000 |
| 328 | IGNIEEIAY | 3.000 |
| 435 | DGKLAAIPL | 3.000 |

TABLE XX-V1-continued

HLA-B3501-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 568 | KSKKGILVN | 3.000 |
| 168 | VVIFEQTQY | 3.000 |
| 226 | QTSSGTFQY | 2.000 |
| 490 | GGSVLVKRM | 2.000 |
| 350 | KIFITVNCL | 2.000 |
| 371 | LPLMIQIDT | 2.000 |
| 4 | DPPFNTRRA | 2.000 |
| 26 | NPLTAATKA | 2.000 |
| 234 | YTLEATKSL | 2.000 |
| 506 | FGPVPSKQM | 2.000 |
| 323 | ESFNTIGNI | 2.000 |
| 178 | VPSLATHSA | 2.000 |
| 28 | LTAATKAMM | 2.000 |
| 83 | GTSEAQSNL | 2.000 |
| 256 | KGQFYAITL | 2.000 |
| 517 | EGTKRVLLY | 2.000 |
| 47 | ALGLLYDYY | 2.000 |
| 317 | DIADYKESF | 2.000 |
| 473 | NLQRTGQVY | 2.000 |
| 102 | KTVPVNLSL | 2.000 |
| 596 | ESMVEGFKV | 1.500 |
| 193 | RSTPDSTYS | 1.500 |
| 173 | QTQYDVPSL | 1.500 |
| 21 | KSYLENPLT | 1.500 |
| 254 | LNKGQFYAI | 1.200 |
| 30 | AATKAMMSI | 1.200 |
| 269 | DNKCFRHPI | 1.200 |
| 500 | RPMEEEFGP | 1.200 |
| 367 | GVKGLPLMI | 1.200 |
| 455 | MPDLHSQPV | 1.200 |
| 279 | KVRSVVMVV | 1.200 |
| 543 | TVKGLMEAI | 1.200 |
| 131 | SAIIPVSGI | 1.200 |
| 333 | EIAYNAVSF | 1.000 |
| 385 | RSNKPIHRA | 1.000 |

TABLE XX-V1-continued

HLA-B3501-9mers-202P5A5
Each peptide is a portion of
SEQ ID NO: 3; each start
position is specified, the length
of peptide is 9 amino acids,
and the end position for each
peptide is the start position
plus eight.

| Start | Subsequence | Score |
|---|---|---|
| 107 | NLSLNQDHL | 1.000 |
| 354 | TVNCLSTDF | 1.000 |
| 430 | CNSSSDGKL | 1.000 |
| 251 | MTYLNKGQF | 1.000 |
| 281 | RSVVMVVFS | 1.000 |
| 179 | PSLATHSAY | 1.000 |
| 457 | DLHSQPVLF | 1.000 |
| 139 | ITVVKAEDF | 1.000 |
| 180 | SLATHSAYL | 1.000 |
| 432 | SSSDGKLAA | 1.000 |
| 463 | VLFIPDVHF | 1.000 |
| 187 | YLKDDQRST | 0.900 |
| 348 | EAKIFITVN | 0.900 |
| 525 | YVRKETDDV | 0.900 |
| 158 | YPRGDGEEQ | 0.900 |
| 369 | KGLPLMIQI | 0.800 |
| 431 | NSSSDGKLA | 0.750 |
| 486 | DEREGGSVL | 0.600 |
| 547 | LMEAISEKY | 0.600 |
| 207 | AATEKFRSA | 0.600 |
| 529 | ETDDVFDAL | 0.600 |
| 195 | TPDSTYSES | 0.600 |
| 526 | VRKETDDVF | 0.600 |

TABLE XX-V2

HLA-B3501-9mers-202P5A5
Each peptide is a portion of
SEQ ID NO: 5; each start
position is specified, the length
of peptide is 9 amino acids,
and the end position for each
peptide is the start position
plus eight.

| Start | Subsequence | Score |
|---|---|---|
| 15 | VPMPSDPPF | 20.000 |
| 6 | DNNKRLVAL | 1.000 |
| 7 | NNKRLVALV | 0.600 |

TABLE XX-V2-continued

HLA-B3501-9mers-202P5A5
Each peptide is a portion of
SEQ ID NO: 5; each start
position is specified, the length
of peptide is 9 amino acids,
and the end position for each
peptide is the start position
plus eight.

| Start | Subsequence | Score |
|---|---|---|
| 9 | KRLVALYPM | 0.400 |
| 4 | ESDNNKRLV | 0.300 |
| 3 | QESDNNKRL | 0.200 |
| 11 | LVALVPMPS | 0.100 |
| 1 | MSQESDNNK | 0.100 |
| 12 | VALVPMPSD | 0.030 |
| 10 | RLVALVPMP | 0.020 |
| 16 | PMPSDPPFN | 0.015 |
| 5 | SDNNKRLVA | 0.010 |
| 14 | LVPMFSDPP | 0.010 |
| 13 | ALVPMPSDP | 0.010 |
| 2 | SQESEDNNR | 0.004 |
| 8 | NKRLVALVP | 0.003 |

TABLE XX-V4

HLA-B3501-9mers-202P5A5
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 1 | TAATKAMMI | 1.200 |
| 2 | AATKAMMII | 1.200 |
| 3 | ATKAMMIIN | 0.300 |
| 9 | IINGDEDSA | 0.150 |
| 8 | MIINGDEDS | 0.100 |
| 5 | KAMMIINGD | 0.060 |
| 6 | AMMIINGDE | 0.010 |
| 7 | MMIINGDED | 0.010 |
| 4 | TKAMMIING | 0.001 |

TABLE XX-V5

HLA-B3501-9mers-202P5A5
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 3 | KIRDEEQKQ | 0.180 |
| 8 | EQKQNRKKG | 0.030 |
| 4 | IRDEEQKQN | 0.009 |
| 1 | ERKIRDEEQ | 0.003 |
| 2 | RKIRDEEQK | 0.003 |
| 5 | RDEEQKQNR | 0.001 |
| 9 | QKQNRKKGK | 0.001 |
| 7 | EEQKQNRKK | 0.001 |
| 6 | DEEQKQNRK | 0.000 |

TABLE XX-V5&6

HLA-B3501-9mers-202P5A5
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 2 | EQKQNRKNG | 0.030 |
| 1 | EEQKQNRKN | 0.010 |
| 3 | QKQNRKNGK | 0.001 |

TABLE XX-V6

HLA-B3501-9mers-202P5A5
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 9 | NGKGQASQT | 0.300 |
| 5 | QNRKNGKGQ | 0.030 |
| 6 | NRKNGKGQA | 0.030 |
| 1 | EERKQNRKN | 0.030 |
| 7 | RKNGKGQAS | 0.020 |
| 8 | KNGKGQASQ | 0.020 |
| 4 | KQNRKNGKG | 0.020 |
| 2 | ERKQNRKNG | 0.003 |
| 3 | RKQNRKNGK | 0.002 |

TABLE XX-V8

HLA-B3501-9mers-202P5A5
Each peptide is a portion of SEQ ID NO: 3;
each start position is specified, the length
of peptide is 9 amino acids, and the end
position for each peptide is the start
position plus eight.

| Start | Subsequence | Score |
|---|---|---|
| 4 | KSPTVMGLM | 20.000 |
| 1 | LMLKSPTVM | 2.000 |
| 7 | TVMGLMEAI | 0.400 |
| 5 | SPTVMGLME | 0.200 |
| 3 | LKSPTVMGL | 0.100 |
| 8 | VMGLMEAIS | 0.100 |
| 2 | MLKSPTVMG | 0.030 |
| 9 | MGLMEAISE | 0.015 |
| 6 | PTVMGLMEA | 0.010 |

TABLE XXI-V1

HLA-B3501-10mers-202P5A5
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 557 | LPVEKIAKLY | 80.000 |
| 568 | KSKKGILVNM | 60.000 |
| 178 | VPSLATHSAY | 40.000 |
| 4 | DPPFNTRRAY | 40.000 |
| 371 | LPLMIQIDTY | 40.000 |
| 26 | NPLTAATKAM | 40.000 |
| 57 | VPRDKRLLSV | 24.000 |
| 500 | RPMEEEFGPV | 24.000 |
| 213 | RSASVGAEEY | 20.000 |
| 385 | RSNKPIHRAY | 20.000 |
| 312 | KQRVLDIADY | 18.000 |
| 388 | KPIHRAYCQI | 16.000 |
| 215 | ASVGAEEYMY | 15.000 |
| 43 | DSAAALGLLY | 10.000 |
| 143 | KAEDFTPVFM | 7.200 |
| 45 | AAALGLLYDY | 6.000 |
| 292 | KNRDEQLKYW | 6.000 |
| 455 | MPDLHSQPVL | 6.000 |
| 46 | AALGLLYDYY | 6.000 |
| 214 | SASVGAEEYM | 6.000 |

TABLE XXI-V1-continued

HLA-B3501-10mers-202P5A5
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 279 | KVRSVVMVVF | 6.000 |
| 14 | TSEDEAWKSY | 6.000 |
| 195 | TPDSTYSESF | 6.000 |
| 167 | RVVIFEQTQY | 6.000 |
| 446 | KSDITYFKTM | 6.000 |
| 191 | DQRSTPDSTY | 6.000 |
| 227 | TSSGTFQYTL | 5.000 |
| 362 | FSSQKGVKGL | 6.000 |
| 11 | RAYTSEDEAW | 4.500 |
| 443 | LQKKSDITYF | 4.500 |
| 432 | SSSDGKLAAI | 4.000 |
| 275 | KPISKVRSVV | 4.000 |
| 245 | KQGEGPMTYL | 4.000 |
| 546 | GLMEAISEKY | 4.000 |
| 538 | MLKSPTVKGL | 3.000 |
| 373 | LMIQIDTYSY | 3.000 |
| 364 | SQKGVKGLPL | 3.000 |
| 277 | ISKVRSVVMV | 3.000 |
| 525 | YVRKETDDVF | 3.000 |
| 327 | TIGNIEEIAY | 3.000 |
| 264 | LSETGDNKCF | 2.250 |
| 497 | RMFRPMEEEF | 2.000 |
| 307 | RQHTAKQRVL | 2.000 |
| 593 | LNMESMVEGF | 2.000 |
| 541 | SPTVKGLMEA | 2.000 |
| 473 | NLQRTGQVYY | 2.000 |
| 465 | FIPDVHFANL | 2.000 |
| 441 | IPLQKKSDIT | 2.000 |
| 589 | DTFILNMESM | 2.000 |
| 472 | ANLQRTGQVY | 2.000 |
| 597 | SMVEGFKVTL | 2.000 |
| 251 | MTYLNKGQFY | 2.000 |
| 92 | SGGENRVQVL | 2.000 |
| 489 | EGGSVLVKRM | 2.000 |
| 225 | DQTSSGTFQY | 2.000 |

TABLE XXI-V1-continued

HLA-B3501-10mers-202P5A5
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 130 | SSAIIPVSGI | 2.000 |
| 125 | ISFPESSAII | 2.000 |
| 493 | VLVKRMFRPM | 2.000 |
| 408 | KIRDEERKQN | 1.800 |
| 172 | EQTQYDVPSL | 1.500 |
| 117 | NSKREQYSIS | 1.500 |
| 334 | IAYNAVSFTW | 1.500 |
| 529 | ETDDVFDALM | 1.200 |
| 29 | TAATKAMMSI | 1.200 |
| 513 | QMKEEGTKRV | 1.200 |
| 586 | SNEDTFILNM | 1.200 |
| 576 | NMDDNIIEHY | 1.200 |
| 127 | FPESSAIIPV | 1.200 |
| 82 | LGTSEAQSNL | 1.000 |
| 106 | VNLSLNQDHL | 1.000 |
| 490 | GGSVLVKRMF | 1.000 |
| 429 | QCNSSSDGKL | 1.000 |
| 353 | ITVNCLSTDF | 1.000 |
| 21 | KSYLENPLTA | 1.000 |
| 91 | LSGGENRVQV | 1.000 |
| 449 | ITYFKTMPDL | 1.000 |
| 556 | GLPVEKIAKL | 1.000 |
| 685 | YSNEDTFILN | 1.000 |
| 138 | GITVVKAEDF | 1.000 |
| 71 | DSQEDQEKRN | 1.000 |
| 99 | QVLKTVPVNL | 1.000 |
| 141 | VVKAEDFTPV | 0.900 |
| 243 | RQKQGEGPMT | 0.900 |
| 310 | TAKQRVLDIA | 0.900 |
| 348 | EAKIFITVNC | 0.900 |
| 366 | KGVKGLPLMI | 0.800 |
| 564 | KLYKKSKKGI | 0.800 |
| 344 | KVNEEAKIFI | 0.800 |
| 108 | LSLNQDHLEN | 0.750 |
| 36 | MSINGDEDSA | 0.750 |
| 598 | MVEGFKVTLM | 0.600 |

TABLE XXI-V1-continued

HLA-B3501-10mers-202P5A5
Each peptide is a portion of SEQ ID NO: 3;
each start position is specified, the length
of peptide is 10 amino acids, and the end
position for each peptide is the start
position plus nine.

| Start | Subsequence | Score |
|---|---|---|
| 116 | ENSKREQYSI | 0.600 |
| 124 | SISFPESSAI | 0.600 |
| 392 | RAYCQIKVFC | 0.600 |
| 114 | HLENSKREQY | 0.600 |
| 95 | ENRVQVLKTV | 0.600 |
| 203 | SFKDAATEKF | 0.600 |
| 207 | AATEKFRSAS | 0.600 |
| 158 | YPRGDGEEQR | 0.600 |
| 118 | SKREQYSISF | 0.600 |

TABLE XXI-V2

HLA-B3501-10mers-202P5A5
Each peptide is a portion of SEQ ID NO: 5;
each start position is specified, the length
of peptide is 10 amino acids, and the end
position for each peptide is the start
position plus nine.

| Start | Subsequence | Score |
|---|---|---|
| 15 | VPMPSDPPFN | 3.000 |
| 14 | LVPMPSDPPF | 1.000 |
| 8 | NKRLVALVPM | 0.600 |
| 2 | SQESDNNKRL | 0.300 |
| 6 | DNNKRLVALV | 0.200 |
| 10 | RLVALVPMPS | 0.200 |
| 4 | ESDNNKRLVA | 0.150 |
| 1 | MSQESDNNKR | 0.150 |
| 5 | SDNNKRLVAL | 0.100 |
| 3 | QESDNNKRLV | 0.040 |
| 12 | VALVPMPSDP | 0.030 |
| 7 | NNKRLVALVP | 0.030 |
| 13 | ALVPMPSDPP | 0.010 |
| 11 | LVALVPMPSD | 0.010 |
| 16 | PMPSDPPFNT | 0.010 |
| 9 | KRLVALVPMP | 0.002 |

TABLE XXI-V4

HLA-B3501-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 2 | TAATKAMMII | 1.200 |
| 1 | LTAATKAMMI | 0.400 |
| 3 | AATKAMMIIN | 0.300 |
| 9 | MIINGDEDSA | 0.150 |
| 10 | IINGDEDSAA | 0.150 |
| 8 | MMIINGDEDS | 0.100 |
| 6 | KAMMIINGDE | 0.060 |
| 4 | ATKAMMIING | 0.030 |
| 7 | AMMIINGDED | 0.010 |
| 5 | TKAMMIINGD | 0.001 |

TABLE XXI-V5

HLA-B3501-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 4 | KIRDEEQKQN | 1.800 |
| 9 | EQKQNRKKGK | 0.030 |
| 2 | ERKIRDEEQK | 0.005 |
| 1 | AERKIRDEEQ | 0.003 |
| 3 | RKIRDEEQKQ | 0.003 |
| 6 | RDEEQKQNRK | 0.001 |
| 8 | EEQKQNRKKG | 0.001 |
| 10 | QKQNRKKGKG | 0.001 |
| 5 | IRDEEQKQNR | 0.001 |
| 7 | DEEQKQNRKK | 0.000 |

TABLE XXI-V5&6

HLA-B3501-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 3 | EQKQNRKNGK | 0.030 |
| 1 | DEEQKQNRKN | 0.003 |
| 4 | QKQNRKNGKG | 0.001 |
| 2 | EEQKQNRKNG | 0.001 |

TABLE XXI-V6

HLA-B3501-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 5 | QNRKNGKGQA | 0.300 |
| 8 | KNGKGQASQT | 0.200 |
| 6 | NRKNGKGQAS | 0.030 |
| 4 | KQNRKNGKGQ | 0.020 |
| 1 | EERKQNRKNG | 0.003 |
| 2 | ERKQNRKNGK | 0.003 |
| 7 | RKNGKGQASQ | 0.002 |
| 3 | RKQNRKNGKG | 0.002 |

TABLE XXI-V8

HLA-B3501-10mers-202P5A5
Each peptide is a portion of SEQ ID NO: 3; each start position is specified, the length of peptide is 10 amino acids, and the end position for each peptide is the start position plus nine.

| Start | Subsequence | Score |
|---|---|---|
| 3 | MLKSPTVMGL | 3.000 |
| 1 | ALMLKSPTVM | 2.000 |
| 6 | SPTVMGLMEA | 2.000 |
| 4 | LKSPTVMGLM | 0.200 |
| 8 | TVMGLMEAIS | 0.100 |
| 5 | KSPTVMGLME | 0.100 |
| 7 | PTVMGLMEAI | 0.040 |
| 9 | VMGLMEAISE | 0.015 |
| 10 | MGLMEAISEK | 0.010 |
| 2 | LMLKSPTVMG | 0.010 |

TABLE XXII-V1

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 15 | SEDEAWKSY | 27 |
| 547 | LMEAISEKY | 27 |
| 558 | PVEKIAKLY | 27 |
| 44 | SAAALGLLY | 26 |
| 577 | MDDNIIEHY | 25 |
| 517 | EGTKRVLLY | 24 |
| 226 | QTSSGTFQY | 23 |
| 292 | KNRDEQLKY | 23 |
| 2 | PSDPPFNTR | 22 |
| 551 | ISEKYGLPV | 22 |
| 386 | SNKPIHRAY | 21 |
| 529 | ETDDVFDAL | 21 |
| 586 | SNEDTFILN | 21 |
| 359 | STDFSSQKG | 20 |
| 102 | KTVPVNLSL | 19 |
| 179 | PSLATHSAY | 19 |
| 214 | SASVGAEEY | 19 |
| 328 | IGNIEEIAY | 19 |
| 443 | LQKKSDITY | 19 |
| 533 | VFDALMLKS | 19 |
| 84 | TSEAQSNLS | 18 |
| 208 | ATEKFRSAS | 18 |
| 216 | SVGAEEYMY | 18 |
| 264 | LSETGDNKC | 18 |
| 372 | PLMIQIDTY | 18 |
| 473 | NLQRTGQVY | 18 |
| 46 | AALGLLYDY | 17 |
| 47 | ALGLLYDYY | 17 |
| 69 | ASDSQEDQE | 17 |
| 150 | VFMAPPVHY | 17 |
| 175 | QYDVPSLAT | 17 |
| 245 | KQGEGPMTY | 17 |
| 295 | DEQLKYWKY | 17 |
| 433 | SSDGKLAAI | 17 |
| 474 | LQRTGQVYY | 17 |

TABLE XXII-V1-continued

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 483 | NTDDEREGG | 17 |
| 5 | PPFNTRRAY | 16 |
| 14 | TSEDEAWKS | 16 |
| 58 | PRDKRLLSV | 16 |
| 115 | LENSKREQY | 16 |
| 168 | VVIFEQTQY | 16 |
| 192 | QRSTPDSTY | 16 |
| 200 | YSESFKDAA | 16 |
| 252 | TYLNKGQFY | 16 |
| 288 | FSEDKNRDE | 16 |
| 446 | KSDITYFKT | 16 |
| 487 | NEDTFILNM | 16 |
| 119 | KREQYSISF | 15 |
| 127 | FPESSAIIP | 15 |
| 182 | ATHSAYLKD | 15 |
| 313 | QRVLDIADY | 15 |
| 345 | VNEEAKIFI | 15 |
| 374 | MIQIDTYSY | 15 |
| 487 | EREGGSVLV | 15 |
| 23 | YLENPLTAA | 14 |
| 72 | SQEDQEKRN | 14 |
| 162 | DGEEQRVVI | 14 |
| 315 | VLDIADYKE | 14 |
| 432 | SSSDGKLAA | 14 |
| 518 | GTKRVLLYV | 14 |
| 576 | NMDDNIIEH | 14 |
| 75 | DQEKRNCLG | 13 |
| 188 | LKDDQRSTP | 13 |
| 204 | FKDAATEKF | 13 |
| 230 | GTFQYTLEA | 13 |
| 235 | TLEATKSLR | 13 |
| 289 | SEDKNRDEQ | 13 |
| 321 | YKESFNTIG | 13 |
| 400 | FCDKGAERK | 13 |

TABLE XXII-V1-continued

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 466 | IPDVHFANL | 13 |
| 501 | PMEEEFGPV | 13 |
| 568 | KSKKGILVN | 13 |

TABLE XXII-V2

HLA-A1-9mers-202P5A5
Each peptide is a portion of SEQ ID NO: 5; each start position is specified, the length of peptide is 9 amino acids, and the end position for each peptide is the start position plus eight.

| Pos | 123456789 | score |
|---|---|---|
| 4 | ESDNNKRLV | 16 |
| 2 | SQESDNNKR | 15 |
| 5 | SDNNKRLVA | 10 |
| 8 | NKRLVALVP | 9 |

TABLE XXII-V4

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 3 | ATKAMMIIN | 11 |

TABLE XXII-V5

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 1 | YLENPLTAA | 14 |
| 19 | DEDSAAALG | 12 |
| 9 | ATKAMMIIN | 11 |
| 17 | NGDEDSAAA | 10 |

TABLE XXII-V5-continued

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 18 | GDEDSAAAL | 10 |
| 6 | LTAATKAMM | 7 |
| 20 | EDSAAALGL | 5 |
| 21 | DSAAALGLL | 6 |

TABLE XXII-V5&6

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 1 | EEQKQNRKN | 5 |

TABLE XXII-V6

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 1 | EERKQNRKN | 5 |
| 4 | KQNRKNGKG | 3 |
| 9 | NGKGQASQT | 3 |
| 6 | NRKNGKGQA | 2 |
| 7 | RKNGKGQAS | 2 |
| 8 | KNGKGQASQ | 2 |

TABLE XXII-V8

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 5 | SPTVMGLME | 10 |
| 4 | KSPTVMGLM | 8 |
| 6 | PTVMGLMEA | 8 |
| 3 | LKSPTVMGL | 5 |
| 9 | MGLMEAISE | 4 |

TABLE XXII-V1

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 536 | ALMLKSPTV | 27 |
| 180 | SLATHSAYL | 26 |
| 49 | GLLYDYYKV | 25 |
| 90 | NLSGGENRV | 25 |
| 350 | KIFITVNCL | 25 |
| 234 | YTLEATKSL | 23 |
| 557 | LPVEKIAKL | 23 |
| 100 | VLKTVPVNL | 22 |
| 131 | SAIIPVSGI | 22 |
| 133 | IIPVSGITV | 22 |
| 326 | NTIGNIEEI | 22 |
| 23 | YLENPLTAA | 21 |
| 591 | FILNMESMV | 21 |
| 102 | KTVPVNLSL | 20 |
| 107 | NLSLNQDHL | 20 |
| 173 | QTQYDVPSL | 20 |
| 433 | SSDGKLAAI | 20 |
| 546 | GLMEAISEK | 20 |
| 573 | ILVNMDDNI | 20 |
| 598 | MVEGFKVTL | 20 |
| 37 | SINGDEDSA | 19 |
| 151 | FMAPPVHYP | 19 |

TABLE XXII-V1-continued

HLA-A1-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 253 | YLNKGQFYA | 19 |
| 275 | HPISDVRSV | 19 |
| 279 | KVRSVVMVV | 19 |
| 518 | GTKRVLLYV | 19 |
| 132 | AIIPVSGIT | 18 |
| 134 | IPVSGITVV | 18 |
| 187 | YLKDDQRST | 18 |
| 278 | SDVRSVVMV | 18 |
| 363 | SSQKGVKGL | 18 |
| 525 | YVRKETDDV | 18 |
| 539 | LKSPTVKGL | 18 |
| 83 | GTSEAQSNL | 17 |
| 272 | CFRHPISKV | 17 |
| 337 | NAVSFTWDV | 17 |
| 522 | VLLYVRKET | 17 |
| 585 | YSNEDTFIL | 17 |
| 597 | SMVEGFKVT | 17 |
| 46 | AALGLLYDY | 16 |
| 63 | LLSVSKASD | 16 |
| 92 | SGGENRVQV | 16 |
| 96 | VQVLKTVPV | 16 |
| 109 | SLNQDHLEN | 16 |
| 124 | SISFPESSA | 16 |
| 222 | YMYDQTSSG | 16 |
| 228 | SSGTFQYTL | 16 |
| 230 | GTFQYTLEA | 16 |
| 310 | TAKQRVLDI | 16 |
| 367 | GVKGLPLMI | 16 |
| 458 | LHSQPVLFI | 16 |
| 461 | QPVLFIPDV | 16 |
| 472 | ANLQRTGQV | 16 |
| 501 | PMEEEFGPV | 16 |
| 538 | MLKSPTVKG | 16 |
| 554 | KYGLPVEKI | 16 |

TABLE XXII-V1-continued

HLA-A1-9mers-202P5A5
Each peptide is a portion
of SEQ ID NO: 3; each
start position is specified,
the length of peptide is 9
amino acids, and the end
position for each peptide
is the start position plus eight.

| Pos | 123456789 | score |
|---|---|---|
| 574 | LVNMDDNII | 16 |
| 24 | LENPLTAAT | 15 |
| 30 | AATKAMMSI | 15 |
| 43 | DSAAALGLL | 15 |
| 45 | AAALGLLYD | 15 |
| 56 | KVPRDKRLL | 15 |
| 96 | NRVQVLKTV | 15 |
| 142 | VKAEDFTPV | 15 |
| 241 | SLRQKQGEG | 15 |
| 276 | PISKVRSVV | 15 |
| 334 | IAYNAVSFT | 15 |
| 352 | FITVNCLST | 15 |
| 370 | GLPLMIQID | 15 |
| 438 | LAAIPLQKK | 15 |
| 453 | KTMPDLHSQ | 15 |
| 463 | VLFIPDVHF | 15 |
| 464 | LFIPDVHFA | 15 |
| 523 | LLYVRKETD | 15 |
| 543 | TVKGLMEAI | 15 |
| 549 | EAISEKYGL | 15 |

TABLE XXIII-V2

HLA-A0201-9mers-202P5A5
Each peptide is a portion
of SEQ ID NO: 5; each
start position is specified,
the length of peptide is 9
amino acids, and the end
position for each peptide
is the start position plus eight.

| Pos | 123456789 | score |
|---|---|---|
| 6 | DNNKRLVAL | 17 |
| 7 | NNKRLVALV | 16 |
| 10 | RLVALVPMP | 16 |
| 13 | ALVPMPSDP | 14 |
| 9 | KRLVALVPM | 31 |
| 12 | VALVPMPSD | 11 |
| 3 | QESDNNKRL | 10 |

TABLE XXIII-V2-continued

HLA-A0201-9mers-202P5A5
Each peptide is a portion
of SEQ ID NO: 5; each
start position is specified,
the length of peptide is 9
amino acids, and the end
position for each peptide
is the start position plus eight.

| Pos | 123456789 | score |
|---|---|---|
| 5 | SDNNKRLVA | 9 |
| 11 | LVALVPMPS | 8 |

TABLE XXIII-V4

A0201-9mers-202P5A5
Each peptide is a portion
of SEQ ID NO: 3; each
start position is specified,
the lenght of peptide is 9
amino acids, and the end
position for each peptide
is the start position plus eight.

| Pos | 123456789 | score |
|---|---|---|
| 9 | IINGDEDSA | 19 |
| 1 | TAATKAMMI | 15 |
| 2 | AATKAMMII | 13 |
| 5 | KAMMIINGD | 12 |
| 7 | MMIINGDED | 12 |
| 8 | MIINGDEDS | 12 |
| 6 | AMMIINGDE | 11 |

TABLE XXIII-V5

A0201-9mers-202P5A5
Each peptide is a portion
of SEQ ID NO: 3; each
start position is specified,
the lenght of peptide is 9
amino acids, and the end
position for each peptide
is the start position plus eight.

| Pos | 123456789 | score |
|---|---|---|
| 3 | KIRDEEQKQ | 12 |

TABLE XXIII-V5&6

A0201-9mers-202P5A5
Each peptide is a portion
of SEQ ID NO: 3; each
start position is specified,
the lenght of peptide is 9
amino acids, and the end
position for each peptide
is the start position plus eight.

| Pos | 123456789 | score |
|---|---|---|
| 3 | AKANRKNGK | 2 |

TABLE XXIII-V6

HLA-A0201-9mers-202P5A5
Each peptide is a portion of SEQ ID NO: 3; each start position is specified, the lenght of peptide is 9 amino acids, and the end position for each peptide is the start position plus eight.

| Pos | 123456789 | score |
|---|---|---|
| 8 | KNGKGQASQ | 7 |
| 4 | KQNRKNGKG | 5 |
| 6 | NRKNGKGQA | 5 |
| 7 | RKNGKGQAS | 5 |
| 9 | NGKGQASQT | 5 |

TABLE XXIII-V8

HLA-A0201-9mers-202P5A5
Each peptide is a portion of SEQ ID NO: 5; each start position is specified, the length of peptide is 9 amino acids, and the end position for each peptide is the start position plus eight.

| Pos | 123456789 | score |
|---|---|---|
| 3 | LKSPTVMGL | 19 |
| 7 | TVMGLMEAI | 17 |
| 1 | LMLKSPTVM | 16 |
| 2 | MLKSPTVMG | 14 |
| 6 | PTVMGLMEA | 13 |
| 8 | VMGLMEAIS | 11 |

TABLE XXIV-V1

HLA-A0203-9mers-202P5A5

| Pos | 123456789 | score |
|---|---|---|
| No Results Found | | |

TABLE XXIV-V2

HLA-A0203-9mers-202P5A5

| Pos | 123456789 | score |
|---|---|---|
| No Results Found | | |

TABLE XXIV-V3

HLA-A0203-9mers-202P5A5

| Pos | 123456789 | score |
|---|---|---|
| No Results Found | | |

TABLE XXIV-V4

HLA-A0203-9mers-202P5A5

| Pos | 123456789 | score |
|---|---|---|
| No Results Found | | |

TABLE XXIV-V5

HLA-A0203-9mers-202P5A5

| Pos | 123456789 | score |
|---|---|---|
| No results found | | |

TABLE XXIV-V5&6

HLA_A0203-9mers-202P5A5

| Pos | 123456789 | score |
|---|---|---|
| No results found | | |

TABLE XXIV-V6

HLA-A0203-9mers-202P5A5

| Pos | 123456789 | score |
|---|---|---|
| No results found | | |

TABLE XXIV-V8

HLA-A0203-9mers-202P5A5

| Pos | 123456789 | score |
|---|---|---|
| No results found | | |

TABLE XXV-V1

HLA-A3-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 437 | KLAAIPLQK | 33 |
| 135 | PVSGITVVK | 30 |
| 314 | RVLDIADYK | 30 |
| 473 | NLQRTGQVY | 26 |
| 263 | TLSETGDNK | 24 |
| 546 | GLMEAISEK | 24 |
| 168 | VVIFEQTQY | 23 |
| 488 | REGGSVLVK | 23 |
| 279 | KVRSVVMVV | 22 |

TABLE XXV-V1-continued

HLA-A3-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 333 | EIAYNAVSF | 22 |
| 532 | DVFDALMLK | 22 |
| 25  | ENPLTAATK | 21 |
| 232 | FQYTLEATK | 21 |
| 372 | PLMIQIDTY | 21 |
| 462 | PVLFIPDVH | 21 |
| 553 | EKYGLPVEK | 21 |
| 556 | GLPVEKIAK | 21 |
| 47  | ALGLLYDYY | 20 |
| 60  | DKRLLSVSK | 20 |
| 218 | SVGAEEYMY | 20 |
| 407 | RKIRDEERK | 20 |
| 468 | DVHFANLQR | 20 |
| 492 | SVLVKRMFR | 20 |
| 523 | LLYVRKETD | 20 |
| 598 | MVEGFKVTL | 20 |
| 50  | LLYDYYKVP | 19 |
| 97  | RVQVLKTVP | 19 |
| 132 | AIIPVSGIT | 19 |
| 149 | PVEMAPPVH | 19 |
| 167 | RVVIFEQTQ | 19 |
| 235 | TLEATKSLR | 19 |
| 271 | KCFRHPISK | 19 |
| 380 | YSYNNRSNK | 19 |
| 457 | DLHSQPVLF | 19 |
| 463 | VLFIPDVHF | 19 |
| 536 | ALMLKSPTV | 19 |
| 558 | PVEKIAKLY | 19 |
| 563 | AKLYKKSKK | 19 |
| 62  | RLLSVSKAS | 18 |
| 94  | GENRVQVLK | 18 |
| 99  | QVLKTVPVN | 18 |
| 245 | KQGEGPMTY | 18 |
| 297 | QLKYWKYWH | 18 |

TABLE XXV-V1-continued

HLA-A3-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 344 | DVNEEAKIF | 18 |
| 367 | GVKGLPLMI | 18 |
| 512 | KQMKEEGTK | 18 |
| 520 | KRVLLYVRK | 18 |
| 537 | LMLKSPTVK | 18 |
| 564 | KLYKKSKKG | 18 |
| 100 | VLKTVPVNL | 17 |
| 133 | IIPVSGITV | 17 |
| 141 | VVKAEDRTP | 17 |
| 203 | SFKDAATEK | 17 |
| 276 | PISKVRSVV | 17 |
| 338 | AVSFTWDVN | 17 |
| 358 | LSTDFSSQK | 17 |
| 374 | MIQIDTYSY | 17 |
| 390 | IHRAYCQIK | 17 |
| 414 | RKQNRKKGK | 17 |
| 521 | RVLLYVRKE | 17 |
| 592 | ILNMESMVE | 17 |
| 44  | SAAALGLLY | 16 |
| 53  | DYYKVPRDK | 16 |
| 56  | KVPRDKRLL | 16 |
| 81  | CLGTSEAQS | 16 |
| 241 | SLRQKQGEG | 16 |
| 292 | KNRDEQLKY | 16 |
| 317 | DIADYKESF | 16 |
| 392 | RAYCQIKVF | 16 |
| 479 | QVYYNTDDE | 16 |
| 486 | DEREGGSVL | 16 |
| 560 | EKIAKLYKK | 16 |
| 562 | IAKLYKKSK | 16 |

TABLE XXV-V2

HLA-A3-9mers-202P5A5
Each peptide is a portion
of SEQ ID NO: 5; each
start position is specified,
the length of peptide is 9
amino acids, and the end
position for each peptide
is the start position plus eight.

| Pos. | 123456789 | score |
|---|---|---|
| 13 | ALVPMPSDP | 20 |
| 10 | RLVALVPMP | 17 |
| 8 | NKRLVALVP | 15 |
| 11 | LVALVPMPS | 15 |
| 1 | MSQESDNNK | 11 |
| 5 | SDNNKRLVA | 11 |
| 14 | LVPMPSDPP | 10 |
| 9 | KRLVALVPM | 9 |

TABLE XXV-V4

HLA-A3-9mers-202P5A5
Each peptide is a portion
of SEQ ID NO: 3; each
start position is specified,
the length of peptide is 9
amino acids, and the end
position for each peptide
is the start position plus eight.

| Pos | 123456789 | score |
|---|---|---|
| 8 | MIINGDEDS | 14 |
| 9 | IINGDEDSA | 14 |
| 1 | TAATKAMMI | 7 |
| 7 | MMIINGDED | 7 |
| 3 | ATKAMMIIN | 6 |

TABLE XXV-V5

HLA-A3-9mers-202P5A5
Each peptide is a portion
of SEQ ID NO: 3; each
start position is specified,
the length of peptide is 9
amino acids, and the end
position for each peptide
is the start position plus eight.

| Pos | 123456789 | score |
|---|---|---|
| 3 | ENPLTAATK | 21 |
| 14 | MIINGDEDS | 14 |
| 15 | IINGDEDSA | 14 |
| 1 | YLENPLTAA | 13 |
| 5 | PLTAATKAM | 13 |

TABLE XXV-V5&6

HLA-A3-9mers-202P5A5
Each peptide is a portion
of SEQ ID NO: 3; each
start position is specified,
the length of peptide is 9
amino acids, and the end
position for each peptide
is the start position plus eight

| Pos | 123456789 | score |
|---|---|---|
| 3 | QKQNRKNGK | 15 |

TABLE XXV-V8

HLA-A3-9mers-202P5A5
Each peptide is a portion
of SEQ ID NO: 3; each
start position is specified,
the length of peptide is 9
amino acids, and the end
position for each peptide
is the start position plus eight

| Pos | 123456789 | score |
|---|---|---|
| 3 | RKQNRKNGK | 17 |
| 9 | NGKGQASQT | 12 |
| 7 | RKNGKGQAS | 11 |
| 8 | KNGKGQASQ | 10 |
| 4 | KQNRKNGKG | 8 |
| 5 | QNRKNGKGQ | 8 |
| 6 | NRKNGKGQA | 8 |

TABLE XXV-V8

HLA-A3-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 2 | MLKSPTVMG | 16 |
| 7 | TVMGLMEAI | 13 |
| 1 | LMLKSPTVM | 8 |
| 5 | SPTVMGLME | 8 |
| 9 | MGLMEAISE | 7 |

TABLE XXVI-V1

HLA-A26-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 344 | DVNEEAKIF | 28 |
| 529 | ETDDVFDAL | 28 |
| 532 | DVFDALMLK | 27 |
| 517 | EGTKRVLLY | 26 |
| 168 | VVIFEQTQY | 25 |
| 333 | EIAYNAVSF | 24 |
| 102 | KTVPVNLSL | 23 |
| 549 | EAISEKYGL | 23 |
| 216 | SVGAEEYMY | 22 |
| 317 | DIADYKESF | 22 |
| 531 | DDVFDALML | 22 |
| 558 | PVEKIAKLY | 22 |
| 43 | DSAAALGLL | 21 |
| 74 | EDQEKRNCL | 21 |
| 139 | ITVVKAEDF | 21 |
| 173 | QTQYDVPSL | 21 |
| 583 | EHYSNEDTF | 21 |
| 589 | DTFILNMES | 21 |
| 177 | DVPSLATHS | 20 |
| 226 | QTSSGTFQY | 20 |
| 266 | ETGDNKCFR | 20 |
| 282 | SVVMVVFSE | 20 |
| 295 | DEQLKYWKY | 20 |
| 350 | KIFITVNCL | 20 |
| 354 | TVNCLSTDF | 20 |
| 468 | DVHFANLQR | 20 |
| 486 | DEREGGSVL | 20 |
| 557 | LPVEKIAKL | 20 |
| 560 | EKIAKLYKK | 20 |
| 16 | EDEAWKSYL | 19 |
| 42 | EDSAAALGL | 19 |
| 83 | GTSEAQSNL | 19 |
| 145 | EDFTPVFMA | 19 |
| 234 | YTLEATKSL | 19 |
| 251 | MTYLNKGQF | 19 |
| 290 | EDKNRDEQL | 19 |
| 323 | ESFNTIGNI | 19 |
| 504 | EEFGPVPSK | 19 |
| 516 | EEGTKRVLL | 19 |
| 598 | MVEGFKVTL | 19 |
| 56 | KVPRDKRLL | 18 |
| 313 | QRVLDIADY | 18 |
| 353 | ITVNCLSTD | 18 |
| 588 | EDTFILNME | 18 |
| 86 | EAQSNLSGG | 17 |
| 103 | TVPVNLSLN | 17 |
| 326 | NTIGNIEEI | 17 |
| 378 | DTYSYNNRS | 17 |
| 435 | DGKLAAIPL | 17 |
| 457 | DLHSQPVLF | 17 |
| 77 | EKRNCLGTS | 16 |
| 95 | ENRVQVLKT | 16 |
| 129 | ESSAIIPVS | 16 |
| 237 | EATKSLRQK | 16 |
| 398 | KVFCDKGAE | 16 |
| 489 | EGGSVLVKR | 16 |
| 542 | PTVKGLMEA | 16 |
| 577 | MDDNIIEHY | 16 |
| 600 | EGFKVTLME | 16 |
| 5 | PPFNTRRAY | 15 |
| 46 | AALGLLYDY | 15 |
| 105 | PVNLSLNQD | 15 |
| 140 | TVVKAEDFT | 15 |
| 164 | EEQRVVIFE | 15 |
| 167 | RVVIFEQTQ | 15 |
| 202 | ESFKDAATE | 15 |
| 210 | EKFRSASVG | 15 |
| 279 | KVRSVVMVV | 15 |
| 285 | MVVFSEDKN | 15 |
| 286 | VVFSEDKNR | 15 |
| 372 | PLMIQIDTY | 15 |

TABLE XXVI-V1-continued

HLA-A26-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 374 | MIQIDTYSY | 15 |
| 386 | SNKPIHRAY | 15 |
| 521 | RVLLYVRKE | 15 |
| 15 | SEDEAWKSY | 14 |
| 44 | SAAALGLLY | 14 |
| 99 | QVLKTVPVN | 14 |
| 149 | PVFMAPPVH | 14 |
| 165 | EQRVVIFEQ | 14 |
| 332 | EEIAYNAVS | 14 |
| 347 | EEAKIFITV | 14 |
| 348 | EAKIFITVN | 14 |
| 448 | DITYFKTMP | 14 |
| 453 | KTMPDLHSQ | 14 |
| 55 | YKVPRDKRL | 13 |
| 115 | LENSKREQY | 13 |
| 121 | ECYSISFPE | 13 |
| 230 | GTFQYTLEA | 13 |
| 245 | KQGEGPMTY | 13 |
| 252 | TYLNKGQFY | 13 |
| 292 | KNRDEQLKY | 13 |
| 314 | RVLDIADYK | 13 |
| 363 | SSQKGVKGL | 13 |
| 367 | GVKGLPLMI | 13 |
| 444 | QKKSDITYF | 13 |
| 450 | TYFKTMPDL | 13 |
| 491 | GSVLVKRMF | 13 |
| 505 | EFGPVPSKQ | 13 |
| 508 | PVPSKQMKE | 13 |
| 518 | GTKRVLLYV | 13 |
| 539 | LKSPTVKGL | 13 |
| 543 | TVKGLMEAI | 13 |
| 547 | LMEAISEKY | 13 |
| 579 | DNIIEHYSN | 13 |
| 594 | NMESMVEGF | 13 |

TABLE XXVI-V2

HLA-A26-9mers-202P5A5
Each peptide is a portion of SEQ ID NO: 5;
each start position is specified, the length
of peptide is 9 amino acids, and the end
position for each peptide is the start
position plus eight.

| Pos | 123456789 | score |
|---|---|---|
| 6 | DNNKRLVAL | 21 |
| 4 | ESDNNKRLV | 11 |
| 3 | QESDNNKRL | 10 |
| 10 | RLVALVPMP | 10 |
| 11 | LVALVPMPS | 10 |
| 14 | LVPMPSDPP | 10 |

TABLE XXVI-V4

HLA-A26-9 mers-202P5A5
Each peptide is a portion of SEQ ID NO: 3; each
start position is specified, the length of peptide
is 9 amino acids, and the end position for each
peptide is the start position plus eight.

| Pos | 123456789 | score |
|---|---|---|
| 3 | ATKAMMIIN | 9 |
| 6 | MIINGDEDS | 8 |
| 4 | TKAMMIING | 8 |
| 5 | KAMMIINGD | 6 |
| 7 | MMIINGDED | 6 |
| 9 | IINGDEDSA | 5 |

TABLE XXVI-V5

HLA-A26-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 21 | DSAAALGLL | 21 |
| 20 | EDSAAALGL | 19 |
| 3 | ENPLTAATK | 11 |
| 18 | GDEDSAAAL | 10 |

TABLE XXVI-V5&6

HLA-A26-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 1 | EEQKQNRKN | 11 |
| 2 | EQKQNRKNG | 11 |

TABLE XXVI-V6

HLA-A26-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 1 | EERKQNRKN | 11 |
| 2 | ERKQNRKNG | 11 |

TABLE XXVI-V8

HLA-A26-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 6 | PTVMGLMEA | 16 |
| 3 | LKSPTVMGL | 13 |
| 7 | TVMGLMEAI | 13 |

TABLE XXVII-V1

HLA-B0702-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 466 | IPDVHFANL | 24 |
| 1 | MPSDPPFNT | 21 |
| 557 | LPVEKIAKL | 21 |
| 134 | IPVSGITVV | 19 |
| 178 | VPSLATHSA | 19 |
| 148 | TPVFMAPPV | 18 |
| 455 | MPDLHSQPV | 18 |
| 4 | DPPFNTRRA | 17 |
| 26 | NPLTAATKA | 17 |
| 275 | HPISKVRSV | 17 |
| 441 | IPLQKKSDI | 17 |
| 461 | QPVLFIPDV | 17 |
| 42 | EDSAAALGL | 16 |
| 246 | QGEGPMTYL | 16 |
| 371 | LPLMIQIDT | 16 |
| 57 | VPRDKRLLS | 15 |
| 158 | YPRGDGEEQ | 15 |
| 365 | QKGVKGLPL | 15 |
| 458 | LHSQPVLFI | 15 |
| 516 | EEGTKRVLL | 15 |
| 102 | KTVPVNLSL | 14 |
| 486 | DEREGGSVL | 14 |
| 515 | KEEGTKRVL | 14 |
| 529 | ETDDVFDAL | 14 |
| 539 | LKSPTVKGL | 14 |
| 598 | MVEGFKVTL | 14 |
| 20 | WKSYLENPL | 13 |
| 153 | APPVHYPRG | 13 |
| 175 | QYDVPSLAT | 13 |
| 509 | VPSKQMKEE | 13 |
| 541 | SPTVKGLME | 13 |
| 5 | PPFNTRRAY | 12 |
| 16 | EDEAWKSYL | 12 |
| 40 | GDEDSAAAL | 12 |
| 43 | DSAAALGLL | 12 |
| 74 | EDQEKRNCL | 12 |
| 83 | GTSEAQSNL | 12 |
| 93 | GGENRVQVL | 12 |
| 95 | ENRVQVLKT | 12 |
| 100 | VLKTVPVNL | 12 |
| 104 | VPVNLSLNQ | 12 |
| 107 | NLSLNQDHL | 12 |
| 144 | AEDFTPVFM | 12 |
| 173 | QTQYDVPSL | 12 |

TABLE XXVII-V1-continued

HLA-B0702-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 180 | SLATHSAYL | 12 |
| 308 | QHTAKQRVL | 12 |
| 350 | KIFITVNCL | 12 |
| 363 | SSQKGVKGL | 12 |
| 430 | CNSSSDGKL | 12 |
| 450 | TYFKTMPDL | 12 |
| 456 | PDLHSQPVL | 12 |
| 500 | RPMEEEFGP | 12 |
| 531 | DDVFDALML | 12 |
| 551 | ISEKYGLPV | 12 |
| 554 | KYGLPVEKI | 12 |
| 23 | YLENPLTAA | 11 |
| 55 | YKVPRDKRL | 11 |
| 56 | KVPRDKRLL | 11 |
| 124 | SISFPESSA | 11 |
| 145 | EDFTPVFMA | 11 |
| 195 | TPDSTYSES | 11 |
| 211 | KFRSASVGA | 11 |
| 227 | TSSGTFQYT | 11 |
| 228 | SSGTFQYTL | 11 |
| 234 | YTLEATKSL | 11 |
| 249 | GPMTYLNKG | 11 |
| 256 | KGQFYAITL | 11 |
| 272 | CFRHPISKV | 11 |
| 276 | PISKVRSVV | 11 |
| 279 | KVRSVVMVV | 11 |
| 280 | VRSVVMVVF | 11 |
| 290 | EDKNRDEQL | 11 |
| 385 | RSNKPIHRA | 11 |
| 388 | KPIHRAYCQ | 11 |
| 432 | SSSDGKLAA | 11 |
| 433 | SSDGKLAAI | 11 |
| 435 | DGKLAAIPL | 11 |
| 463 | VLFIPDVHF | 11 |
| 487 | EREGGSVLV | 11 |
| 507 | GPVPSKQMK | 11 |

TABLE XXVII-V1-continued

HLA-B0702-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 549 | EAISEKYGL | 11 |
| 567 | KKSKKGILV | 11 |
| 585 | YSNEDTFIL | 11 |

TABLE XXVII-V2

HLA-B0702-9mers-202P5A5
Each peptide is a portion of SEQ ID NO: 5;
each start position is specified, the length
of peptide is 9 amino acids, and the end
position for each peptide is the start
position plus eight.

| Pos | 123456789 | score |
|---|---|---|
| 15 | VPMPSDPPF | 20 |
| 6 | DNNKRLVAL | 14 |
| 3 | QESDNNKRL | 12 |
| 5 | SDNNKRLVA | 10 |
| 9 | KRLVALVPM | 10 |

TABLE XXVII-V4

HLA-B0702-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 2 | AATKAMMII | 9 |
| 9 | IINGDEDSA | 9 |
| 1 | TAATKAMMI | 7 |

TABLE XXVII-V5

HLA-B0702-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 4 | NPLTAATKA | 17 |
| 20 | EDSAAALGL | 16 |
| 18 | GDEDSAAAL | 12 |
| 21 | DSAAALGLL | 12 |

TABLE XXVII-V5-continued

HLA-B0702-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 1 | YLENPLTAA | 11 |
| 2 | LENPLTAAT | 10 |
| 5 | PLTAATKAM | 9 |
| 6 | LTAATKAMM | 9 |
| 8 | AATKAMMII | 9 |
| 15 | IINGDEDSA | 9 |
| 16 | INGDEDSAA | 9 |
| 17 | NGDEDSAAA | 9 |

TABLE XXVII-V5&6

HLA-B0702-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 1 | EEQKQNRKN | 2 |
| 2 | EQKQNRKNG | 2 |

TABLE XXVII-V6

HLA-B0702-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 9 | NGKGQASQT | 8 |
| 6 | NRKNGKGQA | 6 |
| 7 | RKNGKGQAS | 5 |
| 1 | EERKQNRKN | 4 |
| 5 | QNRKNGKGQ | 4 |
| 8 | KNGKGQASQ | 4 |

TABLE XXVII-V8

HLA-B0702-9mers-202P5A
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 3 | LKSPTVMGL | 14 |
| 5 | SPTVMGLME | 13 |
| 7 | TVMGLMEAI | 10 |
| 1 | LMLKSPTVM | 9 |
| 4 | KSPTVMGLM | 7 |
| 2 | MLKSPTVMG | 6 |
| 6 | PTVMGLMEA | 6 |

TABLE XXVII-V1

HLA-B08-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 290 | EDKNRDEQL | 30 |
| 566 | YKKSKKGIL | 30 |
| 310 | TAKQRVLDI | 29 |
| 557 | LPVEKIAKL | 29 |
| 100 | VLKTVPVNL | 28 |
| 241 | SLRQKQGEG | 25 |
| 74 | EDQEKRNCL | 24 |
| 57 | VPRDKRLLS | 23 |
| 441 | IPLQKKSDI | 23 |
| 516 | EEGTKRVLL | 23 |
| 277 | ISKVRSVVM | 21 |
| 365 | QKGVKGLPL | 21 |
| 406 | ERKIRDEER | 21 |
| 418 | RKKGKGQAS | 21 |
| 435 | DGKLAAIPL | 21 |
| 93 | GGENRVQVL | 20 |
| 308 | QHTAKQRVL | 20 |
| 55 | YKVPRDKRL | 19 |
| 433 | SSDGKLAAI | 19 |
| 526 | VRKETDDVF | 19 |
| 541 | SPTVKGLME | 19 |
| 601 | GFKVTLMEI | 19 |

TABLE XXVII-V1-continued

HLA-B08-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 139 | ITVVKAEDF | 18 |
| 180 | SLATHSAYL | 18 |
| 209 | TEKFRSASV | 18 |
| 275 | HPISKVRSV | 18 |
| 320 | QYKESFNTI | 18 |
| 466 | IPDVHFANL | 18 |
| 486 | DEREGGSVL | 18 |
| 107 | NLSLNQDHL | 17 |
| 163 | GEEQRVVIF | 17 |
| 185 | SAYLKDDQR | 17 |
| 254 | LNKGQFYAI | 17 |
| 297 | QLKYWKYWH | 17 |
| 348 | EAKIFITVN | 17 |
| 367 | GVKGLPLMI | 17 |
| 416 | QNRKKGKGQ | 17 |
| 444 | QKKSDITYF | 17 |
| 536 | ALMLKSPTV | 17 |
| 538 | MLKSPTVKG | 17 |
| 543 | TVKGLMEAI | 17 |
| 562 | IAKLYKKSK | 17 |
| 564 | KLYKKSKKG | 17 |
| 565 | LYKKSKKGI | 17 |
| 117 | NSKREQYSI | 16 |
| 187 | YLKDDQRST | 16 |
| 207 | AATEKFRSA | 16 |
| 269 | DNKCFRHPI | 16 |
| 318 | IADYKESFN | 16 |
| 401 | CDKGAERKI | 16 |
| 404 | GAERKIRDE | 16 |
| 442 | PLQKKSDIT | 16 |
| 549 | EAISEKYGL | 16 |
| 550 | AISEKYGLP | 16 |
| 350 | KIFITVNCL | 15 |
| 396 | QIKVFCDKG | 15 |
| 493 | VLVKRMFRP | 15 |

TABLE XXVII-V1-continued

HLA-B08-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 523 | LLYVRKETD | 15 |
| 29 | TAATKAMMS | 14 |
| 333 | EIAYNAVSF | 14 |
| 363 | SSQKGVKGL | 14 |
| 388 | KPIHRAYCQ | 14 |
| 463 | VLFIPDVHF | 14 |

TABLE XXVIII-V2

HLA-B08-9mers-202P5A5
Each peptide is a portion of SEQ ID NO: 5;
each start position is specified, the length
of peptide is 9 amino acids, and the end
position for each peptide is the start
position plus eight.

| Pos | 123456789 | score |
|---|---|---|
| 6 | DNNKRLVAL | 20 |
| 15 | VPMPSDPPF | 13 |
| 3 | QESDNNKRL | 12 |
| 5 | SDNNKRLVA | 12 |
| 7 | NNKRLVALV | 11 |

TABLE XXVIII-V4

HLA-B08-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 1 | TAATKAMMI | 20 |
| 2 | AATKAMMII | 10 |
| 3 | ATKAMMIIN | 10 |

TABLE VIII-V5

HLA-B08-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 7 | TAATKAMMI | 20 |
| 18 | GDEDSAAAL | 12 |
| 20 | EDSAAALGL | 12 |
| 8 | AATKAMMII | 10 |
| 9 | ATKAMMIIN | 10 |
| 21 | DSAAALGLL | 10 |

TABLE XXVIII-V5&6

HLA-B08-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 2 | EQKQNRKNG | 13 |
| 3 | QKQNRKNGK | 8 |

TABLE XXVIII-V6

HLA-B08-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 2 | ERKQNRKNG | 13 |
| 4 | KQNRKNGKG | 11 |
| 7 | RKNGKGQAS | 11 |
| 6 | NRKNGKGQA | 10 |
| 9 | NGKGQASQT | 10 |
| 1 | EERKQNRKN | 9 |
| 3 | RKQNRKNGK | 8 |
| 5 | QNRKNGKGQ | 7 |

TABLE XXVIII-V8

HLA-B08-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 2 | MLKSPTVMG | 17 |
| 3 | LKSPTVMGL | 11 |
| 5 | SPTVMGLME | 9 |

TABLE XXIX-V1

HLA-B1510-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 308 | QHTAKQRVL | 24 |
| 583 | EHYSNEDTF | 19 |
| 515 | KEEGTKRVL | 17 |
| 598 | MVEGFKVTL | 16 |
| 55 | YKVPRDKRL | 15 |
| 93 | GGENRVQVL | 15 |
| 274 | RHPISKVRS | 15 |
| 40 | GDEDSAAAL | 14 |
| 113 | DHLENSKRE | 14 |
| 246 | QGEGPMTYL | 14 |
| 450 | TYFKTMPDL | 14 |
| 458 | LHSQPVLFI | 14 |
| 486 | DEREGGSVL | 14 |
| 516 | EEGTKRVLL | 14 |
| 539 | LKSPTVKGL | 14 |
| 16 | EDEAWKSYL | 13 |
| 56 | KVPRDKRLL | 13 |
| 74 | EDQEKRNCL | 13 |
| 83 | GTSEAQSNL | 13 |
| 100 | VLKTVPVNL | 13 |
| 277 | ISKVRSVVM | 13 |
| 280 | VRSVVMVVF | 13 |
| 363 | SSQKGVKGL | 13 |
| 456 | PDLHSQPVL | 13 |
| 466 | IPDVHFANL | 13 |
| 469 | VHFANLQRT | 13 |

TABLE XXIX-V1-continued

HLA-B1510-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|-----|-----------|-------|
| 529 | ETDDVFDAL | 13 |
| 42  | EDSAAALGL | 12 |
| 102 | KTVPVNLSL | 12 |
| 107 | NLSLNQDHL | 12 |
| 156 | VHYPRGDGE | 12 |
| 163 | GEEQRVVIF | 12 |
| 173 | QTQYDVPSL | 12 |
| 183 | THSAYLKDD | 12 |
| 234 | YTLEATKSL | 12 |
| 304 | WHSRQHTAK | 12 |
| 390 | IHRAYCQIK | 12 |
| 490 | GGSVLVKRM | 12 |
| 549 | EAISEKYGL | 12 |
| 557 | LPVEKIAKL | 12 |
| 566 | YKKSKKGIL | 12 |
| 585 | YSNEDTFIL | 12 |
| 20  | WKSYLENPL | 11 |
| 43  | DSAAALGLL | 11 |
| 143 | KAEDFTPVF | 11 |
| 180 | SLATHSAYL | 11 |
| 228 | SSGTFQYTL | 11 |
| 256 | KGQFYAITL | 11 |
| 390 | EDKNRDEQL | 11 |
| 333 | EIAYNAVSF | 11 |
| 350 | KIFITVNCL | 11 |
| 365 | QKGVKGLPL | 11 |
| 430 | CNSSSDGKL | 11 |

TABLE XXIX-V2

HLA-B1510-9mers-202P5A5
Each peptide is a portion of SEQ ID NO: 5;
each start position is specified, the length
of peptide is 9 amino acids, and the end
position for each peptide is the start
position plus eight.

| Pos | 123456789 | score |
|-----|-----------|-------|
| 3   | QESDNNKRL | 15 |
| 6   | DNNKRLVAL | 14 |

TABLE XXIX-V2-continued

HLA-B1510-9mers-202P5A5
Each peptide is a portion of SEQ ID NO: 5;
each start position is specified, the length
of peptide is 9 amino acids, and the end
position for each peptide is the start
position plus eight.

| Pos | 123456789 | score |
|-----|-----------|-------|
| 9   | KRLVALVPM | 9 |
| 15  | VPMPSDPPF | 9 |

TABLE XXIX-V4

HLA-B1510-9mers-202P5A5
Each peptide is a portion of SEQ ID NO: 5;
each start position is specified, the length
of peptide is 9 amino acids, and the end
position for each peptide is the start
position plus eight.

| Pos | 123456789 | score |
|-----|-----------|-------|
| 4   | TKAMMIING | 3 |
| 9   | IINGDEDSA | 3 |
| 1   | TAATKAMMI | 2 |
| 2   | AATKAMMII | 2 |
| 7   | MMIINGDED | 2 |
| 3   | ATKAMMIIN | 1 |
| 5   | KAMMIINGD | 1 |
| 8   | MIINGDEDS | 1 |

TABLE XXIX-V5

HLA-B1510-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|-----|-----------|-------|
| 6   | DEEQKQNRK | 4 |
| 7   | EEQKQNRKK | 4 |
| 8   | EQKQNRKKG | 4 |
| 4   | IRDEEQKQN | 3 |
| 5   | RDEEQKQNR | 3 |
| 1   | ERKIRDEEQ | 2 |
| 3   | KIRDEEQKQ | 1 |
| 9   | QKQNRKKGK | 1 |

TABLE XXIX-V5&6

HLA-B1510-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 1 | EEQKQNRKN | 4 |
| 2 | EQKQNRKNG | 4 |

TABLE XXIX-V6

HLA-B1510-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 1 | EERKQNRKN | 4 |
| 2 | ERKQNRKNG | 4 |
| 5 | QNRKNGKGQ | 2 |
| 6 | NRKNGKGQA | 2 |
| 7 | RKNGKGQAS | 2 |
| 8 | KNGKGQASQ | 2 |
| 3 | RKQNRKNGK | 1 |
| 9 | NGKGQASQT | 1 |

TABLE XXIX-V8

HLA-B1510-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 3 | LKSPTVMGL | 14 |
| 1 | LMLKSPTVM | 10 |
| 4 | KSPTVMGLM | 7 |

TABLE XXX-V1

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 520 | KRVLLYVRK | 28 |
| 119 | KREQYSISF | 27 |
| 273 | FRHPISKVR | 24 |

TABLE XXX-V1-continued

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 313 | QRVLDIADY | 24 |
| 159 | PRGDGEEQR | 23 |
| 280 | VRSVVMVVF | 23 |
| 526 | VRKETDDVF | 23 |
| 192 | QRSTPDSTY | 22 |
| 306 | SRQHTAKQR | 22 |
| 384 | NRSNKPIHR | 22 |
| 406 | ERKIRDEER | 22 |
| 61 | KRLLSVSKA | 20 |
| 392 | RAYCQIKVF | 20 |
| 488 | REGGSVLVK | 20 |
| 83 | GTSEAQSNL | 19 |
| 294 | RDEQLKYWK | 19 |
| 504 | EEFGPVPSK | 19 |
| 546 | GLMEAISEK | 19 |
| 557 | LPVEKIAKL | 19 |
| 102 | KTVPVNLSL | 18 |
| 314 | RVLDIADYK | 18 |
| 407 | RKIRDEERK | 18 |
| 410 | RDEERKQNR | 18 |
| 537 | LMLKSPTVK | 18 |
| 563 | AKLYKKSKK | 18 |
| 94 | GENRVQVLK | 17 |
| 163 | GEEQRVVIF | 17 |
| 271 | KCFRHPISK | 17 |
| 286 | VVFSEDKNR | 17 |
| 350 | KIFITVNCL | 17 |
| 366 | KGVKGLPLM | 17 |
| 400 | FCDKGAERK | 17 |
| 456 | PDLHSQPVL | 17 |
| 491 | GSVLVKRMF | 17 |
| 507 | GPVPSKQMK | 17 |
| 553 | EKYGLPVEK | 17 |
| 560 | EKIAKLYKK | 17 |
| 3 | SDPPFNTRR | 16 |

TABLE XXX-V1-continued

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 40 | GDEDSAAAL | 16 |
| 46 | AALGLLYDY | 16 |
| 78 | KRNCLGTSE | 16 |
| 89 | SNLSGGENR | 16 |
| 96 | NRVQVLKTV | 16 |
| 112 | QDHLENSKR | 16 |
| 168 | VVIFEQTQY | 16 |
| 185 | SAYLKDDQR | 16 |
| 243 | RQKQGEGPM | 16 |
| 292 | KNRDEQLKY | 16 |
| 411 | DEERKQNRK | 16 |
| 417 | NRKKGKGQA | 16 |
| 450 | TYFKTMPDL | 16 |
| 463 | VLFIPDVHF | 16 |
| 487 | EREGGSVLV | 16 |
| 512 | KQMKEEGTK | 16 |
| 513 | QMKEEGTKR | 16 |
| 515 | KEEGTKRVL | 16 |
| 556 | GLPVEKIAK | 16 |
| 10 | RRAYTSEDE | 15 |
| 48 | LGLLYDYYK | 15 |
| 53 | DYYKVPRDK | 15 |
| 55 | YKVPRDKRL | 15 |
| 58 | PRDKRLLSV | 15 |
| 60 | DKRLLSVSK | 15 |
| 70 | SDSQEDQEK | 15 |
| 71 | DSQEDQEKR | 15 |
| 93 | GGENRVQVL | 15 |
| 135 | PVSGITVVK | 15 |
| 232 | FQYTLEATK | 15 |
| 237 | EATKSLRQK | 15 |
| 245 | KQGEGPMTY | 15 |
| 246 | QGEGPMTYL | 15 |
| 251 | MTYLNKGQF | 15 |
| 256 | KGQFYAITL | 15 |
| 299 | KYWKYWHSR | 15 |
| 363 | SSQKGVKGL | 15 |
| 377 | IDTYSYNNR | 15 |
| 380 | YSYNNRSNK | 15 |
| 391 | HRAYCQIKV | 15 |
| 395 | CQIKVFCDK | 15 |
| 412 | EERKQNRKK | 15 |
| 414 | RKQNRKKGK | 15 |
| 437 | KLAAIPLQK | 15 |
| 444 | QKKSDITYF | 15 |
| 486 | DEREGGSVL | 15 |
| 489 | EGGSVLVKR | 15 |
| 490 | GGSVLVKRM | 15 |
| 532 | DVFDALMLK | 15 |
| 549 | EAISEKYGL | 15 |
| 569 | SKKGILVNM | 15 |
| 598 | MVEGFKVTL | 15 |
| 2 | PSDPPFNTR | 14 |
| 25 | ENPLTAATK | 14 |
| 100 | VLKTVPVNL | 14 |
| 125 | ISFPESSAI | 14 |
| 139 | ITVVKAEDF | 14 |
| 143 | KAEDFTPVF | 14 |
| 176 | VDVPSLATH | 14 |
| 203 | SFKDAATEK | 14 |
| 228 | SSGTFQYTL | 14 |
| 234 | YTLEATKSL | 14 |
| 308 | QHTAKQRVL | 14 |
| 323 | ESFNTIGNI | 14 |
| 326 | NTIGNIEEI | 14 |
| 354 | TVNCLSTDF | 14 |
| 369 | KGLPLMIQI | 14 |
| 409 | IRDEERKQN | 14 |
| 413 | ERKQNRKKG | 14 |
| 430 | CNSSSDGKL | 14 |
| 438 | LAAIPLQKK | 14 |

TABLE XXX-V1-continued

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 441 | IPLQKKSDI | 14 |
| 443 | LQKKSDITY | 14 |
| 445 | KKSDITYFK | 14 |
| 466 | IPDVHFANL | 14 |
| 475 | QRTGQVYYN | 14 |
| 480 | VYYNTDDER | 14 |
| 492 | SVLVKRMFR | 14 |
| 496 | KRMFRPMEE | 14 |
| 519 | TKRVLLYVR | 14 |
| 562 | IAKLYKKSK | 14 |
| 587 | NEDTFILNM | 14 |
| 54 | YYKVPRDKR | 13 |
| 56 | KVPRDKRLL | 13 |
| 74 | EDQEKRNCL | 13 |
| 107 | NLSLNQDHL | 13 |
| 111 | NQDHLENSK | 13 |
| 149 | PVFMAPPVH | 13 |
| 152 | MAPPVHYPR | 13 |
| 166 | QRVVIFEQT | 13 |
| 173 | QTQYDVPSL | 13 |
| 181 | LATHSAYLK | 13 |
| 224 | YDQTSSGTF | 13 |
| 248 | EGPMTYLNK | 13 |
| 263 | TLSETGDNK | 13 |
| 285 | SETGDNKCF | 13 |
| 295 | DEQLKYWKY | 13 |
| 333 | EIAYNAVSF | 13 |
| 344 | DVNEEAKIF | 13 |
| 358 | LSTDFSSQK | 13 |
| 367 | GVKGLPLMI | 13 |
| 399 | VFCDKGAER | 13 |
| 435 | DGKLAAIPL | 13 |
| 468 | DVHFANLQR | 13 |
| 474 | LQRTGQVYY | 13 |
| 531 | DDVFDALML | 13 |
| 564 | KYGLPVEKI | 13 |

TABLE XXX-V1-continued

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 576 | NMDDNIIEH | 13 |
| 583 | EHYSNEDTF | 13 |

TABLE XXX-V2

HLA-B2705-9mers-202P5A5
Each peptide is a portion of SEQ ID NO: 5;
each start position is specified, the length
of peptide is 9 amino acids, and the end
position for each peptide is the start
position plus eight.

| Pos | 123456789 | score |
|---|---|---|
| 9 | KRLVALVPM | 24 |
| 1 | MSQESDNNK | 16 |
| 2 | SQESDNNKR | 14 |
| 6 | DNNKRLVAL | 14 |
| 15 | VPMPSDPPF | 14 |
| 3 | QESDNNKRL | 13 |

TABLE XXX-V4

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 2 | AATKAMMII | 10 |
| 1 | TAATKAMMI | 9 |
| 5 | KAMMIINGD | 7 |
| 4 | TKAMMIING | 6 |
| 8 | MIINGDEDS | 5 |
| 9 | IINGDEDSA | 4 |

TABLE XXX-V5

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 5 | RDEEQKQNR | 18 |
| 6 | DEEQKQNRK | 18 |
| 2 | RKIRDEEQK | 17 |
| 4 | IRDEEQKQN | 16 |
| 7 | EEQKQNRKK | 15 |
| 1 | ERKIRDEEQ | 12 |
| 9 | QKQNRKKGK | 11 |

TABLE XXX-V5&6

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 3 | QKQNRKNGK | 12 |
| 1 | EEQKQNRKN | 5 |

TABLE XXX-V6

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 3 | RKQNRKNGK | 16 |
| 2 | ERKQNRKNG | 14 |
| 6 | NRKNGKGQA | 14 |
| 8 | KNGKGQASQ | 10 |
| 7 | RKNGKGQAS | 7 |

TABLE XXX-V8

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 1 | LMLKSPTVM | 16 |
| 3 | LKSPTVMGL | 13 |

TABLE XXX-V8-continued

HLA-B2705-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 4 | KSPTVMGLM | 11 |
| 7 | TVMGLMEAI | 9 |

TABLE XXXI-V1

HLA-B2709-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 119 | KREQYSISF | 20 |
| 58 | PRDKRLLSV | 19 |
| 96 | NRVQVLKTV | 19 |
| 280 | VRSVVMVVF | 19 |
| 487 | EREGGSVLV | 19 |
| 391 | HRAYCQIKV | 18 |
| 526 | VRKETDDVF | 18 |
| 49 | GLLYDYYKV | 15 |
| 61 | KRLLSVSKA | 15 |
| 102 | KTVPVNLSL | 15 |
| 350 | KIFITVNCL | 15 |
| 520 | KRVLLYVRK | 15 |
| 10 | RRAYTSEDE | 14 |
| 40 | GDEDSAAAL | 14 |
| 83 | GTSEAQSNL | 14 |
| 93 | GGENRVQVL | 14 |
| 369 | KGLPLMIQI | 14 |
| 392 | RAYCQIKVF | 14 |
| 531 | DDVFDALML | 14 |
| 55 | YKVPRDKRL | 13 |
| 56 | KVPRDKRLL | 13 |
| 160 | RGDGEEQRV | 13 |
| 163 | GEEQRVVIF | 13 |
| 166 | QRVVIFEQT | 13 |
| 173 | QTQYDVPSL | 13 |
| 256 | KGQFYAITL | 13 |

TABLE XXXI-V1-continued

HLA-B2709-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 307 | RQHTAKQRV | 13 |
| 450 | TYFKTMPDL | 13 |
| 456 | PDLHSQPVL | 13 |
| 475 | QRTGQVYYN | 13 |
| 490 | GGSVLVKRM | 13 |
| 548 | EAISEKYGL | 13 |
| 42 | EDSAAALGL | 12 |
| 78 | KRNCLGTSE | 12 |
| 100 | VLKTVPVNL | 12 |
| 125 | ESFPESSAI | 12 |
| 234 | YTLEATKSL | 12 |
| 243 | RQKQGEGPM | 12 |
| 273 | FRHPISKVR | 12 |
| 279 | KVRSVVMVV | 12 |
| 306 | SRQHTAKQR | 12 |
| 313 | QRVLDIADY | 12 |
| 366 | KGVKGLPLM | 12 |
| 367 | GVKGLPLMI | 12 |
| 409 | IRDEERKQN | 12 |
| 466 | IPDVHFANL | 12 |
| 472 | ANLQRTGQV | 12 |
| 491 | GSVLVKRMF | 12 |
| 496 | KRMFRPMEE | 12 |
| 515 | KEEGTKRVL | 12 |
| 518 | GTKRVLLYV | 12 |
| 539 | LKSPTVKGL | 12 |
| 134 | IPVSGITVV | 11 |
| 139 | ITVVKAEDF | 11 |
| 143 | KAEDFTPVF | 11 |
| 148 | TPVFMAPPV | 11 |
| 159 | PRGDGEEQR | 11 |
| 161 | GDGEEQRVV | 11 |
| 212 | FRSASVGAE | 11 |
| 228 | SSGTFQYTL | 11 |
| 251 | MTYLNKGQF | 11 |
| 275 | HPISKVRSV | 11 |

TABLE XXXI-V1-continued

HLA-B2709-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 278 | SKVRSVVMV | 11 |
| 290 | EDKNRDEQL | 11 |
| 308 | QHTAKQRVL | 11 |
| 323 | ESFNTIGNI | 11 |
| 360 | TDFSSQKGV | 11 |
| 363 | SSQKGVKGL | 11 |
| 365 | QKGVKGLPL | 11 |
| 417 | NRKKGKGQA | 11 |
| 430 | CNSSSDGKL | 11 |
| 435 | DGKLAAIPL | 11 |
| 441 | IPLQKKSDI | 11 |
| 463 | VLFIPDVHF | 11 |
| 516 | EEGTKRVLL | 11 |
| 554 | KYGLPVEKI | 11 |
| 567 | LPVEKIAKL | 11 |
| 566 | YKKSKKGIL | 11 |
| 569 | SKKGILVNM | 11 |
| 573 | ILVNMDDNI | 11 |
| 583 | EHYSNEDTF | 11 |
| 585 | YSNEDTFIL | 11 |
| 598 | MVEGFKVTL | 11 |
| 601 | GFKVTLMEI | 11 |
| 9 | TRRAYTSED | 10 |
| 16 | EDEAWKSYL | 10 |
| 20 | WKSYLENPL | 10 |
| 30 | AATKAMMSI | 10 |
| 43 | DSAAALGLL | 10 |
| 74 | EDQEKRNCL | 10 |
| 92 | SGGENRVQV | 10 |
| 98 | VQVLKTVPV | 10 |
| 107 | NLSLNQDHL | 10 |
| 131 | SAIIPVSGI | 10 |
| 144 | AEDFTPVFM | 10 |
| 170 | IFEQTQYDV | 10 |
| 180 | SLATHSAYL | 10 |

TABLE XXXI-V1-continued

HLA-B2709-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 192 | QRSTPDSTY | 10 |
| 215 | ASVGAEEYM | 10 |
| 242 | LRQKQGEGP | 10 |
| 246 | QGEGPMTYL | 10 |
| 265 | SETGDNKCF | 10 |
| 277 | ISKVRSVVM | 10 |
| 293 | NRDEQLKYW | 10 |
| 310 | TAKQRVLDI | 10 |
| 333 | EIAYNAVSF | 10 |
| 337 | NAVSFTWDV | 10 |
| 384 | NRSNKPIHR | 10 |
| 406 | ERKIRDEER | 10 |
| 413 | ERKQNRKKG | 10 |
| 444 | QKKSDITYF | 10 |
| 457 | DLHSQPVLF | 10 |
| 458 | LHSQPVLFI | 10 |
| 461 | QPVLFIPDV | 10 |
| 486 | DEREGGSVL | 10 |
| 499 | FRPMEEEFG | 10 |
| 529 | ETDDVFDAL | 10 |
| 536 | ALMLKSPTV | 10 |
| 540 | KSPTVKGLM | 10 |
| 551 | ISEKYGLPV | 10 |
| 567 | KKSKKGILV | 10 |
| 587 | NEDTFILNM | 10 |
| 591 | FILNMESMV | 10 |
| 594 | NMESMVEGF | 10 |
| 27 | PLTAATKAM | 9 |
| 90 | NLSGGENRV | 9 |
| 117 | NSKREQYSI | 9 |
| 128 | PESSAIIPV | 9 |
| 133 | IIPVSGITV | 9 |
| 142 | VKAEDFTPV | 9 |
| 162 | DGEEQRVVI | 9 |
| 254 | LNKGQFYAI | 9 |
| 326 | NTIGNIEEI | 9 |

TABLE XXXI-V1-continued

HLA-B2709-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 331 | IEEIAYNAV | 9 |
| 343 | WDVNEEAKI | 9 |
| 344 | DVNEEAKIF | 9 |
| 347 | EEAKIFITV | 9 |
| 389 | PIHRAYCQI | 9 |
| 447 | SDITYFKTM | 9 |
| 498 | MFRPMEEEF | 9 |
| 506 | FGPVPSKQM | 9 |
| 514 | MKEEGTKRV | 9 |
| 574 | LVNMDDNII | 9 |
| 590 | TFILNMESM | 9 |
| 599 | VEGFKVTLM | 9 |

TABLE XXXI-V2

HLA-B2709-9 mers-202P5A5
Each peptide is a portion of SEQ ID NO: 5; each
start position is specified, the length of peptide
is 9 amino acids, and the end position for each
peptide is the start position plus eight.

| Pos | 123456789 | score |
|---|---|---|
| 9 | KRLVALVPM | 23 |
| 3 | QESDNNKRL | 11 |
| 6 | DNNKRLVAL | 11 |

TABLE XXXI-V4

HLA-B2709-9 mers-202P5A5
Each peptide is a portion of SEQ ID NO: 3; each
start position is specified, the length of peptide
is 9 amino acids, and the end position for each
peptide is the start position plus eight.

| Pos | 123456789 | score |
|---|---|---|
| 2 | AATKAMMII | 10 |
| 1 | TAATKAMMI | 9 |

TABLE XXXI-V5

HLA-B2709-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 4 | IRDEEQKQN | 12 |
| 1 | ERKIRDEEQ | 10 |
| 2 | RKIRDEEQK | 7 |
| 5 | RDEEQKQNR | 5 |

TABLE XXXI-V5&6

HLA-B2709-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 2 | EQKQNRKNG | 1 |

TABLE XXXI-V6

HLA-B2709-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 2 | ERKQNRKNG | 11 |
| 6 | NRKNGKGQA | 11 |
| 3 | RKQNRKNGK | 4 |
| 7 | RKNGKGQAS | 4 |

TABLE XXXI-V8

HLA-B2709-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 3 | LKSPTVMGL | 12 |
| 1 | LMLKSPTVM | 10 |
| 4 | KSPTVMGLM | 10 |
| 7 | TVMGLMEAI | 8 |

TABLE XXXII-V1

HLA-B4402-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 516 | EEGTKRVLL | 26 |
| 16 | SEDEAWKSY | 24 |
| 265 | SETGDNKCF | 24 |
| 515 | KEEGTKRVL | 24 |
| 163 | GEEQRVVIF | 23 |
| 115 | LENSKRFQY | 22 |
| 295 | DEQLKYWKY | 22 |
| 486 | DEREGGSVL | 21 |
| 386 | SNKPIHRAY | 18 |
| 5 | PPFNTRRAY | 17 |
| 326 | NTIGNIEEI | 17 |
| 529 | ETDDVFDAL | 17 |
| 539 | LKSPTVKGL | 17 |
| 587 | NEDTFILNM | 17 |
| 24 | LENPLTAAT | 16 |
| 46 | AALGLLYDY | 16 |
| 55 | YKVPRDKRL | 16 |
| 144 | AEDFTPVFM | 16 |
| 323 | ESFNTIGNI | 16 |
| 332 | EEIAYNAVS | 16 |
| 347 | EEAKIFITV | 16 |
| 392 | RAYCQIKVF | 16 |
| 504 | EEFGPVPSK | 16 |
| 517 | EGTKRVLLY | 16 |
| 577 | MDDNIIEHY | 16 |
| 12 | AYTSEDEAW | 15 |
| 42 | EDSAAALGL | 15 |
| 56 | KVPRDKRLL | 15 |
| 102 | KTVPVNLSL | 15 |
| 125 | ISFPESSAI | 15 |
| 128 | PESSAIIPV | 15 |
| 164 | EEQRVVIFE | 15 |
| 247 | GEGPMTYLN | 15 |
| 290 | EDKNRDEQL | 15 |
| 293 | NRDEQLKYW | 15 |
| 296 | EQLKYWKYW | 15 |

TABLE XXXII-V1-continued

HLA-B4402-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 322 | KESFNTIGN | 15 |
| 333 | EIAYNAVSF | 15 |
| 350 | KIFITVNCL | 15 |
| 369 | KGLPLMIQI | 15 |
| 372 | PLMIQIDTY | 15 |
| 405 | AERKIRDEE | 15 |
| 549 | EAISEKYGL | 15 |
| 558 | PVEKIAKLY | 15 |
| 40 | GDEDSAAAL | 14 |
| 47 | ALGLLYDYY | 14 |
| 74 | EDQEKRNCL | 14 |
| 93 | GGENRVQVL | 14 |
| 107 | NLSLNQDHL | 14 |
| 143 | KAEDFTPVF | 14 |
| 168 | VVIFEQTQY | 14 |
| 201 | SESFKDAAT | 14 |
| 219 | AEEYMYDQT | 14 |
| 234 | YTLEATKSL | 14 |
| 256 | KGQFYAITL | 14 |
| 289 | SEDKNRDEQ | 14 |
| 292 | KNRDEQLKY | 14 |
| 313 | QRVLDIADY | 14 |
| 335 | AYNAVSFTW | 14 |
| 346 | NEEAKIFIT | 14 |
| 363 | SSQKGVKGL | 14 |
| 412 | EERKQNRKK | 14 |
| 433 | SSDGKLAAI | 14 |
| 488 | REGGSVLVK | 14 |
| 503 | EEEFGPVPS | 14 |
| 557 | LPVEKIAKL | 14 |
| 583 | EHYSNEDTF | 14 |
| 41 | DEDSAAALG | 13 |
| 44 | SAAALGLLY | 13 |
| 76 | QEKRNCLST | 13 |
| 94 | GENRVQVLK | 13 |

TABLE XXXII-V1-continued

HLA-B4402-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 100 | VLKTVPVNL | 13 |
| 120 | REQYSISFP | 13 |
| 131 | SAIIPVSGI | 13 |
| 150 | VFMAPPVHY | 13 |
| 179 | PSLATHSAY | 13 |
| 192 | QRSTPDSTY | 13 |
| 204 | FKDAATEKF | 13 |
| 214 | SASVGAEEY | 13 |
| 220 | EEYMYDQTS | 13 |
| 226 | QTSSGTFQY | 13 |
| 228 | SSGTFQYTL | 13 |
| 245 | KQGEGPMTY | 13 |
| 251 | MTYLNKGQF | 13 |
| 280 | VRSVVMVVF | 13 |
| 328 | IGNIEEIAY | 13 |
| 331 | IEEIAYNAV | 13 |
| 344 | DVNEEAKIF | 13 |
| 435 | DGKLAAIPL | 13 |
| 444 | QKKSDITYF | 13 |
| 457 | DLHSQPVLF | 13 |
| 463 | VLFIPDVHF | 13 |
| 473 | NLQRTGQVY | 13 |
| 498 | MFRPMEEEF | 13 |
| 528 | KETDDVFDA | 13 |
| 552 | SEKYGLPVE | 13 |
| 598 | MVEGFKVTL | 13 |
| 16 | EDEAWKSYL | 12 |
| 20 | WKSYLENPL | 12 |
| 43 | DSAAALGLL | 12 |
| 73 | QEDQEKRNC | 12 |
| 85 | SEAQSNLSG | 12 |
| 119 | KREQYSISF | 12 |
| 171 | FEQTQYDVP | 12 |
| 180 | SLATHSAYL | 12 |
| 196 | PDSTYSESF | 12 |
| 224 | YDQTSSGTF | 12 |

TABLE XXXII-V1-continued

HLA-B4402-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 236 | LEATKSLRQ | 12 |
| 252 | TYLNKGQFY | 12 |
| 254 | LNKGQFYAI | 12 |
| 308 | QHTAKQRVL | 12 |
| 411 | DEERKQNRK | 12 |
| 430 | CNSSSDGKL | 12 |
| 439 | AAIPLQKKS | 12 |
| 443 | LQKKSDITY | 12 |
| 450 | TYFKTMPDL | 12 |
| 456 | PDLHSQPVL | 12 |
| 466 | IPDVHFANL | 12 |
| 474 | LQRTGQVYY | 12 |
| 491 | GSVLVKRMF | 12 |
| 531 | DDVFDALML | 12 |
| 547 | LMEAISEKY | 12 |
| 548 | MEAISEKYG | 12 |
| 554 | KYGLPVEKI | 12 |
| 594 | NMESMVEGF | 12 |
| 599 | VEGFKVTLM | 12 |

TABLE XXXII-V2

HLA-B4402-9mers-202P5A5
Each peptide is a portion of SEQ ID NO: 5;
each start position is specified, the length
of peptide is 9 amino acids, and the end
position for each peptide is the start
position plus eight.

| Pos | 123456789 | score |
|---|---|---|
| 3 | QESDNNKRL | 25 |
| 6 | DNNKRLVAL | 15 |
| 15 | VPMPSDPPF | 14 |

TABLE XXXII-V4

HLA-B4402-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 2 | AATKAMMII | 11 |
| 1 | TAATKAMMI | 10 |
| 5 | KAMMIINGD | 7 |
| 6 | AMMIINGDE | 5 |

TABLE XXXII-V5

HLA-B4402-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 7 | EEQKQNRKK | 14 |
| 6 | DEEQKQNRK | 11 |
| 8 | EQKQNRKKG | 7 |

TABLE XXXII-V5&6

HLA-B4402-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 1 | EEQKQNRKN | 14 |
| 2 | EQKQNRKNG | 6 |

TABLE XXXII-V6

HLA-B4402-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 1 | EERKQNRKN | 14 |
| 2 | ERKQNRKNG | 6 |

TABLE XXXII-B8

HLA-B4402-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 3 | LKSPTVMGL | 15 |
| 7 | TVMGLMEAI | 12 |

TABLE XXXIIII-V1

HLA-B5101-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 162 | DGEEQRVVI | 26 |
| 134 | IPVSGITVV | 25 |
| 441 | IPLQKKSDI | 25 |
| 310 | TAKQRVLDI | 24 |
| 557 | LPVEKIAKL | 24 |
| 131 | SAIIPVSGI | 22 |
| 275 | HPISKVRSV | 22 |
| 30 | AATKAMMSI | 21 |
| 148 | TPVFMAPPV | 21 |
| 320 | DYKESFNTI | 21 |
| 337 | NAVSFTWDV | 19 |
| 369 | KGLPLMIQI | 19 |
| 392 | RAYCQIKVF | 19 |
| 455 | MPDLHSQPV | 19 |
| 461 | QPVLFIPDV | 19 |
| 466 | IPDVHFANL | 19 |
| 26 | NPLTAATKA | 18 |
| 334 | IAYNAVSFT | 18 |
| 435 | DGKLAAIPL | 18 |
| 4 | DPPFNTRRA | 17 |
| 92 | SGGENRVQV | 17 |
| 93 | GGENRVQVL | 17 |
| 256 | KGQFYAITL | 17 |
| 11 | RAYTSEDEA | 16 |
| 160 | RGDGEEQRV | 16 |
| 206 | DAATEKFRS | 16 |
| 249 | GPMTYLNKG | 16 |

TABLE XXXIIII-V1-continued

HLA-B5101-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 535 | DALMLKSPT | 16 |
| 549 | EAISEKYGL | 16 |
| 96 | NRVQVLKTV | 15 |
| 133 | IIPVSGITV | 15 |
| 186 | SAYLKDDQR | 15 |
| 207 | AATEKFRSA | 15 |
| 280 | YAITLSETG | 15 |
| 279 | KVRSVVMVV | 15 |
| 348 | EAKIFITVN | 15 |
| 371 | LPLMIQIDT | 15 |
| 382 | YNNRSNKPI | 15 |
| 438 | LAAIPLQKK | 15 |
| 458 | LHSQPVLFI | 15 |
| 486 | DEREGGSVL | 15 |
| 565 | LYKKSKKGI | 15 |
| 18 | EAWKSYLEN | 14 |
| 29 | TAATKAMMS | 14 |
| 46 | AALGLLYDY | 14 |
| 57 | VPRDKRLLS | 14 |
| 126 | SFPESSAII | 14 |
| 127 | FPESSAIIP | 14 |
| 143 | KAEDFTPVF | 14 |
| 152 | MAPPVHYPR | 14 |
| 161 | GDGEEQRVV | 14 |
| 181 | LATHSAYLK | 14 |
| 237 | EATKSLRQK | 14 |
| 246 | QGEGPMTYL | 14 |
| 254 | LNKGQFYAI | 14 |
| 269 | DNKCFRHPI | 14 |
| 276 | PISKVRSVV | 14 |
| 345 | VNEEAKIFI | 14 |
| 401 | CDKGAERKI | 14 |
| 554 | KYGLPVEKI | 14 |
| 562 | IAKLYKKSK | 14 |
| 1 | MPSDPPFNT | 13 |

TABLE XXXIIII-V1-continued

HLA-B5101-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 5 | PPFNTRRAY | 13 |
| 33 | KAMMSINGD | 13 |
| 53 | DYYKVPRDK | 13 |
| 125 | ISFPESSAI | 13 |
| 142 | VKAEDFTPV | 13 |
| 154 | PPVHYPRGD | 13 |
| 158 | YPRGDGEEQ | 13 |
| 218 | GAEEYMYDQ | 13 |
| 234 | YTLEATKSL | 13 |
| 318 | IADYKESFN | 13 |
| 323 | ESFNTIGNI | 13 |
| 326 | NTIGNIEEI | 13 |
| 347 | EEAKIFITV | 13 |
| 367 | GVKGLPLMI | 13 |
| 404 | GAERKIRDE | 13 |
| 433 | SSDGKLAAI | 13 |
| 439 | AAIPLQKKS | 13 |
| 509 | VPSKQMKEE | 13 |
| 514 | MKEEGTKRV | 13 |
| 551 | ISEKYGLPV | 13 |
| 555 | YGLPVEKIA | 13 |
| 573 | ILVNMDDNI | 13 |
| 574 | LVNMDDNII | 13 |
| 43 | DSAAALGLL | 12 |
| 44 | SAAALGLLY | 12 |
| 45 | AAALGLLYD | 12 |
| 49 | GLLYDYYKV | 12 |
| 50 | LLYDYYKVP | 12 |
| 68 | KASDSQEDQ | 12 |
| 90 | NLSGGENRV | 12 |
| 100 | VLKTVPVNL | 12 |
| 104 | VPVNLSLNQ | 12 |
| 137 | SGITVVKAE | 12 |
| 153 | APPVHYPRG | 12 |
| 195 | TPDSTYSES | 12 |
| 278 | SKVRSVVMV | 12 |

TABLE XXXIIII-V1-continued

HLA-B5101-9mers-202P5A5
Each peptide is a portion of SEQ ID NO: 3; each start position is specified, the length of peptide is 9 amino acids, and the end position for each peptide is the start position plus eight.

| Pos | 123456789 | score |
|---|---|---|
| 308 | QHTAKQRVL | 12 |
| 343 | WDVNEEAKI | 12 |
| 360 | TDFSSQKGV | 12 |
| 378 | DTYSYNNRS | 12 |
| 456 | PDLHSQPVL | 12 |
| 471 | FANLQRTGQ | 12 |
| 485 | DDEREGGSV | 12 |
| 489 | EGGSVLVKR | 12 |
| 500 | RPMEEEFGP | 12 |
| 515 | KEEGTKRVL | 12 |
| 518 | GTKRVLLYV | 12 |
| 531 | DDVFDALML | 12 |
| 539 | LKSPTVKGL | 12 |
| 541 | SPTVKGLME | 12 |
| 543 | TVKGLMEAI | 12 |
| 591 | FILNMESMV | 12 |
| 601 | GFKVTLMEI | 12 |

TABLE XXXIIII-V2

HLA-B5101-9mers-202P5A5
Each peptide is a portion of SEQ ID NO: 5; each start position is specified, the length of peptide is 9 amino acids, and the end position for each peptide is the start position plus eight.

| Pos | 123456789 | score |
|---|---|---|
| 6 | DNNKRLVAL | 13 |
| 12 | VALVPMPSD | 13 |
| 15 | VPMPSDPPF | 12 |
| 7 | NNKRLVALV | 11 |
| 3 | QESDNNKRL | 10 |
| 4 | ESDNNKRLV | 9 |
| 8 | NKRLVALVP | 8 |

TABLE XXXIIII-V4

HLA-B5101-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 1 | TAATKAMMI | 24 |
| 2 | AATKAMMII | 21 |
| 5 | KAMMIINGD | 12 |

TABLE XXXIIII-V5

HLA-B5101-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 6 | DEEQKQNRK | 7 |
| 4 | IRDEEQKQN | 5 |
| 7 | EEQKQNRKK | 5 |
| 3 | KIRDEEQKQ | 3 |
| 8 | EQKQNRKKG | 3 |

TABLE XXXIIII-V5&6

HLA-B5101-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 1 | EEQKQNRKN | 5 |

TABLE XXXIIII-V6

HLA-B5101-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 9 | NGKGQASQT | 9 |
| 1 | EERKQNRKN | 5 |
| 4 | KQNRKNGKG | 4 |

TABLE XXXIIII-V8

HLA-B5101-9mers-202P5A5
Each peptide is a portion of SEQ ID NO: 3;
each start position is specified, the length
of peptide is 9 amino acids, and the end
position for each peptide is the start
position plus eight.

| Pos | 123456789 | score |
|---|---|---|
| 5 | SPTVMGLME | 12 |
| 7 | TVMGLMEAI | 12 |
| 1 | LMLKSPTVM | 11 |
| 3 | LKSPTVMGL | 11 |
| 9 | MGLMEAISE | 11 |

TABLE XXXIV-V1

HLA-A1-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 14 | TSEDEAWKSY | 29 |
| 43 | DSAAALGLLY | 28 |
| 114 | HLENSKREQY | 27 |
| 294 | RDEQLKYWKY | 27 |
| 576 | NMDDNIIEHY | 25 |
| 516 | EEGTKRVLLY | 24 |
| 291 | DKNRDEQLKY | 23 |
| 215 | ASVGAEEYMY | 22 |
| 251 | MTYLNKGQFY | 22 |
| 84 | TSEAQSNLSG | 21 |
| 442 | PLQKKSDITY | 20 |
| 2 | PSDPPFNTRR | 19 |
| 213 | RSASVGAEEY | 19 |
| 327 | TIGNIEEIAY | 19 |
| 385 | RSNKPIHRAY | 19 |
| 487 | EREGGSVLVK | 19 |
| 359 | STDFSSQKGV | 18 |
| 472 | ANLQRTGQVY | 18 |
| 529 | ETDDVFDALM | 18 |
| 546 | GLMEAISEKY | 18 |
| 586 | SNEDTFILNM | 18 |
| 46 | AALGLLYDYY | 17 |
| 208 | ATEKFRSASV | 17 |
| 235 | TLEATKSLRQ | 17 |

TABLE XXXIV-V1-continued

HLA-A1-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 346 | NEEAKIFITV | 17 |
| 433 | SSDGKLAAIP | 17 |
| 446 | KSDITYFKTM | 17 |
| 530 | TDDVFDALML | 17 |
| 557 | LPVEKIAKLY | 17 |
| 4 | DPPFNTRRAY | 16 |
| 41 | DEDSAAALGL | 16 |
| 45 | AAALGLLYDY | 16 |
| 75 | DQEKRNCLGT | 16 |
| 178 | VPSLATHSAY | 16 |
| 200 | YSESFKDAAT | 16 |
| 244 | QKQGEGPMTY | 16 |
| 288 | FSEDKNRDEQ | 16 |
| 321 | YKESFNTIGN | 16 |
| 473 | NLQRTGQVYY | 16 |
| 483 | NTDDEREGGS | 16 |
| 556 | PVEKIAKLYK | 16 |
| 69 | ASDSQEDQEK | 15 |
| 127 | FPESSAIIPV | 15 |
| 148 | PVFMAPPVHY | 15 |
| 163 | GEEQRVVIFE | 15 |
| 167 | RVVIFEQTQY | 15 |
| 191 | DQRSTPDSTY | 15 |
| 225 | DQTSSGTFQY | 15 |
| 264 | LSETGDNKCF | 15 |
| 312 | KQRVLDIADY | 15 |
| 371 | LPLMIQIDTY | 15 |
| 373 | LMIQIDTYSY | 15 |
| 459 | HSQPVLFIPD | 15 |
| 551 | ISEKYGLPVE | 15 |
| 585 | YSNEDTFILN | 15 |
| 515 | KEEGTKRVLL | 14 |
| 598 | MVEGFKVTLM | 14 |

TABLE XXXIV-V2

HLA-A1-10mers-202P5A5
Each peptide is a portion of SEQ ID NO: 5;
each start position is specified, the length
of peptide is 10 amino acids, and the end
position for each peptide is the start
position plus nine.

| Pos | 1234567890 | score |
|---|---|---|
| 4 | ESDNNKRLVA | 22 |
| 2 | SQESDNNKRL | 13 |

TABLE XXXIV-V4

HLA-A1-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 4 | ATKAMMIING | 11 |
| 1 | LTAATKAMMI | 7 |
| 3 | AATKAMMIIN | 5 |

TABLE XXXIV-V5

HLA-A1-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 7 | DEEQKQNRKK | 13 |
| 5 | IRDEEQKQNR | 10 |
| 6 | RDEEQKQNRK | 10 |

TABLE XXXIV-V5&6

HLA-A1-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 1 | DEEQKQNRKN | 13 |

TABLE XXXIV-V6

HLA-A1-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 1 | DEERKQNRKN | 13 |

TABLE XXXIV-V8

HLA-A1-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 5 | KSPTVMGLME | 12 |
| 4 | IKSPTVMGLM | 6 |
| 7 | PTVMGLMEAI | 6 |
| 9 | VMGLMEAISE | 5 |

TABLE XXXV-V1

HLA-A0201-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 556 | GLPVEKIAKL | 29 |
| 132 | AIIPVSGITV | 26 |
| 597 | SMVEGFKVTL | 26 |
| 133 | IIPVSGITVV | 24 |
| 169 | VIFEQTQYDV | 23 |
| 253 | YLNKGQFYAI | 23 |
| 538 | MLKSPTVKGL | 23 |
| 550 | AISEKYGLPV | 23 |
| 457 | DLHSQPVLFI | 22 |
| 465 | FIPDVHFANL | 22 |
| 330 | NIEEIAYNAV | 21 |
| 483 | VLFIPDVHFA | 21 |
| 573 | ILVNMDDNII | 21 |
| 564 | KLYKKSKKGI | 20 |
| 57 | VPRDKRLLSV | 19 |
| 208 | ATEKFRSASV | 19 |
| 309 | HTAKQRVLDI | 19 |
| 437 | KLAAIPLQKK | 19 |
| 454 | TMPDLHSQPV | 19 |
| 572 | GILVNMDDNI | 19 |
| 23 | YLENPLTAAT | 18 |
| 37 | SINGDEDSAA | 18 |
| 92 | SGGENRVQVL | 18 |
| 99 | QVLKTVPVNL | 18 |
| 124 | SISFPESSAI | 18 |
| 271 | KCFRHPISKV | 18 |
| 349 | AKIFITVNCL | 18 |
| 432 | SSSDGKLAAI | 18 |
| 440 | AIPLQKKSDI | 18 |
| 513 | QMKEEGTKRV | 18 |
| 535 | DALMLKSPTV | 18 |
| 48 | LGLLYDYYKV | 17 |
| 109 | SLNQDHLENS | 17 |
| 130 | SSAIIPVSGI | 17 |
| 222 | YMYDQTSSGT | 17 |
| 277 | ISKVRSVVMV | 17 |
| 449 | ITYFKTMPDL | 17 |
| 460 | SQPVLFIPDV | 17 |
| 592 | ILNMESMVEG | 17 |
| 29 | TAATKAMMSI | 16 |
| 50 | LLYDYYKVPR | 16 |
| 62 | RLLSVSKASD | 16 |
| 91 | LSGGENRVQV | 16 |
| 97 | RVQVLKTVPV | 16 |
| 147 | FTPVFMAPPV | 16 |
| 274 | RHPISKVRSV | 16 |
| 278 | SKVRSVVMVV | 16 |
| 471 | FANLQRTGQV | 16 |
| 537 | LMLKSPTVKG | 16 |
| 546 | GLMEAISEKY | 16 |
| 22 | SYLENPLTAA | 15 |
| 39 | NGDEDSAAAL | 15 |
| 89 | SNLSGGENRV | 15 |

TABLE XXXV-V1-continued

HLA-A0201-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 100 | VLKTVPVNLS | 15 |
| 125 | ISFPESSAII | 15 |
| 135 | PVSGITVVKA | 15 |
| 180 | SLATHSAYLK | 15 |
| 227 | TSSGTFQYTL | 15 |
| 230 | GTFQYTLEAT | 15 |
| 263 | TLSETGDNKC | 15 |
| 359 | STDFSSQKGV | 15 |
| 362 | FSSQKGVKGL | 15 |
| 370 | GLPLMIQIDT | 15 |
| 373 | LMIQIDTYSY | 15 |
| 493 | VLVKRMFRPM | 15 |
| 580 | NIIEHYSNED | 15 |
| 15 | SEDEAWKSYL | 14 |
| 55 | YKVPRDKRLL | 14 |
| 101 | LKTVPVNLSL | 14 |
| 127 | FPESSAIIPV | 14 |
| 141 | VVKAEDFTPV | 14 |
| 151 | FMAPPVHYPR | 14 |
| 187 | YLKDDQRSTP | 14 |
| 319 | ADYKESFNTI | 14 |
| 325 | FNTIGNIEEI | 14 |
| 333 | EIAYNAVSFT | 14 |
| 336 | YNAVSFTWDV | 14 |
| 344 | DVNEEAKIFI | 14 |
| 352 | FITVNCLSTD | 14 |
| 364 | SQKGVKGLPL | 14 |
| 390 | IHRAYCQIKV | 14 |
| 484 | TDDEREGGSV | 14 |
| 515 | KEEGTKRVLL | 14 |
| 622 | VLLYVRKETD | 14 |
| 548 | MEAISEKYGL | 14 |
| 553 | EKYGLPVEKI | 14 |

TABLE XXXV-V2

HLA-A0201-10mers-202P5A5
Each peptide is a portion of SEQ ID NO: 5;
each start position is specified, the length
of peptide is 10 amino acids, and the end
position for each peptide is the start
position plus nine.

| Pos | 1234567890 | score |
|---|---|---|
| 5 | SDNNKRLVAL | 20 |
| 6 | DNNKRLVALV | 16 |
| 13 | ALVPMPSDPP | 14 |
| 3 | QESDNNKRLV | 11 |
| 11 | LVALVPMPSD | 11 |
| 2 | SQESDNNKRL | 10 |
| 8 | NKRLVALVPM | 10 |
| 10 | RLVALVPMPS | 10 |
| 16 | PMPSDPPFNT | 9 |

TABLE XXXV-V4

HLA-A0201-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 10 | IINGDEDSAA | 18 |
| 1 | LTAATKAMMI | 16 |
| 9 | MIINGDEDSA | 16 |
| 2 | TAATKAMMII | 14 |
| 7 | AMMIINGDED | 13 |
| 8 | MMIINGDEDS | 10 |
| 4 | ATKAMMIING | 9 |
| 5 | TKAMMIINGD | 8 |

TABLE XXXV-V6

HLA-A0201-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 4 | KIRDEEQKQN | 9 |
| 1 | AERKIRDEEQ | 4 |
| 3 | RKIRDEEQKQ | 4 |
| 5 | IRDEEQKQNR | 4 |

TABLE XXXV-V5&6

HLA-A0201-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 4 | QKQNRKNGKG | 2 |

TABLE XXXV-V6

HLA-A0201-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 8 | RKNGKGQASQ | 7 |
| 9 | KNGKGQASQT | 5 |
| 6 | QNRKNGKGQA | 4 |
| 10 | NGKGQASQTQ | 3 |

TABLE XXXV-V8

HLA-A0201-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 3 | MLKSPTVMGL | 24 |
| 1 | ALMLKSPTVM | 17 |
| 2 | LMLKSPTVMG | 14 |
| 6 | SPTVMGLMEA | 11 |
| 9 | VMGLMEAISE | 11 |

TABLE XXXVI-V1

HLA-A0203-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 38 | INGDEDSAAA | 27 |
| 22 | SYLENPLTAA | 19 |
| 37 | SINGDEDSAA | 19 |
| 199 | TYSESFKDAA | 19 |
| 431 | NSSSDGKLAA | 19 |
| 23 | YLENPLTAAT | 17 |

TABLE XXXVI-V1-continued

HLA-A0203-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 39 | NGDEDSAAAL | 17 |
| 200 | YSESFKDAAT | 17 |
| 432 | SSSDGKLAAI | 17 |

TABLE XXXVI-V2

HLA-A0203-10 mers-202P5A5
Each peptide is a portion of SEQ ID NO: 5; each
start position is specified, the length of peptide
is 10 amino acids, and the end position for each
peptide is the start position plus nine.

| Pos | 1234567890 | score |
|---|---|---|
| 4 | ESDNNKRLVA | 10 |
| 5 | SDNNKRLVAL | 9 |
| 6 | DNNKRLVALV | 8 |

TABLE XXXVI-V4

HLA-A0203-10 mers-202P5A5
Each peptide is a portion of SEQ ID NO: 3; each
start position is specified, the length of peptide
is 10 amino acids, and the end position for each
peptide is the start position plus nine.

| Pos | 1234567890 | score |
|---|---|---|
| 10 | IINGDEDSAA | 19 |
| 9 | MIINGDEDSA | 10 |

TABLE XXXVI-V5

HLA-A0203-10mers-202P5A5

| Pos | 1234567890 | score |
|---|---|---|
| NoResultsFound. | | |

TABLE XXXVI

V5 & 6-HLA-A0203-10mers-202P5A5

| Pos | 1234567890 | score |
|---|---|---|
| NoResultsFound. | | |

TABLE XXXVI

V6-HLA-A0203-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 6 | QNRKNGKGQA | 10 |
| 7 | NRKNGKGQAS | 9 |
| 8 | RKNGKGQASQ | 8 |

TABLE XXXVI

V8-HLA-A0203-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 6 | SPTVMGLMEA | 10 |
| 7 | PTVMGLMEAI | 9 |
| 8 | TVMGLMEAIS | 8 |

TABLE XXXVII

V1-HLA-A3-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 536 | ALMLKSPTVK | 30 |
| 279 | KVRSVVMVVF | 28 |
| 357 | CLSTDFSSQK | 26 |
| 437 | KLAAIPLQKK | 26 |
| 167 | RVVIFEQTQY | 25 |
| 180 | SLATHSAYLK | 25 |
| 47 | ALGLLYDYYK | 24 |
| 59 | RDKRLLSVSK | 24 |
| 132 | AIIPVSGITV | 24 |
| 561 | KIAKLYKKSK | 24 |
| 24 | LENPLTAATK | 23 |
| 50 | LLYDYYKVPR | 23 |
| 398 | KVFCDKGAER | 23 |
| 473 | NLQRTGQVYY | 23 |
| 558 | PVEKIAKLYK | 23 |
| 62 | RLLSVSKASD | 21 |

TABLE XXXVII-continued

V1-HLA-A3-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 114 | HLENSKREQY | 21 |
| 149 | PVFMAPPVHY | 21 |
| 389 | PIHRAYCQIK | 21 |
| 436 | GKLAAIPLQK | 21 |
| 525 | YVRKETDDVF | 21 |
| 56 | KVPRDKRLLS | 20 |
| 134 | IPVSGITVVK | 20 |
| 187 | YLKDDQRSTP | 20 |
| 283 | VVMVVFSEDK | 20 |
| 442 | PLQKKSDITY | 20 |
| 462 | PVLFIPDVHF | 20 |
| 479 | QVYYNTDDER | 20 |
| 99 | QVLKTVPVNL | 19 |
| 408 | KIRDEERKQN | 19 |
| 487 | EREGGSVLVK | 19 |
| 97 | RVQVLKTVPV | 18 |
| 332 | EEIAYNAVSF | 18 |
| 472 | ANLQRTGQVY | 18 |
| 521 | RVLLYVRKET | 18 |
| 545 | KGLMEAISEK | 18 |
| 550 | AISEKYGLPV | 18 |
| 12 | AYTSEDEAWK | 17 |
| 65 | SVSKASDSQE | 17 |
| 231 | TFQYTLEATK | 17 |
| 241 | SLRQKQGEGP | 17 |
| 262 | ITLSETGDNK | 17 |
| 314 | RVLDIADYKE | 17 |
| 338 | AVSFTWDVNE | 17 |
| 519 | TKRVLLYVRK | 17 |
| 546 | GLMEAISEKY | 17 |
| 552 | SEKYGLPVEK | 17 |
| 562 | IAKLYKKSKK | 17 |
| 564 | KLYKKSKKGI | 17 |
| 21 | KSYLENPLTA | 16 |
| 27 | PLTAATKAMM | 16 |
| 49 | GLLYDYYKVP | 16 |

TABLE XXXVII-continued

V1-HLA-A3-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 63 | LLSVSKASDS | 16 |
| 90 | NLSGGENRVQ | 16 |
| 135 | PVSGITVVKA | 16 |
| 191 | DQRSTPDSTY | 16 |
| 244 | QKQGEGPMTY | 16 |
| 247 | GEGPMTYLNK | 16 |
| 276 | PISKVRSVVM | 16 |
| 313 | QRVLDIADYK | 16 |
| 327 | TIGNIEEIAY | 16 |
| 494 | LVKRMFRPME | 16 |
| 511 | SKQMKEEGTK | 16 |
| 522 | VLLYVRKETD | 16 |
| 543 | TVKGLMEAIS | 16 |
| 555 | YGLPVEKIAK | 16 |
| 591 | FILNMESMVE | 16 |
| 592 | ILNMESMVEG | 16 |
| 23 | YLENPLTAAT | 15 |
| 37 | SINGDEDSAA | 15 |
| 43 | DSAAALGLLY | 15 |
| 52 | YDYYKVPRDK | 15 |
| 81 | CLGTSEAQSN | 15 |
| 93 | GGENRVQVLK | 15 |
| 105 | PVNLSLNQDH | 15 |
| 133 | IIPVSGITVV | 15 |
| 138 | GITVVKAEDF | 15 |
| 235 | TLEATKSLRQ | 15 |
| 312 | KQRVLDIADY | 15 |
| 352 | FITVNCLSTD | 15 |
| 360 | TDFSSQKGVK | 15 |
| 410 | RDEERKQNRK | 15 |
| 440 | AIPLQKKSDI | 15 |
| 523 | LLYVRKETDD | 15 |
| 140 | TVVKAEDFTP | 14 |
| 141 | VVKAEDFTPV | 14 |
| 202 | ESFKDAATEK | 14 |

TABLE XXXVII-continued

V1-HLA-A3-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 213 | RSASVGAEEY | 14 |
| 216 | SVGAEEYMYD | 14 |
| 236 | LEATKSLRQK | 14 |
| 251 | MTYLNKGQFY | 14 |
| 282 | SVVMVVFSED | 14 |
| 285 | MVVFSEDKNR | 14 |
| 367 | GVKGLPLMIQ | 14 |
| 376 | QIDTYSYNNR | 14 |
| 379 | TYSYNNRSNK | 14 |
| 399 | VFCDKGAERK | 14 |
| 488 | REGGSVLVKR | 14 |
| 532 | DVFDALMLKS | 14 |

TABLE XXXVII

V2-HLA-A3-10mers-202P5A5
Each peptide is a portion of SEQ ID NO: 5;
each start position is specified, the length
of peptide is 10 amino acids, and the end
position for each peptide is the start
position plus nine.

| Pos | 1234567890 | score |
|---|---|---|
| 10 | RLVALVPMPS | 18 |
| 13 | ALVPMPSDPP | 16 |
| 7 | NNKRLVALVP | 14 |
| 11 | LVALVPMPSD | 14 |
| 14 | LVPMPSDPPF | 14 |
| 4 | ESDNNKRLVA | 9 |
| 8 | NKRLVALVPM | 8 |

TABLE XXXVII

V4-HLA-A3-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 10 | IINGDEDSAA | 16 |
| 9 | MIINGDEDSA | 14 |

TABLE XXXVII-continued

V4-HLA-A3-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 1 | LTAATKAMMI | 8 |
| 7 | AMMIINGDED | 7 |

TABLE XXXVII

V5-HLA-A3-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 4 | KIRDEEQKQN | 18 |
| 2 | ERKIRDEEQK | 15 |
| 6 | RDEEQKQNRK | 15 |
| 9 | EQKQNRKKGK | 11 |
| 3 | RKIRDEEQKQ | 10 |
| 7 | DEEQKQNRKK | 10 |

TABLE XXXVII

V5 & 6-HLA-A3-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 3 | EQKQNRKNGK | 11 |

TABLE XXXVII

V6-HLA-A3-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 9 | KNGKGQASQT | 12 |
| 3 | ERKQNRKNGK | 11 |
| 8 | RKNGKGQASQ | 11 |
| 5 | KQNRKNGKGQ | 9 |
| 6 | QNRKNGKGQA | 9 |
| 10 | NGKGQASQTQ | 7 |

TABLE XXXVII-continued

V6-HLA-A3-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 4 | RKQNRKNGKG | 6 |
| 7 | NRKNGKGQAS | 6 |

TABLE XXXVII

V8-HLA-A23-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 1 | ALMLKSPTVM | 20 |
| 8 | TVMGLMEAIS | 15 |
| 10 | MGLMEAISEK | 15 |
| 3 | MLKSPTVMGL | 12 |
| 5 | KSPTVMGLME | 10 |

TABLE XXXVIII-V1

HLA-A26-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 167 | RVVIFEQTQY | 25 |
| 516 | EEGTKRVLLY | 25 |
| 532 | DVFDALMLKS | 25 |
| 149 | PVFMAPPVHY | 24 |
| 172 | EQTQYDVPSL | 24 |
| 42 | EDSAAALGLL | 23 |
| 332 | EEIAYNAVSF | 23 |
| 162 | DGEEQRVVIF | 22 |
| 468 | DVHFANLQRT | 22 |
| 191 | DQRSTPDSTY | 21 |
| 225 | DQTSSGTFQY | 21 |
| 344 | DVNEEAKIFI | 21 |
| 589 | DTFILNMESM | 21 |
| 43 | DSAAALGLLY | 20 |
| 177 | DVPSLATHSA | 20 |

TABLE XXXVIII-V1-continued

HLA-A26-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 291 | DKNRDEQLKY | 20 |
| 353 | ITVNCLSTDF | 20 |
| 4 | DPPFNTRRAY | 19 |
| 251 | MTYLNKGQFY | 19 |
| 266 | ETGDNKCFRH | 19 |
| 279 | KVRSVVMVVF | 19 |
| 333 | EIAYNAVSFT | 19 |
| 529 | ETDDVFDALM | 19 |
| 41 | DEDSAAALGL | 18 |
| 99 | QVLKTVPVNL | 18 |
| 102 | KTVPVNLSLN | 18 |
| 378 | DTYSYNNRSN | 18 |
| 462 | PVLFIPDVHF | 18 |
| 485 | DDEREGGSVL | 18 |
| 525 | YVRKETDDVF | 18 |
| 600 | EGFKVTLMEI | 18 |
| 230 | GTFQYTLEAT | 17 |
| 327 | TIGNIEEIAY | 17 |
| 140 | YVVKAEDFTP | 16 |
| 282 | SVVMVVFSED | 16 |
| 349 | AKIFITVNCL | 16 |
| 449 | ITYFKTMPDL | 16 |
| 504 | EEFGPVPSKQ | 16 |
| 517 | EGTKRVLLYV | 16 |
| 531 | DDVFDALMLK | 16 |
| 549 | EAISEKYGLP | 16 |
| 557 | LPVEKIAKLY | 16 |
| 597 | SMVEGFKVTL | 16 |
| 92 | SGGENRVQVL | 15 |
| 95 | ENRVQLKTV | 15 |
| 135 | PVSGITVVKA | 15 |
| 145 | EDFTPVFMAP | 15 |
| 215 | ASVGAEEYMY | 15 |
| 248 | EGPMTYLNKG | 15 |
| 265 | VVFSEDKNRD | 15 |
| 323 | ESFNTIGNIE | 15 |
| 371 | LPLMIQIDTY | 15 |
| 373 | LMIQIDTYSY | 15 |
| 398 | KVFCDKGAER | 15 |
| 487 | EREGGSVLVK | 15 |
| 489 | EGGSVLVKRM | 15 |
| 503 | EEEFGPVPSK | 15 |
| 553 | EKYGLPVEKI | 15 |
| 560 | EKIAKLYKKS | 15 |
| 576 | NMDDNIIEHY | 15 |
| 18 | EAWKSYLENP | 14 |
| 45 | AAALGLLYDY | 14 |
| 60 | DKRLLSVSKA | 14 |
| 164 | EEQRVVIFEQ | 14 |
| 168 | VVIFEQTQYD | 14 |
| 202 | ESFKDAATEK | 14 |
| 210 | EKFRSASVGA | 14 |
| 285 | MVVFSEDKNR | 14 |
| 312 | KQRVLDIADY | 14 |
| 317 | DIADYKESFN | 14 |
| 347 | EEAKIFITVN | 14 |
| 367 | GVKGLPLMIQ | 14 |
| 457 | DLHSQPVLFI | 14 |
| 593 | LNMESMVEGF | 14 |
| 598 | MVEGFKVTLM | 14 |
| 14 | TSEDEAWKSY | 13 |
| 55 | YKVPRDKRLL | 13 |
| 65 | SVSKASDSQE | 13 |
| 118 | SKREQYSISF | 13 |
| 138 | GITVVKAEDF | 13 |
| 182 | ATHSAYLKDD | 13 |
| 309 | HTAKQRVLDI | 13 |
| 316 | LDIADYKESF | 13 |
| 448 | DITYFKTMPD | 13 |
| 465 | FIPDVHFANL | 13 |
| 538 | MLKSPTVKGL | 13 |

TABLE XXXVIII-V1-continued

HLA-A26-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 542 | PTVKGLMEAI | 13 |
| 546 | GLMEAISEKY | 13 |
| 556 | GLPVEKIAKL | 13 |
| 579 | DNIIEHYSNE | 13 |
| 15 | SEDEAWKSYL | 12 |
| 74 | EDQEKRNCLG | 12 |
| 77 | EKRNCLGTSE | 12 |
| 86 | EAQSNLSGGE | 12 |
| 103 | TVPVNLSLNQ | 12 |
| 132 | AIIPVSGITV | 12 |
| 139 | ITVVKAEDFT | 12 |
| 178 | VPSLATHSAY | 12 |
| 221 | EYMYDQTSSG | 12 |
| 237 | EATKSLRQKQ | 12 |
| 314 | RVLDIADYKE | 12 |
| 326 | NTIGNIEEIA | 12 |
| 343 | WDVNEEAKIF | 12 |
| 362 | FSSQKGVKGL | 12 |
| 391 | HRAYCQIKVF | 12 |
| 435 | DGKLAAIPLQ | 12 |
| 442 | PLQKKSDITY | 12 |
| 443 | LQKKSDITYF | 12 |
| 497 | RMFRPMEEEF | 12 |
| 505 | EFGPVPSKQM | 12 |
| 518 | GTKRVLLYVR | 12 |

TABLE XXXVIII-V2

HLA-A26-10mers-202P5A5
Each peptide is a portion of SEQ ID NO: 5;
each start position is specified, the length
of peptide is 10 amino acids, and the end
position for each peptide is the start
position plus nine.

| Pos | 1234567890 | score |
|---|---|---|
| 14 | LVPMPSDPPF | 18 |
| 5 | SDNNKRLVAL | 14 |
| 6 | DNNKRLVALV | 12 |
| 4 | ESDNNKRLVA | 11 |

TABLE XXXVIII-V2-continued

HLA-A26-10mers-202P5A5
Each peptide is a portion of SEQ ID NO: 5;
each start position is specified, the length
of peptide is 10 amino acids, and the end
position for each peptide is the start
position plus nine.

| Pos | 1234567890 | score |
|---|---|---|
| 11 | LVALVPMPSD | 11 |
| 2 | SQESDNNKRL | 10 |

TABLE XXXVIII-V4

HLA-A26-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 4 | ATKAMMIING | 13 |
| 1 | LTAATKAMMI | 9 |
| 9 | MIINGDEDSA | 9 |
| 10 | IINGDEDSAA | 6 |

TABLE XXXVIII-V5

HLA-A26-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 2 | ERKIRDEEQK | 11 |
| 8 | EEQKQNRKKG | 11 |
| 9 | EQKQNRKKGK | 10 |
| 7 | DEEQKQNRKK | 9 |
| 4 | KIRDEEQKQN | 6 |
| 3 | RKIRDEEQKQ | 5 |

TABLE XXXVIII-V5&6

HLA-A26-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 2 | EEQKQNRKNG | 10 |
| 3 | EQKQNRKNGK | 10 |
| 1 | DEEQKQNRKN | 9 |

TABLE XXXVIII-V6

HLA-A26-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 2 | EERKQNRKNG | 10 |
| 3 | ERKQNRKNGK | 10 |
| 1 | DEERKQNRKN | 9 |

TABLE XXXVIII-V8

HLA-A26-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 3 | MLKSPTVMGL | 13 |
| 7 | PTVMGLMEAI | 13 |
| 8 | TVMGLMEAIS | 11 |
| 6 | SPTVMGLMEA | 6 |

TABLE XXXIX-V1

HLA-B0702-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 455 | MPDLHSQPVL | 23 |
| 57 | VPRDKRLLSV | 20 |
| 500 | RPMEEEFGPV | 20 |
| 5 | PPFNTRRAYT | 18 |
| 26 | NPLTAATKAM | 18 |
| 275 | HPISKVRSVV | 18 |
| 127 | FPESSAIIPV | 17 |
| 195 | TPDSTYSESF | 17 |
| 388 | KPIHRAYCQI | 17 |
| 441 | IPLQKKSDIT | 17 |
| 515 | KEEGTKRVLL | 16 |
| 541 | SPTVKGLMEA | 16 |
| 134 | IPVSGITVVK | 15 |
| 364 | SQKGVKGLPL | 15 |
| 42 | EDSAAALGLL | 14 |

TABLE XXXIX-V1-continued

HLA-B0702-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 158 | YPRGDGEEQR | 14 |
| 227 | TSSGTFQYTL | 14 |
| 1 | MPSDPPFNTR | 13 |
| 19 | AWKSYLENPL | 13 |
| 39 | NGDEDSAAAL | 13 |
| 41 | DEDSAAALGL | 13 |
| 92 | SGGENRVQVL | 13 |
| 99 | QVLKTVPVNL | 13 |
| 135 | PVSGITVVKA | 13 |
| 172 | EQTQYDVPSL | 13 |
| 178 | VPSLATHSAY | 13 |
| 245 | KQGEGPMTYL | 13 |
| 349 | AKIFITVNCL | 13 |
| 362 | FSSQKGVKGL | 13 |
| 434 | SDGKLAAIPL | 13 |
| 509 | VPSKQMKEEG | 13 |
| 528 | KETDDVFDAL | 13 |
| 530 | TDDVFDALML | 13 |
| 550 | AISEKYGLPV | 13 |
| 584 | HYSNEDTFIL | 13 |
| 4 | DPPFNTRRAY | 12 |
| 73 | QEDQEKRNCL | 12 |
| 91 | LSGGENRVQV | 12 |
| 101 | LKTVPVNLSL | 12 |
| 148 | TPVFMAPPVH | 12 |
| 153 | APPVHYPRGD | 12 |
| 179 | PSLATHSAYL | 12 |
| 276 | PISKVRSVVM | 12 |
| 279 | KVRSVVMVVF | 12 |
| 289 | SEDKNRDEQL | 12 |
| 307 | RQHTAKQRVL | 12 |
| 449 | ITYFKTMPDL | 12 |
| 465 | FIPDVHFANL | 12 |
| 466 | IPDVHFANLQ | 12 |
| 597 | SMVEGFKVTL | 12 |
| 15 | SEDEAWKSYL | 11 |

TABLE XXXIX-V1-continued

HLA-B0702-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 55 | YKVPRDKRLL | 11 |
| 97 | RVQVLKTVPV | 11 |
| 154 | PPVHYPRGDG | 11 |
| 160 | RGDGEEQRVV | 11 |
| 161 | GDGEEQRVVI | 11 |
| 233 | QYTLEATKSL | 11 |
| 249 | GPMTYLNKGQ | 11 |
| 255 | NKGQFYAITL | 11 |
| 309 | HTAKQRVLDI | 11 |
| 431 | NSSSDGKLAA | 11 |
| 461 | QPVLFIPDVH | 11 |
| 485 | DDEREGGSVL | 11 |
| 507 | GPVPSKQMKE | 11 |
| 514 | MKEEGTKRVL | 11 |
| 538 | MLKSPTVKGL | 11 |
| 548 | MEAISEKYGL | 11 |
| 556 | GLPVEKIAKL | 11 |
| 565 | LYKKSKKGIL | 11 |

TABLE XXXIX-V2

HLA-B0702-10mers-202P5A5
Each peptide is a portion of SEQ ID NO: 5;
each start position is specified, the length
of peptide is 10 amino acids, and the end
position for each peptide is the start
position plus nine.

| Pos | 1234567890 | score |
|---|---|---|
| 15 | VPMPSDPPFN | 14 |
| 5 | SDNNKRLVAL | 13 |
| 4 | ESDNNKRLVA | 12 |
| 8 | NKRLVALVPM | 11 |
| 2 | SQESDNNKRL | 10 |
| 6 | DNNKRLVALV | 9 |
| 3 | QESDNNKRLV | 8 |
| 14 | LVPMPSDPPF | 8 |
| 16 | PMPSDPPFNT | 6 |

TABLE XXXIX-V4

HLA-B0702-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 10 | IINGDEDSAA | 10 |
| 1 | LTAATKAMMI | 8 |
| 2 | TAATKAMMII | 7 |
| 9 | MIINGDEDSA | 6 |

TABLE XXXIX-V5

HLA-B0702-10mers-202P5A5
Each peptide is a portion of SEQ ID NO: 3;
each start position is specified, the length
of peptide is 10 amino acids, and the end
position for each peptide is the start
position plus nine.

| score | 1234567890 | score |
|---|---|---|
| 1 | AERKIRDEEQ | 5 |
| 4 | KIRDEEQKQN | 3 |
| 8 | EEQKQNRKKG | 3 |
| 5 | IRDEEQKQNR | 2 |

TABLE XXXIC-V5 & 6

HLA-B0702-10 mers-202P5A5
Each peptide is a portion of SEQ ID NO: 3; each
start position is specified, the length of peptide
is 10 amino acids, and the end position for each
peptide is the start position plus nine.

| Pos | 1234567890 | score |
|---|---|---|
| 2 | EEQKQNRKNG | 3 |
| 3 | EQKQNRKNGK | 1 |

TABLE XXXIX-V6

HLA-B0702-10 mers-202P5A5
Each peptide is a portion of SEQ ID NO: 3; each
start position is specified, the length of peptide
is 10 amino acids, and the end position for each
peptide is the start position plus nine.

| Pos | 1234567890 | score |
|---|---|---|
| 6 | QNRKNGKGQA | 9 |
| 9 | KNGKGQASQT | 9 |
| 2 | EERKQNRKNG | 5 |
| 8 | RKNGKGQASQ | 4 |

TABLE XXXIX-V8

HLA-B0702-10mers-202P5A5
Each peptide is a portion of SEQ ID NO: 3; each start position is specified, the length of peptide is 10 amino acids, and the end position for each peptide is the start position plus nine.

| score | 1234567890 | score |
|---|---|---|
| 6 | SPTVMGLMEA | 15 |
| 1 | ALMLKSPTVM | 11 |
| 3 | MLKSPTVMGL | 11 |
| 4 | LKSPTVMGLM | 9 |
| 7 | PTVMGLMEAI | 7 |

TABLE XL-V1

HLA-B08-10mers-202P5A5

| Pos | 1234567890 | score |
|---|---|---|
| NoResultsFound. | | |

TABLE XL-V2

HLA-B08-10mers-202P5A5

| Pos | 1234567890 | score |
|---|---|---|
| NoResultsFound. | | |

TABLE XL-V4

HLA-B08-10mers-202P5A5

| Pos | 1234567890 | score |
|---|---|---|
| NoResultsFound. | | |

TABLE XL-V5

HLA-B08-10mers-202P5A5

| Pos | 1234567890 | score |
|---|---|---|
| NoResultsFound. | | |

TABLE XL-V5&6

HLA-B08-10mers-202P5A5

| Pos | 1234567890 | score |
|---|---|---|
| NoResultsFound. | | |

TABLE XL-V6

HLA-B08-10mers-202P5A5

| Pos | 1234567890 | score |
|---|---|---|
| NoResultsFound. | | |

TABLE XL-V8

HLA-B08-10mers-202P5A5

| Pos | 1234567890 | score |
|---|---|---|
| NoResultsFound. | | |

TABLE XLI-V1

HLA-B1510-10mers-202P5A5

| Pos | 1234567890 | score |
|---|---|---|
| NoResultsFound. | | |

TABLE XLI-V2

HLA-B1510-10 mers-202P5A5

| Pos | 1234567890 | score |
|---|---|---|
| NoResultsFound | | |

TABLE XLI-V4

HLA-B1510-10mers-202P5A5

| Pos | 1234567890 | score |
|---|---|---|
| NoResultsFound. | | |

TABLE XLI-V5

HLA-B1510-10mers-202P5A5

| Pos | 1234567890 | score |
|---|---|---|
| NoResultsFound. | | |

TABLE XLI-V5&6

HLA-B1510-10mers-202P5A5

| Pos | 1234567890 | score |
|---|---|---|
| NoResultsFound. | | |

TABLE XLI-V6

HLA-B1510-10 mers-202P5A5

| Pos | 1234567890 | score |
|---|---|---|
| NoResultsFound | | |

TABLE XLI-V8

HLA-B1510-10 mers-202P5A5

| Pos | 1234567890 | score |
|---|---|---|
| NoResultsFound | | |

TABLE XLII-V1

HLA-B2705-10mers-202P5A5

| Pos | 1234567890 | score |
|---|---|---|
| NoResultsFound. | | |

TABLE XLII-V2

HLA-B2705-10mers-202P5A5

| Pos | 1234567890 | score |
|---|---|---|
| NoResultsFound. | | |

TABLE XLII-V4

HLA-B2705-10mers-202P5A5

| Pos | 1234567890 | score |
|---|---|---|
| NoResultsFound. | | |

TABLE XLII-V5

HLA-B2705-10mers-202P5A5

| Pos | 1234567890 | score |
|---|---|---|
| NoResultsFound. | | |

TABLE XLII-V5&6

HLA-B2705-10mers-202P5A5

| Pos | 1234567890 | score |
|---|---|---|
| NoResultsFound. | | |

TABLE XLII-V6

HLA-B2705-10mers-202P5A5

| Pos | 1234567890 | score |
|---|---|---|
| NoResultsFound. | | |

TABLE XLII-V8

HLA-B2705-10mers-202P5A5

| Pos | 1234567890 | score |
|---|---|---|
| NoResultsFound. | | |

TABLE XLIII-V1

HLA-B2709-10mers-202P5A5

| Pos | 1234567890 | score |
|---|---|---|
| NoResultsRound. | | |

TABLE XLIII-V2

HLA-B2709-10mers-202P5A5

| Pos | 1234567890 | score |
|---|---|---|
| NoResultsRound. | | |

TABLE XLI-V4

HLA-B1510-10mers-202P5A5

| Pos | 1234567890 | score |
|---|---|---|
| NoResultsRound. | | |

TABLE XLI-V5

HLA-B1510-10mers-202P5A5

| Pos | 1234567890 | score |
|---|---|---|
| NoResultsRound. | | |

TABLE XLI-V5&6

HLA-B1510-10mers-202P5A5

| Pos | 1234567890 | score |
|---|---|---|
| NoResultsRound. | | |

TABLE XLI-V6

HLA-B1510-10mers-202P5A5

| Pos | 1234567890 | score |
|---|---|---|
| NoResultsRound. | | |

TABLE XLI-V8

HLA-B1510-10mers-202P5A5

| Pos | 1234567890 | score |
|---|---|---|
| NoResultsRound. | | |

TABLE XLIV-V1

HLA-B4402-10mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 332 | EEIAYNAVSF | 27 |
| 516 | EEGTKRVLLY | 26 |
| 515 | KEEGTKRVLL | 25 |
| 528 | KETDDVFDAL | 25 |
| 41 | DEDSAAALGL | 23 |
| 73 | QEDQEKRNCL | 23 |
| 289 | SEDKNRDEQL | 23 |
| 295 | DEQLKYWKYW | 23 |
| 322 | KESFNTIGNI | 23 |
| 15 | SEDEAWKSYL | 22 |
| 582 | IEHYSNEDTF | 21 |
| 548 | MEAISEKYGL | 20 |
| 349 | AKIFITVNCL | 18 |
| 504 | EEFGPVPSKQ | 17 |
| 164 | EEQRVVIFEQ | 16 |
| 347 | EEAKIFITVN | 16 |
| 391 | HRAYCQIKVF | 16 |
| 412 | EERKQNRKKG | 16 |
| 576 | NMDDNIIEHY | 16 |
| 4 | DPPFNTRRAY | 15 |
| 24 | LENPLTAATK | 15 |
| 39 | NGDEDSAAAL | 15 |
| 42 | EDSAAALGLL | 15 |
| 45 | AAALGLLYDY | 15 |
| 46 | AALGLLYDYY | 15 |
| 55 | YKVPRDKRLL | 15 |
| 128 | PESSAIIPVS | 15 |
| 144 | AEDFTPVFMA | 15 |
| 292 | KNRDEQLKYW | 15 |
| 371 | LPLMIQIDTY | 15 |
| 472 | ANLQRTGQVY | 15 |
| 556 | GLPVEKIAKL | 15 |
| 587 | NEDTFILNME | 15 |
| 19 | AWKSYLENPL | 14 |
| 94 | GENRVQVLKT | 14 |
| 149 | PVFMAPPVHY | 14 |
| 178 | VPSLATHSAY | 14 |
| 201 | SESFKDAATE | 14 |
| 203 | SFKDAATEKF | 14 |
| 215 | ASVGAEEYMY | 14 |
| 219 | AEEYMYDQTS | 14 |
| 233 | QYTLEATKSL | 14 |
| 236 | LEATKSLRQK | 14 |
| 247 | GEGPWTYLNK | 14 |
| 255 | NKGQFYAITL | 14 |
| 312 | KQRVLDIADY | 14 |
| 319 | ADYKESFNTI | 14 |
| 327 | TIGNIEEIAY | 14 |
| 343 | WDVNEEAKIF | 14 |
| 346 | NEEAKIFITV | 14 |
| 362 | FSSQKGVKGL | 14 |
| 373 | LMIQIDTYSY | 14 |
| 432 | SSSDGKLAAI | 14 |
| 456 | PDLHSQPVLF | 14 |
| 488 | REGGSVLVKR | 14 |
| 557 | LPVEKIAKLY | 14 |
| 11 | RAYTSEDEAW | 13 |
| 14 | TSEDEAWKSY | 13 |
| 76 | QEKRNCLGTS | 13 |
| 92 | SGGENRVQVL | 13 |
| 99 | QVLKTVPVNL | 13 |
| 114 | HLENSKREQY | 13 |
| 125 | ISFPESSAII | 13 |
| 172 | EQTQYDVPSL | 13 |
| 227 | TSSGTFQYTL | 13 |
| 244 | QKQGEGPMTY | 13 |
| 264 | LSETGDNKCF | 13 |
| 279 | KVRSVVMVVF | 13 |
| 291 | KDNRDEQLKY | 13 |
| 307 | RQHTAKQRVL | 13 |
| 316 | LDIADYKESF | 13 |

TABLE XLIV-V1-continued

HLA-B4402-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 364 | SQKGVKGLPL | 13 |
| 385 | RSNKPIHRAY | 13 |
| 388 | KPIHRAYCQI | 13 |
| 405 | AERKIRDEER | 13 |
| 411 | DEERKQNRKK | 13 |
| 434 | SDGKLAAIPL | 13 |
| 440 | AIPLQKKSDI | 13 |
| 443 | LQKKSDITYF | 13 |
| 455 | MPDLHSQPVL | 13 |
| 465 | FIPDVHFANL | 13 |
| 473 | NLQRTGVVYY | 13 |
| 497 | RMFRPMEEEF | 13 |
| 503 | EEEFGPVPSK | 13 |
| 530 | TDDVFDALML | 13 |
| 538 | MLKSPTVKGL | 13 |
| 552 | SEDYGLPVEK | 13 |
| 553 | EKYGLPVEKI | 13 |
| 584 | HYSNEDTFIL | 13 |
| 597 | SMVEGFKVTL | 13 |
| 600 | EGFKVTLMEI | 13 |

TABLE XLIV-V2

HLA-B4402-10mers-202P5A5
Each peptide is a portion of SEQ ID NO: 5;
each start position is specified, the length
of peptide is 10 amino acids, and the end
position for each peptide is the start
position plus nine.

| Pos | 1234567890 | score |
|---|---|---|
| 5 | SDNNKRLVAL | 16 |
| 3 | QESDNNKRLV | 14 |
| 2 | SQESDNNKRL | 13 |
| 14 | LVPMPSDPPF | 11 |
| 4 | ESDNNKRLVA | 7 |

TABLE XLIV-V4

HLA-B4402-10mers-202P5A5
Each peptide is a portion of SEQ ID NO: 3;
each start position is specified, the length
of peptide is 10 amino acids, and the end
position for each peptide is the start
position plus nine.

| Pos | 1234567890 | score |
|---|---|---|
| 1 | LTAATKAMMI | 9 |
| 2 | TAATKAMMII | 9 |
| 4 | ATKAMMIING | 7 |
| 3 | AATKAMMIIN | 4 |
| 5 | TKAMMIINGD | 4 |
| 7 | AMMIINGDED | 4 |
| 9 | MIINGDEDSA | 4 |

TABLE XLIV-V5

HLA-B4402-10 mers-202P5A5
Each peptide is a portion of SEQ ID NO: 3; each
start position is specified, the length of peptide
is 10 amino acids, and the end position for each
peptide is the start position plus nine.

| Pos | 1234567890 | score |
|---|---|---|
| 8 | EEQKQNRKKG | 16 |
| 1 | AERKIRDEEQ | 13 |
| 7 | DEEQKQNRKK | 12 |

TABLE XLIV-V5&6

HLA-B4402-10 mers-202P5A5
Each peptide is a portion of SEQ ID NO: 3; each
start position is specified, the length of peptide
is 10 amino acids, and the end position for each
peptide is the start position plus nine.

| Pos | 1234567890 | score |
|---|---|---|
| 2 | EEQKQNRKNG | 15 |
| 1 | DEEQKQNRKN | 12 |

TABLE XLIV-V6

HLA-B4402-10 mers-202P5A5
Each peptide is a portion of SEQ ID NO: 3; each
start position is specified, the length of peptide
is 10 amino acids, and the end position for each
peptide is the start position plus nine.

| Pos | 1234567890 | score |
|---|---|---|
| 2 | EERKQNRKNG | 15 |
| 1 | DEERKQNRKN | 13 |

TABLE XLIV-V8

HLA-B4402-10 mers-202P5A5
Each peptide is a portion of SEQ ID NO: 3; each start position is specified, the length of peptide is 10 amino acids, and the end position for each peptide is the start position plus nine.

| Pos | 1234567890 | score |
|---|---|---|
| 3 | MLKSPTVMGL | 11 |
| 7 | PTVMGLMEAI | 10 |
| 1 | ALMLKSPTVM | 7 |
| 4 | LKSPTVMGLM | 5 |

TABLE XLV-V1

HLA-B5101-10 mers-202P5A5

| Pos | 1234567890 | score |
|---|---|---|
| NoResultsFound | | |

TABLE XLV-V2

HLA-B5101-10 mers-202P5A5

| Pos | 1234567890 | score |
|---|---|---|
| NoResultsFound | | |

TABLE XLV-V4

HLA-B5101-10 mers-202P5A5

| Pos | 1234567890 | score |
|---|---|---|
| NoResultsFound | | |

TABLE XLV-V5

HLA-B5101-10 mers-202P5A5

| Pos | 1234567890 | score |
|---|---|---|
| NoResultsFound | | |

TABLE XLV-V5&6

HLA-B5101-10 mers-202P5A5

| Pos | 1234567890 | score |
|---|---|---|
| NoResultsFound | | |

TABLE XLV-V6

HLA-B5101-10 mers-202P5A5

| Pos | 1234567890 | score |
|---|---|---|
| NoResultsFound | | |

TABLE XLV-V8

HLA-B5101-10mers-202P5A5

| Pos | 1234567890 | score |
|---|---|---|
| NoResultsFound | | |

TABLE XLVI-V1

HLA-DRB1-0101-15mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 136 | VSGITVVKAEDFTPV | 31 |
| 352 | FITVNCLSTDFSSQK | 31 |
| 503 | EEEFGPVPSKQMKEE | 31 |
| 95 | ENRVQVLKTVPVNLS | 30 |
| 130 | SSAIIPVSGITVVKA | 30 |
| 175 | QYDVPSLATHSAYLK | 30 |
| 274 | RHPISKVRSVVMVVF | 30 |
| 452 | FKTMPDLHSQPVLFI | 30 |
| 239 | TKSLRQKQGEGPMTY | 28 |
| 4 | DPPFNTRRAYTSEDE | 27 |
| 120 | REQYSISFPESSAII | 27 |
| 230 | GTFQYTLEATKSLRQ | 27 |
| 231 | TFQYTLEATKSLRQK | 27 |
| 531 | DDVFDALMLKSPTVK | 27 |
| 124 | SISFPESSAIIPVSG | 26 |
| 201 | SESFKDAATEKFRSA | 26 |
| 370 | GLPLMIQIDTYSYNN | 26 |
| 432 | SSSDGKLAAIPLQKK | 26 |
| 522 | VLLYVRKETDDVFDA | 26 |
| 144 | AEDFTPVFMAPPVHY | 25 |
| 248 | EGPMTYLNKGQFYAI | 25 |
| 359 | STDFSSQKGVKGLPL | 25 |
| 449 | ITYFKTMPDLHSQPV | 25 |
| 511 | SKQMKEEGTKRVLLY | 25 |
| 541 | SPTVKGLMEAISEKY | 25 |
| 593 | LNMESMVEGFKVTLM | 25 |
| 61 | KRLLSVSKASDSQED | 24 |
| 76 | QEKRNCLGTSEAQSN | 24 |
| 97 | RVQVLKTVPVNLSLN | 24 |
| 122 | QYSISFPESSAIIPV | 24 |

TABLE XLVI-V1-continued

HLA-DRB1-0101-15mers-202P5A5
Each peptide is a portion of SEQ ID NO: 3;
each start position is specified, the length
of peptide is 14 amino acids, and the end
position for each peptide is the start
position plus fourteen.

| Pos | 123456789012345 | score |
|---|---|---|
| 221 | EYMYDQTSSGTFQYT | 24 |
| 277 | ISKVRSVVMVVFSED | 24 |
| 499 | FRPMEEEFGPVPSKQ | 24 |
| 548 | MEAISEKYGLPVEKI | 24 |
| 582 | IEHYSNEDTFILNME | 24 |
| 98 | VQVLKTVPVNLSLNQ | 23 |
| 133 | IIPVSGITVVKAEDF | 23 |
| 362 | FSSQKGVKGLPLMIQ | 23 |
| 438 | LAAIPLQKKSDITYF | 23 |
| 460 | SQPVLFIPDVHFANL | 23 |
| 533 | VFDALMLKSPTVKGL | 23 |
| 571 | KGILVNMDDNIIEHY | 23 |
| 32 | TKAMMSINGDEDSAA | 22 |
| 116 | ENSKREQYSISFPES | 22 |
| 167 | RVVIFEQTQYDVPSL | 22 |
| 220 | EEYMYDQTSSGTFQY | 22 |
| 227 | TSSGTFQYTLEATKS | 22 |
| 328 | IGNIEEIAYNAVSFT | 22 |
| 455 | MPDLHSQPVLFIPDV | 22 |
| 463 | VLFIPDVHFANLQRT | 22 |
| 469 | VHFANLQRTGQVYYN | 22 |
| 468 | DVHFANLQRTGQVYY | 21 |
| 562 | IAKLYKKSKKGILVN | 21 |
| 563 | AKLYKKSKKGILVNM | 21 |
| 589 | DTFILNMESMVEGFK | 21 |
| 33 | KAMMSINGDEDSAAA | 20 |
| 52 | YDYYKVPRDKRLLSV | 20 |
| 58 | PRDKRLLSVSKASDS | 20 |
| 138 | GITVVKAEDFTPVFM | 20 |
| 281 | RSVVMVVFSEDKNRD | 20 |
| 313 | QRVLDIADYKESFNT | 20 |
| 340 | SFTWDVNEEAKIFIT | 20 |
| 371 | LPLMIQIDTYSYNNR | 20 |
| 379 | TYSYNNRSNKPIHRA | 20 |
| 394 | YQDIKVFCDKGAERK | 20 |
| 491 | GSVLVKRMFRPMEEE | 20 |
| 523 | LLYVRKETDDVFDAL | 20 |
| 536 | ALMLKSPTVKGLMEA | 20 |
| 552 | SEKYGLPVEKIAKLY | 20 |
| 17 | DEAWKSYLENPLTAA | 19 |
| 20 | WKSYLENPLTAATKA | 19 |
| 23 | YLENPLTAATKAMMS | 19 |
| 51 | LYDYYKVPRDKRLLS | 19 |
| 128 | PESSAIIPVSGITVV | 19 |
| 250 | PMTYLNKGQFYAITL | 19 |
| 251 | MTYLNKGQFYAITLS | 19 |
| 257 | GQFYAITLSETGDNK | 19 |
| 270 | NKCFRHPISKVRSVV | 19 |
| 338 | AVSFTWDVNEEAKIF | 19 |
| 341 | FTWDVNEEAKIFITV | 19 |
| 348 | EAKIFITVNCLSTDF | 19 |
| 397 | IKVFCDKGAERKIRD | 19 |
| 415 | KQNRKKGKGQASQTQ | 19 |
| 461 | QPVLFIPDVHFANLQ | 19 |
| 495 | KRMFRPMEEEFGPVP | 19 |
| 559 | VEKIAKLYKKSKKGI | 19 |
| 587 | MEDTFILNMESMVEG | 19 |
| 588 | EDTFILNMESMVEGF | 19 |
| 11 | RAYTSEDEAWKSYLE | 18 |
| 35 | MMSINGDEDSAAALG | 18 |
| 39 | NGDEDSAAALGLLYD | 18 |
| 131 | SAIIPVSGITVVKAE | 18 |
| 139 | ITVVKAEDFTPVFMA | 18 |
| 148 | TPVFMAPPVHYPRGD | 18 |
| 153 | APPVHYPRGDGEEQR | 18 |
| 155 | PVHYPRGDGEEQRVV | 18 |
| 168 | VVIFEQTQYDVPSLA | 18 |
| 174 | TQYDVPSLATHSAYL | 18 |
| 197 | DSTYSESFKDAATEK | 18 |
| 298 | LKYWKYWHSRQHTAK | 18 |
| 300 | YWKYWHSRQHTAKQR | 18 |

TABLE XLVI-V1-continued

HLA-DRB1-0101-15mers-202P5A5
Each peptide is a portion of SEQ ID NO: 3;
each start position is specified, the length
of peptide is 14 amino acids, and the end
position for each peptide is the start
position plus fourteen.

| Pos | 123456789012345 | score |
|-----|-----------------|-------|
| 322 | KESFNTIGNIEEIAY | 18 |
| 333 | EIAYNAVSFTWDVNE | 18 |
| 448 | DITYFKTMPDLHSQP | 18 |
| 22  | SYLENPLTAATKAMM | 17 |
| 25  | ENPLTAATKAMMSIN | 17 |
| 45  | AAALGLLYDYYKVPR | 17 |
| 47  | ALGLLYDYYKVPRDK | 17 |
| 79  | RNCLGTSEAQSNLSG | 17 |
| 93  | GGENRVQVLKTVPVN | 17 |
| 107 | NLSLNQDHLENSKRE | 17 |
| 185 | SAYLKDDQRSTPDST | 17 |
| 240 | KSLRQKQGEGPMTYL | 17 |
| 259 | FYAITLSETGDNKCF | 17 |
| 295 | DEQLKYWKYWHSRQH | 17 |
| 342 | TWDVNEEAKIFITVN | 17 |
| 364 | SQKGVKGLPLMIQID | 17 |
| 365 | QKGVKGLPLMIQIDT | 17 |
| 428 | TQCNSSSDGKLAAIP | 17 |
| 482 | YNTDDEREGGSVLVK | 17 |
| 483 | NTDDEREGGSVLVKR | 17 |
| 484 | TDDEREGGSVLVKRM | 17 |
| 488 | REGGSVLVKRMFRPM | 17 |
| 530 | TDDVFDALMLKSPTV | 17 |
| 535 | DALMLKSPTVKGLME | 17 |
| 551 | ISEKYGLPVEKIAKL | 17 |
| 554 | KYGLPVEKIAKLYKK | 17 |
| 564 | KLYKKSKKGILVNMD | 17 |
| 595 | MESMVEGFKVTLMEI | 17 |
| 26  | MPLTAATKAMMSING | 16 |
| 37  | SINGDEDSAAALGLL | 16 |
| 54  | YYKVPRDKRLLSVSK | 16 |
| 59  | RDKRLLSVSKASDSQ | 16 |
| 85  | SEAQSNLSGGENRVQ | 16 |
| 94  | GENRVQVLKTVPVNL | 16 |
| 104 | VPNLSLNQDHLENS  | 16 |
| 145 | EDFTPVFMAPPVHYP | 16 |
| 178 | VPSLATHSAYLKDDQ | 16 |
| 206 | DAATEKFRSASVGAE | 16 |
| 208 | ATEKFRSASVGAEEY | 16 |
| 219 | AEEYMYDQTSSGTFQ | 16 |
| 253 | YLNKGQFYAITLSET | 16 |
| 256 | KGQFYAITLSETGDN | 16 |
| 280 | VRSVVMVVFSEDKNR | 16 |
| 307 | RQHTAKQRVLDIADY | 16 |
| 327 | TIGNIEEIAYNAVSF | 16 |
| 330 | NIEEIAYNAVSFTWD | 16 |
| 349 | AKIFITVNCLSTDFS | 16 |
| 351 | IFITVNCLSTDFSSQ | 16 |
| 391 | HRAYCQIKVFCDKGA | 16 |
| 396 | QIKVFCDKGAERKIR | 16 |
| 431 | NSSSDGKLAAIPLQK | 16 |
| 458 | LHSQPVLFIPDVHFA | 16 |
| 490 | GGSVLVKRMFRPMEE | 16 |
| 495 | VKRMFRPMEEEFGPV | 16 |
| 528 | KETDDVFDALMLKSP | 16 |
| 534 | FDALMLKSPTVKGLM | 16 |
| 542 | PTVKGLMEAISEKYG | 16 |
| 556 | GLPVEKIAKLYKKSK | 16 |
| 570 | KKGILVNMDDNIIEH | 16 |
| 586 | SNEDTFILNMESMVE | 16 |
| 1   | MPSDPPFNTRRAYTS | 15 |
| 19  | AWKSYLENPLTAATK | 15 |
| 24  | LENPLTAATKAMMSI | 15 |
| 57  | VPRDKRLLSVSKASD | 15 |
| 147 | FTPVFMAPPVHYPRG | 15 |
| 166 | QRVVIFEQTQYDVPS | 15 |
| 190 | DDQRSTPDSTYSESF | 15 |
| 211 | KFRSASVGAEEYMYD | 15 |
| 312 | KQRVLDIADYKESFN | 15 |
| 325 | FNTIGNIEEIAYNAV | 15 |
| 347 | EEAKIFITVNCLSTD | 15 |

TABLE XLVI-V1-continued

HLA-DRB1-0101-15mers-202P5A5
Each peptide is a portion of SEQ ID NO: 3;
each start position is specified, the length
of peptide is 14 amino acids, and the end
position for each peptide is the start
position plus fourteen.

| Pos | 123456789012345 | score |
|---|---|---|
| 368 | VKGLPLMIQIDTYSY | 15 |
| 378 | DTYSYNNRSNKPIHR | 15 |
| 435 | DGLKAAIPLQKKSDI | 15 |
| 446 | KSDITYFKTMPDLHS | 15 |
| 487 | EREGGSVLVKRMFRP | 15 |
| 492 | SVLVKRMFRPMEEEF | 15 |
| 500 | RPMEEEFGPVPSKQM | 15 |
| 544 | VKGLMEAISEKYGLP | 15 |
| 545 | KGLMEAISEKYGLPV | 15 |

TABLE XLVI-V2

HLA-DRB1-0101-15mers-202P5A5
Each peptide is a portion of SEQ ID NO: 5;
each start position is specified, the length
of peptide is 14 amino adds, and the end
position for each peptide is the start
position plus fourteen.

| Pos | 123456789012345 | score |
|---|---|---|
| 8 | NKRLVALVPMPSDPP | 31 |
| 11 | LVALVPMPSDPPFNT | 29 |
| 5 | SDNNKRLVALVPMPS | 25 |
| 6 | DNNKRLVALVPMPSD | 17 |
| 12 | VALVPMPSDPPFNTR | 17 |
| 9 | KRLVALVPMPSDPPF | 15 |

TABLE XLVI-V4

HLA-DRB1-0101-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 10 | TKAMMIINGDEDSAA | 25 |
| 11 | KAMMIINGDEDSAAA | 20 |
| 1 | YLENPLTAATKAMMI | 19 |
| 13 | MMIINGDEDSAAALG | 18 |
| 3 | ENPLTAATKAMMIIN | 17 |
| 4 | NPLTAATKAMMIING | 16 |
| 12 | AMMIINGDEDSAAAL | 16 |

TABLE XLVI-V4-continued

HLA-DRB1-0101-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 15 | IINGDEDSAAALGLL | 16 |
| 2 | LENPLTAATKAMMII | 15 |
| 14 | MIINGDEDSAAALGL | 14 |

TABLE XLVI-V5

HLA-DRB1-0101-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 15 | QRQNRKKGKGQASQT | 13 |
| 7 | ERKIRDEEQKQNRKK | 12 |
| 14 | EQKQNRKKGKGQASQ | 12 |
| 4 | KGAERKIRDEEQKQN | 10 |
| 11 | RDEEQKQNRKKGKGQ | 10 |
| 9 | KIRDEEQKQNRKKGK | 6 |

TABLE XLVI-V5&6

HLA-DRB1-0101-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 9 | QKQNRKNGKGQASQT | 13 |
| 1 | ERKIRDEEQKQNRKN | 12 |
| 8 | EQKQNRKNGKGQASQ | 12 |
| 5 | RDEEQKQNRKNGKGQ | 9 |
| 3 | KIRDEEQKQNRKNGK | 6 |

TABLE XLVI-V6

HLA-DRB1-0101-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 10 | KQNRKNGKGQASQTQ | 17 |
| 9 | RKQNRKNGKGQASQT | 13 |

TABLE XLVI-V6-continued

HLA-DRB1-0101-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 13 | RKNGKGQASQTQCNS | 13 |
| 1 | ERKIRDEERKQNRKN | 12 |
| 8 | ERKQNRKNGKGQASQ | 12 |
| 5 | RDEERKQNRKNGKGQ | 11 |
| 12 | NRKNGKGQASQTQCN | 10 |

TABLE XLVI-V8

HLA-DRB1-01010-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 1 | DDVFDALMLKSPTVM | 27 |
| 4 | FDALMLKSPTVMGLM | 24 |
| 11 | SPTVMGLMEAISEKY | 24 |
| 12 | PTVMGLMEAISEKYG | 24 |
| 3 | VFDALMLKSPTVMGL | 23 |
| 6 | ALMLKSPTVMGLMEA | 19 |
| 5 | DALMLKSPTVMGLME | 16 |
| 9 | LKSPTVMGLMEAISE | 16 |
| 14 | VMGLMEAISEKYGLP | 15 |
| 15 | MGLMEAISEKYGLPV | 15 |
| 8 | MLKSPTVMGLMEAIS | 14 |

TABLE XLVII-V1

HLA-DRB1-0301-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 54 | YYKVPRDKRLLSVSK | 29 |
| 185 | SAYLKDDQRSTPDST | 27 |
| 289 | SEDKNRDEQLKYWKY | 27 |
| 572 | GILVNMDDNIIEHYS | 27 |
| 595 | MESMVEGFKVTLMEI | 27 |
| 165 | EQRVVIFEQTQYDVP | 26 |

TABLE XLVII-V1-continued

HLA-DRB1-0301-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 285 | MVVFSEDKNRDEQLK | 26 |
| 325 | FNTIGNIEEIAYNAV | 26 |
| 471 | FANLQRTGQVYYNTD | 26 |
| 112 | QDHLENSKREQYSIS | 25 |
| 248 | EGPMTYLNKGQFYAI | 25 |
| 314 | RVLDIADYKESFNTI | 25 |
| 338 | AVSFTWDVNEEAKIF | 25 |
| 495 | VKRMFRPMEEEFGPV | 24 |
| 35 | MMSINGDEDSAAALG | 22 |
| 37 | SINGDEDSAAALGLL | 22 |
| 47 | ALGLLYDYYKVPRDK | 22 |
| 97 | RVQVLKTVPVNLSLN | 22 |
| 396 | QIKVFCDKGAERKIR | 22 |
| 460 | SQPVLFIPDVHFANL | 22 |
| 60 | DKRLLSVSKASDSQE | 21 |
| 107 | NLSLNQDHLENSKRE | 21 |
| 147 | FTPVFMAPPVHYPRG | 21 |
| 277 | ISKVRSVVMVVFSED | 21 |
| 462 | PVLFIPDVHFANLQR | 21 |
| 554 | KYGLPVEKIAKLYKK | 21 |
| 136 | VSGITVVKAEDFTPV | 20 |
| 355 | VNCLSTDFSSQKGVK | 20 |
| 372 | PLMIQIDTYSYNNRS | 20 |
| 429 | QCNSSSDGKLAAIPL | 20 |
| 463 | VLFIPDVHFANLQRT | 20 |
| 526 | VRKETDDVFDALMLK | 20 |
| 536 | ALMLKSPTVKGLMEA | 20 |
| 544 | VKGLMEAISEKYGLP | 20 |
| 103 | TVPVNLSLNQDHLEN | 19 |
| 140 | TVVKAEDFTPVFMAP | 19 |
| 282 | SVVMVVFSEDKNRDE | 19 |
| 371 | LPLMIQIDTYSYNNR | 19 |
| 405 | AERKIRDEERKQNRK | 19 |
| 440 | AIPLQKKSDITYFKT | 19 |
| 519 | TKRVLLYVRKETDDV | 19 |

TABLE XLVII-V1-continued

HLA-DRB1-0301-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 523 | LLYVRKETDDVFDAL | 19 |
| 17 | DEAWKSYLENPLTAA | 18 |
| 25 | ENPLTAATKAMMSIN | 18 |
| 65 | SVSKASDSQEDQEKR | 18 |
| 156 | VHYPRGDGEEQRVVI | 18 |
| 184 | HSAYLKDDQRSTPDS | 18 |
| 201 | SESFKDAATEKFRSA | 18 |
| 284 | VMVVFSEDKNRDEQL | 18 |
| 406 | ERKIRDEERKQNRKK | 18 |
| 438 | LAAIPLQKKSDITYF | 18 |
| 480 | VYYNTDDEREGGSVL | 18 |
| 520 | KRVLLYVRKETDDVF | 18 |
| 541 | SPTVKGLMEAISEKY | 18 |
| 574 | LVNMDDNIIEHYSNE | 18 |
| 48 | LGLLYDYYKVPRDKR | 17 |
| 53 | DYYKVPRDKRLLSVS | 17 |
| 69 | ASDSQEDQEKRNCLG | 17 |
| 80 | NCLSTSEAQSNLSGG | 17 |
| 88 | QSNLSGGENRVQVLK | 17 |
| 104 | VPVNLSLNQDHLENS | 17 |
| 167 | RVVIFEQTQYDVPSL | 17 |
| 263 | TLSETGDNKCFRHPI | 17 |
| 315 | VLDIADYKESFNTIG | 17 |
| 342 | TWDVNEEAKIFITVN | 17 |
| 348 | EAKITITVNCLSTDF | 17 |
| 368 | VKGLPLMIQIDTYSY | 17 |
| 492 | SVLVKRMFRPMEEEF | 17 |
| 498 | KRMFRPMEEEFGPVP | 17 |
| 513 | QMKEEGTKRVLLYVR | 17 |
| 521 | RVLLYVRKETDDVFD | 17 |
| 545 | KGLMEAISEKYGLPV | 17 |
| 556 | GLPVEKIAKLYKKSK | 17 |
| 562 | IAKLYKKSKKGILVN | 17 |
| 579 | DNIIEHYSNEDTFIL | 17 |
| 592 | ILNMESMVEGFKVTL | 17 |
| 71 | DSQEDQEKRNCLGTS | 16 |

TABLE XLVII-V1-continued

HLA-DRB1-0301-15mers-202P5A5
Each peptide is a portion of SEQ ID NO: 3;
each start position is specified, the length
of peptide is 14 amino adds, and the end
position for each peptide is the start
position plus fourteen.

| Pos | 123456789012345 | score |
|---|---|---|
| 99 | QVLKTVPVNLSLNQD | 16 |
| 213 | RSASVGAEEYMYDQT | 16 |
| 229 | SGTFQYTLEATKSLR | 16 |
| 453 | KTMPDLHSQPVLFIP | 16 |
| 479 | QVYYNTDDEREGGSV | 16 |
| 559 | VEKIAKLYKKSKKGI | 16 |
| 563 | AKLYKKSKKGILVNM | 16 |
| 588 | EDTFILNMESMVEGF | 16 |
| 2 | PSDPPFNTRRAYTSE | 15 |
| 13 | YTSEDEAWKSYLENP | 15 |
| 305 | HSRQHTAKQRVLDIA | 15 |
| 322 | KESFNTIGNIEEIAY | 15 |
| 512 | KQMKEEGTKRVLLYV | 15 |
| 535 | DALMLKSPTVKGLME | 15 |
| 546 | GLMEAISEKYGLPVE | 15 |
| 98 | VQVLKTVPVNLSLNQ | 14 |
| 225 | DQTSSGTFQYTLEAT | 14 |
| 261 | AITLSETGDNKCFRH | 14 |
| 262 | ITLSETGDNKCFRHP | 14 |
| 468 | DVHFANLQRTGQVYY | 14 |
| 488 | REGGSVLVKRMFRPM | 14 |
| 560 | NIIEHYSNEDTFILN | 14 |

TABLE XLVI-V2

HLA-DRB1-0301-15mers-202P5A5
Each peptide is a portion of SEQ ID NO: 5;
each start position is specified, the length
of peptide is 14 amino acids, and the end
position for each peptide is the start
position plus fourteen.

| Pos | 123456789012345 | score |
|---|---|---|
| 14 | LVPMPSDPPFNTRRA | 23 |
| 12 | VALVPMPSDPPFNTR | 20 |
| 11 | LVALVPMPSDPPFNT | 13 |
| 9 | KRLYALVPMPSDPPF | 12 |
| 8 | NKRLVALVPMPSDPP | 11 |

TABLE XLVI-V4

HLA-DRB1-0301-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 13 | MMIINGDEDSAAALG | 22 |
| 15 | IINGDEDSAAALGLL | 22 |
| 3 | ENPLTAATKAMMIIN | 18 |
| 12 | AMMIINGDEDSAAAL | 17 |
| 11 | KAMMIINGDEDSAAA | 12 |
| 10 | TKAMMIINGDEDSAA | 10 |

TABLE XLVI-V5

HLA-DRB1-0301-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 6 | AERKIRDEEQKQNRK | 20 |
| 7 | ERKIRDEEQKQNRKK | 18 |
| 8 | RKIRDEEQKQNRKKG | 9 |
| 9 | KIRDEEQKQNRKKGK | 9 |

TABLE XLVI-V5&6

HLA-DRB1-0301-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 1 | ERKIRDEEQKQNRKN | 18 |
| 2 | RKIRDEEQKQNRKNG | 9 |
| 3 | KIRDEEQKQNRKNGK | 9 |
| 6 | DEEQKQNRKNGKGQA | 8 |
| 7 | EEQKQNRKNGKGQAS | 8 |
| 9 | QKQNRKNGKGQASQT | 8 |

TABLE XLVI-V6

HLA-DRB1-0301-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 1 | ERKIRDEERKQNRKN | 18 |
| 2 | RKIRDEERKQNRKNG | 9 |

TABLE XLVI-V6-continued

HLA-DRB1-0301-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 3 | KIRDEERKQNRKNGK | 9 |
| 5 | RDEERKQNRKNGKGQ | 8 |
| 6 | EERKQNRKNGKGQA | 8 |
| 7 | EERKQNRKNGKGQAS | 8 |
| 9 | KQNRKNGKGQASQT | 8 |
| 11 | QNRKNGKGQASQTQC | 8 |

TABLE XLVI-V8

HLA-DRB1-0301-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 6 | ALMLKSPTVMGLMEA | 20 |
| 14 | VMGLMEAISEKYGLP | 20 |
| 11 | SPTVMGLMEAISEKY | 17 |
| 15 | MGLMEAISEKYGLPV | 17 |
| 5 | DALMLKSPTVMGLME | 14 |
| 4 | FDALMLKSPTVMGLM | 12 |
| 12 | PTVMGLMEAISEKYG | 12 |

TABLE XLVIII-V1

HLA-DR1-0401-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 184 | HSAYLKDDQRSTPDS | 28 |
| 231 | TFQYTLEATKSLRQK | 28 |
| 338 | AVSFTWDVNEEAKIF | 28 |
| 462 | PVLFIPDVHFNALQR | 28 |
| 468 | DVHFANLQRTGQVYY | 28 |
| 503 | EEEFGPVPSKQMKEE | 28 |
| 582 | IEHYSNEDTFILNME | 28 |
| 54 | YYKVPRDKRLLSVSK | 26 |
| 95 | ENRVQVLKTVPVNLS | 26 |
| 175 | QYDVPSLATHSAYLK | 26 |

TABLE XLVIII-V1-continued

HLA-DR1-0401-15 mers-202P5A5
Each peptide is a portion of SEQ ID NO: 3; each
start position is specified, the length of peptide
is 14 amino acids, and the end position for each
peptide is the start position plus fourteen.

| Pos | 123456789012345 | score |
|---|---|---|
| 274 | RHPISKVRSVVMVF | 26 |
| 281 | RSVVMVVFSEDKNRD | 26 |
| 352 | FITVNCLSTDFSSQK | 26 |
| 355 | VNCLSTDFSSQKGVK | 26 |
| 406 | ERKIRDEERKQNRKK | 26 |
| 452 | FKTMPDLHSPVLFI | 26 |
| 511 | SKQMKEEGTKRVLLY | 26 |
| 10 | RRAYTSEDEAWKSYL | 22 |
| 51 | LYDYYKVPRDKRLLS | 22 |
| 201 | SESFKDAATEKFRSA | 22 |
| 219 | AEEYMDQTSSGTFQ | 22 |
| 256 | KGQFYAITLSETGDN | 22 |
| 285 | MVVFSEDKNRDEQLK | 22 |
| 297 | QLKYWKYWHSRQHTA | 22 |
| 300 | YWKYWHSRQHTAKQR | 22 |
| 322 | KESFNTIGNIEEIAY | 22 |
| 349 | AKIFITVNCLSTDFS | 22 |
| 377 | IDTYSYNNRSNKPIH | 22 |
| 21 | KSYLENPLTAATKAM | 20 |
| 25 | ENPLTAATKAMMSIN | 20 |
| 35 | MMSINGDEDSAAALG | 20 |
| 45 | AAALGLLYDYYKVPR | 20 |
| 88 | QSNLSGGENRVQVLK | 20 |
| 98 | VQVLKTVPVNLSLNQ | 20 |
| 101 | LKTVPVNLSLNQDHL | 20 |
| 107 | NLSLNQDHLENSKRE | 20 |
| 122 | QYSISFPESSAIIPV | 20 |
| 130 | SSAIIPVSGITVVKA | 20 |
| 133 | IIPVSGITVVKAEDF | 20 |
| 139 | ITVVKAEDFTPVFMA | 20 |
| 165 | EQRVVIFEQTQYDVP | 20 |
| 166 | QRVVIFEQTQYDVPS | 20 |
| 167 | RVVIFEQTQYDVPSL | 20 |
| 185 | SAYLKDDQRSTPDST | 20 |
| 220 | EEYMDQTSSGTFQY | 20 |
| 233 | QYTLEATKSLRQKQG | 20 |

TABLE XLVIII-V1-continued

HLA-DR1-0401-15 mers-202P5A5
Each peptide is a portion of SEQ ID NO: 3; each
start position is specified, the length of peptide
is 14 amino acids, and the end position for each
peptide is the start position plus fourteen.

| Pos | 123456789012345 | score |
|---|---|---|
| 259 | FYAITLSETGDNKCF | 20 |
| 282 | SVVMVVFSEDKNRDE | 20 |
| 313 | QRVLDIADYKESFNT | 20 |
| 328 | IGNIEEIAYNAVSFT | 20 |
| 342 | TWDVNEEAKIFITVN | 20 |
| 348 | EAKIFITVNCLSTDF | 20 |
| 365 | QKGVKGLPLMIQIDT | 20 |
| 368 | VKGLPLMIQIDTYSY | 20 |
| 371 | LPLMIQIDTYSYNNR | 20 |
| 372 | PLMIQIDTYSYNNRS | 20 |
| 387 | NKPIHRAYCQIKVFC | 20 |
| 394 | YCQIKVFCDKGAERK | 20 |
| 435 | DGKLAAIPLQKKSDI | 20 |
| 446 | KSDITYFKTMPDLHS | 20 |
| 463 | VLFIPDVHFANLQRT | 20 |
| 466 | IPDVHFANLQRTGQV | 20 |
| 519 | TKRVLLYVRKETDDV | 20 |
| 530 | TDDVFDALMLKSPTV | 20 |
| 541 | SPTVKGLMEAISEKY | 20 |
| 544 | VKGLMEAISEKYGLP | 20 |
| 554 | KYGLPVEKIAKLYKK | 20 |
| 556 | GLPVEKIAKLYKKSK | 20 |
| 559 | VEKIAKLYKKSKKGI | 20 |
| 572 | GILVNMDDNIIEHYS | 20 |
| 579 | DNIIEHYSNEDTFIL | 20 |
| 1 | MPSDPPFNTRRAYTS | 18 |
| 18 | EAWKSYLENPLTAAT | 18 |
| 24 | LENPLTAATKAMMSI | 18 |
| 36 | MSINGDEDSAAALGL | 18 |
| 57 | VPRDKRLLSVSKASD | 18 |
| 65 | SVSKASDSQEDQEKR | 18 |
| 71 | DSQEDQEKRNCLGTS | 18 |
| 76 | QEKRNCLGTSEAQSN | 18 |
| 80 | NCLGTSEAQSNLSGG | 18 |
| 81 | CLGTSEAQSNLSGGE | 18 |
| 89 | SNLSGGENRVQVLKT | 18 |

TABLE XLVIII-V1-continued

HLA-DR1-0401-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 104 | VPVNLSLNQDHLENS | 18 |
| 123 | YSISFPESSAIIPVS | 18 |
| 158 | YPRGDEEQRVVIFE | 18 |
| 159 | PRGDEEQRVVIFEQ | 18 |
| 172 | EQTQYDVPSLATHSA | 18 |
| 206 | DAATEKFRSASVGAE | 18 |
| 267 | TGDNKCFRHPISKVR | 18 |
| 305 | HSRQHTAKQRVLDIA | 18 |
| 319 | ADYKESFNTIGNIEE | 18 |
| 329 | GNIEEIAYNAVSFTW | 18 |
| 442 | PLQKKSDITYFKTMP | 18 |
| 533 | VFDALMLKSPTVKGL | 18 |
| 576 | NMDDNIIEHYSNEDT | 18 |
| 586 | SNEDTFILNMESMVE | 18 |
| 250 | PMTYLNKGQFYAITL | 17 |
| 301 | WKYWHSRQHTAKQRV | 17 |
| 379 | TYSYNNRSNKPIHRA | 17 |
| 522 | VLLYVRDETDDVFDA | 17 |
| 17 | DEAWKSYLENPLTAA | 16 |
| 20 | WKSYLENPLTAATKA | 16 |
| 52 | YDYYKVPRKKRLLSV | 16 |
| 120 | REQYSISFPESSAII | 16 |
| 144 | AEDFTPVFMAPPVHY | 16 |
| 155 | PVHYPRGDEEQRVV | 16 |
| 197 | DSTYSESFKDAATEK | 16 |
| 209 | TEKFRSASVGAEEYM | 16 |
| 221 | EYMYDQTSSGTFQYT | 16 |
| 229 | SGTFQYTLEATKSLR | 16 |
| 257 | GQFYAITLSETGDNK | 16 |
| 270 | NKCFRHPISKVRSVV | 16 |
| 298 | LKYWKYWHSRQHTAK | 16 |
| 318 | IADYKESFNTIGNIE | 16 |
| 333 | EIAYNAVSFTWDVNE | 16 |
| 340 | SFTWDVNEEAKIFIT | 16 |
| 391 | HRAYCQIKVFCDKGA | 16 |
| 449 | ITYFKTMPDLHSQPV | 16 |
| 479 | QVYYNTDDEREGGSV | 16 |
| 531 | DDVFDALMLKSPTVK | 16 |
| 552 | SEKYGLPVEKIAKLY | 16 |
| 563 | AKLYKKSKKGILVNM | 16 |
| 588 | EDTFILNMESMVEGF | 16 |
| 32 | TKAMMSINGDEDSAA | 14 |
| 33 | KAMMSINGDEDSAAA | 14 |
| 47 | ALGLLYDYYKVPRDK | 14 |
| 60 | DKRLLSVSKASDSQE | 14 |
| 61 | KRLLSVSKASDSQED | 14 |
| 63 | LLSVSKASDSQEDQE | 14 |
| 79 | RNCLGTSEAQSNLSG | 14 |
| 97 | RVQVLKTVPVNLSLN | 14 |
| 103 | TVPVNLSLNQDHLEN | 14 |
| 112 | QDHLENSKREQYSIS | 14 |
| 131 | SAIIPVSGITVVKAE | 14 |
| 136 | VSGITVVKAEDFTPV | 14 |
| 138 | GITVVKAEDFTPVFM | 14 |
| 147 | FTPVFMAPPVHYPRG | 14 |
| 149 | PVFMAPPVHYPRGDG | 14 |
| 178 | VPSLATHSAYLKDDQ | 14 |
| 214 | SASVGAEEYMYDQTS | 14 |
| 248 | EGPMTYLNKGQFYAI | 14 |
| 251 | MTYLNKGQFYAITLS | 14 |
| 277 | ISKVRSVVMVVFSED | 14 |
| 280 | VRSVVMVVFSEDKNR | 14 |
| 284 | VMVVFSEDKNRDEQL | 14 |
| 295 | DEQLKYWKYWHSRQH | 14 |
| 312 | KQRVLDIADYKESFN | 14 |
| 315 | VLDIADYKESFNTIG | 14 |
| 325 | FNTIGNIEEIAYNAV | 14 |
| 331 | IEEIAYNAVSFTWDV | 14 |
| 370 | GLPLMIQIDTYSYNN | 14 |
| 396 | QIKVFGDKGAERKIR | 14 |
| 438 | LAAIPLQKKSDITYF | 14 |
| 455 | MPDLHSQPVLFIPDV | 14 |

TABLE XLVIII-V1-continued

HLA-DR1-0401-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 460 | SQPVLFIPDVHFANL | 14 |
| 461 | QPVLFIPDVHFANLQ | 14 |
| 471 | FANLQRTGQVYYNTD | 14 |
| 492 | SVLVKRMFRPMEEEF | 14 |
| 499 | FRPMEEEFGPVPSKQ | 14 |
| 520 | KRVLLYVRKETDDVF | 14 |
| 523 | LLYVRKETDDVFDAL | 14 |
| 535 | DALMLKSPTVKGLME | 14 |
| 536 | ALMLKSPTVKGLMEA | 14 |
| 545 | KGLMEAISEKYGLPV | 14 |
| 570 | KKGILVNMDDNIIEH | 14 |
| 571 | KGILVNMDDNIIEHY | 14 |
| 578 | DDNIIEHYSNEDTFI | 14 |
| 589 | DTFILNMESMVEGFK | 14 |
| 590 | TFILNMESMVEGFKV | 14 |
| 592 | ILNMESMVEGFKVTL | 14 |
| 595 | MESMVEGFKVTLMEI | 14 |

TABLE XLVIII-V2

HLA-DR1-0401-15 mers-202P5A5
Each peptide is a portion of SEQ ID NO: 5; each start position is specified, the length of peptide is 14 amino acids, and the end position for each peptide is the start position plus fourteen.

| Pos | 123456789012345 | score |
|---|---|---|
| 8 | NKRLVALVPMPSDPP | 20 |
| 14 | LVPMPSDPPFNTRRA | 20 |
| 9 | KRLVALVPMPSDPPF | 14 |
| 11 | LVALVPMPSDPPFNT | 14 |
| 2 | SQESDNNKRLVALVP | 12 |
| 6 | DNNKRLVALVPMPSD | 12 |

TABLE XLVIII-V4

HLA-DR1-0401-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 3 | ENPLTAATKAMMIIN | 20 |
| 13 | MMIINGDEDSAAALG | 20 |

TABLE XLVIII-V4-continued

HLA-DR1-0401-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 2 | LENPLTAATKAMMII | 18 |
| 14 | MIINGDEDSAAALGL | 18 |
| 10 | TKAMMIINGDEDSAA | 14 |
| 11 | KAMMIINGDEDSAAA | 14 |
| 12 | AMMIINGDEDSAAAL | 14 |
| 6 | LTAATKAMMIINGDE | 12 |
| 9 | ATKAMMIINGDEDSA | 12 |
| 15 | IINGDEDSAAALGLL | 12 |

TABLE XLVIII-V5

HLA-DR1-0401-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 7 | ERKIRDEEQKQNRKK | 26 |
| 4 | KGAERKIRDEEQKQN | 12 |
| 6 | AERKIRDEEQKQNRK | 12 |
| 9 | KIRDEEQKQNRKKGK | 12 |

TABLE XLVIII-V5&6

HLA-DR1-0401-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 1 | ERKIRDEEQKQNRKN | 26 |
| 3 | KIRDEEQKQNRKNGK | 12 |

TABLE XLVIII-V6

HLA-DR1-0401-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 1 | ERKIRDEERKQNRKN | 26 |
| 13 | RKNGKGQASQTQCNS | 12 |

TABLE XLVIII-V6-continued

HLA-DR1-0401-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 14 | KNGKGQASQTQCNSS | 12 |
| 15 | NGKGQASQTQCNSSS | 12 |

TABLE XLVIII-V8

HLA-DR1-0401-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | score |
|---|---|---|
| 11 | SPTVMGLMEAISEKY | 20 |
| 14 | VMGLMEAISEKYGLP | 20 |
| 3 | VFDALMLKSPTVMGL | 18 |
| 1 | DDVFDALMLKSPTVM | 16 |
| 5 | DALMLKSPTVMGLME | 14 |
| 6 | ALMLKSPTVMGLMEA | 14 |
| 15 | MGLMEAISEKYGLPV | 14 |
| 13 | TVMGLMEAISEKYGL | 12 |
| 4 | FDALMLKSPTVMGLM | 9 |

TABLE XLIX-V1

HLA-DRB1-1101-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | Score |
|---|---|---|
| 51 | LYDYYKVPRDKRLLS | 25 |
| 144 | AEDFTPVFMAPPVHY | 24 |
| 197 | DSTYSESFKDAATEK | 24 |
| 468 | DVHFANLQRTGQVVY | 24 |
| 248 | EGPMTYLNKGQFYAI | 22 |
| 271 | KCFRHPISKVRSVVM | 22 |
| 449 | ITYFKTMPDLHSQPV | 22 |
| 496 | KRMFRPMEEEFGPVP | 22 |
| 531 | DDVFDALMLKSPTVK | 22 |
| 54 | YYKVPRDKRLLSVSK | 21 |
| 94 | GENRVQLKTVPVNL | 21 |
| 60 | DKRLLSVSKASDSQE | 20 |

TABLE XLIX-V1-continued

HLA-DRB1-1101-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | Score |
|---|---|---|
| 185 | SAYLKDDQRSTPDST | 20 |
| 297 | QLKYWKYWHSRQHTA | 20 |
| 338 | AVSFTWDVNEEAKIF | 20 |
| 462 | PVLFIPDVHFANLQR | 20 |
| 492 | SVLVKRMFRPMEEEF | 20 |
| 520 | KRVLLYVRKETDDVF | 20 |
| 556 | GLPVEKIAKLYKKSK | 20 |
| 559 | VEKIAKLYKKSKKGI | 20 |
| 98 | VQVLKTVPVNLSLNQ | 19 |
| 133 | IIPVSGITVVKAEDF | 19 |
| 541 | SPTVKGLMEAISEKY | 19 |
| 552 | SEKYGLPVEKIAKLY | 19 |
| 563 | AKLYKKSKKGILVNM | 19 |
| 175 | QYDVPSLATHSAYLK | 18 |
| 301 | WKYWHSRQHTAKQRV | 18 |
| 352 | FITVNCLSTDFSSQK | 18 |
| 377 | IDTYSYNNRSNKPIH | 18 |
| 488 | REGGSVLVKRMFRPM | 18 |
| 545 | KGLMEAISEKYGLPV | 18 |
| 124 | SISFPESSAIIPVSG | 17 |
| 168 | VVIFEQTQYDVPSLA | 17 |
| 284 | VMVVFSEDKNRDEQL | 17 |
| 318 | IADYKESFNTIGNIE | 17 |
| 359 | STDFSSQKGVKGLPL | 17 |
| 361 | DFSSQKGVKGLPLMI | 17 |
| 479 | QVYYNTDDEREGGSV | 17 |
| 4 | DPPFNTRRAYTSEDE | 16 |
| 20 | WKSYLENPLTAATKA | 16 |
| 25 | ENPLTAATKAMMSIN | 16 |
| 120 | REQYSISFPESSAII | 16 |
| 135 | PVSGITVVKAEDFTP | 16 |
| 148 | TPVFMAPPVHYPRGD | 16 |
| 149 | PVFMAPPVHYPRGDG | 16 |
| 203 | SFKDAATEKFRSASV | 16 |
| 205 | KDAATEKFRSASVGA | 16 |
| 219 | AEEYMYDQTSSGTFQ | 16 |

TABLE XLIX-V1-continued

HLA-DRB1-1101-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | Score |
|---|---|---|
| 250 | PMTYLNKGQFYAITL | 16 |
| 256 | KGQFYAITLSETGDN | 16 |
| 257 | GQFYAITLSETGDNK | 16 |
| 300 | YWKYWHSRQHTAKQR | 16 |
| 322 | KESFNTIGNIEEIAY | 16 |
| 333 | EIAYNAVSFTWDVNE | 16 |
| 348 | EAKIFITVNCLSTDF | 16 |
| 349 | AKIFITVNCLSTDFS | 16 |
| 391 | HRAYCQIKVFCDKGA | 16 |
| 480 | VYYNTDDEREGGSVL | 16 |
| 503 | EEEFGPVPSKQMKEE | 16 |
| 519 | TKRVLLYVRKETDDV | 16 |
| 136 | VSGITVVKAEDFTPV | 15 |
| 267 | TGDNKCFRHPISKVR | 15 |
| 277 | ISKVRSVVMVVFSED | 15 |
| 410 | RDEERKQNRKKGKGQ | 15 |
| 412 | EERKQNRKKGKGQAS | 15 |
| 490 | GGSVLVKRMFRPMEE | 15 |
| 48 | LGLLYDYYKVPRDKR | 14 |
| 112 | QDHLENSKREQYSIS | 14 |
| 150 | VFMAPPVHYPRGDGE | 14 |
| 152 | MAPPVHYPRGDGEEQ | 14 |
| 280 | VRSVVMVVFSEDKNR | 14 |
| 342 | TWDVNEEAKIFITVN | 14 |
| 384 | NRSNKPIHRAYCQIK | 14 |
| 406 | ERKIRDEERKQNRKK | 14 |
| 414 | RKQNRKKGKGQASQT | 14 |
| 429 | QCNSSSDGKLAAIPL | 14 |
| 437 | KLAAIPLQKKSDITY | 14 |
| 438 | LAAIPLQKKSDITYF | 14 |
| 445 | KKSDITYFKTMPDLH | 14 |
| 451 | YFKTMPDLHSQPVLF | 14 |
| 489 | EGGSVLVKRMFRPME | 14 |
| 507 | GPVPSKQMKEEGTKR | 14 |
| 530 | TDDVFDALMLKSPTV | 14 |
| 532 | DVFDALMLKSPTVKG | 14 |

TABLE XLIX-V1-continued

HLA-DRB1-1101-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | Score |
|---|---|---|
| 553 | EKYGLPVEKIAKLYK | 14 |
| 562 | IAKLYKKSKKGILVN | 14 |
| 576 | NMDDNIIEHYSNEDT | 14 |
| 586 | SNEDTFILNMESMVE | 14 |
| 592 | ILNMESMVEGFKVTL | 14 |
| 595 | MESMVEGFKVTLMEI | 14 |
| 47 | ALGLLYDYYKVPRDK | 13 |
| 52 | YDYYKVPRDKRLLSV | 13 |
| 58 | PRDKRLLSVSKASDS | 13 |
| 61 | KRLLSVSKASDSQED | 13 |
| 95 | ENRVQVLKTVPVNLS | 13 |
| 230 | GTFQYTLEATKSLRQ | 13 |
| 274 | RHPISKVRSVVMVVF | 13 |
| 278 | SKVRSVVMVVFSEDK | 13 |
| 281 | RSVVMVVFSEDKNRD | 13 |
| 312 | KQRVLDIADYKESFN | 13 |
| 365 | QKGVKGLPLMIQIDT | 13 |
| 393 | AYCQIKVFCDKGAER | 13 |
| 394 | YCQIKVFCDKGAERK | 13 |
| 435 | DGKLAAIPLQKKSDI | 13 |
| 461 | QPVLFIPDVHFANLQ | 13 |
| 499 | FRPMEEEFGPVPSKQ | 13 |
| 535 | DALMLKSPTVKGLME | 13 |
| 571 | KGILVNMDDNIIEHY | 13 |
| 589 | DTFILNMESMVEGFK | 13 |
| 10 | RRAYTSEDEAWKSYL | 12 |
| 29 | TAATKAMMSINGDED | 12 |
| 32 | TKAMMSINGDEDSAA | 12 |
| 33 | KAMMSINGDEDSAAA | 12 |
| 35 | MMSINGDEDSAAALG | 12 |
| 45 | AAALGLLYDYYKVPR | 12 |
| 49 | GLLYDYYKVPRDKRL | 12 |
| 76 | QEKRNCLGTSEAQSN | 12 |
| 107 | NLSLNQDHLENSKRE | 12 |
| 119 | KREQYSISFPESSAI | 12 |
| 127 | FPESSAIIPVSGITV | 12 |

TABLE XLIX-V1-continued

HLA-DRB1-1101-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | Score |
|---|---|---|
| 130 | SSAIIPVSGITVVKA | 12 |
| 138 | GITVVKAEDFTPVFM | 12 |
| 217 | VGAEEYMYDQTSSGT | 12 |
| 231 | TFQYTLEATKSLRQK | 12 |
| 236 | LEATKSLRQKQGEGP | 12 |
| 239 | TKSLRQKQGEGPMTY | 12 |
| 295 | DEQLKYWKYWHSRQH | 12 |
| 313 | QRVLDIADYKESFNT | 12 |
| 325 | FNTIGNIEEIAYNAV | 12 |
| 328 | IGNIEEIAYNAVSFT | 12 |
| 340 | SFTWDVNEEAKIFIT | 12 |
| 368 | VKGLPLMIQIDTYSY | 12 |
| 370 | GLPLMIQIDTYSYNN | 12 |
| 371 | LPLMIQIDTYSYNNR | 12 |
| 397 | IKVFCDKGAERKIRD | 12 |
| 448 | DITYFKTMPDLHSQP | 12 |
| 452 | FKTMPDLHSQPVLFI | 12 |
| 460 | SQPVLFIPDVHFANL | 12 |
| 463 | VLFIPDVHFANLQRT | 12 |
| 478 | GQVYYNTDDEREGGS | 12 |
| 575 | VNMDDNIIEHYSNED | 12 |
| 590 | TFILNMESMVEGFKV | 12 |

TABLE XLIX-V2

HLA-DRB1-1101-15 mers-202P5A5
Each peptide is a portion of SEQ ID NO: 5; each start position is specified, the length of peptide is 14 amino acids, and the end position for each peptide is the start position plus fourteen.

| Pos | 123456789012345 | Score |
|---|---|---|
| 8 | NKRLVALVPMPSDPP | 20 |
| 11 | LVALVPMPSDPPFNT | 18 |
| 2 | SQESDNNKRLVALVP | 15 |
| 5 | SDNNKRLVALVPMPS | 15 |
| 9 | KRLVALVPMPSDPPF | 12 |
| 1 | MSQESDNNKRLVALV | 10 |

TABLE XLIX-V4

HLA-DRB1-1101-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | Score |
|---|---|---|
| 3 | ENPLTAATKAMMIIN | 16 |
| 7 | TAATKAMMIINGDED | 12 |
| 10 | TKAMMIINGDEDSAA | 12 |
| 11 | KAMMIINGDEDSAAA | 12 |
| 12 | AMMIINGDEDSAAAL | 12 |
| 13 | MMIINGDEDSAAALG | 12 |
| 1 | YLENPLTAATKAMMI | 7 |

TABLE XLIX-V5

HLA-DRB1-1101-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | Score |
|---|---|---|
| 11 | RDEEQKQNRKKGKGQ | 15 |
| 13 | EEQKQNRKKGKGQAS | 15 |
| 15 | QKQNRKKGKGQASQT | 14 |
| 1 | FCDKGAERKIRDEEQ | 10 |
| 3 | DKGAERKIRDEEQKQ | 8 |
| 8 | RKIRDEEQKQNRKKG | 8 |
| 12 | DEEQKQNRKKGKGQA | 8 |

TABLE XLIX-V5&6

HLA-DRB1-1101-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | Score |
|---|---|---|
| 5 | RDEEQKQNRKNGKGQ | 14 |
| 9 | QKQNRKNGKGQASQT | 14 |
| 2 | RKIRDEEQKQNRKNG | 8 |
| 6 | DEEQKQNRKNGKGQA | 8 |
| 7 | EQKQNRKNGKGQAS | 7 |
| 1 | ERKIRDEEQKQNRKN | 6 |

TABLE XLIX-V6

HLA-DRB1-1101-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | Score |
|---|---|---|
| 1 | ERKIRDEERKQNRKN | 14 |
| 5 | RDEERKQNRKNGKGQ | 14 |
| 9 | RKQNRKNGKGQASQT | 14 |
| 2 | RKIRDEERKQNRKNG | 8 |
| 6 | DEERKQNRKNGKGQA | 8 |
| 7 | ERKQNRKNGKGQAS  | 7 |
| 10 | KQNRKNGKGQASQTQ | 6 |

TABLE XLIX-V8

HLA-DRB1-1101-15 mers-202P5A5
Each peptide is a portion of SEQ ID NO: 3; each start position is specified, the length of peptide is 14 amino acids, and the end position for each peptide is the start position plus fourteen.

| Pos | 123456789012345 | Score |
|---|---|---|
| 11 | SPTVMGLMEAISEKY | 20 |
| 14 | VMGLMEAISEKYGLP | 20 |
| 3 | VFDALMLKSPTVMGL | 18 |
| 1 | DDVFDALMLKSPTVM | 16 |
| 5 | DALMLKSPTVMGLME | 14 |
| 6 | ALMLKSPTVMGLMEA | 14 |
| 15 | MGLMEAISEKYGLPV | 14 |
| 13 | TVMGLMEAISEKYGL | 12 |
| 4 | FDALMLKSPTVMGLM | 9 |

TABLE L

Protein Characteristics of 202P5A5

| | Bioinformatic Program | Located on the World Wide Web at: | Outcome |
|---|---|---|---|
| ORF | ORF finder | | 1829 bp |
| Protein length | | | 609aa |
| Transmembrane region | TM Pred | ch.embnet.org/ | no TM |
| | HMMTop | enzim.hu/hmmtop/ | no TM |
| | Sosui | genome.ad.jp/SOSui/ | soluble protein |
| | TMHMM | cbs.dtu.dk/services/TMHMM | no TM, extracellular |
| Signal Peptide | Signal P | cbs.dtu.dk/services/SignalP/ | no signal peptide |
| pI | pI/MW tool | expasy.ch/tools/ | pI 6.05 |
| Molecular weight | pI/MW tool | expasy.ch/tools/ | 63.6 kD |
| Localization | PSORT | psort.nibb.ac.jp/ | 76% nuclear, 30% microbody |
| Motifs | PSORT II | psort.nibb.ac.jp/ | 61% nuclear, 22% milochondrial |
| | Pfam | sanger.ac.uk/Pfam/ | CP2 transcription factor |
| | Prints | biochem.ucl.ac.uk/ | Fibronetin type III repeat |
| | Blocks | blocks.fhcrc.org/ | M protein repeat |

TABLE LI

Exon boundaries of transcript 202P5A05 v.1

| Exon Number | Start | End | Length |
|---|---|---|---|
| 1 | 1 | 196 | 196 |
| 2 | 197 | 264 | 68 |
| 3 | 265 | 658 | 394 |
| 4 | 659 | 714 | 56 |
| 5 | 715 | 871 | 157 |
| 6 | 872 | 983 | 112 |
| 7 | 984 | 1078 | 95 |
| 8 | 1079 | 1237 | 159 |
| 9 | 1238 | 1325 | 88 |
| 10 | 1326 | 1465 | 140 |
| 11 | 1466 | 1497 | 32 |
| 12 | 1498 | 1592 | 95 |
| 13 | 1593 | 1678 | 86 |
| 14 | 1679 | 1743 | 65 |
| 15 | 1744 | 4746 | 3002 |

TABLE LII(a)

Nucleotide sequence of transcript variant 202P5A05 v.2 (SEQ ID NO: 96)

| | | | | | |
|---|---|---|---|---|---|
| attggatcaa | acatgtcaca | agagtcggac | aataataaaa | gactagtggc | cctagtgccc | 60 |
| atgcccagtg | accctccatt | caataccccga | agagcctaca | ccagtgagga | tgaagcctgg | 120 |
| aagtcatact | tggagaatcc | cctgacagca | gccaccaagg | ccatgatgag | cattaatggt | 180 |
| gatgaggaca | gtgctgctgc | cctcggcctg | ctctatgact | actacaaggt | tcctcgagac | 240 |
| aagaggctgc | tgtctgtaag | caaagcaagt | gacagccaag | aagaccagga | gaaagaaac | 300 |
| tgccttggca | ccagtgaagc | ccagactaat | ttgagtggag | gagaaaaccg | agtgcaagtc | 360 |
| ctaaagactg | ttccagtgaa | cctttcccta | aatcaagatc | acctggagaa | ttccaagcgg | 420 |
| gaacagtaca | gcatcagctt | ccccgagagc | tctgccatca | tcccggtgtc | gggaatcacg | 480 |
| gtggtgaaag | ctgaagattt | cacaccagtt | ttcatggccc | cacctgtgca | ctatccccgg | 540 |
| ggagatgggg | aagagcaacg | agtggttatc | tttgaacaga | ctcagtatga | cgtgccctcg | 600 |
| ctggccaccc | acagcgccca | tctcaaagac | gaccagcgca | gcactccgga | cagcacatac | 660 |
| agcgagagct | tcaaggacgc | agccacagag | aaatttcgga | gtgcttcagt | tggggctgag | 720 |
| gagtacatgt | atgatcagac | atcaagtggc | acatttcagt | acaccctgga | agccaccaaa | 780 |
| tctctccgtc | agaagcaggg | ggagggcccc | atgacctacc | tcaacaaagg | acagttctat | 840 |
| gccataacac | tcagcgagac | cggagacaac | aaatgcttcc | gacacccat | cagcaaagtc | 900 |
| aggagtgtgg | tgatggtggt | cttcagtgaa | gacaaaaaca | gagatgaaca | gctcaaatac | 960 |
| tggaaatact | ggcactctcg | gcagcatacg | gcgaagcaga | gggtccttga | cattgccgat | 1020 |
| tacaaggaga | gctttaatac | gattggaaac | attgaacaga | ttgcatataa | tgctgtttcc | 1080 |
| tttacctggg | acgtgaatga | agaggcgaag | atttttcatca | ccgtgaattg | cttgagcaca | 1140 |
| gatttctcct | cccaaaaagg | ggtgaaagga | cttcctttga | tgattcagat | tgacacatac | 1200 |
| agttataaca | atcgtagcaa | taaacccatt | catagagctt | attgccagat | caaggtcttc | 1260 |
| tgtgacaaag | gagcagaaag | aaaaatccga | gatgaagagc | ggaagcagaa | caggaagaaa | 1320 |
| gggaaaggcc | aggcatccca | aactcaatgc | aacagctcct | ctgatgggaa | gttggctgcc | 1380 |
| ataccttac | agaagaagag | tgacatcacc | tacttcaaaa | ccatgcctga | tctccactca | 1440 |
| cagccagctc | tcttcatacc | tgatgttcac | tttgcaaacc | tgcagaggac | cggacaggtg | 1500 |
| tattacaaca | cggatgatga | acgagaaggt | ggcagtgtcc | ttgttaaacg | gatgttccgg | 1560 |
| cccatggaag | aggagtttgg | tccagtgcct | tcaaagcaga | tgaaagaaga | agggacaaag | 1620 |
| cgagtgctct | tgtacgtgag | gaaggagact | gacgatgtgt | tcgatgcatt | gatgttgaag | 1680 |
| tctcccacag | tgaagggcct | gatggaagcg | atatctgaga | aatatgggct | gcccgtggag | 1740 |
| aagatagcaa | agctttacaa | gaaaagcaaa | aaaggcatct | tggtgaacat | ggatgacaac | 1800 |
| atcatcgagc | actactcgaa | cgaggacacc | ttcatcctca | acatggagag | catggtggag | 1860 |
| ggcttcaagg | tcacgctcat | ggaaatctag | ccctgggttt | ggcatccgct | ttggctggag | 1920 |
| ctctcagtgc | gttcctccct | gagagagaca | gaagcccag | ccccagaacc | tggagaccca | 1980 |
| tctcccccat | ctcacaactg | ctgttacaag | accgtgctgg | ggagtggggc | aagggacagg | 2040 |
| ccccactgtc | ggtgtgcttg | gcccatccac | tggcacctac | cacggagctg | aagcctgagc | 2100 |
| ccctcaggaa | ggtgccttag | gcctgttgga | ttcctattta | ttgcccacct | tttcctggag | 2160 |
| cccaggtcca | ggcccgccag | gactctgcag | gtcactgcta | gctccagatg | agaccgtcca | 2220 |
| gcgttccccc | ttcaagagaa | acactcatcc | cgaacagcct | aaaaaattcc | catcccttct | 2280 |
| ctctcacccc | tccatatcta | tctcccgagt | ggctggacaa | aatgagctac | gtctgggtgc | 2340 |

TABLE LII(a)-continued

Nucleotide sequence of transcript variant 202P5A05 v.2 (SEQ ID NO: 96)

```
agtagttata ggtggggcaa gaggtggatg cccactttct ggtcagacac ctttaggttg   2400
ctctggggaa ggctgtcttg ctaaatacct ccagggttcc cagcaagtgg ccaccaggcc   2460
ttgtacagga agacattcag tcaccgtgta attagtaaca cagaaagtct gcctgtctgc   2520
attgtacata gtgtttataa tattgtaata atatatttta cctgtggtat gtgggcatgt   2580
ttactgccac tggcctagag gagacacaga cctggagacc gttttaatgg gggttttttgc  2640
ctctgtgcct gttcaagaga cttgcagggt taggtagagg gcctttggga tgttaaggtg   2700
actgcagctg atgccaagat ggactctgca atgggcatac ctgggggctc gttccctgtc   2760
cccagaggaa gcccctctc cttctccatg gcatgactc tccttcgagg ccaccacgtt    2820
tatctcacaa tgatgtgttt tgcttgactt tcccttttgcg ctgtcttgtg ggaaaggtca   2880
ttctgtctga accccagct ccttctccag ctttggctgc gggcatggcc tgagctttct   2940
ggagagcctc tgcagggggt ttgccatcag ggccctgtgg ctgggtctgc tgcagagctc   3000
cttggctatc aggagaatcc tggacactgt actgtgcctc ccagtttaca aacacgccct   3060
ccatctcaag tggcccttta aaaggcctgc tgccatgtga gagctgtgaa cagctcagct   3120
ctgagtcggc aggctggggc ttcctcctgg gccaccagat ggaaggggg tattgtttgc    3180
ctcactcctg gatgctgcgt tttaaggaag tgagtgagaa agaatgtgcc aagatacctg   3240
gctcctgtga aaccagcctc aggagggaaa ctgggagaga gaagctgtgg tctcctgcta  3300
catgccctgg gagctggaag agaaaaacac tccctaaac aatcgcaaaa tgatgaacca    3360
tcatgggcca ctgttctctt tgaggggaca ggtttagggg tttgcgttcg cccttgtggg   3420
ctgaagcact agcttttttgg tagctagaca catcctgcac ccaaaggttc tctacaaagg  3480
cccagattttg tttgtaaagc actatgaccc ttacctggag gcccgctctc taagggcttc 3540
ctgcgctccc acatcatctg tccctgagat gcagagcagg atggagggtc tgcttctagc   3600
tcagctgttt ctccttgagg ttgcggagga attgaattga atgggacaga gggcaggtgc   3660
tgtggccaag aagatctccg agcagcagtg acggggcacc ttgctgtgtg tcctctgggc   3720
atgttaaccc ttctgtgggg ccaaaggttt gcatcgtgga tccagctgtg ctccagtctg   3780
tccctcctc ctccactctg actgccacgc cccggaccag cagcttgggg accctccagg    3840
gtactaatgg ggctctgttc tgagatggac aaattcagtg ttggaaatac atgttgtact   3900
atgcacttcc catgctccta gggttaggaa tagtttcaaa tatgattggc agacataaca   3960
acggcaaata ctcggactgg ggcataggac tccagagtag gaaaaagaca aaagatttgg   4020
cagcctgaca caggcaacct acccctctct ctccagcctc tttatgaaac tgtttgtttg    4080
ccagtcctgc cctaaggcag aagatgaatt gaagatgctg tgcatgtttc ctaagtcctt    4140
gagcaatcat ggtggtgaca attgccacaa gggatatgag gccagtgcca ccagagggtg   4200
gtgccaagtg ccacatccct tccgatccat tccctctgc atcctcggag cacccagtt     4260
tgcctttgat gtgtccgctg tgtatgttag ctgaactttg atgagcaaaa tttcctgagc   4320
gaaacactcc aaagagatag gaaaacttgc cgcctcttct tttttgtcca ttaatcaaac    4380
ttaaataagc ttaaaaaaaa tccatggaag atcatggaca tgtgaaatga gcatttttt    4440
cttttttttt tttaacaaag tctgaactga acagaacaag acttttttcct catacatctc  4500
caaattgttt aaacttactt tatgagtgtt tgtttagaag ttcggaccaa cagaaaaatg  4560
cagtcagatg tcatcttgga attggtttct aaaagagtaa ggcatgtccc tgcccagaaa   4620
cttaggaagc atgaaataaa tcaaatgttt attttccttc ttatttaaaa tcatgcaaat   4680
```

TABLE LII(a)-continued

Nucleotide sequence of transcript variant 202P5A05 v.2 (SEQ ID NO: 96)

```
gcaacagaaa tagagggttt gtgccaaatg ctatgaacgg cccttctta aagacaagca    4740 agggagattg atatatgtac aatttgctct catgttttaa aaaaaaaagg taaatctaac    4800
ttaatagttt tgtaaatggg agaggggaa tctataaact ataaatacag ttattttatt    4860
ttttgtacat ttttaaggag aaaaaaataa atattcataa cataagagga aaa           4913
```

TABLE LIII(a)

Nucleotide sequence alignment of 202P5A05 v.2 (SEQ ID NO: 97) and 202P5A05 v.1 (SEQ ID NO: 98)

```
v.1    1   TAATAAAAGACTAGTGGCCTTAGTGCCCATGCCCAGTGACCCTCCATTCA    50
           ||||||||||||||||||||||||||||||||||||||||||||||||||
v.2   33   taataaaagactagtggccttagtgcccatgcccagtgaccctccattca    82 v.1   51   ATACCCGAAGAGCCTACACCAGTGAGGATGAAGCCTGGAAGTCATACTTG   100
           ||||||||||||||||||||||||||||||||||||||||||||||||||
v.2   83   atacccgaagagcctacaccagtgaggatgaagcctggaagtcatacttg   132 v.1  101   GAGAATCCCCTGACAGCAGCCACCAAGGCCATGATGAGCATTAATGGTGA   150
           ||||||||||||||||||||||||||||||||||||||||||||||||||
v.2  133   gagaatcccctgacagcagccaccaaggccatgatgagcattaatggtga   182 v.1  151   TGAGGACAGTGCTGCTGCCCTCGGCCTGCTCTATGACTACTACAAGGTTC   200
           ||||||||||||||||||||||||||||||||||||||||||||||||||
v.2  183   tgaggacagtgctgctgccctcggcctgctctatgactactacaaggttc   232 v.1  201   CTCGAGACAAGAGGCTGCTGTCTGTAAGCAAAGCAAGTGACAGCCAAGAA   250
           ||||||||||||||||||||||||||||||||||||||||||||||||||
v.2  233   ctcgagacaagaggctgctgtctgtaagcaaagcaagtgacagccaagaa   282 v.1  251   GACCAGGAGAAAAGAAACTGCCTTGGCACCAGTGAAGCCCAGAGTAATTT   300
           ||||||||||||||||||||||||||||||||||||||||||||||||||
v.2  283   gaccaggagaaaagaaactgccttggcaccagtgaagcccagagtaattt   332 v.1  301   GAGTGGAGGAGAAAACCGAGTGCAAGTCCTAAAGACTGTTCCAGTGAACC   350
           ||||||||||||||||||||||||||||||||||||||||||||||||||
v.2  333   gagtggaggagaaaaccgagtgcaagtcctaaagactgttccagtgaacc   382 v.1  351   TTTCCCTAAATCAAGATCACCTGGAGAATTCCAAGCGGGAACAGTACAGC   400
           ||||||||||||||||||||||||||||||||||||||||||||||||||
v.2  383   tttccctaaatcaagatcacctggagaattccaagcgggaacagtacagc   432 v.1  401   ATCAGCTTCCCCGAGAGCTCTGCCATCATCCCGGTGTCGGGAATCACGGT   450
           ||||||||||||||||||||||||||||||||||||||||||||||||||
v.2  433   atcagcttccccgagagctctgccatcatcccggtgtcgggaatcacggt   482 v.1  451   GGTGAAAGCTGAAGATTTCACACCAGTTTTCATGGCCCCACCTGTGCACT   500
           ||||||||||||||||||||||||||||||||||||||||||||||||||
v.2  483   ggtgaaagctgaagatttcacaccagttttcatggccccacctgtgcact   532 v.1  501   ATCCCCGGGGAGATGGGGAAGAGCAACGAGTGGTTATCTTTGAACAGACT   550
           ||||||||||||||||||||||||||||||||||||||||||||||||||
v.2  533   atccccggggagatggggaagagcaacgagtggttatctttgaacagact   582 v.1  551   CAGTATGACGTGCCCTCGCTGGCCACCCACAGCGCCTATCTCAAAGACGA   600
           ||||||||||||||||||||||||||||||||||||||||||||||||||
v.2  583   cagtatgacgtgccctcgctggccacccacagcgcctatctcaaagacga   632 v.1  601   CCAGCGCAGCACTCCGGACAGCACATACAGCGAGAGCTTCAAGGACGCAG   650
           ||||||||||||||||||||||||||||||||||||||||||||||||||
v.2  633   ccagcgcagcactccggacagcacatacagcgagagcttcaaggacgcag   682 v.1  651   CCACAGAGAAATTTCGGAGTGCTTCAGTTGGGGCTGAGGAGTACATGTAT   700
           ||||||||||||||||||||||||||||||||||||||||||||||||||
v.2  683   ccacagagaaatttcggagtgcttcagttggggctgaggagtacatgtat   732 v.1  701   GATCAGACATCAAGTGGCACATTTCAGTACACCCTGGAAGCCACCAAATC   750
           ||||||||||||||||||||||||||||||||||||||||||||||||||
v.2  733   gatcagacatcaagtggcacatttcagtacaccctggaagccaccaaatc   782
```

TABLE LIII(a)-continued

Nucleotide sequence alignment of 202P5A05 v.2 (SEQ ID NO: 97)
and 202P5A05 v.1 (SEQ ID NO: 98)

```
v.1   751  TCTCCGTCAGAAGCAGGGGGAGGGCCCCATGACCTACCTCAACAAAGGAC   800
           ||||||||||||||||||||||||||||||||||||||||||||||||||
v.2   783  tctccgtcagaagcaggggagggccccatgacctacctcaacaaaggac    832 v.1   801  AGTTCTATGCCATAACACTCAGCGAGACCGGAGACAACAAATGCTTCCGA   850
           ||||||||||||||||||||||||||||||||||||||||||||||||||
v.2   833  agttctatgccataacactcagcgagaccggagacaacaaatgcttccga   882 v.1   851  CACCCCATCAGCAAAGTCAGGAGTGTGGTGATGGTGGTCTTCAGTGAAGA   900
           ||||||||||||||||||||||||||||||||||||||||||||||||||
v.2   883  caccccatcagcaaagtcaggagtgtggtgatggtggtcttcagtgaaga   932 v.1   901  CAAAAACAGAGATGAACAGCTCAAATACTGGAAATACTGGCACTCTCGGC   950
           ||||||||||||||||||||||||||||||||||||||||||||||||||
v.2   933  caaaaacagagatgaacagctcaaatactggaaatactggcactctcggc   982 v.1   951  AGCATACGGCGAAGCAGAGGGTCCTTGACATTGCCGATTACAAGGAGAGC   1000
           ||||||||||||||||||||||||||||||||||||||||||||||||||
v.2   983  agcatacggcgaagcagagggtccttgacattgccgattacaaggagagc   1032 v.1   1001 TTTAATACGATTGGAAACATTGAAGAGATTGCATATAATGCTGTTTCCTT   1050
           ||||||||||||||||||||||||||||||||||||||||||||||||||
v.2   1033 tttaatacgattggaaacattgaagagattgcatataatgctgtttcctt   1082 v.1   1051 TACCTGGGACGTGAATGAAGAGGCGAAGATTTTCATCACCGTGAATTGCT   1100
           ||||||||||||||||||||||||||||||||||||||||||||||||||
v.2   1083 tacctgggacgtgaatgaagaggcgaagattttcatcaccgtgaattgct   1132 v.1   1101 TGAGCACAGATTTCTCCTCCCAAAAAGGGGTGAAAGGACTTCCTTTGATG   1150
           ||||||||||||||||||||||||||||||||||||||||||||||||||
v.2   1133 tgagcacagatttctcctcccaaaaaggggtgaaaggacttcctttgatg   1182 v.1   1151 ATTCAGATTGACACATACAGTTATAACAATCGTAGCAATAAACCCATTCA   1200
           ||||||||||||||||||||||||||||||||||||||||||||||||||
v.2   1183 attcagattgacacatacagttataacaatcgtagcaataaacccattca   1232 v.1   1201 TAGAGCTTATTGCCAGATCAAGGTCTTCTGTGACAAAGGAGCAGAAAGAA   1250
           ||||||||||||||||||||||||||||||||||||||||||||||||||
v.2   1233 tagagcttattgccagatcaaggtcttctgtgacaaaggagcagaaagaa   1282 v.1   1251 AAATCCGAGATGAAGAGCGGAAGCAGAACAGGAAGAAAGGGAAAGGCCAG   1300
           ||||||||||||||||||||||||||||||||||||||||||||||||||
v.2   1283 aaatccgagatgaagagcggaagcagaacaggaagaaagggaaaggccag   1332 v.1   1301 GCCTCCCAAACTCAATGCAACAGCTCCTCTGATGGGAAGTTGGCTGCCAT   1350
           ||||||||||||||||||||||||||||||||||||||||||||||||||
v.2   1333 gcctcccaaactcaatgcaacagctcctctgatgggaagttggctgccat   1382 v.1   1351 ACCTTTACAGAAGAAGAGTGACATCACCTACTTCAAAACCATGCCTGATC   1400
           ||||||||||||||||||||||||||||||||||||||||||||||||||
v.2   1383 acctttacagaagaagagtgacatcacctacttcaaaaccatgcctgatc   1432 v.1   1401 TCCACTCACAGCCAGTTCTCTTCATACCTGATGTTCACTTTGCAAACCTG   1450
           ||||||||||||||||||||||||||||||||||||||||||||||||||
v.2   1433 tccactcacagccagttctcttcatacctgatgttcactttgcaaacctg   1482 v.1   1451 CAGAGGACCGGACAGGTGTATTACAACACGGATGATGAACGAGAAGGTGG   1500
           ||||||||||||||||||||||||||||||||||||||||||||||||||
v.2   1483 cagaggaccggacaggtgtattacaacacggatgatgaacgagaaggtgg   1532 v.1   1501 CAGTGTCCTTGTTAAACGGATGTTCCGGCCCATGGAAGAGGAGTTTGGTC   1550
           ||||||||||||||||||||||||||||||||||||||||||||||||||
v.2   1533 cagtgtccttgttaaacggatgttccggcccatggaagaggagtttggtc   1582 v.1   1551 CAGTGCCTTCAAAGCAGATGAAAGAAGAAGGGACAAAGCGAGTGCTCTTG   1600
           ||||||||||||||||||||||||||||||||||||||||||||||||||
v.2   1583 cagtgccttcaaagcagatgaaagaagaagggacaaagcgagtgctcttg   1632 v.1   1601 TACGTGAGGAAGGAGACTGACGATGTGTTCGATGCATTGATGTTGAAGTC   1650
           ||||||||||||||||||||||||||||||||||||||||||||||||||
v.2   1633 tacgtgaggaaggagactgacgatgtgttcgatgcattgatgttgaagtc   1682
```

TABLE LIII(a)-continued

Nucleotide sequence alignment of 202P5A05 v.2 (SEQ ID NO: 97) and 202P5A05 v.1 (SEQ ID NO: 98)

```
v.1  1651  TCCCACAGTGAAGGGCCTGATGGAAGCGATATCTGAGAAATATGGGCTGC  1700
           ||||||||||||||||||||||||||||||||||||||||||||||||||
v.2  1683  tcccacagtgaagggcctgatggaagcgatatctgagaaatatgggctgc  1732 v.1  1701  CCGTGGAGAAGATAGCAAAGCTTTACAAGAAAAGCAAAAAAGGCATCTTG  1750
           ||||||||||||||||||||||||||||||||||||||||||||||||||
v.2  1733  ccgtggagaagatagcaaagctttacaagaaaagcaaaaaaggcatcttg  1782 v.1  1751  GTGAACATGGATGACAACATCATCGAGCACTACTCGAACGAGGACACCTT  1800
           ||||||||||||||||||||||||||||||||||||||||||||||||||
v.2  1783  gtgaacatggatgacaacatcatcgagcactactcgaacgaggacacctt  1832 v.1  1801  CATCCTCAACATGGAGAGCATGGTGGAGGGCTTCAAGGTCACGCTCATGG  1850
           ||||||||||||||||||||||||||||||||||||||||||||||||||
v.2  1833  catcctcaacatggagagcatggtggagggcttcaaggtcacgctcatgg  1882 v.1  1851  AAATCTAGCCCTGGGTTTGGCATCCGCTTTGGCTGGAGCTCTCAGTGCGT  1900
           ||||||||||||||||||||||||||||||||||||||||||||||||||
v.2  1883  aaatctagccctgggtttggcatccgctttggctggagctctcagtgcgt  1932 v.1  1901  TCCTCCCTGAGAGAGACAGAAGCCCCAGCCCCAGAACCTGGAGACCCATC  1950
           ||||||||||||||||||||||||||||||||||||||||||||||||||
v.2  1933  tcctccctgagagagacagaagccccagccccagaacctggagacccatc  1982 v.1  1951  TCCCCCATCTCACAACTGCTGTTACAAGACCGTGCTGGGGAGTGGGGCAA  2000
           ||||||||||||||||||||||||||||||||||||||||||||||||||
v.2  1983  tcccccatctcacaactgctgttacaagaccgtgctggggagtggggcaa  2032 v.1  2001  GGGACAGGCCCCACTGTCGGTGTGCTTGGCCCATCCACTGGCACCTACCA  2050
           ||||||||||||||||||||||||||||||||||||||||||||||||||
v.2  2033  gggacaggccccactgtcggtgtgcttggcccatccactggcacctacca  2082 v.1  2051  CGGAGCTGAAGCCTGAGCCCCTCAGGAAGGTGCCTTAGGCCTGTTGGATT  2100
           ||||||||||||||||||||||||||||||||||||||||||||||||||
v.2  2083  cggagctgaagcctgagcccctcaggaaggtgccttaggcctgttggatt  2132 v.1  2101  CCTATTTATTGCCCACCTTTTCCTGGAGCCCAGGTCCAGGCCCGCCAGGA  2150
           ||||||||||||||||||||||||||||||||||||||||||||||||||
v.2  2133  cctatttattgcccaccttttcctggagcccaggtccaggcccgccagga  2182 v.1  2151  CTCTGCAGGTCACTGCTAGCTCCAGATGAGACCGTCCAGCGTTCCCCCTT  2200
           ||||||||||||||||||||||||||||||||||||||||||||||||||
v.2  2183  ctctgcaggtcactgctagctccagatgagaccgtccagcgttccccctt  2232 v.1  2201  CAAGAGAAACACTCATCCCGAACAGCCTAAAAAATTCCCATCCCTTCTCT  2250
           ||||||||||||||||||||||||||||||||||||||||||||||||||
v.2  2233  caagagaaacactcatcccgaacagcctaaaaaattcccatcccttctct  2282 v.1  2251  CTCACCCCTCCATATCTATCTCCCGAGTGGCTGGACAAAATGAGCTACGT  2300
           ||||||||||||||||||||||||||||||||||||||||||||||||||
v.2  2283  ctcacccctccatatctatctcccgagtggctggacaaaatgagctacgt  2332 v.1  2301  CTGGGTGCAGTAGTTATAGGTGGGGCAAGAGGTGGATGCCCACTTTCTGG  2350
           ||||||||||||||||||||||||||||||||||||||||||||||||||
v.2  2333  ctgggtgcagtagttataggtggggcaagaggtggatgcccactttctgg  2382 v.1  2351  TCAGACACCTTTAGGTTGCTCTGGGGAAGGCTGTCTTGCTAAATACCTCC  2400
           ||||||||||||||||||||||||||||||||||||||||||||||||||
v.2  2383  tcagacacctttaggttgctctggggaaggctgtcttgctaaataccctcc  2432 v.1  2401  AGGGTTCCCAGCAAGTGGCCACCAGGCCTTGTACAGGAAGACATTCAGTC  2450
           ||||||||||||||||||||||||||||||||||||||||||||||||||
v.2  2433  agggttcccagcaagtggccaccaggccttgtacaggaagacattcagtc  2482 v.1  2451  ACCGTGTAATTAGTAACACAGAAAGTCTGCCTGTCTGCATTGTACATAGT  2500
           ||||||||||||||||||||||||||||||||||||||||||||||||||
v.2  2483  accgtgtaattagtaacacagaaagtctgcctgtctgcattgtacatagt  2532 v.1  2501  GTTTATAATATTGTAATAATATATTTTACCTGTGGTATGTGGGCATGTTT  2550
           ||||||||||||||||||||||||||||||||||||||||||||||||||
v.2  2533  gtttataatattgtaataatatattttacctgtggtatgtgggcatgttt  2582
```

TABLE LIII(a)-continued

Nucleotide sequence alignment of 202P5A05 v.2 (SEQ ID NO: 97) and 202P5A05 v.1 (SEQ ID NO: 98)

```
v.1  2551  ACTGCCACTGGCCTAGAGGAGACACAGACCTGGAGACCGTTTTAATGGGG  2600
           ||||||||||||||||||||:|||||:||||| || || |||||||||||
v.2  2583  actgccactggcctagaggagacacagacctggagaccgttttaatgggg  2632 v.1  2601  GTTTTTGCCTCTGTGCCTGTTCAAGAGACTTGCAGGGCTAGGTAGAGGGC  2630
           |||||||||||||||||||| ||||:||||||::| || ||||||| |||
v.2  2633  gttttcctctgtgcctgttcaagagacttgcagggctaggtagagggc    2682 v.1  2651  CTTTGGGATGTTAAGGTGACTGCAGCTGATGCCAAGATGGACTCTGCAAT  2700
           |||||||||||||||||||| ||||| |||||||| | || |||||| |||
v.2  2683  ctttgggatgttaaggtgactgcagctgatgccaagatggactctgcaat  2732 v.1  2701  GGGCATACCTGGGGGCTCGTTCCCTGTCCCCAGAGGAAGCCCCCTCTCCT  2750
           ||||||||||||||||||||| |||||| ||||::| || |||||| |||
v.2  2733  gggcatacctgggggctcgttccctgtccccagaggaagccccctctcct  2782 v.1  2751  TCTCCATGGGCATGACTCTCCTTCGAGGCCACCACCTTTATCTCACAATG  2800
           ||||||||||||||||||| |||||:||||||||:| |||||||||:|||
v.2  2783  tctccatgggcatgactctccttcgaggccaccacgtttatctcacaatg  2832 v.1  2801  ATGTGTTTTGCTTGACTTTCCCTTTGCGCTGTCTCGTGGGAAAGGTCATT  2850
           ||||||||||||||||||||||| |||||||||||| |||||||||||||
v.2  2833  atgtgttttgcttgactttcccttttgcgctgtctcgtgggaaaggtcatt  2882 v.1  2851  CTGTCTGAGACCCCAGCTCCTTCTCCAGCTTTGGCTGCGGGCATGGCCTG  2900
           |||||||||||||||||||| |||| |||||||| |||||||||||||||
v.2  2883  ctgtctgagacccccagctccttctccagctttggctgcgggcatggcctg  2932 v.1  2901  AGCTTTCTGGAGAGCCTCTGCAGGGGGTTTGCCATCAGGGCCCTGTCCCT  2950
           ||||||||||||||||||||| |||| ||||||| | ||||||||||| |
v.2  2933  agctttctggagagcctctgcaggggggtttgccatcagggccctgtggct  2982 v.1  2951  GGGTCTGCTGCAGAGCTCCTTGGCTATCAGGAGAATCCTGGACACTGTAC  3000
           |||| |||| |||| ||||||||||| |||| |||| || ||||| | ||
v.2  2983  gggtctgctgcagagctccttggctatcaggagaatcctggacactgtac  3032 v.1  3001  TGTGCCTCCCAGTTTACAAACACGCCCTTCATCTCAAGTGGCCCTTTAAA  3050
           |||||||| ||||| ||||| |||||||||||||||||||||||||||||
v.2  3033  tgtgcctcccagtttacaaacacgcccttcatctcaagtggcccttttaaa  3082 v.1  3051  AGGCCTGCTGCCATGTGAGAGCTGTGAACAGCTCAGCTCTGAGTCGGCAG  3100
           |||||||| ||||| |||| |||| |||||||||||||||||||||||||
v.2  3083  aggcctgctgccatgtgagagctgtgaacagctcagctctgagtcggcag  3132 v.1  3101  GCTGGGGCTTCCTCCTGGGCCACCAGATGGAAAGGGGGTATTGTTTGCCT  3150
           ||||||||||| |||| ||||| |||||| |||| ||| |||| | || ||
v.2  3133  gctggggcttcctcctgggccaccagatggaaaggggggtattgtttgcct  3182 v.1  3151  CACTCCTGGATGCTGCGTTTTAAGGAAGTGAGTGAGAAAGAATGTGCCAA  3200
           |||||||| ||||||||||||||||||||| || :||||||||||||||||
v.2  3183  cactcctggatgctgcgttttaaggaagtgagtgagaaagaatgtgccaa  3232 v.1  3201  GATACCTGGCTCCTCTGAAACCAGCCTCAGGAGGGAAACTGGGAGAGAGA  3250
           || |||| |||| ||||||||||||:|||| |||| |||| |||| :|||
v.2  3233  gatacctggctcctgtgaaaccagcctcaggagggaaactgggagagaga  3282 v.1  3251  AGCTGTGGTCTCCTGCTACATGCCCTGGGAGCTGGAAGAGAAAAACACTC  3300
           ||||||||||||||:|||| :||||||| |||| :|||| ||||||||||
v.2  3283  agctgtggtctcctgctacatgccctgggagctggaagagaaaaacactc  3332 v.1  3301  CCCTAAACAATCGCAAAATGATGAACCATCATGGGCCACTGTTCTCTTTG  3350
           |||||||||||||||||||||||||||||| || |||||||||||| |||
v.2  3333  ccctaaacaatcgcaaaatgatgaaccatcatgggccactgttctctttg  3382 v.1  3351  AGGGGACAGGTTTAGGGGTTTGCGTTCGCCCTTGTGGGCTGAAGCACTAG  3400
           |||| |||| ||||| ||||| |||| |||||||||||||||||||||||
v.3  3383  aggggacaggtttaggggtttgcgttcgcccttgtgggctgaagcactag  3432 v.1  3401  CTTTTTGGTAGCTAGACACATCCTGCACCCAAAGGTTCTCTACAAAGGCC  3450
           |||||||| ||||||||||||||||||||||| || | |||||||| | |
v.2  3433  cttttggtagctagacacatcctgcacccaaaggttctctacaaaggcc  3482
```

TABLE LIII(a)-continued

Nucleotide sequence alignment of 202P5A05 v.2 (SEQ ID NO: 97) and 202P5A05 v.1 (SEQ ID NO: 98)

```
v.1  3451  CAGATTTGTTTGTAAAGCACTTTGACTCTTACCTGGAGGCCCGCTCTCTA  3500
           ||||||||||||||||||||||||||||||||||||| ||||| ||||||
v.2  3483  cagatttgtttgtaaagcactttgactcttacctggaggcccgctctcta  3532 v.1  3501  AGGGCTTCCTGCGCTCCCACCTCATCTGTCCCTGAGATGCAGAGCAGGAT  3550
           ||||| |||||||||||||||||||||||||||||| || |||||| |||
v.2  3533  agggcttcctgcgctcccacctcatctgtccctgagatgcagagcaggat  3582 v.1  3551  GGAGGGTCTGCTTCTAGCTCAGCTGTTTCTCCTTGAGGTTGCGGAGGAAT  3600
           ||||| |||| ||||||||||||||||| |||||| || | ||||||||| ||
v.2  3503  ggagggtctgcttctagctcagctgtttctccttgaggttgcggaggaat  3632 v.1  3601  TGAATTGAATGGGACAGAGGGCAGGTGCTGTGGCCAAGAAGATCTCCGAG  3650
           ||||| |||| |||||||||||||| |||| || ||||||||||||||||| ||
v.2  3633  tgaattgaatgggacagagggcaggtgctgtggccaagaagatctccgag  3682 v.1  3651  CAGCAGTGACGGGCCACCTTGCTGTGTGTCCTCTGGGCATGTTAACCCTT  3700
           | |||||||| |||||||||||||| |||| || || || ||||||||||||||
v.2  3683  cagcagtgacgggccaccttgctgtgtgtcctctgggcatgttaaccctt  3732 v.1  3701  CTGTGGGGCCAAAGGTTTGCATCGTGGATCCAGCTGTGCTCCAGTCTGTC  3750
           | |||||||||||||||||||||||||||||||||||||||||||||||
v.2  3733  ctgtggggccaaaggtttgcatcgtggatccagctgtgctccagtctgtc  3782 v.1  3751  CCCTCCTCCTCCACTCTGACTGCCACGCCCCGGACCAGCAGCTTGGGGAC  3800
           | ||||||||||||||||||||| |||| |||||||||||||||||||||
v.2  3783  ccctcctcctccactctgactgccacgccccggaccagcagcttggggac  3832 v.1  3801  CCTCCAGGGTACTAATGGGGCTCTGTTCTGAGATGGACAAATTCAGTGTT  3850
           | |||||||||||||||||||||| |||| |||||||||||||||||||| ||
v.2  3833  cctccagggtactaatggggctctgttctgagatggacaaattcagtgtt  3882 v.1  3851  GGAAATACATGTTGTACTATGCACTTCCCATGCTCCTAGGGTTAGGAATA  3900
           ||||||||||| |||||||||||| |||| |||| || |||||||||||| ||
v.2  3883  ggaaatacatgttgtactatgcacttcccatgctcctagggttaggaata  3932 v.1  3901  GTTTCAAACATGATTCGCAGACATAACAACGGCAAATACTCGGACTGGGG  3950
           ||||| |||| |||| |||||| |||| |||| |||| || | ||||||||||
v.2  3933  gtttcaaacatgattggcagacataacaacggcaaatactcggactgggg  3982 v.1  3951  CATAGGACTCCAGAGTAGGAAAAAGACAAAAGATTTGGCAGCCTGACACA  4000
           ||||| |||||||||||||||||||||||||||||||||||||||||||| 
v.2  3983  cataggactccagagtaggaaaaagacaaaagatttggcagcctgacaca  4032 v.1  4001  GGCAACCTACCCCTCTCTCTCCAGCCTCTTTATCAAACTGTTTGTTTGCC  4050
           ||||||||| |||| |||||||| |||||||||  |||||||| ||||||
v.2  4033  ggcaacctaccoctctctcttcagcctctttatgaaactgtttgtttgcc  4082 v.1  4061  AGTCCTGCCCTAAGGCAGAACATCAATTGAAGATGCTGTGCATGTTTCCT  4100
           ||||||||||||||| |||| |||| |||| |||| || | || |||||||:||
v.3  4083  agtcctgccctaaggcagaacatcaattgaagatgctgtgcatgtttcct  4132 v.1  4101  AAGTCCTTGAGCAATCATGGTGGTGACAATTGCCACAAGGGATATGAGGC  4150
           | ||||||||:||||| |||| |||| |||||||||| |||| |||||||||
v.2  4133  aagtccttgagcaatcatggtggtgacaattgccacaagggatatgaggc  4182 v.1  4151  CAGTGCCACCAGAGGGTGGTGCCAAGTGCCACATCCCTTCCGATCCATTC  4200
           |||||||||| |||| |||||:|||| |||| || ||||||||||| ||
v.2  4183  cagtgccaccagagggtggtgccaagtgccacatcccttccgatccattc  4232 v.1  4201  CCCTCTGCATCCTCGGAGCACCCCAGTTTGCCTTTGATGTGTCCGCTGTG  4250
           ||||||||||||| |||||||||||||||||||| | |||||||||||||
v.2  4233  ccctctgcatcctcggagcaccccagtttgcctttgatgtgtccgctgtg  4282 v.1  4251  TATGTTAGCTGAACTTTGATGAGCAAAATTTCCTGAGCGAAACACTCCAA  4300
           ||||| |||||||||||| ||||||||||| ||||||| ||||||||||| 
v.2  4283  tatgttagctgaactttgatgagcaaaatttcctgagcgaaacactccaa  4332 v.1  4301  AGAGATAGGAAAACTTGCCGCCTCTTCTTTTTTGTCCCTTAATCAAACTC  4350
           ||||| ||| |||| ||||||||||||| |||||| ||||||:||
v.2  4333  agagataggaaaacttgccgcctcttcttttttgtcccttaatcaaactc  4382
```

TABLE LIII(a)-continued

Nucleotide sequence alignment of 202P5A05 v.2 (SEQ ID NO: 97) and 202P5A05 v.1 (SEQ ID NO: 98)

```
v.1   4351  AAATAAGCTTAAAAAAAATCCATGGAAGATCATGGACATGTGAAATGAGC  4400
            ||||||||||||||||||||||||||||||||| || |||| |||||||| |
v.2   4383  aaataagcttaaaaaaaatccatggaagatcatggacatgtgaaatgagc  4432 v.1   4401  ATTTTTTTCTTTTTTTTTTTTAACAAAGTCTGAACTGAACAGAACAAGAC  4450
            |||||||||||||||| ||||| |||| |||||||| | || |||| | || |
v.2   4433  atttttttctttttttttttttaacaaagtctgaactgaacagaacaagac  4482 v.1   4451  TTTTTCCTCATACATCTCCAAATTGTTTAAACTTACTTTATGAGTGTTTG  4500
            ||||  ||||||||||||||| ||||  ||:||||||||||  |||| | || |
v.2   4483  tttttcctcatacatctccaaattgtttaaacttactttatgagtgtttg  4532 v.1   4501  TTTAGAAGTTCGGACCAACAGAAAAATGCAGTCAGATGTCATCTTGGAAT  4550
            |||||||||  ||||  |||||||||||||:| || ||||  |||| | || ||
v.2   4533  tttagaagttcggaccaacagaaaaatgcagtcagatgtcatcttggaat  4582 v.1   4551  TGGTTTCTAAAAGAGTAAGGCATGTCCCTGCCCAGAAACTTAGGAAGCAT  4600
            |||  |||||||  ||||  |||||||||||||||||:|||:| ||:||
v.2   4583  tggtttctaaaagagtaaggcatgtccctgcccagaaacttaggaagcat  4632 v.1   4601  GAAATAAATCAAATGTTTATTTTCCTTCTTATTTAAAATCATGCAAATGC  4650
            |||  |||  ||||:||||||||||| || |  ||  ||||:||||||||||
v.2   4633  gaaataaatcaaatgtttattttccttcttatttaaaatcatgcaaatgc  4682 v.1   4651  AACAGAAATAGAGGGTTTGTGCCAAATGCTATGAACGGCCCTTTCTTAAA  4700
            |||  |||  ||||:|||||||||| || |  || ||||:||||||||||||
v.2   4683  aacagaaatagagggtttgtgccaaatgctatgaacggcccctttcttaaa  4732 v.1   4701  GACAAGCAAGGGAGATTGATATATGTACAATTTGCTCTCATGTTTT       4746
            | ||||  ||||:||||:|||||  ||||  |||| |||||||||||
v.2   4733  gacaagcaagggagattgatatatgtacaatttgctctcatgttttt     4778
```

TABLE LIV(a)

Peptide sequences of protein coded by 202P5A05 v.2 (SEQ ID NO: 99)

```
MSQESDNNKR LVALVPMPSD PPFNTRRAYT SEDEAWKSYL ENPLTAATKA MMSINGDECS    60

AAALGLLYDY YKVPRCKRLL SVSKASDSQE DQEKRNCLGT SEAQSNLSGG ENRVQVLKTV  120

PVNLSLNQBH LENSKREQYS ISFPESSALT PVSGITVVKA EDFTEVFMAP PVHYPRGDGE  180

EQRVVTFEQT QYDVPSLATH SAYLKDDQRS TPDSTYSESF KDAATEKFRS ASVCAEEYMY  240

DQTSSGTFQY TLEATKSLRQ KQGEGPMTYL NKGQFYAITS SERGDNNCFR HPISKVRSVV  300

MVVFSEDKNR DEQLKYWKYW HRSQETAKQR VLDIADYKES FNTIGKTEET AYNAVSETND  360

VNEEAKIFIT VNCLSTDFSS QKGVKGLTLM TQIDTYSYNN RSNKPIHRAY CQIKVFCDKG  420

ZERKIRDEER KQNRKKCKCQ ASQTQCNSSS DCKLAATFLQ KKSDITYFKT MPDLHSQPVL  480

FIPDVHFANL QRTGQVYYNT DDEREGGSVL VKRMFRPMEF RFGPVPSKQM KEEGVKRVLL  540

YVRKETDDVF DALMLKSPTV KGLMEAISEK YGLPVEKIAK LYKKSKKGIL VNMDDNIIEH  600

YSNEDTFILN MESMVEGFKV TLMEI                                         625
```

TABLE LV(a)

Amino acid sequence alignment of 202P5A05 v.2 (SEQ ID NO: 100) and 202P5A05 v.1 (SEQ ID NO: 101)

```
v.1    1   MPSDPPFNTRRAYTSEDEAWKSYLENPLTAATKAMKSINGDEDSAAALGL    50
           ||||||||||||||||||||| ||||||||||||||||||||:|| ||| |
v.2   17   MPSDPPFNTRRAYTSEDEAWKSYLENPLTAATKAMKSINGDEDSAAALGL    60 v.1   51   LYDYYKVPRDKRLLSVSKASDSQEDQEKRNCLGESEAQSNLSGGENRVQV   100
           |||||||||||| ||||  |||| ||||||| ||||||  |||:||||  |||
v.2   67   LYDYYKVPRDKRLLSVSKASDSQEDQEKRNCLGESEAQSNLSGGENRVQV   166 v.1  101   LKTVPVNLSLNQDHLENSKREQYSISFPESSAIEPVSGETVVKAEDFTPV   130
           |||| ||||  |||| ||||| |||||| |||| || ||| ||| | ||||
v.2  117   LKTVPVNLSLNQDHLENSKREQYSISFPESSAIEPVSGETVVKAEDFTPV   216 v.1  151   FMAPPVHYPRGDEEQRVVIFECTOYDVFSLATHSAYLKDDQRSTPDSTY   200
           ||||:|||||||  |||||||||||  |||||||||||||  ||||||||||||
v.2  167   FMAPPVHYPRGDEEQRVVIFECTOYDVFSLATHSAYLKDDQRSTPDSTY   216 v.1  201   SESFKDAAFEKFRSASVGAEEYMYDQTSSGTFQYTLEATKSLRQKQGEGP   250
           |||||||||| ||||  |||||||||||||:|| |||||||||||||||||
v.2  217   SESFKDAAFEKFRSASVGAEEYMYDQTSSGTEQYTLEATKSLRQKQGEGP   286 v.1  251   MTYLNKGQFYAITLSETGDNKCFRHPISKVRSVVMVVFSEDKNRDEQLKY   300
           ||| |||| |||||||||||||||||||||||||||||||||||||||||||||
v.2  267   MTYLNKGQFYAITLSETGDNKCFRHPISKVRSVVMVVFSEDKNRDEQLKY   316 v.1  301   WKYWFSRQHTAKQRVLDLADYKESFNTTGNTEETAYNAVSFTWDVNEEAK   350
           ||| ||||  |||||||||||||| |||||||||||||  |||||||||||||
v.2  317   WKYWFSRQHTAKQRVLDLADYKESFNTTGNTEETAYNAVSFTWDVNEEAK   366 v.1  351   TFZTVNCLSTDFSSQKGVKGLPLMIQIDPYSYNNRSKKPIHRAYCQIKVF   400
           || ||||||||||||||| |||||||||||| ||||||||||||||||||||
v.2  367   TFZTVNCLSTDFSSQKGVKGLPLMIQIDPYSYNNRSKKPIHRAYCQIKVF   416 v.1  401   CDKGAERKTRDEERKQNRKKGKGQASQTQCKSSSDGKLAATPLQKKSDIT   450
           |||||||||| || |||||:|||||||||| |||| ||||  ||||||||
v.2  417   CDKGAERKTRDEERKQNRKKGKGQASQTQCKSSSDGKLAATPLQKKSDIT   466 v.1  451   YFKTMPDIHSQPVLFTPDVHFANLQRTGQVYYNTDDEREGGSVLVKRMFR   500
           |||| || | |||| |||||||||||||||||||||||||||||||||||||
v.2  467   YFKTMPDIHSQPVLFTPDVHFANLQRTGQVYYNTDDEREGGSVLVKRMFR   466 v.1  501   PMEEEFGPVPSKQMKEEGTKRVLLYVRKETDDVFDALMLKSFTVKGLMEA   550
           || |||||||||||||||| |||||:|||| ||||||| | ||||||
v.2  517   PMEEEFGPVPSKQMKEEGTKRVLLYVRKETDDVFDALMLKSFTVKGLMEA   566 v.1  551   ISEKYGLPVEKIAKLYKKSKKGILVNMDDNIIEHYSNEDTFILNMESMVE   600
           |||| || |||| | ||:||||||||||| |||| ||||||:||:|||||
v.2  567   ISEKYGLPVEKIAKLYKKSKKGILVNMDDNIIEHYSNEDTFILNMESMVE   616 v.1  601   GFKVTLMEI                                          609
           ||||||| ||
v.2  617   GFKVTLMEI                                          625
```

TABLE LII(b)

Nucleotide sequence of transcript variant 202P5A05 v.3 (SEQ ID NO: 102)

```
attggatcaa acatgtcaca agagtcggac aagtaagtgg atcacacgcg ccggctgctg    60
ctactactac cactttgggc tgatggcaac tgtaataaaa gactagtggc cttagtgccc   120
atgcccagtg accctccatt caatacccga agagcctaca ccagtgagga tgaagcctgg   180
aagtcatact tggagaatcc cctgacagca gccaccaagg ccatgatgag cattaatggt   240
gatgaggaca gtgctgctgc cctcggcctg ctctatgact actacaaggt tcctcgagac   300
aagaggctgc tgtctgtaag caaagcaagt gacagccaag aagaccagga gaaagaaac    360
tgccttggca ccagtgaagc ccagagtaat ttgagtggag gagaaaaccg agtgcaagtc   420
```

TABLE LII(b)-continued

Nucleotide sequence of transcript
variant 202P5A05 v.3 (SEQ ID NO: 102)

```
ctaaagactg ttccagtgaa cctttccta  aatcaagatc acctggagaa ttccaagcgg   480
gaacagtaca gcatcagcta ccccgagagc tctgccatca tcccggtgtc gggaatcacg   540
gtggtgaaag ctgaagattt cacaccagtt ttcatggccc cacctgtgca ctatccccgg   600
ggagatgggg aagagcaacg agtggttatc tttgaacaga ctcagtatga cgtgccctcg    60
ctggccaccc acagcgccta tctcaaagac gaccagcgca gcactccgga cagcacatac   720
agcgagagct tcaaggacgc agccacagag aaatttcgga gtgcttcagt tggggctgag   780
gagtacatgt atgatcagac atcaagtggc acatttcagt acaccctgga agccaccaaa   840
tctctccgtc agaagcaggg ggagggcccc atgacctacc tcaacaaagg acagttctct   900
gccataacac tcagcgagac cggagacaac aaatgcttcc gacaccccat cagcaaagtc  1020
tggaaatact ggcactctcg gcagcatacg gcgaagcaga gggtccttga cattgccgat  1080
tacaaggaga gctttaatac gattggaaac attgaagaga ttgcatataa tgctgtttcc  1140
tttacctggg acgtgaatga agaggcgaag attttcatca ccgtgaattg cttgagcaca  1200
gatttctcct cccaaaaagg ggtgaaagga cttcctttga tgattcagat tgacacatac  1260
agttataaca atcgtagcaa taaacccatt catagagctt attgccagat caaggtcttc  1320
tgtgacaaag gagcagaaag aaaaatccga gatgaagagc ggaagcagaa caggaagaaa  1380
gggaaaggcc aggcctccca aactcaatgc aacagctcct ctgatgggaa gttggctgcc  1440
atacctttac agaagaagag tgacatcacc tacttcaaaa ccatgcctga tctccactca  1500
cagccagttc tcttcatacc tgatgttcac tttgcaaacc tgcagaggac cggacaggtg  1560
tattacaaca cggatgatga acgagaaggt ggcagtgtcc ttgttaaacg gatgttccgg  1620
cccatggaag aggagtttgg tccagtgcct tcaaagcaga tgaaagaaga agggacaaag  1680
cgagtgctct tgtacgtgag gaaggagact gacgatgtgt tcgatgcatt gatgttgaag  1740
tctcccacag tgaagggcct gatggaagcg atatctgaga aatatgggct gcccgtggag  1800
aagatagcaa agctttacaa gaaaagcaaa aaaggcatct tggtgaacat ggatgacaac  1860
atcatcgagc actactcgaa cgaggacacc ttcatcctca acatggagag catggtggag  1920
ggcttcaagg tcacgctcat ggaaatctag ccctgggttt ggcatccgct ttggctggag  1980
ctctcagtgc gttcctccct gagagagaca gaagcccccag ccccagaacc tggagaccca  2040
tctcccccat ctcacaactg ctgttacaag accgtgctgg ggagtggggc aagggatagg  2100
ccccactgtc ggtgtgcttg gcccatccac tggcacctac cacggagctg aagcctgagc  2160
ccctcaggaa ggtgccttag gcctgttgga ttcctattta ttgcccacct tttcctggag  2220
cccaggtcca ggcccgccag gactatgcag gtcactgcta gctccagatg agaccgtcca  2280
gcgttccccc ttcaagagaa acactcatcc cgaacagcct aaaaaattcc catcccttct  2340
ctctcacccc tccatatcta tctcccgagt ggctggacaa aatgagctac gtctgggtgc  2400
agtagttata ggtggggcaa gaggtggatg cccactttct ggtcagacac ctttaggttg  2460
ctctggggaa ggctgtcttg ctaaatacct ccagggttcc cagcaagtgg ccaccaggcc  2520
ctgtacagga agacattcag tcaccgtgta attagtaaca cagaaagtct gcctgtctgc  2580
attgtacata gtgtttataa tattgtaata atatatttta cctgtggtat gtgggcatgt  2640
ctactgccac tggcctagag gagacacaga cctggagacc gttttaatgg gggtttgtgc  2700
ctctgtgccc gttcaagaga cttgcagggc taggtagagg gcctttggga tgttaaggtg  2760
actgcagctg atgccaagat ggactctgca atgggcatac ctgggggctc gttccctgtc  2820
```

TABLE LII(b)-continued

Nucleotide sequence of transcript
variant 202P5A05 v.3 (SEQ ID NO: 102)

```
cccagaggaa gcccctctc cttctccatg ggcatgactc tccttcgagg ccaccacgtt  2880
tatctcacaa tgatgtgttt tgcttgactt tcccttttgcg ctgtctcgtg ggaaaggtca  2940
ttctgtctga gaccccagct ccttctccag ctttggctgc gggcatggcc tgagctttct  3000
ggagagcctc tgcaggggt ttgccatcag ggccctgtgg ctgggtctgc tgcagagctc  3060
cttggctatc aggagaatcc cggacactgt actgtgcctc ccagtttaca aacacgccct  3120
tcatctcaag tggcccttta aaaggcctgc tgccatgtga gagctgtgaa cagctcagct  3180
ctgagtcggc aggctggggc ctcctcctgg gccaccagat ggaaggggg tattgtttgc  3240
ctcactcctg gatgctgcgt tttaaggaag tgagtgagaa agaatgtgcc aagatacctg  3300
gctcctgtga aaccagcctc aggagggaaa ctgggagaga gaagctgtgg tctcctgcta  3360
catgccctgg gagctggaag agaaaaacac tcccctaaac aatcgcaaaa tgatgaacca  3420
tcatgggcca ctgttctctt tgaggggaca ggtttagggg tttgcgttcg cccttgtggg  3480
ctgaagcact agcttttttgg tagctagaca catcctgcac ccaaaggttc tctacaaagg  3540
cccagatttg tttgtaaagc actttgactc ttacctggag gcccgctctc taagggcttc  3600
ctgcgctccc accttatctg tccctgagat gcagagcagg atggagggtc tgcttctagc  3660
tcagctgtta ctccttgagg ttgcggagga attgaattga atgggacaga gggcaggtgc  3720
tgtggccaag aagatctccg agcagcagtg acggggcacc ttgctgtgtg tcctctgggc  3780
atgttaaccc ttctgtgggg acaaaggttt gcatcgtgga tccagctgtg ctccagtctg  3840
tccctcctc ctccactctg actgccacgc cccggaccag cagcttgggg accctccagg  3900
gtactaatgg ggtctgttc cgagatggac aaattcagtg ttggaaatac atgttgtact  3960
atgcacttcc catgctccta gggttaggaa tagtttcaaa catgattggc agacataaca  4020
acggcaaata cccggactgg ggcataggac tccagagtag gaaaaagaca aaagatttgg  4080
cagcctgaca caggcaacct accctctct ctccagcctc tttatgaaac tgtttgtttg  4140
ccagtcctgc cctaaggcag aagatgaatt gaagatgctg tgcatgtttc ctaagtcctt  4200
gagcaatcat ggtggtgaca attgccacaa gggatatgag gccagtgcca ccagagggtg  4260
gtgccaagtg ccacatccct tccgatccat tcccctctgc atcctcggag caccccagtt  4320
tgcctttgat gtgtccgctg tgtatgtaag ctgaactttg atgagcaaaa tttcctgagc  4380
gaaacactcc aaagagatag gaaaacttgc cgcctcttct tttttgtccc ttaatcaaac  4440
tcaaataagc ttaaaaaaaa tccatggaag atcatggaca tgtgaaatga gcattttttt  4500
cttttttttt tttaacaaag tctgaactga acagaacaag acttttttcct catacatctc  4560
caaattgttt aaacttactt tatgagtgtt tgtttagaag ttcggaccaa cagaaaaatg  4620
cagtcagatg tcatcttgga attggtttct aaaagagtaa ggcatgtccc tgcccagaaa  4680
cttaggaagc atgaaataaa tcaaatgttt attttccttc ttatttaaaa tcatgcaaat  4740
gcaacagaaa tagagggttt gtgccaaatg ctatgaacgg cccttcctta aagacaagca  4800
agggagattg atatatgtac aatttgctct catgttttaa aaaaaaaagg taaatgtaac  4860
ttaatagttt tgtaaatggg agaggggaa tctataaact ataaatacag ttattttttt  4920
ttttgtacat ttttaaggag aaaaaaataa atattcataa cataagagga aaa         4973
```

TABLE LIII(b)

Nucleotide sequence alignment of 202P5A05 v.3 (SEQ ID NO: 103)
and 202P5A05 v.1 (SEG ID NO: 104)

```
v.1    1  TAATAAAAGACTAGTGGCCTTAGTGCCCATGCCCAGTGACCCTCCATTCA    50
          || | ||||||:|| ||||| |||||:|||| |||| |||||
v.3   93  taataaaagactagtggccttagtgcccatgcccagtgaccctccattca   142 v.1   51  ATACCCGAAGAGCCTACACCAGTGAGGATGAAGCCTGGAAGTCATACTTG   100
          || | ||||||| |:||| |||| |||| |||| ||||| |||||||||
v.3  143  atacccgaagagcctacaccagtgaggatgaagcctggaagtcatacttg   192 v.1  101  CACAATCCCCTCACAGCAGCCACCAAGGCCATGATGAGCATTAATGGTGA   150
          || | ||||||| |:||| |||| |||| |||| |||||  ||||||||
v.3  193  gagaatcccctgacagcagccaccaaggccatgatgagcattaatggtga   242 v.1  151  TGAGGACAGTGCTGCTGCCCTCGGCCTGCTCTATGACTACTACAAGGTTC   200
          ||||||||||||| ||  |||||||||||||||||||||| :|| |||||
v.3  243  tgaggacagtgctgctgccctcggcctgctctatgactactacaaggttc   292 v.1  201  CTCGAGACAAGAGGCTGCTGTCTGTAAGCAAAGCAAGTGACAGCCAAGAA   250
          | ||||||||||||| |||| |||||||||||||||| || |||||  ||
v.3  293  ctcgagacaagaggctgctgtctgtaagcaaagcaagtgacagccaagaa   342 v.1  251  GACCAGGACAAAAGAAACTGCCTTGGCACCAGTGAAGCCCAGAGTAATTT   300
          ||||||| |||||||||||||||||||||||||||||||||||||||||
v.3  343  gaccaggagaaaagaaactgccttggcaccagtgaagcccagagtaattt   392 v.1  301  CAGTGGAGGAGAAAACCGAGTGCAAGTCCTAAAGACTGTTCCAGTGAACC   350
          |||| ||||||||||| |||||||||||||||||||||| |||||||| |||
v.3  393  gagtggaggagaaaaccgagtgcaagtcctaaagactgttccagtgaacc   442 v.1  351  TTTCCCTAAATCAAGATCACCTGGAGAATTCCAAGCGGGAACAGTACAGC   400
          ||||||||| |||| ||||| |||| ||||||||||| || ||||||||
v.3  443  tttccctaaatcaagatcacctggagaattccaagcgggaacagtacagc   492 v.1  401  ATCAGCTTCCCCCAGAGCTCTGCCATCATCCCGGTGTCGGGAATCACGGT   450
          |||| |||||||||||||||||||||| ||||| || |||||||||||
v.3  493  atcagcttccccgagagctctgccatcatcccggtgtcgggaatcacggt   542 v.1  451  GGTGAAAGCTGAAGATTTCACACCAGTTTTCATGGCGCCACCTGTGCACT   500
          ||| ||||||||||||||||||||||||||||||||  |  ||||||||
v.3  543  ggtgaaagctgaagatttcacaccagttttcatggccccacctgtgcact   592 v.1  501  ATCCCCGGGGAGATGGGGAAGAGCAACGAGTGGTTATCTTTGAACAGACT   550
          ||||||| |||| ||||| |||||||  || || |||||||||||||| |||||
v.3  593  atccccggggagatggggaagagcaatgagtggttatctttgaacagact   642 v.1  551  CAGTATGACGTGCCCTCGCTGGCCACCCACAGCGCCTATCTCAAAGACGA   600
          |||| | ||||||||||||||||||||||| ||||||||| |||||||| ||
v.3  643  cagtctgacgtgccctcgctggccacccacagcgcctatctcaaagacga   692 v.1  601  CCAGCCCAGCACTCCGGACAGCACATACAGCGAGAGCTTCAAGGACGCAG   650
          |||| | |||||||||||||||||||| ||||| ||||||||||||| ||
v.3  693  ccagcgcagcactccggacagcacatacagcgagagcttcaaggacgcag   742 v.1  651  CCACAGAGAAATTTCGGAGTGCTTCAGTTGGGGCTGAGGAGTACATGTAT   700
          |||||| |||||||||||||||||||||| |||||||||||||||||||
v.3  743  ccacagacaaatttcggagtgcttcagttggggctgaggagtacatgtat   792 v.1  701  GATCAGACATCAAGTGGCACATTTCACTACACCCTGGAAGCCACCAAATC   750
          ||||||||||||||||||||||||| ||| |||||||||||||||||| ||
v.3  793  gatcagacatcaagtggcacatttcagtacaccctggaagccaccaaatg   842 v.1  751  TCTCCCTCAGAAGCAGGGGGAGGGCCCCATGACCTACCTCAACAAAGGAC   800
          |||||| |||||||||||||||||||||||||||||||| ||||||||||
v.3  843  tctccgtcagaagcaggggagggccccatgacctacctcaacaaaggac   892 v.1  801  AGTTCTATGCCATAACACTCAGCGAGACCCGAGACAACAAATGCTTCCGA   850
          ||||||||||||| ||||||||||||||| |||||||||||||||||||
v.3  893  agttctatgccataatactcagcgagaccggagacaacaaatgcttccga   942 v.1  851  CACCCCATCAGCAAAGTCAGGAGTGTGGTGATGGTGGTCTTCAGTGAAGA   900
          |||||||||||||||||||||||||||||||| | ||||||||||| ||
v.3  943  caccccatcagcaaagtcaggagtgtggtgatggtggtcttcagtgaaga   992
```

TABLE LIII(b)-continued

Nucleotide sequence alignment of 202P5A05 v.3 (SEQ ID NO: 103) and 202P5A05 v.1 (SEG ID NO: 104)

```
v.1    901  CAAAAACAGAGATGAACAGCCCAAATACTGGAAATACTGGCACTCTCGGC   950
            |||||  |||| ||||  ||| ||||||||||||||||| |||||||||
v.3    993  caaaaacagagatgaacagctcaaatactggaaatactggcactctcggc  1042 v.1    951  AGCATACGGCGAAGCAGAGGGTCCTTGACATTGCCGATTACAAGGAGAGC  1000
            |||| |||| |||| |||| ||||| |||| |||| ||:|||| ||||||| ||
v.3   1043  agcatacggcgaagcagagggtccttgacattgccgattacaaggagagc  1092 v.1   1001  TTTAATACGATTGGAAACATTGAAGAGATTGCATATAATGCTGTTTCCTT  1050
            |||  |||||||||||||||||||||| |||||||||||||| ||||||||||
v.3   1093  tttaatacgattggaaacattgaagagattgcatataatgctgtttcctt  1142 v.1   1051  TACCTGGCACGTGAATGAACAGGCGAAGATTTTCATCACCGTGAATTGCT  1100
            ||||  ||||  ||||||||||||| ||||| |||| || | || ||||||||||
v.3   1143  tacctgggacgtgaatgaagaggcgaagattttcatcaccgtgaattgct  1192 v.1   1101  TGAGCACAGATTTCTCCTCCCAAAAAGGGGTGAAAGGACTTCCCTTGATG  1150
            |||||||||| |||| |||| |||||||||| ||:|||| |||| | || |
v.3   1193  tgagcacagatttctcctcccaaaaaggggtgaaaggacttcctttgatg  1242 v.1   1151  ATTCAGATTGACACATACAGTTATAACAATCGTAGCAATAAACCCATTCA  1200
            ||| ||||  |||||||||||| ||:| |||||||||:|||||  ||| |
v.3   1243  attcagattgacacacacagttataacaatcgtagcaataaacccattca  1292 v.1   1201  TAGAGCTTATTGCCAGATCAAGGTCTTCTGTGACAAAGGAGCAGAAAGAA  1250
            |||||||||||| |||| |||| |||| ||||||||:|||| | |||||
v.3   1293  tagagcttattgccagatcaaggtcttctgtgacaaaggagcagaaagaa  1342 v.1   1251  AAATCCGAGATGAAGAGCGGAAGCAGAACAGGAAGAAAGGGAAAGGCCAG  1300
            || |||| |||||||||||||||||||| | |||||||| ||||||||||| ||
v.3   1343  aaatccgagatgaagagcggaagcagaacaggaagaaagggaaaggccag  1392 v.1   1301  GCCTCCCAAACTCAATGCAACAGCTCCTCTGATGGGAAGTTGGCTGCCAT  1350
            ||||||||||||||||||||||||| || ||||||||||||||||||||||
v.3   1393  gcctcccaaactcaatgcaacagctcctctgatgggaagttggctgccat  1442 v.1   1351  ACCTTTACAGAAGAAGAGTGACATCACCTACTTCAAAACCATGCCTCATC  1400
            |||||||||||||||||||||||||||| |||| |||||||||||| ||||
v.3   1443  acctttacagaagaagagtgacatcacctacttcaaaaccatgcctgatc  1492 v.1   1401  TCCACTCACAGCCAGTTCTCTTCATACCTGATGTTCACTTTGCAAACCTG  1450
            |||:||||;|||||||| ||||| |||| |||| ||||:||||||||||||
v.3   1493  tccactcacagccagttctcttcatacctgatgttcactttgcaaacctg  1542 v.1   1451  CAGAGGACCGGACAGGTGTATTACAACACGCATGATGAACGAGAAGGTGG  1500
            ||||||||||||||||| |||| |||| |||| ||||||| ||||||||||
v.3   1543  cagaggaccggacaggtgtattacaacacgatgatgaacgagaaggtgg  1592 v.1   1501  CAGTGTCCTTGTTAAACGGATGTTCCGGCCCATGGAAGAGGAGTTTGGTC  1550
            | ||| ||||:|||| ||||| |||| |||| || | ||||||||||||||
v.3   1593  cagtgtccttgttaaacggatgttccggcccatggaagaggagtttggtc  1642 v.1   1551  CAGTGCCTTCAAAGCAGATGAAAGAAGAAGGGACAAAGCGAGTGCTCTTG  1600
            | |||| ||||||||||||||| ||||| |||||||||||| ||||| |||||
v.3   1643  cagtgccttcaaagcagatgaaagaagaagggacaaagcgactcctcttg  1692 v.1   1601  TACGTGAGGAAGGAGACTGACGATGTGTTCGATGCATTGATGTTGAAGTC  1650
            ||||||| |||||||||| ||||||||| |||| |||| || |||||| ||
v.3   1693  tacgtgaggaaggagactgacgatgtgttcgatgcattgatgttgaagtc  1742 v.1   1651  TCCCACAGTGAAGGGCCTGATGGAAGCGATATCTGAGAAATATCGGCTGC  1700
            || | ||||||||| |:|||||||| |||| |||||||||||||| | ||||:|
V.3   1743  tcccacagtgaagggcctgatggaagcgatatctgagaaatatgggctgc  1792 v.1   1701  CCGTGGAGAAGATACCAAAGCTTTACAAGAAAAGCAAAAAACCCATCTTG  1750
            ||||||| ||||  |||| ||||||||||||||||||||||| ||:|:||| |
V.3   1793  ccgtggagaagatagcaaagctttacaagaaaagcaaaaaaggcatcttg  1842 v.1   1751  GTGAACATGGATGACAACATCATCGAGCACTACTCGAACGAGGACACCTT  1800
            |||||||||||||||||||||||||||| ||||||||| ||||||||||||
V.3   1843  gtgaacatggatgacaacatcatcgagcactactcgaacgaggacacctt  1892
```

TABLE LIII(b)-continued

Nucleotide sequence alignment of 202P5A05 v.3 (SEQ ID NO: 103)
and 202P5A05 v.1 (SEG ID NO: 104)

```
v.1   1801  CATCCTCAACATGGAGAGCATGGTGGAGGGCTTCAAGGTCACGCTCATGG  1850
            || ||||  ||||||||||||||||||||||| |||||||||||||||||
V.3   1893  catcctcaacatggagagcatggtggagggcttcaaggtcacgctcatgg  1942 v.1   1851  AAATCTAGCCCTGGGTTTGGCATCCGCTTTGGCTGGAGCTCTCAGTGCGT  1900
            || ||||  |||||||||||||||||||||||||||||||||||||||||
v.3   1943  aaatctagccctgggtttggcatccgctttggctggagctctcagtgcgt  1992 v.1   1901  TCCTCCCTGAGAGAGACAGAAGCCCCAGCCCCAGAACCTGGAGACCCATC  1950
            ||| | ||  |||||||||||||||||||||||| ||||||||||||||
v.3   1993  tcctccctgagagagacagaagcccagcccagaacctggagacccatc  2042 v.1   1951  TCCCCCATCTCACAACTGCTGTTACAAGACCGTCCTGGGGAGTGGGGCAA  2000
            || || | |||| ||||||||||||||||| || |||||||||||||||
V.3   2043  tcccccatctcacaactgctgttacaagaccgtgctggggagtggggcaa  2092 v.1   2001  GGGACAGGCCCCACTCTCGGTGTGCTTGGCCCATCCACTGGCACCTACCA  2050
            ||| | || ||||||||||| || || |||||||||||||| |||||||
V.3   2093  gggacaggccccactgtcggtgtgcttggcccatccactggcacctacca  2142 v.1   2051  CCCACCTGAAGCCTGAGCCCCTCAGGAAGGTGCCTTAGGCCTGTTGGATT  2100
            ||| | || ||||||||||||||||| |||||||||||||||||||||
v.3   2413  cggagctgaagcctgagcccctcaggaaggtgccttaggcctgttggatt  2192 v.1   2101  CCTATTTATTGCCCACCTTTTCCTGGAGCCCAGGTCCAGGCCCGCCAGGA  2150
            || ||||  || ||||||||||| ||||| |||||||||| ||||||||
v.3   2193  cctatttattgcccaccttttcctggagcccaggtccaggcccgccagga  2242 v.1   2151  CTCTGCAGGTCACTGCTAGCTCCAGATGAGACCGTCCAGCGTTCCCCCTT  2200
            ||||||||||||||||||||||||||||||||||||||||||||||||||
v.3   2243  ctctgcaggtcactgctagctccagatgagaccgtccagcgttccccctt  2292 v.1   2201  CAAGAGAAACACTCATCCCGAACAGCCTAAAAAATTCCCATCCCTTCTCT  2250
            ||||||||||||||||||||||||||||||||||||||||||||||||||
v.3   2293  caagagaaacactcatcccgaacagcctaaaaaattcccatcccttctct  2342 v.1   2251  CTCACCCCTCCATATCTATCTCCCGAGTGGCTGGACAAAATGAGCTACGT  2300
            ||||||||||||||||||||||||||||||||||||||||||||||||||
v.3   2343  ctcacccctccatatctatctcccgagtggctggacaaaatgagctacgt  2392 v.1   2301  CTGGGTGCAGTAGTTATAGGTGGGGCAAGAGGTGGATGCCCACTTTCTGG  2350
            ||||||||||||||||||||||||||||||||||||||||||||||||||
v.3   2393  ctgggtgcagtagttataggtggggcaagaggtggatgcccactttctgg  2442 v.1   2351  TCAGACACCTTTAGGTTGCTCTGGGGAAGGCTGTCTTGCTAAATACCTCC  2400
            ||||||||||||||||||||||||||||||||||||||||||||||||||
v.3   2443  tcagacacctttaggttgctctggggaaggctgtcttgctaaatacctcc  2492 v.1   2401  AGGGTTCCCAGCAAGTGGCCACCAGGCCTTGTACAGGAAGACATTCAGTC  2450
            ||||||||||||||||||||||||||||||||||||||||||||||||||
v.3   2493  agggttcccagcaagtggccaccaggccttgtacaggaagacattcagtc  2542 v.1   2451  ACCGTGTAATTAGTAACACAGAAAGTCTGCCTGTCTGCATTGTACATAGT  2500
            ||||||||||||||||||||||||||||||||||||||||||||||||||
v.3   2543  accgtgtaattagtaacacagaaagtctgcctgtctgcattgtacatagt  2592 v.1   2501  GTTTATAATATTGTAATAATATATTTTACCTGTGGTATGTGGGCATGTTT  2550
            ||||||||||||||||||||||||||||||||||||||||||||||||||
v.3   2593  gtttataatattgtaataatatattttacctgtggtatgtgggcatgttt  2642 v.1   2551  ACTGCCACTGGCCTAGAGGAGACACAGACCTGGAGACCGTTTTAATGGGG  2600
            ||||||||||||||||||||||||||||||||||||||||||||||||||
v.3   2643  actgccactggcctagaggagacacagacctggagaccgttttaatgggg  2692 v.1   2601  GTTTTTGCCTCTGTGCCTGTTCAAGAGACTTGCAGGGCTAGGTAGAGGGC  2650
            ||||||||||||||||||||||||||||||||||||||||||||||||||
v.3   2693  gttttgcctctgtgcctgttcaagagacttgcagggctaggtagagggc  2742 v.1   2651  CTTTGGGATGTTAAGGTGACTGCAGCTGATGCCAAGATGGACTCTGCAAT  2700
            ||||||||||||||||||||||||||||||||||||||||||||||||||
v.3   2743  ctttgggatgttaaggtgactgcagctgatgccaagatggactctgcaat  2792
```

TABLE LIII(b)-continued

Nucleotide sequence alignment of 202P5A05 v.3 (SEQ ID NO: 103) and 202P5A05 v.1 (SEG ID NO: 104)

```
v.1  2701  GGGCATACCTGGGGGCTCGTTCCCTGTCCCCAGAGGAAGCCCCCTCTCCT  2750
           ||||||||||||||||||||||||||||||||||||||||||||||||||
v.3  2793  gggcatacctgggggctcgttccctgtccccagaggaagccccctctcct  2842 v.1  2751  TCTCCATGGGCATGACTCTCCTTCGAGGCCACCACGTTTATCTCACAATG  2800
           ||||||||||||||||||||||||||||||||||||||||||||||||||
v.3  2843  tctccatgggcatgactctccttcgaggccaccacgtttatctcacaatg  2892 v.1  2801  ATGTGTTTTGCTTGACTTTCCCTTTGCGCTGTCTCGTGGGAAAGGTCATT  2850
           ||||||||||||||||||||||||||||||||||||||||||||||||||
v.3  2893  atgtgttttgcttgactttccctttgcgctgtctcgtgggaaaggtcatt  2942 v.1  2851  CTGTCTGAGACCCCAGCTCCTTCTCCAGCTTTGGCTGCGGGCATGGCCTG  2900
           ||||||||||||||||||||||||||||||||||||||||||||||||||
v.3  2943  ctgtctgagaccccagctccttctccagctttggctgcgggcatggcctg  2992 v.1  2901  AGCTTTCTGGAGAGCCTCTGCAGGGGGTTTGCCATCAGGGCCCTGTGGCT  2950
           ||||||||||||||||||||||||||||||||||||||||||||||||||
v.3  2993  agctttctggagagcctctgcagggggtttgccatcagggccctgtggct  3042 v.1  2951  GGGTCTGCTGCAGAGCTCCTTGGCTATCAGGAGAATCCTGGACACTGTAC  3000
           ||||||||||||||||||||||||||||||||||||||||||||||||||
v.3  3043  gggtctgctgcagagctccttggctatcaggagaatcctggacactgtac  3092 v.1  3001  TGTGCCTCCCAGTTTACAAACACGCCCTTCATCTCAAGTGGCCCTTTAAA  3050
           ||||||||||||||||||||||||||||||||||||||||||||||||||
v.3  3093  tgtgcctcccagtttacaaacacgcccttcatctcaagtggccctttaaa  3142 v.1  3051  AGGCCTGCTGCCATGTGAGAGCTGTGAACAGCTCAGCTCTGAGTCGGCAG  3100
           ||||||||||||||||||||||||||||||||||||||||||||||||||
v.3  3143  aggcctgctgccatgtgagagctgtgaacagctcagctctgagtcggcag  3192 v.1  3101  GCTGGGGCTTCCTCCTGGGCCACCAGATGGAAAGGGGGTATTGTTTGCCT  3150
           ||||||||||||||||||||||||||||||||||||||||||||||||||
v.3  3193  gctggggcttcctcctgggccaccagatggaaagggggtattgtttgcct  3242 v.1  3151  CACTCCTGGATGCTGCGTTTTAAGGAAGTGAGTGAGAAAGAATGTGCCAA  3200
           ||||||||||||||||||||||||||||||||||||||||||||||||||
v.3  3242  cactcctggatgctgcgttttaaggaagtgagtgagaaagaatgtgccaa  3292 v.1  3201  GATACCTGGCTCCTGTGAAACCAGCCTCAGGAGGGAAACTGGGAGAGAGA  3250
           ||||||||||||||||||||||||||||||||||||||||||||||||||
v.3  3293  gatacctggctcctgtgaaaccagcctcaggagggaaactgggagagaga  3342 v.1  3251  AGCTGTGGTCTCCTGCTACATGCCCTGGGAGCTGGAAGAGAAAAACACTC  3300
           ||||||||||||||||||||||||||||||||||||||||||||||||||
v.3  3343  agctgtggtctcctgctacatgccctgggagctggaagagaaaaacactc  3392 v.1  3301  CCCTAAACAATCGCAAAATGATGAACCATCATGGGCCACTGTTCTCTTTG  3350
           ||||||||||||||||||||||||||||||||||||||||||||||||||
v.3  3393  ccctaaacaatcgcaaaatgatgaaccatcatgggccactgttctctttg  3442 v.1  3351  AGGGGACAGGTTTAGGGGTTTGCGTTCGCCCTTGTGGGCTGAAGCACTAG  3400
           ||||||||||||||||||||||||||||||||||||||||||||||||||
v.3  3443  aggggacaggtttaggggtttgcgttcgcccttgtgggctgaagcactag  3492 v.1  3401  CTTTTTGGTAGCTAGACACATCCTGCACCCAAAGGTTCTCTACAAAGGCC  3450
           ||||||||||||||||||||||||||||||||||||||||||||||||||
v.3  3493  cttttggtagctagacacatcctgcacccaaaggttctctacaaaggcc  3542 v.1  3451  CAGATTTGTTTGTAAAGCACTTTGACTCTTACCTGGAGGCCCGCTCTCTA  3500
           ||||||||||||||||||||||||||||||||||||||||||||||||||
v.3  3543  cagatttgtttgtaaagcactttgactcttacctggaggcccgctctcta  3592 v.1  3501  AGGGCTTCCTGCGCTCCCACCTCATCTGTCCCTGAGATGCAGAGCAGGAT  3550
           ||||||||||||||||||||||||||||||||||||||||||||||||||
v.3  3593  agggcttcctgcgctcccacctcatctgtccctgagatgcagagcaggat  3642 v.1  3551  GGAGGGTCTGCTTCTAGCTCAGCTGTTTCTCCTTGAGGTTGCGGAGGAAT  3600
           ||||||||||||||||||||||||||||||||||||||||||||||||||
v.3  3643  ggagggtctgcttctagctcagctgtttctccttgaggttgcggaggaat  3692
```

TABLE LIII(b)-continued

Nucleotide sequence alignment of 202P5A05 v.3 (SEQ ID NO: 103) and 202P5A05 v.1 (SEG ID NO: 104)

```
v.1  3601  TGAATTGAATGGGACAGAGGGCAGGTGCTGTGGCCAAGAAGATCTCCGAG  3650
           ||||||||||||||||||||||||||||||||||||||||||||||||||
v.3  3693  tgaattgaatgggacagagggcaggtgctgtggccaagaagatctccgag  3742 v.1  3651  CAGCAGTGACGGGGCACCTTGCTGTGTGTCCTCTGGGCATGTTAACCCTT  3700
           ||||||||||||||||||||||||||||||||||||||||||||||||||
v.3  3743  cagcagtgacggggcaccttgctgtgtgtcctctgggcatgttaaccctt  3792 v.1  3701  CTGTGGGGCCAAAGGTTTGCATCGTGGATCCAGCTGTGCTCCAGTCTGTC  3750
           |||||||| |||||||||||||||||||||||||||||||||||||||||
v.3  3793  ctgtggggccaaaggtttgcatcgtggatccagctgtgctccagtctgtc  3842 v.1  3751  CCCTCCTCCTCCACTCTGACTGCCACGCCCCGGACCAGCAGCTTGGGGAC  3800
           |||||||| |||| |||| ||||| ||||||||| |||| |||| |||||||
v.3  3843  ccctcctcctccactctgactgccacgccccggaccagcagcttggggac  3892 v.1  3801  CCTCCAGGGTACTAATGGGGCTCTGTTCTGAGATGGACAAATTCAGTGTT  3850
           |||||||| |||| |||||||||||| || |||| |||| |||| ||||||||
v.3  3893  cctccagggtactaatggggctctgttctgagatggacaaattcagtgtt  3942 v.1  3851  GGAAATACATGTTGTACTATGCACTTCCCATGCTCCTAGGGTTAGGAATA  3900
           ||||||||||||||||||||||||||||||||||||||||||||||||||
v.3  3943  ggaaatacatgttgtactatgcacttcccatgctcctagggttaggaata  3992 v.1  3901  GTTTCAAACATGATTGGCAGACATAACAACGGCAAATACTCGGACTGGGG  3950
           |||||||||||||||||||||||| || | || |||| |||||||||||| |||
v.3  3993  gtttcaaacatgattggcagacataacaacggcaaatactcggactgggg  4042 v.1  3951  CATAGGACTCCAGAGTAGGAAAAAGACAAAAGATTTGGCACCCTGACACA  4000
           |||||||||||||||||||||| || | || ||||||||||| |||||||||
v.3  4043  cataggactccagagtaggaaaaagacaaaagatttggcagcctgacaca  4092 v.1  4001  GGCAACCTACCCCTCTCTCTCCAGCCTCTTTATGAAACTGTTTGTTTGCC  4050
           |||||||||||||||||||||||||| | | || ||||||||||||| |||
v.3  4093  ggcaacctacccctctctctccagcctctttatgaaactgtttgtttgcc  4142 v.1  4051  AGTCCTGCCCTAAGGCAGAAGATGAATTGAAGATGCTGTGCATGTTTCCT  4100
           ||||||||||||||||||||||||||||||||||||||||||||||||||
v.3  4143  agtcctgccctaaggcagaagatgaattgaagatgctgtgcatgtttcct  4192 v.1  4101  AAGTCCTTGAGCAATCATGGTGGTGACAATTGCCACAAGGGATATGAGGC  4150
           |||||||||||||||||||||| || | || |||| |||||||||| |||
v.3  4193  aagtccttgagcaatcatggtggtgacaattgccacaagggatatgaggc  4242 v.1  4151  CAGTGCCACCAGAGGGTGGTGCCAAGTGCCACATCCCTTCCGATCCATTC  4200
           |||||||||||||||||||||||||||||||||| |||| |||||||||| |||
v.3  4243  cagtgccaccagagggtggtgccaagtgccacatcccttccgatccattc  4292 v.1  4201  CCCTCTGCATCCTCGGAGGACCCCAGTTTGCCTTTCATGTGTCCGGTGTG  4250
           || |||| |||||| ||||| ||||||||||| |||| |||| |||| :|||
v.3  4293  ccctctgcatcctcggagcaccccagtttgcctttgatgtgtccgctgtg  4342 v.1  4251  TATGTTAGCTGAACTTTGATGAGCAAAATTTCCTGAGCGAAACACTCCAA  4300
           |||||||| |||||||||||||||||| |||||||||||||||||||| |||||||||
v.3  4343  tatgttagctgaactttgatgagcaaaatttcctgagcgaaacactccaa  4392 v.1  4301  AGAGATAGGAAAACTTGCCGCCTCTTCTTTTTTGTCCCTTAATCAAACTC  4350
           |||||||||||||||| ||||| |||||||||||||||||||||||||||
v.3  4393  agagataggaaaacttgccgcctcttctttttgtcccttaatcaaactc  4442 v.1  4351  AAATAAGCTTAAAAAAAATCCATGGAAGATCATGGACATCTGAAATGAGC  4400
           |:|||| |||||||||||| || |||||||||| |||| |||||||||||||||
v.3  4443  aaataagcttaaaaaaaatccatggaagatcatggacatgtgaaatgagc  4492 v.1  4401  ATTTTTTTCTTTTTTTTTTTAACAAACTCTCAACTGAACAGAACAAGAC   4450
           | ||||||||| ||||||||||||||||||||| ||||||||||||||||
v.3  4493  atttttttcttttttttttttaacaaagtctgaactgaacagaacaagac  4542 v.1  4451  TTTTTCCTCATACATCTCCAAATTGTTTAAACTTACTTTATGAGTGTTTG  4500
           ||||| |||||||||||| || | ||||||||| ||||||||||||||||||||
v.3  4543  ttttcctcatacatctccaaattgtttaaacttactttatgagtgtttg  4592
```

TABLE LIII(b)-continued

Nucleotide sequence alignment of 202P5A05 v.3 (SEQ ID NO: 103) and 202P5A05 v.1 (SEG ID NO: 104)

```
v.1  4501  TTTAGAAGTTCGGACCAACAGAAAAATGCAGTCAGATGTCATCTTGGAAT  4550
           ||||||||||||||||||||||||||||||||||||||||||||||||||
v.3  4593  tttagaagttcggaccaacagaaaaatgcagtcagatgtcatcttggaat  4642 v.1  4551  TGGTTTCTAAAAGAGTAAGGCATGTCCCTGCCCAGAAACTTAGGAAGCAT  4600
           ||||||||||||||||||||||||||||||||||||||||||||||||||
v.3  4643  tggtttctaaaagagtaaggcatgtccctgcccagaaacttaggaagcat  4692 v.1  4601  GAAATAAATCAAATGTTTATTTTCCTTCTTATTTAAAATCATGCAAATGC  4650
           ||||||||||||||||||||||||||||||||||||||||||||||||||
v.3  4693  gaaataaatcaaatgtttattttccttcttatttaaaatcatgcaaatgc  4742 v.1  4651  AACAGAAATAGAGGGTTTGTGCCAAATGCTATGAACGGCCCTTTCTTAAA  4700
           ||||||||||||||||||||||||||||||||||||||||||||||||||
v.3  4743  aacagaaatagagggtttgtgccaaatgctatgaacggccctttcttaaa  4792 v.1  4701  GACAAGCAAGGGAGATTGATATATGTACAATTTGCTCTCATGTTTT      4746
           ||||||||||||||||||||||||||||||||||||||||||||||
v.3  4793  gacaagcaagggagattgatatatgtacaatttgctctcatgttttt     4838
```

TABLE LIV(b)

Peptide sequences of protein coded by 202P5A05 v.3 (SEQ ID NO: 105)

```
MPSDPPFNTR RAYTSEDEAW KSYLENPLTA ATKAMMSING DEDSAAALGL LYDYYKVPRD   60
KRLLSVSKAS DSQEDQEKRN CLGTSEAQSN LSGGENRVQV LKTVPVNLSL NQDHLENSKR  120
EQYSISFPES SAIIPVSGIT VVKAEDFTPV FMAPPVHYPR GDGEEQRVVI FEQTQYDVPS  180
LATHSAYLKD DQRSTPDSTY SESFKDAATE KFRSASVGAE EYMYDQTSSG TFQYTLEATK  240
SLRQKQGEGP MTYLNKGQFY AITLSETGDN KCFRHPISKV RSVVMVVFSE DKNRDEQLKY  300
WKYWHSRQHT AKQRVLDIAD YKESFNTIGN IEEIAYNAVS FTWDVNEEAK IFITVNCLST  360
DFSSQKGVKG LPLMIQIDTY SYNNRSNKPI HRAYCQIKVF CDKGAERKIR DEERKQNRKK  420
GKGQASQTQC NSSSDGKLAA IPLQKKSDIT YFKTMPDLHS QPVLFIPDVH FANLQRTGQV  480
YYNTDDEREG GSVLVKRMFR PMEEEFGPVP SKQMKEEGTK RVLLYVRKET DDVFDALMLK  540
SPTVKGLMEA ISEKYGLPVE KIAKLYKKSK KGILVNMDDN IIEHYSNEDT FILNMESMVE  600
GFKVTLMEI                                                         609
```

TABLE LV(b)

Amino acid sequence alignment of 202P5A05 v.3 (SEQ ID NO: 106) and 202P5A05 v.1 (SEQ ID NO: 107)

```
v.1  1    MPSDPPFNTRRAYTSEDEAWKSYLENPLTAATKAMMSINGDEDSAAALGL   50
          ||||||||||||||||||||||||||||||||||||||||||||||||||
V.3  1    MPSDPPFNTRRAYTSEDEAWKSYLENPLTAATKAMMSINGDEDSAAALGL   50 v.1  51   LYDYYKVPRDKRLLSVSKASDSQEDQEKRNCLGTSEAQSNLSGGENRVQV  100
          ||||||||||||||||||||||||||||||||||||||||||||||||||
V.3  51   LYDYYKVPRDKRLLSVSKASDSQEDQEKRNCLGTSEAQSNLSGGENRVQV  100 v.1  101  LKTVPVNLSLNQDHLENSKREQYSISFPESSAIIPVSGITVVKAEDFTPV  150
          ||||||||||||||||||||||||||||||||||||||||||||||||||
V.3  101  LKTVPVNLSLNQDHLENSKREQYSISFPESSAIIPVSGITVVKAEDFTPV  150 v.1  151  FMAPPVHYPRGDGEEQRVVIFEQTQYDVPSLATHSAYLKDDQRSTPDSTY  200
          ||||||||||||||||||||||||||||||||||||||||||||||||||
V.3  151  FMAPPVHYPRGDGEEQRVVIFEQTQYDVPSLATHSAYLKDDQRSTPDSTY  200 v.1  201  SESFKDAATEKFRSASVGAEEYMYDQTSSGTFQYTLEATKSLRQKQGEGP  250
          ||||||||||||||||||||||||||||||||||||||||||||||||||
V.3  201  SESFKDAATEKFRSASVGAEEYMYDQTSSGTFQYTLEATKSLRQKQGEGP  250
```

TABLE LV(b)-continued

Amino acid sequence alignment of 202P5A05 v.3 (SEQ ID NO: 106) and 202P5A05 v.1 (SEQ ID NO: 107)

```
v.1  251  MTYLNKGQFYAITLSETGDNKCFRHPISKVRSVVMVVFSEDKNRDEQLKY  300
          ||||||||||||||||||||||||||||||||||||||||||||||||||
V.3  251  MTYLNKGQFYAITLSETGDNKCFRHPISKVRSVVMVVFSEDKNRDEQLKY  300 v.1  301  WKYWHSRQHTAKQRVLDIADYKESFNTIGNIEEIAYNAVSFTWDVNEEAK  350
          ||||||||||||||||||||||||||||||||||||||||||||||||||
V.3  301  WKYWHSRQHTAKQRVLDIADYKESFNTIGNIEEIAYNAVSFTWDVNEEAK  350 v.1  351  IFITVNCLSTDFSSQKGVKGLPLMIQIDTYSYNNRSNKPIHRAYCQIKVF  400
          ||||||||||||||||||||||||||||||||||||||||||||||||||
V.3  351  IFITVNCLSTDFSSQKGVKGLPLMIQIDTYSYNNRSNKPIHRAYCQIKVF  400 v.1  401  CDKGAERKIRDEERKQNRKKGKGQASQTQCNSSSDGKLAAIPLQKKSDIT  450
          ||||||||||||||||||||||||||||||||||||||||||||||||||
V.3  401  CDKGAERKIRDEERKQNRKKGKGQASQTQCNSSSDGKLAAIPLQKKSDIT  450 v.1  451  YFKTMPDLHSQPVLFIPDVHFANLQRTGQVYYNTDDEREGGSVLVKRMFR  500
          ||||||||||||||||||||||||||||||||||||||||||||||||||
V.3  451  YFKTMPDLHSQPVLFIPDVHFANLQRTGQVYYNTDDEREGGSVLVKRMFR  500 v.1  501  PMEEEFGPVPSKQMKEEGTKRVLLYVRKETDDVFDALMLKSPTVKGLMEA  550
          ||||||||||||||||||||||||||||||||||||||||||||||||||
V.3  501  PMEEEFGPVPSKQMKEEGTKRVLLYVRKETDDVFDALMLKSPTVKGLMEA  550 v.1  551  ISEKYGLPVEKIAKLYKKSKKGILVNMDDNIIEHYSNEDTFILNMESMVE  600
          ||||||||||||||||||||||||||||||||||||||||||||||||||
V.3  551  ISEKYGLPVEKIAKLYKKSKKGILVNMDDNIIEHYSNEDTFILNMESMVE  600 v.1  601  GFKVTLMEI                                           609
          |||||||||
V.3  601  GFKVTLMEI                                           609
```

TABLE LVI

SNP and codon changes in 202P5A5 v.1, v.2, and v.3,. *AA: amino acid; **—: deletion of the corresponding base.

| | v.1 | | | | v.2 | | v.3 | | |
|---|---|---|---|---|---|---|---|---|---|
| SNP | Position | AA* change | AA position | Variant relative to v.1 | Position | AA change | AA position | Position | AA change | AA positon |
| g/t | 138 | S/I | 37 | v.4 | 170 | S/I | 53 | 230 | S/I | 37 |
| a/g | 1269 | R/Q | 414 | v.5 | 1301 | R/Q | 430 | 1361 | R/Q | 414 |
| a/c | 1288 | K/N | 420 | v.6 | 1320 | K/N | 436 | 1380 | K/N | 420 |
| a/g | 1552 | P/P | 508 | v.7 | 1584 | P/P | 524 | 1644 | P/P | 508 |
| a/t | 1662 | K/M | 545 | v.8 | 1694 | K/M | 561 | 1754 | K/M | 545 |
| g/a | 1899 | | Outside ORF | v.9 | 1931 | | Outside ORF | 1991 | | Outside ORF |
| t/c | 2057 | | Outside ORF | v.10 | 2089 | | Outside ORF | 2149 | | Outside ORF |
| c/t | 2143 | | Outside ORF | v.11 | 2175 | | Outside ORF | 2235 | | Outside ORF |
| g/a | 2144 | | Outside ORF | v.12 | 2176 | | Outside ORF | 2236 | | Outside ORF |
| c/t | 2249 | | Outside ORF | v.13 | 2281 | | Outside ORF | 2341 | | Outside ORF |
| —/at** | 2269-70 | | Outside ORF | v.14 | 2301-2 | | Outside ORF | 2361-2 | | Outside ORF |
| a/g | 2576 | | Outside ORF | v.15 | 2608 | | Outside ORF | 2668 | | Outside ORF |
| t/c | 2812 | | Outside ORF | v.16 | 2848 | | Outside ORF | 2908 | | Outside ORF |
| g/a | 2836 | | Outside ORF | v.17 | 2868 | | Outside ORF | 2928 | | Outside ORF |
| t/c | 3059 | | Outside ORF | v.18 | 3091 | | Outside ORF | 3151 | | Outside ORF |
| g/a | 3101 | | Outside ORF | v.19 | 3133 | | Outside ORF | 3193 | | Outside ORF |
| a/c | 3309 | | Outside | v.20 | 3341 | | Outside | 3401 | | Outside |

TABLE LVI-continued

SNP and codon changes in 202P5A5 v.1, v.2, and v.3,. *AA: amino acid; **—: deletion of the corresponding base.

| | v.1 | | | v.2 | | v.3 | |
|---|---|---|---|---|---|---|---|
| SNP | Position | AA* change | Variant relative to v.1 | AA Position | AA change position | AA Position change | AA positon |
| t/c | 3332 | Outside ORF | v.21 | 3364 | Outside ORF | 3424 | Outside ORF |
| a/— | 3427 | Outside ORF | v.22 | 3459 | Outside ORF | 3459 | Outside ORF |
| c/t | 4208 | Outside ORF | v.23 | 4240 | Outside ORF | 4300 | Outside ORF |
| c/t | 4264 | Outside ORF | v.24 | 4296 | Outside ORF | 4356 | Outside ORF |
| c/t | 4409 | Outside ORF | v.25 | 4441 | Outside ORF | 4501 | Outside ORF |
| a/t | 4646 | Outside ORF | v.26 | 4677 | Outside ORF | 4737 | Outside ORF |

The invention claimed is:

1. A method for detecting, in a sample, the presence of a 202P5A5 mRNA, comprising the steps of:
   producing cDNA from the sample by reverse transcription using at least one primer;
   amplifying the cDNA so produced using sense and antisense primers to amplify a 202P5A5 cDNA that encodes the amino acid of SEQ ID NO: 3, wherein the cDNA consists of residues 29-1858 of SEQ ID NO: 2, with or without the stop codon, wherein the nucleotide at each of positions 138 and 1269 is G and the nucleotide at each of positions 1288 and 1662 is A, and the nucleotide at position 1552 is A or G; and
   detecting the presence of the amplified 202P5A5 cDNA, thereby detecting the presence of a 202P5A5 mRNA.

2. The method of claim 1, wherein the sample is taken from a patient who has or who is suspected of having cancer.

3. The method of claim 2, further comprising:
   performing the producing, amplifying and detecting steps on a corresponding normal sample; and
   determining whether the 202P5A5 mRNA is elevated, whereby the detection of an elevated 202P5A5 mRNA from the patient tissue sample relative to the normal sample indicates the presence or status of a cancer.

4. The method of claim 3, wherein the cancer occurs in a tissue selected from among prostate, bladder, colon, lung, ovary, breast, stomach, cervix, lymphoma, bone, and skin.

5. The method of claim 2, wherein the patient tissue sample is from a tissue selected from among prostate, bladder, colon, lung, ovary, breast, stomach, cervix, lymphoma, bone, and skin.

6. The method of claim 1, wherein the sample is a biological sample from a patient tissue, the tissue selected from among prostate, bladder, colon, lung, ovary, breast, stomach, cervix, lymphoma, bone, and skin.

7. A method for detecting, in a sample, the presence of a 202P5A5 polynucleotide, comprising steps of:
   contacting the sample with a substance that specifically binds to the polynucleotide consisting of residues 29-1858 of SEQ ID NO: 2, with or without the stop codon, wherein the nucleotide at each of positions 138 and 1269 is and the nucleotide at each of positions 1288 and 1662 is A, and the nucleotide at position 1552 is A or G; and determining that there is a complex of the substance with the polynucleotide in the sample, thereby detecting the presence of the 202P5A5 polynucleotide.

8. The method of claim 7, wherein the sample is taken from a patient who has or who is suspected of having cancer.

9. The method of claim 7, wherein the sample is a biological sample from a patient tissue, the tissue selected from among prostate, bladder, colon, lung, ovary, breast, stomach, cervix, lymphoma, bone, and skin.

* * * * *

SEQUENCE LISTING

```
<160> NUMBER OF SEQ ID NOS: 108

<210> SEQ ID NO 1
<211> LENGTH: 186
<212> TYPE: DNA
<213> ORGANISM: Homo sapiens

<400> SEQUENCE: 1
gatcatggat ttttttaag cttatttgag tttgattaag ggacaaaaaa gaagaggcgg    60
caagttttcc tatctctttg gagtgtttcg ctcaggaaat tttgctcatc aaaattcagc   120
taacatacac agcggacaca tcaaaggcaa actggggtgc tccgaggatg cagaggggaa   180
tggatc                                                             186

<210> SEQ ID NO 2
<211> LENGTH: 4746
<212> TYPE: DNA
<213> ORGANISM: Homo sapiens
<220> FEATURE:
<221> NAME/KEY: CDS
<222> LOCATION: (29)...(1858)
<220> FEATURE:
<221> NAME/KEY: misc_feature
<222> LOCATION: 138
<223> OTHER INFORMATION: v.4:   K = G or T
<220> FEATURE:
<221> NAME/KEY: misc_feature
<222> LOCATION: 1269
<223> OTHER INFORMATION: v.5:   r = G or A
<220> FEATURE:
<221> NAME/KEY: misc_feature
<222> LOCATION: 1288
<223> OTHER INFORMATION: v.6:   m = A or C
<220> FEATURE:
<221> NAME/KEY: misc_feature
<222> LOCATION: 1552
<223> OTHER INFORMATION: v.7:   r = A or G
<220> FEATURE:
<221> NAME/KEY: misc_feature
<222> LOCATION: 1662
<223> OTHER INFORMATION: v.8:   w = A or T
<220> FEATURE:
<221> NAME/KEY: misc_feature
<222> LOCATION: (0)...(0)
```

```
<223> OTHER INFORMATION: Pos. 1899;  v.9:   r = G or A
<220> FEATURE:
<221> NAME/KEY: misc_feature
<222> LOCATION: (0)...(0)
<223> OTHER INFORMATION: Pos. 2057;  v.10:  y = T or C
<220> FEATURE:
<221> NAME/KEY: misc_feature
<222> LOCATION: (0)...(0)
<223> OTHER INFORMATION: Pos. 2143;  v.11:  y = C or T
<220> FEATURE:
<221> NAME/KEY: misc_feature
<222> LOCATION: (0)...(0)
<223> OTHER INFORMATION: Pos. 2144;  v.12:  r = G or A
<220> FEATURE:
<221> NAME/KEY: misc_feature
<222> LOCATION: (0)...(0)
<223> OTHER INFORMATION: Pos. 2249;  v.13:  y = C or T
<220> FEATURE:
<221> NAME/KEY: misc_feature
<222> LOCATION: (0)...(0)
<223> OTHER INFORMATION: Pos. 2576;  v.15:  r = A or G
<220> FEATURE:
<221> NAME/KEY: misc_feature
<222> LOCATION: (0)...(0)
<223> OTHER INFORMATION: Pos. 2812;  v.16:  y = T or C
<220> FEATURE:
<221> NAME/KEY: misc_feature
<222> LOCATION: (0)...(0)
<223> OTHER INFORMATION: Pos. 2836;  v.17:  r = G or A
<220> FEATURE:
<221> NAME/KEY: misc_feature
<222> LOCATION: (0)...(0)
<223> OTHER INFORMATION: Pos. 3059;  v.18:  y = T or C
<220> FEATURE:
<221> NAME/KEY: misc_feature
<222> LOCATION: (0)...(0)
<223> OTHER INFORMATION: Pos. 3101;  v.19:  r = G or A
<220> FEATURE:
<221> NAME/KEY: misc_feature
<222> LOCATION: (0)...(0)
<223> OTHER INFORMATION: Pos. 3309;  v.20:  m = A or C
<220> FEATURE:
<221> NAME/KEY: misc_feature
<222> LOCATION: (0)...(0)
<223> OTHER INFORMATION: Pos. 3332;  v.21:  y = T or C
      Pos. 4208;  v.23:  y = C or T
      Pos. 4264;  v.24:  y = C or T
      Pos. 4409;  v.25:  y = C or T
<220> FEATURE:
<221> NAME/KEY: misc_feature
<222> LOCATION: (0)...(0)
<223> OTHER INFORMATION: Pos. 4645;  v.26:  w = A or T

<400> SEQUENCE: 2
taataaaaga ctagtggcct tagtgccc atg ccc agt gac cct cca ttc aat          52
                                Met Pro Ser Asp Pro Pro Phe Asn
                                  1               5 acc cga aga gcc tac acc agt gag gat gaa gcc tgg aag tca tac ttg         100
Thr Arg Arg Ala Tyr Thr Ser Glu Asp Glu Ala Trp Lys Ser Tyr Leu
         10                  15                  20 gag aat ccc ctg aca gca gcc acc aag gcc atg atg akc att aat ggt         148
Glu Asn Pro Leu Thr Ala Ala Thr Lys Ala Met Met Ser Ile Asn Gly
 25                  30                  35                  40 gat gag gac agt gct gct gcc ctc ggc ctg ctc tat gac tac tac aag         196
Asp Glu Asp Ser Ala Ala Ala Leu Gly Leu Leu Tyr Asp Tyr Tyr Lys
                 45                  50                  55 gtt cct cga gac aag agg ctg ctg tct gta agc aaa gca agt gac agc         244
Val Pro Arg Asp Lys Arg Leu Leu Ser Val Ser Lys Ala Ser Asp Ser
             60                  65                  70 caa gaa gac cag gag aaa aga aac tgc ctt ggc acc agt gaa gcc cag         292
Gln Glu Asp Gln Glu Lys Arg Asn Cys Leu Gly Thr Ser Glu Ala Gln
         75                  80                  85 agt aat ttg agt gga gga gaa aac cga gtg caa gtc cta aag act gtt         340
```

```
Ser Asn Leu Ser Gly Gly Glu Asn Arg Val Gln Val Leu Lys Thr Val
     90                  95                 100 cca gtg aac ctt tcc cta aat caa gat cac ctg gag aat tcc aag cgg      388
Pro Val Asn Leu Ser Leu Asn Gln Asp His Leu Glu Asn Ser Lys Arg
105             110                 115                 120 gaa cag tac agc atc agc ttc ccc gag agc tct gcc atc atc ccg gtg      436
Glu Gln Tyr Ser Ile Ser Phe Pro Glu Ser Ser Ala Ile Ile Pro Val
            125                 130                 135 tcg gga atc acg gtg gtg aaa gct gaa gat ttc aca cca gtt ttc atg      484
Ser Gly Ile Thr Val Val Lys Ala Glu Asp Phe Thr Pro Val Phe Met
                140                 145                 150 gcc cca cct gtg cac tat ccc cgg gga gat ggg gaa gag caa cga gtg      532
Ala Pro Pro Val His Tyr Pro Arg Gly Asp Gly Glu Glu Gln Arg Val
            155                 160                 165 gtt atc ttt gaa cag act cag tat gac gtg ccc tcg ctg gcc acc cac      580
Val Ile Phe Glu Gln Thr Gln Tyr Asp Val Pro Ser Leu Ala Thr His
170                 175                 180 agc gcc tat ctc aaa gac gac cag cgc agc act ccg gac agc aca tac      628
Ser Ala Tyr Leu Lys Asp Asp Gln Arg Ser Thr Pro Asp Ser Thr Tyr
185                 190                 195                 200 agc gag agc ttc aag gac gca gcc aca gag aaa ttt cgg agt gct tca      676
Ser Glu Ser Phe Lys Asp Ala Ala Thr Glu Lys Phe Arg Ser Ala Ser
            205                 210                 215 gtt ggg gct gag gag tac atg tat gat cag aca tca agt ggc aca ttt      724
Val Gly Ala Glu Glu Tyr Met Tyr Asp Gln Thr Ser Ser Gly Thr Phe
                220                 225                 230 cag tac acc ctg gaa gcc acc aaa tct ctc cgt cag aag cag ggg gag      772
Gln Tyr Thr Leu Glu Ala Thr Lys Ser Leu Arg Gln Lys Gln Gly Glu
            235                 240                 245 ggc ccc atg acc tac ctc aac aaa gga cag ttc tat gcc ata aca ctc      820
Gly Pro Met Thr Tyr Leu Asn Lys Gly Gln Phe Tyr Ala Ile Thr Leu
250                 255                 260 agc gag acc gga gac aac aaa tgc ttc cga cac ccc atc agc aaa gtc      868
Ser Glu Thr Gly Asp Asn Lys Cys Phe Arg His Pro Ile Ser Lys Val
265                 270                 275                 280 agg agt gtg gtg atg gtg gtc ttc agt gaa gac aaa aac aga gat gaa      916
Arg Ser Val Val Met Val Val Phe Ser Glu Asp Lys Asn Arg Asp Glu
            285                 290                 295 cag ctc aaa tac tgg aaa tac tgg cac tct cgg cag cat acg gcg aag      964
Gln Leu Lys Tyr Trp Lys Tyr Trp His Ser Arg Gln His Thr Ala Lys
                300                 305                 310 cag agg gtc ctt gac att gcc gat tac aag gag agc ttt aat acg att     1012
Gln Arg Val Leu Asp Ile Ala Asp Tyr Lys Glu Ser Phe Asn Thr Ile
            315                 320                 325 gga aac att gaa gag att gca tat aat gct gtt tcc ttt acc tgg gac     1060
Gly Asn Ile Glu Glu Ile Ala Tyr Asn Ala Val Ser Phe Thr Trp Asp
330                 335                 340 gtg aat gaa gag gcg aag att ttc atc acc gtg aat tgc ttg agc aca     1108
Val Asn Glu Glu Ala Lys Ile Phe Ile Thr Val Asn Cys Leu Ser Thr
345                 350                 355                 360 gat ttc tcc tcc caa aaa ggg gtg aaa gga ctt cct ttg atg att cag     1156
Asp Phe Ser Ser Gln Lys Gly Val Lys Gly Leu Pro Leu Met Ile Gln
            365                 370                 375 att gac aca tac agt tat aac aat cgt agc aat aaa ccc att cat aga     1204
Ile Asp Thr Tyr Ser Tyr Asn Asn Arg Ser Asn Lys Pro Ile His Arg
            380                 385                 390 gct tat tgc cag atc aag gtc ttc tgt gac aaa gga gca gaa aga aaa     1252
Ala Tyr Cys Gln Ile Lys Val Phe Cys Asp Lys Gly Ala Glu Arg Lys
395                 400                 405 atc cga gat gaa gag crg aag cag aac agg aag aam ggg aaa ggc cag     1300
```

```
                 Ile Arg Asp Glu Glu Arg Lys Gln Asn Arg Lys Lys Gly Lys Gly Gln
                     410                 415                 420 gcc tcc caa act caa tgc aac agc tcc tct gat ggg aag ttg gct gcc              1348
Ala Ser Gln Thr Gln Cys Asn Ser Ser Ser Asp Gly Lys Leu Ala Ala
425                 430                 435                 440 ata cct tta cag aag aag agt gac atc acc tac ttc aaa acc atg cct              1396
Ile Pro Leu Gln Lys Lys Ser Asp Ile Thr Tyr Phe Lys Thr Met Pro
                445                 450                 455 gat ctc cac tca cag cca gtt ctc ttc ata cct gat gtt cac ttt gca              1444
Asp Leu His Ser Gln Pro Val Leu Phe Ile Pro Asp Val His Phe Ala
                460                 465                 470 aac ctg cag agg acc gga cag gtg tat tac aac acg gat gat gaa cga              1492
Asn Leu Gln Arg Thr Gly Gln Val Tyr Tyr Asn Thr Asp Asp Glu Arg
                475                 480                 485 gaa ggt ggc agt gtc ctt gtt aaa cgg atg ttc cgg ccc atg gaa gag              1540
Glu Gly Gly Ser Val Leu Val Lys Arg Met Phe Arg Pro Met Glu Glu
            490                 495                 500 gag ttt ggt ccr gtg cct tca aag cag atg aaa gaa gaa ggg aca aag              1588
Glu Phe Gly Pro Val Pro Ser Lys Gln Met Lys Glu Glu Gly Thr Lys
505                 510                 515                 520 cga gtg ctc ttg tac gtg agg aag gag act gac gat gtg ttc gat gca              1636
Arg Val Leu Leu Tyr Val Arg Lys Glu Thr Asp Asp Val Phe Asp Ala
                525                 530                 535 ttg atg ttg aag tct ccc aca gtg awg ggc ctg atg gaa gcg ata tct              1684
Leu Met Leu Lys Ser Pro Thr Val Lys Gly Leu Met Glu Ala Ile Ser
                540                 545                 550 gag aaa tat ggg ctg ccc gtg gag aag ata gca aag ctt tac aag aaa              1732
Glu Lys Tyr Gly Leu Pro Val Glu Lys Ile Ala Lys Leu Tyr Lys Lys
                555                 560                 565 agc aaa aaa ggc atc ttg gtg aac atg gat gac aac atc atc gag cac              1780
Ser Lys Lys Gly Ile Leu Val Asn Met Asp Asp Asn Ile Ile Glu His
        570                 575                 580 tac tcg aac gag gac acc ttc atc ctc aac atg gag agc atg gtg gag              1828
Tyr Ser Asn Glu Asp Thr Phe Ile Leu Asn Met Glu Ser Met Val Glu
585                 590                 595                 600 ggc ttc aag gtc acg ctc atg gaa atc tag ccctgggttt ggcatccgct                1878
Gly Phe Lys Val Thr Leu Met Glu Ile *
                605 ttggctggag ctctcagtgc rttcctccct gagagagaca gaagcccag ccccagaacc             1938 tggagaccca tctcccccat ctcacaactg ctgttacaag accgtgctgg ggagtgggc             1998 aagggacagg ccccactgtc ggtgtgcttg gcccatccac tggcacctac cacggagcyg            2058 aagcctgagc ccctcaggaa ggtgccttag gcctgttgga ttcctattta ttgcccacct            2118 tttcctggag cccaggtcca ggccyrccag gactctgcag gtcactgcta gctccagatg            2178 agaccgtcca gcgttccccc ttcaagagaa acactcatcc cgaacagcct aaaaaattcc            2238 catcccttct ytctcacccc tccatatcta tctcccgagt ggctggacaa aatgagctac            2298 gtctgggtgc agtagttata ggtggggcaa gaggtggatg cccactttct ggtcagacac            2358 ctttaggttg ctctgggaa ggctgtcttg ctaaatacct ccagggttcc cagcaagtgg            2418 ccaccaggcc ttgtacagga agacattcag tcaccgtgta attagtaaca cagaaagtct            2478 gcctgtctgc attgtacata gtgtttataa tattgtaata atatattta cctgtggtat             2538 gtgggcatgt ttactgccac tggcctgag gagacacrga cctggagacc gttttaatgg             2598 gggttttgc ctctgtgcct gttcaagaga cttgcagggc taggtagagg gcctttggga             2658 tgttaaggtg actgcagctg atgccaagat ggactctgca atgggcatac ctggggggctc           2718 gttccctgtc cccagaggaa gcccctctc cttctccatg ggcatgactc tccttcgagg             2778
```

```
ccaccacgtt tatctcacaa tgatgtgttt tgcytgactt tcccttttgcg ctgtctcrtg    2838 ggaaaggtca ttctgtctga acccccagct ccttctccag ctttggctgc gggcatggcc    2898
tgagctttct ggagagcctc tgcaggggggt ttgccatcag ggccctgtgg ctgggtctgc    2958
tgcagagctc cttggctatc aggagaatcc tggacactgt actgtgcctc ccagtttaca    3018
aacacgccct tcatctcaag tggccctta aaaggcctgc ygccatgtga gagctgtgaa    3078
cagctcagct ctgagtcggc agrctggggc ttcctcctgg gccaccagat ggaaaggggg    3138
tattgtttgc ctcactcctg gatgctgcgt tttaaggaag tgagtgagaa agaatgtgcc    3198
aagatacctg gctcctgtga aaccagcctc aggagggaaa ctgggagaga gaagctgtgg    3258
tctcctgcta catgccctgg gagctggaag agaaaaacac tccctaaac matcgcaaaa    3318 tgatgaacca tcaygggcca ctgttctctt tgaggggaca ggtttagggg tttgcgttcg    3378
cccttgtggg ctgaagcact agcttttttgg tagctagaca catcctgcac ccaaaggttc    3438
tctacaaagg cccagatttg tttgtaaagc actttgactc ttacctggag gcccgctctc    3498
taagggcttc ctgcgctccc acctcatctg tccctgagat gcagagcagg atggagggtc    3558
tgcttctagc tcagctgttt ctccttgagg ttgcggagga attgaattga atgggacaga    3618
gggcaggtgc tgtggccaag aagatctccg agcagcagtg acggggcacc ttgctgtgtg    3678
tcctctgggc atgttaaccc ttctgtgggg ccaaaggttt gcatcgtgga tccagctgtg    3738
ctccagtctg tcccctcctc ctccactctg actgccacgc cccggaccag cagcttgggg    3798
accctccagg gtactaatgg ggctctgttc tgagatggac aaattcagtg ttggaaatac    3858
atgttgtact atgcacttcc catgctccta gggttaggaa tagtttcaaa catgattggc    3918
agacataaca acggcaaata ctcggactgg ggcataggac tccagagtag gaaaaagaca    3978
aaagatttgg cagcctgaca caggcaacct accctctct ctccagcctc tttatgaaac    4038
tgtttgtttg ccagtcctgc cctaaggcag aagatgaatt gaagatgctg tgcatgtttc    4098
ctaagtcctt gagcaatcat ggtggtgaca attgccacaa gggatatgag gccagtgcca    4158
ccagagggtg gtgccaagtg ccacatccct tccgatccat tccctctgy atcctcggag    4218 cacccccagtt tgcctttgat gtgtccgctg tgtatgttag ctgaaytttg atgagcaaaa    4278
tttcctgagc gaaacactcc aaagagatag gaaaacttgc cgcctcttct ttttttgtccc    4338 ttaatcaaac tcaaataagc ttaaaaaaaa tccatggaag atcatggaca tgtgaaatga    4398 gcatttttt yttttttttt tttaacaaag tctgaactga acagaacaag acttttttcct    4458 catacatctc caaattgttt aaacttactt tatgagtgtt tgtttagaag ttcggaccaa    4518
cagaaaaatg cagtcagatg tcatcttgga attggtttct aaaagagtaa ggcatgtccc    4578
tgcccagaaa cttaggaagc atgaaataaa tcaaatgttt attttccttc ttatttaaaa    4638
tcatgcwaat gcaacagaaa tagagggttt gtgccaaatg ctatgaacgg cccttttctta    4698 aagacaagca agggagattg atatatgtac aatttgctct catgtttt                4746
```

<210> SEQ ID NO 3
<211> LENGTH: 609
<212> TYPE: PRT
<213> ORGANISM: Homo sapiens
<220> FEATURE:
<221> NAME/KEY: VARIANT
<222> LOCATION: 37
<223> OTHER INFORMATION: v.4: S=I
<220> FEATURE:
<221> NAME/KEY: VARIANT
<222> LOCATION: 414
<223> OTHER INFORMATION: v.5: R=Q

```
<220> FEATURE:
<221> NAME/KEY: VARIANT
<222> LOCATION: 420
<223> OTHER INFORMATION: v.6:  K=N
<220> FEATURE:
<221> NAME/KEY: VARIANT
<222> LOCATION: 545
<223> OTHER INFORMATION: v.8:  K=M

<400> SEQUENCE: 3
```

| | | | | | | | | | | | | | | |
|---|---|---|---|---|---|---|---|---|---|---|---|---|---|---|
|Met|Pro|Ser|Asp|Pro|Pro|Phe|Asn|Thr|Arg|Arg|Ala|Tyr|Thr|Ser|Glu|
|1| | | |5| | | | |10| | | | |15|
|Asp|Glu|Ala|Trp|Lys|Ser|Tyr|Leu|Glu|Asn|Pro|Leu|Thr|Ala|Ala|Thr|
| | | |20| | | | |25| | | | |30| | |
|Lys|Ala|Met|Met|Ser|Ile|Asn|Gly|Asp|Glu|Asp|Ser|Ala|Ala|Ala|Leu|
| | | |35| | | | |40| | | | |45| | |
|Gly|Leu|Leu|Tyr|Asp|Tyr|Tyr|Lys|Val|Pro|Arg|Asp|Lys|Arg|Leu|Leu|
| |50| | | | |55| | | | |60| | | | |
|Ser|Val|Ser|Lys|Ala|Ser|Asp|Ser|Gln|Glu|Asp|Gln|Glu|Lys|Arg|Asn|
|65| | | | |70| | | | |75| | | | |80|
|Cys|Leu|Gly|Thr|Ser|Glu|Ala|Gln|Ser|Asn|Leu|Ser|Gly|Gly|Glu|Asn|
| | | | |85| | | | |90| | | | |95| |
|Arg|Val|Gln|Val|Leu|Lys|Thr|Val|Pro|Val|Asn|Leu|Ser|Leu|Asn|Gln|
| | | |100| | | | |105| | | | |110| | |
|Asp|His|Leu|Glu|Asn|Ser|Lys|Arg|Glu|Gln|Tyr|Ser|Ile|Ser|Phe|Pro|
| | | |115| | | | |120| | | | |125| | |
|Glu|Ser|Ser|Ala|Ile|Ile|Pro|Val|Ser|Gly|Ile|Thr|Val|Val|Lys|Ala|
| |130| | | | |135| | | | |140| | | | |
|Glu|Asp|Phe|Thr|Pro|Val|Phe|Met|Ala|Pro|Pro|Val|His|Tyr|Pro|Arg|
|145| | | | |150| | | | |155| | | | |160|
|Gly|Asp|Gly|Glu|Glu|Gln|Arg|Val|Val|Ile|Phe|Glu|Gln|Thr|Gln|Tyr|
| | | | |165| | | | |170| | | | |175| |
|Asp|Val|Pro|Ser|Leu|Ala|Thr|His|Ser|Ala|Tyr|Leu|Lys|Asp|Asp|Gln|
| | | |180| | | | |185| | | | |190| | |
|Arg|Ser|Thr|Pro|Asp|Ser|Thr|Tyr|Ser|Glu|Ser|Phe|Lys|Asp|Ala|Ala|
| | | |195| | | | |200| | | | |205| | |
|Thr|Glu|Lys|Phe|Arg|Ser|Ala|Ser|Val|Gly|Ala|Glu|Glu|Tyr|Met|Tyr|
| |210| | | | |215| | | | |220| | | | |
|Asp|Gln|Thr|Ser|Ser|Gly|Thr|Phe|Gln|Tyr|Thr|Leu|Glu|Ala|Thr|Lys|
|225| | | | |230| | | | |235| | | | |240|
|Ser|Leu|Arg|Gln|Lys|Gln|Gly|Glu|Gly|Pro|Met|Thr|Tyr|Leu|Asn|Lys|
| | | | |245| | | | |250| | | | |255| |
|Gly|Gln|Phe|Tyr|Ala|Ile|Thr|Leu|Ser|Glu|Thr|Gly|Asp|Asn|Lys|Cys|
| | | |260| | | | |265| | | | |270| | |
|Phe|Arg|His|Pro|Ile|Ser|Lys|Val|Arg|Ser|Val|Val|Met|Val|Val|Phe|
| | |275| | | | |280| | | | |285| | | |
|Ser|Glu|Asp|Lys|Asn|Arg|Asp|Glu|Gln|Leu|Lys|Tyr|Trp|Lys|Tyr|Trp|
| |290| | | | |295| | | | |300| | | | |
|His|Ser|Arg|Gln|His|Thr|Ala|Lys|Gln|Arg|Val|Leu|Asp|Ile|Ala|Asp|
|305| | | | |310| | | | |315| | | | |320|
|Tyr|Lys|Glu|Ser|Phe|Asn|Thr|Ile|Gly|Asn|Ile|Glu|Glu|Ile|Ala|Tyr|
| | | | |325| | | | |330| | | | |335| |
|Asn|Ala|Val|Ser|Phe|Thr|Trp|Asp|Val|Asn|Glu|Glu|Ala|Lys|Ile|Phe|
| | | |340| | | | |345| | | | |350| | |
|Ile|Thr|Val|Asn|Cys|Leu|Ser|Thr|Asp|Phe|Ser|Gln|Lys|Gly|Val|
| | | |355| | | | |360| | | | |365| |

```
Lys Gly Leu Pro Leu Met Ile Gln Ile Asp Thr Tyr Ser Tyr Asn Asn
        370             375                 380

Arg Ser Asn Lys Pro Ile His Arg Ala Tyr Cys Gln Ile Lys Val Phe
385             390                 395                 400

Cys Asp Lys Gly Ala Glu Arg Lys Ile Arg Asp Glu Glu Arg Lys Gln
                405                 410                 415

Asn Arg Lys Lys Gly Lys Gly Gln Ala Ser Gln Thr Gln Cys Asn Ser
            420                 425                 430

Ser Ser Asp Gly Lys Leu Ala Ala Ile Pro Leu Gln Lys Lys Ser Asp
        435                 440                 445

Ile Thr Tyr Phe Lys Thr Met Pro Asp Leu His Ser Gln Pro Val Leu
    450                 455                 460

Phe Ile Pro Asp Val His Phe Ala Asn Leu Gln Arg Thr Gly Gln Val
465             470                 475                 480

Tyr Tyr Asn Thr Asp Asp Glu Arg Glu Gly Gly Ser Val Leu Val Lys
                485                 490                 495

Arg Met Phe Arg Pro Met Glu Glu Phe Gly Pro Val Pro Ser Lys
                500                 505                 510

Gln Met Lys Glu Glu Gly Thr Lys Arg Val Leu Leu Tyr Val Arg Lys
            515                 520                 525

Glu Thr Asp Asp Val Phe Asp Ala Leu Met Leu Lys Ser Pro Thr Val
    530                 535                 540

Lys Gly Leu Met Glu Ala Ile Ser Glu Lys Tyr Gly Leu Pro Val Glu
545             550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
            580                 585                 590

Leu Asn Met Glu Ser Met Val Glu Gly Phe Lys Val Thr Leu Met Glu
        595                 600                 605

Ile

<210> SEQ ID NO 4
<211> LENGTH: 4913
<212> TYPE: DNA
<213> ORGANISM: Homo sapiens
<220> FEATURE:
<221> NAME/KEY: CDS
<222> LOCATION: (13)...(1890)

<400> SEQUENCE: 4
attggatcaa ac atg tca caa gag tcg gac aat aat aaa aga cta gtg gcc        51
              Met Ser Gln Glu Ser Asp Asn Asn Lys Arg Leu Val Ala
                1               5                   10 tta gtg ccc atg ccc agt gac cct cca ttc aat acc cga aga gcc tac          99
Leu Val Pro Met Pro Ser Asp Pro Pro Phe Asn Thr Arg Arg Ala Tyr
    15                  20                  25 acc agt gag gat gaa gcc tgg aag tca tac ttg gag aat ccc ctg aca         147
Thr Ser Glu Asp Glu Ala Trp Lys Ser Tyr Leu Glu Asn Pro Leu Thr
30                  35                  40                  45 gca gcc acc aag gcc atg atg agc att aat ggt gat gag gac agt gct         195
Ala Ala Thr Lys Ala Met Met Ser Ile Asn Gly Asp Glu Asp Ser Ala
                50                  55                  60 gct gcc ctc ggc ctg ctc tat gac tac tac aag gtt cct cga gac aag         243
Ala Ala Leu Gly Leu Leu Tyr Asp Tyr Tyr Lys Val Pro Arg Asp Lys
            65                  70                  75 agg ctg ctg tct gta agc aaa gca agt gac agc caa gaa gac cag gag         291
Arg Leu Leu Ser Val Ser Lys Ala Ser Asp Ser Gln Glu Asp Gln Glu
```

-continued

```
              80                  85                  90
aaa aga aac tgc ctt ggc acc agt gaa gcc cag agt aat ttg agt gga         339
Lys Arg Asn Cys Leu Gly Thr Ser Glu Ala Gln Ser Asn Leu Ser Gly
     95                 100                 105 gga gaa aac cga gtg caa gtc cta aag act gtt cca gtg aac ctt tcc         387
Gly Glu Asn Arg Val Gln Val Leu Lys Thr Val Pro Val Asn Leu Ser
110                 115                 120                 125 cta aat caa gat cac ctg gag aat tcc aag cgg gaa cag tac agc atc         435
Leu Asn Gln Asp His Leu Glu Asn Ser Lys Arg Glu Gln Tyr Ser Ile
                130                 135                 140 agc ttc ccc gag agc tct gcc atc atc ccg gtg tcg gga atc acg gtg         483
Ser Phe Pro Glu Ser Ser Ala Ile Ile Pro Val Ser Gly Ile Thr Val
            145                 150                 155 gtg aaa gct gaa gat ttc aca cca gtt ttc atg gcc cca cct gtg cac         531
Val Lys Ala Glu Asp Phe Thr Pro Val Phe Met Ala Pro Pro Val His
        160                 165                 170 tat ccc cgg gga gat ggg gaa gag caa cga gtg gtt atc ttt gaa cag         579
Tyr Pro Arg Gly Asp Gly Glu Glu Gln Arg Val Val Ile Phe Glu Gln
    175                 180                 185 act cag tat gac gtg ccc tcg ctg gcc acc cac agc gcc tat ctc aaa         627
Thr Gln Tyr Asp Val Pro Ser Leu Ala Thr His Ser Ala Tyr Leu Lys
190                 195                 200                 205 gac gac cag cgc agc act ccg gac agc aca tac agc gag agc ttc aag         675
Asp Asp Gln Arg Ser Thr Pro Asp Ser Thr Tyr Ser Glu Ser Phe Lys
                210                 215                 220 gac gca gcc aca gag aaa ttt cgg agt gct tca gtt ggg gct gag gag         723
Asp Ala Ala Thr Glu Lys Phe Arg Ser Ala Ser Val Gly Ala Glu Glu
            225                 230                 235 tac atg tat gat cag aca tca agt ggc aca ttt cag tac acc ctg gaa         771
Tyr Met Tyr Asp Gln Thr Ser Ser Gly Thr Phe Gln Tyr Thr Leu Glu
        240                 245                 250 gcc acc aaa tct ctc cgt cag aag cag ggg gag ggc ccc atg acc tac         819
Ala Thr Lys Ser Leu Arg Gln Lys Gln Gly Glu Gly Pro Met Thr Tyr
    255                 260                 265 ctc aac aaa gga cag ttc tat gcc ata aca ctc agc gag acc gga gac         867
Leu Asn Lys Gly Gln Phe Tyr Ala Ile Thr Leu Ser Glu Thr Gly Asp
270                 275                 280                 285 aac aaa tgc ttc cga cac ccc atc agc aaa gtc agg agt gtg gtg atg         915
Asn Lys Cys Phe Arg His Pro Ile Ser Lys Val Arg Ser Val Val Met
                290                 295                 300 gtg gtc ttc agt gaa gac aaa aac aga gat gaa cag ctc aaa tac tgg         963
Val Val Phe Ser Glu Asp Lys Asn Arg Asp Glu Gln Leu Lys Tyr Trp
            305                 310                 315 aaa tac tgg cac tct cgg cag cat acg gcg aag cag agg gtc ctt gac        1011
Lys Tyr Trp His Ser Arg Gln His Thr Ala Lys Gln Arg Val Leu Asp
        320                 325                 330 att gcc gat tac aag gag agc ttt aat acg att gga aac att gaa gag        1059
Ile Ala Asp Tyr Lys Glu Ser Phe Asn Thr Ile Gly Asn Ile Glu Glu
    335                 340                 345 att gca tat aat gct gtt tcc ttt acc tgg gac gtg aat gaa gag gcg        1107
Ile Ala Tyr Asn Ala Val Ser Phe Thr Trp Asp Val Asn Glu Glu Ala
350                 355                 360                 365 aag att ttc atc acc gtg aat tgc ttg agc aca gat ttc tcc tcc caa        1155
Lys Ile Phe Ile Thr Val Asn Cys Leu Ser Thr Asp Phe Ser Ser Gln
                370                 375                 380 aaa ggg gtg aaa gga ctt cct ttg atg att cag att gac aca tac agt        1203
Lys Gly Val Lys Gly Leu Pro Leu Met Ile Gln Ile Asp Thr Tyr Ser
            385                 390                 395 tat aac aat cgt agc aat aaa ccc att cat aga gct tat tgc cag atc        1251
Tyr Asn Asn Arg Ser Asn Lys Pro Ile His Arg Ala Tyr Cys Gln Ile
```

```
                    400                 405                 410
aag gtc ttc tgt gac aaa gga gca gaa aga aaa atc cga gat gaa gag      1299
Lys Val Phe Cys Asp Lys Gly Ala Glu Arg Lys Ile Arg Asp Glu Glu
        415                 420                 425 cgg aag cag aac agg aag aaa ggg aaa ggc cag gcc tcc caa act caa      1347
Arg Lys Gln Asn Arg Lys Lys Gly Lys Gly Gln Ala Ser Gln Thr Gln
430                 435                 440                 445 tgc aac agc tcc tct gat ggg aag ttg gct gcc ata cct tta cag aag      1395
Cys Asn Ser Ser Ser Asp Gly Lys Leu Ala Ala Ile Pro Leu Gln Lys
                450                 455                 460 aag agt gac atc acc tac ttc aaa acc atg cct gat ctc cac tca cag      1443
Lys Ser Asp Ile Thr Tyr Phe Lys Thr Met Pro Asp Leu His Ser Gln
            465                 470                 475 cca gtt ctc ttc ata cct gat gtt cac ttt gca aac ctg cag agg acc      1491
Pro Val Leu Phe Ile Pro Asp Val His Phe Ala Asn Leu Gln Arg Thr
        480                 485                 490 gga cag gtg tat tac aac acg gat gat gaa cga gaa ggt ggc agt gtc      1539
Gly Gln Val Tyr Tyr Asn Thr Asp Asp Glu Arg Glu Gly Gly Ser Val
    495                 500                 505 ctt gtt aaa cgg atg ttc cgg ccc atg gaa gag gag ttt ggt cca gtg      1587
Leu Val Lys Arg Met Phe Arg Pro Met Glu Glu Glu Phe Gly Pro Val
510                 515                 520                 525 cct tca aag cag atg aaa gaa gaa ggg aca aag cga gtg ctc ttg tac      1635
Pro Ser Lys Gln Met Lys Glu Glu Gly Thr Lys Arg Val Leu Leu Tyr
                530                 535                 540 gtg agg aag gag act gac gat gtg ttc gat gca ttg atg ttg aag tct      1683
Val Arg Lys Glu Thr Asp Asp Val Phe Asp Ala Leu Met Leu Lys Ser
            545                 550                 555 ccc aca gtg aag ggc ctg atg gaa gcg ata tct gag aaa tat ggg ctg      1731
Pro Thr Val Lys Gly Leu Met Glu Ala Ile Ser Glu Lys Tyr Gly Leu
        560                 565                 570 ccc gtg gag aag ata gca aag ctt tac aag aaa agc aaa aaa ggc atc      1779
Pro Val Glu Lys Ile Ala Lys Leu Tyr Lys Lys Ser Lys Lys Gly Ile
    575                 580                 585 ttg gtg aac atg gat gac aac atc atc gag cac tac tcg aac gag gac      1827
Leu Val Asn Met Asp Asp Asn Ile Ile Glu His Tyr Ser Asn Glu Asp
590                 595                 600                 605 acc ttc atc ctc aac atg gag agc atg gtg gag ggc ttc aag gtc acg      1875
Thr Phe Ile Leu Asn Met Glu Ser Met Val Glu Gly Phe Lys Val Thr
                610                 615                 620 ctc atg gaa atc tag ccctgggttt ggcatccgct ttggctggag ctctcagtgc      1930
Leu Met Glu Ile *
            625 gttcctccct gagagagaca gaagcccag ccccagaacc tggagaccca tctcccccat      1990 ctcacaactg ctgttacaag accgtgctgg ggagtgggc aagggacagg ccccactgtc      2050 ggtgtgcttg gcccatccac tggcacctac cacggagctg aagcctgagc ccctcaggaa      2110 ggtgccttag gcctgttgga ttcctattta ttgcccacct tttcctggag cccaggtcca      2170 ggcccgccag gactctgcag gtcactgcta gctccagatg agaccgtcca gcgttccccc      2230 ttcaagagaa acactcatcc cgaacagcct aaaaaattcc catcccttct ctctcacccc      2290 tccatatcta tctcccgagt ggctggacaa aatgagctac gtctgggtgc agtagttata      2350 ggtgggcaa gaggtggatg cccacttttct ggtcagacac ctttaggttg ctctggggaa      2410 ggctgtcttg ctaaatacct ccagggttcc cagcaagtgg ccaccaggcc ttgtacagga      2470 agacattcag tcaccgtgta attagtaaca cagaaagtct gcctgtctgc attgtacata      2530 gtgtttataa tattgtaata atatatttta cctgtggtat gtgggcatgt ttactgccac      2590
```

```
tggcctagag gagacacaga cctggagacc gttttaatgg gggtttttgc ctctgtgcct    2650
gttcaagaga cttgcagggc taggtagagg gcctttggga tgttaaggtg actgcagctg    2710
atgccaagat ggactctgca atgggcatac ctgggggctc gttccctgtc cccagaggaa    2770 gcccctctc  cttctccatg gcatgactc  tccttcgagg ccaccacgtt tatctcacaa    2830
tgatgtgttt tgcttgactt tccctttgcg ctgtctcgtg ggaaaggtca ttctgtctga    2890
gaccccagct cctctccag  ctttggctgc gggcatggcc tgagcttcct ggagagcctc    2950
tgcagggggt ttgccatcag ggccctgtgg ctgggtctgc tgcagagctc cttggctatc    3010
aggagaatcc tggacactgt actgtgcctc ccagtttaca aacacgccct tcatctcaag    3070
tggcccttta aaaggcctgc tgccatgtga gagctgtgaa cagctcagct ctgagtcggc    3130 aggctgggc  ttcctcctgg gccaccagat ggaaagggg  tattgtttgc ctcactcctg    3190
gatgctgcgt tttaaggaag tgagtgagaa agaatgtgcc aagatacctg gctcctgtga    3250
aaccagcctc aggagggaaa ctgggagaga gaagctgtgg tctcctgcta catgccctgg    3310
gagctggaag agaaaaacac tcccctaaac aatcgcaaaa tgatgaacca tcatgggcca    3370
ctgttctctt tgagggggaca ggtttagggg tttgcgttcg cccttgtggg ctgaagcact    3430 agcttttgg  tagctagaca catcctgcac ccaaaggttc tctacaaagg cccagatttg    3490
tttgtaaagc actttgactc ttacctggag gcccgctctc taagggcttc ctgcgctccc    3550
acctcatctg tccctgagat gcagagcagg atggagggtc tgcttctagc tcagctgttt    3610
ctccttgagg ttgcggagga attgaattga atgggacaga gggcaggtgc tgtggccaag    3670
aagatctccg agcagcagtg acgggcacc  ttgctgtgtg tcctctgggc atgttaaccc    3730
ttctgtgggg ccaaaggttt gcatcgtgga tccagctgtg ctccagtctg tcccctcctc    3790
ctccactctg actgccacgc cccggaccag cagcttgggg accctccagg gtactaatgg    3850
ggctctgttc tgagatggac aaattcagtg ttgaaatac  atgttgtact atgcacttcc    3910
catgctccta gggttaggaa tagtttcaaa catgattggc agacataaca acggcaaata    3970
ctcggactgg ggcataggac tccagagtag gaaaaagaca aaagatttgg cagcctgaca    4030
caggcaacct acccctctct ctccagcctc tttatgaaac tgtttgtttg ccagtcctgc    4090
cctaaggcag aagatgaatt gaagatgctg tgcatgtttc ctaagtcctt gagcaatcat    4150
ggtggtgaca attgccacaa gggatatgag gccagtgcca ccagagggtg gtgccaagtg    4210
ccacatccct tccgatccat tcccctctgc atcctcggag caccccagtt tgcctttgat    4270
gtgtccgctg tgtatgttag ctgaactttg atgagcaaaa tttcctgagc gaaacactcc    4330
aaagagatag gaaaacttgc cgcctcttct ttttttgtccc ttaatcaaac tcaaataagc    4390
ttaaaaaaaa tccatggaag atcatggaca tgtgaaatga gcattttttt cttttttttt    4450
tttaacaaag tctgaactga acagaacaag actttttcct catacatctc caaattgttt    4510
aaacttactt tatgagtgtt tgtttagaag ttcggaccaa cagaaaaatg cagtcagatg    4570
tcatcttgga attggtttct aaaagagtaa ggcatgtccc tgcccagaaa cttaggaagc    4630
atgaaataaa tcaaatgttt attttccttc ttatttaaaa tcatgcaaat gcaacagaaa    4690
tagagggttt gtgccaaatg ctatgaacgg ccctttctta aagacaagca agggagattg    4750
atatatgtac aatttgctct catgttttaa aaaaaaagg  taaatgtaac ttaatagttt    4810
tgtaaatggg agagggggaa tctataaact ataaatacag ttattttatt ttttgtacat    4870
ttttaaggag aaaaaaataa atattcataa cataagagga aaa                     4913
```

<210> SEQ ID NO 5

<211> LENGTH: 625
<212> TYPE: PRT
<213> ORGANISM: Homo sapiens

<400> SEQUENCE: 5

```
Met Ser Gln Glu Ser Asp Asn Asn Lys Arg Leu Val Ala Leu Val Pro
1               5                   10                  15

Met Pro Ser Asp Pro Pro Phe Asn Thr Arg Arg Ala Tyr Thr Ser Glu
            20                  25                  30

Asp Glu Ala Trp Lys Ser Tyr Leu Glu Asn Pro Leu Thr Ala Ala Thr
        35                  40                  45

Lys Ala Met Met Ser Ile Asn Gly Asp Glu Asp Ser Ala Ala Ala Leu
50                  55                  60

Gly Leu Leu Tyr Asp Tyr Tyr Lys Val Pro Arg Asp Lys Arg Leu Leu
65                  70                  75                  80

Ser Val Ser Lys Ala Ser Asp Ser Gln Glu Asp Gln Glu Lys Arg Asn
                85                  90                  95

Cys Leu Gly Thr Ser Glu Ala Gln Ser Asn Leu Ser Gly Glu Asn
            100                 105                 110

Arg Val Gln Val Leu Lys Thr Val Pro Val Asn Leu Ser Leu Asn Gln
            115                 120                 125

Asp His Leu Glu Asn Ser Lys Arg Glu Gln Tyr Ser Ile Ser Phe Pro
    130                 135                 140

Glu Ser Ser Ala Ile Ile Pro Val Ser Gly Ile Thr Val Val Lys Ala
145                 150                 155                 160

Glu Asp Phe Thr Pro Val Phe Met Ala Pro Pro Val His Tyr Pro Arg
                165                 170                 175

Gly Asp Gly Glu Glu Gln Arg Val Val Ile Phe Glu Gln Thr Gln Tyr
            180                 185                 190

Asp Val Pro Ser Leu Ala Thr His Ser Ala Tyr Leu Lys Asp Asp Gln
        195                 200                 205

Arg Ser Thr Pro Asp Ser Thr Tyr Ser Glu Ser Phe Lys Asp Ala Ala
210                 215                 220

Thr Glu Lys Phe Arg Ser Ala Ser Val Gly Ala Glu Glu Tyr Met Tyr
225                 230                 235                 240

Asp Gln Thr Ser Ser Gly Thr Phe Gln Tyr Thr Leu Glu Ala Thr Lys
                245                 250                 255

Ser Leu Arg Gln Lys Gln Gly Glu Gly Pro Met Thr Tyr Leu Asn Lys
            260                 265                 270

Gly Gln Phe Tyr Ala Ile Thr Leu Ser Glu Thr Gly Asp Asn Lys Cys
        275                 280                 285

Phe Arg His Pro Ile Ser Lys Val Arg Ser Val Val Met Val Val Phe
290                 295                 300

Ser Glu Asp Lys Asn Arg Asp Glu Gln Leu Lys Tyr Trp Lys Tyr Trp
305                 310                 315                 320

His Ser Arg Gln His Thr Ala Lys Gln Arg Val Leu Asp Ile Ala Asp
                325                 330                 335

Tyr Lys Glu Ser Phe Asn Thr Ile Gly Asn Ile Glu Glu Ile Ala Tyr
            340                 345                 350

Asn Ala Val Ser Phe Thr Trp Asp Val Asn Glu Glu Ala Lys Ile Phe
        355                 360                 365

Ile Thr Val Asn Cys Leu Ser Thr Asp Phe Ser Ser Gln Lys Gly Val
370                 375                 380

Lys Gly Leu Pro Leu Met Ile Gln Ile Asp Thr Tyr Ser Tyr Asn Asn
385                 390                 395                 400
```

```
Arg Ser Asn Lys Pro Ile His Arg Ala Tyr Cys Gln Ile Lys Val Phe
                405                 410                 415

Cys Asp Lys Gly Ala Glu Arg Lys Ile Arg Asp Glu Glu Arg Lys Gln
            420                 425                 430

Asn Arg Lys Lys Gly Lys Gly Gln Ala Ser Gln Thr Gln Cys Asn Ser
        435                 440                 445

Ser Ser Asp Gly Lys Leu Ala Ala Ile Pro Leu Gln Lys Lys Ser Asp
450                 455                 460

Ile Thr Tyr Phe Lys Thr Met Pro Asp Leu His Ser Gln Pro Val Leu
465                 470                 475                 480

Phe Ile Pro Asp Val His Phe Ala Asn Leu Gln Arg Thr Gly Gln Val
                485                 490                 495

Tyr Tyr Asn Thr Asp Asp Glu Arg Glu Gly Gly Ser Val Leu Val Lys
            500                 505                 510

Arg Met Phe Arg Pro Met Glu Glu Phe Gly Pro Val Pro Ser Lys
        515                 520                 525

Gln Met Lys Glu Glu Gly Thr Lys Arg Val Leu Leu Tyr Val Arg Lys
530                 535                 540

Glu Thr Asp Asp Val Phe Asp Ala Leu Met Leu Lys Ser Pro Thr Val
545                 550                 555                 560

Lys Gly Leu Met Glu Ala Ile Ser Glu Lys Tyr Gly Leu Pro Val Glu
                565                 570                 575

Lys Ile Ala Lys Leu Tyr Lys Lys Ser Lys Lys Gly Ile Leu Val Asn
            580                 585                 590

Met Asp Asp Asn Ile Ile Glu His Tyr Ser Asn Glu Asp Thr Phe Ile
        595                 600                 605

Leu Asn Met Glu Ser Met Val Glu Gly Phe Lys Val Thr Leu Met Glu
    610                 615                 620

Ile
625

<210> SEQ ID NO 6
<211> LENGTH: 4973
<212> TYPE: DNA
<213> ORGANISM: Homo sapiens
<220> FEATURE:
<221> NAME/KEY: CDS
<222> LOCATION: (121)...(1950)

<400> SEQUENCE: 6
attggatcaa acatgtcaca agagtcggac aagtaagtgg atcacacgcg ccggctgctg      60
ctactactac cactttgggc tgatggcaac tgtaataaaa gactagtggc cttagtgccc     120 atg ccc agt gac cct cca ttc aat acc cga aga gcc tac acc agt gag      168
Met Pro Ser Asp Pro Pro Phe Asn Thr Arg Arg Ala Tyr Thr Ser Glu
1               5                   10                  15 gat gaa gcc tgg aag tca tac ttg gag aat ccc ctg aca gca gcc acc      216
Asp Glu Ala Trp Lys Ser Tyr Leu Glu Asn Pro Leu Thr Ala Ala Thr
            20                  25                  30 aag gcc atg atg agc att aat ggt gat gag gac agt gct gct gcc ctc      264
Lys Ala Met Met Ser Ile Asn Gly Asp Glu Asp Ser Ala Ala Ala Leu
        35                  40                  45 ggc ctg ctc tat gac tac tac aag gtt cct cga gac aag agg ctg ctg      312
Gly Leu Leu Tyr Asp Tyr Tyr Lys Val Pro Arg Asp Lys Arg Leu Leu
    50                  55                  60 tct gta agc aaa gca agt gac agc caa gaa gac cag gag aaa aga aac      360
Ser Val Ser Lys Ala Ser Asp Ser Gln Glu Asp Gln Glu Lys Arg Asn
65                  70                  75                  80
```

-continued

| | |
|---|---|
| tgc ctt ggc acc agt gaa gcc cag agt aat ttg agt gga gga gaa aac<br>Cys Leu Gly Thr Ser Glu Ala Gln Ser Asn Leu Ser Gly Gly Glu Asn<br>85 90 95 | 408 |
| cga gtg caa gtc cta aag act gtt cca gtg aac ctt tcc cta aat caa<br>Arg Val Gln Val Leu Lys Thr Val Pro Val Asn Leu Ser Leu Asn Gln<br>100 105 110 | 456 |
| gat cac ctg gag aat tcc aag cgg gaa cag tac agc atc agc ttc ccc<br>Asp His Leu Glu Asn Ser Lys Arg Glu Gln Tyr Ser Ile Ser Phe Pro<br>115 120 125 | 504 |
| gag agc tct gcc atc atc ccg gtg tcg gga atc acg gtg gtg aaa gct<br>Glu Ser Ser Ala Ile Ile Pro Val Ser Gly Ile Thr Val Val Lys Ala<br>130 135 140 | 552 |
| gaa gat ttc aca cca gtt ttc atg gcc cca cct gtg cac tat ccc cgg<br>Glu Asp Phe Thr Pro Val Phe Met Ala Pro Pro Val His Tyr Pro Arg<br>145 150 155 160 | 600 |
| gga gat ggg gaa gag caa cga gtg gtt atc ttt gaa cag act cag tat<br>Gly Asp Gly Glu Glu Gln Arg Val Val Ile Phe Glu Gln Thr Gln Tyr<br>165 170 175 | 648 |
| gac gtg ccc tcg ctg gcc acc cac agc gcc tat ctc aaa gac gac cag<br>Asp Val Pro Ser Leu Ala Thr His Ser Ala Tyr Leu Lys Asp Asp Gln<br>180 185 190 | 696 |
| cgc agc act ccg gac agc aca tac agc gag agc ttc aag gac gca gcc<br>Arg Ser Thr Pro Asp Ser Thr Tyr Ser Glu Ser Phe Lys Asp Ala Ala<br>195 200 205 | 744 |
| aca gag aaa ttt cgg agt gct tca gtt ggg gct gag gag tac atg tat<br>Thr Glu Lys Phe Arg Ser Ala Ser Val Gly Ala Glu Glu Tyr Met Tyr<br>210 215 220 | 792 |
| gat cag aca tca agt ggc aca ttt cag tac acc ctg gaa gcc acc aaa<br>Asp Gln Thr Ser Ser Gly Thr Phe Gln Tyr Thr Leu Glu Ala Thr Lys<br>225 230 235 240 | 840 |
| tct ctc cgt cag aag cag ggg gag ggc ccc atg acc tac ctc aac aaa<br>Ser Leu Arg Gln Lys Gln Gly Glu Gly Pro Met Thr Tyr Leu Asn Lys<br>245 250 255 | 888 |
| gga cag ttc tat gcc ata aca ctc agc gag acc gga gac aac aaa tgc<br>Gly Gln Phe Tyr Ala Ile Thr Leu Ser Glu Thr Gly Asp Asn Lys Cys<br>260 265 270 | 936 |
| ttc cga cac ccc atc agc aaa gtc agg agt gtg gtg atg gtg gtc ttc<br>Phe Arg His Pro Ile Ser Lys Val Arg Ser Val Val Met Val Val Phe<br>275 280 285 | 984 |
| agt gaa gac aaa aac aga gat gaa cag ctc aaa tac tgg aaa tac tgg<br>Ser Glu Asp Lys Asn Arg Asp Glu Gln Leu Lys Tyr Trp Lys Tyr Trp<br>290 295 300 | 1032 |
| cac tct cgg cag cat acg gcg aag cag agg gtc ctt gac att gcc gat<br>His Ser Arg Gln His Thr Ala Lys Gln Arg Val Leu Asp Ile Ala Asp<br>305 310 315 320 | 1080 |
| tac aag gag agc ttt aat acg att gga aac att gaa gag att gca tat<br>Tyr Lys Glu Ser Phe Asn Thr Ile Gly Asn Ile Glu Glu Ile Ala Tyr<br>325 330 335 | 1128 |
| aat gct gtt tcc ttt acc tgg gac gtg aat gaa gag gcg aag att ttc<br>Asn Ala Val Ser Phe Thr Trp Asp Val Asn Glu Glu Ala Lys Ile Phe<br>340 345 350 | 1176 |
| atc acc gtg aat tgc ttg agc aca gat ttc tcc tcc caa aaa ggg gtg<br>Ile Thr Val Asn Cys Leu Ser Thr Asp Phe Ser Ser Gln Lys Gly Val<br>355 360 365 | 1224 |
| aaa gga ctt cct ttg atg att cag att gac aca tac agt tat aac aat<br>Lys Gly Leu Pro Leu Met Ile Gln Ile Asp Thr Tyr Ser Tyr Asn Asn<br>370 375 380 | 1272 |
| cgt agc aat aaa ccc att cat aga gct tat tgc cag atc aag gtc ttc<br>Arg Ser Asn Lys Pro Ile His Arg Ala Tyr Cys Gln Ile Lys Val Phe<br>385 390 395 400 | 1320 |

```
tgt gac aaa gga gca gaa aga aaa atc cga gat gaa gag cgg aag cag      1368
Cys Asp Lys Gly Ala Glu Arg Lys Ile Arg Asp Glu Glu Arg Lys Gln
                405                 410                 415 aac agg aag aaa ggg aaa ggc cag gcc tcc caa act caa tgc aac agc      1416
Asn Arg Lys Lys Gly Lys Gly Gln Ala Ser Gln Thr Gln Cys Asn Ser
                420                 425                 430 tcc tct gat ggg aag ttg gct gcc ata cct tta cag aag aag agt gac      1464
Ser Ser Asp Gly Lys Leu Ala Ala Ile Pro Leu Gln Lys Lys Ser Asp
                435                 440                 445 atc acc tac ttc aaa acc atg cct gat ctc cac tca cag cca gtt ctc      1512
Ile Thr Tyr Phe Lys Thr Met Pro Asp Leu His Ser Gln Pro Val Leu
                450                 455                 460 ttc ata cct gat gtt cac ttt gca aac ctg cag agg acc gga cag gtg      1560
Phe Ile Pro Asp Val His Phe Ala Asn Leu Gln Arg Thr Gly Gln Val
465                 470                 475                 480 tat tac aac acg gat gat gaa cga gaa ggt ggc agt gtc ctt gtt aaa      1608
Tyr Tyr Asn Thr Asp Asp Glu Arg Glu Gly Gly Ser Val Leu Val Lys
                485                 490                 495 cgg atg ttc cgg ccc atg gaa gag gag ttt ggt cca gtg cct tca aag      1656
Arg Met Phe Arg Pro Met Glu Glu Glu Phe Gly Pro Val Pro Ser Lys
                500                 505                 510 cag atg aaa gaa gaa ggg aca aag cga gtg ctc ttg tac gtg agg aag      1704
Gln Met Lys Glu Glu Gly Thr Lys Arg Val Leu Leu Tyr Val Arg Lys
                515                 520                 525 gag act gac gat gtg ttc gat gca ttg atg ttg aag tct ccc aca gtg      1752
Glu Thr Asp Asp Val Phe Asp Ala Leu Met Leu Lys Ser Pro Thr Val
                530                 535                 540 aag ggc ctg atg gaa gcg ata tct gag aaa tat ggg ctg ccc gtg gag      1800
Lys Gly Leu Met Glu Ala Ile Ser Glu Lys Tyr Gly Leu Pro Val Glu
545                 550                 555                 560 aag ata gca aag ctt tac aag aaa agc aaa aaa ggc atc ttg gtg aac      1848
Lys Ile Ala Lys Leu Tyr Lys Lys Ser Lys Lys Gly Ile Leu Val Asn
                565                 570                 575 atg gat gac aac atc atc gag cac tac tcg aac gag gac acc ttc atc      1896
Met Asp Asp Asn Ile Ile Glu His Tyr Ser Asn Glu Asp Thr Phe Ile
                580                 585                 590 ctc aac atg gag agc atg gtg gag ggc ttc aag gtc acg ctc atg gaa      1944
Leu Asn Met Glu Ser Met Val Glu Gly Phe Lys Val Thr Leu Met Glu
                595                 600                 605 atc tag ccctgggttt ggcatccgct ttggctggag ctctcagtgc gttcctccct       2000
Ile * gagagagaca gaagcccag ccccagaacc tggagaccca tctcccccat ctcacaactg     2060
ctgttacaag accgtgctgg ggagtgggc aagggacagg ccccactgtc ggtgtgcttg     2120
gcccatccac tggcacctac cacggagctg aagcctgagc ccctcaggaa ggtgccttag   2180
gcctgttgga ttcctattta ttgcccacct tttcctggag cccaggtcca ggcccgccag    2240
gactctgcag gtcactgcta gctccagatg agaccgtcca gcgttccccc ttcaagagaa    2300
acactcatcc cgaacagcct aaaaaattcc catcccttct ctctcacccc tccatatcta    2360
tctcccgagt ggctggacaa aatgagctac gtctgggtgc agtagttata ggtggggcaa    2420
gaggtggatg cccactttct ggtcagacac ctttaggttg ctctggggaa ggctgtcttg    2480
ctaaatacct ccagggttcc cagcaagtgg ccaccaggcc ttgtacagga agacattcag    2540
tcaccgtgta attagtaaca cagaaagtct gcctgtctgc attgtacata gtgtttataa    2600
tattgtaata atatatttta cctgtggtat gtgggcatgt ttactgccac tggcctagag    2660
gagacacaga cctggagacc gttttaatgg gggttttgc ctctgtgcct gttcaagaga     2720
```

-continued

```
cttgcagggc taggtagagg gcctttggga tgttaaggtg actgcagctg atgccaagat    2780
ggactctgca atgggcatac ctgggggctc gttccctgtc cccagaggaa gcccctctc     2840 cttctccatg gcatgactc tccttcgagg ccaccacgtt tatctcacaa tgatgtgttt     2900
tgcttgactt tcccttttgcg ctgtctcgtg ggaaaggtca ttctgtctga accccagct    2960 ccttctccag ctttggctgc gggcatggcc tgagctttct ggagagcctc tgcaggggt     3020 ttgccatcag ggccctgtgg ctgggtctgc tgcagagctc cttggctatc aggagaatcc    3080
tggacactgt actgtgcctc ccagtttaca aacacgccct tcatctcaag tggccctta    3140 aaaggcctgc tgccatgtga gagctgtgaa cagctcagct ctgagtcggc aggctggggc    3200
ttcctcctgg gccaccagat ggaaaggggg tattgtttgc ctcactcctg gatgctgcgt    3260
tttaaggaag tgagtgagaa agaatgtgcc aagatacctg gctcctgtga aaccagcctc    3320
aggagggaaa ctgggagaga gaagctgtgg tctcctgcta catgccctgg gagctggaag    3380
agaaaaacac tcccctaaac aatcgcaaaa tgatgaacca tcatgggcca ctgttctctt    3440 tgagggaca ggtttagggg tttgcgttcg cccttgtggg ctgaagcact agcttttgg      3500 tagctagaca catcctgcac ccaaaggttc tctacaaagg cccagatttg tttgtaaagc    3560
actttgactc ttacctggag gcccgctctc taagggcttc ctgcgctccc acctcatctg    3620
tccctgagat gcagagcagg atggagggtc tgcttctagc tcagctgttt ctccttgagg    3680
ttgcggagga attgaattga atgggacaga gggcaggtgc tgtggccaag aagatctccg    3740
agcagcagtg acggggcacc ttgctgtgtg tcctctgggc atgttaaccc ttctgtgggg    3800
ccaaaggttt gcatcgtgga tccagctgtg ctccagtctg tccctcctc ctccactctg     3860 actgccacgc cccggaccag cagcttgggg accctccagg gtactaatgg ggctctgttc    3920
tgagatggac aaattcagtg ttggaaatac atgttgtact atgcacttcc catgctccta    3980
gggttaggaa tagtttcaaa catgattggc agacataaca acggcaaata ctcggactgg    4040
ggcataggac tccagagtag gaaaaagaca aaagatttgg cagcctgaca caggcaacct    4100 accctctct ctccagcctc tttatgaaac tgtttgtttg ccagtcctgc cctaaggcag     4160
aagatgaatt gaagatgctg tgcatgtttc ctaagtcctt gagcaatcat ggtggtgaca    4220
attgccacaa gggatatgag gccagtgcca ccagagggtg gtgccaagtg ccacatccct    4280
tccgatccat tcccctctgc atcctcggag caccccagtt tgcctttgat gtgtccgctg    4340
tgtatgttag ctgaactttg atgagcaaaa tttcctgagc gaaacactcc aaagagatag    4400
gaaaacttgc cgcctcttct tttttgtccc ttaatcaaac tcaaataagc ttaaaaaaaa    4460
tccatggaag atcatggaca tgtgaaatga gcattttttt cttttttttt tttaacaaag    4520
tctgaactga acagaacaag acttttttcct catacatctc caaattgttt aaacttactt    4580
tatgagtgtt tgtttagaag ttcggaccaa cagaaaaatg cagtcagatg tcatcttgga    4640 attggttct aaaagagtaa ggcatgtccc tgcccagaaa cttaggaagc atgaaataaa      4700
tcaaatgttt attttccttc ttatttaaaa tcatgcaaat gcaacagaaa tagagggttt    4760
gtgccaaatg ctatgaacgg ccctttctta aagacaagca agggagattg atatatgtac    4820
aatttgctct catgttttaa aaaaaaaagg taaatgtaac ttaatagttt tgtaaatggg    4880
agagggggaa tctataaact ataaatacag ttatttttatt ttttgtacat ttttaaggag   4940
aaaaaaataa atattcataa cataagagga aaa                                 4973
```

<210> SEQ ID NO 7
<211> LENGTH: 609
<212> TYPE: PRT

<213> ORGANISM: Homo sapiens

<400> SEQUENCE: 7

```
Met Pro Ser Asp Pro Pro Phe Asn Thr Arg Arg Ala Tyr Thr Ser Glu
 1               5                  10                  15
Asp Glu Ala Trp Lys Ser Tyr Leu Glu Asn Pro Leu Thr Ala Ala Thr
            20                  25                  30
Lys Ala Met Met Ser Ile Asn Gly Asp Glu Asp Ser Ala Ala Ala Leu
        35                  40                  45
Gly Leu Leu Tyr Asp Tyr Tyr Lys Val Pro Arg Asp Lys Arg Leu Leu
50                  55                  60
Ser Val Ser Lys Ala Ser Asp Ser Gln Glu Asp Gln Glu Lys Arg Asn
65                  70                  75                  80
Cys Leu Gly Thr Ser Glu Ala Gln Ser Asn Leu Ser Gly Gly Glu Asn
                85                  90                  95
Arg Val Gln Val Leu Lys Thr Val Pro Val Asn Leu Ser Leu Asn Gln
            100                 105                 110
Asp His Leu Glu Asn Ser Lys Arg Glu Gln Tyr Ser Ile Ser Phe Pro
        115                 120                 125
Glu Ser Ser Ala Ile Ile Pro Val Ser Gly Ile Thr Val Val Lys Ala
130                 135                 140
Glu Asp Phe Thr Pro Val Phe Met Ala Pro Val His Tyr Pro Arg
145                 150                 155                 160
Gly Asp Gly Glu Glu Gln Arg Val Val Ile Phe Glu Gln Thr Gln Tyr
                165                 170                 175
Asp Val Pro Ser Leu Ala Thr His Ser Ala Tyr Leu Lys Asp Asp Gln
            180                 185                 190
Arg Ser Thr Pro Asp Ser Thr Tyr Ser Glu Ser Phe Lys Asp Ala Ala
        195                 200                 205
Thr Glu Lys Phe Arg Ser Ala Ser Val Gly Ala Glu Glu Tyr Met Tyr
210                 215                 220
Asp Gln Thr Ser Ser Gly Thr Phe Gln Tyr Thr Leu Glu Ala Thr Lys
225                 230                 235                 240
Ser Leu Arg Gln Lys Gln Gly Glu Gly Pro Met Thr Tyr Leu Asn Lys
                245                 250                 255
Gly Gln Phe Tyr Ala Ile Thr Leu Ser Glu Thr Gly Asp Asn Lys Cys
            260                 265                 270
Phe Arg His Pro Ile Ser Lys Val Arg Ser Val Val Met Val Val Phe
        275                 280                 285
Ser Glu Asp Lys Asn Arg Asp Glu Gln Leu Lys Tyr Trp Lys Tyr Trp
290                 295                 300
His Ser Arg Gln His Thr Ala Lys Gln Arg Val Leu Asp Ile Ala Asp
305                 310                 315                 320
Tyr Lys Glu Ser Phe Asn Thr Ile Gly Asn Ile Glu Glu Ile Ala Tyr
                325                 330                 335
Asn Ala Val Ser Phe Thr Trp Asp Val Asn Glu Glu Ala Lys Ile Phe
            340                 345                 350
Ile Thr Val Asn Cys Leu Ser Thr Asp Phe Ser Ser Gln Lys Gly Val
        355                 360                 365
Lys Gly Leu Pro Leu Met Ile Gln Ile Asp Thr Tyr Ser Tyr Asn Asn
370                 375                 380
Arg Ser Asn Lys Pro Ile His Arg Ala Tyr Cys Gln Ile Lys Val Phe
385                 390                 395                 400
Cys Asp Lys Gly Ala Glu Arg Lys Ile Arg Asp Glu Glu Arg Lys Gln
```

```
                    405                 410                 415
Asn Arg Lys Lys Gly Lys Gly Gln Ala Ser Gln Thr Gln Cys Asn Ser
            420                 425                 430

Ser Ser Asp Gly Lys Leu Ala Ala Ile Pro Leu Gln Lys Lys Ser Asp
        435                 440                 445

Ile Thr Tyr Phe Lys Thr Met Pro Asp Leu His Ser Gln Pro Val Leu
450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Phe Gly Pro Val Pro Ser Lys
            500                 505                 510

Gln Met Lys Glu Glu Gly Thr Lys Arg Val Leu Leu Tyr Val Arg Lys
        515                 520                 525

Glu Thr Asp Asp Val Phe Asp Ala Leu Met Leu Lys Ser Pro Thr Val
530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
            580                 585                 590

Leu Asn Met Glu Ser Met Val Glu Gly Phe Lys Val Thr Leu Met Glu
        595                 600                 605

Ile

<210> SEQ ID NO 8
<211> LENGTH: 4748
<212> TYPE: DNA
<213> ORGANISM: Homo sapiens
<220> FEATURE:
<221> NAME/KEY: CDS
<222> LOCATION: (29)...(1858)

<400> SEQUENCE: 8
taataaaaga ctagtggcct tagtgcccc atg ccc agt gac cct cca ttc aat      52
                                Met Pro Ser Asp Pro Pro Phe Asn
                                 1               5 acc cga aga gcc tac acc agt gag gat gaa gcc tgg aag tca tac ttg     100
Thr Arg Arg Ala Tyr Thr Ser Glu Asp Glu Ala Trp Lys Ser Tyr Leu
     10                  15                  20 gag aat ccc ctg aca gca gcc acc aag gcc atg atg agc att aat ggt     148
Glu Asn Pro Leu Thr Ala Ala Thr Lys Ala Met Met Ser Ile Asn Gly
 25                  30                  35                  40 gat gag gac agt gct gct gcc ctc ggc ctg ctc tat gac tac tac aag     196
Asp Glu Asp Ser Ala Ala Ala Leu Gly Leu Leu Tyr Asp Tyr Tyr Lys
                 45                  50                  55 gtt cct cga gac aag agg ctg ctg tct gta agc aaa gca agt gac agc     244
Val Pro Arg Asp Lys Arg Leu Leu Ser Val Ser Lys Ala Ser Asp Ser
             60                  65                  70 caa gaa gac cag gag aaa aga aac tgc ctt ggc acc agt gaa gcc cag     292
Gln Glu Asp Gln Glu Lys Arg Asn Cys Leu Gly Thr Ser Glu Ala Gln
         75                  80                  85 agt aat ttg agt gga gga gaa aac cga gtg caa gtc cta aag act gtt     340
Ser Asn Leu Ser Gly Gly Glu Asn Arg Val Gln Val Leu Lys Thr Val
     90                  95                 100 cca gtg aac ctt tcc cta aat caa gat cac ctg gag aat tcc aag cgg     388
```

-continued

| | | |
|---|---|---|
| Pro Val Asn Leu Ser Leu Asn Gln Asp His Leu Glu Asn Ser Lys Arg<br>105                    110                    115                    120 | | |
| gaa cag tac agc atc agc ttc ccc gag agc tct gcc atc atc ccg gtg<br>Glu Gln Tyr Ser Ile Ser Phe Pro Glu Ser Ser Ala Ile Ile Pro Val<br>                    125                    130                    135 | 436 | |
| tcg gga atc acg gtg gtg aaa gct gaa gat ttc aca cca gtt ttc atg<br>Ser Gly Ile Thr Val Val Lys Ala Glu Asp Phe Thr Pro Val Phe Met<br>            140                    145                    150 | 484 | |
| gcc cca cct gtg cac tat ccc cgg gga gat ggg gaa gag caa cga gtg<br>Ala Pro Pro Val His Tyr Pro Arg Gly Asp Gly Glu Glu Gln Arg Val<br>                155                    160                    165 | 532 | |
| gtt atc ttt gaa cag act cag tat gac gtg ccc tcg ctg gcc acc cac<br>Val Ile Phe Glu Gln Thr Gln Tyr Asp Val Pro Ser Leu Ala Thr His<br>170                    175                    180 | 580 | |
| agc gcc tat ctc aaa gac gac cag cgc agc act ccg gac agc aca tac<br>Ser Ala Tyr Leu Lys Asp Asp Gln Arg Ser Thr Pro Asp Ser Thr Tyr<br>185                    190                    195                    200 | 628 | |
| agc gag agc ttc aag gac gca gcc aca gag aaa ttt cgg agt gct tca<br>Ser Glu Ser Phe Lys Asp Ala Ala Thr Glu Lys Phe Arg Ser Ala Ser<br>                    205                    210                    215 | 676 | |
| gtt ggg gct gag gag tac atg tat gat cag aca tca agt ggc aca ttt<br>Val Gly Ala Glu Glu Tyr Met Tyr Asp Gln Thr Ser Ser Gly Thr Phe<br>            220                    225                    230 | 724 | |
| cag tac acc ctg gaa gcc acc aaa tct ctc cgt cag aag cag ggg gag<br>Gln Tyr Thr Leu Glu Ala Thr Lys Ser Leu Arg Gln Lys Gln Gly Glu<br>                235                    240                    245 | 772 | |
| ggc ccc atg acc tac ctc aac aaa gga cag ttc tat gcc ata aca ctc<br>Gly Pro Met Thr Tyr Leu Asn Lys Gly Gln Phe Tyr Ala Ile Thr Leu<br>250                    255                    260 | 820 | |
| agc gag acc gga gac aac aaa tgc ttc cga cac ccc atc agc aaa gtc<br>Ser Glu Thr Gly Asp Asn Lys Cys Phe Arg His Pro Ile Ser Lys Val<br>265                    270                    275                    280 | 868 | |
| agg agt gtg gtg atg gtg gtc ttc agt gaa gac aaa aac aga gat gaa<br>Arg Ser Val Val Met Val Val Phe Ser Glu Asp Lys Asn Arg Asp Glu<br>                    285                    290                    295 | 916 | |
| cag ctc aaa tac tgg aaa tac tgg cac tct cgg cag cat acg gcg aag<br>Gln Leu Lys Tyr Trp Lys Tyr Trp His Ser Arg Gln His Thr Ala Lys<br>            300                    305                    310 | 964 | |
| cag agg gtc ctt gac att gcc gat tac aag gag agc ttt aat acg att<br>Gln Arg Val Leu Asp Ile Ala Asp Tyr Lys Glu Ser Phe Asn Thr Ile<br>                315                    320                    325 | 1012 | |
| gga aac att gaa gag att gca tat aat gct gtt tcc ttt acc tgg gac<br>Gly Asn Ile Glu Glu Ile Ala Tyr Asn Ala Val Ser Phe Thr Trp Asp<br>330                    335                    340 | 1060 | |
| gtg aat gaa gag gcg aag att ttc atc acc gtg aat tgc ttg agc aca<br>Val Asn Glu Glu Ala Lys Ile Phe Ile Thr Val Asn Cys Leu Ser Thr<br>345                    350                    355                    360 | 1108 | |
| gat ttc tcc tcc caa aaa ggg gtg aaa gga ctt cct ttg atg att cag<br>Asp Phe Ser Ser Gln Lys Gly Val Lys Gly Leu Pro Leu Met Ile Gln<br>                365                    370                    375 | 1156 | |
| att gac aca tac agt tat aac aat cgt agc aat aaa ccc att cat aga<br>Ile Asp Thr Tyr Ser Tyr Asn Asn Arg Ser Asn Lys Pro Ile His Arg<br>            380                    385                    390 | 1204 | |
| gct tat tgc cag atc aag gtc ttc tgt gac aaa gga gca gaa aga aaa<br>Ala Tyr Cys Gln Ile Lys Val Phe Cys Asp Lys Gly Ala Glu Arg Lys<br>395                    400                    405 | 1252 | |
| atc cga gat gaa gag cgg aag cag aac agg aag aaa ggg aaa ggc cag<br>Ile Arg Asp Glu Glu Arg Lys Gln Asn Arg Lys Lys Gly Lys Gly Gln<br>410                    415                    420 | 1300 | |
| gcc tcc caa act caa tgc aac agc tcc tct gat ggg aag ttg gct gcc | 1348 | |

| | | | | | | | | | | | | | | |
|---|---|---|---|---|---|---|---|---|---|---|---|---|---|---|
|Ala|Ser|Gln|Thr|Gln|Cys|Asn|Ser|Ser|Asp|Gly|Lys|Leu|Ala|Ala|
|425| | | |430| | | |435| | | |440| | |

```
ata cct tta cag aag aag agt gac atc acc tac ttc aaa acc atg cct    1396
Ile Pro Leu Gln Lys Lys Ser Asp Ile Thr Tyr Phe Lys Thr Met Pro
            445                 450                 455 gat ctc cac tca cag cca gtt ctc ttc ata cct gat gtt cac ttt gca    1444
Asp Leu His Ser Gln Pro Val Leu Phe Ile Pro Asp Val His Phe Ala
                460                 465                 470 aac ctg cag agg acc gga cag gtg tat tac aac acg gat gat gaa cga    1492
Asn Leu Gln Arg Thr Gly Gln Val Tyr Tyr Asn Thr Asp Asp Glu Arg
            475                 480                 485 gaa ggt ggc agt gtc ctt gtt aaa cgg atg ttc cgg ccc atg gaa gag    1540
Glu Gly Gly Ser Val Leu Val Lys Arg Met Phe Arg Pro Met Glu Glu
        490                 495                 500 gag ttt ggt cca gtg cct tca aag cag atg aaa gaa gaa ggg aca aag    1588
Glu Phe Gly Pro Val Pro Ser Lys Gln Met Lys Glu Glu Gly Thr Lys
505                 510                 515                 520 cga gtg ctc ttg tac gtg agg aag gag act gac gat gtg ttc gat gca    1636
Arg Val Leu Leu Tyr Val Arg Lys Glu Thr Asp Asp Val Phe Asp Ala
            525                 530                 535 ttg atg ttg aag tct ccc aca gtg aag ggc ctg atg gaa gcg ata tct    1684
Leu Met Leu Lys Ser Pro Thr Val Lys Gly Leu Met Glu Ala Ile Ser
                540                 545                 550 gag aaa tat ggg ctg ccc gtg gag aag ata gca aag ctt tac aag aaa    1732
Glu Lys Tyr Gly Leu Pro Val Glu Lys Ile Ala Lys Leu Tyr Lys Lys
            555                 560                 565 agc aaa aaa ggc atc ttg gtg aac atg gat gac aac atc atc gag cac    1780
Ser Lys Lys Gly Ile Leu Val Asn Met Asp Asp Asn Ile Ile Glu His
        570                 575                 580 tac tcg aac gag gac acc ttc atc ctc aac atg gag agc atg gtg gag    1828
Tyr Ser Asn Glu Asp Thr Phe Ile Leu Asn Met Glu Ser Met Val Glu
585                 590                 595                 600 ggc ttc aag gtc acg ctc atg gaa atc tag ccctgggttt ggcatccgct      1878
Gly Phe Lys Val Thr Leu Met Glu Ile  *
            605 ttggctggag ctctcagtgc gttcctccct gagagagaca gaagcccag ccccagaacc   1938
tggagaccca tctcccccat ctcacaactg ctgttacaag accgtgctgg ggagtggggc  1998
aagggacagg ccccactgtc ggtgtgcttg gcccatccac tggcacctac cacgagctg   2058
aagcctgagc ccctcaggaa ggtgccttag gcctgttgga ttcctattta ttgcccacct  2118
tttcctggag cccaggtcca ggcccgccag gactctgcag gtcactgcta gctccagatg  2178
agaccgtcca gcgttccccc ttcaagagaa acactcatcc cgaacagcct aaaaaattcc  2238
catcccttct ctctcacccc tccatatcta tatctcccga gtggctggac aaaatgagct  2298
acgtctgggt gcagtagtta taggtggggc aagaggtgga tgcccacttt ctggtcagac  2358
acctttaggt tgctctgggg aaggctgtct tgctaaatac ctccagggtt cccagcaagt  2418
ggccaccagg ccttgtacag gaagacattc agtcaccgtg taattagtaa cacagaaagt  2478
ctgcctgtct gcattgtaca tagtgtttat aatattgtaa taatatattt tacctgtggt  2538
atgtgggcat gtttactgcc actggcctag aggagacaca gacctggaga ccgttttaat  2598
gggggttttt gcctctgtgc ctgttcaaga gacttgcagg gctaggtaga gggcctttgg  2658
gatgttaagg tgactgcagc tgatgccaag atggactctg caatgggcat acctgggggc  2718
tcgttccctg tccccagagg aagccccctc tccttctcca tgggcatgac tctccttcga  2778
ggccaccacg tttatctcac aatgatgtgt tttgcttgac tttcccttttg cgctgtctcg  2838
tgggaaaggt cattctgtct gagaccccag ctccttctcc agctttggct gcgggcatgg  2898
```

-continued

```
cctgagcttt ctggagagcc tctgcagggg gtttgccatc agggccctgt ggctgggtct   2958
gctgcagagc tccttggcta tcaggagaat cctggacact gtactgtgcc tcccagttta   3018
caaacacgcc cttcatctca agtggccctt taaaaggcct gctgccatgt gagagctgtg   3078

aacagctcag ctctgagtcg gcaggctggg gcttcctcct gggccaccag atggaaaggg   3138
ggtattgttt gcctcactcc tggatgctgc gttttaagga agtgagtgag aaagaatgtg   3198
ccaagatacc tggctcctgt gaaaccagcc tcaggaggga aactgggaga gagaagctgt   3258
ggtctcctgc tacatgccct gggagctgga agagaaaaac actcccctaa acaatcgcaa   3318
aatgatgaac catcatgggc cactgttctc tttgagggga caggtttagg ggtttgcgtt   3378
cgcccttgtg ggctgaagca ctagcttttt ggtagctaga cacatcctgc acccaaaggt   3438
tctctacaaa ggcccagatt tgtttgtaaa gcactttgac tcttacctgg aggcccgctc   3498
tctaagggct tcctgcgctc ccacctcatc tgtccctgag atgcagagca ggatggaggg   3558
tctgcttcta gctcagctgt ttctccttga ggttgcggag gaattgaatt gaatgggaca   3618
gagggcaggt gctgtggcca agaagatctc cgagcagcag tgacggggca ccttgctgtg   3678
tgtcctctgg gcatgttaac ccttctgtgg ggccaaaggt ttgcatcgtg gatccagctg   3738
tgctccagtc tgtcccctcc tcctccactc tgactgccac gccccggacc agcagcttgg   3798
ggaccctcca gggtactaat ggggctctgt tctgagatgg acaaattcag tgttggaaat   3858
acatgttgta ctatgcactt cccatgctcc tagggttagg aatagtttca aacatgattg   3918
gcagacataa caacggcaaa tactcggact ggggcatagg actccagagt aggaaaaaga   3978
caaaagattt ggcagcctga cacaggcaac ctacccctct ctctccagcc tctttatgaa   4038
actgtttgtt tgccagtcct gccctaaggc agaagatgaa ttgaagatgc tgtgcatgtt   4098
tcctaagtcc ttgagcaatc atggtggtga caattgccac aagggatatg aggccagtgc   4158
caccagaggg tggtgccaag tgccacatcc cttccgatcc attcccctct gcatcctcgg   4218
agcaccccag tttgcctttg atgtgtccgc tgtgtatgtt agctgaactt tgatgagcaa   4278
aatttcctga gcgaaacact ccaaagagat aggaaaactt gccgcctctt ctttttttgtc   4338
ccttaatcaa actcaaataa gcttaaaaaa aatccatgga agatcatgga catgtgaaat   4398
gagcattttt ttcttttttt tttttaacaa agtctgaact gaacagaaca agactttttc   4458
ctcatacatc tccaaattgt ttaaacttac tttatgagtg tttgtttaga agttcggacc   4518
aacagaaaaa tgcagtcaga tgtcatcttg gaattggttt ctaaaagagt aaggcatgtc   4578
cctgcccaga aacttaggaa gcatgaaata aatcaaatgt ttattttcct tcttatttaa   4638
aatcatgcaa atgcaacaga aatagagggt ttgtgccaaa tgctatgaac ggccctttct   4698
taaagacaag caagggagat tgatatatgt acaatttgct ctcatgtttt              4748
```

<210> SEQ ID NO 9
<211> LENGTH: 609
<212> TYPE: PRT
<213> ORGANISM: Homo sapiens

<400> SEQUENCE: 9

```
Met Pro Ser Asp Pro Pro Phe Asn Thr Arg Arg Ala Tyr Thr Ser Glu
 1               5                  10                  15

Asp Glu Ala Trp Lys Ser Tyr Leu Glu Asn Pro Leu Thr Ala Ala Thr
            20                  25                  30

Lys Ala Met Met Ser Ile Asn Gly Asp Glu Asp Ser Ala Ala Ala Leu
        35                  40                  45
```

-continued

```
Gly Leu Leu Tyr Asp Tyr Tyr Lys Val Pro Arg Asp Lys Arg Leu Leu
         50                   55                  60

Ser Val Ser Lys Ala Ser Asp Ser Gln Glu Asp Gln Glu Lys Arg Asn
 65                   70                  75                  80

Cys Leu Gly Thr Ser Glu Ala Gln Ser Asn Leu Ser Gly Gly Glu Asn
                     85                  90                  95

Arg Val Gln Val Leu Lys Thr Val Pro Val Asn Leu Ser Leu Asn Gln
                100                 105                 110

Asp His Leu Glu Asn Ser Lys Arg Glu Gln Tyr Ser Ile Ser Phe Pro
                115                 120                 125

Glu Ser Ser Ala Ile Ile Pro Val Ser Gly Ile Thr Val Val Lys Ala
                130                 135                 140

Glu Asp Phe Thr Pro Val Phe Met Ala Pro Val His Tyr Pro Arg
145                 150                 155                 160

Gly Asp Gly Glu Glu Gln Arg Val Val Ile Phe Glu Gln Thr Gln Tyr
                    165                 170                 175

Asp Val Pro Ser Leu Ala Thr His Ser Ala Tyr Leu Lys Asp Asp Gln
                180                 185                 190

Arg Ser Thr Pro Asp Ser Thr Tyr Ser Glu Ser Phe Lys Asp Ala Ala
                195                 200                 205

Thr Glu Lys Phe Arg Ser Ala Ser Val Gly Ala Glu Glu Tyr Met Tyr
210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                    245                 250                 255

Gly Gln Phe Tyr Ala Ile Thr Leu Ser Glu Thr Gly Asp Asn Lys Cys
                260                 265                 270

Phe Arg His Pro Ile Ser Lys Val Arg Ser Val Val Met Val Val Phe
                275                 280                 285

Ser Glu Asp Lys Asn Arg Asp Glu Gln Leu Lys Tyr Trp Lys Tyr Trp
290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                    325                 330                 335

Asn Ala Val Ser Phe Thr Trp Asp Val Asn Glu Glu Ala Lys Ile Phe
                340                 345                 350

Ile Thr Val Asn Cys Leu Ser Thr Asp Phe Ser Ser Gln Lys Gly Val
                355                 360                 365

Lys Gly Leu Pro Leu Met Ile Gln Ile Asp Thr Tyr Ser Tyr Asn Asn
370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Arg Lys Gln
                    405                 410                 415

Asn Arg Lys Lys Gly Lys Gly Gln Ala Ser Gln Thr Gln Cys Asn Ser
                420                 425                 430

Ser Ser Asp Gly Lys Leu Ala Ala Ile Pro Leu Gln Lys Lys Ser Asp
                435                 440                 445

Ile Thr Tyr Phe Lys Thr Met Pro Asp Leu His Ser Gln Pro Val Leu
                450                 455                 460

Phe Ile Pro Asp Val His Phe Ala Asn Leu Gln Arg Thr Gly Gln Val
465                 470                 475                 480
```

```
Tyr Tyr Asn Thr Asp Asp Glu Arg Glu Gly Gly Ser Val Leu Val Lys
            485                 490                 495

Arg Met Phe Arg Pro Met Glu Glu Phe Gly Pro Val Pro Ser Lys
        500                 505                 510

Gln Met Lys Glu Glu Gly Thr Lys Arg Val Leu Leu Tyr Val Arg Lys
            515                 520                 525

Glu Thr Asp Asp Val Phe Asp Ala Leu Met Leu Lys Ser Pro Thr Val
        530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
            580                 585                 590

Leu Asn Met Glu Ser Met Val Glu Gly Phe Lys Val Thr Leu Met Glu
        595                 600                 605

Ile

<210> SEQ ID NO 10
<211> LENGTH: 4745
<212> TYPE: DNA
<213> ORGANISM: Homo sapiens
<220> FEATURE:
<221> NAME/KEY: CDS
<222> LOCATION: (29)...(1858)

<400> SEQUENCE: 10
taataaaaga ctagtggcct tagtgccc atg ccc agt gac cct cca ttc aat          52
                                Met Pro Ser Asp Pro Pro Phe Asn
                                 1               5 acc cga aga gcc tac acc agt gag gat gaa gcc tgg aag tca tac ttg         100
Thr Arg Arg Ala Tyr Thr Ser Glu Asp Glu Ala Trp Lys Ser Tyr Leu
     10                  15                  20 gag aat ccc ctg aca gca gcc acc aag gcc atg atg agc att aat ggt         148
Glu Asn Pro Leu Thr Ala Ala Thr Lys Ala Met Met Ser Ile Asn Gly
 25                  30                  35                  40 gat gag gac agt gct gct gcc ctc ggc ctg ctc tat gac tac tac aag         196
Asp Glu Asp Ser Ala Ala Ala Leu Gly Leu Leu Tyr Asp Tyr Tyr Lys
                 45                  50                  55 gtt cct cga gac aag agg ctg ctg tct gta agc aaa gca agt gac agc         244
Val Pro Arg Asp Lys Arg Leu Leu Ser Val Ser Lys Ala Ser Asp Ser
             60                  65                  70 caa gaa gac cag gag aaa aga aac tgc ctt ggc acc agt gaa gcc cag         292
Gln Glu Asp Gln Glu Lys Arg Asn Cys Leu Gly Thr Ser Glu Ala Gln
 75                  80                  85 agt aat ttg agt gga gga gaa aac cga gtg caa gtc cta aag act gtt         340
Ser Asn Leu Ser Gly Gly Glu Asn Arg Val Gln Val Leu Lys Thr Val
         90                  95                 100 cca gtg aac ctt tcc cta aat caa gat cac ctg gag aat tcc aag cgg         388
Pro Val Asn Leu Ser Leu Asn Gln Asp His Leu Glu Asn Ser Lys Arg
105                 110                 115                 120 gaa cag tac agc atc agc ttc ccc gag agc tct gcc atc atc ccg gtg         436
Glu Gln Tyr Ser Ile Ser Phe Pro Glu Ser Ser Ala Ile Ile Pro Val
                125                 130                 135 tcg gga atc acg gtg gtg aaa gct gaa gat ttc aca cca gtt ttc atg         484
Ser Gly Ile Thr Val Val Lys Ala Glu Asp Phe Thr Pro Val Phe Met
            140                 145                 150 gcc cca cct gtg cac tat ccc cgg gga gat ggg gaa gag caa cga gtg         532
Ala Pro Pro Val His Tyr Pro Arg Gly Asp Gly Glu Glu Gln Arg Val
```

-continued

```
                155                 160                 165
gtt atc ttt gaa cag act cag tat gac gtg ccc tcg ctg gcc acc cac        580
Val Ile Phe Glu Gln Thr Gln Tyr Asp Val Pro Ser Leu Ala Thr His
    170                 175                 180 agc gcc tat ctc aaa gac gac cag cgc agc act ccg gac agc aca tac        628
Ser Ala Tyr Leu Lys Asp Asp Gln Arg Ser Thr Pro Asp Ser Thr Tyr
185                 190                 195                 200 agc gag agc ttc aag gac gca gcc aca gag aaa ttt cgg agt gct tca        676
Ser Glu Ser Phe Lys Asp Ala Ala Thr Glu Lys Phe Arg Ser Ala Ser
        205                 210                 215 gtt ggg gct gag gag tac atg tat gat cag aca tca agt ggc aca ttt        724
Val Gly Ala Glu Glu Tyr Met Tyr Asp Gln Thr Ser Ser Gly Thr Phe
            220                 225                 230 cag tac acc ctg gaa gcc acc aaa tct ctc cgt cag aag cag ggg gag        772
Gln Tyr Thr Leu Glu Ala Thr Lys Ser Leu Arg Gln Lys Gln Gly Glu
        235                 240                 245 ggc ccc atg acc tac ctc aac aaa gga cag ttc tat gcc ata aca ctc        820
Gly Pro Met Thr Tyr Leu Asn Lys Gly Gln Phe Tyr Ala Ile Thr Leu
250                 255                 260 agc gag acc gga gac aac aaa tgc ttc cga cac ccc atc agc aaa gtc        868
Ser Glu Thr Gly Asp Asn Lys Cys Phe Arg His Pro Ile Ser Lys Val
265                 270                 275                 280 agg agt gtg gtg atg gtg gtc ttc agt gaa gac aaa aac aga gat gaa        916
Arg Ser Val Val Met Val Val Phe Ser Glu Asp Lys Asn Arg Asp Glu
                285                 290                 295 cag ctc aaa tac tgg aaa tac tgg cac tct cgg cag cat acg gcg aag        964
Gln Leu Lys Tyr Trp Lys Tyr Trp His Ser Arg Gln His Thr Ala Lys
        300                 305                 310 cag agg gtc ctt gac att gcc gat tac aag gag agc ttt aat acg att       1012
Gln Arg Val Leu Asp Ile Ala Asp Tyr Lys Glu Ser Phe Asn Thr Ile
            315                 320                 325 gga aac att gaa gag att gca tat aat gct gtt tcc ttt acc tgg gac       1060
Gly Asn Ile Glu Glu Ile Ala Tyr Asn Ala Val Ser Phe Thr Trp Asp
        330                 335                 340 gtg aat gaa gag gcg aag att ttc atc acc gtg aat tgc ttg agc aca       1108
Val Asn Glu Glu Ala Lys Ile Phe Ile Thr Val Asn Cys Leu Ser Thr
345                 350                 355                 360 gat ttc tcc tcc caa aaa ggg gtg aaa gga ctt cct ttg atg att cag       1156
Asp Phe Ser Ser Gln Lys Gly Val Lys Gly Leu Pro Leu Met Ile Gln
                365                 370                 375 att gac aca tac agt tat aac aat cgt agc aat aaa ccc att cat aga       1204
Ile Asp Thr Tyr Ser Tyr Asn Asn Arg Ser Asn Lys Pro Ile His Arg
        380                 385                 390 gct tat tgc cag atc aag gtc ttc tgt gac aaa gga gca gaa aga aaa       1252
Ala Tyr Cys Gln Ile Lys Val Phe Cys Asp Lys Gly Ala Glu Arg Lys
            395                 400                 405 atc cga gat gaa gag cgg aag cag aac agg aag aaa ggg aaa ggc cag       1300
Ile Arg Asp Glu Glu Arg Lys Gln Asn Arg Lys Lys Gly Lys Gly Gln
410                 415                 420 gcc tcc caa act caa tgc aac agc tcc tct gat ggg aag ttg gct gcc       1348
Ala Ser Gln Thr Gln Cys Asn Ser Ser Ser Asp Gly Lys Leu Ala Ala
425                 430                 435                 440 ata cct tta cag aag aag agt gac atc acc tac ttc aaa acc atg cct       1396
Ile Pro Leu Gln Lys Lys Ser Asp Ile Thr Tyr Phe Lys Thr Met Pro
                445                 450                 455 gat ctc cac tca cag cca gtt ctc ttc ata cct gat gtt cac ttt gca       1444
Asp Leu His Ser Gln Pro Val Leu Phe Ile Pro Asp Val His Phe Ala
        460                 465                 470 aac ctg cag agg acc gga cag gtg tat tac aac acg gat gat gaa cga       1492
Asn Leu Gln Arg Thr Gly Gln Val Tyr Tyr Asn Thr Asp Asp Glu Arg
```

```
                475                 480                 485
gaa ggt ggc agt gtc ctt gtt aaa cgg atg ttc cgg ccc atg gaa gag      1540
Glu Gly Gly Ser Val Leu Val Lys Arg Met Phe Arg Pro Met Glu Glu
    490                 495                 500 gag ttt ggt cca gtg cct tca aag cag atg aaa gaa gaa ggc aca aag      1588
Glu Phe Gly Pro Val Pro Ser Lys Gln Met Lys Glu Glu Gly Thr Lys
505                 510                 515                 520 cga gtg ctc ttg tac gtg agg aag gag act gac gat gtg ttc gat gca      1636
Arg Val Leu Leu Tyr Val Arg Lys Glu Thr Asp Asp Val Phe Asp Ala
                525                 530                 535 ttg atg ttg aag tct ccc aca gtg aag ggc ctg atg gaa gcg ata tct      1684
Leu Met Leu Lys Ser Pro Thr Val Lys Gly Leu Met Glu Ala Ile Ser
                540                 545                 550 gag aaa tat ggg ctg ccc gtg gag aag ata gca aag ctt tac aag aaa      1732
Glu Lys Tyr Gly Leu Pro Val Glu Lys Ile Ala Lys Leu Tyr Lys Lys
                555                 560                 565 agc aaa aaa ggc atc ttg gtg aac atg gat gac aac atc atc gag cac      1780
Ser Lys Lys Gly Ile Leu Val Asn Met Asp Asp Asn Ile Ile Glu His
            570                 575                 580 tac tcg aac gag gac acc ttc atc ctc aac atg gag agc atg gtg gag      1828
Tyr Ser Asn Glu Asp Thr Phe Ile Leu Asn Met Glu Ser Met Val Glu
585                 590                 595                 600 ggc ttc aag gtc acg ctc atg gaa atc tag ccctgggttt ggcatccgct        1878
Gly Phe Lys Val Thr Leu Met Glu Ile *
                605 ttggctggag ctctcagtgc gttcctccct gagagagaca gaagcccag ccccagaacc     1938 tggagaccca tctcccccat ctcacaactg ctgttacaag accgtgctgg ggagtggggc    1998 aagggacagg ccccactgtc ggtgtgcttg gcccatccac tggcacctac cacggagctg    2058 aagcctgagc ccctcaggaa ggtgccttag gcctgttgga ttcctattta ttgcccacct    2118 tttcctggag cccaggtcca ggcccgccag gactctgcag gtcactgcta gctccagatg    2178 agaccgtcca gcgttccccc ttcaagagaa acactcatcc cgaacagcct aaaaaattcc    2238 catcccttct ctctcacccc tccatatcta tctcccgagt ggctggacaa aatgagctac    2298 gtctgggtgc agtagttata ggtggggcaa gaggtggatg cccactttct ggtcagacac    2358 ctttaggttg ctctggggaa ggctgtcttg ctaaatacct ccagggttcc cagcaagtgg    2418 ccaccaggcc ttgtacagga agacattcag tcaccgtgta attagtaaca cagaaagtct    2478 gcctgtctgc attgtacata gtgtttataa tattgtaata atatatttta cctgtggtat    2538 gtgggcatgt ttactgccac tggcctagag gagacacaga cctggagacc gttttaatgg    2598 gggttttgc ctctgtgcct gttcaagaga cttgcagggc taggtagagg gcctttggga     2658 tgttaaggtg actgcagctg atgccaagat ggactctgca atgggcatac ctgggggctc    2718 gttccctgtc cccagaggaa gcccctctc cttctccatg gcatgactc tccttcgagg      2778 ccaccacgtt tatctcacaa tgatgtgttt gcttgactt tccctttgcg ctgtctcgtg     2838 ggaaaggtca ttctgtctga gaccccagct ccttctccag ctttggctgc gggcatggcc    2898 tgagcttttct ggagagcctc tgcagggggt ttgccatcag ggccctgtgg ctgggtctgc   2958 tgcagagctc cttggctatc aggagaatcc tggacactgt actgtgcctc ccagtttaca    3018 aacacgccct tcatctcaag tggccctttta aaaggcctgc tgccatgtga gagctgtgaa   3078 cagctcagct ctgagtcggc aggctggggc ttcctcctgg gccaccagat ggaaagggg     3138 tattgtttgc ctcactcctg gatgctgcgt tttaaggaag tgagtgagaa agaatgtgcc    3198 aagatacctg gctcctgtga aaccagcctc aggagggaaa ctgggagaga gaagctgtgg    3258
```

```
tctcctgcta catgccctgg gagctggaag agaaaaacac tccoctaaac aatcgcaaaa    3318
tgatgaacca tcatgggcca ctgttctctt tgaggggaca ggtttagggg tttgcgttcg    3378
cccttgtggg ctgaagcact agcttttttgg tagctagaca catcctgcac ccaaaggttc   3438
tctacaaagg cccagatttg tttgtaaagc actttgactc ttacctggag cccgctctc    3498
taagggcttc ctgcgctccc acctcatcgt ccctgagatg cagagcagga tggagggtct   3558
gcttctagct cagctgtttc tccttgaggt tgcggaggaa ttgaattgaa tgggacagag   3618
ggcaggtgct gtggccaaga agatctccga gcagcagtga cggggcacct tgctgtgtgt   3678
cctctgggca tgttaaccct tctgtggggc caaaggtttg catcgtggat ccagctgtgc   3738
tccagtctgt ccctcctcc tccactctga ctgccacgcc ccggaccagc agcttgggga   3798
ccctccaggg tactaatggg gctctgttct gagatggaca aattcagtgt tggaaataca   3858
tgttgtacta tgcacttccc atgctcctag ggttaggaat agtttcaaac atgattggca   3918
gacataacaa cggcaaatac tcggactggg gcataggact ccagagtagg aaaaagacaa   3978
aagatttggc agcctgacac aggcaaccta ccctctctc tccagcctct ttatgaaact    4038
gtttgtttgc cagtcctgcc ctaaggcaga agatgaattg aagatgctgt gcatgtttcc   4098
taagtccttg agcaatcatg gtggtgacaa ttgccacaag ggatatgagg ccagtgccac   4158
cagagggtgg tgccaagtgc cacatcccctt ccgatccatt ccctctgca tcctcggagc   4218
accccagttt gcctttgatg tgtccgctgt gtatgttagc tgaactttga tgagcaaaat   4278
ttcctgagcg aaacactcca agagatagg aaaacttgcc gcctcttctt ttttgtccct    4338
taatcaaact caaataagct taaaaaaaat ccatggaaga tcatggacat gtgaaatgag   4398
cattttttc ttttttttttt ttaacaaagt ctgaactgaa cagaacaaga ctttttcctc    4458
atacatctcc aaattgttta aacttacttt atgagtgttt gtttagaagt tcggaccaac   4518
agaaaaatgc agtcagatgt catcttggaa ttggtttcta aaagagtaag gcatgtccct   4578
gcccagaaac ttaggaagca tgaaataaat caaatgttta ttttccttct tatttaaaat   4638
catgcaaatg caacagaaat agagggtttg tgccaaatgc tatgaacggc cctttcttaa   4698
agacaagcaa gggagattga tatatgtaca atttgctctc atgttttt                4745

<210> SEQ ID NO 11
<211> LENGTH: 609
<212> TYPE: PRT
<213> ORGANISM: Homo sapiens

<400> SEQUENCE: 11

Met Pro Ser Asp Pro Pro Phe Asn Thr Arg Ala Tyr Thr Ser Glu
 1               5                  10                  15

Asp Glu Ala Trp Lys Ser Tyr Leu Glu Asn Pro Leu Thr Ala Ala Thr
            20                  25                  30

Lys Ala Met Met Ser Ile Asn Gly Asp Glu Asp Ser Ala Ala Ala Leu
        35                  40                  45

Gly Leu Leu Tyr Asp Tyr Tyr Lys Val Pro Arg Asp Lys Arg Leu Leu
    50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
            100                 105                 110

Asp His Leu Glu Asn Ser Lys Arg Glu Gln Tyr Ser Ile Ser Phe Pro
```

```
                    115                 120                 125
Glu Ser Ser Ala Ile Ile Pro Val Ser Gly Ile Thr Val Val Lys Ala
130                 135                 140

Glu Asp Phe Thr Pro Val Phe Met Ala Pro Val His Tyr Pro Arg
145                 150                 155                 160

Gly Asp Gly Glu Glu Gln Arg Val Val Ile Phe Glu Gln Thr Gln Tyr
                165                 170                 175

Asp Val Pro Ser Leu Ala Thr His Ser Ala Tyr Leu Lys Asp Asp Gln
                180                 185                 190

Arg Ser Thr Pro Asp Ser Thr Tyr Ser Glu Ser Phe Lys Asp Ala Ala
                195                 200                 205

Thr Glu Lys Phe Arg Ser Ala Ser Val Gly Ala Glu Glu Tyr Met Tyr
210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
                260                 265                 270

Phe Arg His Pro Ile Ser Lys Val Arg Ser Val Val Met Val Val Phe
                275                 280                 285

Ser Glu Asp Lys Asn Arg Asp Glu Gln Leu Lys Tyr Trp Lys Tyr Trp
290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
                340                 345                 350

Ile Thr Val Asn Cys Leu Ser Thr Asp Phe Ser Ser Gln Lys Gly Val
                355                 360                 365

Lys Gly Leu Pro Leu Met Ile Gln Ile Asp Thr Tyr Ser Tyr Asn Asn
370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Arg Lys Gln
                405                 410                 415

Asn Arg Lys Lys Gly Lys Gly Gln Ala Ser Gln Thr Gln Cys Asn Ser
                420                 425                 430

Ser Ser Asp Gly Lys Leu Ala Ala Ile Pro Leu Gln Lys Lys Ser Asp
                435                 440                 445

Ile Thr Tyr Phe Lys Thr Met Pro Asp Leu His Ser Gln Pro Val Leu
450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Glu Phe Gly Pro Val Pro Ser Lys
                500                 505                 510

Gln Met Lys Glu Glu Gly Thr Lys Arg Val Leu Leu Tyr Val Arg Lys
                515                 520                 525

Glu Thr Asp Asp Val Phe Asp Ala Leu Met Leu Lys Ser Pro Thr Val
530                 535                 540
```

-continued

```
Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Gly Ile Leu Val Asn
                565                 570                 575

Met Asp Asp Asn Ile Ile Glu His Tyr Ser Asn Glu Asp Thr Phe Ile
                580                 585                 590

Leu Asn Met Glu Ser Met Val Glu Gly Phe Lys Val Thr Leu Met Glu
            595                 600                 605

Ile

<210> SEQ ID NO 12
<211> LENGTH: 609
<212> TYPE: PRT
<213> ORGANISM: Homo sapiens

<400> SEQUENCE: 12

Met Pro Ser Asp Pro Pro Phe Asn Thr Arg Arg Ala Tyr Thr Ser Glu
1               5                   10                  15

Asp Glu Ala Trp Lys Ser Tyr Leu Glu Asn Pro Leu Thr Ala Ala Thr
                20                  25                  30

Lys Ala Met Met Ser Ile Asn Gly Asp Glu Asp Ser Ala Ala Ala Leu
            35                  40                  45

Gly Leu Leu Tyr Asp Tyr Tyr Lys Val Pro Arg Asp Lys Arg Leu Leu
50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
                100                 105                 110

Asp His Leu Glu Asn Ser Lys Arg Glu Gln Tyr Ser Ile Ser Phe Pro
            115                 120                 125

Glu Ser Ser Ala Ile Ile Pro Val Ser Gly Ile Thr Val Val Lys Ala
130                 135                 140

Glu Asp Phe Thr Pro Val Phe Met Ala Pro Pro Val His Tyr Pro Arg
145                 150                 155                 160

Gly Asp Gly Glu Glu Gln Arg Val Val Ile Phe Glu Gln Thr Gln Tyr
                165                 170                 175

Asp Val Pro Ser Leu Ala Thr His Ser Ala Tyr Leu Lys Asp Asp Gln
            180                 185                 190

Arg Ser Thr Pro Asp Ser Thr Tyr Ser Glu Ser Phe Lys Asp Ala Ala
        195                 200                 205

Thr Glu Lys Phe Arg Ser Ala Val Gly Ala Glu Glu Tyr Met Tyr
210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Met Val Val Phe
        275                 280                 285

Ser Glu Asp Lys Asn Arg Asp Glu Gln Leu Lys Tyr Trp Lys Tyr Trp
290                 295                 300

His Ser Arg Gln His Thr Ala Lys Gln Arg Val Leu Asp Ile Ala Asp
```

```
                305                 310                 315                 320
Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
                340                 345                 350

Ile Thr Val Asn Cys Leu Ser Thr Asp Phe Ser Ser Gln Lys Gly Val
                355                 360                 365

Lys Gly Leu Pro Leu Met Ile Gln Ile Asp Thr Tyr Ser Tyr Asn Asn
            370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Arg Lys Gln
                405                 410                 415

Asn Arg Lys Lys Gly Lys Gly Gln Ala Ser Gln Thr Gln Cys Asn Ser
                420                 425                 430

Ser Ser Asp Gly Lys Leu Ala Ala Ile Pro Leu Gln Lys Lys Ser Asp
            435                 440                 445

Ile Thr Tyr Phe Lys Thr Met Pro Asp Leu His Ser Gln Pro Val Leu
        450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Glu Phe Gly Pro Val Pro Ser Lys
                500                 505                 510

Gln Met Lys Glu Glu Gly Thr Lys Arg Val Leu Leu Tyr Val Arg Lys
                515                 520                 525

Glu Thr Asp Asp Val Phe Asp Ala Leu Met Leu Lys Ser Pro Thr Val
            530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
                580                 585                 590

Leu Asn Met Glu Ser Met Val Glu Gly Phe Lys Val Thr Leu Met Glu
            595                 600                 605

Ile

<210> SEQ ID NO 13
<211> LENGTH: 625
<212> TYPE: PRT
<213> ORGANISM: Homo sapiens

<400> SEQUENCE: 13

Met Ser Gln Glu Ser Asp Asn Asn Lys Arg Leu Val Ala Leu Val Pro
1               5                   10                  15

Met Pro Ser Asp Pro Pro Phe Asn Thr Arg Arg Ala Tyr Thr Ser Glu
                20                  25                  30

Asp Glu Ala Trp Lys Ser Tyr Leu Glu Asn Pro Leu Thr Ala Ala Thr
            35                  40                  45

Lys Ala Met Met Ser Ile Asn Gly Asp Glu Asp Ser Ala Ala Ala Leu
        50                  55                  60

Gly Leu Leu Tyr Asp Tyr Tyr Lys Val Pro Arg Asp Lys Arg Leu Leu
65                  70                  75                  80
```

-continued

Ser Val Ser Lys Ala Ser Asp Ser Gln Glu Asp Gln Glu Lys Arg Asn
                85              90              95

Cys Leu Gly Thr Ser Glu Ala Gln Ser Asn Leu Ser Gly Gly Glu Asn
                100             105             110

Arg Val Gln Val Leu Lys Thr Val Pro Val Asn Leu Ser Leu Asn Gln
                115             120             125

Asp His Leu Glu Asn Ser Lys Arg Glu Gln Tyr Ser Ile Ser Phe Pro
            130             135             140

Glu Ser Ser Ala Ile Ile Pro Val Ser Gly Ile Thr Val Val Lys Ala
145             150             155             160

Glu Asp Phe Thr Pro Val Phe Met Ala Pro Val His Tyr Pro Arg
                165             170             175

Gly Asp Gly Glu Glu Gln Arg Val Val Ile Phe Glu Gln Thr Gln Tyr
                180             185             190

Asp Val Pro Ser Leu Ala Thr His Ser Ala Tyr Leu Lys Asp Asp Gln
            195             200             205

Arg Ser Thr Pro Asp Ser Thr Tyr Ser Glu Ser Phe Lys Asp Ala Ala
    210             215             220

Thr Glu Lys Phe Arg Ser Ala Ser Val Gly Ala Glu Glu Tyr Met Tyr
225             230             235             240

Asp Gln Thr Ser Ser Gly Thr Phe Gln Tyr Thr Leu Glu Ala Thr Lys
                245             250             255

Ser Leu Arg Gln Lys Gln Gly Glu Gly Pro Met Thr Tyr Leu Asn Lys
                260             265             270

Gly Gln Phe Tyr Ala Ile Thr Leu Ser Glu Thr Gly Asp Asn Lys Cys
            275             280             285

Phe Arg His Pro Ile Ser Lys Val Arg Ser Val Val Met Val Val Phe
    290             295             300

Ser Glu Asp Lys Asn Arg Asp Glu Gln Leu Lys Tyr Trp Lys Tyr Trp
305             310             315             320

His Ser Arg Gln His Thr Ala Lys Gln Arg Val Leu Asp Ile Ala Asp
                325             330             335

Tyr Lys Glu Ser Phe Asn Thr Ile Gly Asn Ile Glu Glu Ile Ala Tyr
                340             345             350

Asn Ala Val Ser Phe Thr Trp Asp Val Asn Glu Glu Ala Lys Ile Phe
            355             360             365

Ile Thr Val Asn Cys Leu Ser Thr Asp Phe Ser Ser Gln Lys Gly Val
370             375             380

Lys Gly Leu Pro Leu Met Ile Gln Ile Asp Thr Tyr Ser Tyr Asn Asn
385             390             395             400

Arg Ser Asn Lys Pro Ile His Arg Ala Tyr Cys Gln Ile Lys Val Phe
                405             410             415

Cys Asp Lys Gly Ala Glu Arg Lys Ile Arg Asp Glu Glu Arg Lys Gln
            420             425             430

Asn Arg Lys Lys Gly Lys Gly Gln Ala Ser Gln Thr Gln Cys Asn Ser
            435             440             445

Ser Ser Asp Gly Lys Leu Ala Ala Ile Pro Leu Gln Lys Lys Ser Asp
    450             455             460

Ile Thr Tyr Phe Lys Thr Met Pro Asp Leu His Ser Gln Pro Val Leu
465             470             475             480

Phe Ile Pro Asp Val His Phe Ala Asn Leu Gln Arg Thr Gly Gln Val
                485             490             495

Tyr Tyr Asn Thr Asp Asp Glu Arg Glu Gly Gly Ser Val Leu Val Lys

```
                    500             505             510
Arg Met Phe Arg Pro Met Glu Glu Phe Gly Pro Val Pro Ser Lys
            515                 520                 525

Gln Met Lys Glu Glu Gly Thr Lys Arg Val Leu Leu Tyr Val Arg Lys
        530                 535                 540

Glu Thr Asp Asp Val Phe Asp Ala Leu Met Leu Lys Ser Pro Thr Val
545                 550                 555                 560

Lys Gly Leu Met Glu Ala Ile Ser Glu Lys Tyr Gly Leu Pro Val Glu
                565                 570                 575

Lys Ile Ala Lys Leu Tyr Lys Lys Ser Lys Lys Gly Ile Leu Val Asn
            580                 585                 590

Met Asp Asp Asn Ile Ile Glu His Tyr Ser Asn Glu Asp Thr Phe Ile
        595                 600                 605

Leu Asn Met Glu Ser Met Val Glu Gly Phe Lys Val Thr Leu Met Glu
    610                 615                 620

Ile
625

<210> SEQ ID NO 14
<211> LENGTH: 609
<212> TYPE: PRT
<213> ORGANISM: Homo sapiens

<400> SEQUENCE: 14

Met Pro Ser Asp Pro Pro Phe Asn Thr Arg Arg Ala Tyr Thr Ser Glu
1               5                   10                  15

Asp Glu Ala Trp Lys Ser Tyr Leu Glu Asn Pro Leu Thr Ala Ala Thr
            20                  25                  30

Lys Ala Met Met Ile Ile Asn Gly Asp Glu Asp Ser Ala Ala Ala Leu
        35                  40                  45

Gly Leu Leu Tyr Asp Tyr Tyr Lys Val Pro Arg Asp Lys Arg Leu Leu
    50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
            100                 105                 110

Asp His Leu Glu Asn Ser Lys Arg Glu Gln Tyr Ser Ile Ser Phe Pro
        115                 120                 125

Glu Ser Ser Ala Ile Ile Pro Val Ser Gly Ile Thr Val Val Lys Ala
    130                 135                 140

Glu Asp Phe Thr Pro Val Phe Met Ala Pro Pro Val His Tyr Pro Arg
145                 150                 155                 160

Gly Asp Gly Glu Glu Gln Arg Val Val Ile Phe Glu Gln Thr Gln Tyr
                165                 170                 175

Asp Val Pro Ser Leu Ala Thr His Ser Ala Tyr Leu Lys Asp Asp Gln
            180                 185                 190

Arg Ser Thr Pro Asp Ser Thr Tyr Ser Glu Ser Phe Lys Asp Ala Ala
        195                 200                 205

Thr Glu Lys Phe Arg Ser Ala Ser Val Gly Ala Glu Glu Tyr Met Tyr
    210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
```

Gly Gln Phe Tyr Ala Ile Thr Leu Ser Glu Thr Gly Asp Asn Lys Cys
            245                 250                 255
                260

Phe Arg His Pro Ile Ser Lys Val Arg Ser Val Val Met Val Val Phe
                275                 280                 285

Ser Glu Asp Lys Asn Arg Asp Glu Gln Leu Lys Tyr Trp Lys Tyr Trp
        290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                    325                 330                 335

Asn Ala Val Ser Phe Thr Trp Asp Val Asn Glu Glu Ala Lys Ile Phe
                340                 345                 350

Ile Thr Val Asn Cys Leu Ser Thr Asp Phe Ser Ser Gln Lys Gly Val
                355                 360                 365

Lys Gly Leu Pro Leu Met Ile Gln Ile Asp Thr Tyr Ser Tyr Asn Asn
370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Arg Lys Gln
                405                 410                 415

Asn Arg Lys Lys Gly Lys Gly Gln Ala Ser Gln Thr Gln Cys Asn Ser
                420                 425                 430

Ser Ser Asp Gly Lys Leu Ala Ala Ile Pro Leu Gln Lys Lys Ser Asp
            435                 440                 445

Ile Thr Tyr Phe Lys Thr Met Pro Asp Leu His Ser Gln Pro Val Leu
            450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Phe Gly Pro Val Pro Ser Lys
                500                 505                 510

Gln Met Lys Glu Glu Gly Thr Lys Arg Val Leu Leu Tyr Val Arg Lys
            515                 520                 525

Glu Thr Asp Asp Val Phe Asp Ala Leu Met Leu Lys Ser Pro Thr Val
            530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
                580                 585                 590

Leu Asn Met Glu Ser Met Val Glu Gly Phe Lys Val Thr Leu Met Glu
            595                 600                 605

Ile

<210> SEQ ID NO 15
<211> LENGTH: 609
<212> TYPE: PRT
<213> ORGANISM: Homo sapiens

<400> SEQUENCE: 15

Met Pro Ser Asp Pro Pro Phe Asn Thr Arg Arg Ala Tyr Thr Ser Glu
1               5                   10                  15

```
Asp Glu Ala Trp Lys Ser Tyr Leu Glu Asn Pro Leu Thr Ala Ala Thr
             20                  25                  30

Lys Ala Met Met Ser Ile Asn Gly Asp Glu Asp Ser Ala Ala Ala Leu
         35                  40                  45

Gly Leu Leu Tyr Asp Tyr Tyr Lys Val Pro Arg Asp Lys Arg Leu Leu
     50                  55                  60

Ser Val Ser Lys Ala Ser Asp Ser Gln Glu Asp Gln Glu Lys Arg Asn
 65                  70                  75                  80

Cys Leu Gly Thr Ser Glu Ala Gln Ser Asn Leu Ser Gly Gly Glu Asn
                 85                  90                  95

Arg Val Gln Val Leu Lys Thr Val Pro Val Asn Leu Ser Leu Asn Gln
             100                 105                 110

Asp His Leu Glu Asn Ser Lys Arg Glu Gln Tyr Ser Ile Ser Phe Pro
         115                 120                 125

Glu Ser Ser Ala Ile Ile Pro Val Ser Gly Ile Thr Val Val Lys Ala
 130                 135                 140

Glu Asp Phe Thr Pro Val Phe Met Ala Pro Pro Val His Tyr Pro Arg
145                 150                 155                 160

Gly Asp Gly Glu Glu Gln Arg Val Val Ile Phe Glu Gln Thr Gln Tyr
                 165                 170                 175

Asp Val Pro Ser Leu Ala Thr His Ser Ala Tyr Leu Lys Asp Asp Gln
             180                 185                 190

Arg Ser Thr Pro Asp Ser Thr Tyr Ser Glu Ser Phe Lys Asp Ala Ala
         195                 200                 205

Thr Glu Lys Phe Arg Ser Ala Ser Val Gly Ala Glu Glu Tyr Met Tyr
 210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                 245                 250                 255

Gly Gln Phe Tyr Ala Ile Thr Leu Ser Glu Thr Gly Asp Asn Lys Cys
             260                 265                 270

Phe Arg His Pro Ile Ser Lys Val Arg Ser Val Val Met Val Val Phe
         275                 280                 285

Ser Glu Asp Lys Asn Arg Asp Glu Gln Leu Lys Tyr Trp Lys Tyr Trp
 290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                 325                 330                 335

Asn Ala Val Ser Phe Thr Trp Asp Val Asn Glu Glu Ala Lys Ile Phe
             340                 345                 350

Ile Thr Val Asn Cys Leu Ser Thr Asp Phe Ser Ser Gln Lys Gly Val
         355                 360                 365

Lys Gly Leu Pro Leu Met Ile Gln Ile Asp Thr Tyr Ser Tyr Asn Asn
 370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Glu Gln Lys Gln
                 405                 410                 415

Asn Arg Lys Lys Gly Lys Gly Gln Ala Ser Gln Thr Gln Cys Asn Ser
             420                 425                 430

Ser Ser Asp Gly Lys Leu Ala Ala Ile Pro Leu Gln Lys Lys Ser Asp
```

```
                435                 440                 445
Ile Thr Tyr Phe Lys Thr Met Pro Asp Leu His Ser Gln Pro Val Leu
450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Ser Val Leu Val Lys
                485                 490                 495

Arg Met Phe Arg Pro Met Glu Glu Glu Phe Gly Pro Val Pro Ser Lys
                500                 505                 510

Gln Met Lys Glu Glu Gly Thr Lys Arg Val Leu Leu Tyr Val Arg Lys
                515                 520                 525

Glu Thr Asp Asp Val Phe Asp Ala Leu Met Leu Lys Ser Pro Thr Val
530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Gly Ile Leu Val Asn
                565                 570                 575

Met Asp Asp Asn Ile Ile Glu His Tyr Ser Asn Glu Asp Thr Phe Ile
                580                 585                 590

Leu Asn Met Glu Ser Met Val Glu Gly Phe Lys Val Thr Leu Met Glu
                595                 600                 605

Ile

<210> SEQ ID NO 16
<211> LENGTH: 609
<212> TYPE: PRT
<213> ORGANISM: Homo sapiens

<400> SEQUENCE: 16

Met Pro Ser Asp Pro Pro Phe Asn Thr Arg Ala Tyr Thr Ser Glu
1               5                   10                  15

Asp Glu Ala Trp Lys Ser Tyr Leu Glu Asn Pro Leu Thr Ala Ala Thr
                20                  25                  30

Lys Ala Met Met Ser Ile Asn Gly Asp Glu Asp Ser Ala Ala Ala Leu
                35                  40                  45

Gly Leu Leu Tyr Asp Tyr Tyr Lys Val Pro Arg Asp Lys Arg Leu Leu
50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
                100                 105                 110

Asp His Leu Glu Asn Ser Lys Arg Glu Gln Tyr Ser Ile Ser Phe Pro
                115                 120                 125

Glu Ser Ser Ala Ile Ile Pro Val Ser Gly Ile Thr Val Val Lys Ala
                130                 135                 140

Glu Asp Phe Thr Pro Val Phe Met Ala Pro Pro Val His Tyr Pro Arg
145                 150                 155                 160

Gly Asp Gly Glu Glu Gln Arg Val Val Ile Phe Glu Gln Thr Gln Tyr
                165                 170                 175

Asp Val Pro Ser Leu Ala Thr His Ser Ala Tyr Leu Lys Asp Asp Gln
                180                 185                 190

Arg Ser Thr Pro Asp Ser Thr Tyr Ser Glu Ser Phe Lys Asp Ala Ala
                195                 200                 205
```

```
Thr Glu Lys Phe Arg Ser Ala Ser Val Gly Ala Glu Tyr Met Tyr
    210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                    245                 250                 255

Gly Gln Phe Tyr Ala Ile Thr Leu Ser Glu Thr Gly Asp Asn Lys Cys
                260                 265                 270

Phe Arg His Pro Ile Ser Lys Val Arg Ser Val Val Met Val Val Phe
                275                 280                 285

Ser Glu Asp Lys Asn Arg Asp Glu Gln Leu Lys Tyr Trp Lys Tyr Trp
    290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                    325                 330                 335

Asn Ala Val Ser Phe Thr Trp Asp Val Asn Glu Glu Ala Lys Ile Phe
                340                 345                 350

Ile Thr Val Asn Cys Leu Ser Thr Asp Phe Ser Ser Gln Lys Gly Val
                355                 360                 365

Lys Gly Leu Pro Leu Met Ile Gln Ile Asp Thr Tyr Ser Tyr Asn Asn
370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Arg Lys Gln
                    405                 410                 415

Asn Arg Lys Asn Gly Lys Gly Gln Ala Ser Gln Thr Cys Asn Ser
                420                 425                 430

Ser Ser Asp Gly Lys Leu Ala Ala Ile Pro Leu Gln Lys Lys Ser Asp
                435                 440                 445

Ile Thr Tyr Phe Lys Thr Met Pro Asp Leu His Ser Gln Pro Val Leu
    450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Phe Gly Pro Val Pro Ser Lys
                500                 505                 510

Gln Met Lys Glu Glu Gly Thr Lys Arg Val Leu Leu Tyr Val Arg Lys
    515                 520                 525

Glu Thr Asp Asp Val Phe Asp Ala Leu Met Leu Lys Ser Pro Thr Val
    530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
                580                 585                 590

Leu Asn Met Glu Ser Met Val Glu Gly Phe Lys Val Thr Leu Met Glu
                595                 600                 605

Ile

<210> SEQ ID NO 17
```

```
<211> LENGTH: 609
<212> TYPE: PRT
<213> ORGANISM: Homo sapiens

<400> SEQUENCE: 17

Met Pro Ser Asp Pro Pro Phe Asn Thr Arg Arg Ala Tyr Thr Ser Glu
 1               5                  10                  15

Asp Glu Ala Trp Lys Ser Tyr Leu Glu Asn Pro Leu Thr Ala Ala Thr
            20                  25                  30

Lys Ala Met Met Ser Ile Asn Gly Asp Glu Asp Ser Ala Ala Ala Leu
        35                  40                  45

Gly Leu Leu Tyr Asp Tyr Tyr Lys Val Pro Arg Asp Lys Arg Leu Leu
50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
            100                 105                 110

Asp His Leu Glu Asn Ser Lys Arg Glu Gln Tyr Ser Ile Ser Phe Pro
        115                 120                 125

Glu Ser Ser Ala Ile Ile Pro Val Ser Gly Ile Thr Val Val Lys Ala
130                 135                 140

Glu Asp Phe Thr Pro Val Phe Met Ala Pro Pro Val His Tyr Pro Arg
145                 150                 155                 160

Gly Asp Gly Glu Glu Gln Arg Val Val Ile Phe Glu Gln Thr Gln Tyr
                165                 170                 175

Asp Val Pro Ser Leu Ala Thr His Ser Ala Tyr Leu Lys Asp Asp Gln
            180                 185                 190

Arg Ser Thr Pro Asp Ser Thr Tyr Ser Glu Ser Phe Lys Asp Ala Ala
        195                 200                 205

Thr Glu Lys Phe Arg Ser Ala Ser Val Gly Ala Glu Glu Tyr Met Tyr
210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Val Met Val Val Phe
        275                 280                 285

Ser Glu Asp Lys Asn Arg Asp Glu Gln Leu Lys Tyr Trp Lys Tyr Trp
290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Ile Ala Tyr
                325                 330                 335

Asn Ala Val Ser Phe Thr Trp Asp Val Asn Glu Glu Ala Lys Ile Phe
            340                 345                 350

Ile Thr Val Asn Cys Leu Ser Thr Asp Phe Ser Ser Gln Lys Gly Val
        355                 360                 365

Lys Gly Leu Pro Leu Met Ile Gln Ile Asp Thr Tyr Ser Tyr Asn Asn
370                 375                 380

Arg Ser Asn Lys Pro Ile His Arg Ala Tyr Cys Gln Ile Lys Val Phe
385                 390                 395                 400
```

```
Cys Asp Lys Gly Ala Glu Arg Lys Ile Arg Asp Glu Glu Arg Lys Gln
            405                 410                 415

Asn Arg Lys Lys Gly Lys Gly Gln Ala Ser Gln Thr Gln Cys Asn Ser
            420                 425                 430

Ser Ser Asp Gly Lys Leu Ala Ala Ile Pro Leu Gln Lys Lys Ser Asp
            435                 440                 445

Ile Thr Tyr Phe Lys Thr Met Pro Asp Leu His Ser Gln Pro Val Leu
        450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Ser Val Leu Val Lys
                485                 490                 495

Arg Met Phe Arg Pro Met Glu Glu Glu Phe Gly Pro Val Pro Ser Lys
                500                 505                 510

Gln Met Lys Glu Glu Gly Thr Lys Arg Val Leu Leu Tyr Val Arg Lys
            515                 520                 525

Glu Thr Asp Asp Val Phe Asp Ala Leu Met Leu Lys Ser Pro Thr Val
            530                 535                 540

Met Gly Leu Met Glu Ala Ile Ser Glu Lys Tyr Gly Leu Pro Val Glu
545                 550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
            580                 585                 590

Leu Asn Met Glu Ser Met Val Glu Gly Phe Lys Val Thr Leu Met Glu
            595                 600                 605

Ile

<210> SEQ ID NO 18
<211> LENGTH: 609
<212> TYPE: PRT
<213> ORGANISM: Homo sapiens

<400> SEQUENCE: 18

Met Pro Ser Asp Pro Pro Phe Asn Thr Arg Arg Ala Tyr Thr Ser Glu
1               5                   10                  15

Asp Glu Ala Trp Lys Ser Tyr Leu Glu Asn Pro Leu Thr Ala Ala Thr
            20                  25                  30

Lys Ala Met Met Ser Ile Asn Gly Asp Glu Asp Ser Ala Ala Ala Leu
        35                  40                  45

Gly Leu Leu Tyr Asp Tyr Tyr Lys Val Pro Arg Asp Lys Arg Leu Leu
    50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
            100                 105                 110

Asp His Leu Glu Asn Ser Lys Arg Glu Gln Tyr Ser Ile Ser Phe Pro
        115                 120                 125

Glu Ser Ser Ala Ile Ile Pro Val Ser Gly Ile Thr Val Val Lys Ala
    130                 135                 140

Glu Asp Phe Thr Pro Val Phe Met Ala Pro Pro Val His Tyr Pro Arg
145                 150                 155                 160
```

-continued

```
Gly Asp Gly Glu Glu Gln Arg Val Val Ile Phe Gln Thr Gln Tyr
                165                 170                 175

Asp Val Pro Ser Leu Ala Thr His Ser Ala Tyr Leu Lys Asp Gln
            180                 185                 190

Arg Ser Thr Pro Asp Ser Thr Tyr Ser Glu Ser Phe Lys Asp Ala Ala
        195                 200                 205

Thr Glu Lys Phe Arg Ser Ala Ser Val Gly Ala Glu Glu Tyr Met Tyr
    210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Val Met Val Val Phe
        275                 280                 285

Ser Glu Asp Lys Asn Arg Asp Glu Gln Leu Lys Tyr Trp Lys Tyr Trp
    290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
            340                 345                 350

Ile Thr Val Asn Cys Leu Ser Asp Phe Ser Ser Lys Gly Val
        355                 360                 365

Lys Gly Leu Pro Leu Met Ile Gln Ile Asp Thr Tyr Ser Tyr Asn Asn
    370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Arg Lys Gln
                405                 410                 415

Asn Arg Lys Lys Gly Lys Gly Gln Ala Ser Gln Thr Gln Cys Asn Ser
            420                 425                 430

Ser Ser Asp Gly Lys Leu Ala Ala Ile Pro Leu Gln Lys Lys Ser Asp
        435                 440                 445

Ile Thr Tyr Phe Lys Thr Met Pro Asp Leu His Ser Gln Pro Val Leu
    450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Phe Gly Pro Val Pro Ser Lys
            500                 505                 510

Gln Met Lys Glu Glu Gly Thr Lys Arg Val Leu Leu Tyr Val Arg Lys
        515                 520                 525

Glu Thr Asp Asp Val Phe Asp Ala Leu Met Leu Lys Ser Pro Thr Val
    530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
            580                 585                 590
```

```
Leu Asn Met Glu Ser Met Val Glu Gly Phe Lys Val Thr Leu Met Glu
        595                 600                 605
Ile

<210> SEQ ID NO 19
<211> LENGTH: 609
<212> TYPE: PRT
<213> ORGANISM: Homo sapiens

<400> SEQUENCE: 19

Met Pro Ser Asp Pro Pro Phe Asn Thr Arg Arg Ala Tyr Thr Ser Glu
  1               5                  10                  15

Asp Glu Ala Trp Lys Ser Tyr Leu Glu Asn Pro Leu Thr Ala Ala Thr
             20                  25                  30

Lys Ala Met Met Ile Ile Asn Gly Asp Glu Asp Ser Ala Ala Ala Leu
         35                  40                  45

Gly Leu Leu Tyr Asp Tyr Lys Val Pro Arg Asp Lys Arg Leu Leu
     50                  55                  60

Ser Val Ser Lys Ala Ser Asp Ser Gln Glu Asp Gln Glu Lys Arg Asn
 65                 70                  75                  80

Cys Leu Gly Thr Ser Glu Ala Gln Ser Asn Leu Ser Gly Gly Glu Asn
             85                  90                  95

Arg Val Gln Val Leu Lys Thr Val Pro Val Asn Leu Ser Leu Asn Gln
        100                 105                 110

Asp His Leu Glu Asn Ser Lys Arg Glu Gln Tyr Ser Ile Ser Phe Pro
    115                 120                 125

Glu Ser Ser Ala Ile Ile Pro Val Ser Gly Ile Thr Val Val Lys Ala
130                 135                 140

Glu Asp Phe Thr Pro Val Phe Met Ala Pro Pro Val His Tyr Pro Arg
145                 150                 155                 160

Gly Asp Gly Glu Glu Gln Arg Val Val Ile Phe Glu Gln Thr Gln Tyr
                165                 170                 175

Asp Val Pro Ser Leu Ala Thr His Ser Ala Tyr Leu Lys Asp Asp Gln
            180                 185                 190

Arg Ser Thr Pro Asp Ser Thr Tyr Ser Glu Ser Phe Lys Asp Ala Ala
        195                 200                 205

Thr Glu Lys Phe Arg Ser Ala Ser Val Gly Ala Glu Glu Tyr Met Tyr
    210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Met Val Val Phe
        275                 280                 285

Ser Glu Asp Lys Asn Arg Asp Glu Gln Leu Lys Tyr Trp Lys Tyr Trp
    290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
            340                 345                 350
```

-continued

```
Ile Thr Val Asn Cys Leu Ser Thr Asp Phe Ser Ser Gln Lys Gly Val
            355                 360                 365
Lys Gly Leu Pro Leu Met Ile Gln Ile Asp Thr Tyr Ser Tyr Asn Asn
    370                 375                 380
Arg Ser Asn Lys Pro Ile His Arg Ala Tyr Cys Gln Ile Lys Val Phe
385                 390                 395                 400
Cys Asp Lys Gly Ala Glu Arg Lys Ile Arg Asp Glu Glu Lys Gln
                405                 410                 415
Asn Arg Lys Asn Gly Lys Gly Gln Ala Ser Gln Thr Gln Cys Asn Ser
                420                 425                 430
Ser Ser Asp Gly Lys Leu Ala Ala Ile Pro Leu Gln Lys Lys Ser Asp
            435                 440                 445
Ile Thr Tyr Phe Lys Thr Met Pro Asp Leu His Ser Gln Pro Val Leu
    450                 455                 460
Phe Ile Pro Asp Val His Phe Ala Asn Leu Gln Arg Thr Gly Gln Val
465                 470                 475                 480
Tyr Tyr Asn Thr Asp Asp Glu Arg Glu Gly Ser Val Leu Val Lys
                485                 490                 495
Arg Met Phe Arg Pro Met Glu Glu Phe Gly Pro Val Pro Ser Lys
                500                 505                 510
Gln Met Lys Glu Glu Gly Thr Lys Arg Val Leu Leu Tyr Val Arg Lys
            515                 520                 525
Glu Thr Asp Asp Val Phe Asp Ala Leu Met Leu Lys Ser Pro Thr Val
    530                 535                 540
Met Gly Leu Met Glu Ala Ile Ser Glu Lys Tyr Gly Leu Pro Val Glu
545                 550                 555                 560
Lys Ile Ala Lys Leu Tyr Lys Lys Ser Lys Lys Gly Ile Leu Val Asn
                565                 570                 575
Met Asp Asp Asn Ile Ile Glu His Tyr Ser Asn Glu Asp Thr Phe Ile
                580                 585                 590
Leu Asn Met Glu Ser Met Val Glu Gly Phe Lys Val Thr Leu Met Glu
            595                 600                 605
Ile

<210> SEQ ID NO 20
<211> LENGTH: 609
<212> TYPE: PRT
<213> ORGANISM: Homo sapiens

<400> SEQUENCE: 20

Met Pro Ser Asp Pro Pro Phe Asn Thr Arg Arg Ala Tyr Thr Ser Glu
  1               5                  10                  15
Asp Glu Ala Trp Lys Ser Tyr Leu Glu Asn Pro Leu Thr Ala Ala Thr
                20                  25                  30
Lys Ala Met Met Ser Ile Asn Gly Asp Glu Asp Ser Ala Ala Ala Leu
            35                  40                  45
Gly Leu Leu Tyr Asp Tyr Tyr Lys Val Pro Arg Asp Lys Arg Leu Leu
    50                  55                  60
Ser Val Ser Lys Ala Ser Asp Ser Gln Glu Asp Gln Glu Lys Arg Asn
65                  70                  75                  80
Cys Leu Gly Thr Ser Glu Ala Gln Ser Asn Leu Ser Gly Gly Glu Asn
                85                  90                  95
Arg Val Gln Val Leu Lys Thr Val Pro Val Asn Leu Ser Leu Asn Gln
                100                 105                 110
Asp His Leu Glu Asn Ser Lys Arg Glu Gln Tyr Ser Ile Ser Phe Pro
```

```
                115                 120                 125
Glu Ser Ser Ala Ile Ile Pro Val Ser Gly Ile Thr Val Lys Ala
130                 135                 140

Glu Asp Phe Thr Pro Val Phe Met Ala Pro Val His Tyr Pro Arg
145                 150                 155                 160

Gly Asp Gly Glu Glu Gln Arg Val Val Ile Phe Glu Gln Thr Gln Tyr
            165                 170                 175

Asp Val Pro Ser Leu Ala Thr His Ser Ala Tyr Leu Lys Asp Asp Gln
                180                 185                 190

Arg Ser Thr Pro Asp Ser Thr Tyr Ser Glu Ser Phe Lys Asp Ala Ala
            195                 200                 205

Thr Glu Lys Phe Arg Ser Ala Ser Val Gly Ala Glu Glu Tyr Met Tyr
210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Val Met Val Val Phe
            275                 280                 285

Ser Glu Asp Lys Asn Arg Asp Glu Gln Leu Lys Tyr Trp Lys Tyr Trp
290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
            340                 345                 350

Ile Thr Val Asn Cys Leu Ser Thr Asp Phe Ser Ser Gln Lys Gly Val
            355                 360                 365

Lys Gly Leu Pro Leu Met Ile Gln Ile Asp Thr Tyr Ser Tyr Asn Asn
370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Arg Lys Gln
                405                 410                 415

Asn Arg Lys Lys Gly Lys Gly Gln Ala Ser Gln Thr Gln Cys Asn Ser
            420                 425                 430

Ser Ser Asp Gly Lys Leu Ala Ala Ile Pro Leu Gln Lys Lys Ser Asp
            435                 440                 445

Ile Thr Tyr Phe Lys Thr Met Pro Asp Leu His Ser Gln Pro Val Leu
            450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Glu Phe Gly Pro Val Pro Ser Lys
            500                 505                 510

Gln Met Lys Glu Glu Gly Thr Lys Arg Val Leu Leu Tyr Val Arg Lys
            515                 520                 525

Glu Thr Asp Asp Val Phe Asp Ala Leu Met Leu Lys Ser Pro Thr Val
530                 535                 540
```

-continued

```
Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Gly Ile Leu Val Asn
            565                 570                 575

Met Asp Asp Asn Ile Ile Glu His Tyr Ser Asn Glu Asp Thr Phe Ile
            580                 585                 590

Leu Asn Met Glu Ser Met Val Glu Gly Phe Lys Val Thr Leu Met Glu
        595                 600                 605

Ile

<210> SEQ ID NO 21
<211> LENGTH: 609
<212> TYPE: PRT
<213> ORGANISM: Homo sapiens

<400> SEQUENCE: 21

Met Pro Ser Asp Pro Pro Phe Asn Thr Arg Arg Ala Tyr Thr Ser Glu
1               5                   10                  15

Asp Glu Ala Trp Lys Ser Tyr Leu Glu Asn Pro Leu Thr Ala Ala Thr
            20                  25                  30

Lys Ala Met Met Ser Ile Asn Gly Asp Glu Asp Ser Ala Ala Ala Leu
        35                  40                  45

Gly Leu Leu Tyr Asp Tyr Tyr Lys Val Pro Arg Asp Lys Arg Leu Leu
50                  55                  60

Ser Val Ser Lys Ala Ser Asp Ser Gln Glu Asp Gln Asp Lys Arg Asn
65                  70                  75                  80

Cys Leu Gly Thr Ser Glu Ala Gln Ile Asn Leu Ser Gly Gly Glu Asn
                85                  90                  95

Arg Val Gln Val Leu Lys Thr Val Pro Val Asn Leu Cys Leu Ser Gln
            100                 105                 110

Asp His Met Glu Asn Ser Lys Arg Glu Gln Tyr Ser Val Ser Ile Thr
        115                 120                 125

Glu Ser Ser Ala Val Ile Pro Val Ser Gly Ile Thr Val Val Lys Ala
130                 135                 140

Glu Asp Phe Thr Pro Val Phe Met Ala Pro Val His Tyr Pro Arg
145                 150                 155                 160

Ala Asp Ser Glu Glu Gln Arg Val Val Ile Phe Glu Gln Thr Gln Tyr
                165                 170                 175

Asp Leu Pro Ser Ile Ala Ser His Ser Ser Tyr Leu Lys Asp Asp Gln
            180                 185                 190

Arg Ser Thr Pro Asp Ser Thr Tyr Ser Glu Ser Phe Lys Asp Gly Ala
        195                 200                 205

Ser Glu Lys Phe Arg Ser Thr Val Gly Ala Asp Glu Tyr Thr Tyr
210                 215                 220

Asp Gln Thr Gly Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Met Val Val Phe
        275                 280                 285

Ser Glu Asp Lys Asn Arg Asp Glu Gln Leu Lys Tyr Trp Lys Tyr Trp
290                 295                 300

His Ser Arg Gln His Thr Ala Lys Gln Arg Val Leu Asp Ile Ala Asp
```

```
                   305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
                340                 345                 350

Ile Thr Val Asn Cys Leu Ser Thr Asp Phe Ser Ser Gln Lys Gly Val
                355                 360                 365

Lys Gly Leu Pro Leu Met Ile Gln Ile Asp Thr Tyr Ser Tyr Asn Asn
            370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Arg Lys Gln
                405                 410                 415

Asn Arg Lys Lys Gly Lys Gly Gln Ala Ser Gln Ala Gln Cys Asn Asn
                420                 425                 430

Ser Ser Asp Gly Lys Met Ala Ala Ile Pro Leu Gln Lys Lys Ser Asp
            435                 440                 445

Ile Thr Tyr Phe Lys Thr Met Pro Asp Leu His Ser Gln Pro Val Leu
        450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Ser Ser Val Leu Val Lys
                485                 490                 495

Arg Met Phe Arg Pro Met Glu Glu Phe Gly Pro Thr Pro Ser Lys
                500                 505                 510

Gln Ile Lys Glu Glu Asn Val Lys Arg Val Leu Leu Tyr Val Arg Lys
            515                 520                 525

Glu Asn Asp Asp Val Phe Asp Ala Leu Met Leu Lys Ser Pro Thr Val
        530                 535                 540

Lys Gly Leu Met Glu Ala Leu Ser Glu Lys Tyr Gly Leu Pro Val Glu
545                 550                 555                 560

Lys Ile Thr Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
                580                 585                 590

Leu Asn Met Glu Ser Met Val Glu Gly Phe Lys Ile Thr Leu Met Glu
            595                 600                 605

Ile

<210> SEQ ID NO 22
<211> LENGTH: 403
<212> TYPE: PRT
<213> ORGANISM: Homo sapiens

<400> SEQUENCE: 22

Met Pro Ser Asp Pro Pro Phe Asn Thr Arg Arg Ala Tyr Thr Ser Glu
1               5                   10                  15

Asp Glu Ala Trp Lys Ser Tyr Leu Glu Asn Pro Leu Thr Ala Ala Thr
                20                  25                  30

Lys Ala Met Met Ser Ile Asn Gly Asp Glu Asp Ser Ala Ala Ala Leu
            35                  40                  45

Gly Leu Leu Tyr Asp Tyr Tyr Lys Val Pro Arg Asp Lys Arg Leu Leu
        50                  55                  60

Ser Val Ser Lys Ala Ser Asp Ser Gln Glu Asp Gln Glu Lys Arg Asn
65                  70                  75                  80
```

```
Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
            100                 105                 110

Asp His Leu Glu Asn Ser Lys Arg Glu Gln Tyr Ser Ile Ser Phe Pro
        115                 120                 125

Glu Ser Ser Ala Ile Ile Pro Val Ser Gly Ile Thr Val Val Lys Ala
130                 135                 140

Glu Asp Phe Thr Pro Val Phe Met Ala Pro Val His Tyr Pro Arg
145                 150                 155                 160

Gly Asp Gly Glu Glu Gln Arg Val Val Ile Phe Glu Gln Thr Gln Tyr
                165                 170                 175

Asp Val Pro Ser Leu Ala Thr His Ser Ala Tyr Leu Lys Asp Asp Gln
            180                 185                 190

Arg Ser Thr Pro Asp Ser Thr Tyr Ser Glu Ser Phe Lys Asp Ala Ala
        195                 200                 205

Thr Glu Lys Phe Arg Ser Ala Ser Val Gly Ala Glu Glu Tyr Met Tyr
210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Val Met Val Val Phe
        275                 280                 285

Ser Glu Asp Lys Asn Arg Asp Glu Gln Leu Lys Tyr Trp Lys Tyr Trp
290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
            340                 345                 350

Ile Thr Val Asn Cys Leu Ser Thr Asp Phe Ser Ser Gln Lys Gly Val
        355                 360                 365

Lys Gly Leu Pro Leu Met Ile Gln Ile Asp Thr Tyr Ser Tyr Asn Asn
370                 375                 380

Arg Ser Asn Lys Pro Ile His Arg Ala Tyr Cys Gln Ile Lys Val Phe
385                 390                 395                 400

Cys Asp Lys

<210> SEQ ID NO 23
<211> LENGTH: 403
<212> TYPE: PRT
<213> ORGANISM: Homo sapiens

<400> SEQUENCE: 23

Met Pro Ser Asp Pro Pro Phe Asn Thr Arg Arg Ala Tyr Thr Ser Glu
1               5                   10                  15

Asp Glu Ala Trp Lys Ser Tyr Leu Glu Asn Pro Leu Thr Ala Ala Thr
                20                  25                  30

Lys Ala Met Met Ser Ile Asn Gly Asp Glu Asp Ser Ala Ala Ala Leu
            35                  40                  45
```

-continued

```
Gly Leu Leu Tyr Asp Tyr Tyr Lys Val Pro Arg Asp Lys Arg Leu Leu
 50                  55                  60

Ser Val Ser Lys Ala Ser Asp Ser Gln Glu Asp Gln Asp Lys Arg Asn
 65                  70                  75                  80

Cys Leu Gly Thr Ser Glu Ala Gln Ile Asn Leu Ser Gly Gly Glu Asn
                 85                  90                  95

Arg Val Gln Val Leu Lys Thr Val Pro Val Asn Leu Cys Leu Ser Gln
            100                 105                 110

Asp His Met Glu Asn Ser Lys Arg Glu Gln Tyr Ser Val Ser Ile Thr
        115                 120                 125

Glu Ser Ser Ala Val Ile Pro Val Ser Gly Ile Thr Val Val Lys Ala
130                 135                 140

Glu Asp Phe Thr Pro Val Phe Met Ala Pro Val His Tyr Pro Arg
145                 150                 155                 160

Ala Asp Ser Glu Glu Gln Arg Val Val Ile Phe Glu Gln Thr Gln Tyr
                165                 170                 175

Asp Leu Pro Ser Ile Ala Ser His Ser Ser Tyr Leu Lys Asp Asp Gln
            180                 185                 190

Arg Ser Thr Pro Asp Ser Thr Tyr Ser Glu Ser Phe Lys Asp Gly Ala
        195                 200                 205

Ser Glu Lys Phe Arg Ser Thr Ser Val Gly Ala Asp Glu Tyr Thr Tyr
210                 215                 220

Asp Gln Thr Gly Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Val Met Val Val Phe
        275                 280                 285

Ser Glu Asp Lys Asn Arg Asp Glu Gln Leu Lys Tyr Trp Lys Tyr Trp
290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
            340                 345                 350

Ile Thr Val Asn Cys Leu Ser Thr Asp Phe Ser Ser Gln Lys Gly Val
        355                 360                 365

Lys Gly Leu Pro Leu Met Ile Gln Ile Asp Thr Tyr Ser Tyr Asn Asn
370                 375                 380

Arg Ser Asn Lys Pro Ile His Arg Ala Tyr Cys Gln Ile Lys Val Phe
385                 390                 395                 400

Cys Asp Lys

<210> SEQ ID NO 24
<211> LENGTH: 14
<212> TYPE: PRT
<213> ORGANISM: Tetanus toxoid

<400> SEQUENCE: 24

Gln Tyr Ile Lys Ala Asn Ser Lys Phe Ile Gly Ile Thr Glu
  1               5                  10
```

```
<210> SEQ ID NO 25
<211> LENGTH: 21
<212> TYPE: PRT
<213> ORGANISM: Plasmodium falciparum

<400> SEQUENCE: 25

Asp Ile Glu Lys Lys Ile Ala Lys Met Glu Lys Ala Ser Ser Val Phe
1               5                   10                  15

Asn Val Val Asn Ser
            20

<210> SEQ ID NO 26
<211> LENGTH: 16
<212> TYPE: PRT
<213> ORGANISM: Streptococcus

<400> SEQUENCE: 26

Gly Ala Val Asp Ser Ile Leu Gly Gly Val Ala Thr Tyr Gly Ala Ala
1               5                   10                  15

<210> SEQ ID NO 27
<211> LENGTH: 12
<212> TYPE: PRT
<213> ORGANISM: Artificial Sequence
<220> FEATURE:
<223> OTHER INFORMATION: Pan-DR-binding epitope
<220> FEATURE:
<221> NAME/KEY: VARIANT
<222> LOCATION: 1, 12
<223> OTHER INFORMATION: Xaa = D-alanine or L-alanine
<220> FEATURE:
<221> NAME/KEY: VARIANT
<222> LOCATION: 3
<223> OTHER INFORMATION: Xaa = cyclohexylalanine, phenylalanine, or
      tyrosine

<400> SEQUENCE: 27

Xaa Lys Xaa Val Ala Ala Trp Thr Leu Lys Ala Xaa
1               5                   10

<210> SEQ ID NO 28
<211> LENGTH: 14
<212> TYPE: DNA
<213> ORGANISM: Artificial Sequence
<220> FEATURE:
<223> OTHER INFORMATION: Primer

<400> SEQUENCE: 28
ttttgatcaa gctt                                                         14

<210> SEQ ID NO 29
<211> LENGTH: 42
<212> TYPE: DNA
<213> ORGANISM: Artificial Sequence
<220> FEATURE:
<223> OTHER INFORMATION: Primer

<400> SEQUENCE: 29
ctaatacgac tcactatagg gctcgagcgg ccgcccgggc ag                           42

<210> SEQ ID NO 30
<211> LENGTH: 12
<212> TYPE: DNA
<213> ORGANISM: Artificial Sequence
<220> FEATURE:
<223> OTHER INFORMATION: Primer

<400> SEQUENCE: 30
```
gatcctgccc gg                                                          12

<210> SEQ ID NO 31
<211> LENGTH: 40
<212> TYPE: DNA
<213> ORGANISM: Artificial Sequence
<220> FEATURE:
<223> OTHER INFORMATION: Primer

<400> SEQUENCE: 31
gtaatacgac tcactatagg gcagcgtggt cgcggccgag                             40

<210> SEQ ID NO 32
<211> LENGTH: 10
<212> TYPE: DNA
<213> ORGANISM: Artificial Sequence
<220> FEATURE:
<223> OTHER INFORMATION: Primer

<400> SEQUENCE: 32
gatcctcggc                                                             10

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
ctaatacgac tcactatagg gc                                               22

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
tcgagcggcc gcccgggcag ga                                               22

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
agcgtggtcg cggccgagga                                                  20

<210> SEQ ID NO 36
<211> LENGTH: 25
<212> TYPE: DNA
<213> ORGANISM: Artificial Sequence
<220> FEATURE:
<223> OTHER INFORMATION: Primer

<400> SEQUENCE: 36
atatcgccgc gctcgtcgtc gacaa                                            25

<210> SEQ ID NO 37
<211> LENGTH: 26
<212> TYPE: DNA
<213> ORGANISM: Artificial Sequence
<220> FEATURE:

```
<223> OTHER INFORMATION: Primer

<400> SEQUENCE: 37
agccacacgc agctcattgt agaagg                                          26

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
catttcacat gtccatgatc ttcc                                            24

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
ctttgatgtg tccgctgtgt atgt                                            24

<210> SEQ ID NO 40
<211> LENGTH: 24
<212> TYPE: DNA
<213> ORGANISM: Artificial Sequence
<220> FEATURE:
<223> OTHER INFORMATION: FLAG Epitope tag

<400> SEQUENCE: 40
gattacaagg atgacgacga taag                                            24

<210> SEQ ID NO 41
<211> LENGTH: 4
<212> TYPE: PRT
<213> ORGANISM: Homo sapiens

<400> SEQUENCE: 41

Asn Leu Ser Gly
 1

<210> SEQ ID NO 42
<211> LENGTH: 4
<212> TYPE: PRT
<213> ORGANISM: Homo sapiens

<400> SEQUENCE: 42

Asn Leu Ser Leu
 1

<210> SEQ ID NO 43
<211> LENGTH: 4
<212> TYPE: PRT
<213> ORGANISM: Homo sapiens

<400> SEQUENCE: 43

Asn Arg Ser Asn
 1

<210> SEQ ID NO 44
<211> LENGTH: 4
<212> TYPE: PRT
<213> ORGANISM: Homo sapiens
```

<400> SEQUENCE: 44

Asn Ser Ser Ser
 1

<210> SEQ ID NO 45
<211> LENGTH: 15
<212> TYPE: PRT
<213> ORGANISM: Homo sapiens

<400> SEQUENCE: 45

Ala Ser Val Gly Ala Glu Glu Tyr Met Tyr Asp Gln Thr Ser Ser
 1               5                  10                  15

<210> SEQ ID NO 46
<211> LENGTH: 15
<212> TYPE: PRT
<213> ORGANISM: Homo sapiens

<400> SEQUENCE: 46

Val Gly Ala Glu Glu Tyr Met Tyr Asp Gln Thr Ser Ser Gly Thr
 1               5                  10                  15

<210> SEQ ID NO 47
<211> LENGTH: 15
<212> TYPE: PRT
<213> ORGANISM: Homo sapiens

<400> SEQUENCE: 47

Arg Val Leu Asp Ile Ala Asp Tyr Lys Glu Ser Phe Asn Thr Ile
 1               5                  10                  15

<210> SEQ ID NO 48
<211> LENGTH: 15
<212> TYPE: PRT
<213> ORGANISM: Homo sapiens

<400> SEQUENCE: 48

Asp Asp Asn Ile Ile Glu His Tyr Ser Asn Glu Asp Thr Phe Ile
 1               5                  10                  15

<210> SEQ ID NO 49
<211> LENGTH: 4
<212> TYPE: PRT
<213> ORGANISM: Homo sapiens

<400> SEQUENCE: 49

Arg Lys Glu Thr
 1

<210> SEQ ID NO 50
<211> LENGTH: 4
<212> TYPE: PRT
<213> ORGANISM: Homo sapiens

<400> SEQUENCE: 50

Thr Ser Glu Asp
 1

<210> SEQ ID NO 51
<211> LENGTH: 4
<212> TYPE: PRT
<213> ORGANISM: Homo sapiens

<400> SEQUENCE: 51

Ser Glu Asp Glu
1

<210> SEQ ID NO 52
<211> LENGTH: 4
<212> TYPE: PRT
<213> ORGANISM: Homo sapiens

<400> SEQUENCE: 52

Ser Tyr Leu Glu
1

<210> SEQ ID NO 53
<211> LENGTH: 4
<212> TYPE: PRT
<213> ORGANISM: Homo sapiens

<400> SEQUENCE: 53

Ser Gln Glu Asp
1

<210> SEQ ID NO 54
<211> LENGTH: 4
<212> TYPE: PRT
<213> ORGANISM: Homo sapiens

<400> SEQUENCE: 54

Ser Gly Gly Glu
1

<210> SEQ ID NO 55
<211> LENGTH: 4
<212> TYPE: PRT
<213> ORGANISM: Homo sapiens

<400> SEQUENCE: 55

Ser Lys Arg Glu
1

<210> SEQ ID NO 56
<211> LENGTH: 4
<212> TYPE: PRT
<213> ORGANISM: Homo sapiens

<400> SEQUENCE: 56

Ser Phe Pro Glu
1

<210> SEQ ID NO 57
<211> LENGTH: 4
<212> TYPE: PRT
<213> ORGANISM: Homo sapiens

<400> SEQUENCE: 57

Thr Gln Tyr Asp
1

<210> SEQ ID NO 58
<211> LENGTH: 4
<212> TYPE: PRT
<213> ORGANISM: Homo sapiens

<400> SEQUENCE: 58

Ser Thr Pro Asp
1

```
<210> SEQ ID NO 59
<211> LENGTH: 4
<212> TYPE: PRT
<213> ORGANISM: Homo sapiens

<400> SEQUENCE: 59

Thr Tyr Ser Glu
1

<210> SEQ ID NO 60
<211> LENGTH: 4
<212> TYPE: PRT
<213> ORGANISM: Homo sapiens

<400> SEQUENCE: 60

Ser Phe Lys Asp
1

<210> SEQ ID NO 61
<211> LENGTH: 4
<212> TYPE: PRT
<213> ORGANISM: Homo sapiens

<400> SEQUENCE: 61

Thr Leu Ser Glu
1

<210> SEQ ID NO 62
<211> LENGTH: 4
<212> TYPE: PRT
<213> ORGANISM: Homo sapiens

<400> SEQUENCE: 62

Ser Ser Ser Asp
1

<210> SEQ ID NO 63
<211> LENGTH: 4
<212> TYPE: PRT
<213> ORGANISM: Homo sapiens

<400> SEQUENCE: 63

Thr Met Pro Asp
1

<210> SEQ ID NO 64
<211> LENGTH: 4
<212> TYPE: PRT
<213> ORGANISM: Homo sapiens

<400> SEQUENCE: 64

Thr Asp Asp Glu
1

<210> SEQ ID NO 65
<211> LENGTH: 4
<212> TYPE: PRT
<213> ORGANISM: Homo sapiens

<400> SEQUENCE: 65

Ser Asn Glu Asp
1

<210> SEQ ID NO 66
<211> LENGTH: 4
```

```
<212> TYPE: PRT
<213> ORGANISM: Homo sapiens

<400> SEQUENCE: 66

Ser Met Val Glu
 1

<210> SEQ ID NO 67
<211> LENGTH: 4
<212> TYPE: PRT
<213> ORGANISM: Homo sapiens

<400> SEQUENCE: 67

Thr Leu Met Glu
 1

<210> SEQ ID NO 68
<211> LENGTH: 8
<212> TYPE: PRT
<213> ORGANISM: Homo sapiens

<400> SEQUENCE: 68

Arg Ser Thr Pro Asp Ser Thr Tyr
 1               5

<210> SEQ ID NO 69
<211> LENGTH: 9
<212> TYPE: PRT
<213> ORGANISM: Homo sapiens

<400> SEQUENCE: 69

Lys Asn Arg Asp Glu Gln Leu Lys Tyr
 1               5

<210> SEQ ID NO 70
<211> LENGTH: 8
<212> TYPE: PRT
<213> ORGANISM: Homo sapiens

<400> SEQUENCE: 70

Arg Val Leu Asp Ile Ala Asp Tyr
 1               5

<210> SEQ ID NO 71
<211> LENGTH: 7
<212> TYPE: PRT
<213> ORGANISM: Homo sapiens

<400> SEQUENCE: 71

Lys Lys Ser Asp Ile Thr Tyr
 1               5

<210> SEQ ID NO 72
<211> LENGTH: 6
<212> TYPE: PRT
<213> ORGANISM: Homo sapiens

<400> SEQUENCE: 72

Gly Thr Ser Glu Ala Gln
 1               5

<210> SEQ ID NO 73
<211> LENGTH: 6
<212> TYPE: PRT
<213> ORGANISM: Homo sapiens
```

-continued

```
<400> SEQUENCE: 73

Gly Gln Phe Tyr Ala Ile
1               5

<210> SEQ ID NO 74
<211> LENGTH: 6
<212> TYPE: PRT
<213> ORGANISM: Homo sapiens

<400> SEQUENCE: 74

Gly Leu Met Glu Ala Ile
1               5

<210> SEQ ID NO 75
<211> LENGTH: 6
<212> TYPE: PRT
<213> ORGANISM: Homo sapiens

<400> SEQUENCE: 75

Gly Ile Leu Val Asn Met
1               5

<210> SEQ ID NO 76
<211> LENGTH: 17
<212> TYPE: PRT
<213> ORGANISM: Homo sapiens

<400> SEQUENCE: 76

Arg Lys Ile Arg Asp Glu Glu Arg Lys Gln Asn Arg Lys Lys Gly Lys
1               5                   10                  15

Gly

<210> SEQ ID NO 77
<211> LENGTH: 609
<212> TYPE: PRT
<213> ORGANISM: Homo sapiens

<400> SEQUENCE: 77

Met Pro Ser Asp Pro Pro Phe Asn Thr Arg Arg Ala Tyr Thr Ser Glu
1               5                   10                  15

Asp Glu Ala Trp Lys Ser Tyr Leu Glu Asn Pro Leu Thr Ala Ala Thr
                20                  25                  30

Lys Ala Met Met Ser Ile Asn Gly Asp Glu Asp Ser Ala Ala Ala Leu
            35                  40                  45

Gly Leu Leu Tyr Asp Tyr Tyr Lys Val Pro Arg Asp Lys Arg Leu Leu
        50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
                100                 105                 110

Asp His Leu Glu Asn Ser Lys Arg Glu Gln Tyr Ser Ile Ser Phe Pro
            115                 120                 125

Glu Ser Ser Ala Ile Ile Pro Val Ser Gly Ile Thr Val Val Lys Ala
        130                 135                 140

Glu Asp Phe Thr Pro Val Phe Met Ala Pro Val His Tyr Pro Arg
145                 150                 155                 160

Gly Asp Gly Glu Glu Gln Arg Val Val Ile Phe Glu Gln Thr Gln Tyr
                165                 170                 175
```

```
Asp Val Pro Ser Leu Ala Thr His Ser Ala Tyr Leu Lys Asp Asp Gln
            180                 185                 190

Arg Ser Thr Pro Asp Ser Thr Tyr Ser Glu Ser Phe Lys Asp Ala Ala
        195                 200                 205

Thr Glu Lys Phe Arg Ser Ala Ser Val Gly Ala Glu Glu Tyr Met Tyr
    210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
                260                 265                 270

Phe Arg His Pro Ile Ser Lys Val Arg Ser Val Val Met Val Val Phe
            275                 280                 285

Ser Glu Asp Lys Asn Arg Asp Glu Gln Leu Lys Tyr Trp Lys Tyr Trp
    290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
                340                 345                 350

Ile Thr Val Asn Cys Leu Ser Thr Asp Phe Ser Ser Gln Lys Gly Val
            355                 360                 365

Lys Gly Leu Pro Leu Met Ile Gln Ile Asp Thr Tyr Ser Tyr Asn Asn
370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Glu Arg Lys Gln
                405                 410                 415

Asn Arg Lys Lys Gly Lys Gly Gln Ala Ser Gln Thr Gln Cys Asn Ser
                420                 425                 430

Ser Ser Asp Gly Lys Leu Ala Ala Ile Pro Leu Gln Lys Lys Ser Asp
            435                 440                 445

Ile Thr Tyr Phe Lys Thr Met Pro Asp Leu His Ser Gln Pro Val Leu
450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Glu Phe Gly Pro Val Pro Ser Lys
                500                 505                 510

Gln Met Lys Glu Glu Gly Thr Lys Arg Val Leu Leu Tyr Val Arg Lys
            515                 520                 525

Glu Thr Asp Asp Val Phe Asp Ala Leu Met Leu Lys Ser Pro Thr Val
    530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Gly Ile Leu Val Asn
                565                 570                 575

Met Asp Asp Asn Ile Ile Glu His Tyr Ser Asn Glu Asp Thr Phe Ile
            580                 585                 590

Leu Asn Met Glu Ser Met Val Glu Gly Phe Lys Val Thr Leu Met Glu
```

-continued

```
            595                 600                 605
Ile
```

<210> SEQ ID NO 78
<211> LENGTH: 24
<212> TYPE: PRT
<213> ORGANISM: Homo sapiens

<400> SEQUENCE: 78

Met Ser Gln Glu Ser Asp Asn Asn Lys Arg Leu Val Ala Leu Val Pro
 1               5                  10                  15

Met Pro Ser Asp Pro Pro Phe Asn
            20

<210> SEQ ID NO 79
<211> LENGTH: 25
<212> TYPE: PRT
<213> ORGANISM: Homo sapiens

<400> SEQUENCE: 79

Met Ser Gln Glu Ser Asp Asn Asn Lys Arg Leu Val Ala Leu Val Pro
 1               5                  10                  15

Met Pro Ser Asp Pro Pro Phe Asn Thr
            20                  25

<210> SEQ ID NO 80
<211> LENGTH: 30
<212> TYPE: PRT
<213> ORGANISM: Homo sapiens

<400> SEQUENCE: 80

Met Ser Gln Glu Ser Asp Asn Asn Lys Arg Leu Val Ala Leu Val Pro
 1               5                  10                  15

Met Pro Ser Asp Pro Pro Phe Asn Thr Arg Arg Ala Tyr Thr
            20                  25                  30

<210> SEQ ID NO 81
<211> LENGTH: 17
<212> TYPE: PRT
<213> ORGANISM: Homo sapiens

<400> SEQUENCE: 81

Thr Ala Ala Thr Lys Ala Met Met Ile Ile Asn Gly Asp Glu Asp Ser
 1               5                  10                  15

Ala

<210> SEQ ID NO 82
<211> LENGTH: 19
<212> TYPE: PRT
<213> ORGANISM: Homo sapiens

<400> SEQUENCE: 82

Leu Thr Ala Ala Thr Lys Ala Met Met Ile Ile Asn Gly Asp Glu Asp
 1               5                  10                  15

Ser Ala Ala

<210> SEQ ID NO 83
<211> LENGTH: 29
<212> TYPE: PRT
<213> ORGANISM: Homo sapiens

<400> SEQUENCE: 83

```
Tyr Leu Glu Asn Pro Leu Thr Ala Ala Thr Lys Ala Met Met Ile Ile
 1               5                  10                  15

Asn Gly Asp Glu Asp Ser Ala Ala Ala Leu Gly Leu Leu
            20                  25
```

<210> SEQ ID NO 84
<211> LENGTH: 17
<212> TYPE: PRT
<213> ORGANISM: Homo sapiens

<400> SEQUENCE: 84

```
Glu Arg Lys Ile Arg Asp Glu Glu Gln Lys Gln Asn Arg Lys Lys Gly
 1               5                  10                  15

Lys
```

<210> SEQ ID NO 85
<211> LENGTH: 19
<212> TYPE: PRT
<213> ORGANISM: Homo sapiens

<400> SEQUENCE: 85

```
Ala Glu Arg Lys Ile Arg Asp Glu Glu Gln Lys Gln Asn Arg Lys Lys
 1               5                  10                  15

Gly Lys Gly
```

<210> SEQ ID NO 86
<211> LENGTH: 29
<212> TYPE: PRT
<213> ORGANISM: Homo sapiens

<400> SEQUENCE: 86

```
Phe Cys Asp Lys Gly Ala Glu Arg Lys Ile Arg Asp Glu Glu Gln Lys
 1               5                  10                  15

Gln Asn Arg Lys Lys Gly Lys Gly Gln Ala Ser Gln Thr
            20                  25
```

<210> SEQ ID NO 87
<211> LENGTH: 17
<212> TYPE: PRT
<213> ORGANISM: Homo sapiens

<400> SEQUENCE: 87

```
Glu Glu Arg Lys Gln Asn Arg Lys Asn Gly Lys Gly Gln Ala Ser Gln
 1               5                  10                  15

Thr
```

<210> SEQ ID NO 88
<211> LENGTH: 19
<212> TYPE: PRT
<213> ORGANISM: Homo sapiens

<400> SEQUENCE: 88

```
Asp Glu Glu Arg Lys Gln Asn Arg Lys Asn Gly Lys Gly Gln Ala Ser
 1               5                  10                  15

Gln Thr Gln
```

<210> SEQ ID NO 89
<211> LENGTH: 29
<212> TYPE: PRT
<213> ORGANISM: Homo sapiens

<400> SEQUENCE: 89

Glu Arg Lys Ile Arg Asp Glu Glu Arg Lys Gln Asn Arg Lys Asn Gly
1               5                   10                  15

Lys Gly Gln Ala Ser Gln Thr Gln Cys Asn Ser Ser Ser
            20                  25

<210> SEQ ID NO 90
<211> LENGTH: 11
<212> TYPE: PRT
<213> ORGANISM: Homo sapiens

<400> SEQUENCE: 90

Glu Glu Gln Lys Gln Asn Arg Lys Asn Gly Lys
1               5                   10

<210> SEQ ID NO 91
<211> LENGTH: 13
<212> TYPE: PRT
<213> ORGANISM: Homo sapiens

<400> SEQUENCE: 91

Asp Glu Glu Gln Lys Gln Asn Arg Lys Asn Gly Lys Gly
1               5                   10

<210> SEQ ID NO 92
<211> LENGTH: 23
<212> TYPE: PRT
<213> ORGANISM: Homo sapiens

<400> SEQUENCE: 92

Glu Arg Lys Ile Arg Asp Glu Glu Gln Lys Gln Asn Arg Lys Asn Gly
1               5                   10                  15

Lys Gly Gln Ala Ser Gln Thr
            20

<210> SEQ ID NO 93
<211> LENGTH: 17
<212> TYPE: PRT
<213> ORGANISM: Homo sapiens

<400> SEQUENCE: 93

Leu Met Leu Lys Ser Pro Thr Val Met Gly Leu Met Glu Ala Ile Ser
1               5                   10                  15

Glu

<210> SEQ ID NO 94
<211> LENGTH: 19
<212> TYPE: PRT
<213> ORGANISM: Homo sapiens

<400> SEQUENCE: 94

Ala Leu Met Leu Lys Ser Pro Thr Val Met Gly Leu Met Glu Ala Ile
1               5                   10                  15

Ser Glu Lys

<210> SEQ ID NO 95
<211> LENGTH: 26
<212> TYPE: PRT
<213> ORGANISM: Homo sapiens

<400> SEQUENCE: 95

Phe Asp Ala Leu Met Leu Lys Ser Pro Thr Val Met Gly Leu Met Glu
1               5                   10                  15

Ala Ile Ser Glu Lys Tyr Gly Leu Pro Val

<210> SEQ ID NO 96
<211> LENGTH: 4913
<212> TYPE: DNA
<213> ORGANISM: Homo sapiens

<400> SEQUENCE: 96

```
attggatcaa acatgtcaca agagtcggac aataataaaa gactagtggc cttagtgccc      60
atgcccagtg accctccatt caatacccga agagcctaca ccagtgagga tgaagcctgg     120
aagtcatact tggagaatcc cctgacagca gccaccaagg ccatgatgag cattaatggt     180
gatgaggaca gtgctgctgc cctcggcctg ctctatgact actacaaggt tcctcgagac     240
aagaggctgc tgtctgtaag caaagcaagt gacagccaag aagaccagga aaaagaaac      300
tgccttggca ccagtgaagc ccagagtaat ttgagtggag agaaaaccg agtgcaagtc      360
ctaaagactt ttccagtgaa cctttcccta aatcaagatc acctggagaa ttccaagcgg     420
gaacagtaca gcatcagctt ccccgagagc tctgccatca tcccggtgtc gggaatcacg     480
gtggtgaaag ctgaagattt cacaccagtt ttcatggccc cacctgtgca ctatccccgg     540
ggagatgggg aagagcaacg agtggttatc tttgaacaga ctcagtatga cgtgccctcg     600
ctggccaccc acagcgccta tctcaaagac gaccagcgca gcactccgga cagcacatac     660
agcgagagct tcaaggacgc agccacagag aaatttcgga gtgcttcagt tggggctgag     720
gagtacatgt atgatcagac atcaagtggc acatttcagt acaccctgga agccaccaaa     780
tctctccgtc agaagcaggg ggagggcccc atgacctacc tcaacaaagg acagttctat     840
gccataacac tcagcgagac cggagacaac aaatgcttcc gacacccat cagcaaagtc      900
aggagtgtgg tgatggtggt cttcagtgaa gacaaaaaca gagatgaaca gctcaaatac     960
tggaaatact ggcactctcg gcagcatacg gcgaagcaga gggtccttga cattgccgat    1020
tacaaggaga gctttaatac gattggaaac attgaagaga ttgcatataa tgctgttttcc   1080
tttacctggg acgtgaatga agaggcgaag attttcatca ccgtgaattg cttgagcaca    1140
gatttctcct cccaaaaagg ggtgaaagga cttcctttga tgattcagat tgacacatac    1200
agttataaca atcgtagcaa taaacccatt catagagctt attgccagat caaggtcttc    1260
tgtgacaaag gagcagaaag aaaaatccga gatgaagagc ggaagcagaa caggaagaaa    1320
gggaaaggcc aggcctccca aactcaatgc aacagctcct ctgatgggaa gttggctgcc    1380
ataccttta cagaagaagag tgacatcacc tacttcaaaa ccatgcctga tctccactca    1440
cagccagttc tcttcatacc tgatgttcac tttgcaaacc tgcagaggac cggacaggtg    1500
tattacaaca cggatgatga acgagaaggt ggcagtgtcc ttgttaaacg gatgttccgg    1560
cccatggaag aggagtttgg tccagtgcct tcaaagcaga tgaaagaaga agggacaaag    1620
cgagtgctct tgtacgtgag gaaggagact gacgatgtgt tcgatgcatt gatgttgaag    1680
tctcccacag tgaagggcct gatggaagcg atatctgaga aatatggct gcccgtggag    1740
aagatagcaa agctttacaa gaaaagcaaa aaaggcatct tggtgaacat ggatgacaac    1800
atcatcgagc actactcgaa cgaggacacc ttcatcctca acatggagag catggtggag    1860
ggcttcaagg tcacgctcat ggaaatctag ccctgggttt ggcatccgct ttggctggag    1920
ctctcagtgc gttcctccct gagagagaca gaagcccag ccccagaacc tggagaccca    1980
tctcccccat ctcacaactg ctgttacaag accgtgctgg ggagtggggc aagggacagg    2040
ccccactgtc ggtgtgcttg gcccatccac tggcacctac cacggagctg aagcctgagc    2100
```

```
ccctcaggaa ggtgccttag gcctgttgga ttcctatttta ttgcccacct tttcctggag    2160
cccaggtcca ggcccgccag gactctgcag gtcactgcta gctccagatg agaccgtcca    2220
gcgttccccc ttcaagagaa acactcatcc cgaacagcct aaaaaattcc catcccttct    2280
ctctcacccc tccatatcta tctcccgagt ggctggacaa aatgagctac gtctgggtgc    2340
agtagttata ggtggggcaa gaggtggatg cccactttct ggtcagacac ctttaggttg    2400
ctctggggaa ggctgtcttg ctaaataccc tcagggttcc cagcaagtgg ccaccaggcc    2460
ttgtacagga agacattcag tcaccgtgta attagtaaca cagaaagtct gcctgtctgc    2520
attgtacata gtgttttataa tattgtaata atatattta cctgtggtat gtgggcatgt    2580
ttactgccac tggcctagag gagacacaga cctggagacc gttttaatgg gggttttttgc   2640 ctctgtgcct gttcaagaga cttgcagggc taggtagagg gcctttggga tgttaaggtg    2700
actgcagctg atgccaagat ggactctgca atgggcatac ctgggggctc gttccctgtc    2760
cccagaggaa gccccctctc cttctccatg ggcatgactc tccttcgagg ccaccacgtt    2820
tatctcacaa tgatgtgttt tgcttgactt tccctttgcg ctgtctcgtg ggaaaggtca    2880
ttctgtctga gacccagct ccttctccag ctttggctgc gggcatggcc tgagcttct     2940 ggagagcctc tgcaggggt ttgccatcag ggccctgtgg ctgggtctgc tgcagagctc     3000
cttggctatc aggagaatcc tggacactgt actgtgcctc ccagtttaca aacacgccct    3060
tcatctcaag tggcccttta aaaggcctgc tgccatgtga gagctgtgaa cagctcagct    3120
ctgagtcggc aggctgggc ttcctcctgg gccaccagat ggaaggggg tattgtttgc      3180 ctcactcctg gatgctgcgt tttaaggaag tgagtgagaa agaatgtgcc aagatacctg    3240
gctcctgtga aaccagcctc aggagggaaa ctgggagaga gaagctgtgg tctcctgcta    3300
catgccctgg gagctggaag agaaaaacac tcccctaaac aatcgcaaaa tgatgaacca    3360
tcatgggcca ctgttctctt tgaggggaca ggtttagggg tttgcgttcg cccttgtggg    3420
ctgaagcact agctttttgg tagctagaca catcctgcac ccaaaggttc tctacaaagg    3480
cccagatttg tttgtaaagc actttgactc ttacctggag gcccgctctc taagggcttc    3540
ctgcgctccc acctcatctg tccctgagat gcagagcagg atgagggtc tgcttctagc    3600 tcagctgttt ctccttgagg ttgcggagga attgaattga atgggacaga gggcaggtgc    3660
tgtggccaag aagatctccg agcagcagtg acggggcacc ttgctgtgtg tcctctgggc    3720
atgttaaccc ttctgtgggg ccaaaggttt gcatcgtgga tccagctgtg ctccagtctg    3780
tcccctcctc ctccactctg actgccacgc cccggaccag cagcttgggg accctccagg    3840
gtactaatgg ggctctgttc tgagatggac aaattcagtg ttggaaatac atgttgtact    3900
atgcacttcc catgctccta gggttaggaa tagtttcaaa catgattggc agacataaca    3960
acggcaaata ctcggactgg ggcataggac tccagagtag gaaaaagaca aaagatttgg    4020
cagcctgaca caggcaacct acccctctct ctccagcctc tttatgaaac tgtttgtttg    4080
ccagtcctgc cctaaggcag aagatgaatt gaagatgctg tgcatgtttc ctaagtcctt    4140
gagcaatcat ggtggtgaca attgccacaa gggatatgag gccagtgcca ccagagggtg    4200
gtgccaagtg ccacatccct tccgatccat tcccctctgc atcctcggag cacccccagtt   4260 tgcctttgat gtgtccgctg tgtatgttag ctgaactttg atgagcaaaa tttcctgagc    4320
gaaacactcc aaagagatag gaaaacttgc cgcctcttct tttttgtccc ttaatcaaac    4380
tcaaataagc ttaaaaaaaa tccatggaag atcatggaca tgtgaaatga gcattttttt    4440
cttttttttt tttaacaaag tctgaactga acagaacaag acttttttcct catacatctc    4500
```

| | | |
|---|---|---|
| caaattgttt aaacttactt tatgagtgtt tgtttagaag ttcggaccaa cagaaaaatg | 4560 | |
| cagtcagatg tcatcttgga attggtttct aaaagagtaa ggcatgtccc tgcccagaaa | 4620 | |
| cttaggaagc atgaaataaa tcaaatgttt attttccttc ttatttaaaa tcatgcaaat | 4680 | |
| gcaacagaaa tagagggttt gtgccaaatg ctatgaacgg cccttcttta agacaagca | 4740 | |
| agggagattg atatatgtac aatttgctct catgttttaa aaaaaaaagg taaatgtaac | 4800 | |
| ttaatagttt tgtaaatggg agaggggaa tctataaact ataaatacag ttatttatt | 4860 | |
| ttttgtacat ttttaaggag aaaaaaataa atattcataa cataagagga aaa | 4913 | |

<210> SEQ ID NO 97
<211> LENGTH: 4746
<212> TYPE: DNA
<213> ORGANISM: Homo sapiens

<400> SEQUENCE: 97

| | | |
|---|---|---|
| taataaaaga ctagtggcct tagtgcccat gcccagtgac cctccattca atacccgaag | 60 | |
| agcctacacc agtgaggatg aagcctggaa gtcatacttg gagaatcccc tgacagcagc | 120 | |
| caccaaggcc atgatgagca ttaatggtga tgaggacagt gctgctgccc tcggcctgct | 180 | |
| ctatgactac tacaaggttc ctcgagacaa gaggctgctg tctgtaagca aagcaagtga | 240 | |
| cagccaagaa gaccaggaga aaagaaactg ccttggcacc agtgaagccc agagtaattt | 300 | |
| gagtggagga gaaaaccgag tgcaagtcct aaagactgtt ccagtgaacc tttccctaaa | 360 | |
| tcaagatcac ctggagaatt ccaagcggga acagtacagc atcagcttcc ccgagagctc | 420 | |
| tgccatcatc ccggtgtcgg aatcacggt ggtgaaagct gaagatttca ccagttttt | 480 | |
| catggcccca cctgtgcact atccccgggg agatggggaa gagcaacgag tggttatctt | 540 | |
| tgaacagact cagtatgacg tgccctcgct ggccacccac agcgcctatc tcaaagacga | 600 | |
| ccagcgcagc actccggaca gcacatacag cgagagcttc aaggacgcag ccacagagaa | 660 | |
| atttcggagt gcttcagttg gggctgagga gtacatgtat gatcagacat caagtggcac | 720 | |
| atttcagtac accctggaag ccaccaaatc tctccgtcag aagcagggg agggcccat | 780 | |
| gacctacctc aacaaaggac agttctatgc cataacactc agcgagaccg agacaacaa | 840 | |
| atgcttccga caccccatca gcaaagtcag gagtgtggtg atggtggtct tcagtgaaga | 900 | |
| caaaaacaga gatgaacagc tcaaatactg gaaatactgg cactctcggc agcatacggc | 960 | |
| gaagcagagg gtccttgaca ttgccgatta caaggagagc tttaatacga ttggaaacat | 1020 | |
| tgaagagatt gcatataatg ctgtttcctt tacctgggac gtgaatgaag aggcgaagat | 1080 | |
| tttcatcacc gtgaattgct tgagcacaga tttctcctcc caaaaagggg tgaaaggact | 1140 | |
| tcctttgatg attcagattg acacatacag ttataacaat cgtagcaata aacccattca | 1200 | |
| tagagcttat tgccagatca aggtcttctg tgacaaagga gcagaaagaa aaatccgaga | 1260 | |
| tgaagagcgg aagcagaaca ggaagaaagg gaaaggccag gcctcccaaa ctcaatgcaa | 1320 | |
| cagctcctct gatgggaagt tggctgccat acctttacag aagaagagtg acatcaccta | 1380 | |
| cttcaaaacc atgcctgatc tccactcaca gccagttctc ttcatacctg atgttcactt | 1440 | |
| tgcaaacctg cagaggaccg gacaggtgta ttacaacacg gatgatgaac gagaaggtgg | 1500 | |
| cagtgtcctt gttaaacgga tgttccggcc catggaagag gagtttggtc cagtgccttc | 1560 | |
| aaagcagatg aaagaagaag ggacaaagcg agtgctcttg tacgtgagga aggagactga | 1620 | |
| cgatgtgttc gatgcattga tgttgaagtc tccacagtg aagggcctga tggaagcgat | 1680 | |
| atctgagaaa tatgggctgc cgtggagaa gatagcaaag ctttacaaga aaagcaaaaa | 1740 | |

```
aggcatcttg gtgaacatgg atgacaacat catcgagcac tactcgaacg aggacacctt    1800
catcctcaac atggagagca tggtggaggg cttcaaggtc acgctcatgg aaatctagcc    1860
ctgggtttgg catccgcttt ggctggagct ctcagtgcgt tcctccctga gagagacaga    1920
agccccagcc ccagaacctg gagacccatc tcccccatct cacaactgct gttacaagac    1980
cgtgctgggg agtggggcaa gggacaggcc ccactgtcgg tgtgcttggc ccatccactg    2040
gcacctacca cggagctgaa gcctgagccc tcaggaagg tgccttaggc ctgttggatt     2100
cctatttatt gcccacccttt tcctggagcc caggtccagg cccgccagga ctctgcaggt   2160
cactgctagc tccagatgag accgtccagc gttccccctt caagagaaac actcatcccg    2220
aacagcctaa aaaattccca tcccttctct ctcacccctc catatctatc tcccgagtgg    2280
ctggacaaaa tgagctacgt ctgggtgcag tagttatagg tggggcaaga ggtggatgcc    2340
cactttctgg tcagacacct ttaggttgct ctggggaagg ctgtcttgct aaatacctcc    2400
agggttccca gcaagtggcc accaggcctt gtacaggaag acattcagtc accgtgtaat    2460
tagtaacaca gaaagtctgc ctgtctgcat tgtacatagt gtttataata ttgtaataat    2520
atattttacc tgtggtatgt gggcatgttt actgccactg gcctagagga gacacagacc    2580
tggagaccgt tttaatgggg gttttttgcct ctgtgcctgt tcaagagact tgcagggcta   2640
ggtagagggc ctttgggatg ttaaggtgac tgcagctgat gccaagatgg actctgcaat    2700
gggcatacct gggggctcgt tccctgtccc cagaggaagc cccctctcct tctccatggg    2760
catgactctc cttcgaggcc accacgttta tctcacaatg atgtgttttg cttgactttc    2820
cctttgcgct gtctcgtggg aaaggtcatt ctgtctgaga ccccagctcc ttctccagct    2880
ttggctgcgg gcatggcctg agcttttctgg agagcctctg cagggggttt gccatcaggg   2940
ccctgtggct gggtctgctg cagagctcct tggctatcag gagaatcctg gacactgtac    3000
tgtgcctccc agtttacaaa cacgcccttc atctcaagtg gcccttttaaa aggcctgctg   3060 ccatgtgaga gctgtgaaca gctcagctct gagtcggcag gctggggctt cctcctgggc    3120
caccagatgg aaaggggggta ttgttttgcct cactcctgga tgctgcgttt taaggaagtg   3180
agtgagaaag aatgtgccaa gatacctggc tcctgtgaaa ccagcctcag gagggaaact    3240
gggagagaga agctgtggtc tcctgctaca tgccctggga gctggaagag aaaaacactc    3300
cactaaacaa tcgcaaaatg atgaaccatc atgggccact gttctctttg aggggacagg    3360 tttagggggtt tgcgttcgcc cttgtgggct gaagcactag cttttttggta gctagacaca    3420 tcctgcaccc aaaggttctc tacaaagcc cagatttgtt tgtaaagcac tttgactctt      3480
acctggaggc ccgctctcta agggcttcct gcgctcccac ctcatctgtc cctgagatgc    3540
agagcaggat ggagggtctg cttctagctc agctgtttct ccttgaggtt gcggaggaat    3600
tgaattgaat gggacagagg gcaggtgctg tggccaagaa gatctccgag cagcagtgac    3660
ggggcacctt gctgtgtgtc ctctgggcat gttaaccctt ctgtggggcc aaaggtttgc    3720
atcgtggatc cagctgtgct ccagtctgtc ccctcctcct ccactctgac tgccacgccc    3780
cggaccagca gctggggac cctccagggt actaatgggg ctctgttctg agatggacaa     3840
attcagtgtt ggaaatacat gttgtactat gcacttccca tgctcctagg gttaggaata    3900
gtttcaaaca tgattggcag acataacaac ggcaaatact cggactgggg cataggactc    3960
cagagtagga aaaagacaaa agatttggca gcctgacaca ggcaacctac ccctctctct    4020
ccagcctctt tatgaaactg tttgtttgcc agtcctgccc taaggcagaa gatgaattga    4080
agatgctgtg catgtttcct aagtccttga gcaatcatgg tggtgacaat tgccacaagg    4140
```

-continued

| | |
|---|---|
| gatatgaggc cagtgccacc agagggtggt gccaagtgcc acatcccttc cgatccattc | 4200 |
| ccctctgcat cctcggagca ccccagtttg cctttgatgt gtccgctgtg tatgttagct | 4260 |
| gaactttgat gagcaaaatt tcctgagcga aacactccaa agagatagga aaacttgccg | 4320 |
| cctcttcttt tttgtcccctt aatcaaactc aaataagctt aaaaaaaatc catgaaagat | 4380 |
| catggacatg tgaaatgagc attttttttct tttttttttt taacaaagtc tgaactgaac | 4440 |
| agaacaagac ttttttcctca tacatctcca aattgtttaa acttacttta tgagtgtttg | 4500 |
| tttagaagtt cggaccaaca gaaaaatgca gtcagatgtc atcttggaat tggtttctaa | 4560 |
| aagagtaagg catgtccctg cccagaaact taggaagcat gaaataaatc aaatgtttat | 4620 |
| tttccttctt atttaaaatc atgcaaatgc aacagaaata gagggtttgt gccaaatgct | 4680 |
| atgaacggcc ctttcttaaa gacaagcaag ggagattgat atatgtacaa tttgctctca | 4740 |
| tgttttt | 4746 |

<210> SEQ ID NO 98
<211> LENGTH: 4746
<212> TYPE: DNA
<213> ORGANISM: Homo sapiens

<400> SEQUENCE: 98

| | |
|---|---|
| taataaaaga ctagtggcct tagtgcccat gcccagtgac cctccattca atacccgaag | 60 |
| agcctacacc agtgaggatg aagcctggaa gtcatacttg gagaatcccc tgacagcagc | 120 |
| caccaaggcc atgatgagca ttaatggtga tgaggacagt gctgctgccc tcggcctgct | 180 |
| ctatgactac tacaaggttc ctcgagacaa gaggctgctg tctgtaagca agcaagtga | 240 |
| cagccaagaa gaccaggaga aagaaactg ccttggcacc agtgaagccc agagtaattt | 300 |
| gagtggagga gaaaaccgag tgcaagtcct aaagactgtt ccagtgaacc tttccctaaa | 360 |
| tcaagatcac ctggagaatt ccaagcggga acagtacagc atcagcttcc ccgagagctc | 420 |
| tgccatcatc ccggtgtcgg aatcacggt ggtgaaagct gaagatttca caccagtttt | 480 |
| catggcccca cctgtgcact atccccgggg agatggggaa gagcaacgag tggttatctt | 540 |
| tgaacagact cagtatgacg tgccctcgct ggccacccac agcgcctatc tcaaagacga | 600 |
| ccagcgcagc actccggaca gcacatacag cgagagcttc aaggacgcag ccacagagaa | 660 |
| atttcggagt gcttcagttg gggctgagga gtacatgtat gatcagacat caagtggcac | 720 |
| atttcagtac accctggaag ccaccaaatc tctccgtcag aagcaggggg agggccccat | 780 |
| gacctacctc aacaaaggac agttctatgc cataacactc agcgagaccg agacaacaa | 840 |
| atgcttccga caccccatca gcaaagtcag gagtgtggtg atggtggtct tcagtgaaga | 900 |
| caaaaacaga gatgaacagc tcaaatactg gaaatactgg cactctcggc agcatacggc | 960 |
| gaagcagagg gtccttgaca ttgccgatta caaggagagc tttaatacga ttggaaacat | 1020 |
| tgaagagatt gcatataatg ctgtttcctt tacctgggac gtgaatgaag aggcgaagat | 1080 |
| tttcatcacc gtgaattgct tgagcacaga tttctcctcc caaaaagggg tgaaaggact | 1140 |
| tcctttgatg attcagattg acacatacag ttataacaat cgtagcaata aacccattca | 1200 |
| tagagcttat tgccagatca aggtcttctg tgacaaagga gcagaaagaa aaatccgaga | 1260 |
| tgaagagcgg aagcagaaca ggaagaaagg gaaaggccag gcctcccaaa ctcaatgcaa | 1320 |
| cagctcctct gatgggaagt tggctgccat acctttacag aagaagagtg acatcaccta | 1380 |
| cttcaaaacc atgcctgatc tccactcaca gccagttctc ttcatacctg atgttcactt | 1440 |
| tgcaaacctg cagaggaccg gacaggtgta ttacaacacg gatgatgaac gagaaggtgg | 1500 |

```
cagtgtcctt gttaaacgga tgttccggcc catggaagag gagtttggtc cagtgccttc    1560
aaagcagatg aaagaagaag ggacaaagcg agtgctcttg tacgtgagga aggagactga    1620
cgatgtgttc gatgcattga tgttgaagtc tcccacagtg aagggcctga tggaagcgat    1680
atctgagaaa tatgggctgc ccgtggagaa gatagcaaag ctttacaaga aaagcaaaaa    1740
aggcatcttg gtgaacatgg atgacaacat catcgagcac tactcgaacg aggacacctt    1800
catcctcaac atggagagca tggtggaggg cttcaaggtc acgctcatgg aaatctagcc    1860
ctgggtttgg catccgcttt ggctggagct ctcagtgcgt tcctccctga gagagacaga    1920
agccccagcc ccagaacctg gagacccatc tcccccatct cacaactgct gttacaagac    1980
cgtgctgggg agtggggcaa gggacaggcc ccactgtcgg tgtgcttggc ccatccactg    2040
gcacctacca cggagctgaa gcctgagccc tcaggaagg tgccttaggc ctgttggatt     2100
cctatttatt gcccacccttt tcctggagcc caggtccagg cccgccagga ctctgcaggt   2160
cactgctagc tccagatgag accgtccagc gttccccctt caagagaaac actcatcccg    2220
aacagcctaa aaaattccca tcccttctct ctcaccccctc catatctatc tcccgagtgg   2280
ctggacaaaa tgagctacgt ctgggtgcag tagttatagg tggggcaaga ggtgatgcc     2340 cactttctgg tcagacacct ttaggttgct ctggggaagg ctgtcttgct aaatacctcc    2400
agggttccca gcaagtggcc accaggcctt gtacaggaag acattcagtc accgtgtaat    2460
tagtaacaca gaaagtctgc ctgtctgcat tgtacatagt gtttataata ttgtaataat    2520
atattttacc tgtggtatgt gggcatgttt actgccactg gcctagagga gacacagacc    2580
tggagaccgt tttaatgggg gttttttgcct ctgtgcctgt tcaagagact tgcagggcta   2640
ggtagagggc ctttgggatg ttaaggtgac tgcagctgat gccaagatgg actctgcaat    2700
gggcatacct gggggctcgt tccctgtccc cagaggaagc cccctctcct tctccatggg    2760
catgactctc cttcgaggcc accacgttta tctcacaatg atgtgttttg cttgactttc    2820
cctttgcgct gtctcgtggg aaaggtcatt ctgtctgaga ccccagctcc ttctccagct    2880
ttggctgcgg gcatgccctg agcttttctgg agagcctctg caggggggttt gccatcaggg   2940 ccctgtggct gggtctgctg cagagctcct tggctatcag gagaatcctg acactgtac     3000 tgtgcctccc agtttacaaa cacgcccttc atctcaagtg gccctttaaa aggcctgctg    3060
ccatgtgaga gctgtgaaca gctcagctct gagtcggcag gctggggctt cctcctgggc    3120
caccagatgg aaaggggggta ttgttttgcct cactcctgga tgctgcgttt taaggaagtg   3180
agtgagaaag aatgtgccaa gatacctggc tcctgtgaaa ccagcctcag gagggaaact    3240
gggagagaga agctgtggtc tcctgctaca tgccctggga gctggaagag aaaaacactc    3300
ccctaaacaa tcgcaaaatg atgaaccatc atgggccact gttctctttg aggggacagg    3360
tttaggggtt tgcgttcgcc cttgtgggct gaagcactag cttttttggta gctagacaca   3420 tcctgcaccc aaaggttctc tacaaaggcc cagatttgtt tgtaaagcac tttgactctt    3480
acctggaggc ccgctctcta agggcttcct gcgctcccac ctcatctgtc cctgagatgc    3540
agagcaggat ggagggtctg cttctagctc agctgtttct ccttgaggtt gcggaggaat    3600
tgaattgaat gggacagagg gcaggtgctg tggccaagaa gatctccgag cagcagtgac    3660 ggggcaccctt gctgtgtgtc ctctgggcat gttaacccctt ctgtggggcc aaaggttttgc   3720 atcgtggatc cagctgtgct ccagtctgtc ccctcctcct ccactctgac tgccacgccc    3780
cggaccagca gcttggggac cctccagggt actaatgggg ctctgttctg agatggacaa    3840
attcagtgtt ggaaatacat gttgtactat gcacttccca tgctcctagg gttaggaata    3900
```

-continued

```
gtttcaaaca tgattggcag acataacaac ggcaaatact cggactgggg cataggactc    3960
cagagtagga aaaagacaaa agatttggca gcctgcacac aggcaacctac ccctctctct    4020 ccagcctctt tatgaaactg tttgtttgcc agtcctgccc taaggcagaa gatgaattga    4080
agatgctgtg catgtttcct aagtccttga gcaatcatgg tggtgacaat tgccacaagg    4140
gatatgaggc cagtgccacc agagggtggt gccaagtgcc acatcccttc cgatccattc    4200
ccctctgcat cctcggagca ccccagtttg ccttttgatgt gtccgctgtg tatgttagct    4260
gaactttgat gagcaaaatt tcctgagcga aacactccaa agagatagga aaacttgccg    4320
cctcttcttt tttgtccctt aatcaaactc aaataagctt aaaaaaaatc catggaagat    4380
catggacatg tgaaatgagc attttttttct tttttttttt taacaaagtc tgaactgaac    4440
agaacaagac ttttttcctca tacatctcca aattgtttaa acttacttta tgagtgtttg    4500
tttagaagtt cggaccaaca gaaaaatgca gtcagatgtc atcttggaat tggtttctaa    4560
aagagtaagg catgtccctg cccagaaact taggaagcat gaaataaatc aaatgtttat    4620
tttccttctt atttaaaatc atgcaaatgc aacagaaata gagggtttgt gccaaatgct    4680
atgaacggcc ctttcttaaa gacaagcaag ggagattgat atatgtacaa tttgctctca    4740
tgttttt                                                              4746
```

<210> SEQ ID NO 99
<211> LENGTH: 625
<212> TYPE: PRT
<213> ORGANISM: Homo sapiens

<400> SEQUENCE: 99

```
Met Ser Gln Glu Ser Asp Asn Asn Lys Arg Leu Val Ala Leu Val Pro
1               5                   10                  15

Met Pro Ser Asp Pro Pro Phe Asn Thr Arg Arg Ala Tyr Thr Ser Glu
            20                  25                  30

Asp Glu Ala Trp Lys Ser Tyr Leu Glu Asn Pro Leu Thr Ala Ala Thr
        35                  40                  45

Lys Ala Met Met Ser Ile Asn Gly Asp Glu Asp Ser Ala Ala Ala Leu
    50                  55                  60

Gly Leu Leu Tyr Asp Tyr Tyr Lys Val Pro Arg Asp Lys Arg Leu Leu
65                  70                  75                  80

Ser Val Ser Lys Ala Ser Asp Ser Gln Glu Asp Gln Glu Lys Arg Asn
                85                  90                  95

Cys Leu Gly Thr Ser Glu Ala Gln Ser Asn Leu Ser Gly Gly Glu Asn
            100                 105                 110

Arg Val Gln Val Leu Lys Thr Val Pro Val Asn Leu Ser Leu Asn Gln
        115                 120                 125

Asp His Leu Glu Asn Ser Lys Arg Glu Gln Tyr Ser Ile Ser Phe Pro
    130                 135                 140

Glu Ser Ser Ala Ile Ile Pro Val Ser Gly Ile Thr Val Val Lys Ala
145                 150                 155                 160

Glu Asp Phe Thr Pro Val Phe Met Ala Pro Val His Tyr Pro Arg
                165                 170                 175

Gly Asp Gly Glu Glu Gln Arg Val Val Ile Phe Glu Gln Thr Gln Tyr
            180                 185                 190

Asp Val Pro Ser Leu Ala Thr His Ser Ala Tyr Leu Lys Asp Asp Gln
        195                 200                 205

Arg Ser Thr Pro Asp Ser Thr Tyr Ser Glu Ser Phe Lys Asp Ala Ala
    210                 215                 220
```

-continued

Thr Glu Lys Phe Arg Ser Ala Ser Val Gly Ala Glu Tyr Met Tyr
225                 230                 235                 240

Asp Gln Thr Ser Ser Gly Thr Phe Gln Tyr Thr Leu Glu Ala Thr Lys
            245                 250                 255

Ser Leu Arg Gln Lys Gln Gly Glu Gly Pro Met Thr Tyr Leu Asn Lys
        260                 265                 270

Gly Gln Phe Tyr Ala Ile Thr Leu Ser Glu Thr Gly Asp Asn Lys Cys
    275                 280                 285

Phe Arg His Pro Ile Ser Lys Val Arg Ser Val Val Met Val Val Phe
290                 295                 300

Ser Glu Asp Lys Asn Arg Asp Glu Gln Leu Lys Tyr Trp Lys Tyr Trp
305                 310                 315                 320

His Ser Arg Gln His Thr Ala Lys Gln Arg Val Leu Asp Ile Ala Asp
            325                 330                 335

Tyr Lys Glu Ser Phe Asn Thr Ile Gly Asn Ile Glu Glu Ile Ala Tyr
        340                 345                 350

Asn Ala Val Ser Phe Thr Trp Asp Val Asn Glu Glu Ala Lys Ile Phe
    355                 360                 365

Ile Thr Val Asn Cys Leu Ser Thr Asp Phe Ser Ser Gln Lys Gly Val
370                 375                 380

Lys Gly Leu Pro Leu Met Ile Gln Ile Asp Thr Tyr Ser Tyr Asn Asn
385                 390                 395                 400

Arg Ser Asn Lys Pro Ile His Arg Ala Tyr Cys Gln Ile Lys Val Phe
            405                 410                 415

Cys Asp Lys Gly Ala Glu Arg Lys Ile Arg Asp Glu Glu Arg Lys Gln
        420                 425                 430

Asn Arg Lys Lys Gly Lys Gly Gln Ala Ser Gln Thr Gln Cys Asn Ser
    435                 440                 445

Ser Ser Asp Gly Lys Leu Ala Ala Ile Pro Leu Gln Lys Lys Ser Asp
450                 455                 460

Ile Thr Tyr Phe Lys Thr Met Pro Asp Leu His Ser Gln Pro Val Leu
465                 470                 475                 480

Phe Ile Pro Asp Val His Phe Ala Asn Leu Gln Arg Thr Gly Gln Val
            485                 490                 495

Tyr Tyr Asn Thr Asp Asp Glu Arg Glu Gly Gly Ser Val Leu Val Lys
        500                 505                 510

Arg Met Phe Arg Pro Met Glu Glu Glu Phe Gly Pro Val Pro Ser Lys
    515                 520                 525

Gln Met Lys Glu Glu Gly Thr Lys Arg Val Leu Leu Tyr Val Arg Lys
530                 535                 540

Glu Thr Asp Asp Val Phe Asp Ala Leu Met Leu Lys Ser Pro Thr Val
545                 550                 555                 560

Lys Gly Leu Met Glu Ala Ile Ser Glu Lys Tyr Gly Leu Pro Val Glu
            565                 570                 575

Lys Ile Ala Lys Leu Tyr Lys Lys Ser Lys Lys Gly Ile Leu Val Asn
        580                 585                 590

Met Asp Asp Asn Ile Ile Glu His Tyr Ser Asn Glu Asp Thr Phe Ile
    595                 600                 605

Leu Asn Met Glu Ser Met Val Glu Gly Phe Lys Val Thr Leu Met Glu
610                 615                 620

Ile
625

<210> SEQ ID NO 100

```
<211> LENGTH: 609
<212> TYPE: PRT
<213> ORGANISM: Homo sapiens

<400> SEQUENCE: 100
```

| | | | | | | | | | | | | | | |
|---|---|---|---|---|---|---|---|---|---|---|---|---|---|---|
|Met|Pro|Ser|Asp|Pro|Phe|Asn|Thr|Arg|Arg|Ala|Tyr|Thr|Ser|Glu|
|1| | | |5| | | | |10| | | | |15|
|Asp|Glu|Ala|Trp|Lys|Ser|Tyr|Leu|Glu|Asn|Pro|Leu|Thr|Ala|Thr|
| | | |20| | | | |25| | | | |30| |
|Lys|Ala|Met|Met|Ser|Ile|Asn|Gly|Asp|Glu|Asp|Ser|Ala|Ala|Leu|
| | | | |35| | | | |40| | | | |45|
|Gly|Leu|Leu|Tyr|Asp|Tyr|Tyr|Lys|Val|Pro|Arg|Asp|Lys|Arg|Leu|Leu|
| |50| | | | |55| | | | |60| | | |
|Ser|Val|Ser|Lys|Ala|Ser|Asp|Ser|Gln|Glu|Asp|Gln|Glu|Lys|Arg|Asn|
|65| | | | |70| | | | |75| | | | |80|
|Cys|Leu|Gly|Thr|Ser|Glu|Ala|Gln|Ser|Asn|Leu|Ser|Gly|Gly|Glu|Asn|
| | | | |85| | | | |90| | | | |95| |
|Arg|Val|Gln|Val|Leu|Lys|Thr|Val|Pro|Val|Asn|Leu|Ser|Leu|Asn|Gln|
| | | | |100| | | | |105| | | | |110| |
|Asp|His|Leu|Glu|Asn|Ser|Lys|Arg|Glu|Gln|Tyr|Ser|Ile|Ser|Phe|Pro|
| | |115| | | | |120| | | | |125| | | |
|Glu|Ser|Ser|Ala|Ile|Ile|Pro|Val|Ser|Gly|Ile|Thr|Val|Val|Lys|Ala|
|130| | | | |135| | | | |140| | | | | |
|Glu|Asp|Phe|Thr|Pro|Val|Phe|Met|Ala|Pro|Pro|Val|His|Tyr|Pro|Arg|
|145| | | | |150| | | | |155| | | | |160|
|Gly|Asp|Gly|Glu|Glu|Gln|Arg|Val|Val|Ile|Phe|Glu|Gln|Thr|Gln|Tyr|
| | | | |165| | | | |170| | | | |175| |
|Asp|Val|Pro|Ser|Leu|Ala|Thr|His|Ser|Ala|Tyr|Leu|Lys|Asp|Asp|Gln|
| | |180| | | | |185| | | | |190| | | |
|Arg|Ser|Thr|Pro|Asp|Ser|Thr|Tyr|Ser|Glu|Ser|Phe|Lys|Asp|Ala|Ala|
| |195| | | | |200| | | | |205| | | | |
|Thr|Glu|Lys|Phe|Arg|Ser|Ala|Ser|Val|Gly|Ala|Glu|Glu|Tyr|Met|Tyr|
|210| | | | |215| | | | |220| | | | | |
|Asp|Gln|Thr|Ser|Ser|Gly|Thr|Phe|Gln|Tyr|Thr|Leu|Glu|Ala|Thr|Lys|
|225| | | | |230| | | | |235| | | | |240|
|Ser|Leu|Arg|Gln|Lys|Gln|Gly|Glu|Gly|Pro|Met|Thr|Tyr|Leu|Asn|Lys|
| | | | |245| | | | |250| | | | |255| |
|Gly|Gln|Phe|Tyr|Ala|Ile|Thr|Leu|Ser|Glu|Thr|Gly|Asp|Asn|Lys|Cys|
| | |260| | | | |265| | | | |270| | | |
|Phe|Arg|His|Pro|Ile|Ser|Lys|Val|Arg|Ser|Val|Val|Met|Val|Val|Phe|
| |275| | | | |280| | | | |285| | | | |
|Ser|Glu|Asp|Lys|Asn|Arg|Asp|Glu|Gln|Leu|Lys|Tyr|Trp|Lys|Tyr|Trp|
|290| | | | |295| | | | |300| | | | | |
|His|Ser|Arg|Gln|His|Thr|Ala|Lys|Gln|Arg|Val|Leu|Asp|Ile|Ala|Asp|
|305| | | | |310| | | | |315| | | | |320|
|Tyr|Lys|Glu|Ser|Phe|Asn|Thr|Ile|Gly|Asn|Ile|Glu|Glu|Ile|Ala|Tyr|
| | | | |325| | | | |330| | | | |335| |
|Asn|Ala|Val|Ser|Phe|Thr|Trp|Asp|Val|Asn|Glu|Glu|Ala|Lys|Ile|Phe|
| | |340| | | | |345| | | | |350| | | |
|Ile|Thr|Val|Asn|Cys|Leu|Ser|Thr|Asp|Phe|Ser|Ser|Gln|Lys|Gly|Val|
| |355| | | | |360| | | | |365| | | | |
|Lys|Gly|Leu|Pro|Leu|Met|Ile|Gln|Ile|Asp|Thr|Tyr|Ser|Tyr|Asn|Asn|
|370| | | | |375| | | | |380| | | | | |
|Arg|Ser|Asn|Lys|Pro|Ile|His|Arg|Ala|Tyr|Cys|Gln|Ile|Lys|Val|Phe|
|385| | | | |390| | | | |395| | | | |400|

```
Cys Asp Lys Gly Ala Glu Arg Lys Ile Arg Asp Glu Glu Arg Lys Gln
                405                 410                 415

Asn Arg Lys Lys Gly Lys Gly Gln Ala Ser Gln Thr Gln Cys Asn Ser
            420                 425                 430

Ser Ser Asp Gly Lys Leu Ala Ala Ile Pro Leu Gln Lys Lys Ser Asp
        435                 440                 445

Ile Thr Tyr Phe Lys Thr Met Pro Asp Leu His Ser Gln Pro Val Leu
    450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Ser Val Leu Val Lys
                485                 490                 495

Arg Met Phe Arg Pro Met Glu Glu Glu Phe Gly Pro Val Pro Ser Lys
                500                 505                 510

Gln Met Lys Glu Glu Gly Thr Lys Arg Val Leu Leu Tyr Val Arg Lys
                515                 520                 525

Glu Thr Asp Asp Val Phe Asp Ala Leu Met Leu Lys Ser Pro Thr Val
                530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
                580                 585                 590

Leu Asn Met Glu Ser Met Val Glu Gly Phe Lys Val Thr Leu Met Glu
                595                 600                 605

Ile

<210> SEQ ID NO 101
<211> LENGTH: 609
<212> TYPE: PRT
<213> ORGANISM: Homo sapiens

<400> SEQUENCE: 101

Met Pro Ser Asp Pro Pro Phe Asn Thr Arg Arg Ala Tyr Thr Ser Glu
1               5                   10                  15

Asp Glu Ala Trp Lys Ser Tyr Leu Glu Asn Pro Leu Thr Ala Ala Thr
            20                  25                  30

Lys Ala Met Met Ser Ile Asn Gly Asp Glu Asp Ser Ala Ala Ala Leu
        35                  40                  45

Gly Leu Leu Tyr Asp Tyr Tyr Lys Val Pro Arg Asp Lys Arg Leu Leu
    50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
            100                 105                 110

Asp His Leu Glu Asn Ser Lys Arg Glu Gln Tyr Ser Ile Ser Phe Pro
        115                 120                 125

Glu Ser Ser Ala Ile Ile Pro Val Ser Gly Ile Thr Val Val Lys Ala
    130                 135                 140

Glu Asp Phe Thr Pro Val Phe Met Ala Pro Pro Val His Tyr Pro Arg
145                 150                 155                 160
```

-continued

```
Gly Asp Gly Glu Glu Gln Arg Val Val Ile Phe Gln Thr Gln Tyr
                165                 170                 175

Asp Val Pro Ser Leu Ala Thr His Ser Ala Tyr Leu Lys Asp Gln
            180                 185                 190

Arg Ser Thr Pro Asp Ser Thr Tyr Ser Glu Ser Phe Lys Asp Ala Ala
        195                 200                 205

Thr Glu Lys Phe Arg Ser Ala Ser Val Gly Ala Glu Glu Tyr Met Tyr
    210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Val Met Val Val Phe
        275                 280                 285

Ser Glu Asp Lys Asn Arg Asp Glu Gln Leu Lys Tyr Trp Lys Tyr Trp
    290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
            340                 345                 350

Ile Thr Val Asn Cys Leu Ser Thr Asp Phe Ser Ser Gln Lys Gly Val
        355                 360                 365

Lys Gly Leu Pro Leu Met Ile Gln Ile Asp Thr Tyr Ser Tyr Asn Asn
    370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Arg Lys Gln
                405                 410                 415

Asn Arg Lys Lys Gly Lys Gly Gln Ala Ser Gln Thr Gln Cys Asn Ser
            420                 425                 430

Ser Ser Asp Gly Lys Leu Ala Ala Ile Pro Leu Gln Lys Lys Ser Asp
        435                 440                 445

Ile Thr Tyr Phe Lys Thr Met Pro Asp Leu His Ser Gln Pro Val Leu
    450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Phe Gly Pro Val Pro Ser Lys
            500                 505                 510

Gln Met Lys Glu Glu Gly Thr Lys Arg Val Leu Leu Tyr Val Arg Lys
        515                 520                 525

Glu Thr Asp Asp Val Phe Asp Ala Leu Met Leu Lys Ser Pro Thr Val
    530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
            580                 585                 590
```

Leu Asn Met Glu Ser Met Val Glu Gly Phe Lys Val Thr Leu Met Glu
        595                 600                 605

Ile

<210> SEQ ID NO 102
<211> LENGTH: 4973
<212> TYPE: DNA
<213> ORGANISM: Homo sapiens

<400> SEQUENCE: 102

| | | | | | |
|---|---|---|---|---|---|
| attggatcaa | acatgtcaca | agagtcggac | aagtaagtgg | atcacacgcg | ccggctgctg | 60 |
| ctactactac | cactttgggc | tgatggcaac | tgtaataaaa | gactagtggc | cttagtgccc | 120 |
| atgcccagtg | accctccatt | caataccga | agagcctaca | ccagtgagga | tgaagcctgg | 180 |
| aagtcatact | tggagaatcc | cctgacagca | gccaccaagg | ccatgatgag | cattaatggt | 240 |
| gatgaggaca | gtgctgctgc | cctcggcctg | ctctatgact | actacaaggt | tcctcgagac | 300 |
| aagaggctgc | tgtctgtaag | caaagcaagt | gacagccaag | aagaccagga | gaaaagaaac | 360 |
| tgccttggca | ccagtgaagc | ccagagtaat | ttgagtggag | gagaaaaccg | agtgcaagtc | 420 |
| ctaaagactg | ttccagtgaa | cctttcccta | aatcaagatc | acctggagaa | ttccaagcgg | 480 |
| gaacagtaca | gcatcagctt | ccccgagagc | tctgccatca | tcccggtgtc | gggaatcacg | 540 |
| gtggtgaaag | ctgaagattt | cacaccagtt | ttcatggccc | cacctgtgca | ctatcccgg  | 600 |
| ggagatgggg | aagagcaacg | agtggttatc | tttgaacaga | ctcagtatga | cgtgccctcg | 660 |
| ctggccaccc | acagcgccta | tctcaaagac | gaccagcgca | gcactccgga | cagcacatac | 720 |
| agcgagagct | tcaaggacgc | agccacagag | aaatttcgga | gtgcttcagt | tggggctgag | 780 |
| gagtacatgt | atgatcagac | atcaagtggc | acatttcagt | acacccgtgga | agccaccaaa | 840 |
| tctctccgtc | agaagcaggg | ggagggcccc | atgacctacc | tcaacaaagg | acagttctat | 900 |
| gccataacac | tcagcgagac | cggagacaac | aaatgcttcc | gacacccat  | cagcaaagtc | 960 |
| aggagtgtgg | tgatggtggt | cttcagtgaa | gacaaaaaca | gagatgaaca | gctcaaatac | 1020 |
| tggaaatact | ggcactctcg | gcagcatacg | gcgaagcaga | gggtccttga | cattgccgat | 1080 |
| tacaaggaga | gctttaatac | gattggaaac | attgaagaga | ttgcatataa | tgctgtttcc | 1140 |
| tttacctggg | acgtgaatga | agaggcgaag | atttcatca  | ccgtgaattg | cttgagcaca | 1200 |
| gatttctcct | cccaaaaagg | ggtgaaagga | cttcctttga | tgattcagat | tgacacatac | 1260 |
| agttataaca | atcgtagcaa | taaacccatt | catagagctt | attgccagat | caaggtcttc | 1320 |
| tgtgacaaag | gagcagaaag | aaaaatccga | gatgaagagc | ggaagcagaa | caggaagaaa | 1380 |
| gggaaaggcc | aggcctccca | aactcaatgc | aacagctcct | ctgatgggaa | gttggctgcc | 1440 |
| ataccttttac | agaagaagag | tgacatcacc | tacttcaaaa | ccatgcctga | tctccactca | 1500 |
| cagccagttc | tcttcatacc | tgatgttcac | tttgcaaacc | tgcagaggac | cggacaggtg | 1560 |
| tattacaaca | cggatgatga | acgagaaggt | ggcagtgtcc | ttgttaaacg | gatgttccgg | 1620 |
| cccatggaag | aggagtttgg | tccagtgcct | tcaaagcaga | tgaaagaaga | agggacaaag | 1680 |
| cgagtgctct | tgtacgtgag | gaaggagact | gacgatgtgt | tcgatgcatt | gatgttgaag | 1740 |
| tctcccacag | tgaagggcct | gatggaagcg | atatctgaga | aatatgggct | gcccgtggag | 1800 |
| aagatagcaa | agctttacaa | gaaaagcaaa | aaaggcatct | tggtgaacat | ggatgacaac | 1860 |
| atcatcgagc | actactcgaa | cgaggacacc | ttcatcctca | acatggagag | catggtggag | 1920 |
| ggcttcaagg | tcacgctcat | ggaaatctag | ccctgggttt | ggcatccgct | ttggctggag | 1980 |

```
ctctcagtgc gttcctccct gagagagaca gaagccccag ccccagaacc tggagaccca    2040
tctcccccat ctcacaactg ctgttacaag accgtgctgg ggagtggggc aagggacagg    2100
ccccactgtc ggtgtgcttg cccatccac tggcacctac cacggagctg aagcctgagc     2160
ccctcaggaa ggtgccttag gcctgttgga ttcctattta ttgcccacct tttcctggag    2220
cccaggtcca ggcccgccag gactctgcag gtcactgcta gctccagatg agaccgtcca    2280
gcgttccccc ttcaagagaa acactcatcc cgaacagcct aaaaaattcc catcccttct    2340
ctctcaccc tccatatcta tctcccgagt ggctggacaa aatgagctac gtctgggtgc     2400
agtagttata ggtggggcaa gaggtggatg cccactttct ggtcagacac ctttaggttg    2460
ctctggggaa ggctgtcttg ctaaatacct ccagggttcc cagcaagtgg ccaccaggcc    2520
ttgtacagga agacattcag tcaccgtgta attagtaaca cagaaagtct gcctgtctgc    2580
attgtacata gtgtttataa tattgtaata atatatttta cctgtggtat gtgggcatgt    2640
ttactgccac tggcctagag gagacacaga cctggagacc gttttaatgg gggttttttgc   2700
ctctgtgcct gttcaagaga cttgcagggc taggtagagg gcctttggga tgttaaggtg    2760
actgcagctg atgccaagat ggactctgca atgggcatac ctgggggctc gttccctgtc    2820
cccagaggaa gcccctctc cttctccatg gcatgactc tccttcgagg ccaccacgtt      2880
tatctcacaa tgatgtgttt tgcttgactt tcccttgcg ctgtctcgtg ggaaaggtca     2940
ttctgtctga accccagct ccttctccag ctttggctgc gggcatggcc tgagctttct    3000
ggagagcctc tgcaggggt ttgccatcag ggccctgtgg ctgggtctgc tgcagagctc    3060
cttggctatc aggagaatcc tggacactgt actgtgcctc ccagtttaca aacacgccct    3120
tcatctcaag tggccctta aaaggcctgc tgccatgtga gagctgtgaa cagctcagct    3180
ctgagtcggc aggctggggc ttcctcctgg gccaccagat ggaaggggg tattgtttgc     3240
ctcactcctg gatgctgcgt tttaaggaag tgagtgagaa agaatgtgcc aagatacctg    3300
gctcctgtga accagcctc aggagggaaa ctggagaga gaagctgtgg tctcctgcta     3360
catgccctgg gagctggaag agaaaaacac tcccctaaac aatcgcaaaa tgatgaacca    3420
tcatgggcca ctgttctctt tgaggggaca ggtttagggg tttgcgttcg cccttgtggg    3480
ctgaagcact agcttttgg tagctagaca catcctgcac ccaaaggttc tctacaaagg     3540
cccagatttg tttgtaaagc actttgactc ttacctggag gcccgctctc taagggcttc    3600
ctgcgctccc acctcatctg tccctgagat gcagagcagg atggagggtc tgcttctagc    3660
tcagctgttt ctccttgagg ttgcggagga attgaattga atgggacaga gggcaggtgc    3720
tgtggccaag aagatctccg agcagcagtg acggggcacc ttgctgtgtg tcctctgggc    3780
atgttaaccc ttctgtgggg ccaaaggttt gcatcgtgga tccagctgtg ctccagtctg    3840
tcccctcctc ctccactctg actgccacgc cccggaccag cagcttgggg accctccagg    3900
gtactaatgg ggctctgttc tgagatggac aaattcagtg ttggaaatac atgttgtact    3960
atgcacttcc catgctccta gggttaggaa tagtttcaaa catgattggc agacataaca    4020
acggcaaata ctcggactgg ggcataggac tccagagtag gaaaaagaca aaagatttgg    4080
cagcctgaca caggcaacct acccctctct ctccagcctc tttatgaaac tgtttgtttg    4140
ccagtcctgc cctaaggcag aagatgaatt gaagatgctg tgcatgtttc ctaagtcctt    4200
gagcaatcat ggtggtgaca attgccacaa gggatatgag gccagtgcca ccagagggtg    4260
gtgccaagtg ccacatccct tccgatccat tcccctctgc atcctcggag caccccagtt    4320
tgcctttgat gtgtccgctg tgtatgttag ctgaactttg atgagcaaaa tttcctgagc    4380
```

-continued

```
gaaacactcc aaagagatag gaaaacttgc cgcctcttct tttttgtccc ttaatcaaac    4440
tcaaataagc ttaaaaaaaa tccatggaag atcatggaca tgtgaaatga gcatttttt     4500 cttttttttt tttaacaaag tctgaactga acagaacaag acttttttcct catacatctc   4560 caaattgttt aaacttactt tatgagtgtt tgtttagaag ttcggaccaa cagaaaaatg    4620
cagtcagatg tcatcttgga attggtttct aaaagagtaa ggcatgtccc tgcccagaaa    4680
cttaggaagc atgaaataaa tcaaatgttt attttccttc ttatttaaaa tcatgcaaat    4740
gcaacagaaa tagagggttt gtgccaaatg ctatgaacgg ccctttctta aagacaagca    4800
agggagattg atatatgtac aatttgctct catgttttaa aaaaaaaagg taaatgtaac    4860
ttaatagttt tgtaaatggg agaggggaa tctataaact ataaatacag ttattttatt     4920
ttttgtacat ttttaaggag aaaaaaataa atattcataa cataagagga aaa            4973

<210> SEQ ID NO 103
<211> LENGTH: 4746
<212> TYPE: DNA
<213> ORGANISM: Homo sapiens

<400> SEQUENCE: 103
taataaaaga ctagtggcct tagtgcccat gcccagtgac cctccattca atacccgaag      60
agcctacacc agtgaggatg aagcctggaa gtcatacttg gagaatcccc tgacagcagc     120
caccaaggcc atgatgagca ttaatggtga tgaggacagt gctgctgccc tcggcctgct     180
ctatgactac tacaaggttc ctcgagacaa gaggctgctg tctgtaagca agcaagtga     240 cagccaagaa gaccaggaga aagaaactg ccttggcacc agtgaagccc agagtaattt      300
gagtggagga gaaaaccgag tgcaagtcct aaagactgtt ccagtgaacc tttccctaaa    360
tcaagatcac ctggagaatt ccaagcggga acagtacagc atcagcttcc ccgagagctc    420
tgccatcatc ccggtgtcgg gaatcacggt ggtgaaagct gaagatttca caccagttt     480 catggcccca cctgtgcact atccccgggg agatggggaa gagcaacgag tggttatctt    540
tgaacagact cagtatgacg tgccctcgct ggccacccac agcgcctatc tcaaagacga    600
ccagcgcagc actccggaca gcacatacag cgagagcttc aaggacgcag ccacagaaaa    660
atttcggagt gcttcagttg gggctgagga gtacatgtat gatcagacat caagtggcac    720
atttcagtac accctggaag ccaccaaatc tctccgtcag aagcaggggg agggcccat     780 gacctacctc aacaaaggac agttctatgc cataacactc agcgagaccg agacaacaa     840 atgcttccga caccccatca gcaaagtcag gagtgtggtg atggtggtct tcagtgaaga    900
caaaaacaga gatgaacagc tcaaatactg gaaatactgg cactctcggc agcatacggc    960
gaagcagagg tccttgaca ttgccgatta caaggagagc tttaatacga ttggaaacat    1020
tgaagagatt gcatataatg ctgttttcctt tacctgggac gtgaatgaag aggcgaagat    1080
tttcatcacc gtgaattgct tgagcacaga tttctcctcc caaaaggggg tgaaaggact    1140
tcctttgatg attcagattg acacatacag ttataacaat cgtagcaata aacccattca    1200
tagagcttat tgccagatca aggtcttctg tgacaaagga gcagaaagaa aaatccgaga    1260
tgaagagcgg aagcagaaca ggaagaaagg gaaaggccag gcctcccaaa ctcaatgcaa    1320 cagctccttct gatgggaagt tggctgccat acctttacag aagaagagtg acatcaccta    1380
cttcaaaacc atgcctgatc tccactcaca gccagttctc ttcatacctg atgttcactt    1440
tgcaaacctg cagaggaccg gacaggtgta ttacaacacg gatgatgaac gagaaggtgg    1500
cagtgtcctt gttaaacgga tgttccggcc catggaagag gagtttggtc cagtgccttc    1560
```

```
aaagcagatg aaagaagaag ggacaaagcg agtgctcttg tacgtgagga aggagactga   1620
cgatgtgttc gatgcattga tgttgaagtc tcccacagtg aagggcctga tggaagcgat   1680
atctgagaaa tatgggctgc ccgtggagaa gatagcaaag ctttacaaga aaagcaaaaa   1740
aggcatcttg gtgaacatgg atgacaacat catcgagcac tactcgaacg aggacacctt   1800
catcctcaac atggagagca tggtggaggg cttcaaggtc acgctcatgg aaatctagcc   1860
ctgggtttgg catccgcttt ggctggagct ctcagtgcgt tcctccctga gagagacaga   1920
agccccagcc ccagaacctg agacccatc tcccccatct cacaactgct gttacaagac   1980
cgtgctgggg agtggggcaa gggacaggcc ccactgtcgg tgtgcttggc ccatccactg   2040
gcacctacca cggagctgaa gcctgagccc ctcaggaagg tgccttaggc ctgttggatt   2100
cctatttatt gcccaccttt tcctggagcc caggtccagg cccgccagga ctctgcaggt   2160
cactgctagc tccagatgag accgtccagc gttcccccctt caagagaaac actcatcccg   2220
aacagcctaa aaaattccca tcccttctct ctcacccctc catatctatc tcccgagtgg   2280
ctggacaaaa tgagctacgt ctgggtgcag tagttatagg tggggcaaga ggtggatgcc   2340
cactttctgg tcagacacct ttaggttgct ctggggaagg ctgtcttgct aaatacctcc   2400
agggttccca gcaagtggcc accaggcctt gtacaggaag acattcagtc accgtgtaat   2460
tagtaacaca gaaagtctgc ctgtctgcat tgtacatagt gttttataata ttgtaataat   2520 atattttacc tgtggtatgt gggcatgttt actgccactg gcctagagga gacacagacc   2580
tggagaccgt tttaatgggg gttttttgcct ctgtgcctgt tcaagagact tgcagggcta   2640
ggtagagggc ctttgggatg ttaaggtgac tgcagctgat gccaagatgg actctgcaat   2700
gggcatacct gggggctcgt tccctgtccc cagaggaagc cccctctcct tctccatggg   2760
catgactctc cttcgaggcc accacgttta tctcacaatg atgtgttttg cttgactttc   2820
cctttgcgct gtctcgtggg aaaggtcatt ctgtctgaga ccccagctcc ttctccagct   2880
ttggctgcgg gcatggcctg agcttttctgg agagcctctg caggggggttt gccatcaggg   2940 ccctgtggct gggtctgctg cagagctcct tggctatcag gagaatcctg gacactgtac   3000
tgtgcctccc agtttacaaa cacgcccttc atctcaagtg gccctttaaa aggcctgctg   3060
ccatgtgaga gctgtgaaca gctcagctct gagtcggcag gctggggctt cctcctgggc   3120
caccagatgg aaaggggta ttgtttgcct cactcctgga tgctgcgttt taaggaagtg   3180
agtgagaaag aatgtgccaa gatacctggc tcctgtgaaa ccagcctcag gagggaaact   3240
gggagagaga agctgtggtc tcctgctaca tgccctggga gctggaagag aaaaacactc   3300
ccctaaacaa tcgcaaaatg atgaaccatc atgggccact gttctctttg aggggacagg   3360 tttagggggtt tgcgttcgcc cttgtgggct gaagcactag cttttttggta gctagacaca   3420 tcctgcaccc aaaggttctc tacaaaggcc cagatttgtt tgtaaagcac tttgactctt   3480
acctggaggc ccgctctcta agggcttcct gcgctcccac ctcatctgtc cctgagatgc   3540
agagcaggat ggagggtctg cttctagctc agctgtttct ccttgaggtt gcggaggaat   3600
tgaattgaat gggacagagg gcaggtgctg tggccaagaa gatctccgag cagcagtgac   3660
ggggcacctt gctgtgtgtc ctctgggcat gttaaccctt ctgtggggcc aaaggtttgc   3720
atcgtggatc cagctgtgct ccagtctgtc ccctcctcct ccactctgac tgccacgccc   3780
cggaccagca gcttggggac cctccagggt actaatgggg ctctgttctg agatggacaa   3840
attcagtgtt ggaaatacat gttgtactat gcacttccca tgctcctagg gttaggaata   3900
gtttcaaaca tgattggcag acataacaac ggcaaatact cggactgggg cataggactc   3960
```

-continued

| | |
|---|---|
| cagagtagga aaaagacaaa agatttggca gcctgacaca ggcaacctac ccctctctct | 4020 |
| ccagcctctt tatgaaactg tttgtttgcc agtcctgccc taaggcagaa gatgaattga | 4080 |
| agatgctgtg catgtttcct aagtccttga gcaatcatgg tggtgacaat tgccacaagg | 4140 |
| gatatgaggc cagtgccacc agagggtggt gccaagtgcc acatcccttc cgatccattc | 4200 |
| ccctctgcat cctcggagca ccccagtttg cctttgatgt gtccgctgtg tatgttagct | 4260 |
| gaactttgat gagcaaaatt tcctgagcga aacactccaa agagatagga aaacttgccg | 4320 |
| cctcttcttt tttgtccctt aatcaaactc aaataagctt aaaaaaaatc catggaagat | 4380 |
| catggacatg tgaaatgagc attttttct tttttttttt taacaaagtc tgaactgaac | 4440 |
| agaacaagac ttttcctca tacatctcca aattgtttaa acttacttta tgagtgtttg | 4500 |
| tttagaagtt cggaccaaca gaaaaatgca gtcagatgtc atcttggaat tggtttctaa | 4560 |
| aagagtaagg catgtccctg cccagaaact taggaagcat gaaataaatc aaatgtttat | 4620 |
| tttccttctt atttaaaatc atgcaaatgc aacagaaata gagggtttgt gccaaatgct | 4680 |
| atgaacggcc ctttcttaaa gacaagcaag ggagattgat atatgtacaa tttgctctca | 4740 |
| tgtttt | 4746 |

<210> SEQ ID NO 104
<211> LENGTH: 4746
<212> TYPE: DNA
<213> ORGANISM: Homo sapiens

<400> SEQUENCE: 104

| | |
|---|---|
| taataaaaga ctagtggcct tagtgcccat gcccagtgac cctccattca atacccgaag | 60 |
| agcctacacc agtgaggatg aagcctggaa gtcatacttg gagaatcccc tgacagcagc | 120 |
| caccaaggcc atgatgagca ttaatggtga tgaggacagt gctgctgccc tcggcctgct | 180 |
| ctatgactac tacaaggttc ctcgagacaa gaggctgctg tctgtaagca agcaagtga | 240 |
| cagccaagaa gaccaggaga aaagaaactg ccttggcacc agtgaagccc agagtaattt | 300 |
| gagtggagga gaaaaccgag tgcaagtcct aaagactgtt ccagtgaacc tttccctaaa | 360 |
| tcaagatcac ctggagaatt ccaagcggga acagtacagc atcagcttcc ccgagagctc | 420 |
| tgccatcatc ccggtgtcgg gaatcacggt ggtgaaagct gaagatttca caccagtttt | 480 |
| catggcccca cctgtgcact atccccgggg agatggggaa gagcaacgag tggttatctt | 540 |
| tgaacagact cagtatgacg tgccctcgct ggccacccac agcgcctatc tcaaagacga | 600 |
| ccagcgcagc actccggaca gcacatacag cgagagcttc aaggacgcag ccacagagaa | 660 |
| atttcggagt gcttcagttg gggctgagga gtacatgtat gatcagacat caagtggcac | 720 |
| atttcagtac accctggaag ccaccaaatc tctccgtcag aagcaggggg agggcccat | 780 |
| gacctacctc aacaaaggac agttctatgc cataacactc agcgagaccg agacaacaa | 840 |
| atgcttccga caccccatca gcaaagtcag gagtgtggtg atggtggtct tcagtgaaga | 900 |
| caaaaacaga gatgaacagc tcaaatactg gaaatactgg cactctcggc agcatacggc | 960 |
| gaagcagagg gtccttgaca ttgccgatta caaggagagc tttaatacga ttggaaacat | 1020 |
| tgaagagatt gcatataatg ctgtttcctt tacctgggac gtgaatgaag aggcgaagat | 1080 |
| tttcatcacc gtgaattgct tgagcacaga tttctcctcc caaaaagggg tgaaaggact | 1140 |
| tcctttgatg attcagattg acacatacag ttataacaat cgtagcaata aacccattca | 1200 |
| tagagcttat tgccagatca aggtcttctg tgacaaagga gcagaaagaa aaatccgaga | 1260 |
| tgaagagcgg aagcagaaca ggaagaaagg gaaaggccag gcctcccaaa ctcaatgcaa | 1320 |

-continued

```
cagctcctct gatgggaagt tggctgccat acctttacag aagaagagtg acatcaccta   1380
cttcaaaacc atgcctgatc tccactcaca gccagttctc ttcatacctg atgttcactt   1440
tgcaaacctg cagaggaccg gacaggtgta ttacaacacg gatgatgaac gagaaggtgg   1500
cagtgtcctt gttaaacgga tgttccggcc catggaagag gagtttggtc cagtgccttc   1560
aaagcagatg aaagaagaag ggacaaagcg agtgctcttg tacgtgagga aggagactga   1620
cgatgtgttc gatgcattga tgttgaagtc tcccacagtg aagggcctga tggaagcgat   1680
atctgagaaa tatgggctgc cgtggagaa gatagcaaag ctttacaaga aagcaaaaa    1740
aggcatcttg gtgaacatgg atgacaacat catcgagcac tactcgaacg aggacacctt   1800
catcctcaac atggagagca tggtggaggg cttcaaggtc acgctcatgg aaatctagcc   1860
ctgggtttgg catccgcttt ggctggagct ctcagtgcgt tcctccctga gagagacaga   1920
agccccagcc ccagaacctg agacccatc tcccccatct cacaactgct gttacaagac   1980
cgtgctgggg agtggggcaa ggacaggcc ccactgtcgg tgtgcttggc ccatccactg    2040
gcacctacca cggagctgaa gcctgagccc ctcaggaagg tgccttaggc ctgttggatt   2100
cctatttatt gcccaccttt tcctggagcc caggtccagg cccgccagga ctctgcaggt   2160
cactgctagc tccagatgag accgtccagc gttccccctt caagagaaac actcatcccg   2220
aacagcctaa aaaattccca tcccttctct ctcaccctc catatctatc tcccgagtgg    2280
ctggacaaaa tgagctacgt ctgggtgcag tagttatagg tggggcaaga ggtggatgcc   2340
cactttctgg tcagacacct ttaggttgct ctggggaagg ctgtcttgct aaatacctcc   2400
agggttccca gcaagtggcc accaggcctt gtacaggaag acattcagtc accgtgtaat   2460
tagtaacaca gaaagtctgc ctgtctgcat tgtacatagt gtttataata ttgtaataat   2520
atattttacc tgtggtatgt gggcatgttt actgccactg gcctagagga gacacagacc   2580
tggagaccgt tttaatgggg gttttttgcct ctgtgcctgt tcaagagact tgcagggcta   2640
ggtagagggc cttgggatg ttaaggtgac tgcagctgat gccaagatgg actctgcaat    2700
gggcatacct gggggctcgt tccctgtccc cagaggaagc cccctctcct tctccatggg   2760
catgactctc cttcgaggcc accacgttta tctcacaatg atgtgttttg cttgactttc   2820
cctttgcgct gtctcgtggg aaaggtcatt ctgtctgaga ccccagctcc ttctccagct   2880
ttggctgcgg gcatggcctg agctttctgg agagcctctg caggggttt gccatcaggg    2940
ccctgtggct gggtctgctg cagagctcct tggctatcag gagaatcctg gacactgtac   3000
tgtgcctccc agtttacaaa cacgcccttc atctcaagtg gccctttaaa aggcctgctg   3060
ccatgtgaga gctgtgaaca gctcagctct gagtcggcag gctggggctt cctcctgggc   3120
caccagatga aaagggggta ttgtttgcct cactcctgga tgctgcgttt taaggaagtg   3180
agtgagaaag aatgtgccaa gatacctggc tcctgtgaaa ccagcctcag gagggaaact   3240
gggagagaga agctgtggtc tcctgctaca tgccctggga gctggaagag aaaaacactc   3300
ccctaaacaa tcgcaaaatg atgaaccatc atgggccact gttctctttg agggacagg    3360
tttaggggtt tgcgttcgcc cttgtgggct gaagcactag cttttttggta gctagacaca   3420
tcctgcaccc aaaggttctc tacaaaggcc cagatttgtt tgtaaagcac tttgactctt   3480
acctggaggc ccgctctcta agggcttcct gcgctcccac ctcatctgtc cctgagatgc   3540
agagcaggat ggagggtctg cttctagctc agctgtttct ccttgaggtt gcggaggaat   3600
tgaattgaat gggacagagg gcaggtgctg tggccaagaa gatctccgag cagcagtgac   3660
ggggcacctt gctgtgtgtc ctctgggcat gttaacccctt ctgtggggcc aaaggtttgc   3720
```

-continued

```
atcgtggatc cagctgtgct ccagtctgtc ccctcctcct ccactctgac tgccacgccc    3780
cggaccagca gcttggggac cctccagggt actaatgggg ctctgttctg agatggacaa    3840
attcagtgtt ggaaatacat gttgtactat gcacttccca tgctcctagg gttaggaata    3900
gtttcaaaca tgattggcag acataacaac ggcaaatact cggactgggg cataggactc    3960
cagagtagga aaagacaaa agatttggca gcctgacaca ggcaacctac ccctctctct    4020
ccagcctctt tatgaaactg tttgtttgcc agtcctgccc taaggcagaa gatgaattga    4080
agatgctgtg catgtttcct aagtccttga gcaatcatgg tggtgacaat tgccacaagg    4140
gatatgaggc cagtgccacc agagggtggt gccaagtgcc acatcccttc cgatccattc    4200
ccctctgcat cctcggagca ccccagtttg cctttgatgt gtccgctgtg tatgttagct    4260
gaactttgat gagcaaaatt tcctgagcga aacactccaa agagatagga aaacttgccg    4320
cctcttcttt tttgtcccctt aatcaaactc aaataagctt aaaaaaaatc catggaagat    4380
catggacatg tgaaatgagc atttttttct tttttttttt taacaaagtc tgaactgaac    4440
agaacaagac ttttcctca tacatctcca aattgtttaa acttacttta tgagtgtttg    4500
tttagaagtt cggaccaaca gaaaaatgca gtcagatgtc atcttggaat tggtttctaa    4560
aagagtaagg catgtccctg cccagaaact taggaagcat gaaataaatc aaatgtttat    4620
tttccttctt atttaaaatc atgcaaatgc aacagaaata gagggtttgt gccaaatgct    4680
atgaacggcc ctttcttaaa gacaagcaag ggagattgat atatgtacaa tttgctctca    4740
tgtttt    4746
```

<210> SEQ ID NO 105
<211> LENGTH: 609
<212> TYPE: PRT
<213> ORGANISM: Homo sapiens

<400> SEQUENCE: 105

```
Met Pro Ser Asp Pro Pro Phe Asn Thr Arg Arg Ala Tyr Thr Ser Glu
 1               5                  10                  15

Asp Glu Ala Trp Lys Ser Tyr Leu Glu Asn Pro Leu Thr Ala Ala Thr
            20                  25                  30

Lys Ala Met Met Ser Ile Asn Gly Asp Glu Asp Ser Ala Ala Ala Leu
        35                  40                  45

Gly Leu Leu Tyr Asp Tyr Tyr Lys Val Pro Arg Asp Lys Arg Leu Leu
    50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
            100                 105                 110

Asp His Leu Glu Asn Ser Lys Arg Glu Gln Tyr Ser Ile Ser Phe Pro
        115                 120                 125

Glu Ser Ser Ala Ile Ile Pro Val Ser Gly Ile Thr Val Val Lys Ala
    130                 135                 140

Glu Asp Phe Thr Pro Val Phe Met Ala Pro Val His Tyr Pro Arg
145                 150                 155                 160

Gly Asp Gly Glu Glu Gln Arg Val Val Ile Phe Glu Gln Thr Gln Tyr
                165                 170                 175

Asp Val Pro Ser Leu Ala Thr His Ser Ala Tyr Leu Lys Asp Asp Gln
            180                 185                 190
```

```
Arg Ser Thr Pro Asp Ser Thr Tyr Ser Glu Ser Phe Lys Asp Ala Ala
        195                 200                 205

Thr Glu Lys Phe Arg Ser Ala Ser Val Gly Ala Glu Glu Tyr Met Tyr
210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
            245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Val Met Val Val Phe
        275                 280                 285

Ser Glu Asp Lys Asn Arg Asp Glu Gln Leu Lys Tyr Trp Lys Tyr Trp
290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
            325                 330                 335

Asn Ala Val Ser Phe Thr Trp Asp Val Asn Glu Glu Ala Lys Ile Phe
            340                 345                 350

Ile Thr Val Asn Cys Leu Ser Thr Asp Phe Ser Ser Gln Lys Gly Val
        355                 360                 365

Lys Gly Leu Pro Leu Met Ile Gln Ile Asp Thr Tyr Ser Tyr Asn Asn
370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Glu Arg Lys Gln
            405                 410                 415

Asn Arg Lys Lys Gly Lys Gly Gln Ala Ser Gln Thr Gln Cys Asn Ser
            420                 425                 430

Ser Ser Asp Gly Lys Leu Ala Ala Ile Pro Leu Gln Lys Lys Ser Asp
        435                 440                 445

Ile Thr Tyr Phe Lys Thr Met Pro Asp Leu His Ser Gln Pro Val Leu
450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Ser Val Leu Val Lys
            485                 490                 495

Arg Met Phe Arg Pro Met Glu Glu Glu Phe Gly Pro Val Pro Ser Lys
            500                 505                 510

Gln Met Lys Glu Glu Gly Thr Lys Arg Val Leu Leu Tyr Val Arg Lys
        515                 520                 525

Glu Thr Asp Asp Val Phe Asp Ala Leu Met Leu Lys Ser Pro Thr Val
530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Gly Ile Leu Val Asn
            565                 570                 575

Met Asp Asp Asn Ile Ile Glu His Tyr Ser Asn Glu Asp Thr Phe Ile
            580                 585                 590

Leu Asn Met Glu Ser Met Val Glu Gly Phe Lys Val Thr Leu Met Glu
        595                 600                 605

Ile
```

-continued

```
<210> SEQ ID NO 106
<211> LENGTH: 609
<212> TYPE: PRT
<213> ORGANISM: Homo sapiens

<400> SEQUENCE: 106
```

Met Pro Ser Asp Pro Pro Phe Asn Thr Arg Ala Tyr Thr Ser Glu
1               5                   10                  15

Asp Glu Ala Trp Lys Ser Tyr Leu Glu Asn Pro Leu Thr Ala Ala Thr
            20                  25                  30

Lys Ala Met Met Ser Ile Asn Gly Asp Glu Asp Ser Ala Ala Ala Leu
                35                  40                  45

Gly Leu Leu Tyr Asp Tyr Tyr Lys Val Pro Arg Asp Lys Arg Leu Leu
    50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
            100                 105                 110

Asp His Leu Glu Asn Ser Lys Arg Glu Gln Tyr Ser Ile Ser Phe Pro
        115                 120                 125

Glu Ser Ser Ala Ile Ile Pro Val Ser Gly Ile Thr Val Val Lys Ala
130                 135                 140

Glu Asp Phe Thr Pro Val Phe Met Ala Pro Val His Tyr Pro Arg
145                 150                 155                 160

Gly Asp Gly Glu Glu Gln Arg Val Val Ile Phe Glu Gln Thr Gln Tyr
                165                 170                 175

Asp Val Pro Ser Leu Ala Thr His Ser Ala Tyr Leu Lys Asp Asp Gln
            180                 185                 190

Arg Ser Thr Pro Asp Ser Thr Tyr Ser Glu Ser Phe Lys Asp Ala Ala
        195                 200                 205

Thr Glu Lys Phe Arg Ser Ala Ser Val Gly Ala Glu Glu Tyr Met Tyr
210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Val Met Val Val Phe
        275                 280                 285

Ser Glu Asp Lys Asn Arg Asp Glu Gln Leu Lys Tyr Trp Lys Tyr Trp
290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
            340                 345                 350

Ile Thr Val Asn Cys Leu Ser Thr Asp Phe Ser Ser Gln Lys Gly Val
        355                 360                 365

Lys Gly Leu Pro Leu Met Ile Gln Ile Asp Thr Tyr Ser Tyr Asn Asn
370                 375                 380

```
Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Glu Arg Lys Gln
                405                 410                 415

Asn Arg Lys Lys Gly Lys Gly Gln Ala Ser Gln Thr Gln Cys Asn Ser
            420                 425                 430

Ser Ser Asp Gly Lys Leu Ala Ala Ile Pro Leu Gln Lys Lys Ser Asp
        435                 440                 445

Ile Thr Tyr Phe Lys Thr Met Pro Asp Leu His Ser Gln Pro Val Leu
    450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Phe Gly Pro Val Pro Ser Lys
            500                 505                 510

Gln Met Lys Glu Glu Gly Thr Lys Arg Val Leu Leu Tyr Val Arg Lys
                515                 520                 525

Glu Thr Asp Asp Val Phe Asp Ala Leu Met Leu Lys Ser Pro Thr Val
530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Ser Lys Lys Gly Ile Leu Val Asn
            565                 570                 575

Met Asp Asp Asn Ile Ile Glu His Tyr Ser Asn Glu Asp Thr Phe Ile
        580                 585                 590

Leu Asn Met Glu Ser Met Val Glu Gly Phe Lys Val Thr Leu Met Glu
        595                 600                 605

Ile

<210> SEQ ID NO 107
<211> LENGTH: 609
<212> TYPE: PRT
<213> ORGANISM: Homo sapiens

<400> SEQUENCE: 107

Met Pro Ser Asp Pro Pro Phe Asn Thr Arg Arg Ala Tyr Thr Ser Glu
1               5                   10                  15

Asp Glu Ala Trp Lys Ser Tyr Leu Glu Asn Pro Leu Thr Ala Ala Thr
            20                  25                  30

Lys Ala Met Met Ser Ile Asn Gly Asp Glu Asp Ser Ala Ala Ala Leu
        35                  40                  45

Gly Leu Leu Tyr Asp Tyr Tyr Lys Val Pro Arg Asp Lys Arg Leu Leu
    50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
            100                 105                 110

Asp His Leu Glu Asn Ser Lys Arg Glu Gln Tyr Ser Ile Ser Phe Pro
        115                 120                 125

Glu Ser Ser Ala Ile Ile Pro Val Ser Gly Ile Thr Val Val Lys Ala
    130                 135                 140

Glu Asp Phe Thr Pro Val Phe Met Ala Pro Pro Val His Tyr Pro Arg
```

```
                145                 150                 155                 160
Gly Asp Gly Glu Glu Gln Arg Val Val Ile Phe Glu Gln Thr Gln Tyr
                165                 170                 175
Asp Val Pro Ser Leu Ala Thr His Ser Ala Tyr Leu Lys Asp Asp Gln
                180                 185                 190
Arg Ser Thr Pro Asp Ser Thr Tyr Ser Glu Ser Phe Lys Asp Ala Ala
                195                 200                 205
Thr Glu Lys Phe Arg Ser Ala Ser Val Gly Ala Glu Glu Tyr Met Tyr
                210                 215                 220
Asp Gln Thr Ser Ser Gly Thr Phe Gln Tyr Thr Leu Glu Ala Thr Lys
225                 230                 235                 240
Ser Leu Arg Gln Lys Gln Gly Glu Gly Pro Met Thr Tyr Leu Asn Lys
                245                 250                 255
Gly Gln Phe Tyr Ala Ile Thr Leu Ser Glu Thr Gly Asp Asn Lys Cys
                260                 265                 270
Phe Arg His Pro Ile Ser Lys Val Arg Ser Val Val Met Val Val Phe
                275                 280                 285
Ser Glu Asp Lys Asn Arg Asp Glu Gln Leu Lys Tyr Trp Lys Tyr Trp
                290                 295                 300
His Ser Arg Gln His Thr Ala Lys Gln Arg Val Leu Asp Ile Ala Asp
305                 310                 315                 320
Tyr Lys Glu Ser Phe Asn Thr Ile Gly Asn Ile Glu Glu Ile Ala Tyr
                325                 330                 335
Asn Ala Val Ser Phe Thr Trp Asp Val Asn Glu Glu Ala Lys Ile Phe
                340                 345                 350
Ile Thr Val Asn Cys Leu Ser Thr Asp Phe Ser Ser Gln Lys Gly Val
                355                 360                 365
Lys Gly Leu Pro Leu Met Ile Gln Ile Asp Thr Tyr Ser Tyr Asn Asn
                370                 375                 380
Arg Ser Asn Lys Pro Ile His Arg Ala Tyr Cys Gln Ile Lys Val Phe
385                 390                 395                 400
Cys Asp Lys Gly Ala Glu Arg Lys Ile Arg Asp Glu Glu Arg Lys Gln
                405                 410                 415
Asn Arg Lys Lys Gly Lys Gly Gln Ala Ser Gln Thr Gln Cys Asn Ser
                420                 425                 430
Ser Ser Asp Gly Lys Leu Ala Ala Ile Pro Leu Gln Lys Lys Ser Asp
                435                 440                 445
Ile Thr Tyr Phe Lys Thr Met Pro Asp Leu His Ser Gln Pro Val Leu
450                 455                 460
Phe Ile Pro Asp Val His Phe Ala Asn Leu Gln Arg Thr Gly Gln Val
465                 470                 475                 480
Tyr Tyr Asn Thr Asp Asp Glu Arg Glu Gly Gly Ser Val Leu Val Lys
                485                 490                 495
Arg Met Phe Arg Pro Met Glu Glu Phe Gly Pro Val Pro Ser Lys
                500                 505                 510
Gln Met Lys Glu Glu Gly Thr Lys Arg Val Leu Leu Tyr Val Arg Lys
                515                 520                 525
Glu Thr Asp Asp Val Phe Asp Ala Leu Met Leu Lys Ser Pro Thr Val
                530                 535                 540
Lys Gly Leu Met Glu Ala Ile Ser Glu Lys Tyr Gly Leu Pro Val Glu
545                 550                 555                 560
Lys Ile Ala Lys Leu Tyr Lys Lys Ser Lys Lys Gly Ile Leu Val Asn
                565                 570                 575
```

```
Met Asp Asp Asn Ile Ile Glu His Tyr Ser Asn Glu Asp Thr Phe Ile
            580                 585                 590

Leu Asn Met Glu Ser Met Val Glu Gly Phe Lys Val Thr Leu Met Glu
        595                 600                 605

Ile

<210> SEQ ID NO 108
<211> LENGTH: 609
<212> TYPE: PRT
<213> ORGANISM: Homo sapiens

<400> SEQUENCE: 108

Met Pro Ser Asp Pro Phe Asn Thr Arg Arg Ala Tyr Thr Ser Glu
1               5                   10                  15

Asp Glu Ala Trp Lys Ser Tyr Leu Glu Asn Pro Leu Thr Ala Ala Thr
            20                  25                  30

Lys Ala Met Met Ser Ile Asn Gly Asp Glu Asp Ser Ala Ala Ala Leu
        35                  40                  45

Gly Leu Leu Tyr Asp Tyr Tyr Lys Val Pro Arg Asp Lys Arg Leu Leu
    50                  55                  60

Ser Val Ser Lys Ala Ser Asp Ser Gln Glu Asp Gln Glu Lys Arg Asn
65                  70                  75                  80

Cys Leu Gly Thr Ser Glu Ala Gln Ser Asn Leu Ser Gly Gly Glu Asn
                85                  90                  95

Arg Val Gln Val Leu Lys Thr Val Pro Val Asn Leu Ser Leu Asn Gln
            100                 105                 110

Asp His Leu Glu Asn Ser Lys Arg Glu Gln Tyr Ser Ile Ser Phe Pro
        115                 120                 125

Glu Ser Ser Ala Ile Ile Pro Val Ser Gly Ile Thr Val Val Lys Ala
    130                 135                 140

Glu Asp Phe Thr Pro Val Phe Met Ala Pro Pro Val His Tyr Pro Arg
145                 150                 155                 160

Gly Asp Gly Glu Glu Gln Arg Val Val Ile Phe Glu Gln Thr Gln Tyr
                165                 170                 175

Asp Val Pro Ser Leu Ala Thr His Ser Ala Tyr Leu Lys Asp Asp Gln
            180                 185                 190

Arg Ser Thr Pro Asp Ser Thr Tyr Ser Glu Ser Phe Lys Asp Ala Ala
        195                 200                 205

Thr Glu Lys Phe Arg Ser Ala Ser Val Gly Ala Glu Glu Tyr Met Tyr
    210                 215                 220

Asp Gln Thr Ser Ser Gly Thr Phe Gln Tyr Thr Leu Glu Ala Thr Lys
225                 230                 235                 240

Ser Leu Arg Gln Lys Gln Gly Glu Gly Pro Met Thr Tyr Leu Asn Lys
                245                 250                 255

Gly Gln Phe Tyr Ala Ile Thr Leu Ser Glu Thr Gly Asp Asn Lys Cys
            260                 265                 270

Phe Arg His Pro Ile Ser Lys Val Arg Ser Val Val Met Val Val Phe
        275                 280                 285

Ser Glu Asp Lys Asn Arg Asp Glu Gln Leu Lys Tyr Trp Lys Tyr Trp
    290                 295                 300

His Ser Arg Gln His Thr Ala Lys Gln Arg Val Leu Asp Ile Ala Asp
305                 310                 315                 320

Tyr Lys Glu Ser Phe Asn Thr Ile Gly Asn Ile Glu Glu Ile Ala Tyr
                325                 330                 335

Asn Ala Val Ser Phe Thr Trp Asp Val Asn Glu Glu Ala Lys Ile Phe
```

-continued

```
                    340                 345                 350
Ile Thr Val Asn Cys Leu Ser Thr Asp Phe Ser Ser Gln Lys Gly Val
        355                 360                 365

Lys Gly Leu Pro Leu Met Ile Gln Ile Asp Thr Tyr Ser Tyr Asn Asn
        370                 375                 380

Arg Ser Asn Lys Pro Ile His Arg Ala Tyr Cys Gln Ile Lys Val Phe
385                 390                 395                 400

Cys Asp Lys Gly Ala Glu Arg Lys Ile Arg Asp Glu Glu Arg Lys Gln
                405                 410                 415

Asn Arg Lys Lys Gly Lys Gly Gln Ala Ser Gln Thr Gln Cys Asn Ser
            420                 425                 430

Ser Ser Asp Gly Lys Leu Ala Ala Ile Pro Leu Gln Lys Lys Ser Asp
        435                 440                 445

Ile Thr Tyr Phe Lys Thr Met Pro Asp Leu His Ser Gln Pro Val Leu
    450                 455                 460

Phe Ile Pro Asp Val His Phe Ala Asn Leu Gln Arg Thr Gly Gln Val
465                 470                 475                 480

Tyr Tyr Asn Thr Asp Asp Glu Arg Glu Gly Gly Ser Val Leu Val Lys
                485                 490                 495

Arg Met Phe Arg Pro Met Glu Glu Glu Phe Gly Pro Val Pro Ser Lys
                500                 505                 510

Gln Met Lys Glu Glu Gly Thr Lys Arg Val Leu Leu Tyr Val Arg Lys
            515                 520                 525

Glu Thr Asp Asp Val Phe Asp Ala Leu Met Leu Lys Ser Pro Thr Val
        530                 535                 540

Lys Gly Leu Met Glu Ala Ile Ser Glu Lys Tyr Gly Leu Pro Val Glu
545                 550                 555                 560

Lys Ile Ala Lys Leu Tyr Lys Lys Ser Lys Lys Gly Ile Leu Val Asn
                565                 570                 575

Met Asp Asp Asn Ile Ile Glu His Tyr Ser Asn Glu Asp Thr Phe Ile
            580                 585                 590

Leu Asn Met Glu Ser Met Val Glu Gly Phe Lys Val Thr Leu Met Glu
        595                 600                 605

Ile
```